US012576159B2

(12) United States Patent
Reichert et al.

(10) Patent No.: US 12,576,159 B2

(45) Date of Patent: Mar. 17, 2026

(54) ANTI-HUMAN PD-1 ANTIBODY CRYSTALS AND METHODS OF USE THEREOF

(71) Applicant: Merck Sharp & Dohme LLC, Rahway, NJ (US)

(72) Inventors: Paul Reichert, Montville, NJ (US); Winifred W. Prosise, Ramsey, NJ (US); Xiaoyu Yang, Basking Ridge, NJ (US); Corey Strickland, Martinsville, NJ (US); Chakravarthy Nachu Narasimhan, Scotch Plains, NJ (US); Thierry O. Fischmann, Scotch Plains, NJ (US); Erika R. Walsh, Scotch Plains, NJ (US); Yongchao Su, Hillsborough, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 934 days.

(21) Appl. No.: 17/287,588

(22) PCT Filed: Oct. 28, 2019

(86) PCT No.: PCT/US2019/058339

§ 371 (c)(1),
(2) Date: Apr. 22, 2021

(87) PCT Pub. No.: WO2020/092233

PCT Pub. Date: May 7, 2020

(65) Prior Publication Data

US 2021/0317215 A1 Oct. 14, 2021

Related U.S. Application Data

(60) Provisional application No. 62/753,615, filed on Oct. 31, 2018.

(51) Int. Cl.
*C30B 29/58* (2006.01)
*A61K 31/522* (2006.01)
(Continued)

(52) U.S. Cl.
CPC ........ *A61K 47/6849* (2017.08); *A61K 31/522* (2013.01); *A61K 45/06* (2013.01);
(Continued)

(58) Field of Classification Search
CPC . C30B 29/58; C07B 2200/13; C07B 16/2818; C07B 2299/00; A61K 45/06;
(Continued)

(56) References Cited

U.S. PATENT DOCUMENTS 4,401,820 A 8/1983 Chibata et al.
4,816,567 A 3/1989 Cabilly et al.
(Continued)

FOREIGN PATENT DOCUMENTS

AU 2010200784 A1 3/2010
CA 2918888 A1 1/2015
(Continued)

OTHER PUBLICATIONS

Baker, M., Upping the ante on antibodies, Nature Biotechnology, 2005, pp. 1065-1072, vol. 23.
(Continued)

*Primary Examiner* — Robert M Kunemund
(74) *Attorney, Agent, or Firm* — Jonathan B. Fitzgerald; Emily K. Sauter

(57) ABSTRACT

The invention provides methods for producing crystalline an anti-PD-1 monoclonal antibody (mAb), wherein the mAb is pembrolizumab or a pembrolizumab variant, comprising (1) mixing a solution comprising (a) the mAb, (b) polyethylene glycol (PEG), and (c) an additive selected from the group consisting of: caffeine, theophylline, 2' deoxyguanosine-5'-
(Continued)

monophosphate, a bioactive gibberellin, and a pharmaceutically acceptable salt of said bioactive gibberellin, to form a crystallization solution, (2) incubating the crystallization solution for a period of time sufficient for crystal formation; and (3) optionally harvesting the crystalline anti-PD-1 mAb from the solution. In specific embodiments, the PEG is PEG 3350 and the additive is caffeine. The invention also relates to the novel anti-human PD-1 mAb crystals produced by the methods described herein. Characterization of re-dissolved crystalline suspensions using several biochemical methods showed the bio-physical properties of the re-dissolved mAb crystals were consistent with the intact antibody starting sample. The crystals and methods of the invention are amenable to multiple pharmaceutical applications such as purification, storage, formulation, and drug delivery.

7 Claims, 13 Drawing Sheets

Specification includes a Sequence Listing.

(51) Int. Cl.

| | |
|---|---|
| ***A61K 45/06*** | (2006.01) |
| ***A61K 47/10*** | (2017.01) |
| ***A61K 47/68*** | (2017.01) |
| ***A61P 35/00*** | (2006.01) |
| ***C07K 16/28*** | (2006.01) |
| *A61K 39/00* | (2006.01) |

(52) U.S. Cl.
CPC .............. *A61K 47/10* (2013.01); *A61P 35/00* (2018.01); *C07K 16/2818* (2013.01); *C30B 29/58* (2013.01); *A61K 2039/545* (2013.01); *C07B 2200/13* (2013.01); *C07K 2299/00* (2013.01)

(58) Field of Classification Search
CPC .. A61K 47/10; A61K 31/522; A61K 47/6849; A61P 35/00; A61P 2039/545
See application file for complete search history.

(56) References Cited

U.S. PATENT DOCUMENTS

| | | | |
|---|---|---|---|
| 5,262,296 | A | 11/1993 | Ogawa et al. |
| 5,762,905 | A | 6/1998 | Burton et al. |
| 6,171,586 | B1 | 1/2001 | Lam et al. |
| 6,267,958 | B1 | 7/2001 | Andya et al. |
| 6,329,511 | B1 | 12/2001 | Vasquez et al. |
| 6,818,216 | B2 | 11/2004 | Young et al. |
| 6,875,432 | B2 | 4/2005 | Liu et al. |
| 7,247,707 | B2 | 7/2007 | Besman et al. |
| 7,364,736 | B2 | 4/2008 | Boyle et al. |
| 7,374,762 | B2 | 5/2008 | Amphlett et al. |
| 7,375,193 | B2 | 5/2008 | Baca et al. |
| 7,563,869 | B2 | 7/2009 | Honjo et al. |
| 7,592,004 | B2 | 9/2009 | Kaisheva et al. |
| 7,615,213 | B2 | 11/2009 | Kasaian et al. |
| 7,635,473 | B2 | 12/2009 | Warne et al. |
| 7,662,384 | B2 | 2/2010 | Ramakrishnan et al. |
| 7,666,413 | B2 | 2/2010 | Liu et al. |
| 7,691,379 | B2 | 4/2010 | Allan et al. |
| 7,705,132 | B2 | 4/2010 | Rehder et al. |
| 7,740,842 | B2 | 6/2010 | Arvinte et al. |
| 7,833,525 | B2 | 11/2010 | Shenoy et al. |
| 7,959,922 | B2 | 6/2011 | Bakker et al. |
| 7,960,516 | B2 | 6/2011 | Matheus et al. |
| 7,993,645 | B2 | 8/2011 | Benson et al. |
| 7,998,477 | B2 | 8/2011 | Yakovlevsky et al. |
| 8,034,906 | B2 | 10/2011 | Borhani et al. |
| 8,067,547 | B2 | 11/2011 | Ewert et al. |
| 8,142,776 | B2 | 3/2012 | Liu et al. |
| 8,168,760 | B2 | 5/2012 | Borhani et al. |
| 8,216,583 | B2 | 7/2012 | Kruase et al. |
| 8,221,759 | B2 | 7/2012 | Pilkington et al. |
| 8,263,080 | B2 | 9/2012 | Katsikis et al. |
| 8,293,883 | B2 | 10/2012 | Presta |
| 8,354,509 | B2 | 1/2013 | Carven et al. |
| 8,399,712 | B2 | 3/2013 | Schultheiss |
| 8,568,720 | B2 | 10/2013 | Morichika et al. |
| 8,580,297 | B2 | 11/2013 | Essler et al. |
| 8,747,847 | B2 | 6/2014 | Rotem-Yehudar et al. |
| 8,933,075 | B2 | 1/2015 | Wang et al. |
| 9,220,776 | B2 | 12/2015 | Sharma et al. |
| 9,278,131 | B2 | 3/2016 | Dauty et al. |
| 9,592,297 | B2 | 3/2017 | Xiang et al. |
| 9,605,051 | B2 | 3/2017 | Soane et al. |
| 9,713,641 | B2 | 7/2017 | Hicklin et al. |
| 9,782,470 | B2 | 10/2017 | Bhambhani et al. |
| 9,926,371 | B2 | 3/2018 | Liu et al. |
| 10,072,072 | B2 | 9/2018 | Vora et al. |
| 10,444,520 | B2 | 10/2019 | Dholakia et al. |
| 10,787,518 | B2 | 9/2020 | Bernett et al. |
| 11,034,765 | B2 | 6/2021 | Galler et al. |
| 11,633,476 | B2 | 4/2023 | Sharma et al. |
| 2003/0138417 | A1 | 7/2003 | Kaisheva et al. |
| 2004/0091490 | A1 | 5/2004 | Johnson et al. |
| 2005/0101770 | A1 | 5/2005 | Presta |
| 2005/0175986 | A1 | 8/2005 | Gross et al. |
| 2006/0029599 | A1 | 2/2006 | Kaisheva et al. |
| 2006/0057702 | A1 | 3/2006 | Rosenthal et al. |
| 2006/0088523 | A1 | 4/2006 | Andya et al. |
| 2006/0210557 | A1 | 9/2006 | Luisi et al. |
| 2006/0210567 | A1 | 9/2006 | Collins et al. |
| 2006/0246004 | A1 | 11/2006 | Adams et al. |
| 2006/0286103 | A1 | 12/2006 | Kolhe et al. |
| 2007/0009526 | A1 | 1/2007 | Benson et al. |
| 2007/0009541 | A1 | 1/2007 | Amphlett et al. |
| 2007/0048315 | A1 | 3/2007 | Presta |
| 2007/0053900 | A1 | 3/2007 | Liu et al. |
| 2007/0059803 | A1 | 3/2007 | Oppmann et al. |
| 2007/0065437 | A1 | 3/2007 | Elson et al. |
| 2007/0184050 | A1 | 8/2007 | Ishikawa et al. |
| 2007/0190047 | A1 | 8/2007 | Brych et al. |
| 2008/0003220 | A1 | 1/2008 | Gokarn |
| 2008/0050375 | A1 | 2/2008 | Davies et al. |
| 2008/0057070 | A1 | 3/2008 | Long et al. |
| 2008/0112953 | A1 | 5/2008 | Mcauley et al. |
| 2008/0124326 | A1 | 5/2008 | Rehder et al. |
| 2008/0152658 | A1 | 6/2008 | Dagan et al. |
| 2008/0213282 | A1 | 9/2008 | Jacob |
| 2008/0248048 | A1 | 10/2008 | Fish et al. |
| 2008/0254026 | A1 | 10/2008 | Long et al. |
| 2008/0286270 | A1 | 11/2008 | Oliver et al. |
| 2008/0311119 | A1 | 12/2008 | Maloney et al. |
| 2009/0042315 | A1 | 2/2009 | Li et al. |
| 2009/0060906 | A1 | 3/2009 | Barry et al. |
| 2009/0130119 | A1 | 5/2009 | Abate et al. |
| 2009/0162352 | A1 | 6/2009 | Adler et al. |
| 2009/0181027 | A1 | 7/2009 | Dal Monte et al. |
| 2009/0208492 | A1 | 8/2009 | O'Connor et al. |
| 2009/0217401 | A1 | 8/2009 | Korman et al. |
| 2009/0285802 | A1 | 11/2009 | Igawa et al. |
| 2009/0291076 | A1 | 11/2009 | Morichika et al. |
| 2009/0304706 | A1 | 12/2009 | Lu et al. |
| 2009/0311253 | A1 | 12/2009 | Ghayur et al. |
| 2010/0021461 | A1 | 1/2010 | Burke et al. |
| 2010/0068209 | A1 | 3/2010 | Maggio |
| 2010/0137213 | A1 | 6/2010 | Fernandez et al. |
| 2010/0209434 | A1 | 8/2010 | Bishop et al. |
| 2010/0209437 | A1 | 8/2010 | Elson et al. |
| 2010/0226928 | A1 | 9/2010 | Dani |
| 2010/0266617 | A1 | 10/2010 | Carven et al. |
| 2010/0272731 | A1 | 10/2010 | Presta et al. |
| 2010/0278822 | A1 | 11/2010 | Fraunhofer et al. |
| 2010/0286038 | A1 | 11/2010 | Antochshuk et al. |
| 2010/0303827 | A1 | 12/2010 | Sharma et al. |
| 2010/0316638 | A1 | 12/2010 | Gurny et al. |
| 2011/0014203 | A1 | 1/2011 | Nilsson et al. |
| 2011/0059079 | A1 | 3/2011 | Babuka et al. |

(56) References Cited

U.S. PATENT DOCUMENTS

| | | | |
|---|---|---|---|
| 2011/0060290 | A1 | 3/2011 | Bonk et al. |
| 2011/0086038 | A1 | 4/2011 | Hope et al. |
| 2011/0123550 | A1 | 5/2011 | Shibayama et al. |
| 2011/0189275 | A1 | 8/2011 | Schultheiss |
| 2011/0226650 | A1 | 9/2011 | Gokarn et al. |
| 2011/0229490 | A1 | 9/2011 | Li et al. |
| 2011/0256135 | A1 | 10/2011 | Fraunhofer et al. |
| 2011/0300135 | A1 | 12/2011 | Lobo et al. |
| 2011/0318343 | A1 | 12/2011 | Kaisheva et al. |
| 2012/0039876 | A1 | 2/2012 | Oliver et al. |
| 2012/0076784 | A1 | 3/2012 | Matheus et al. |
| 2012/0128687 | A1 | 5/2012 | Adler et al. |
| 2012/0148576 | A1 | 6/2012 | Sharma et al. |
| 2012/0183531 | A1 | 7/2012 | Lucas et al. |
| 2012/0231972 | A1 | 9/2012 | Golyshin et al. |
| 2013/0022625 | A1 | 1/2013 | Igawa et al. |
| 2013/0058958 | A1 | 3/2013 | Bowen et al. |
| 2013/0108651 | A1 | 5/2013 | Carven et al. |
| 2013/0186797 | A1 | 7/2013 | Walsh |
| 2014/0044708 | A1 | 2/2014 | Dauty et al. |
| 2014/0044727 | A1 | 2/2014 | Monck et al. |
| 2014/0178401 | A1 | 6/2014 | Nabozny et al. |
| 2014/0206845 | A1 | 7/2014 | Kameoka et al. |
| 2014/0227250 | A1 | 8/2014 | Li et al. |
| 2014/0234296 | A1 | 8/2014 | Sharma et al. |
| 2014/0314714 | A1 | 10/2014 | Honjo et al. |
| 2014/0348841 | A1 | 11/2014 | Schebye et al. |
| 2015/0071936 | A1 | 3/2015 | Mendiratta et al. |
| 2015/0086537 | A1 | 3/2015 | Adler et al. |
| 2015/0086559 | A1 | 3/2015 | Mueller et al. |
| 2015/0100030 | A1 | 4/2015 | Dix et al. |
| 2015/0110783 | A1 | 4/2015 | Lu et al. |
| 2015/0258209 | A1 | 9/2015 | Benz et al. |
| 2015/0290325 | A1 | 10/2015 | Kashi et al. |
| 2015/0307606 | A1 | 10/2015 | Basarkar et al. |
| 2015/0359900 | A1 | 12/2015 | Wang et al. |
| 2016/0022814 | A1 | 1/2016 | Petit et al. |
| 2016/0045615 | A1 | 2/2016 | Li et al. |
| 2016/0090419 | A1 | 3/2016 | Morichika et al. |
| 2016/0166685 | A1 | 6/2016 | Cheung et al. |
| 2016/0176963 | A1 | 6/2016 | Maurer et al. |
| 2016/0222116 | A1 | 8/2016 | Korman |
| 2016/0289315 | A1 | 10/2016 | Mirza et al. |
| 2016/0304607 | A1 | 10/2016 | Sadineni et al. |
| 2016/0355589 | A1 | 12/2016 | Williams et al. |
| 2017/0051039 | A1 | 2/2017 | Gombotz et al. |
| 2017/0056347 | A1 | 3/2017 | Glick et al. |
| 2017/0089914 | A1 | 3/2017 | Loo et al. |
| 2017/0097333 | A1 | 4/2017 | Bhagwat et al. |
| 2017/0210792 | A1 | 7/2017 | Mason et al. |
| 2017/0210812 | A1 | 7/2017 | Wong et al. |
| 2017/0216433 | A1 | 8/2017 | Li et al. |
| 2017/0218069 | A1 | 8/2017 | Rosengren et al. |
| 2017/0306025 | A1 | 10/2017 | Du et al. |
| 2017/0360929 | A1 | 12/2017 | Sinha et al. |
| 2018/0044419 | A9 | 2/2018 | Rosengren et al. |
| 2018/0237524 | A1 | 8/2018 | Reichert et al. |
| 2018/0333493 | A1 | 11/2018 | Shenoy |
| 2018/0339045 | A1 | 11/2018 | Li et al. |
| 2019/0010231 | A1 | 1/2019 | Rothe et al. |
| 2019/0330363 | A1 | 10/2019 | Jansson et al. |
| 2020/0055938 | A1 | 2/2020 | Desai et al. |
| 2020/0147213 | A1 | 5/2020 | Sharma et al. |
| 2020/0206350 | A1 | 7/2020 | Chu et al. |
| 2020/0262922 | A1 | 8/2020 | Bhattacharya et al. |
| 2020/0354453 | A1 | 11/2020 | De et al. |
| 2021/0155913 | A1 | 5/2021 | Park |
| 2021/0317215 | A1 | 10/2021 | Reichert et al. |
| 2021/0363270 | A1 | 11/2021 | Park |
| 2021/0380694 | A1 | 12/2021 | Forrest, Jr. et al. |
| 2022/0002410 | A1 | 1/2022 | Antochshuk et al. |
| 2022/0089738 | A1 | 3/2022 | Krishnamachari et al. |
| 2022/0233693 | A1 | 7/2022 | Huang et al. |
| 2022/0378916 | A1 | 12/2022 | Chu et al. |

FOREIGN PATENT DOCUMENTS

| | | | | |
|---|---|---|---|---|
| CA | 3131052 | A1 | 10/2020 | |
| CN | 101172100 | A | 5/2008 | |
| CN | 101970499 | A | 2/2011 | |
| CN | 102753570 | A | 10/2012 | |
| CN | 107249624 | A * | 10/2017 | ............. A61P 35/00 |
| EP | 1801123 | A2 | 6/2007 | |
| EP | 2116265 | A2 | 11/2009 | |
| EP | 2275119 | B1 | 9/2013 | |
| EP | 3117837 | A1 | 6/2017 | |
| EP | 3785701 | A1 | 3/2021 | |
| JP | 2005502589 | A | 1/2005 | |
| JP | 2010507670 | A | 3/2010 | |
| JP | 2014515017 | A | 6/2014 | |
| KR | 20180069056 | A | 6/2018 | |
| RU | 2589691 | C2 | 7/2016 | |
| WO | 1989011297 | A1 | 11/1989 | |
| WO | 199704801 | A1 | 2/1997 | |
| WO | 2000053631 | A1 | 9/2000 | |
| WO | 2001018051 | A2 | 3/2001 | |
| WO | 2001030393 | A2 | 3/2001 | |
| WO | 2002072636 | A2 | 9/2002 | |
| WO | 03009817 | A2 | 2/2003 | |
| WO | 2003009817 | A1 | 2/2003 | |
| WO | 2003039485 | A2 | 5/2003 | |
| WO | 2003086310 | A2 | 10/2003 | |
| WO | 2004007520 | A2 | 1/2004 | |
| WO | 2004018312 | A1 | 3/2004 | |
| WO | 2004055164 | A2 | 7/2004 | |
| WO | 2004056875 | A1 | 7/2004 | |
| WO | 2004071517 | A2 | 8/2004 | |
| WO | 2004081190 | A2 | 9/2004 | |
| WO | 2005120571 | A2 | 12/2005 | |
| WO | 2006121168 | A1 | 11/2006 | |
| WO | 2006133486 | A1 | 12/2006 | |
| WO | 2007019232 | A2 | 2/2007 | |
| WO | 2007024846 | A2 | 3/2007 | |
| WO | 2007092772 | A2 | 8/2007 | |
| WO | 2007110339 | A1 | 10/2007 | |
| WO | 2007147019 | A2 | 12/2007 | |
| WO | 2008057240 | A2 | 5/2008 | |
| WO | 2008076321 | A1 | 6/2008 | |
| WO | 2008079290 | A2 | 7/2008 | |
| WO | 2008086395 | A2 | 7/2008 | |
| WO | 2008103473 | A1 | 8/2008 | |
| WO | 2008121301 | A1 | 10/2008 | |
| WO | 2008153610 | A2 | 12/2008 | |
| WO | 2008156712 | A1 | 12/2008 | |
| WO | 2008157409 | A1 | 12/2008 | |
| WO | 2009009407 | A1 | 1/2009 | |
| WO | 2009043933 | A1 | 4/2009 | |
| WO | 2009084659 | A1 | 7/2009 | |
| WO | 2009101611 | A1 | 8/2009 | |
| WO | 2009120684 | A1 | 10/2009 | |
| WO | 2009126688 | A2 | 10/2009 | |
| WO | 2010032220 | A1 | 3/2010 | |
| WO | 2010062372 | A2 | 6/2010 | |
| WO | 2010069858 | A1 | 6/2010 | |
| WO | 2010102241 | A1 | 9/2010 | |
| WO | 2010129469 | A1 | 11/2010 | |
| WO | 2010148337 | A1 | 12/2010 | |
| WO | 2011012637 | A2 | 2/2011 | |
| WO | 2011017070 | A1 | 2/2011 | |
| WO | 2011024862 | A1 | 3/2011 | |
| WO | 2011029892 | A2 | 3/2011 | |
| WO | 2011034822 | A1 | 3/2011 | |
| WO | 2011056772 | A1 | 5/2011 | |
| WO | 2011080209 | A2 | 7/2011 | |
| WO | 2011089062 | A2 | 7/2011 | |
| WO | 2011139718 | A1 | 11/2011 | |
| WO | 2012010799 | A1 | 1/2012 | |
| WO | 2012018538 | A2 | 2/2012 | |
| WO | 2012076670 | A2 | 6/2012 | |
| WO | 2012135035 | A1 | 10/2012 | |
| WO | 2012135408 | A1 | 10/2012 | |
| WO | 2012165917 | A1 | 12/2012 | |
| WO | 2013016648 | A2 | 1/2013 | |
| WO | 2013063468 | A1 | 5/2013 | |

(56) References Cited

FOREIGN PATENT DOCUMENTS

| | | | |
|---|---|---|---|
| WO | 2013167720 A1 | 11/2013 | |
| WO | 2014004436 A2 | 1/2014 | |
| WO | 2014036076 A1 | 3/2014 | |
| WO | 2015011199 A1 | 1/2015 | |
| WO | 2015038777 A1 | 3/2015 | |
| WO | 2015038782 A1 | 3/2015 | |
| WO | 2015038811 A2 | 3/2015 | |
| WO | 2015038818 A2 | 3/2015 | |
| WO | 2015042246 A1 | 3/2015 | |
| WO | 2015048520 A1 | 4/2015 | |
| WO | 2016015675 A1 | 2/2016 | |
| WO | 2016024228 A1 | 2/2016 | |
| WO | 2016028656 A1 | 2/2016 | |
| WO | 2016028672 A1 | 2/2016 | |
| WO | 2016035006 A1 | 3/2016 | |
| WO | 2016100882 A1 | 6/2016 | |
| WO | 2016118654 A1 | 7/2016 | |
| WO | 2016140717 A1 | 9/2016 | |
| WO | 2016153839 A1 | 9/2016 | |
| WO | WO-2016137850 A1 * | 9/2016 | A61P 35/00 |
| WO | 2016168716 A1 | 10/2016 | |
| WO | 2016176504 A1 | 11/2016 | |
| WO | 2016196173 A1 | 12/2016 | |
| WO | 2016200782 A1 | 12/2016 | |
| WO | 2017015560 A2 | 1/2017 | |
| WO | 2017030823 A2 | 2/2017 | |
| WO | 2017037203 A1 | 3/2017 | |
| WO | 2017040864 A1 | 3/2017 | |
| WO | 2017048824 A1 | 3/2017 | |
| WO | 2017054646 A1 | 4/2017 | |
| WO | 2017055547 A1 | 4/2017 | |
| WO | 2017079150 A1 | 5/2017 | |
| WO | 2017112621 A1 | 6/2017 | |
| WO | 2017131496 A1 | 8/2017 | |
| WO | 2017198741 A1 | 11/2017 | |
| WO | 2018091729 A2 | 5/2018 | |
| WO | 2018116198 A1 | 6/2018 | |
| WO | 2018158332 A1 | 9/2018 | |
| WO | 2018160722 A1 | 9/2018 | |
| WO | 2018183928 A1 | 10/2018 | |
| WO | 2018187057 A1 | 10/2018 | |
| WO | 2018204343 A1 | 11/2018 | |
| WO | 2018204368 A1 | 11/2018 | |
| WO | 2018204374 A1 | 11/2018 | |
| WO | 2018204405 A1 | 11/2018 | |
| WO | 2018222718 A1 | 12/2018 | |
| WO | 2018222722 A2 | 12/2018 | |
| WO | 2020022791 A1 | 1/2020 | |
| WO | 2020028011 A1 | 2/2020 | |
| WO | 2020096917 A1 | 5/2020 | |
| WO | 2020097141 A1 | 5/2020 | |
| WO | 2020197230 A1 | 10/2020 | |
| WO | 2021118930 A2 | 6/2021 | |

OTHER PUBLICATIONS

Benvenuti, Manuela, Crystallization of soluble proteins in vapor diffusion for x-ray crystallography, Nature Protocols, 2007, 1633-1651, 2(7).

Bernstein, J., Bioavailability, Polymorphism of molecular crystals, 2007, 324-330 (translated pp. 1-9), Ch. 7.3.2.

Bernstein, J., Bioavailability, Polymorphism of molecular crystals, 2007, 324-330, Ch. 7.3.2.

Caira, Crystalline Polymorphism of organic compounds, Topics in Current Chemistry, 1998, 163-208, 198.

Drenth, Jan, Crystallizing a Protein, Principles of Protein X-Ray Crystallography, 1999, 1-21, Chapter 1, 2nd Edition.

Emsley et al., Features and development of Coot, Biological Crystallography, 2010, pp. 486-501, D66.

Hamid et al., Safety and Tumor Responses with Lambrolizumab (Anti-PD-1) in Melanoma, New Eng. J. Med., 2013, 134-144, 369(2).

Harris et al., Crystallographic Structure of an Intact IgG1 Monoclonal Antibody, Journal of Molecular Biochemistry, 1998, pp. 861-872, vol. 275.

Harris et al., Refined Structure of an Intact IgG2a Monoclonal Antibody, Biochemistry—American Chemical Society, 1997, pp. 1581-1597, vol. 36.

Karagianni, A. et al, Pharmaceutical Cocrystals: New Solid Phase Modification Approaches for the Formulation of APIs, Pharmaceutics, 2018, 1-30, 10(1).

Mcpherson, et al., Current approaches to macromolecular crystallization, Eur. J. Biochem., 1990, pp. 1-23, vol. 189.

Moon, Andrea F., A synergistic approach to protein crystallization: Combination of a fixed-arm carrier with surface entropy reduction, Protein Science, 2010, 901-913, 19.

Murshudov et al., Refinement of Macromolecular Structures by the Maximum-Likelihood Method, Acta Cryst., 1997, pp. 240-255, D53.

Nonappa, et al., Caffeine as a Gelator, Gels, 2016, 1-10, 2.

Ollmann Saphire et al., Crystallization and preliminary structure determination of an intact human immunoglobulin, b12: an antibody that broadly neutralizes primary isolates of HIV-1, Acta Crystallographica Section D: Biological Crystallography, 2001, pp. 168-171, D57.

Trilisky, Egor, Crystallization and Liquid-Liquid Phase Separation of Monoclonal Antibodies and Fc-Fusion Proteins: Screening Results, Biotechnology Progress, 2011, 1054-1067, vol. 27, No. 4.

Vonrhein et al., Data processing and analysis with the autoPROC toolbox, Acta Crystallographica Section D, Biological Crystallography, 2011, pp. 293-302, D67.

WHO Drug Information, vol. 27, No. 2, pp. 161-162 (2013).

Cleland, Jeffrey L. et al., A Specific Molar Ratio of Stabilizer to Protein is Required for Storage Stability of a Lyophilized Monoclonal Antibody, Journal of Pharmaceutical Sciences, 90(3), 310-321, 2001.

FDA insert for KEYTRUDA (pembrolizumab). May 2017. (Year: 2017) 46 pages.

Telikepalli, Srivalli N. et al., Structural Characterization of IgG1 mAb Aggregates and Particles Generated Under Various Stress Conditions, J Pharm Sci, 103(3), 796-809, 2014.

Morar-Mitrica, Sorina et al., Development of a stable low-dose aglycosylated antibody formulation to minimize protein loss during intravenous administration, mAbs, 7:4, 792-803, 2015.

Bittner, Beate et al., Subcutaneous Administration of Biotherapeutics: An Overview of Current Challenges and Opportunities, BioDrugs, 32, 425-440, 2018.

Larson, S. B. et al., Progress in the Development of an Alternative Approach to Macromolecular Crystallization, Crystal Growth and Design, 8(8), 3038-3052, 2008.

Third-Party Observation against WO22066832-PCTUS2021051641, 22 pages.

Shpilberg, O. et al., Subcutaneous administration of rituximab (MabThera) and trastuzumab (Herceptin) using hyaluronidase, British Journal of Cancer, 109, 1556-1561, 2013.

Ahamed, Tangir, Phase Behavior of an Intact Monoclonal Antibody, Biochemical Journal, 2007, 610-619, 93.

Altschul, Stephen F., A Protein Alignment Scoring System Sensitive at All Evolutionary Distances, J Mol Evol, 1993, 290-300, 36.

Armstrong, NA, Sucrose, Handbook of Pharmaceutical Excipients, 2009, 703-707, 6th Edition.

Banks et al., Removal of cysteinylation from an unpaired sulfhydryl in the variable region of a recombinant monoclonal IgG1 antibody improves homogeneity, stability, and biological activity, J Pharm Sci, 2008, 775-790, 97(2).

Banks, Douglas D. et al., The Effect of Sucrose Hydrolysis on the Stability of Protein Therapeutics during Accelerated Formulation Studies, J. Pharm. Sci., 2009, 4501-4510, 98(12).

Basu et al., Protein crystals for the delivery of biopharmaceuticals, Expert Opinion on Biological Therapy, 2004, pp. 301-317, vol. 4(3).

BENLYSTA prescribing information, Mar. 2011.

Bhambhani, Akhilesh, Formulation Design and High-Throughput Excipient Selection Based on Structural Integrity and Conformational

(56) References Cited

OTHER PUBLICATIONS

Stability of Dilute and Highly Concentrated IgG1 Monoclonal Antibody Solutions, Journal of Pharmaceutical Sciences, 2012, 1120-1135, vol. 101, No. 3.
Borwankar, A.U. et al., Viscosity Reduction of a Concentrated Monoclonal Antibody with Arginine•HCl and Arginine•Glutamate, Ind. Eng. Chem. Res., 2016, 11225-11234, 55(43).
Bowman, Edward P. et al., Rationale and safety of anti-interleukin-23 and anti-interleukin-17A therapy, Curr Opin Infect Dis, 2006, 245-252, 19(3).
Carpenter, John F. et al., Rational Design of Stable Lyophilized Protein Formulations: Some Practical Advice, Pharmaceutical Research, 1997, 969-975, 14(8).
Carpenter, John F., Application of infrared spectroscopy to development of stable lyophilized protein formations, European Journal of Pharmaceutics and Biopharmaceutics, 1998, 231-238, 45.
Chang, B.S. and Hershenson, S., Practical approaches to protein formulation development in "Rationale Design of stable protein formulations-theory and practice", Kluwer Academic/Plenum Publishers, 2002, 1-25.
Chang, Byeong et al., Physical Instability in Peptide and Protein Pharmaceuticals, Formulation and Process Development Strategies for Manufacturing Biopharmaceuticals, 2010, 69-104, Chapter 3.
Chauhan, Veeren M., Advancements in the co-formulation of biologic therapeutics, Journal of Controlled Release, 2020, pp. 397-405, vol. 327.
Chauvin et al., TIGIT and PD-1 impair tumor antigen-specific CD8 T cells in melanoma patients, Journal of Clinical Investigation, 2015, pp. 2046-2058, vol. 125(5).
Chen, et al., Influence of histidine on the stability and physical properties of a fully human antibody in aqueous and solid forms, 2003, 1952-1960, 20(12), Pharm Res.
Cordoba et al., Non-enzymatic hinge region fragmentation of antibodies in solution, 2005, 115-121, 818(2), J Chromatogr B Analyt Technol Biomed Life Sci.
Costantino, Henry R., The Secondary Structure and Aggregation of Lyophilized Tetanus Toxoid, Journal of Pharmaceutical Sciences, 1996, 1290-1293, vol. 85, No. 12.
Cua, Daniel J. et al., TGF-beta, a 'double agent' in the immune pathology war, Nat. Immunol., 2006, 557-559, 7(6).
Cudney, R., Protein Crystallization and Dumb Luck, The Rigaku Journal, 1999, 1-7, vol. 16, No. 1.
Daugherty et al., Formulation and delivery issues for monoclonal antibody therapeutics, Advanced Drug Delivery Reviews, 2006, pp. 686-706, vol. 58, No. 5-6.
Daugherty, Ann L. et al., Formulation and Delivery Issues for Monoclonal Antibody Therapeutics, Current Trends in Monoclonal Antibody Development and Manufacturing, 2010, 103-129, Chapter 8.
Davagnino, Juan et al., Acid hydrolysis of monoclonal antibodies, J. Immunol. Methods, 1995, 177-180, 185(2).
Davies et al., Structural Determinants of Unique Properties of Human IgG4-Fc, Journal of Molecular Biology, 2014, pp. 630-644, vol. 426(3).
Dayhoff, M.O., A Model of Evolutionary Change in Proteins, Atlas of Protein Sequence and Structure, 1978, 345-352, 22.
Dear et al., Contrasting the Influence of Cationic Amino Acids on the Viscosity and Stability of a Highly Concentrated Monoclonal Antibody, Pharm. Res., 2017, 193-207, vol. 34.
Dembo, Amir, Limit Distribution of Maximal Non-Aligned Two-Sequence Segmental Score, The Annals of Probability, 1994, 2022-2039, vol. 22, No. 4.
European Medicines Agency, European Public Assessment Report (EPAR) Avastin, Scientific Discussion. Jan. 24, 2006, pp. 1-61.
European Search Report, application No. 12763896.03, mailed Nov. 5, 2014, 6 pages.
Falconer, Robert J. et al., Stabilization of a monoclonal antibody during purification and formulation by addition of basic amino acid excipients, J Chem Technol Biorechnol, 2011, 942-948, 86.
FDA label for AMJEVITA (Adalimumab), Sep. 2016, p. 1-61.
FDA label for ARZERRA (Ofatumumab), Oct. 2009, p. 1-13.
FDA label for AVASTIN (Bevacizumab), Sep. 2011, p. 1-25.
FDA label for BAVENCIO (Avelumab), Mar. 2017, p. 1-20.
FDA label for CAMPATH or LEMTRADA (Alemtuzumab), Sep. 2014, p. 1-18.
FDA label for CIMZIA (Certolizumab), Jan. 2017, p. 1-40.
FDA label for DRAZALEX (Daratumumab), Nov. 2016, p. 1-26.
FDA label for HUMIRA (Adalimumab), Jan. 2008, p. 1-34.
FDA label for KADCYLA (Ado-Trastuzumab Emtansine), Aug. 29, 2013, p. 1-26.
FDA label for MYLOTARG (Gemtuzumab Ozogamicin), Aug. 2005, p. 1-21.
FDA label for OPDIVO (Nivolumab), Dec. 2017, p. 1-73.
FDA label for PRAXBIND (Idarucizumab), Oct. 2015, p. 1-10.
FDA label for PROLIA (Denosumab), Sep. 2011, p. 1-20.
FDA label for PROSTASCINT (Capromab Pendetide), Jun. 2012, p. 1-16.
FDA label for PROTRAZZA (Necitumumab), Nov. 2015, p. 1-12.
FDA label for RAXIBACUMAB, Dec. 2012, p. 1-14.
FDA label for REOPRO (Abciximab), dated Nov. 4, 1997, p. 1-17.
FDA label for REPATHA (Evolocumab), Aug. 2015, p. 1-34.
FDA label for RITUXAN (Rituximab), Feb. 2010, p. 1-35.
FDA label for SIMULECT (Basiliximab), May 1998, p. 1-7.
FDA label for SOLIRIS (Eculizumab), Sep. 2011, p. 1-24.
FDA label for TYSABRI (Natalizumab), Jan. 2012, p. 1-32.
FDA label for VECTIBIX (Panitumumab), Jun. 2017, p. 1-31.
FDA label for ZEVALIN (Ibritumomab Tiuxetan), Sep. 2009, p. 1-11.
FDA label of Adcetris, Nov. 2014, pp. 1-19.
FDA label of Benlysta, Mar. 2012, pp. 1-22.
FDA label of Blincyto, Dec. 2014, pp. 1-24.
FDA label of CINQAIR, Mar. 2016, pp. 1-16.
FDA label of EMPLICITI, Nov. 2015, pp. 1-22.
FDA label of Entyvio, May 2014, pp. 1-21.
FDA label of ERBITUX, Jan. 2012, pp. 1-31.
FDA label of FASENRA, Nov. 2017, pp. 1-8.
FDA label of Ilaris, Mar. 2012, pp. 1-13.
FDA label of KEVZARA, May 2017, pp. 1-45.
FDA label of Nucala, Nov. 2015, pp. 1-28.
FDA label of OCREVUS, Mar. 2017, pp. 1-18.
FDA label of Raptiva, Mar. 2009, pp. 1-36.
FDA label of Remicade, Feb. 2011, pp. 1-47.
FDA label of SILIQ, Feb. 2017, pp. 1-22.
FDA label of SYLVANT, 2014, pp. 1-16.
FDA label of TALTZ Mar. 2016, pp. 1-25.
FDA label of Xolair, 2007, pp. 1-20.
FDA label of YERVOY, Oct. 2015, pp. 1-32.
FDA label of ZINBRYTA, May 2016, pp. 1-32.
FDA label of ZINPLAVA, Oct. 2016, pp. 1-11.
Fukuda, Masakazu et al., Thermodynamic and Fluorescence Analyses to Determine Mechanisms of IgG1 Stabilization and Destabilization by Arginine, Pharm. Res., 2014, 992-1001, 31.
Garber, Ellen et al., A broad range of Fab stabilities within a host of therapeutic IgGs, Biochemical and Biophysical Research Communications, 2007, 751-757, 355.
Ghosh et al., Natalizumab for active Crohns disease, New England J. Med., 2003, pp. 24-32, 348.
Giege, et al., Crystallogenesis of Biological Macromolecules: Facts and Perspectives, Acta Cryst., 1994, pp. 339-350, D50.
Gikanga, Benson et al., Manufacturing of High-Concentration Monoclonal Antibody Formulations via Spray Drying—the Road to Manufacturing Scale, PDS J Pharm Sci and Tech, 2015, 59-73, 69.
Gizzi, Patrick et al., Molecular Tailored Histidine-Based Complexing Surfactants: From Micelles to Hydrogels, Eur. J. Org. Chem., 2009, 3953-3963, N/A.
Grillo, Adeolla O., Late Stage Formulation Development and Characterization of Biopharmaceuticals, Formulation and Process Development Strategies for Manufacturing Biopharmaceuticals, 2010, 161-171, Chapter 7.
Guo, Zheng et al., Structure-Activity Relationship for Hydrophobic Salts as Viscosity-Lowering Excipients for Concentrated Solutions of Monoclonal Antibodies, Pharm Res, 2012, 3102-3109, 29.

(56) References Cited

OTHER PUBLICATIONS

Harris et al., Comparison of the conformations of two intact monoclonal antibodies with hinges, Immunological Reviews, 1998, pp. 35-43, vol. 163.
Harris et al., Crystallization of Intact Monoclonal Antibodies, Proteins: Structure, Function, and Genetics, 1995, pp. 285-289, vol. 23, No. 2.
Harris, Reed J. et al., Identification of multiple sources of charge heterogeneity in a recombinant antibody, Journal of Chromatography B, 2001, 233-245, 752(2).
He et al., Humanization and Pharmacokinetics of a Monoclonal Antibody with Specificity for both E- and P-Selectin, J. Immunol., 1998, pp. 1029-1035, 160.
Herold, ANTI-CD3 Monoclonal Antibody in New-Onset Type 1 Diabetes Mellitus, New England Journal of Medicine, 2002, pp. 1692-1698, 346.
International Search Report of the International Searching Authority for International Application No. PCT/US2013/073825, mailed Feb. 7, 2014 (3 pages).
Introduction to the textbook which contains D16, Nicholas W. Warne, 2010.
Ionescu, Roxana et al., Kinetics of Chemical Degradation in Monoclonal Antibodies: Relationship between Rates at the Molecular and Peptide Levels, Anal. Chem., 2010, 3198-3206, 82(8).
Izutsu, Ken-Ichi et al., Excipient crystallinity and its protein-structure—stabilizing effect during freeze-drying, Journal of Pharmacy and Pharmacology, 2002, 1033-1039, 54.
Jezek, Jan et al., Viscosity of concentrated therapeutic protein compositions, Advanced Drug Delivery Reviews, 2011, 1107-1117, 63.
Jones, Andrew J.S., Analysis of Polypeptides and proteins, Advanced Drug Delivery Reviews, 1993, 29-90, 10.
Jorgensen, Lene et al., Recent trends in stabilising peptides and proteins in pharmaceutical formulation—considerations in the choice of excipients, Expert Opinion on Drug Delivery, 2009, 1219-1230, 6(11).
Joshi, Sangeeta B. et al., An Empirical Phase Diagram/ High Throughput Screening Approach to the Characterization and Formulation of Biopharmaceuticals, Formulation and Process Development Strategies for Manufacturing Biopharmaceuticals, 2010, 173-205, Chapter 8.
Kaithamana, Shashi, Induction of Experimental Autoimmune Graves' Disease in BALB/c Mice, The Journal of Immunology, 1999, 5157-5164, 163.
Kang, Jichao et al., Rapid formulation development for monoclonal antibodies, Bio Process International, 2016, 40-45, 14(4).
KEYTRUDA (Merck & Co., Inc., Whitehouse Station, NJ USA; initial U.S. approval 2014, updated Sep. 2017) 49 pages.
Kheddo, Priscilla et al., The effect of arginine glutamate on the stability of monoclonal antibodies in solution, Int. J. Pharmaceutics, 2014, 126-133, 473.
Kohler et al., Continuous Cultures of Fused Cells Secreting Antibody of Predefined Specificity, Nature, 1975, pp. 495-497, vol. 256.
Krishnan, Development of Formulations for Therapeutic Monoclonal Antibodies and Fc Fusion Proteins, Chugai Exhibit 2014, 2010, pp. 1-48.
Krishnan, Sampathkumar et al., Development of Formulations for Therapeutic Monoclonal Antibodies and Fc Fusion Proteins, Formulation and Process Development Strategies for Manufacturing Biopharmaceuticals, 2010, 383-427, Chapter 16.
Kundrot, C.E., Which strategy for a protein crystallization project?, Cellular Molecular Life Science, 2004, 525-536, 61.
Lam, Xanthe M. et al., Antioxidants for Prevention of Methionine Oxidation in Recombinant Monoclonal Antibody HER2, J. Pharm. Sci., 1997, 1250-1255, 86(11).
Langrish, Claire L. et al., IL-12 and IL-23: master regulators of innate and adaptive immunity, Immunol. Rev., 2004, 96-105, 202.
Le Doussal et al., Enhanced in vivo targeting of an asymmetric bivalent hapten to double-antigen-positive mouse B cells with monoclonal antibody conjugate cocktails, J. Immunol., 1991, pp. 169-175, 146.
Liu, Dingjiang et al., Structure and Stability Changes of Human IgG1 Fc as a Consequence of Methionine Oxidation, Biochemistry, 2008, 5088-5100, 47(18).
Liu, Hongcheng et al., Heterogeneity of Monoclonal Antibodies, J. Pharm. Sci., 2008, 2426-2447, 97(7).
Liu, Jun et al., Reversible Self-Association Increases the Viscosity of a Concentrated Monoclonal Antibody in Aqueous Solution, Journal of Pharmaceutical Sciences, 2005, 1928-1940, 94(9).
Liu, Y. Diana et al., Human IgG2 Antibody Disulfide Rearrangement in Vivo, J. Biol. Chem., 2008, 29266-29272, 283(43).
Mach, Henryk et al., Addressing new analytical challenges in protein formulation development, European Journal of Pharmaceutics and Biopharmaceutics, 2011, 196-207, 78.
Manning, Mark Cornell et al., Prediction of Protein Aggregation Propensities from Primary Sequence Information, Formulation and Process Development Strategies for Manufacturing Biopharmaceuticals, 2010, 329-347, Chapter 14.
Manzini, B. et al., Polymer-supported syntheses of oxo-crown ethers and derivatives containing a-amino-acid residues, Reactive & Functional Polymers, 2008, 1297-1306, 68(9).
Mccoy et al., Phaser crystallographic software, Journal of Applied Crystallography, 2007, pp. 658-674, vol. 40.
Mcdermott, et al., PD-1 as a potential target in cancer therapy, Cancer Medicine, 2013, pp. 662-673, WO.
Menne, Kerstin M.L., A comparison of signal sequence prediction methods using a test set of signal peptides, Bioinformatics Applications Note, 2000, 741-742, 16.
Milgrom et al., Treatment of allergic asthma with monoclonal anti IgE antibody, New England Journal Med., 1999, pp. 1966-1973, 341.
Morissette, Sherry L. et al., High-throughput crystallization: polymorphs, salts, co-crystals and solvates of pharmaceutical solids, Advanced Drug Delivery Reviews, 2004, 275-300, 56.
Murakami, Monica S., Cell Cycle Regulation, Oncogenes, and Antineoplastic Drugs, The Molecular Basis of Cancer, 1995, 3-17, Chapter 1.
Nayar, Rajiv et al., Efficient Approaches to Formulation Development of Biopharmaceuticals, Formulation and Process Development Strategies for Manufacturing Biopharmaceuticals, 2010, 309-328, Chapter 13.
Ollmann Saphire et al., Crystal Structure of a Neutralizing Human IgG Against HIV-1: A Template for Vaccine Design, Science, 2001, pp. 1155-1159, vol. 293.
Pearlman, Rodney, Analysis of Protein Drugs, Peptide and Protein Drug Delivery, 1991, 247-301, Chapter 6.
Perchiacca, Joseph M. et al., Aggregation-resistant domain antibodies engineered with charged mutations near the edges of the complementarity-determining regions, Protein Engineering, Design & Selection, 2012, 591-601, 25(10).
Perez-Ramirez, Bernardo et al., Preformulation Research: Assessing Protein Solution Behavior Early During Therapeutic Development, Formulation and Process Development Strategies for Manufacturing Biopharmaceuticals, 2010, 119-146, Chapter 5.
Poole, Raewyn M., Pembrolizumab: First Global Approval, Drugs, 2014, 1973-1981, 74(16).
Portielje, IL-12: a promising adjuvant for cancer vaccination, Cancer Immunol Immunother, 2003, 133-144, 52.
Presta, Leonard G. et al., Selection, design, and engineering of therapeutic antibodies, J. Allergy Clin. Immunol., 2005, 731-736, 116(4).
Presta, Leonard G., Engineering of therapeutic antibodies to minimize immunogenicity and optimize function, Advanced Drug Delivery Reviews, 2006, 640-656, 58.
Prestrelski, Steven J., Optimization of Lyophilization Conditions for Recombinant Human Interleukin-2 by Dried State Conformational Analysis Using Fourier-Transform Infrared Spectroscopy, Pharmaceutical Research, 1995, 1250-1259, vol. 12, No. 9.
PROLIA prescribing information, Jun. 2010.

(56) References Cited

OTHER PUBLICATIONS

Qing, G. et al., Chiral Effect at Protein/Graphene Interface: A Bioinspired Perspective To Understand Amyloid Formation, Journal of the American Chemical Society, 2014, 10736-10742, 136(30).
Reich, Gabriele. Chapter 10: "Pharmaceutical Formulation and Clinical Application". D19 is a chapter from the textbook "Handbook of Therapeutic Antibodies, vol. 1", published by Wiley & Sons in 2007.
Reichert, et al., Monoclonal antibody successes in the clinic, Nature Biotechnology, 2005, pp. 1073-1078, vol. 23.
Reissner, K. J. et al., Deamidation and isoaspartate formation in proteins: unwanted alterations or surreptitious signals?, Cell. Mol. Life Sci., 2003, 1281-1295, 60.
Remmele, Richard L., Interleukin-1 Receptor (IL-1R) Liquid Formulation Development Using Differential Scanning Calorimetry, Pharmaceutical Research, 1998, 200-208, vol. 15, No. 2.
Rustandi, Richard R. et al., Applications of CE SDS gel in development of biopharmaceutical-antibody-based products, Electrophoresis, 2008, 3612-3620, 29(17).
Sane, Samir U. et al., Raman Spectroscopic Characterization of Drying-Induced Structural Changes in a Therapeutic Antibody: Correlating Structural Changes with Long-Term Stability, Journal of Pharmaceutical Sciences, 2004, 1005-1018, 93(4).
Scapin et al., Structure of full-length human anti-PD1 therapeutic IgG4 antibody pembrolizumab, Nature Structural & Molecular Biology, 2015, pp. 953-958, vol. 22, No. 12.
Schermeyer, Marie-Therese et al., Characterization of highly concentrated antibody solution—A toolbox for the description of protein long-term solution stability, MABS, 2017, 1169-1185, 9(7).
Seifert, Tina et al., Chroman-4-one- and Chromone-Based Sirtuin 2 Inhibitors with Antiproliferative Properties in Cancer Cells, Journal of Medicinal Chemistry, 2014, 9870-9888, 57.
Shahrokh, Zahra, Approaches to Analysis of Aggregates and Demonstrating Mass Balance in Pharmaceutical Protein (Basic Fibroblast Growth Factor) Formulations, Journal of Pharmaceutical Sciences, 1994, 1645-1650, vol. 83, No. 12.
Sharma et al., Preparation, purification and crystallization of antibody Fabs and single-chain Fv domains, Immunology Methods Manual: The Comprehensive Sourcebook of Techniques, 1997, pp. 15-37, vol. 1.
Shire, Steven J. et al., Formulation and manufacturing of biologics, Current Opinion in Biotechnology, 2009, 708-714, 20.
Shire, Steven J. et al., High Concentration Antibody Formulations, Formulation and Process Development Strategies for Manufacturing Biopharmaceuticals, 2010, 349-381, Chapter 15.
Shire, Steven J., et al., Challenges in the Development of High Protein Concentration Formulations, Journal of Pharmaceutical Sciences, 2004, 1390-1402, 93(6).
Sigma-Aldrich, Co., Products for Life Science Research, 2001, 1-47, N/A.
Slamon et al., Use of chemotherapy plus a monoclonal antibody against HER2 for metastatic breast cancer that overexpresses HER2, New England J. Med., 2001, pp. 783-792, 344.
Sluzky, Victoria, Chomatographic Methods for Quantitative Analysis of Native, Denatured, and Aggregated Basic Fibroblast Growth Factor in Solution Formulations, Pharmaceutical Research, 1994, 485-490, vol. 11, No. 4.
Study NCT01295827 posted in Feb. 2011 on ClinicalTrials.gov (see p. 6 "First Posted"), 14 pages.
Sule, S.V. et al., Solution pH That Minimizes Self-Association of Three Monoclonal Antibodies Is Strongly Dependent on Ionic Strength, Mol. Pharmaceutics, 2012, 744-751, 9.
Sumit Goswami, Developments and Challenges for mAb-based Therapeutics, Antibodies, 2013, 452-500, 2.
Sworn statement of Chakravarthy Nachu Narasimhan, 2 pages.
Te Booy, Marcel, Evaluation of the Physical Stability of Freeze-Dried Sucrose-Containing Formulations by Differential Scanning Calorimetry, Pharmaceutical Research, 1992, 109-114, vol. 9, No. 1.
Tomar, Dheeraj S., Molecular basis of high viscosity in concentrated antibody solutions: Strategies for high concentration drug product development, mAbs, 2016, 216-228, vol. 8, No. 2.
Topalian et al., Survival, Durable Tumor Remission, and Long-Term Safety in Patients With Advanced Melanoma Receiving Nivolumab, Clinical Journal of Oncology, 2014, pp. 1020-1030, vol. 32, No. 10.
Topp, Elizabeth M. et al., Chemical Instability in Peptide and Protein Pharmaceuticals, Formulation and Process Development Strategies for Manufacturing Biopharmaceuticals, 2010, 41-67, Chapter 2.
Tyagi, R. et al., The use of chemical modification and chemical crosslinking to stabilize proteins (enzymes), Biochemistry, 1998, 395-407, 63(3).
TYSABRI prescribing information, Nov. 2004.
Uchiyama, Susumu, Liquid formulation for antibody drugs, Biochimica et Biophysica Acta, 2014, 2041-2052, 1844.
Usami, A., The effect of pH, hydrogen peroxide and temperature on the stability of human monoclonal antibody, Journal of Pharmaceutical and Biomedical Analysis, 1996, 1133-1140, 14.
Vermeer, Arnoldus W. P. et al., The Thermal Stability of Immunoglobulin: Unfolding and Aggregation of a Multi-Domain Protein, Biophysical Journal, 2000, 394-404, 78(1).
Vlasak, Josef et al., Fragmentation of monoclonal antibodies, MABS, 2011, 253-263, 3(3).
Vlasak, Josef et al., Identification and characterization of asparagine deamidation in the light chain CDR1 of a humanized IgG1 antibody, Anal. Biochem., 2009, 145-154, 392(2).
Von Heijne et al., A new method for predkting signal sequence cleavage sites, Nucleic Acids Res., 1986, pp. 4683-4690, 14.
Walily, EL, Simultaneous determination of tenoxicam and 2-aminopyridine using derivative spectrophotometry and high-performance liquid chromatography, Journal of Pharmaceutical and Biomedical Analysis, 1997, 1923-1928, 15.
Wang et al., Antibody structure, instability, and formulation, J. Pharm. Sci., 2007, 1-26, 96(1).
Wang, B. et al., Amino acid endcapped poly(p-dioxanone): synthesis and crystallization, J Polym Res, 2013, 1-9, 20(4).
Wang, Instability, stabilization, and formulation of liquid protein pharmaceuticals, Int J Pharm, 1999, pp. 129-188, vol. 185, No. 2.
Wang, Shujing et al., Viscosity-Lowering Effect of Amino Acids and Salts on Highly Concentrated Solutions of Two IgG1 Monoclonal Antibodies, Mol. Pharmaceutics, 2015, 4478-4487, 12.
Warne, Development of high concentration protein biopharmaceuticals: the use of platform approaches in formulation development, 2011, 208-212, 78(2), Eur J Pharm Biopharm.
Warne, Nicholas W., Formulation Development of Phase 1-2 Biopharmaceuticals: An Efficient and Timely Approach, John Wiley & Sons, Inc., 2010, 147-159, Chapter 6.
Weber, Patricia C., Overview of Protein Crystallization Methods, Methods in Enzymology, 1997, 13-22, 276.
Webster, Simon, Predicting Long-Term Storage Stability of Therapeutic Proteins, Pharmaceutical Technology, 2013, 1-7, 37(11).
Wei, Ziping et al., Identification of a Single Tryptophan Residue as Critical for Binding Activity in a Humanized Monoclonal Antibody against Respiratory Syncytial Virus, Anal. Chem., 2007, 2797-2805, 79(7).
Wiekowski, Maria T. et al., Ubiquitous Transgenic Expression of the IL-23 Subunit p19 Induces Multiorgan Inflammation, Runting, Infertility, and Premature Death, J. Immunol., 2001, 7563-7570, 166(12).
Wolchok et al., Nivolumab plus Ipilimumab in Advanced Melanoma, The New England Journal of Medicine, 2013, pp. 122-133, vol. 369(2).
Written Opinion, International Application No. PCT/US12/31063, date of mailing Jun. 22, 2012.
Yang et al., A Randomized Trial of Bevacizumab, an Anti-Vascular Endothelial Growth Factor Antibody, for Metastatic Renal Cancer, New England Journal of Medicine, 2003, pp. 427-434, 349.
Yang, M. et al., Crystalline monoclonal antibodies for subcutaneous delivery, Proceedings of the the National Academy of Sciences, Jun. 10, 2003, 6934-6939, 100-12.

(56) References Cited

OTHER PUBLICATIONS

Yu, Lei et al., Investigation of N-terminal glutamate cyclization of recombinant monoclonal antibody in formulation development, J. Pharm Biomed. Anal., 2006, 455-463, 42(4).
Yu, Lian, Amorphous pharmaceutical solids: preparation, characterization and stabilization, Advanced Drug Delivery Reviews, 2001, 27-42, 48.
Zang, Yuguo, Towards Protein Crystallization as a Process Step in Downstream Processing of Therapeutic Antibodies: Screening and Optimization at Microbatch Scale, PLoS One, 2011, 1-8, 6(9).
Zhang, J. et al., Synthesis and characterization of heterotelechelic poly(ethylene glycol)s with amino acid at one end and hydroxyl group at another end, Journal of Applied Polymer Science, 2008, 2432-2439, 110(4).
Zhou, Shuxia et al., Biotherapeutic Formulation Factors Affecting Metal Leachables from Stainless Steel Studied by Design of Experiments, AAPS PharmSciTech, 2012, 284-294, 13(1).
Hada, Shavron et al., Evaluation of antioxidants in protein formulation against oxidative stress using various biophysical methods, International Journal of Biological Macromolecules, 82, (2016), pp. 192-200.
Zhiqiang Ma, et al., Pterostilbene exerts anticancer activity on non-small-cell lung cancer via activating endoplasmic reticulum stress, Nature: Scientific Reports, 7:8091, 1-14, 2017.
Agarkhed, Meera et al., Effect of Polysorbate 80 Concentration on Thermal and Photostability of a Monoclonal Antibody, AAPS Pharm Sci Tech, 14(1), 1-9, 2013.
FDA insert for KEYTRUDA (pembrolizumab). Jul. 2018. (Year: 2018) 54 pages.
Gervasi, V., et al., Parenteral protein formulations: An overview of approved products within the European Union, European Journal of Pharmaceutics and Biopharmaceutics, vol. 131, p. 8-24, 2018.
Karimi-Jafari, Maryam, et al., Creating Cocrystals: A Review of Pharmaceutical CocrystalPreparation Routes and Applications, Cryst. Growth Des., vol. 18, 6370-6387, 2018.
Li, Z., et al., Coadsorption of a Monoclonal Antibody and Nonionic Surfactant at the SiO2/Water Interface, ACS Applied Materials & Interfaces, vol. 10, No. 51, p. 44257-44266, Dec. 26, 2018.
Thipparaboina, Rajesh, et al., Multidrug co-crystals: towards the development of effective therapeutic hybrids, Drug Discovery Today, vol. 21, No. 3, 481-490, Mar. 2016.
Wade, A., et al., Antioxidant characteristics of L-histidine, Journal of Nutritional Biochemistry, vol. 9, No. 6, p. 308-315, 1998.
Chayen, Naomi E. et al., Protein crystallization: from purified protein to diffraction-quality crystal, Nature Methods, 5(2), 147-153, 2008.
Beirowskl, Jakob et al., Freeze-Drying of Nanosuspensions, Part 3: Investigation of Factors Compromising Storage Stability of Highly Concentrated Drug Nanosuspensions, Journal of Pharmaceutical Sciences, 101, 354-362, 2012.
Challener, Cynthia A., For Lyophilization, Excipients Really Do Matter, BioPharm International, 30(1), 32-35, 2017.
FDA, Pembrolizumab (Keytruda) May 10, 2017, FDA, N/A, 2 pages, 2017.
Ji, J.A et al., Methionine, Tryptophan, and Histidine Oxidation in a Model Protein, PTH: Mechanisms and Stabilization, J Pharm Sci, 98(12), 4485-4500, 2009.
Manning, Mark Cornell et al., Stability of Protein Pharmaceuticals: An Update, Pharmaceutical Research, 27 (4), 544-575, 2010.
Miguel López-Lázaro, The migration ability of stem cells can explain the existence of cancer of unknown primary site. Rethinking metastasis, Oncoscience, 2(5), 467-475, 2015.
Niedziela-Majka, Anita et al., High-Throughput Screening of Formulations to Optimize the Thermal Stability of a Therapeutic Monoclonal Antibody, Journal of Biomolecular Screening, 20(4), 552-559, 2015.
Peter B. Dirks, Brain Tumor Stem Cells: Bringing Order to the Chaos of Brain Cancer, J Clin Oncol, 26, 2916-2924, 2008.
Rosengren, Sanna et al., Abstract 4886: PEGylated recombinant hyaluronidase PH20(PEGPH20) enhances checkpoint inhibitor efficacy insyngeneic mouse models of cancer, AACR; Cancer Res, 76 (14 Supplement): 4886, 2 pages, 2016.
Schneider, Kai-Thomas et al., Shelf-Life Extension of Fc-Fused Single Chain Fragment Variable Antibodies by Lyophilization, Front. Cell. Infect. Microbiol., 11:717689, 1-16, 2021.
Singh, Surinder M. et al., Effect of Polysorbate 20 and Polysorbate 80 on the Higher Order Structure of a Monoclonal Antibody and its Fab and Fc Fragments Probed Using 2D NMR Spectroscopy, J Pharm Sci, 106(12), 3486-3498, 2017.
Tang, Xiaolong et al., Anti-GPC3 antibody-modified sorafenib-loaded nanoparticles significantly inhibited HepG2 hepatocellular carcinoma, Drug Delivery, 25:1, 1484-1494, 2018.
Tran, B. et al., Survival comparison between glioblastoma multiforme and other incurable cancers, Journal of Clinical Neuroscience, 17, 417-421, 2010.
Viola, Margarida et al., Subcutaneous delivery of monoclonal antibodies: How do we get there?, Journal of Controlled Release, 286, 301-314, 2018.
Wang, Mengchang et al., Silence of MCL-1 upstream signaling by shRNA abrogates multiple myeloma growth, Experimental Hematology & Oncology, 3:27, 1-7, 2014.
Hampton Research Corp., Silver Bullets—Solutions for Crystal Growth, Hampton Research Corp., HR2-096, 1-16, 1991.
Shukla, Diwakar et al., Interaction of Arginine with Proteins and the Mechanism by Which It Inhibits Aggregation, J. Phys. Chem. B., 114, 13426-13438, 2010.

* cited by examiner

VIS

UV–TPEF

SHG

VIS

UV–TPEF

SHG

| | Sample Name | Breakloose Force (N) | Force at Point 1 (N) | Force at Point 2 (N) | Force at Point 3 (N) | Force at Point 4 (N) |
|---|---|---|---|---|---|---|
| 1 | Pembro crystalline_150mg_mL | | 3.311 | 3.518 | 3.617 | 3.757 |
| 2 | Pembro crystalline_175mg_mL | 3.963 | 3.696 | 3.571 | 3.793 | 3.973 |
| 3 | Pembro crystalline_200mg_mL | 7.078 | 4.519 | 4.668 | 4.933 | 5.158 |
| Mean | | 5.52 | 3.842 | 3.919 | 4.114 | 4.296 |
| Standard deviation | | 2.20258 | 0.61703 | 0.64927 | 0.71435 | 0.7547 |

ANTI-HUMAN PD-1 ANTIBODY CRYSTALS AND METHODS OF USE THEREOF

FIELD OF THE INVENTION

The invention relates to methods for producing crystalline suspensions of anti-PD-1 monoclonal antibodies. The invention further relates to antibody crystals produced by the methods herein, pharmaceutical compositions comprising the crystals and methods of use thereof.

CROSS-REFERENCE TO RELATED APPLICATIONS

This application is a National Stage application of International Patent Application No. PCT/US2019/058339, filed Oct. 28, 2019, which claims priority to U.S. Provisional Patent Application No. 62/753,615, filed Oct. 31, 2018.

REFERENCE TO SEQUENCE LISTING SUBMITTED ELECTRONICALLY

The sequence listing of the present application is submitted electronically via EFS-Web as an ASCII formatted sequence listing with a file name "24638USPCT-SEQLIST-23MAR2021", with a creation date of Mar. 23, 2021, and a size of 10 KB. This sequence listing submitted via EFS-Web is part of the specification and is herein incorporated by reference in its entirety.

BACKGROUND OF THE INVENTION

Therapeutic and diagnostic antibodies have become the fastest growing area of the biopharmaceutical industry. A critical aspect to the success of antibodies as therapeutic agents is the development of improved methods to express, purify and characterize these proteins. In general, antibody therapeutics are large (typically >150 kDa) and complex in nature and must be administered in stoichiometric rather than catalytic quantities. Production and purification scales have thus reached levels of production that were previously assumed impossible. There is also a need for the development of stable formulations and delivery strategies for such large amounts of a complex molecule.

Development of stable formulations comprising a high concentration of active agent, such as an antibody or antigen-binding fragment, is particularly important for biological formulations intended for subcutaneous administration to a patient, since the volume of solution delivered to a patient is greatly reduced. Subcutaneous administration is the preferred method of administration of many antibodies, in part because it may enable self-administration or easier administration by a medical professional (e.g. pharmacist, doctor, or nurse). Therapeutic antibodies are traditionally prepared in lyophilized form or in solution. Lyophilized forms may exhibit enhanced long-term stability, but require reconstitution prior to use, making them less than ideal for self-administration. On the other hand, stable liquid formulations are more challenging to develop and often require cold storage prior to use.

Immune checkpoint therapies targeting the programmed death receptor-1 (PD-1) axis have resulted in groundbreaking improvements in clinical response in multiple human cancers (Brahmer et al., *N Engl J Med* 2012, 366: 2455-65; Garon et al. *N Engl J Med* 2015, 372: 2018-28; Hamid et al., *N Engl J Med* 2013, 369: 134-44; Robert et al., *Lancet* 2014, 384: 1109-17; Robert et al., *N Engl J Med* 2015, 372: 2521-32; Robert et al., *N Engl J Med* 2015, 372: 320-30; Topalian et al., *N Engl J Med* 2012, 366: 2443-54; Topalian et al., *J Clin Oncol* 2014, 32: 1020-30; Wolchok et al., *N Engl J Med* 2013, 369: 122-33). The interaction of the PD-1 receptor on T-cells with its ligands, PD-L1 and PD-L2, on tumor and immune infiltrating cells regulates T-cell mediated immune responses and may play a role in immune escape by human tumors (Pardoll D M. Nat Rev Cancer 2012, 12: 252-64). Binding of PD-1 to either of its ligands results in delivery of an inhibitory stimulus to the T cell. Immune therapies targeting the PD-1 axis include monoclonal antibodies directed to the PD-1 receptor (KEYTRUDA™ (pembrolizumab), Merck and Co., Inc., Kenilworth, NJ and OPDIVO™ (nivolumab), Bristol-Myers Squibb, Princeton, NJ) and also those that bind to the PD-L1 ligand (MPDL3280A; TECENTRIQ™ (atezolizumab), Genentech, San Francisco, CA). Both therapeutic approaches have demonstrated anti-tumor effects in numerous cancer types.

The need exists for improved stable formulations of anti-PD-1 antibodies for use, e.g., in the treatment of patients with cancer. Preferably, such antibody formulations will not require reconstitution prior to administration. In addition, such formulations will enable administration of a higher concentration of the antibody than would be readily achievable using typical solution formulations, and will preferably support high concentrations with sufficiently low viscosity to be conveniently delivered subcutaneously.

SUMMARY OF THE INVENTION

In one aspect, the invention relates to a method for producing crystalline anti-PD-1 monoclonal antibody (mAb) comprising: (a) mixing: (i) an aqueous buffered solution comprising about 5 mg/mL to about 80 mg/mL of the mAb, wherein the anti-PD-1 mAb is pembrolizumab or a pembrolizumab variant, (ii) polyethylene glycol (PEG), and (iii) an additive selected from the group consisting of: caffeine, theophylline, 2' deoxyguanosine-5'-monophosphate, a bioactive gibberellin, such as gibberellin A3, and a pharmaceutically acceptable salt of the gibberellin; to form a crystallization solution, wherein the crystallization solution has a pH of about 6.0 to about 8.8 and comprises about 2% to about 40% weight per volume (w/v) PEG and about 0.1% to about 0.30% w/v additive; (b) incubating the crystallization solution for a period of time sufficient for crystal formation; and (c) optionally harvesting the crystalline anti-PD-1 mAb from the solution.

In some embodiments, the mAb is pembrolizumab. In further embodiments, the mAb is a pembrolizumab variant that maintains the ability to bind to PD-1 and the ability to bind to the additive.

In specific embodiments, the additive is caffeine.

In some embodiments, the crystallization solution further comprises about 1% to about 10% dextran sodium sulfate.

In one aspect, the invention relates to an isolated anti-PD-1 crystal made by the methods of the invention.

In another aspect, the invention relates to an isolated crystal comprising pembrolizumab complexed with caffeine, wherein the crystal is characterized by space group $P222_1$ a=43.8 Å b=113.9 Å c=175.0 Å, α=β=γ=90°.

In another aspect, the invention relates to crystalline pembrolizumab comprising pembrolizumab complexed to caffeine, characterized by solid state NMR $^{13}C$ spectrum exhibiting peaks at about 182.16, 181.54, 179.99, 109.36, 108.23, 103.58, 76.88 and 76.04 ppm.

In another aspect, the invention relates to crystalline pembrolizumab comprising pembrolizumab complexed to caffeine, characterized by solid state NMR $^{13}C$ spectrum exhibiting peaks at about 183.07, 182.16, 181.54, 180.55, 179.99, 110.70, 110.15, 109.36, 108.23, 103.58, 101.49, 99.75, 98.56, 76.88, 76.04, 74.97, 74.41, 73.52, 72.69, 13.85, 13.27, 12.26 and 11.13 ppm.

Also provided herein are compositions comprising the anti-PD-1 mAb crystals of the invention and a pharmaceutically acceptable carrier.

In one aspect, the invention provides methods of treating cancer and/or infectious disease by administering the crystals or the compositions of the invention to a patient in need thereof. In specific embodiments, the compositions are administered to the patient via intravenous infusion. In alternative embodiments, the crystals are administered to the patient via subcutaneous injection.

BRIEF DESCRIPTION OF THE DRAWINGS

FIG. 1A provides a visible image of the crystals taken at 200× magnification. FIGS. 1B and 1C provide images produced using the UV-TPEF and the SHG mode of the SONICC™ imaging system, respectively. A positive image from SHG and UV-TPEF indicates protein crystals.

FIG. 2A shows crystals formed with 0.20% caffeine, 12% PEG 3350, 50 mM HEPES, pH 6.8. FIG. 2B shows crystals formed with 0.2% theophylline+0.2% ethanolamine+10% PEG 3350. FIG. 2C shows crystals formed using 0.2% theophylline+0.2% 2'deoxyguanosine 5-monophosphate sodium salt hydrate+16% PEG 3350.

DETAILED DESCRIPTION OF THE INVENTION

Figure 1A:
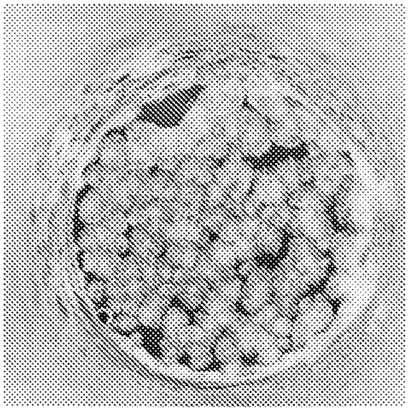
FIGS. 1A-1C show photomicrographs of crystals within a pembrolizumab crystalline suspension, obtained by vapor diffusion at 30° C. using a precipitant solution of Silver Bullet Bio crystallization reagent A2, and 12.5% w/v PEG 3350, 0.05M HEPES buffer at pH 6.8. See EXAMPLE 1. The photomicrographs, at 200× magnification, were taken after 30 days using a SONICC™ imaging system.

The invention provides crystalline forms of pembrolizumab antibodies, and variants thereof, suspensions of these crystals, and pharmaceutical formulations of these suspensions. Highly purified pembrolizumab monoclonal antibody was used in high throughput (HT) vapor diffusion sparse matrix screening experiments. Novel crystalline suspensions were obtained at 30° C. and at room temperature using various additives. The present invention also provides methods for preparing said novel monoclonal antibody (mAb) crystalline suspensions, wherein the mAb is pembrolizumab or a variant thereof, e.g., using bulk crystallization (batch and dialysis) in high yield.

In one aspect, the invention relates to a method for producing crystalline anti-PD-1 mAb comprising: (a) mixing: (i) an aqueous buffered solution comprising about 5 mg/mL to about 80 mg/mL of the mAb, (ii) polyethylene glycol (PEG), and (iii) an additive selected from the group consisting of: caffeine, theophylline, 2' deoxyguanosine-5'-monophosphate, a bioactive gibberellin, and a pharmaceutically acceptable salt of a bioactive gibberellin; to form a crystallization solution, wherein the crystallization solution has a pH of about 6.0 to about 8.8 and comprises about 5% to about 40% weight per volume (w/v) PEG and about 0.10% to about 0.30% w/v additive; (b) incubating the crystallization solution for a period of time sufficient for crystal formation; and (c) optionally harvesting the crystalline anti-PD-1 mAb from the solution. The resulting crystalline suspensions comprise anti-PD-1 mAb crystals, e.g. pembrolizumab crystals, having a particle size of 0.5-200 microns following harvest. In particular embodiments, the method further comprises the step of homogenizing the crystals formed in step (b). In still further embodiments, the crystalline anti-PD-1 mAb is harvested from the crystallization solution, or at least partially purified from the crystallization solution and the harvested or purified crystals are then homogenized. The resulting anti-PD-1 mAb crystals, e.g. pembrolizumab crystals, have a particle size following homogenization of from about 0.5 to about 50 microns.

The invention further provides various methods for making the crystalline pembrolizumab antibody of the invention, as described in greater detail in Examples 1-18. Examples 1 and 2 provide methods based on vapor diffusion, which is useful for screening to determine crystallization conditions. Such methods are also suitable for generation of large crystals for use in X-ray diffraction studies, e.g. to determine the three dimensional structure of the anti-PD-1 antibody. In some embodiments, dextran sodium sulfate is added to the crystallization solution to allow more control over nucleation; thus allowing growth of larger crystals.

Examples 5, 11, and 15-17 provide crystallization methods suited to large-scale production, such as batch crystallization and bulk dialysis crystallization, which are useful for commercial scale production of crystalline pembrolizumab, or a pembrolizumab variant, for therapeutic use. A method of harvesting crystals of the present invention using centrifugation is provided, e.g., in Examples 11, 14 and 15, but filtration methods know in the art, such as hollow fiber tangential flow filtration, may also be used to harvest crystals, e.g., at commercial scale.

Although the specific disclosed embodiments employ a 1:1 and/or 1:3 mixture of an antibody solution with a precipitant solution, any modification of the disclosed methods that result in approximately the same concentrations of solution components in the final crystallization solution (from which crystals arise) would be equivalent. For example, the concentrations of the components in the precipitant solution may be proportionally increased or decreased if using a precipitant solution (a solution comprising PEG and an additive, as defined herein) that comprises less than or more than 50% of the final volume of the crystallization solution, respectively.

The crystallization methods of the present invention also provide a process for purifying pembrolizumab or pembrolizumab variant antibodies, even if such crystals are re-dissolved prior to use. In one embodiment, a pembrolizumab antibody is produced and at least partially purified by methods described herein and known in the art. The antibody is then crystallized, e.g. by batch crystallization or by bulk dialysis. The crystalline antibody is then recovered and washed, e.g. as described in Example 5 (or by filtration), and re-dissolved in buffer, e.g., 10 mM histidine buffer pH 5.4, or any suitable buffer for the intended use of the purified antibody. For therapeutic uses, suitable pharmaceutically acceptable buffers and excipients are used.

The crystallization methods of the present invention also provide a method of storing purified pembrolizumab antibodies, even if such crystals are re-dissolved prior to use. In one embodiment, a pembrolizumab or pembrolizumab variant antibody is produced and at least partially purified by methods described herein and known in the art. The antibody is then crystallized, e.g. by batch crystallization or by bulk dialysis. The resulting concentrated pembrolizumab crystalline suspension is stored as a stable concentrated preparation suitable for shipping and reformulating at global formulation sites.

Crystalline pembrolizumab antibodies of the present invention have several advantageous properties for use in therapy including the ability to be formulated at high concentrations with a low viscosity. This high concentration can enable more efficient administration to a subject, e.g. by subcutaneous injection. The crystalline suspensions of the present invention, can be used to prepare pharmaceutical formulations up to 300-400 mg/mL, enabling higher dosing with lower injection volume, and thus less discomfort. Crystalline suspensions of the present invention may be delivered by subcutaneous injection using small bore needles, such as 27 G insulin syringes. The reduced volume, decreased viscosity and use of a smaller needle are all likely to decrease patient discomfort upon subcutaneous administration.

Crystalline pembrolizumab antibodies of the present invention also have other advantageous properties. Suspensions of the crystalline pembrolizumab antibodies show comparable stability to the starting solution formulation and may allow for a longer shelf-life. Additionally, the ability to store the suspensions of the crystals of present invention at room temperature may offer significant advantages in handling of drug product and supply chain management.

Previous crystalline suspensions of pembrolizumab were made using a high salt process. See WO 2016/137850. The novel pembrolizumab crystals of the invention do not require the use of high salt, which is advantageous for a pharmaceutical manufacturing process since high levels of salt are not suitable for a pharmaceutical formulations intended for subcutaneous administration.

I. Definitions and Abbreviations

As used throughout the specification and appended claims, the following abbreviations apply:

CDR Complementarity determining region
CHO Chinese hamster ovary
CP Cross polarizing
CPS Combined positive score
DFS Disease free survival
ELISA Enzyme-linked immunosorbent assay
FR Framework region
GRAS Generally regarded as safe
HEPES Hydroxyethyl-piperazineethane-sulfonic acid buffer
HT High throughput
IEX Ion exchange
IHC Immunohistochemistry or immunohistochemical
IPTG Isopropyl β-d-1-thiogalactopyranoside
IV Intravenous
mAb Monoclonal antibody
MAS Magic angle spinning
NCI National Cancer Institute
NMR Nuclear magnetic resonance
PBS Phosphate buffered saline
PD Progressive disease
PD-1 Programmed Death 1
PD-L1 Programmed Cell Death 1 Ligand 1
PD-L2 Programmed Cell Death 1 Ligand 2
PEG Polyethylene glycol
PFS Progression free survival
PK Pharmacokinetic
PR Partial response
OR Overall response
OS Overall survival
Q2W One dose every two weeks
Q3W One dose every three weeks
QD One dose per day
RECIST Response Evaluation Criteria in Solid Tumors RPLC Reversed-phase liquid chromatography
RPM Revolutions per minute
SC Subcutaneous
SD Stable disease or standard deviation, as dictated by the context
SHG Second harmonic generation
SONICC Second Order Nonlinear Imaging of Chiral Crystals
T/C Treated over control tumor volume ratio
TPS Tumor proportion score
UV-TPEF Ultraviolet Two-Photon Excited Fluorescence
VH Immunoglobulin heavy chain variable region
VK Immunoglobulin kappa light chain variable region
w/v Weight per volume So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used throughout the specification and in the appended claims, the singular forms "a," "an," and "the" include the plural reference unless the context clearly dictates otherwise.

Reference to "or" indicates either or both possibilities unless the context clearly dictates one of the indicated possibilities. In some cases, "and/or" was employed to highlight either or both possibilities.

"Treat" or "treating" means to administer a composition of the invention to a patient in order to induce a positive therapeutic effect. The terms do not necessarily indicate a total elimination of all disease or disorder symptoms. "Treating" a cancer or immune condition refers to administration of a crystalline suspension or composition of the invention to a patient having an immune condition or cancerous condition, or diagnosed with or predisposed to a cancer or a pathogenic infection (e.g. viral, bacterial, fungal), to achieve at least one positive therapeutic effect, such as for example, reduced number of cancer cells, reduced tumor size, reduced rate of cancer cell infiltration into peripheral organs, or reduced rate of tumor metastasis or tumor growth. "Treatment" may include one or more of the following: inducing/increasing an antitumor immune response, stimulating an immune response to a pathogen, toxin, and/or self-antigen, stimulating an immune response to a viral infection, decreasing the number of one or more tumor markers, inhibiting the growth or survival of tumor cells, eliminating or reducing the size of one or more cancerous lesions or tumors, decreasing the level of one or more tumor markers, ameliorating, reducing the severity or duration of the cancer, prolonging the survival of a patient relative to the expected survival in a similar untreated patient.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

Positive therapeutic effects in cancer can be measured in a number of ways (See, W. A. Weber, *J. Nucl. Med.* 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by administration of a formulation of the invention is any of progression free survival (PFS), disease free survival (DFS) or overall survival (OS). PFS, also referred to as "Time to Tumor Progression" indicates the length of time during and after treatment that the cancer does not grow, and includes the amount of time patients have experienced a complete response or a partial response, as well as the amount of time patients have experienced stable disease. DFS refers to the length of time during and after treatment that the patient remains free of disease. OS refers to a prolongation in life expectancy as compared to naive or untreated individuals or patients. While an embodiment of the formulations, treatment methods, and uses of the present invention may not be effective in achieving a positive therapeutic effect in every patient, it should do so in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

The term "patient" (alternatively referred to as "subject" or "individual" herein) refers to a mammal (e.g., rat, mouse, dog, cat, rabbit) capable of being treated with the formulations of the invention, most preferably a human. The term "patient" may also include non-human animals including livestock animals and domestic animals including, but not limited to, cattle, horses, sheep, swine, goats, rabbits, cats, dogs, and other mammals in need of treatment. In some embodiments, the patient is an adult patient. In other embodiments, the patient is a pediatric patient. A patient "in need of treatment" is an individual diagnosed with, suspected of having, or predisposed to a disease or disorder in which a crystalline suspension or composition of the invention is intended to treat, or a patient for whom prevention of a disorder is desired.

The term "antibody" refers to any form of antibody that exhibits the desired biological activity. Thus, it is used in the broadest sense and specifically covers, but is not limited to, monoclonal antibodies (including full length monoclonal antibodies), polyclonal antibodies, humanized, fully human antibodies, and chimeric antibodies. "Parental antibodies" are antibodies obtained by exposure of an immune system to an antigen prior to modification of the antibodies for an intended use, such as humanization of an antibody for use as a human therapeutic antibody.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The variable regions of each light/heavy chain pair form the antibody binding site. Thus, in general, an intact antibody has two binding sites. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; $5^{th}$ ed.; NIH Publ. No. 91-3242 (1991); Kabat (1978) *Adv. Prot. Chem.* 32:1-75; Kabat, et al., (1977) *J Biol. Chem.* 252: 6609-6616; Chothia, et al., (1987) *J Mol. Biol.* 196:901-917 or Chothia, et al., (1989) *Nature* 342:878-883.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein, i.e. human PD-1, with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 molecule, if it binds to polypeptides comprising that sequence but does not bind to proteins lacking that sequence.

The term "pharmaceutically effective amount" or "therapeutically effective amount" means an amount whereby sufficient therapeutic composition or formulation is introduced to a patient to treat a disease or condition. One skilled in the art recognizes that this level may vary according the patient's characteristics such as age, weight, etc. The term "effective amount," when used with a crystalline suspension or composition of the invention, means an amount of suspension or composition sufficient to treat a pathological condition that it was intended to treat, e.g., a cancerous condition or inflammatory disorder. An "effective amount" of a crystal or composition of the invention means an amount sufficient to elicit the response being sought in a cell, tissue, system, animal or human. In one embodiment, the effective amount is a "therapeutically effective amount" for the alleviation of the symptoms of the disease or condition being treated. When the active compound (i.e., active ingredient) is administered as the salt, references to the amount of active ingredient are to the free acid or free base form of the compound.

The term "about", when modifying the quantity (e.g., mM, or M) of a substance or composition, the percentage (v/v or w/v) of a formulation component, the pH of a solution/formulation, or the value of a parameter characterizing a step in a method, or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of ±0.1%, 0.5%, 1%, 2%, 3%, 4%, 5%, or 10%. In certain embodiments, the term "about" for the purposes of solid state NMR means±0.1 ppm.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, Hodgkin's lymphoma, non-Hodgkin's lymphoma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer.

"Concentration", when used with reference to a crystalline antibody suspension of the present invention, refers to the amount of antibody (e.g., pembrolizumab) present in a given macroscopic unit volume of solution. The term concentration is used in its customary sense despite the inherent heterogeneity of the suspension, as compared to a traditional solution. The concentration of antibody in a crystalline suspension is equal to the concentration of an equivalent sample in which the antibody is not in crystalline form.

"Anti-PD-1 mAb crystal" or "crystalline anti-PD-1 mAb," as used herein, refers to a crystal containing the antibody arranged in a lattice structure that repeats periodically in three dimensions. In contrast, a solid, amorphous form of the mAb, e.g., such as produced by lyophilizing a mAb dissolved in a solution, does not display the optical properties such as refractive index and birefringence that are typical of a crystalline antibody form.

An "antibody solution" refers to a solution of an anti-human PD-1 antibody, e.g. pembrolizumab, which is used to generate the crystalline antibody of the present invention. "Precipitant solution" refers to a second solution that is mixed with the antibody solution, typically at a 1:1 volume ratio (i.e. equal volumes of the two solutions are mixed) to create a "crystallization solution" from which antibodies grow. The concentrations of the antibody and precipitant solutions are provided herein for a 1:1 mixture, for convenience, but one skilled in the art would recognize that the volume ratio used to make the mixture can be changed, and thus so can the concentrations of the solutions making up the mixture. Such modifications are within the scope of the invention if they generate the same crystallization conditions (i.e. the same crystallization solution) as the mixtures described herein.

With regard to crystallization methods based on dialysis, "dialysis solution" refers to the solution against which a solution of pembrolizumab (the "antibody solution") is dialyzed to drive formation of the crystalline antibody of the present invention. "Retentate" refers to the antibody solution after dialysis, which may include crystals of the antibody, which are harvested. The antibody solution/retentate are on one side of the dialysis membrane, and the dialysis solution is on the opposite side.

The term "homogenize" means to reduce crystal particles in size using mechanical means; thus resulting in smaller particles that are more uniform and evenly distributed. Homogenization can be performed through any known means such as through the use of a homogenizer, or by forcing the crystalline particles through a smaller orifice (Venturi effect), such as a syringe, to break the particles into a smaller size.

The terms "micron" and "micrometer" are used interchangeably herein and each means 1/1000000th of a meter.

"PD-L1" or "PD-L2" expression means any detectable level of expression of the designated PD-L protein on the cell surface or of the designated PD-L mRNA within a cell or tissue. PD-L protein expression may be detected with a diagnostic PD-L antibody in an immunohistochemical (IHC) assay of a tumor tissue section or by flow cytometry. Alternatively, PD-L protein expression by tumor cells may be detected by PET imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and real-time quantitative RT-PCR.

Several approaches have been described for quantifying PD-L1 protein expression in IHC assays of tumor tissue sections. See, e.g., Thompson, R. H., et al., *Proc. Nat. Acad. Sci USA* 101 (49): 17174-17179 (2004); Thompson, R. H. et al., *Cancer Res.* 66: 3381-3385 (2006); Gadiot, J., et al., *Cancer* 117: 2192-2201 (2011); Taube, J. M. et al., *Sci Transl Med* 4: 127ra37 (2012); and Toplian, S. L. et al., *New Eng. J Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. In some embodiment, PD-L1 expression in tumor cells is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

A tissue section from a tumor that has been stained by IHC with a diagnostic PD-L1 antibody may also be scored for PD-L1 protein expression by assessing PD-L1 expression in both the tumor cells and infiltrating immune cells in the tissue section using a scoring process. See WO 2014/165422. One PD-L1 scoring process comprises examining each tumor nest in the tissue section for staining, and assigning to the tissue section one or both of a modified H score (MHS) and a modified proportion score (MPS). To assign the MHS, four separate percentages are estimated across all of the viable tumor cells and stained mononuclear inflammatory cells in all of the examined tumor nests: (a) cells that have no staining (intensity=0), (b) weak staining (intensity=1+), (c) moderate staining (intensity=2+) and (d) strong staining (intensity=3+). A cell must have at least partial membrane staining to be included in the weak, moderate or strong staining percentages. The estimated percentages, the sum of which is 100%, are then input into the formula of 1×(percent of weak staining cells)+2×(percent of moderate staining cells)+3×(percent of strong staining cells), and the result is assigned to the tissue section as the MHS. The MPS is assigned by estimating, across all of the viable tumor cells and stained mononuclear inflammatory cells in all of the examined tumor nests, the percentage of cells that have at least partial membrane staining of any intensity, and the resulting percentage is assigned to the tissue section as the MPS. In some embodiments, the tumor is designated as positive for PD-L1 expression if the MHS or the MPS is positive.

"CPS" or "combined positive score" refers to an algorithm for determining a PD-L1 expression score from a tumor sample of a patient. The CPS is useful in selecting patients for treatment with particular treatment regimens including methods of treatment comprising administration of an anti-PD-1 antibody in which expression of PD-L1 is associated with a higher response rate in a particular patient population relative to same patient population that does not express PD-L1. The CPS is determined by determining the number of viable PD-L1 positive tumor cells, the number of viable PD-L1 negative tumor cells, and the number of viable PD-L1 positive mononuclear inflammatory cells (MIC) in a tumor tissue from a patient having a tumor and calculating the CPS using the following formula:

$$\frac{(\#\ PD\text{-}L1 \text{ positive tumor cells}) + (\#\ PD\text{-}L1 \text{ positive } MIC)}{(\#\ PD\text{-}L1 \text{ positive tumor cells}) + (PD\text{-}L1 \text{ negative tumor cells})} \times 100\%.$$

TPS or "tumor proportion score" is the percentage of tumor cells expressing PD-L1 on the cell membrane. TPS typically includes the percentage of neoplastic cells expressing PD-L1 at any intensity (weak, moderate, or strong), which can be determining using an immunohistochemical assay using a diagnostic anti-human PD-L1 mAb, e.g. antibody 20C3 and antibody 22C3, described, supra. Cells are considered to express PD-L1 if membrane staining is present, including cells with partial membrane staining.

The level of PD-L mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue. In some preferred embodiments, PD-L1 expression in a tumor sample is determined to be elevated if PD-L1 protein (and/or PD-L1 mRNA) in the sample is at least 10%, 20%, 30%, 40% or 50% greater than in the control.

"Pembrolizumab" is an IgG4 monoclonal antibody with the structure described in *WHO Drug Information*, Vol. 27, No. 2, pages 161-162 (2013) (Merck Sharp & Dohme Corp., Whitehouse Station, NJ). Each light chain of pembrolizumab comprises light chain complementarity determining regions (CDRs) comprising a sequence of amino acids as set forth in SEQ ID NOs: 1, 2 and 3 and heavy chain CDRs comprising a sequence of amino acids as set forth in SEQ ID NOs: 4, 5 and 6. The variable chain light ($V_L$) and heavy ($V_H$) chains of pembrolizumab comprise a sequence of amino acids as set forth in SEQ ID NO:7 and SEQ ID NO:8, respectively and the full length light and heavy chains comprise or consist of a sequence of amino acids as set forth in SEQ ID NO:9 and SEQ ID NO:10, respectively. Pembrolizumab is approved by the U.S. FDA for the treatment of patients with unresectable or metastatic melanoma, for the adjuvant treatment of patients with melanoma with involvement of lymph node(s) following complete resection and for the treatment of certain patients with recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, esophageal cancer, hepatocellular carcinoma, Merkel cell carcinoma, renal cell carcinoma, endometrial carcinoma, small cell lung cancer, and non-small cell lung cancer, as described in the Prescribing Information for KEYTRUDA™ (Merck & Co., Inc., Whitehouse Station, NJ USA; initial U.S. approval 2014, updated September 2019).

As used herein, a "pembrolizumab variant" refers to a derivative of a pembrolizumab antibody that (1) substantially retains its biological activity of binding to antigen (i.e., human PD-1) and inhibiting its activity (e.g., blocking the binding of PD-1 to PD-L1 and/or PD-L2) and (2) retains the ability of the antibody to bind to an additive that is used in the crystallization solution in the methods of the invention, wherein the additive is caffeine, theophylline, 2' deoxyguanosine-5'-monophosphate, a bioactive gibberellin, such as gibberellin A3, or a pharmaceutically acceptable salt thereof. In embodiments of the invention, the pembrolizumab variant comprises light chain and heavy chain sequences that are identical to those in pembrolizumab (SEQ ID NO:9 and 10, respectively), except for having up to 10, up to 9, up to 8, up to 7, up to 6, up to 5, up to 4, up to 3, up to 2, 1, 2, 3, 4, 5, 6, 7, 8, 9, or 10 conservative amino acid substitutions at amino acid positions that are located outside of the light chain CDRs and outside of the heavy chain CDRs, e.g., the variant positions are located in the framework regions or the constant region. In further embodiments, a pembrolizumab variant has up to 10, up to 9, up to 8, up to 7, up to 6, up to 5, up to 4, up to 3, up to 2, 1, 2, 3, 4, 5, 6, 7, 8, 9, or 10 conservative amino acid substitutions that are located outside the pembrolizumab light and heavy chain CDRs and are further outside of the pembrolizumab residues that bind to caffeine, i.e. outside of TYR 436 and ASN 434 of the pembrolizumab heavy chain (positions 434 and 436 of SEQ ID NO: 10). In other words, pembrolizumab and a pembrolizumab variant comprise identical CDR sequences, but differ from each other due to having a conservative amino acid substitution at no more than ten other positions in their full length light and heavy chain sequences, respectively. A pembrolizumab variant is substantially the same as pembrolizumab with respect to the following properties: binding affinity to PD-1, ability to block the binding of each of PD-L1 and PD-L2 to PD-1, and ability to bind to an additive selected from: caffeine, theophylline, 2' deoxyguanosine-5'-monophosphate, a bioactive gibberellin, such as gibberellin A3, and a pharmaceutically acceptable salt of said bioactive gibberellin.

A "precipitant" is a compound that decreases the solubility of a polypeptide, such as an antibody, in a concentrated solution. In batch crystallization methods, the precipitant may be included in the "precipitant solution," and in bulk dialysis methods the precipitant may be included in the "dialysis solution." Precipitants induce crystallization by forming an energetically unfavorable precipitant-depleted layer around the polypeptide molecules. To minimize the relative amount of this depletion layer, the polypeptides form associations and, ultimately, crystals. This process is explained in Weber (1991) Advances in Protein Chemistry 41:1. Various precipitants are known in the art. In the methods of the invention, the precipitant is polyethylene glycol (e.g. PEG 3350).

In addition to precipitants, one or more additives which facilitate crystallization is added to the polypeptide precipitant solution or crystallization solution selected from: caffeine, theophylline, 2' deoxyguanosine-5'-monophosphate, a bioactive gibberellin, and a pharmaceutically acceptable salt of the bioactive gibberellin. Two of the additives useful in the methods of the invention, caffeine and theophylline, were found to share structural similarity as shown below:

Caffeine

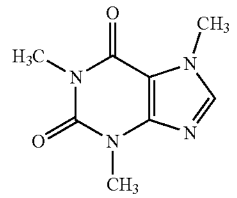

Theophylline

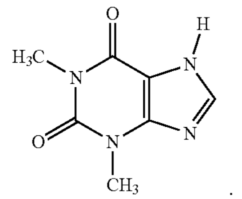

It is also shown herein that gibberellin A3 (alternatively, GA3 or gibberellic acid) is a useful reagent in the crystallization methods of the methods of the invention. Gibberellins (also known as GAs) are a class of hormones found in plants, which share a common diterpenoid acid structure and regulate various developmental processes. "Bioactive gibberellins," are involved in different aspects of plant germination and share the following structural traits: 1) a hydroxyl group on C-3β, 2) a carboxyl group on C-6, and 3) a lactone between C-4 and C-10 (see below). Based on the similar structure and function of the "bioactive gibberellins," which comprise gibberellin A1 (GA1), gibberellin A3 (GA3), gibberellin A4 (GA4), and gibberellin A7 (GA7), or pharmaceutically acceptable salts thereof, it is expected that any bioactive gibberellin or pharmaceutically acceptable salt thereof would be useful in the methods of the invention.

Gibberellin A1

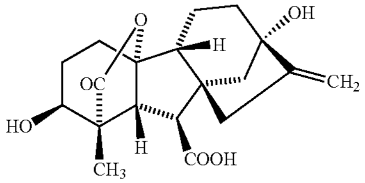

Gibberellin A3

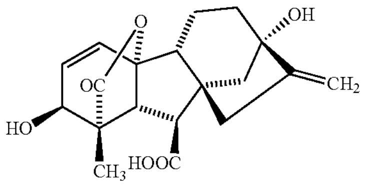

Gibberellin A4

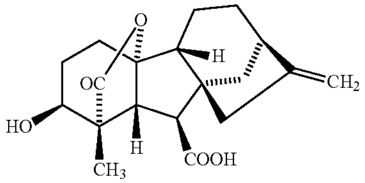

Gibberellin A7

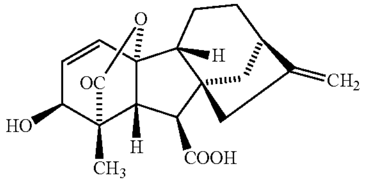

In addition to precipitants, one or more additional excipients may be added to the polypeptide precipitant solution or crystallization solution. Excipients include buffers, such as Tris or HEPES, to adjust the pH of the solution (and hence surface charge on the peptide), salts, such as sodium chloride, lithium chloride and sodium citrate, to reduce the solubility of the polypeptide.

"Tissue Section" refers to a single part or piece of a tissue sample, e.g., a thin slice of tissue cut from a sample of a normal tissue or of a tumor.

"Tris" (2-Amino-2-hydroxymethyl-propane-1,3-diol) as used herein is synonymous with TRIS, Tris base, Trizma, Trisamine, THAM, Tromethamine, Trometamol, Trometh-ane, and Trisaminol.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The humanized forms of rodent antibodies will generally comprise the same CDR sequences of the parental rodent antibodies, although certain amino acid substitutions may be included to increase affinity, increase stability of the humanized antibody, or for other reasons.

Antibodies useful in the compositions of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J Allergy Clin. Immunol.* 116:731 at 734-35.

"Hypervariable region" refers to the amino acid residues of an antibody that are responsible for antigen-binding and are variable in sequence between different antibodies. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain as measured by the Kabat numbering system (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) *J. Mol. Biol.* 196: 901-917). As used herein, the term "framework" or "FR" residues refers to those variable domain residues other than the hypervariable region residues defined herein as CDR residues. CDR and FR residues are determined according to the standard sequence definition of Kabat. Kabat et al. (1987) Sequences of Proteins of Immunological Interest, National Institutes of Health, Bethesda Md.

"Conservatively modified variants" or "conservative substitution" refers to substitutions of amino acids are known to those of skill in this art and may be made generally without altering the biological activity of the resulting molecule, even in essential regions of the polypeptide. Such exemplary substitutions are preferably made in accordance with those set forth in Table 1 as follows:

TABLE 1

Exemplary Conservative Amino Acid Substitutions

| Original residue | Conservative substitution |
| --- | --- |
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

In addition, those of skill in this art recognize that, in general, single amino acid substitutions in non-essential regions of a polypeptide do not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J Mol. Biol.* 222: 581-597, for example. See also Presta (2005) *J. Allergy Clin. Immunol.* 116:731.

The term "buffer" encompasses those agents which maintain the solution pH of the formulations of the invention in an acceptable range, or, for lyophilized formulations of the invention, provide an acceptable solution pH prior to lyophilization.

The term "pharmaceutical formulation" refers to preparations which are in such form as to permit the active ingredients to be effective, and which contains no additional components which are toxic to the subjects to which the formulation would be administered.

"Pharmaceutically acceptable" refers to excipients (vehicles, additives) and compositions that can reasonably be administered to a subject to provide an effective dose of the active ingredient employed and that are "generally regarded as safe" e.g., that are physiologically tolerable and do not typically produce an allergic or similar untoward reaction, such as gastric upset and the like, when administered to a human. In another embodiment, this term refers to molecular entities and compositions approved by a regulatory agency of the federal or a state government or listed in the U.S. Pharmacopeia or another generally recognized pharmacopeia for use in animals, and more particularly in humans.

"Room temperature," or "RT" as used herein refers to a temperature in the range of about 18° C. to about 25° C. (about 64 to about 77° F.).

A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period. For example, in one embodiment, a stable formulation is a formulation with no significant changes observed at a refrigerated temperature (2-8° C.) for at least 12 months. In another embodiment, a stable formulation is a formulation with no significant changes observed at a refrigerated temperature (2-8° C.) for at least 18 months. In another embodiment, stable formulation is a formulation with no significant changes observed at room temperature (23-27° C.) for at least 3 months. In another embodiment, stable formulation is a formulation with no significant changes observed at room temperature (23-27° C.) for at least 6 months. In another embodiment, stable formulation is a formulation with no significant changes observed at room temperature (23-27° C.) for at least 12 months. In another embodiment, stable formulation is a formulation with no significant changes observed at room temperature (23-27° C.) for at least 18 months.

As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a crystalline anti-PD-1 antibody, e.g., crystalline pembrolizumab or a variant thereof, or its salt (e.g., the product isolated from a reaction mixture affording the crystalline anti-PD-1 antibody or salt) consists of the crystalline anti-PD-1 antibody or salt. The level of purity of the crystalline anti-PD-1 antibody and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A crystalline anti-PD-1 antibody or salt of 100% purity is one which is free of detectable impurities as determined by a standard method of analysis.

II. Anti-PD-1 Antibodies for Use in the Methods of the Invention

In the methods of producing anti-PD-1 mAb crystals, and the methods of use/methods of treatment of the invention the anti-human PD-1 antibody is pembrolizumab or a pembrolizumab variant. The amino acid sequences of pembrolizumab are provided in Table 2.

TABLE 2

Pembrolizumab Antibody Sequences

| Antibody Feature | Amino Acid Sequence | SEQ ID NO. |
|---|---|---|
| **Pembrolizumab Light Chain** | | |
| CDR1 | RASKGVSTSGYSYLH | 1 |
| CDR2 | LASYLES | 2 |
| CDR3 | QHSRDLPLT | 3 |
| Variable Region | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIK | 7 |
| Light Chain | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC | 9 |

TABLE 2-continued

Pembrolizumab Antibody Sequences

| Antibody Feature | Amino Acid Sequence | SEQ ID NO. |
|---|---|---|
| **Pembrolizumab Heavy Chain** | | |
| CDR1 | NYYMY | 4 |
| CDR2 | GINPSNGGTNFNEKFKN | 5 |
| CDR3 | RDYRFDMGFDY | 6 |
| Variable Region | QVQLVQSGVEVKKPGASVKVSCKASGYTFTNYYM YWVRQAPGQGLEWMGGINPSNGGTNFNEKFKNRV TLTTDSSTTTAYMELKSLQFDDTAVYYCARRDYR FDMGFDYWGQGTTVTVSS | 8 |
| Heavy Chain | QVQLVQSGVEVKKPGASVKVSCKASGYTFTNYYM YWVRQAPGQGLEWMGGINPSNGGTNFNEKFKNRV TLTTDSSTTTAYMELKSLQFDDTAVYYCARRDYR FDMGFDYWGQGTTVTVSSASTKGPSVFPLAPCSR STSESTAALGCLVKDYFPEPVTVSWNSGALTSGV HTFPAVLQSSGLYSLSSVVTVPSSSLGTKTYTCN VDHKPSNTKVDKRVESKYGPPCPPCPAPEFLGGP SVFLFPPKPKDTLMISRTPEVTCVVVDVSQEDPE VQFNWYVDGVEVHNAKTKPREEQFNSTYRVVSVL TVLHQDWLNGKEYKCKVSNKGLPSSIEKTISKAK GQPREPQVYTLPPSQEEMTKNQVSLTCLVKGFYP SDIAVEWESNGQPENNYKTTPPVLDSDGSFFLYS RLTVDKSRWQEGNVFSCSVMHEALHNHYTQKSLS LSLGK | 10 |

The crystalline anti-PD-1 mAbs of the invention comprise three light chain CDRs (CDRL1, CDRL2 and CDRL3) and three heavy chain CDRs (CDRH1, CDRH2 and CDRH3). In one embodiment, the three light chain CDRs are SEQ ID NO:1, SEQ ID NO:2, and SEQ ID NO:3 and the three heavy chain CDRs are SEQ ID NO:4, SEQ ID NO:5 and SEQ ID NO:6.

In certain embodiments, the invention provides a crystalline anti-PD-1 mAb comprising a light chain variable region ($V_L$) comprising SEQ ID NO:7 or a variant of SEQ ID NO:7 and a heavy chain variable region ($V_H$) comprising SEQ ID NO:8 or a variant of SEQ ID NO: 8. In some embodiments, a variant light chain or heavy chain variable region sequence is identical to the reference sequence except having one, two, three, four, five, six, seven, eight, nine or ten amino acid substitutions. In particular embodiments, the amino acid substitutions are conservative amino acid substitutions. The substitutions in the pembrolizumab variants are in the framework region (i.e., outside of the CDRs) or the constant region and are outside of any residues that would inhibit binding of the pembrolizumab variant to the additive used in the methods herein and thus inhibit crystallization.

In one embodiment of the invention, the crystalline anti-human PD-1 antibody comprises a light chain variable region ($V_L$) comprising or consisting of SEQ ID NO:7 and a heavy chain variable region ($V_H$) comprising or consisting of SEQ ID NO:8.

In another embodiment, the crystalline anti-PD-1 mAb of the invention comprises a $V_L$ domain and/or a $V_H$ domain with at least 99%, 98%, 97%, 96%, 95%, 94%, 93%, 92%, 91% or 90%, sequence homology to the $V_L$ domain or $V_H$ domain described above, and exhibits specific binding to PD-1. In another embodiment, the crystalline anti-PD-1 mAb comprises $V_L$ and $V_H$ domains having up to 1, 2, 3, 4, 5, 6, 7, 8, 9, or 10 or more amino acid substitutions, and exhibits specific binding to PD-1.

In any of the embodiments above, the anti-PD-1 crystals of the invention may comprise a full-length anti-PD-1 antibody (e.g. pembrolizumab) or may be an antigen binding fragment comprising a short truncation that (1) comprises the light chain CDRs of SEQ ID NO: 1, SEQ ID NO:2, and SEQ ID NO:3 and the heavy chain CDRs of SEQ ID NO:4, SEQ ID NO:5 and SEQ ID NO:6, (2) specifically binds human PD-1 and (3) specifically binds to the additive used in the methods of the invention. In certain embodiments, the anti-PD-1 antibody is a full-length anti-PD-1 antibody selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Different constant domains may be appended to the $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

In embodiments of the invention, the crystalline anti-PD-1 mAb is an anti-PD-1 antibody comprising a light chain comprising or consisting of a sequence of amino acid residues as set forth in SEQ ID NO:9 and a heavy chain comprising or consisting of a sequence of amino acid residues as set forth in SEQ ID NO:10. In some embodiments of the invention, the crystalline anti-PD-1 mAb of the invention is crystalline pembrolizumab or a pembrolizumab biosimilar.

In further embodiments, the crystalline anti-PD-1 mAb is a pembrolizumab variant having up to 10, up to 9, up to 8, up to 7, up to 6, up to 5, up to 4, up to 3, up to 2, 1, 2, 3, 4, 5, 6, 7, 8, 9, or 10 conservative amino acid substitutions that are located outside the pembrolizumab light and heavy chain CDRs and are further outside of the pembrolizumab residues that bind to caffeine, i.e. outside of TYR 436 and ASN 434 of the pembrolizumab heavy chain (positions 434 and 436 of SEQ ID NO: 10).

Ordinarily, amino acid sequence variants of the crystalline pembrolizumab variants of the invention will have an amino acid sequence having at least 90% amino acid sequence identity with the amino acid sequence of the reference antibody (e.g. heavy chain, light chain, $V_H$, or $V_L$ sequence), more preferably at least 95, 98, or 99%. Identity or homology with respect to a sequence is defined herein as the percentage of amino acid residues in the candidate sequence that are identical with the anti-PD-1 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

Sequence identity refers to the degree to which the amino acids of two polypeptides are the same at equivalent positions when the two sequences are optimally aligned. Sequence identity can be determined using a BLAST algorithm wherein the parameters of the algorithm are selected to give the largest match between the respective sequences over the entire length of the respective reference sequences. The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, DC; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, DC; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

III. Methods of Producing Crystalline Antibody Suspensions

In one aspect, the invention relates to methods for producing crystalline anti-PD-1 monoclonal antibody (mAb) comprising: (a) mixing: (i) an aqueous buffered solution comprising about 5 mg/mL to about 80 mg/mL of the mAb, wherein the anti-PD-1 mAb is pembrolizumab or a pembrolizumab variant, (ii) polyethylene glycol (PEG), and (iii) an additive selected from the group consisting of: caffeine, theophylline, 2' deoxyguanosine-5'-monophosphate, a bioactive gibberellin, and a pharmaceutically acceptable salt of the gibberellin; to form a crystallization solution, wherein the crystallization solution has a pH of about 6.0 to about 8.8 and comprises about 2% to about 40% weight per volume (w/v) PEG and about 0.1% to about 0.30% w/v additive; (b) incubating the crystallization solution for a period of time sufficient for crystal formation; and (c) optionally harvesting the crystalline anti-PD-1 mAb from the solution.

In specific embodiments of the invention, the method comprises the step of harvesting the crystalline anti-PD-1 mAb from the solution. Methods of harvesting the crystals are known to one of skill in the art and include centrifugation, decantation, lyophilization and filtration, such as hollow fiber tangential flow filtration.

In some embodiments, the method further comprises the step of homogenizing the anti-PD-1 mAb crystals after they are harvested from the crystallization solution. The step of homogenization provides anti-PD-1 mAb crystals with a smaller particle size, e.g. 0.5 to 50 microns. Such smaller particle crystals can be used, for example, in high concentration pharmaceutical formulations.

In some embodiments, the method further comprises the step of homogenizing the anti-PD-1 mAb crystals without first harvesting said crystals from the crystallization solution. In this method, the crystallization solution can be homogenized after incubation for a sufficient time for crystal formation, e.g. forced through a syringe, without first harvesting. The smaller size anti-PD-1 mAb crystals can optionally be harvested following homogenization.

In specific embodiments of the invention, the PEG and the additive are mixed together to form a precipitant solution before being mixed with the aqueous buffered solution comprising the mAb. The precipitant solution and the aqueous buffered solution comprising the mAb are then mixed together to form a crystallization solution.

In alternative embodiments of the invention, the PEG is mixed into the aqueous buffered solution comprising the mAb to form a PEG-mAb solution. The additive, either as a solid or a solution, is then added to the PEG-mAb solution to form the crystallization solution.

In other embodiments, the aqueous buffered solution comprising the mAb is mixed with the additive to form an aqueous buffered solution comprising mAb and additive. This solution is then mixed with the PEG, either as a solid or a solution.

In any of the above embodiments, the additive is caffeine, theophylline, 2' deoxyguanosine-5'-monophosphate, a bioactive gibberellin, or a pharmaceutically acceptable salt of the gibberellin.

In one embodiment, the additive is caffeine.

In another embodiment, the additive is theophylline.

In yet another embodiment, the additive is 2' deoxyguanosine-5'-monophosphate.

In a further embodiment, the additive is a bioactive gibberellin or a pharmaceutically acceptable salt thereof. In specific embodiments, the bioactive gibberellin is gibberellin A1, a pharmaceutically acceptable salt of gibberellin A1, gibberellin A3, a pharmaceutically acceptable salt of gibberellin A3, gibberellin A4, a pharmaceutically acceptable salt of gibberellin A4, gibberellin A7, or a pharmaceutically acceptable salt of gibberellin A7.

In particular embodiments, the additive is gibberellin A3 or a pharmaceutically acceptable salt thereof. In some embodiments, the additive is gibberellin A3. In other embodiments, the additive is a sodium salt of gibberellin A3. In other embodiments, the additive is a potassium salt of gibberellin A3. In other embodiments, the additive is an ammonium salt of gibberellin A3.

The amount of additive in the final crystallization solution is from about 0.10% to about 0.30% w/v. In other embodiments, the amount of additive is from about 0.15% to about 0.30% w/v, from about 0.175% to about 0.30% w/v, from about 0.20% to about 0.30% w/v, from about 0.225% to about 0.30% w/v, from about 0.25% to about 0.30% w/v, from about 0.10% to about 0.25% w/v, from about 0.10% to about 0.275% w/v, from about 0.10% to about 0.25% w/v, from about 0.10% to about 0.225% w/v or from about 0.10% to about 0.20% w/v. In further embodiments, the amount of additive is about 0.10% w/v, about 0.125% w/v, about 0.15% w/v, about 0.175% w/v, about 0.20% w/v, about 0.225% w/v, about 0.25% w/v, about 0.275% w/v, or about 0.30% w/v.

In one embodiment, the additive is caffeine, which is present in the final crystallization solution in an amount of about 0.15% w/v to about 0.30% w/v.

In another embodiment, the additive is theophylline, which is present in the final crystallization solution in an amount of about 0.25% w/v to about 0.30% w/v.

In any of the above embodiments, the crystallization solution may further comprise about 1% to about 10% w/v dextran sodium sulfate, which slows the rate of nucleation and allows the growth of larger crystals. In certain cases, it may be desirable to make larger crystals, for example, for use in characterization studies such as x-ray crystallography. In further embodiments, the crystallization solution comprises about 1%, about 1.5% w/v, about 2% w/v, about 2.5% w/v, about 3% w/v, about 3.5% w/v, about 4% w/v, about 4.5% w/v, about 5% w/v, about 5.5% w/v, about 6% w/v, about 6.5% w/v, about 7% w/v, about 7.5% w/v, about 8% w/v, about 8.5% v, about 9% w/v, about 9.5% w/v, or about 10% w/v dextran sodium sulfate. In alternative embodiments the crystallization solution comprises about 1% to about 9% w/v, about 1% to about 8% w/v, about 1% to about 7% w/v, about 1% to about 6% w/v, about 1% to about 5% w/v, about 1% to about 4% w/v, about 1% to about 3% w/v, about 1% to about 2% w/v, about 2% to about 10% w/v, about 2% to about 9% w/v, about 2% to about 8% w/v, about 2% to about 7% w/v, about 2% to about 6% w/v, about 2% to about 5% w/v, about 2% to about 4%, about 2% to about 3%, about 3% to about 10%, about 3% to about 9%, about 3% to about 8% w/v, about 3% to about 7% w/v, about 3% to about 6% w/v, about 3% to about 5% w/v, about 3% to about 4% w/v, about 4% to about 10% w/v, about 4% to about 9% w/v, about 4% to about 8% w/v, about 4% to about 7% w/v, about 4% to about 6% w/v, about 4% to about 5% w/v, about 5% to about 10% w/v, about 5% to about 9% w/v, about 5% to about 8% w/v, about 5% to about 7% w/v, about 5% to about 6% w/v, about 6% to about 10% w/v, about 6% to about 9% w/v, about 6% to about 8% w/v, about 6% to about 7% w/v, about 7% to about 10% w/v, about 7% to about 9% w/v, about 7% to about 8% w/v, about 8% to about 10% w/v, about 8% to about 8% w/v, or about 9% to about 10% w/v dextran sodium sulfate.

In any of the above embodiments of the invention, the crystallization solution comprises about 2% to about 40% w/v PEG. The average molecular weight of the PEG is from about 2,500 to about 35,000. In particular embodiments, the PEG is PEG 3,350. In alternate embodiments, the PEG is PEG 2,500 (i.e., has an average mol. wt. of 2500), PEG 3,000, PEG 4,000, PEG 5,000, PEG 6,000, PEG 7,000, PEG 8,000, PEG 9,000, PEG 10,000, PEG 12,000, PEG 14000, PEG 15,000, PEG 1600, PEG 1800, PEG 20,000, PEG 22,000, PEG 24,000, PEG 25,000, PEG 26,000, PEG 28,000, PEG 30,000, PEG 32,000, PEG 34,000, or PEG 35,000.

The amount of PEG in the crystallization solution is from about 2% to about 40% w/v; however, one skilled in the art will realize that use of different molecular weight PEGs for the methods of the invention alters the amount of PEG. In some embodiments, the PEG is present in the crystallization solution in an amount of about 5% to about 15% w/v. In alternative embodiments, the PEG is present in the crystallization solution in an amount of about 10% to about 30% w/v. In further embodiments, the PEG is present in the crystallization solution in an amount of about 5% to about 35% w/v, about 5% to about 30% w/v, about 5% to about 25% w/v, about 5% to about 10% w/v, about 10% to about 40% w/v, about 5% to about 35% w/v, about 10% to about 30% w/v, about 10% to about 25% w/v, about 10% to about 20% w/v, about 10% to about 15% w/v, about 15% to about 40% w/v, about 15% to about 35% w/v, about 15% to about 30% w/v, about 15% to about 25% w/v, about 15% to about 20% w/v, about 20% to about 40% w/v, about 20% to about 35% w/v, about 20% to about 30% w/v, about 20% to about 25% w/v, about 25% to about 40% w/v, about 25% to about 35% w/v, about 25% to about 30% w/v, about 30% to about 40% w/v, or about 30% to about 35% w/v.

In the methods of the invention, the crystallization solution is made by combining: (1) an aqueous buffered solution comprising an anti-PD-1 mAb (i.e. pembrolizumab or a pembrolizumab variant), (2) PEG, and (3) an additive, as described herein; wherein the components of the crystallization solution can be added in any order. In embodiments of the invention, the aqueous buffered solution comprising the anti-PD-1 mAb has a pH of about 6.0 to about 8.8. In further embodiments, the pH is about 6.0, about 6.2, about 6.4, about 6.6, about 6.8, about 7.0, about 7.2, about 7.4, about 7.6, about 7.8, about 8.0, about 8.2, about 8.4, about 8.6, or about 8.8. In further embodiments, the pH of the aqueous buffered solution comprising the anti-PD-1 mAb is from about 5.0 to about 6.0. In additional embodiments, the pH is from about 6.8 to about 8.4.

In still further embodiments, the pH of the aqueous buffered solution comprising the anti-PD-1 mAb is from about 6.2 to about 8.8, from about 6.2 to about 8.6, from about 6.2 to about 8.4, from about 6.2 to about 8.2, from about 6.2 to about 8.0, from about 6.2 to about 7.8, from about 6.2 to about 7.6, from about 6.2 to about 7.4, from about 6.2 to about 7.2, from about 6.2 to about 7.0, from about 6.2 to about 6.8, from about 6.2 to about 6.6, from about 6.2 to about 6.4, about 6.4 to about 8.8, from about 6.4 to about 8.6, from about 6.4 to about 8.4, from about 6.4 to about 8.2, from about 6.4 to about 8.0, from about 6.4 to about 7.8, from about 6.4 to about 7.6, from about 6.4 to about 7.4, from about 6.4 to about 7.2, from about 6.4 to about 7.0, from about 6.4 to about 6.8, from about 6.4 to about 6.6, from about 6.6 to about 8.8, from about 6.6 to about 8.6, from about 6.6 to about 8.4, from about 6.6 to about 8.2, from about 6.6 to about 8.0, from about 6.6 to about 7.8, from about 6.6 to about 7.6, from about 6.6 to about 7.4, from about 6.6 to about 7.2, from about 6.6 to about 7.0, from about 6.6 to about 6.8, from about 6.8 to about 8.8, from about 6.8 to about 8.6, from about 6.8 to about 8.4, from about 6.8 to about 8.2, from about 6.8 to about 8.0, from about 6.8 to about 7.8, from about 6.8 to about 7.6, from about 6.8 to about 7.4, from about 6.8 to about 7.2, from about 6.8 to about 7.0, from about 7.0 to about 8.8, from about 7.0 to about 8.6, from about 7.0 to about 8.4, from about 7.0 to about 8.2, from about 7.0 to about 8.0, from about 7.0 to about 7.8, from about 7.0 to about 7.6, from about 7.0 to about 7.4, from about 7.0 to about 7.2, from about 7.2 to about 8.8, from about 7.2 to about 8.6, from about 7.2 to about 8.4, from about 7.2 to about 8.2, from about 7.2 to about 8.0, from about 7.2 to about 7.8, from about 7.2 to about 7.6, from about 7.2 to about 7.4, from about 7.4 to about 8.8, from about 7.4 to about 8.6, from about 7.4 to about 8.4, from about 7.4 to about 8.2, from about 7.4 to about 8.0, from about 7.4 to about 7.8, from about 7.4 to about 7.6, from about 7.6 to about 8.8, from about 7.6 to about 8.6, from about 7.6 to about 8.4, from about 7.6 to about 8.2, from about 7.6 to about 8.0, from about 7.6 to about 7.8, from about 7.8 to about 8.8, from about 7.8 to about 8.6, from about 7.8 to about 8.4, from about 7.8 to about 8.2, or from about 7.8 to about 8.0.

In specific embodiments of any of the methods herein, the aqueous buffered solution comprising the mAb further comprises histidine buffer at a pH of about 5.0 to about 6.0. In specific embodiments, the aqueous buffered solution comprising the mAb further comprises 20 mM histidine buffer at pH 5.4.

In particular embodiments of the methods of the invention, the pH of the crystallization solution and the amount of PEG present in the solution is selected from the group consisting of.

a) pH of the crystallization solution is about 6.0 and the amount of PEG is about 2% to about 4% w/v,
b) pH of the crystallization solution is about 6.4 and the amount of PEG is about 2% to about 6% w/v,
c) pH of the crystallization solution is from about 6.8 to 8.4 and the amount of PEG is about 6% to about 12% w/v, and
d) pH of the crystallization solution is about 8.8 and the amount of PEG is about 10% to about 12% w/v.

In certain embodiments of the method above, the PEG is PEG 3350.

In embodiments of the methods of the invention, the solution concentration of the anti-PD-1 mAb in the crystallization solution is from about 5 mg/mL to about 50 mg/mL. In further embodiments, the solution concentration of the anti-PD-1 mAb in the crystallization solution is from about 5 mg/mL to about 45 mg/mL, about 5 mg/mL to about 40 mg/mL, about 5 mg/mL to about 35 mg/mL, about 5 mg/mL to about 30 mg/mL, about 5 mg/mL to about 25 mg/mL, about 5 mg/mL to about 20 mg/mL, about 5 mg/mL to about 15 mg/mL, about 5 mg/mL to about 10 mg/mL, about 10 mg/mL to about 50 mg/mL, about 10 mg/mL to about 45 mg/mL, about 10 mg/mL to about 40 mg/mL, about 10 mg/mL to about 35 mg/mL, about 10 mg/mL to about 30 mg/mL, about 10 mg/mL to about 25 mg/mL, about 10 mg/mL to about 20 mg/mL, about 10 mg/mL to about 15 mg/mL, about 15 mg/mL to about 50 mg/mL, about 15 mg/mL to about 45 mg/mL, about 15 mg/mL to about 40 mg/mL, about 15 mg/mL to about 35 mg/mL, about 15 mg/mL to about 30 mg/mL, about 15 mg/mL to about 25 mg/mL, about 15 mg/mL to about 20 mg/mL, about 20 mg/mL to about 50 mg/mL, about 20 mg/mL to about 45 mg/mL, about 20 mg/mL to about 40 mg/mL, about 20 mg/mL to about 35 mg/mL, about 20 mg/mL to about 30 mg/mL, about 20 mg/mL to about 25 mg/mL, about 25 mg/mL to about 50 mg/mL, about 25 mg/mL to about 45 mg/mL, about 25 mg/mL to about 40 mg/mL, about 25 mg/mL to about 35 mg/mL, about 25 mg/mL to about 30 mg/mL, about 30 mg/mL to about 50 mg/mL, about 30 mg/mL to about 45 mg/mL, about 30 mg/mL to about 40 mg/mL, about 30 mg/mL to about 35 mg/mL, about 35 mg/mL to about 50 mg/mL, about 35 mg/mL to about 45 mg/mL, about 35 mg/mL to about 40 mg/mL, about 40 mg/mL to about 50 mg/mL, or about 40 mg/mL to about 45 mg/mL.

In particular embodiments of any of the methods of the invention, the crystallization solution further comprises from about 25 mM to about 250 mM HEPES buffer. In some embodiments, the crystallization solution further comprises about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 110 mM, about 120 mM, about 125 mM, about 130 mM, about 140 mM, about 150 mM, about 160 mM, about 170 mM, about 175 mM, about 180 mM, about 190 mM, about 200 mM, about 210 mM, about 220 mM, about 225 mM, about 230 mM, about 240 mM, about 245 mM, or about 250 mM HEPES buffer.

In other embodiments of the methods of the invention, the crystallization solution further comprises Tris buffer (i.e. instead of HEPES buffer) in any of the amounts specified above. In alternative embodiments, the crystallization solution further comprises PIPES, MOPS, TES, DIPSO, MOBS, or TAPSO buffer.

Following mixture of (1) the aqueous buffered solution comprising the anti-PD-1 mAb, (2) PEG, and (3) the additive, the crystallization solution is incubated at a temperature of from about 2° C. to about 37° C. for a length of time sufficient for crystal formation. In certain embodiments, the incubation temperature of the crystallization solution is from about 18° C. to about 25° C. In still other embodiments, the incubation temperature of the crystallization solution is from about 2° C. to about 35° C., about 2° C. to about 30° C., about 2° C. to about 25° C., about 2° C. to about 20° C., about 2° C. to about 15° C., about 2° C. to about 10° C., about 5° C. to about 37° C., about 5° C. to about 35° C., about 5° C. to about 30° C., about 5° C. to about 25° C., about 5° C. to about 20° C., about 5° C. to about 15° C., about 5° C. to about 10° C., about 10° C. to about 37° C., about 10° C. to about 35° C., about 10° C. to about 30° C., about 10° C. to about 25° C., about 10° C. to about 20° C., about 10° C. to about 15° C., about 15° C. to about 37° C., about 15° C. to about 35° C., about 15° C. to about 30° C., about 15° C. to about 25° C., about 15° C. to about 20° C., about 20° C. to about 37° C., about 20° C. to about 35° C., about 20° C. to about 30° C., about 20° C. to about 25° C., about 25° C. to about 37° C., about 25° C. to about 35° C., about 25° C. to about 30° C., about 30° C. to about 37° C., or about 30° C. to about 35° C.

In further embodiments, the crystallization solution is heated to about 50° C. where it remains in solution, and then cooled, where it only crystallizes upon cooling to a temperature of about 37° C. or lower.

In still further embodiments, the crystallization solution is heated to about 50° C., then cooled to a temperature of about 18° C. to about 25° C. or cooled to a temperature of about 25° C. or lower.

In additional embodiments, the crystallization solution is heated to about 50° C., then cooled to a temperature of about 4° C.

In particular embodiments of the method of the invention, the incubation temperature is ramped from about 4° C. to about 10-40° C.

In any of the methods herein, the crystallization solution is incubated for a period of time sufficient for crystal formation. Crystal formation can be detected, for example, by visual inspection, or by use of SONICC™ imaging. In particular embodiments, the crystallization solution is incubated for about 15 minutes or more. In some embodiments, the crystallization solution is incubated for about 2 hours or more. In some embodiments, the crystallization solution is incubated overnight. In some embodiments, the crystallization solution is incubated 18 hours or more. In particular embodiments, the crystallization solution is incubated for about 30 minutes or more, about 1 hour or more, about 3 hours or more, about 4 hours or more, about 5 hours or more, about 6 hours or more, about 7 hours or more, about 8 hours or more, about 9 hours or more, about 10 hours or more, about 11 hours or more, about 12 hours or more, about 13 hours or more, about 14 hours or more, about 15 hours or more, about 16 hours or more, about 17 hours or more, about 20 hours or more, or about 24 hours or more. In additional embodiments, the crystallization solution is incubated for about 2 days, 3 days, 4 days, 5 days, 1 week, 10 days, 2 weeks, 15 days, 3 weeks or more than 3 weeks.

In particular embodiments of any of the methods described herein, the crystallization solution is rotated or agitated during incubation.

Various methods of protein crystallization are known. Giege et al. (1994) *Acta Crystallogr.* D50:339; McPherson (1990); *Eur. J. Biochem.* 189:1. Such techniques include hanging drop vapor diffusion (McPherson (1976) J. Biol. Chem. 251:6300), sitting drop vapor diffusion, microbatch and dialysis.

Both hanging drop and sitting drop vapor diffusion entail a droplet containing purified protein, buffer, and precipitant being allowed to equilibrate with a larger reservoir containing similar buffers and precipitants in higher concentrations. Initially, the droplet of protein solution contains an insufficient concentration of precipitant for crystallization, but as water vaporizes from the drop and transfers to the reservoir, the precipitant concentration increases to a level optimal for crystallization. Since the system is in equilibrium, these optimum conditions are maintained until the crystallization is complete. The hanging drop method differs from the sitting drop method in the vertical orientation of the protein solution drop within the system.

In the microbatch method, polypeptide is mixed with precipitants to achieve supersaturation, and the vessel is sealed and set aside until crystals appear.

In the dialysis method, polypeptide is retained on one side of a dialysis membrane which is placed into contact with a solution containing precipitant. Equilibration across the membrane increases the precipitant concentration thereby causing the polypeptide to reach supersaturation levels.

Some of these techniques were used to prepare pembrolizumab crystals of the invention, as described in greater detail in the Examples.

In particular embodiments of any of the methods described herein, the crystallization solution is produced by vapor diffusion or batch crystallization.

In particular embodiments of any of the methods of producing crystalline anti-PD-1 monoclonal antibody described herein, the method further comprises the step of seeding the crystallization solution with crystals of the anti-PD-1 mAb prior to or during the incubation step.

The anti-PD-1 mAb crystals may be analyzed by various methods to examine or characterize their physical properties, such as crystal size, shape, surface morphology, total surface area and porosity. Such analytical techniques include, e.g., electron diffraction and sold state nuclear magnetic resonance (ssNMR), light microscopy, transmission electron microscopy, scanning electron microscopy, atomic force microscopy, and various light scattering techniques. In addition, The biological activity and/or biophysical properties of the anti-PD-1 mAb in crystals of the invention may be analyzed by "re-dissolving" or solubilizing the antibody crystal in a buffer suitable for the desired analytical technique. For example, the solubilized anti-PD-1 mAb may be analyzed by one or more of ELISA, size exclusion chromatography, SDS PAGE, and dynamic light scattering.

IV. Anti-PD-1 Crystalline Antibody Suspensions and Compositions

In one aspect, the invention provides an isolated crystal formed by any method of the invention, i.e. any method of producing anti-PD-1 mAb crystals described herein.

The invention also relates to an isolated crystal comprising pembrolizumab complexed with caffeine, wherein the crystal is characterized by space group $P222_1$ $\underline{a}$=43.8 Å $\underline{b}$=113.9 Å c=175.0 Å, α=β=γ=90°.

In one embodiment, the invention provides a pembrolizumab crystal, comprising a polypeptide, wherein said polypeptide is characterized by structure coordinates comprising a root mean square deviation (RMSD) of conserved residue backbone atoms of less than about 2.0 angstroms when superimposed on backbone atoms described by structural coordinates of Table 7.

In some embodiments, the pembrolizumab crystal or pembrolizumab variant crystal of the invention has a particle size from about 0.5 to 200 microns following harvest. In particular embodiments, the anti-PD-1 mAb crystals, e.g.

pembrolizumab crystals, are homogenized following crystallization, resulting in a particle size following homogenization of from about 0.5 to about 50 microns.

Figure 10A:
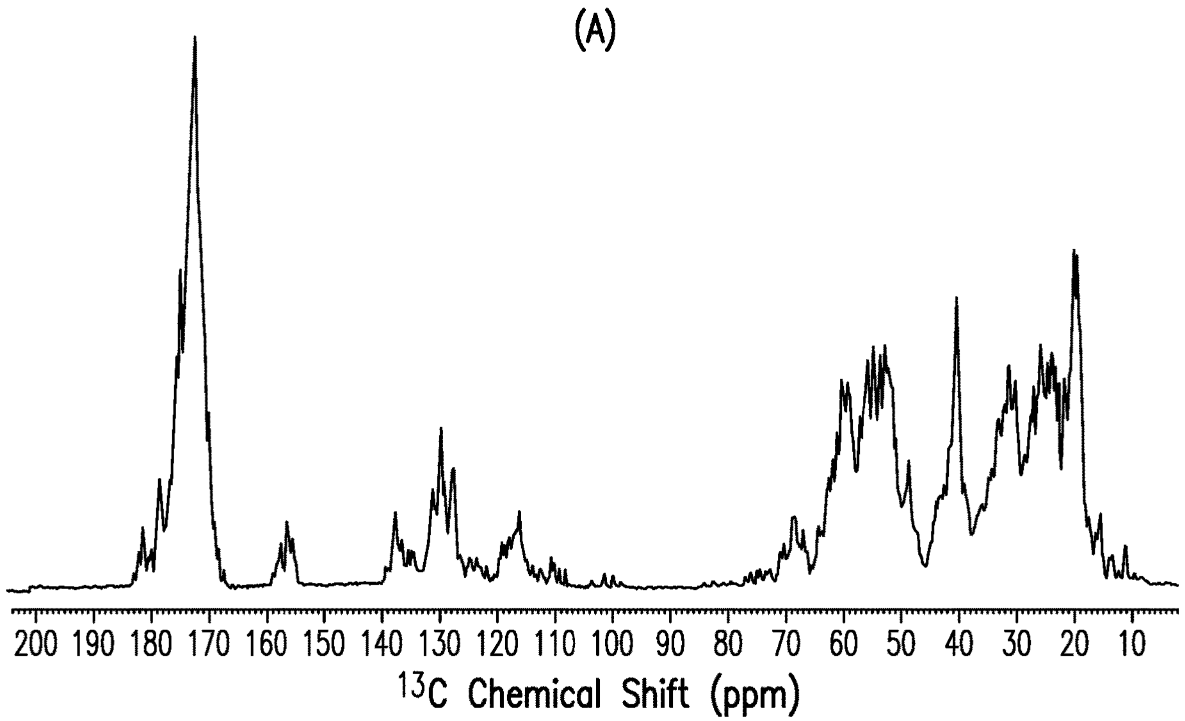
FIG. 10A depict a solid state $^{13}C$ NMR CP MAS a pembrolizumab crystalline suspension, prepared as described in EXAMPLE 11.

In one embodiment, the invention relates to crystalline pembrolizumab comprising pembrolizumab complexed to caffeine, characterized by solid state NMR $^{13}C$ spectrum exhibiting peaks at about 182.16, 181.54, 179.99, 109.36, 108.23, 103.58, 76.88 and 76.04 ppm. In another embodiment, provided is crystalline pembrolizumab complexed to caffeine, characterized by a solid state NMR $^{13}C$ spectrum exhibit peaks at about 183.07, 182.16, 181.54, 180.55, 179.99, 110.70, 110.15, 109.36, 108.23, 103.58, 101.49, 99.75, 98.56, 76.88, 76.04, 74.97, 74.41, 73.52, 72.69, 13.85, 13.27, 12.26 and 11.13 ppm. In another embodiment, the crystalline pembrolizumab is characterized by solid state NMR $^{13}C$ spectrum as shown in FIG. 10A.

In another aspect, the invention relates to a pharmaceutical composition comprising the novel anti-PD-1 crystals of the invention (i.e. the novel pembrolizumab crystals or pembrolizumab variant crystals) and a pharmaceutically acceptable carrier. To prepare pharmaceutical compositions, the anti-PD-1 mAb crystals of the invention, or anti-PD-1 mAb solubilized from such crystals, are mixed with at least one pharmaceutically acceptable carrier or excipient. See, e.g., Remington's Pharmaceutical Sciences and U.S. Pharmacopeia: National Formulary, Mack Publishing Company, Easton, PA (1984). It is not required that the anti-PD-1 mAb crystals used in a pharmaceutical composition of the invention have any particular diffraction quality, as long as the biological activity and stability of the antibody are maintained within the desired range.

In some embodiments, the excipient(s) are added directly to the crystallization liquor during or after crystallization. In other embodiments, the crystals are first harvested from the liquor, washed by suspension in a stabilizing solution, harvested from the stabilizing solution and then suspended in a liquid solution which comprises the excipient(s). The composition of the liquid may be any pharmaceutically acceptable medium, and may include, e.g., aqueous solutions and water in oil mixtures.

Pharmaceutical compositions of crystals in a solid form may be prepared by drying a liquid suspension comprising the crystals and the desired excipient(s), e.g., by passing a stream of nitrogen, air or inert gas over the crystals, by air drying, vacuum drying or lyophilization. The moisture content in the final product will typically be less than 10%, 7%, 5% or 3% by weight.

A pharmaceutical composition comprising pembrolizumab that has been solubilized from pembrolizumab crystals in a liquid suspension or in a dried solid may be prepared by adding a desired quantity of the crystals to a pharmaceutically acceptable dissolution buffer and incubating at 4° C. until the crystals have dissolved. In an embodiment, the dissolution buffer comprises 10 mM histidine, pH 5.6, 0.02% polysorbate 80 w/v and up to 4% sucrose w/v. In an embodiment, any particulates in the resulting composition are removed prior to administration, e.g., by centrifugation or filtration.

In particular embodiments, the pharmaceutical composition is a crystalline suspension and the concentration of the anti-PD-1 mAb is from about 5-400 mg/mL. In additional embodiments, the concentration of the anti-PD-1 mAb is ≥75 mg/mL, ≥100 mg/mL, ≥125 mg/mL, ≥150 mg/mL, ≥175 mg/mL, ≥200 mg/mL, ≥225 mg/mL, ≥250 mg/mL, ≥275 mg/mL, ≥300 mg/mL, ≥325 mg/mL, or ≥350 mg/mL.

In particular embodiments, the pharmaceutical compositions of the invention further include about 5 mM to about 50 mM buffer. In some embodiments, the amount of buffer is about 5 mM, about 10 mM, about 15 mM, about 20 mM, about 25 mM, about 30 mM, about 35 mM, about 40 mM, about 45 mM, or about 50 mM.

In specific embodiments, the pharmaceutical compositions of the invention further comprise about 0.01% to about 0.10% w/v non-ionic surfactant. In some embodiments, the amount of non-ionic surfactant is from about 0.01% to about 0.05% w/v, about 0.01% to about 0.04% w/v, 0.02% to about 0.05% w/v, or 0.02% to about 0.04% w/v. In further embodiments, the pharmaceutical compositions of the invention do not comprise any surfactant.

V. Methods of Use

In one aspect, the invention relates to a method of treating cancer in a patient in need thereof, the method comprising administering to the subject an effective amount of (1) an anti-PD-1 mAb crystal of the invention; i.e. a crystal of pembrolizumab or a crystal of a pembrolizumab variant made by the methods described herein, or (2) a composition comprising an anti-PD-1 mAb crystal of the invention and a pharmaceutically acceptable carrier, to the patient. In some embodiments of the invention, the pembrolizumab crystal is dissolved into solution prior to administration to the patient (e.g. formulated as an aqueous formulation). In specific embodiments of this method, the composition is administered to the subject via intravenous administration. In other embodiments, the composition is administered to the subject by subcutaneous administration.

In some embodiments of the methods of treatment herein, the dosage of anti-PD-1 mAb is 200 mg, which is administered to the patient about every 3 weeks. In alternative embodiments, the dosage of crystalline mAb is 400 mg, which is administered to the patient about every 6 weeks.

In some embodiments of the invention, the pembrolizumab crystal, pembrolizumab variant crystal, or composition comprising the pembrolizumab crystal, or pembrolizumab variant crystal, is administered to the patient once every three weeks for 12 weeks or more. In other embodiments, the crystal or composition of the invention or is administered to the patient once every three weeks for 15 weeks or more, 18 weeks or more, 21 weeks or more, 24 weeks or more, 27 weeks or more, 30 weeks or more, 33 weeks or more, 36 weeks or more, 39 weeks or more, 42 weeks or more, 45 weeks or more, 48 weeks or more, 51 weeks or more, 54 weeks or more, 57 weeks or more, 60 weeks or more, 63 weeks or more, 66 weeks or more, 69 weeks or more, 72 weeks or more, 75 weeks or more, 78 weeks or more, 81 weeks or more, 84 weeks or more, 87 weeks or more, or 90 weeks or more.

In other embodiments of the invention, the pembrolizumab crystal, pembrolizumab variant crystal, or composition comprising the pembrolizumab crystal, or pembrolizumab variant crystal, is administered to the patient once every six weeks for 12 weeks or more. In other embodiments, the crystal or composition of the invention or is administered to the patient once every six weeks for 18 weeks or more, 24 weeks or more, 30 weeks or more, 36 weeks or more, 42 weeks or more, 48 weeks or more, 54 weeks or more, 60 weeks or more, 66 weeks or more, 72 weeks or more, 78 weeks or more, 84 weeks or more, 90 weeks or more, 96 weeks or more, 102 weeks or more, 108 weeks or more, 114 weeks or more, 120 weeks or more, 126 weeks or more, or 132 weeks or more.

In a first embodiment (Embodiment E1), the invention comprises a method of treating cancer in a human patient comprising administering an effective amount of a pembrolizumab crystal of the invention to the patient.

In a second embodiment (Embodiment E2), the invention comprises a method of treating melanoma in a human patient comprising administering an effective amount of a pembrolizumab crystal of the invention to the patient.

In a sub-embodiment of Embodiment E2, the melanoma is unresectable or metastatic.

In a further sub-embodiment of Embodiment E2, the melanoma is adjuvant melanoma. In specific embodiments, the melanoma is resected stage III melanoma.

In a third embodiment (Embodiment E3), the invention comprises a method of treating metastatic non-small cell lung cancer (NSCLC) in a human patient comprising administering an effective amount of a pembrolizumab crystal of the invention to the patient.

In a sub-embodiment of Embodiment E3, the NSCLC is squamous. In alternative embodiments, the NSCLC is non-squamous.

In a sub-embodiment of Embodiment E3, the method further comprises administering carboplatin-paclitaxel or nab-paclitaxel to the patient.

In a sub-embodiment of Embodiment E3 (Embodiment E3-A), the patient has a tumor with high PD-L1 expression [(Tumor Proportion Score (TPS)≥50%)] and was not previously treated with platinum-containing chemotherapy.

In a further sub-embodiment of Embodiment E3 (Embodiment E3-B), the patient has a tumor with PD-L1 expression (TPS≥1%) and was previously treated with platinum-containing chemotherapy. In specific embodiments of Embodiment E3-B, the patient had disease progression on or after receiving platinum-containing chemotherapy.

In certain embodiments of Embodiment E3, the patient has a tumor with PD-L1 expression (TPS≥1%) and was not previously treated with platinum-containing chemotherapy.

In certain embodiments of Embodiment E3 (including Embodiment E3-A and E3-B), the PD-L1 TPS is determined by an FDA-approved test.

In certain embodiments of Embodiment E3 (including Embodiment E3-A and E3-B), the patient's tumor has no EGFR or ALK genomic aberrations.

In certain embodiments of Embodiment E3 (including Embodiment E3-A and E3-B), the patient's tumor has an EGFR or ALK genomic aberration and had disease progression on or after receiving treatment for the EGFR or ALK aberration(s) prior to receiving the anti-PD-1 antibody, or antigen binding fragment thereof.

In a fourth embodiment (Embodiment E4), the invention comprises a method of treating metastatic non-small cell lung cancer (NSCLC) in a human patient comprising: (1) administering an effective amount of a pembrolizumab crystal of the invention to the patient, and (2) administering pemetrexed and carboplatin to the patient. In sub-embodiments of Embodiment E4, the patient was not previously treated with an anti-cancer therapeutic prior to starting the combination treatment regimen with the pembrolizumab crystal of the invention, in combination with pemetrexed and carboplatin.

In a certain embodiments of Embodiment E3 and E4 (including sub-embodiments thereof), the patient has non-squamous non-small cell lung cancer.

In sub-embodiments of Embodiment E4, pemetrexed is administered to the patient in an amount of 500 mg/m2.

In sub-embodiments of Embodiment E4, pemetrexed is administered to the patient via intravenous infusion every 21 days. In specific embodiments, the infusion time is about 10 minutes.

In a sub-embodiments of Embodiment E4 (Embodiment E4-A), the invention further comprises administering about 400 μg to about 1000 μg of folic acid to the patient once per day, beginning about 7 days prior to administering pemetrexed to the patient and continuing until about 21 days after the patient is administered the last dose of pemetrexed. In certain embodiments the folic acid is administered orally.

In a sub-embodiments of Embodiments E4 and E4-A (Embodiment E4-B), the invention further comprises administering about 1 mg of vitamin B12 to the patient about 1 week prior to the first administration of pemetrexed and about every three cycles of pemetrexed administration (i.e., approximately every 9 weeks). In certain embodiments the vitamin B12 is administered intramuscularly.

In a sub-embodiments of Embodiments E4, E4-A and E4-B (Embodiment E4-C), the invention further comprises administering about 4 mg of dexamethasone to the patient twice a day on the day before, the day of, and the day after pemetrexed administration. In certain embodiments the dexamethasone is administered orally.

In a fifth embodiment (Embodiment E5), the invention comprises a method of treating recurrent or metastatic head and neck squamous cell cancer (HNSCC) in a human patient comprising administering an effective amount of a pembrolizumab crystal of the invention to the patient.

In certain sub-embodiments of Embodiment E5, the patient was not previously treated with platinum-containing chemotherapy and the patient's tumor expresses PD-L1 (Combined Positive Score (CPS)≥20).

In certain sub-embodiments of Embodiment E5, the patient has recurrent or metastatic HNSCC.

In a sub-embodiments of Embodiment E5, the patient was previously treated with platinum-containing chemotherapy. In certain embodiments, the patient had disease progression on or after platinum-containing chemotherapy.

In a sixth embodiment (Embodiment E6), the invention comprises a method of treating refractory classical Hodgkin lymphoma (cHL) in a human patient comprising administering an effective amount of a pembrolizumab crystal of the invention to the patient.

In a seventh embodiment (Embodiment E7), the invention comprises a method of treating classical Hodgkin lymphoma (cHL) in a human patient comprising administering an effective amount of a pembrolizumab crystal of the invention to the patient, wherein the patient has relapsed after 3 or more lines of therapy for cHL.

In a sub-embodiments of Embodiments E6 and E7, the patient is an adult patient.

In alternative sub-embodiments of Embodiments E6 and E7, the patient is a pediatric patient.

In an eighth embodiment (Embodiment E8), the invention comprises a method of treating locally advanced or metastatic urothelial carcinoma in a human patient comprising administering an effective amount of a pembrolizumab crystal of the invention to the patient.

In sub-embodiments of Embodiment E8, the patient is not eligible for cisplatin-containing chemotherapy.

In sub-embodiments of Embodiment E8, the patient has a tumor that expresses PD-L1. In some embodiments, the PD-L1 expression level is characterized by a CPS≥10.

In sub-embodiments of Embodiment E8, the patient has disease progression during or following platinum-containing chemotherapy or within 12 months of neoadjuvant or adjuvant treatment with platinum-containing chemotherapy.

In a ninth embodiment (Embodiment E9), the invention comprises a method of treating unresectable or metastatic, microsatellite instability-high (MSI-H) or mismatch repair deficient solid tumors in a human patient comprising administering an effective amount of a pembrolizumab crystal of the invention to the patient.

In a sub-embodiment of Embodiment E9, the patient had disease progression following prior anti-cancer treatment.

In a tenth embodiment (Embodiment E10), the invention comprises a method of treating unresectable or metastatic, microsatellite instability-high (MSI-H) or mismatch repair deficient colorectal cancer in a human patient comprising administering an effective amount of a pembrolizumab crystal of the invention to the patient.

In a sub-embodiment of Embodiment E10, the patient had disease progression following prior treatment with a fluoropyrimidine, oxaliplatin, and irinotecan.

In an eleventh embodiment (Embodiment E11), the invention comprises a method of treating recurrent locally advanced or metastatic gastric cancer in a human patient comprising administering an effective amount of a pembrolizumab crystal of the invention to the patient.

In a twelfth embodiment (Embodiment E12), the invention comprises a method of treating recurrent locally advanced or metastatic gastroesophageal junction adenocarcinoma in a human patient comprising administering an effective amount of a pembrolizumab crystal of the invention to the patient.

In sub-embodiments of Embodiments E11 and E12, the patient's tumor expresses PD-L1 [Combined Positive Score (CPS)≥1].

In sub-embodiments of Embodiments E11 and E12, the patient has disease progression on or after two or more prior lines of therapy including fluoropyrimidine- and platinum-containing chemotherapy.

In sub-embodiments of Embodiments E11 and E12, the patient has disease progression on or after two or more prior lines of therapy including HER2/neu-targeted therapy.

In a thirteenth embodiment (Embodiment E13), the invention comprises a method of treating cervical cancer in a human patient comprising administering an effective amount of a pembrolizumab crystal of the invention to the patient.

In a sub-embodiment of Embodiment E13, the patient has recurrent or metastatic cervical cancer.

In a further sub-embodiment of Embodiment E13, the patient had disease progression on or after chemotherapy.

In another sub-embodiment of Embodiment E13 the patient has a tumor that expresses PD-L1 [CPS≥1].

In a fourteenth embodiment (Embodiment E14), the invention comprises a method of treating cancer in a human patient comprising administering an effective amount of a pembrolizumab crystal of the invention to the patient, wherein the patient has a cancer selected from the group consisting of: melanoma, lung cancer, head and neck cancer, bladder cancer, breast cancer, gastrointestinal cancer, multiple myeloma, hepatocellular cancer, lymphoma, renal cancer, mesothelioma, ovarian cancer, esophageal cancer, anal cancer, biliary tract cancer, colorectal cancer, cervical cancer, thyroid cancer, Merkel cell carcinoma, and salivary cancer.

In a fifteenth embodiment (Embodiment E15), the invention comprises a method of treating cancer in a human patient comprising administering an effective amount of a pembrolizumab crystal of the invention to the patient, wherein the patient has a small-cell lung cancer.

In a sub-embodiment of Embodiment E15, the patient has metastatic SCLC. In certain sub-embodiments, the patient was previously treated with platinum-based chemotherapy with disease progression on or after platinum-based chemotherapy and at least one other prior line of therapy. In certain sub-embodiments, the patient had disease progression on or after the platinum-based chemotherapy and at least one other prior line of therapy.

In a sixteenth embodiment (Embodiment E16), the invention comprises a method of treating non-Hodgkin lymphoma in a human patient comprising administering an effective amount of a pembrolizumab crystal of the invention to the patient.

In a sub-embodiment of Embodiment E16, the non-Hodgkin lymphoma is mediastinal large B-cell lymphoma. In some embodiments, the non-Hodgkin lymphoma is primary mediastinal large B-cell lymphoma (PMBCL) that is refractory. In other embodiments, the patients has PMBCL and has relapsed after 2 or more prior lines of therapy.

In a seventeenth embodiment (Embodiment E17), the invention comprises a method of treating breast cancer in a human patient comprising administering an effective amount of a pembrolizumab crystal of the invention to the patient.

In a sub-embodiment of Embodiment E17, the breast cancer is triple negative breast cancer.

In a sub-embodiment of Embodiment E17, the breast cancer is ER+/HER2− breast cancer.

In an eighteenth embodiment (Embodiment E18), the invention comprises a method of treating nasopharyngeal cancer in a human patient comprising administering an effective amount of a pembrolizumab crystal of the invention to the patient.

In a nineteenth embodiment (Embodiment E19), the invention comprises a method of treating thyroid cancer in a human patient comprising administering an effective amount of a pembrolizumab crystal of the invention to the patient.

In a twentieth embodiment (Embodiment E20), the invention comprises a method of treating salivary cancer in a human patient comprising administering an effective amount of a pembrolizumab crystal of the invention to the patient.

In a twenty-first embodiment (Embodiment E21), the invention comprises a method of treating Merkel cell carcinoma (MCC) in a human patient comprising administering an effective amount of a pembrolizumab crystal of the invention to the patient. In sub-embodiments the MCC is recurrent locally advanced or metastatic.

In a twenty-second embodiment (Embodiment E22), the invention comprises a method of treating cancer in a human patient comprising administering an effective amount of a pembrolizumab crystal of the invention to the patient, wherein the cancer is selected from the group consisting of melanoma, non-small cell lung cancer, relapsed or refractory classical Hodgkin lymphoma, head and neck squamous cell carcinoma, cervical cancer, urothelial cancer, esophageal cancer, gastric cancer, primary mediastinal large B-cell lymphoma, and hepatocellular carcinoma.

In a twenty-third embodiment (Embodiment E23), the invention comprises a method of treating cancer in a human patient comprising administering an effective amount of a pembrolizumab crystal of the invention to the patient, wherein the cancer is a heme malignancy.

In a sub-embodiment of Embodiment E23, the heme malignancy is selected from the group consisting of acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin lymphoma (HL), mantle cell lymphoma (MCL), multiple myeloma (MM), myeloid cell leukemia-1 protein (MCL-1), myelodysplastic syndrome (MDS), non-Hodgkin lymphoma (NHL), and small lymphocytic lymphoma (SLL).

In a twenty-fourth embodiment (Embodiment E24), the invention comprises a method of treating cancer in a human patient comprising administering an effective amount of a pembrolizumab crystal of the invention to the patient, wherein the patient has a tumor with a high mutational burden.

In a twenty-sixth embodiment (Embodiment E26), the invention comprises a method of treating hepatocellular carcinoma in a human patient comprising administering an effective amount of a pembrolizumab crystal of the invention to the patient. In a sub-embodiment of Embodiment E26, the patient was previously treated with sorafenib.

In a twenty-seventh embodiment (Embodiment E27), the invention comprises a method of treating renal cancer in a human patient comprising administering an effective amount of a pembrolizumab crystal of the invention to the patient. In sub-embodiments of Embodiment E27, the renal cancer is clear cell renal cell carcinoma.

In a twenty-eighth embodiment (Embodiment E28), the invention comprises a method of treating esophageal cancer in a human patient comprising administering an effective amount of a pembrolizumab crystal of the invention to the patient. In a sub-embodiment of Embodiment E28, the esophageal cancer is recurrent locally advanced or metastatic squamous cell carcinoma of the esophagus. In a further sub-embodiment, the patient had disease progression after one or more lines of systemic therapy. In a further sub-embodiment, the patient's tumors express PD-L1 [Combined Positive Score (CPS)≥10].

In a twenty-ninth embodiment (Embodiment E29), the invention comprises a method of treating ovarian carcinoma in a human patient comprising administering an effective amount of a pembrolizumab crystal of the invention to the patient.

In a thirtieth embodiment (Embodiment E30), the invention comprises a method of treating colorectal cancer in a human patient comprising administering an effective amount of a pembrolizumab crystal of the invention to the patient.

In a thirty-first embodiment (Embodiment E31), the invention comprises a method of treating cancer in a human patient comprising administering an effective amount of a pembrolizumab crystal of the invention to the patient, wherein the cancer is selected from the group consisting of: melanoma, lung cancer, head and neck cancer, bladder cancer, breast cancer, gastrointestinal cancer, multiple myeloma, lymphoma, renal cancer, mesothelioma, ovarian cancer, esophageal cancer, anal cancer, biliary tract cancer, colorectal cancer, cervical cancer, thyroid cancer, salivary cancer, prostate cancer (e.g. hormone refractory prostate adenocarcinoma), pancreatic cancer, colon cancer, esophageal cancer, liver cancer, thyroid cancer, endometrial cancer, hepatocellular carcinoma, Merkel cell carcinoma glioblastoma, glioma, and other neoplastic malignancies.

In any of the methods of the invention described herein, the "pembrolizumab crystal of the invention" or the "anti-PD-1 crystalline mAb of the invention" can be any pembrolizumab crystals, or pembrolizumab variant crystals of the invention (i.e. a crystal described herein or made by the methods described herein), or composition comprising a pembrolizumab crystal or pembrolizumab variant crystal of the invention, as described in Section II of the Detailed Description of the Invention herein, entitled "*Anti-PD-1 Antibodies for Use in the Methods of the Invention*" or as described in Section IV, entitled "*Anti-PD-1Crystalline Antibody Suspensions and Compositions.*"

Malignancies that demonstrate improved disease-free and overall survival in relation to the presence of tumor-infiltrating lymphocytes in biopsy or surgical material, e.g. melanoma, colorectal, liver, kidney, stomach/esophageal, breast, pancreas, and ovarian cancer are encompassed in the methods and treatments described herein. Such cancer subtypes are known to be susceptible to immune control by T lymphocytes. Additionally, included are refractory or recurrent malignancies whose growth may be inhibited using the antibodies described herein.

In some embodiments, the compositions of the invention are administered to a subject having a cancer characterized by elevated expression of PD-L1 and/or PD-L2 in tested tissue samples, including: ovarian, renal, colorectal, pancreatic, breast, liver, gastric, esophageal cancers and melanoma. Additional cancers that can benefit from treatment with the compositions of the invention include those associated with persistent infection with viruses such as human immunodeficiency viruses, hepatitis viruses class A, B and C, Epstein Barr virus, human papilloma viruses that are known to be causally related to for instance Kaposi's sarcoma, liver cancer, nasopharyngeal cancer, lymphoma, cervical, vulval, anal, penile and oral cancers.

Additional aspects include methods of using an anti-PD-1 mAb crystal or pharmaceutical composition of the invention to treat a patient having, suspected of having, or at risk for having an infection or infectious disease. Thus, the invention provides a method for treating chronic infection in a mammalian subject comprising administering an effective amount of an anti-PD-1 crystalline mAb of the invention or composition comprising an anti-PD-1 crystalline mAb of the invention to the subject. In some specific embodiments of this method, the composition is administered to the subject via intravenous administration. In other embodiments, the composition is administered to the subject by subcutaneous administration.

In this aspect, the compositions of the invention can be used alone, or in combination with vaccines, to stimulate the immune response to pathogens, toxins, and self-antigens. The compositions of the invention can be used to stimulate immune response to viruses infectious to humans, including but not limited to: human immunodeficiency viruses, hepatitis viruses class A, B and C, Epstein Barr virus, human cytomegalovirus, human papilloma viruses, and herpes viruses. Compositions of the invention that comprise antagonist anti-PD-1 antibodies or antibody fragments can be used to stimulate immune response to infection with bacterial or fungal parasites, and other pathogens. Viral infections with hepatitis B and C and HIV are among those considered to be chronic viral infections.

The anti-PD-1 mAb crystals and compositions of the invention may be administered to a patient in combination with one or more "additional therapeutic agents". The additional therapeutic agent may be a biotherapeutic agent (including but not limited to antibodies to VEGF, EGFR, Her2/neu, VEGF receptors, other growth factor receptors, CD20, CD40, CD-40L, OX-40, 4-1BB, and ICOS), a growth inhibitory agent, an immunogenic agent (for example, attenuated cancerous cells, tumor antigens, antigen presenting cells such as dendritic cells pulsed with tumor derived antigen or nucleic acids, immune stimulating cytokines (for example, IL-2, IFN$\alpha$2, GM-CSF), and cells transfected with genes encoding immune stimulating cytokines such as but not limited to GM-CSF).

As noted above, in some embodiments of the methods of the invention, the method further comprises administering an additional therapeutic agent. In particular embodiments, the additional therapeutic agent is an anti-LAG3 antibody or antigen binding fragment thereof, an anti-GITR antibody, or antigen binding fragment thereof, an anti-TIGIT antibody, or antigen binding fragment thereof, an anti-CD27 antibody or antigen binding fragment thereof. In one embodiment, the additional therapeutic agent is a Newcastle disease viral vector expressing IL-12. In a further embodiment, the additional therapeutic agent is dinaciclib. In still further embodiments, the additional therapeutic agent is a STING agonist. In still further embodiments, the additional therapeutic agent is a PARP inhibitor. In still further embodiments, the additional therapeutic agent is a multi-tyrosine kinase inhibitor. In additional embodiments, the additional therapeutic agent is a MEK inhibitor. In additional embodiments, the additional therapeutic agent is a CXCR2 antagonist. In additional embodiments, the additional therapeutic agent is navarixin. In additional embodiments, the additional therapeutic agent is olarparib. In additional embodiments, the additional therapeutic agent is selumetinib. In additional embodiments, the additional therapeutic agent is axitinib.

Suitable routes of administration for the additional therapeutic agent may, for example, include parenteral delivery, including intramuscular, subcutaneous, as well as intrathecal, direct intraventricular, intravenous, intraperitoneal. Drugs can be administered in a variety of conventional ways, such as intraperitoneal, parenteral, intra-arterial or intravenous injection.

Selecting a dosage of the additional therapeutic agent depends on several factors, including the serum or tissue turnover rate of the entity, the level of symptoms, the immunogenicity of the entity, and the accessibility of the target cells, tissue or organ in the individual being treated. The dosage of the additional therapeutic agent should be an amount that provides an acceptable level of side effects. Accordingly, the dose amount and dosing frequency of each additional therapeutic agent (e.g. biotherapeutic or chemotherapeutic agent) will depend in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert et al. (2003) *New Engl. J Med.* 348:601-608; Milgrom et al. (1999) *New Engl. J. Med.* 341:1966-1973; Slamon et al. (2001) *New Engl. J Med.* 344:783-792; Beniaminovitz et al. (2000) *New Engl. J Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Various literature references are available to facilitate selection of pharmaceutically acceptable carriers or excipients for the additional therapeutic agent. See, e.g., *Remington's Pharmaceutical Sciences and U.S. Pharmacopeia: National Formulary*, Mack Publishing Company, Easton, PA (1984); Hardman et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY.

In some embodiments, the additional therapeutic agent is administered by continuous infusion, or by doses at intervals of, e.g., one day, 1-7 times per week, one week, two weeks, three weeks, monthly, bimonthly, etc. A preferred dose protocol is one involving the maximal dose or dose frequency that avoids significant undesirable side effects. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J Med.* 349:427-434; Herold et al. (2002) *New Engl. J Med.* 346:1692-1698; Liu et al. (1999) *J. Neurol. Neurosurg. Psych.* 67:451-456; Portielji et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

In certain embodiments, dosing will comprise administering to a subject escalating doses of 1.0, 3.0, and 10 mg/kg of the additional therapeutic agent, over the course of treatment. The formulation can be a reconstituted liquid formulation, or it can be a liquid formulation not previously lyophilized. Time courses can vary, and can continue as long as desired effects are obtained. In certain embodiments, dose escalation will continue up to a dose of about 10 mg/kg. In certain embodiments, the subject will have a histological or cytological diagnosis of melanoma, or other form of solid tumor, and in certain instances, a subject may have non-measurable disease. In certain embodiments, the subject will have been treated with other chemotherapeutics, while in other embodiments, the subject will be treatment naïve.

In certain embodiments, the dosing regimen will comprise administering a dose of from about 0.005 mg/kg to about 10 mg/kg, with intra-patient dose escalation. In certain embodiments, a dose of 5 mg/kg or 10 mg/kg will be administered at intervals of every 3 weeks, or every 2 weeks. In yet additional embodiments, a dose of 3 mg/kg will be administered at three week intervals for melanoma patients or patients with other solid tumors. In these embodiments, patients should have non-resectable disease; however, patients may have had previous surgery.

In certain embodiments, a subject will be administered a 30 minute IV infusion of any of the pharmaceutical formulations described herein. In certain embodiments for the escalating dose, the dosing interval will be about 28 days (±1 day) between the first and second dose. In certain embodiments, the interval between the second and third doses will be about 14 days (±2 days). In certain embodiments, the dosing interval will be about 14 days (±2 days), for doses subsequent to the second dose.

Subcutaneous administration may performed by injected using a syringe, or using other injection devices (e.g. the Inject-Ease® device); injector pens; or needleless devices (e.g. MediJector and BioJector®).

Embodiments of the invention also include one or more of the anti-PD-1 mAb crystals of the invention (e.g. crystalline pembrolizumab or a pembrolizumab variant) or formulations comprising the crystals described herein or made by the methods described herein (i) for use in, (ii) for use as a medicament or composition for, or (iii) for use in the preparation of a medicament for: (a) therapy (e.g., of the human body); (b) medicine; (c) induction of or increasing of an antitumor immune response (d) decreasing the number of one or more tumor markers in a patient; (e) halting or delaying the growth of a tumor or a blood cancer; (f) halting or delaying the progression of PD-1-related disease; (g) halting or delaying the progression cancer; (h) stabilization of PD-1-related disease; (i) inhibiting the growth or survival of tumor cells; (j) eliminating or reducing the size of one or more cancerous lesions or tumors; (k) reduction of the progression, onset or severity of PD-1-related disease; (1) reducing the severity or duration of the clinical symptoms of PD-1-related disease such as cancer (m) prolonging the survival of a patient relative to the expected survival in a similar untreated patient n) inducing complete or partial remission of a cancerous condition or other PD-1 related disease, (o) treatment of cancer, or (p) treatment of infection or infectious disease.

All publications mentioned herein are incorporated by reference for the purpose of describing and disclosing methodologies and materials that might be used in connection with the present invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

Example 1

High Throughput Crystallization Screening of Pembrolizumab

A number of small molecule reagents were screened, including amino acids, peptides, organic salts and acids, and biologically active small molecules, for their ability to promote crystallization of pembrolizumab (Hampton Research Silver Bullet Bio screen from Hampton Research (catalog #HR2-088)). A solution comprising pembrolizumab (44 mg/mL) in 10 mM histidine, pH 5.6 was screened in a 1536 unique crystallization plate (microbatch-under-oil) (Luft et al., *Journal of Structural Biology* 142: 170-179 (2003)) using 0.2 µl pembrolizumab and 0.2 µl screening solution. The screening solutions can be broken down into three main categories: (1) salt, buffer (36 salts at three concentrations combined with eight buffers); (2) PEG, salt, buffer (eight PEGs at two concentrations, combined with 36 salts and eight buffers) and (3) PEG, Silver Bullets Bio reagents. The Silver Bullets Bio screen is composed of 96 solutions in a single deep well block (Greiner 780261) high throughput format. Each reagent was a mixture of small molecules or macromolecular digest in 0.02 M HEPES sodium pH 6.8 buffer. Each solution contained between 2 and 20 small molecules. The Silver Bullets Bio screen was diluted 1:10 in 15% PEG 3350, 0.02 M HEPES, pH 6.8 as the precipitating agent. Experiments were performed at each of 4° C., 20-22° C. and 30° C. The plate wells were monitored microscopically for crystal formation over time.

After 1 month, several molecules were identified that induced crystallization of pembrolizumab. The crystals were visualized using a SONICC™ imaging system (Formulatrix, Bedford, MA). Second Order Nonlinear Imaging of Chiral Crystals (SONICC) is an imaging technology for visualizing protein crystals, which finds and identifies protein crystals. Two technologies, Second Harmonic Generation (SHG), which probes crystallinity, and Ultraviolet Two-Photon Excited Fluorescence (UV-TPEF) which is specific to proteinaceous samples, are combined together to positively identify protein crystals. Crystals appear white against a stark black background, enabling the identification of crystals even in murky environments. SONICC is also capable of detecting extremely small crystals, or microcrystals, defined as having at least one dimension <1 µm.

One of the molecules identified at 30° C., ammonium phosphate monobasic, was also identified as a crystallization agent compatible with a high salt process developed previously. See WO 2016/137850. Additionally, novel crystallization agents as mixtures were identified that were different than the molecules used with the previous high salt process. The mixtures that were useful in producing crystals and the temperatures at which the crystallization screen was positive for crystals are provided in Table 3, below.

TABLE 3

Results of Crystallization Screen

| Mixture | Components | Temp. |
|---|---|---|
| A2 | 0.016% L-carnitine hydrochloride, 0.016% Tannic acid, 0.016% aspartame, 0.016% caffeine, 0.16% p-coumaric acid, 0.16% 4-hydroxy-L-proline and 0.02M HEPES, pH 6.8, 15% PEG 3350 | 30° C. |
| B5 | 0.02% nicotinic acid, 0.02% inosine 5'-monophosphate disodium salt, 0.02% Gibberellin $A_3$, 0.02% O-phospho-L-tyrosine, 0.02% caffeine and 0.02M HEPES, pH 6.8, 15% PEG 3350 | 30° C. |
| C1 | 0.02% 2-deoxyguanosine, 0.02% ethanolamine, 0.02% theophylline, 0.02% isopropyl, 0.02% 1 thio-β-D galactopyranoside, 0.02% oxalacetic acid and 0.02M HEPES, pH 6.8, 15% PEG 3350 | 30° C. and Room Temp. |

TABLE 3-continued

| Results of Crystallization Screen | | |
|---|---|---|
| Mixture | Components | Temp. |
| D3 | 0.02% thiamine pyrophosphate, 0.02% D-gluscosamic acid, 0.02% choline base solution, 0.02% theophylline, 0.02% ethanolamine and 0.02M HEPES, pH 6.8, 15% PEG 3350, at 30° C. and room temperature. | 30° C. and Room Temp. |

Figure 1B:
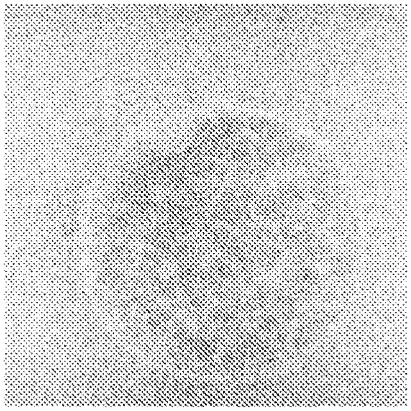
Figure 1C:
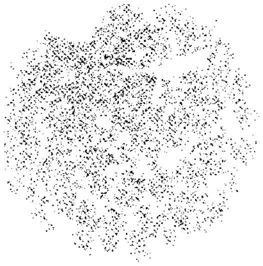

Four molecules were identified for further study: caffeine, theophylline, 2' deoxyguanosine-5'-monophosphate and Gibberellin A3. At 4° C., no crystals were observed with any of the molecules tested in this screen. Images of the crystals formed with Silver Buller Bio A2 as the crystallization additive are provided in FIG. 1.

Example 2

Confirmation of Crystallization Agents Using Drop Vapor Diffusion

A sitting drop vapor diffusion experiment (96 well −3 drop Swissci plate) was performed to confirm the crystallization agents identified in EXAMPLE 1. Antibody solutions comprising 44 mg/mL of pembrolizumab were prepared in in 10 mM histidine, pH 5.6 Several different cocktails were prepared comprising 50 mM HEPES, pH 6.8, 12-15% w/v PEG 3350, and one additive per cocktail solution (total volume 0.6 μL). The drop ratio varied as follows: drop 1: 0.4 μL cocktail+0.2 μL pembrolizumab, drop 2: 0.3 μL cocktail+0.3 μL pembrolizumab, and drop 3: 0.2 μL cocktail+0.4 μL pembrolizumab. The experiment was performed at 23° C. The plate wells were monitored microscopically for crystal formation over time.

Figure 2C:
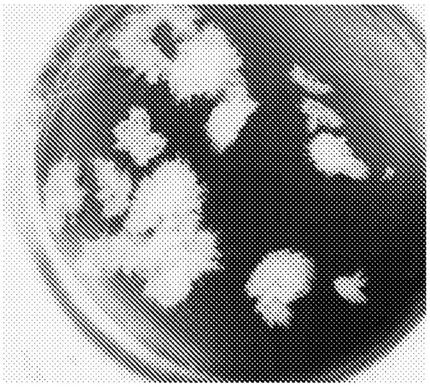
FIGS. 2A-2C provide visible photomicrographs taken at 200× magnification of crystals within a pembrolizumab crystalline suspension produced using drop vapor diffusion, as described in EXAMPLE 2.
Figure 2B:
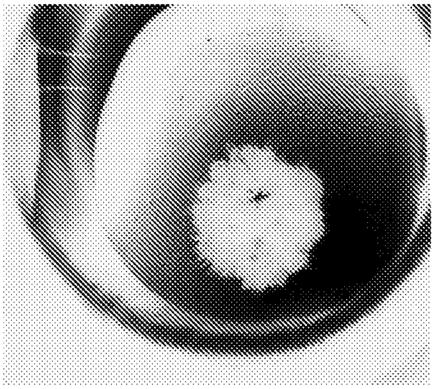
Figure 2A:
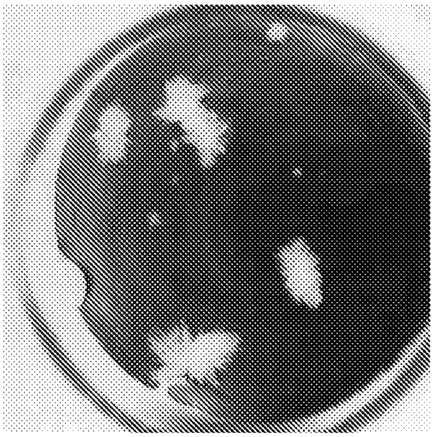

Results confirmed that 0.1 to 0.18% caffeine alone aids crystallization of pembrolizumab in the presence of 12-15% w/v PEG 3350, and 50 mM HEPES, pH 6.8. 0.15% Caffeine w/v and 0.15% w/v Gibberellin A3, either mixed together or independently, were also effective at producing pembrolizumab crystals in the presence of 12-15% w/v PEG 3350, 50 mM HEPES, pH 6.8. Theophylline did not produce crystals at 0.15% w/v, but was effective at crystallizing pembrolizumab at higher concentrations of 0.25% and 0.30% w/v in the presence of 12-15% w/v PEG 3350, 50 mM HEPES, pH 6.8. Paired with other Silver Bullet agents, 0.15% w/v theophylline did produce crystals when mixed with 0.2% w/v 2' deoxyguanosine 5'-monophosphate sodium salt hydrate, 0.2% ethanolamine, 0.2% IPTG, 0.2% thiamine pyrophosphate, 0.2% choline base solution. See FIG. 2. The 50 mM HEPES buffer and 12-15% w/v PEG 3350 alone did not produce any crystals.

Example 3

Batch Crystallization of Pembrolizumab

Experiments were designed to determine optimal micro batch crystallization conditions for producing a crystal suspension of pembrolizumab with a uniform particle size distribution of 10-50 microns.

A pembrolizumab stock solution in 10 mM histidine buffer, pH 5.6 was concentrated in a concentrator to reach a final protein concentration of 44 mg/mL. The concentrated solution was diluted to 20 mg/mL pembrolizumab in histidine buffer. A 2.5% w/v caffeine solution was prepared by adding 1.25 g caffeine (Sigma catalog number C7731-250G) to 50 mL of 20 mM histidine, pH 5.4 and heating the resulting mixture to 40° C. until the caffeine was dissolved and a solution was formed.

0.2% caffeine in 10 mM tris, pH 8.0 was added to a 20 mg/mL pembrolizumab solution (50 mM histidine buffer, pH 5.4) with cocktails 16% PEG 3350, 50 mM HEPES and varying pH 6.8-7.4 in 0.1 intervals. Batch crystallization was set up at a 1:1, 1:2 and 1:3 pembrolizumab: cocktail ratio with a total volume of 200 μL in a 1.5 mL in Eppendorf tubes. Tubes were placed either on a rotating platform or on a stir plate. All experiments were conducted at room temperature with the exception of an early batch plate at 4° C. which produced no crystals and mostly precipitate.

For the experiments conducted at room temperature, crystals formed within the first day, and continued to form over 18 hours. A small volume of crystallization solution was extracted for imaging on a batch plate. The best observed conditions for obtaining single needle crystals 10-50 microns was 15 mg/mL pembrolizumab, 0.20% caffeine, 14% PEG 3350, 50 mM HEPES, and pH 7.3 at room temperature for 18 hours.

Example 4

Batch Crystallization Scale-Up Experiment (1 mL scale)—Comparison of Static and Rotation Methods Two 1 mL batch crystallization experiments were setup by mixing 333 μl of 19.4 mg/mL pembrolizumab, 0.175% caffeine, 50 mM histidine, pH 5.5 (part A) with 666 μL of 50 mM HEPES, pH 7.7, 10.18% PEG 3350 (part B) in a 1.5 mL eppendorf tube. Preparation of Part A solution: A solution of 44 mg/mL pembrolizumab was diluted to 20 mg/mL with 50 mm histidine, pH 5.5. To 1.4 mL of the dilute solution was added 112 μl of 2.5% caffeine in 10 mM histidine, pH 5.5. The final composition for part A was 19.4 mg/mL pembrolizumab, 7% caffeine, 50 mM histidine, pH 5.5. Preparation of Part B solution: Using an Optimatrix maker liquid handing system a 50 mM HEPES, pH 7, 10.18% PEG 3350 solution was prepared.

One tube was incubated under static conditions and the other tube was placed on a Labnet Mini LabRoller H5500 at 30° C. for 18 hours. Microscopic inspection at 200× of the experiments showed clusters of crystals under static conditions while a uniform suspension of needle crystals (10-30 microns) was observed for the rotated sample, indicating that rotation was a preferable step compared to static incubation.

Example 5

Batch Crystallization of Pembrolizumab Using Caffeine/PEG 3350 Process (10 mL Scale Batch)

Figure 3:
FIG. 3 provides a photomicrograph of the pembrolizumab crystals at 200× magnification that resulted from a crystallization method (10 mL scale) that included incubating pembrolizumab with 9.8% PEG 3350, 45 mM HEPES, pH 7.7, 0.23% caffeine for 18 hours at 30° C. See Example 5.
Figure 4A:
FIGS. 4A-4F provide images of crystalline suspensions made with 10.18% PEG 3350, 50 mM HEPES, pH 7.2 solution, as described in EXAMPLE 6. Images show crystals made following incubation of the crystallization solution at 2° C. and 50° C., characterized using the visible (FIGS. 4A and 4D), UV-TPEF (FIGS. 4B and 4E) and SHG modes (FIGS. 4C and 4F) of the SONICC™ imaging system, respectively.
Figure 4B:
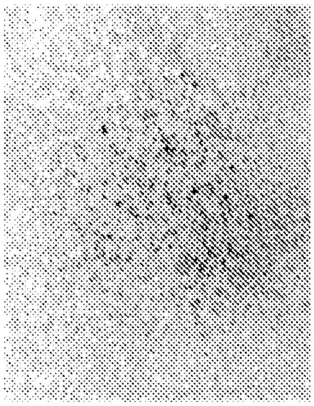
Figure 4C:
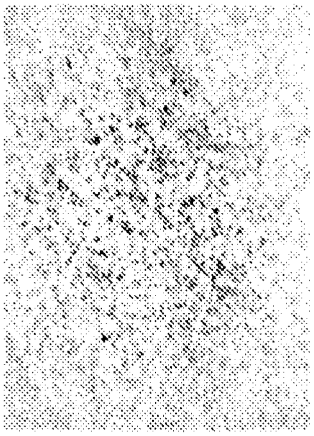
Figure 4D:
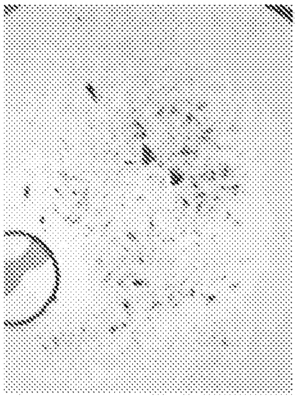
Figure 4E:
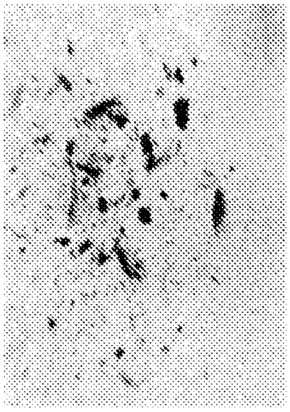
Figure 4F:
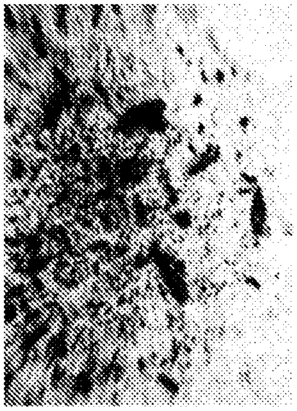

A 20 mg/mL solution of pembrolizumab was prepared by diluting a 44 mg/mL stock solution of pembrolizumab with 20 mM histidine buffer pH 5.4 to a total volume of 3.33 mL. To this solution was added 6.66 mL of 13% PEG 3350, 50 mM HEPES, pH 7.7 and 1.0 mL of 2.5% caffeine in 20 mM histidine buffer, pH 5.4. The final composition of the resulting solution was 6.7 mg/mL pembrolizumab, 9.8% PEG 3350, 45 mM HEPES, pH 7.7, 6.6 mM histidine, 0.23% caffeine. The solution was placed on a Labnet Mini LabRoller H5500 rotisserie at 24 RPM at 30° C. The solution was initially clear, but turbidity was observed after 18 hours. The turbid suspension was inspected microscopically and the formation of micro-needles was confirmed by microscopic inspection at 200×. A photomicrograph of the derived crystals is provided in FIG. 3.

Further processing of the derived crystalline suspension was performed to remove non-crystallized pembrolizumab and excess caffeine from the suspension and to measure the crystallization yield.

A 1 mL aliquot of the crystalline suspension was centrifuged at 3,000 RPM for 3 minutes in a microfuge. The resulting pellet was re-suspended in 1 mL of 13% PEG 3350, 50 mM HEPES, pH 7.7 and the supernatant was labeled wash 1. The suspension was centrifuged at 3,000 RPM for 3 minutes in a microfuge. The resulting pellet was re-suspended in 1 mL of 13% PEG 3350, 50 mM HEPES, pH 7.7 and the supernatant was labeled wash 2. The suspension was centrifuged at 3,000 RPM for 3 minutes in a microfuge. The resulting pellet was re-dissolved in 1 mL of cold 20 mM histidine buffer, pH 5.4. The pellet dissolved within 5 minutes.

Protein concentration was determined using a nano drop spectrophotometer using an extinction coefficient of 1.4. The mother liquor protein concentration was 78 mg/mL (distortion due to caffeine), Wash 1: 24 mg/mL (distortion due to caffeine), Wash 2: 3.87 mg/m mL 1 (distortion due to caffeine) and the final re-dissolved crystals: 6.2 mg/ml (280:260 nm ratio of 0.52 which is the same for starting pembrolizumab solution). The overall yield was 94% based on the protein determination.

Example 6

Temperature Range 0-50° C. Crystallizability Screening

A solution of 44 mg/mL pembrolizumab in 20 mM histidine buffer, pH 5.4 (0.2 micron filtered) was prepared using sterile non pyrogenic water solution.

A solution of 2.5% caffeine, 20 mM histidine, pH 5.4 was prepared by adding 1.25 g caffeine (Sigma; Lot #SLBK4804V) to 50 mL 20 mM histidine (Sigma; H-8000), pH 5.4. The mixture was heated to 60° C. until the caffeine went into solution. The resulting solution was allowed to cool to room temperature before usage.

A solution of 10.18% PEG 3350, 50 mM HEPES, pH 7.4 was prepared by adding 2.5 mL of 1M HEPES (1 M solution, pH 7.4; Hampton Research HR2-941-27), pH 7.4 and 10.2 mL of 50% PEG 3350 to 37.3 mL sterile water for injection. The resulting solution was 0.2 micron filtered.

To 33 μl of the pembrolizumab solution (44 mg/mL) in 20 mM histidine buffer, pH 5.4 was added 66 μl of 10.18% PEG 3350, 50 mM HEPES, pH 7.4 solution at room temperature. To the resulting solution was added 10 μl of 2.5% caffeine, 20 mM histidine buffer, pH 5.4. 1.45 mg pembrolizumab, 6 mM histidine, pH 5.4, 6.1% PEG 3350, 30 mM HEPES, 0.23% caffeine (measured pH 7.2) mixture (in solution) was incubated at 2° C. (wet ice) or at 50° C. (in a water bath) for 18 hours. Crystals were observed microscopically in the 2° C. sample. The 50° C. sample was clear for 18 hours and crystallized upon cooling to room temperature within 1 hour.

SONICC™ analyses were run on a 1/16 dilutions of both samples in 10.18% PEG 3350, 50 mM HEPES, pH 7.4 solution shown in the attached SONICC™ analyses. Both experiments showed positive UV and SHG imaging, consistent with protein chiral crystals. See FIG. 4.

Example 7 pH Ranging Crystallizability Studies

This study was designed to investigate the pH of solution to determine which pH range is effective at producing crystals.

Using a Formulatrix Formulator™ liquid handling instrument, a pH 6.0 to 8.8 grid was dispensed into a 96 well micro-batch plate (Hampton HR267) using 50 mM HEPES buffer across each row and 1-12% PEG 3350 into each column, with a final volume of 66 μl in each well. 33 μl of a solution comprising pembrolizumab (44 mg/mL) in 20 M histidine buffer, pH 5.4 was added at room temperature to each well, followed by 10 μl of 2.5% caffeine, 20 mM histidine buffer, pH 5.4. 1.45 mg pembrolizumab, 6 mM histidine pH 5.4, 0.23% caffeine plate components were mixed by 7× aspiration and dispensing steps. The mixture (in solution) was incubated at 22° C. for 18 hours and crystal formation was confirmed using SONICC™ analysis.

Crystals were observed across the entire pH range from pH 6.0 to 8.8. At the lower pH range of between 6.0 and 6.4, fewer crystals were observed than at higher pH and a mix of crystals and precipitate was observed. The best crystals based on size and quality were observed at pH 6.7-8.0. Above pH 8.0 crystals were observed, but only when a higher % PEG was used. Crystallinity was confirmed using SONICC imaging. See Table 4.

TABLE 4

Results from pH Ranging Studies

| pH | Crystals confirmed by SONICC ™ | Results: Low PEG Concentration | Results: High PEG Concentration |
|---|---|---|---|
| 6.0 | + | Crystals (2-4%) | Precipitate (6-12%) |
| 6.4 | + | Crystals (2-6%) | Precipitate (8-12%) |
| 6.8 | + | Clear (2-4%) | Crystals (4-12%) |
| 7.2 | + | Clear (2-4%) | Crystals (6-12%) |
| 7.6 | + | Clear (2-4%) | Crystals (6-12%) |
| 8.0 | + | Clear (2-4%) | Crystals (6-12%) |
| 8.4 | + | Clear (2-4%) | Crystals (6-12%) |
| 8.8 | + | Clear (2-8%) | Crystals (10-12%) |

Example 8

Crystallizability Screening Using Various Molecular Weight PEGs

A solution of 44 mg/mL pembrolizumab in 20 mM histidine buffer, pH 5.4 (0.2 micron filtered) was prepared using sterile non pyrogenic water solution.

A solution of 2.5% caffeine, 20 mM histidine, pH 5.4 was prepared by adding 1.25 g caffeine (Sigma; Lot #SLBK4804V) to 50 mL 20 mM histidine (Sigma; H-8000), pH 5.4, heat to 60° C. till solution. The solution was allowed to cool to room temperature before usage.

A solution of 10.18% PEG 3350, 50 mM HEPES, pH 7.4 was prepared by adding 2.5 mL of 1M HEPES (1 M solution, pH 7.4; Hampton Research HR2-941-27), pH 7.4 and 10.2 mL of 50% PEG 3350 to 37.3 mL sterile water for injection. The resulting solution was 0.2 micron filtered.

Using a Formulatrix Formulator™ liquid handling instrument, a linear gradient of 1-12% PEG 200, 400, 3000, 3350, 8000, 10,000 and 20,000 and 50 mM HEPES, pH 7.2 was varied in each column and was dispensed into a 96 well micro-batch plate (Hampton HR267) to a final volume of 66 μl in each well. 33 μl of pembrolizumab (44 mg/mL) in 20 mM histidine buffer, pH 5.4 was added at room temperature, followed by 10 μl of 2.5% caffeine, 20 mM histidine buffer, pH 5.4. The plate components were mixed by 7× aspiration and dispensing steps. The mixture (in solution) was incubated at 22° C. for 18 hours.

Crystals were observed microscopically in all the rows except for the PEG 200 and PEG 400 rows. SONICC™ analyses were run using an aliquot in a Whatman Fast Frame 4 slide well plate. All wells comprising PEG molecules with molecular weight from 3,000 to 20,000 showed positive UV and SHG imaging consistent with protein chiral crystals. See Table 5.

TABLE 5

Crystallization Screen with Various Molecular Weight PEG Molecules

| PEG MW | PEG Source (Catalog #) | Crystals confirmed by SONICC ™ Analysis |
|---|---|---|
| 200 | Hampton Research HR2-601 | – |
| 400 | Hampton Research HR2-603 | – |
| 3000 | Rigaku 1008056 | + |
| 3350 | Rigaku 1008055 | + |
| 8000 | Hampton Research HR2-535 | + |
| 10,000 | Hampton Research HR2-607 | + |
| 20,000 | Rigaku CS-300 | + |

Example 9

Monoclonal Antibody Crystallization Screening

This study was performed to determine if the PEG/caffeine conditions described above, which were useful for crystallizing pembrolizumab, would also be effective at crystallizing other monoclonal antibodies.

Several human recombinant monoclonal antibodies (10-40 mg/mL) were screened in a 1536 unique crystallization plate using a micro batch-under-oil method as described in Luft et al. (*Journal of Structural Biology* 142 (2003) 170-179)), using 0.2 μl monoclonal antibodies (10-40 mg/mL) and 0.2 μl precipitating solution (commercially available screens including the Silver Bullets Bio screen. Crystallization screens were performed at 4° C., room temperature, and 30° C. After 1 month, except for pembrolizumab, none of the screened monoclonal antibodies crystallized under the 0.16-0.2% caffeine, 12-15% PEG 3350, 0.05M HEPES, pH 6.8 conditions at any of the temperatures tested, including the anti-PD-1 antibody nivolumab. A list of the mAb targets, as well as the IgG type is provided in Table 6.

TABLE 6

Crystallization Screen Using Different Antibodies

| mAb Target | IgG type | Crystallization with PEG/Caffeine |
|---|---|---|
| IL23 | 1 | – |
| PD-1 (pembrolizumab) | 4 | + |
| PD-1 (nivolumab) | 4 | – |
| GITR | 4 | – |
| GITR | 1 | – |
| LAG3 | 4 | – |
| IGF-1R | 4 | – |
| cCAM | 4 | – |
| RSV | 1 | – |
| FXIa | 4 | – |
| CTLA4 | 1 | – |
| FXIa | 4 | – |

Example 10

Preparation of Pembrolizumab Crystals Suitable for X-Ray Diffraction Analyses A Hampton Research additive screen consisting of 96 unique additives (HR2-138) was set up using a base condition of 12% PEG 3350, 0.1M HEPES, pH 6.8, 0.2% caffeine (72 μL) in a sitting drop vapor diffusion plate adding 10% of the additive screen (8 μL) to the reservoir solution. A Crystal Gryphon (Art Robbins Instruments, LLC, Sunnyvale, CA) was used to mix the reservoir solution and to dispense 0.4, 0.3 and 0.2 μl of the individual drop wells 1-3 to a 3 well Intelli-plate 96. Pembrolizumab (20 mg/mL) was added to the 3 drops of the individual drop wells at 0.2, 0.3 and 0.4 μl, respectively thereby creating drop ratios of 2:1, 1:1 and 1:2 reservoirs to pembrolizumab against each complimentary reservoir solution. The plate was incubated at 14° C. After 1 day, crystals appeared in many of the wells, the well comprising dextran sodium sulfate as an additive (condition E3 from the Hampton additive screen) produced a thicker needle crystal than the other additives.

Figure 5:
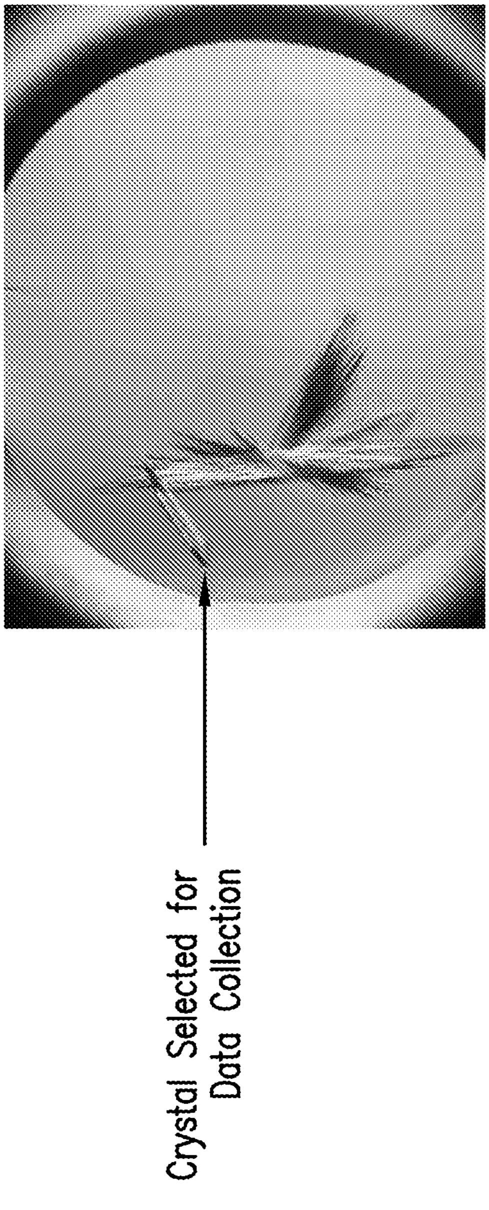
FIG. 5 shows a photomicrograph of pembrolizumab crystals made using the procedure described in EXAMPLE 10. The crystal selected for complete structural characterization is shown.

Prior to data collection, crystals were harvested at room temperature and transferred to a cryoprotectant solution made of the precipitant cocktail augmented with 20% ethylene glycol. After soaking for approximately 20 seconds in this cryoprotectant solution, the crystals were fished using a cryo-loop and frozen in liquid nitrogen. The frozen crystal was then mounted onto the goniometer at the SER-CAT beamline at the Advanced Photon Source (APS) at Argonne National Laboratory (Argonne, IL, USA) equipped with a nitrogen cooled stream. X-ray diffraction was collected using a Rayonix MX300 HS detector. Complete characterization of the pembrolizumab crystal made using the following conditions was conducted: 12% PEG 3350, 0.1M HEPES pH 6.8, 0.2% caffeine, 3% dextran sodium sulfate, 20 mg/mL pembrolizumab, 1:1 ratio (0.3 μl pembrolizumab/0.3 μl 12% PEG 3350, 0.1M HEPES pH 6.8, 0.2% caffeine, 3% dextran sodium sulfate). Data were integrated and scaled using the autoPROC program (Global Phasing), which was set up to use XDS for integration, POINTLESS to confirm the space group, AIMLESS for scaling, STARANISO for anisotropy analysis and conversion to amplitudes. A photomicrograph of the crystal is shown in FIG. 5.

The characteristics of the PEG/caffeine crystal and data collection statistics are provided below:

| Data Collection Statistics | | | |
|---|---|---|---|
| Space group | $P222_1$ | | |
| Unit cell | a = 43.8 Å b = 113.9 Å c = 175.0 Å, α = β = γ = 90° | | |
| Low resolution limit: | 174.96 | 174.96 | 2.45 |
| High resolution limit: | 2.22 | 6.87 | 2.22 |
| Rmerge: | 0.14 | 0.05 | 0.90 |
| Rmeas (within I+/I−) | 0.15 | 0.05 | 1.07 |
| Rmeas (all I+ & I−) | 0.15 | 0.05 | 1.05 |
| Rpim (within I+/I−) | 0.07 | 0.02 | 0.71 |
| Rpim (all I+ & I−) | 0.05 | 0.02 | 0.53 |
| Total no. observations | 294309 | 13831 | 6287 |
| Total number unique | 33863 | 1682 | 1693 |
| Mean(I)/sd(I) | 14.1 | 34.8 | 1.3 |
| Completeness (spherical) | 76.4 | 99.9 | 15.1 |
| Completeness (ellipsoidal) | 90.6 | 99.9 | 38.2 |
| Multiplicity | 8.7 | 8.2 | 3.7 |

Figure 6A:
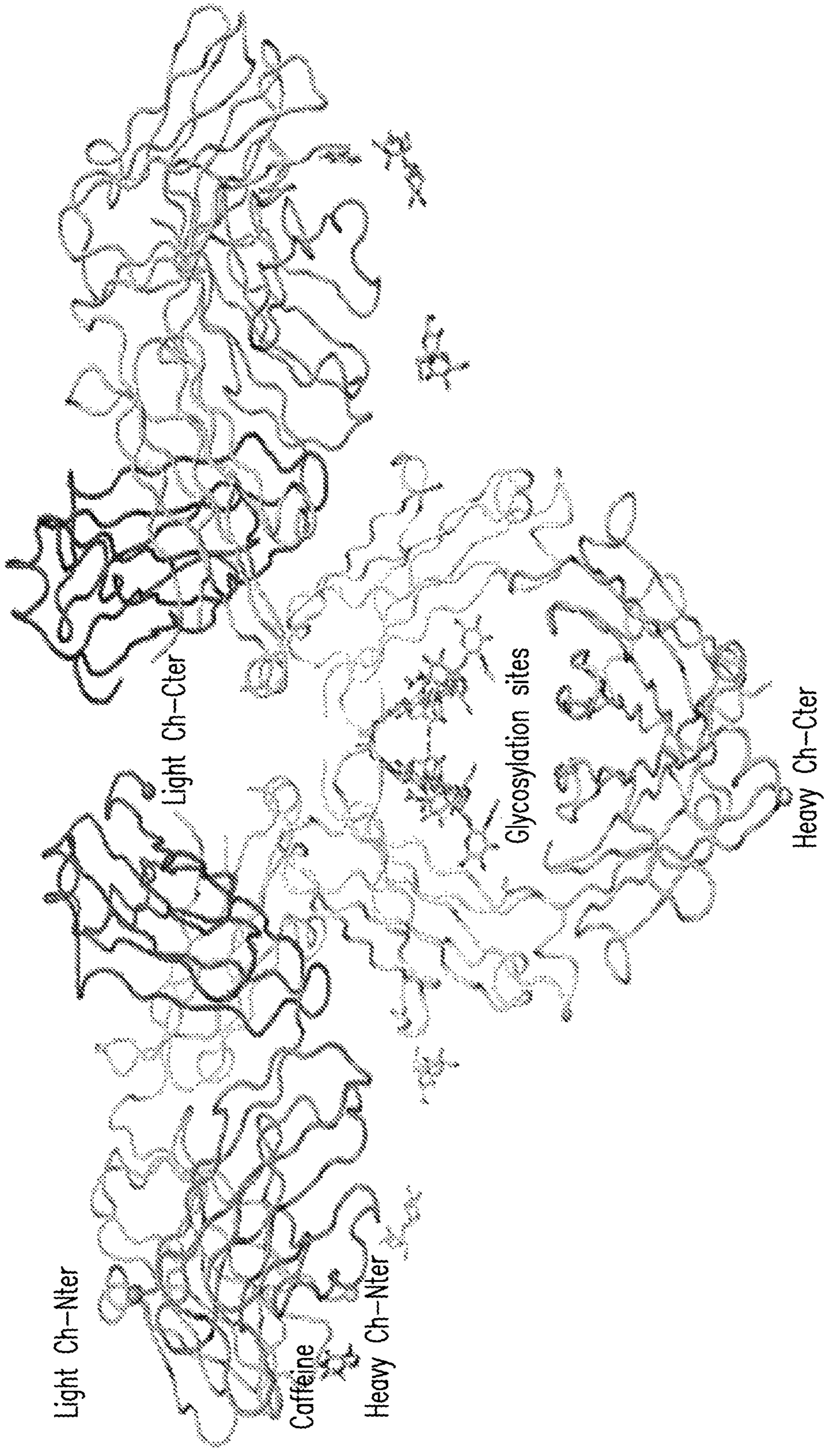
FIG. 6A shows a pictorial representation of the pembrolizumab/caffeine complex in the low salt/PEG/caffeine crystal form described in EXAMPLE 10. The protein backbone is shown as a ribbon; the glycosyls attached to the protein as well as ordered molecules of caffeine bound to the protein are depicted as sticks. In the color version of FIG. 6A, the protein backbone is shown as a ribbon colored as follows: orange VL, magenta CL, green VH, cyan CH1, yellow CH2, grey CH3.
Figure 6B:
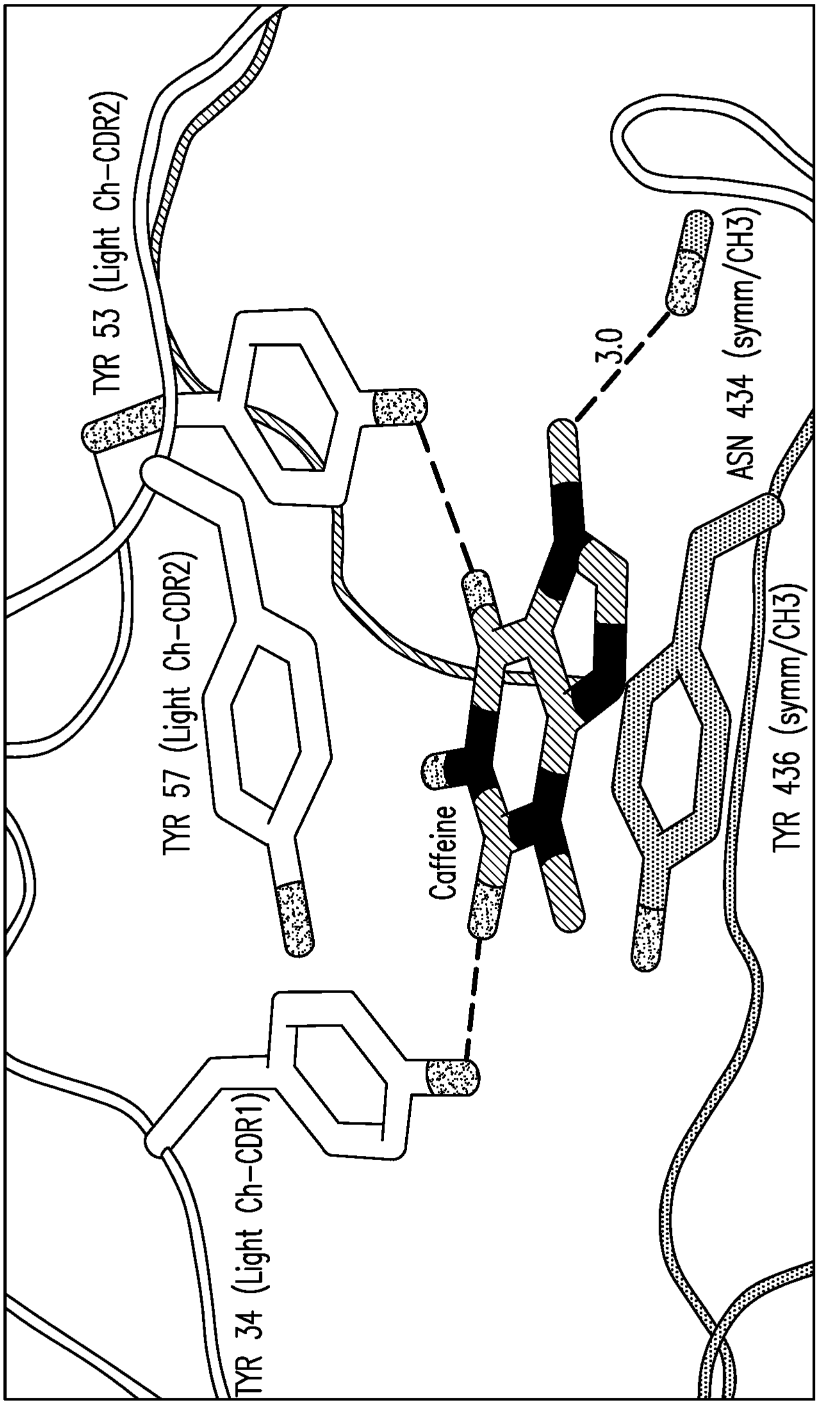
FIG. 6B shows a close-up view of the caffeine molecule found ordered and mediating crystal contacts. The protein backbone is represented as a ribbon with the side-chains surrounding the caffeine molecule, which is depicted as sticks. In the color version, the color convention is identical to FIG. 6A

Packing analysis using the MATTHEWS program showed that the asymmetric unit contains one half of the antibody, the other half being generated by application of a crystal 2-fold symmetry. The crystal structure was solved using molecular replacement package MOLREP using the PDB entry 5DK3 as the search model. The search was performed by looking successively for each rigid moiety, keeping parts of the antibody already positioned as fixed coordinates. The moieties were positioned in the following order: VL and VH, CL and $CH_1$, $CH_2$, $CH_3$. Refinement was done using the program autoBUSTER as part of the Global Phasing package. A pictoral representation of the antibody is set forth in FIG. 6A. A close-up view showing the interactions of caffeine with its environment in the crystal is set forth in FIG. 6B.

Complete structural information and characterization for the pembrolizumab crystal is provided in Table 7.

| | |
|---|---|
| Resolution limits: | 0.81-2.22 Å |
| Number of reflections | 33,850 (76.3%) |
| Number of reflections in test set | 1,635 (4.83%) |
| Number of non-H protein atoms | 4,970 |
| Number of solvent atoms | 395 |
| R-factor | 0.202 |
| R-firee | 0.255 |
| RMSD bond length | 0.010 Å |
| RMSD bond angles | 1.14° |

TABLE 7

| Three-dimensional crystal coordinates for caffeine-pembrolizumab complex. Atomic Coordinates of Caffeine/Pembrolizumab Crystal Complex | | | | | | | | | | |
|---|---|---|---|---|---|---|---|---|---|---|
| LINK | ND2 | ASN B | 297 | C1 | NAG B | 505 | 1555 | 1555 | 1.440 | |
| LINK | O4 | NAG B | 505 | C1 | NAG B | 506 | 1555 | 1555 | 1.420 | |
| LINK | O4 | NAG B | 506 | C1 | BMA B | 507 | 1555 | 1555 | 1.400 | |
| LINK | O3 | BMA B | 507 | C1 | MAN B | 509 | 1555 | 1555 | 1.430 | |
| LINK | O6 | BMA B | 507 | C1 | MAN B | 508 | 1555 | 1555 | 1.410 | |
| LINK | O2 | MAN B | 508 | C1 | NAG B | 511 | 1555 | 1555 | 1.420 | |
| LINK | O2 | MAN B | 509 | C1 | NAG B | 510 | 1555 | 1555 | 1.430 | |
| SSBOND | 1 | CYS A | 23 | CYS A | 92 | | 1555 | 1555 | 2.51 | |
| SSBOND | 2 | CYS A | 138 | CYS A | 198 | 1555 | 1555 | 2.02 | | |
| SSBOND | 3 | CYS A | 218 | CYS B | 134 | 1555 | 1555 | 2.04 | | |
| SSBOND | 4 | CYS B | 22 | CYS B | 96 | 1555 | 1555 | 2.08 | | |
| SSBOND | 5 | CYS B | 147 | CYS B | 203 | 1555 | 1555 | 2.06 | | |
| SSBOND | 8 | CYS B | 261 | CYS B | 321 | 1555 | 1555 | 2.04 | | |
| SSBOND | 9 | CYS B | 367 | CYS B | 425 | 1555 | 1555 | 2.02 | | |
| CRYST1 | 43.800 | 113.900 | 175.000 | 90.00 | 90.00 | 90.00 | P 2 2 21 | | | |
| SCALE1 | 0.022831 | −0.000000 | −0.000000 | −0.00000 | | | | | | |
| SCALE2 | −0.000000 | 0.008780 | −0.000000 | 0.00000 | | | | | | |
| SCALE3 | 0.000000 | −0.000000 | 0.005714 | −0.00000 | | | | | | |
| ATOM | 1 | N | GLU A | 1 | −26.263 | −8.828 | −13.703 | 1.00 | 39.43 | N |
| ATOM | 2 | CA | GLU A | 1 | −25.789 | −10.208 | −13.557 | 1.00 | 38.22 | C |
| ATOM | 3 | C | GLU A | 1 | −26.819 | −11.112 | −12.858 | 1.00 | 40.67 | C |
| ATOM | 4 | O | GLU A | 1 | −27.646 | −10.607 | −12.098 | 1.00 | 42.85 | O |
| ATOM | 5 | CB | GLU A | 1 | −24.457 | −10.250 | −12.768 | 1.00 | 38.53 | C |
| ATOM | 6 | CG | GLU A | 1 | −24.495 | −9.532 | −11.423 | 1.00 | 50.72 | C |
| ATOM | 7 | CD | GLU A | 1 | −23.385 | −9.913 | −10.460 | 1.00 | 76.48 | C |
| ATOM | 8 | OE1 | GLU A | 1 | −23.709 | −10.371 | −9.340 | 1.00 | 74.46 | O |
| ATOM | 9 | OE2 | GLU A | 1 | −22.195 | −9.735 | −10.812 | 1.00 | 68.49 | O |
| ATOM | 10 | N | ILE A | 2 | −26.707 | −12.449 | −13.054 | 1.00 | 32.05 | N |
| ATOM | 11 | CA | ILE A | 2 | −27.541 | −13.451 | −12.372 | 1.00 | 28.85 | C |
| ATOM | 12 | C | ILE A | 2 | −26.896 | −13.688 | −10.990 | 1.00 | 27.94 | C |
| ATOM | 13 | O | ILE A | 2 | −25.716 | −14.060 | −10.900 | 1.00 | 26.83 | O |
| ATOM | 14 | CB | ILE A | 2 | −27.654 | −14.787 | −13.184 | 1.00 | 30.71 | C |
| ATOM | 15 | CG1 | ILE A | 2 | −28.180 | −14.534 | −14.616 | 1.00 | 30.84 | C |
| ATOM | 16 | CG2 | ILE A | 2 | −28.490 | −15.851 | −12.422 | 1.00 | 29.21 | C |
| ATOM | 17 | CD1 | ILE A | 2 | −28.272 | −15.801 | −15.519 | 1.00 | 28.45 | C |
| ATOM | 18 | N | VAL A | 3 | −27.673 | −13.473 | −9.916 | 1.00 | 21.67 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 19 | CA | VAL A | 3 | −27.211 | −13.628 | −8.531 | 1.00 | 17.31 | C |
| ATOM | 20 | C | VAL A | 3 | −27.766 | −14.942 | −8.031 | 1.00 | 21.55 | C |
| ATOM | 21 | O | VAL A | 3 | −28.956 | −15.181 | −8.218 | 1.00 | 23.80 | O |
| ATOM | 22 | CB | VAL A | 3 | −27.684 | −12.411 | −7.665 | 1.00 | 18.83 | C |
| ATOM | 23 | CG1 | VAL A | 3 | −27.285 | −12.551 | −6.189 | 1.00 | 15.22 | C |
| ATOM | 24 | CG2 | VAL A | 3 | −27.161 | −11.099 | −8.243 | 1.00 | 18.64 | C |
| ATOM | 25 | N | LEU A | 4 | −26.931 | −15.792 | −7.404 | 1.00 | 16.70 | N |
| ATOM | 26 | CA | LEU A | 4 | −27.359 | −17.082 | −6.867 | 1.00 | 16.80 | C |
| ATOM | 27 | C | LEU A | 4 | −27.413 | −16.969 | −5.352 | 1.00 | 23.50 | C |
| ATOM | 28 | O | LEU A | 4 | −26.463 | −16.479 | −4.760 | 1.00 | 25.22 | O |
| ATOM | 29 | CB | LEU A | 4 | −26.380 | −18.203 | −7.279 | 1.00 | 15.89 | C |
| ATOM | 30 | CG | LEU A | 4 | −26.185 | −18.377 | −8.787 | 1.00 | 19.65 | C |
| ATOM | 31 | CD1 | LEU A | 4 | −25.154 | −19.375 | −9.073 | 1.00 | 17.68 | C |
| ATOM | 32 | CD2 | LEU A | 4 | −27.512 | −18.750 | −9.488 | 1.00 | 22.34 | C |
| ATOM | 33 | N | THR A | 5 | −28.524 | −17.382 | −4.736 | 1.00 | 20.31 | N |
| ATOM | 34 | CA | THR A | 5 | −28.708 | −17.366 | −3.302 | 1.00 | 20.71 | C |
| ATOM | 35 | C | THR A | 5 | −28.833 | −18.796 | −2.767 | 1.00 | 25.41 | C |
| ATOM | 36 | O | THR A | 5 | −29.791 | −19.502 | −3.077 | 1.00 | 24.17 | O |
| ATOM | 37 | CB | THR A | 5 | −29.961 | −16.569 | −2.916 | 1.00 | 25.46 | C |
| ATOM | 38 | OG1 | THR A | 5 | −29.879 | −15.297 | −3.537 | 1.00 | 29.16 | O |
| ATOM | 39 | CG2 | THR A | 5 | −30.076 | −16.380 | −1.403 | 1.00 | 14.13 | C |
| ATOM | 40 | N | GLN A | 6 | −27.907 | −19.183 | −1.897 | 1.00 | 22.26 | N |
| ATOM | 41 | CA | GLN A | 6 | −27.947 | −20.492 | −1.279 | 1.00 | 21.43 | C |
| ATOM | 42 | C | GLN A | 6 | −28.603 | −20.432 | 0.087 | 1.00 | 25.67 | C |
| ATOM | 43 | O | GLN A | 6 | −28.441 | −19.467 | 0.837 | 1.00 | 24.82 | O |
| ATOM | 44 | CB | GLN A | 6 | −26.537 | −21.068 | −1.175 | 1.00 | 21.31 | C |
| ATOM | 45 | CG | GLN A | 6 | −26.069 | −21.516 | −2.531 | 1.00 | 24.46 | C |
| ATOM | 46 | CD | GLN A | 6 | −24.731 | −22.127 | −2.459 | 1.00 | 28.91 | C |
| ATOM | 47 | OE1 | GLN A | 6 | −23.739 | −21.447 | −2.701 | 1.00 | 27.87 | O |
| ATOM | 48 | NE2 | GLN A | 6 | −24.663 | −23.378 | −2.007 | 1.00 | 14.08 | N |
| ATOM | 49 | N | SER A | 7 | −29.352 | −21.463 | 0.409 | 1.00 | 23.85 | N |
| ATOM | 50 | CA | SER A | 7 | −29.971 | −21.567 | 1.709 | 1.00 | 25.39 | C |
| ATOM | 51 | C | SER A | 7 | −29.978 | −23.037 | 2.182 | 1.00 | 31.41 | C |
| ATOM | 52 | O | SER A | 7 | −30.064 | −23.965 | 1.378 | 1.00 | 30.77 | O |
| ATOM | 53 | CB | SER A | 7 | −31.377 | −20.972 | 1.713 | 1.00 | 30.10 | C |
| ATOM | 54 | OG | SER A | 7 | −32.330 | −21.860 | 1.162 | 1.00 | 38.70 | O |
| ATOM | 55 | N | PRO A | 8 | −29.902 | −23.264 | 3.502 | 1.00 | 29.03 | N |
| ATOM | 56 | CA | PRO A | 8 | −29.612 | −22.275 | 4.542 | 1.00 | 27.58 | C |
| ATOM | 57 | C | PRO A | 8 | −28.110 | −21.961 | 4.474 | 1.00 | 30.86 | C |
| ATOM | 58 | O | PRO A | 8 | −27.332 | −22.693 | 3.847 | 1.00 | 28.80 | O |
| ATOM | 59 | CB | PRO A | 8 | −29.987 | −23.021 | 5.820 | 1.00 | 28.97 | C |
| ATOM | 60 | CG | PRO A | 8 | −29.639 | −24.459 | 5.509 | 1.00 | 33.56 | C |
| ATOM | 61 | CD | PRO A | 8 | −29.846 | −24.643 | 4.033 | 1.00 | 29.95 | C |
| ATOM | 62 | N | ALA A | 9 | −27.689 | −20.873 | 5.094 | 1.00 | 28.39 | N |
| ATOM | 63 | CA | ALA A | 9 | −26.252 | −20.585 | 5.168 | 1.00 | 25.51 | C |
| ATOM | 64 | C | ALA A | 9 | −25.542 | −21.760 | 5.904 | 1.00 | 24.92 | C |
| ATOM | 65 | O | ALA A | 9 | −24.440 | −22.135 | 5.512 | 1.00 | 21.91 | O |
| ATOM | 66 | CB | ALA A | 9 | −26.021 | −19.278 | 5.900 | 1.00 | 25.52 | C |
| ATOM | 67 | N | THR A | 10 | −26.192 | −22.347 | 6.961 | 1.00 | 21.77 | N |
| ATOM | 68 | CA | THR A | 10 | −25.647 | −23.507 | 7.698 | 1.00 | 20.94 | C |
| ATOM | 69 | C | THR A | 10 | −26.690 | −24.616 | 7.802 | 1.00 | 22.68 | C |
| ATOM | 70 | O | THR A | 10 | −27.807 | −24.361 | 8.200 | 1.00 | 21.58 | O |
| ATOM | 71 | CB | THR A | 10 | −25.178 | −23.134 | 9.127 | 1.00 | 30.70 | C |
| ATOM | 72 | OG1 | THR A | 10 | −24.339 | −21.982 | 9.082 | 1.00 | 32.12 | O |
| ATOM | 73 | CG2 | THR A | 10 | −24.408 | −24.283 | 9.810 | 1.00 | 27.26 | C |
| ATOM | 74 | N | LEU A | 11 | −26.315 | −25.835 | 7.492 | 1.00 | 21.24 | N |
| ATOM | 75 | CA | LEU A | 11 | −27.184 | −26.997 | 7.620 | 1.00 | 23.61 | C |
| ATOM | 76 | C | LEU A | 11 | −26.607 | −27.928 | 8.740 | 1.00 | 27.28 | C |
| ATOM | 77 | O | LEU A | 11 | −25.503 | −28.446 | 8.584 | 1.00 | 28.92 | O |
| ATOM | 78 | CB | LEU A | 11 | −27.223 | −27.701 | 6.254 | 1.00 | 24.46 | C |
| ATOM | 79 | CG | LEU A | 11 | −28.299 | −28.749 | 6.036 | 1.00 | 32.05 | C |
| ATOM | 80 | CD1 | LEU A | 11 | −29.687 | −28.144 | 6.118 | 1.00 | 33.08 | C |
| ATOM | 81 | CD2 | LEU A | 11 | −28.129 | −29.423 | 4.656 | 1.00 | 35.07 | C |
| ATOM | 82 | N | SER A | 12 | −27.318 | −28.100 | 9.870 | 1.00 | 21.03 | N |
| ATOM | 83 | CA | SER A | 12 | −26.828 | −28.938 | 10.981 | 1.00 | 21.49 | C |
| ATOM | 84 | C | SER A | 12 | −27.490 | −30.315 | 11.003 | 1.00 | 25.91 | C |
| ATOM | 85 | O | SER A | 12 | −28.666 | −30.427 | 11.308 | 1.00 | 27.66 | O |
| ATOM | 86 | CB | SER A | 12 | −27.043 | −28.222 | 12.303 | 1.00 | 25.20 | C |
| ATOM | 87 | OG | SER A | 12 | −26.432 | −26.950 | 12.214 | 1.00 | 35.91 | O |
| ATOM | 88 | N | LEU A | 13 | −26.730 | −31.363 | 10.686 | 1.00 | 21.67 | N |
| ATOM | 89 | CA | LEU A | 13 | −27.242 | −32.726 | 10.539 | 1.00 | 21.36 | C |
| ATOM | 90 | C | LEU A | 13 | −26.275 | −33.752 | 11.117 | 1.00 | 25.58 | C |
| ATOM | 91 | O | LEU A | 13 | −25.142 | −33.428 | 11.480 | 1.00 | 23.40 | O |
| ATOM | 92 | CB | LEU A | 13 | −27.425 | −33.017 | 9.027 | 1.00 | 21.35 | C |
| ATOM | 93 | CG | LEU A | 13 | −28.425 | −32.126 | 8.253 | 1.00 | 25.22 | C |
| ATOM | 94 | CD1 | LEU A | 13 | −28.277 | −32.316 | 6.777 | 1.00 | 25.07 | C |
| ATOM | 95 | CD2 | LEU A | 13 | −29.860 | −32.395 | 8.666 | 1.00 | 27.09 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 96 | N | SER A | 14 | −26.714 | −35.009 | 11.150 | 1.00 | 25.30 | N |
| ATOM | 97 | CA | SER A | 14 | −25.935 | −36.121 | 11.673 | 1.00 | 26.42 | C |
| ATOM | 98 | C | SER A | 14 | −25.501 | −37.095 | 10.550 | 1.00 | 32.77 | C |
| ATOM | 99 | O | SER A | 14 | −26.217 | −37.217 | 9.545 | 1.00 | 30.92 | O |
| ATOM | 100 | CB | SER A | 14 | −26.771 | −36.873 | 12.700 | 1.00 | 31.82 | C |
| ATOM | 101 | OG | SER A | 14 | −26.919 | −36.092 | 13.882 | 1.00 | 45.13 | O |
| ATOM | 102 | N | PRO A | 15 | −24.352 | −37.826 | 10.724 | 1.00 | 29.67 | N |
| ATOM | 103 | CA | PRO A | 15 | −23.963 | −38.832 | 9.718 | 1.00 | 29.61 | C |
| ATOM | 104 | C | PRO A | 15 | −25.085 | −39.854 | 9.532 | 1.00 | 33.22 | C |
| ATOM | 105 | O | PRO A | 15 | −25.662 | −40.274 | 10.515 | 1.00 | 34.57 | O |
| ATOM | 106 | CB | PRO A | 15 | −22.694 | −39.456 | 10.305 | 1.00 | 31.16 | C |
| ATOM | 107 | CG | PRO A | 15 | −22.163 | −38.412 | 11.246 | 1.00 | 33.66 | C |
| ATOM | 108 | CD | PRO A | 15 | −23.379 | −37.791 | 11.839 | 1.00 | 29.33 | C |
| ATOM | 109 | N | GLY A | 16 | −25.466 | −40.119 | 8.285 | 1.00 | 28.05 | N |
| ATOM | 110 | CA | GLY A | 16 | −26.571 | −41.004 | 7.958 | 1.00 | 28.94 | C |
| ATOM | 111 | C | GLY A | 16 | −27.821 | −40.278 | 7.488 | 1.00 | 34.37 | C |
| ATOM | 112 | O | GLY A | 16 | −28.652 | −40.888 | 6.803 | 1.00 | 35.89 | O |
| ATOM | 113 | N | GLU A | 17 | −27.972 | −38.970 | 7.831 | 1.00 | 29.19 | N |
| ATOM | 114 | CA | GLU A | 17 | −29.142 | −38.198 | 7.435 | 1.00 | 28.44 | C |
| ATOM | 115 | C | GLU A | 17 | −29.068 | −37.672 | 5.994 | 1.00 | 32.69 | C |
| ATOM | 116 | O | GLU A | 17 | −27.981 | −37.477 | 5.427 | 1.00 | 32.10 | O |
| ATOM | 117 | CB | GLU A | 17 | −29.377 | −37.028 | 8.405 | 1.00 | 29.34 | C |
| ATOM | 118 | CG | GLU A | 17 | −29.663 | −37.479 | 9.834 | 1.00 | 40.29 | C |
| ATOM | 119 | CD | GLU A | 17 | −30.232 | −36.405 | 10.745 | 1.00 | 64.60 | C |
| ATOM | 120 | OE1 | GLU A | 17 | −31.298 | −36.652 | 11.354 | 1.00 | 76.92 | O |
| ATOM | 121 | OE2 | GLU A | 17 | −29.619 | −35.317 | 10.849 | 1.00 | 48.75 | O |
| ATOM | 122 | N | ARG A | 18 | −30.263 | −37.449 | 5.415 | 1.00 | 28.91 | N |
| ATOM | 123 | CA | ARG A | 18 | −30.464 | −36.864 | 4.099 | 1.00 | 27.20 | C |
| ATOM | 124 | C | ARG A | 18 | −30.250 | −35.329 | 4.210 | 1.00 | 30.72 | C |
| ATOM | 125 | O | ARG A | 18 | −30.881 | −34.660 | 5.034 | 1.00 | 30.74 | O |
| ATOM | 126 | CB | ARG A | 18 | −31.878 | −37.184 | 3.594 | 1.00 | 27.75 | C |
| ATOM | 127 | CG | ARG A | 18 | −32.344 | −36.390 | 2.362 | 1.00 | 41.48 | C |
| ATOM | 128 | CD | ARG A | 18 | −33.687 | −36.898 | 1.854 | 1.00 | 49.18 | C |
| ATOM | 129 | NE | ARG A | 18 | −33.502 | −37.845 | 0.747 | 1.00 | 67.44 | N |
| ATOM | 130 | CZ | ARG A | 18 | −33.756 | −37.616 | −0.544 | 1.00 | 84.13 | C |
| ATOM | 131 | NH1 | ARG A | 18 | −34.244 | −36.441 | −0.941 | 1.00 | 70.93 | N |
| ATOM | 132 | NH2 | ARG A | 18 | −33.527 | −38.561 | −1.449 | 1.00 | 74.74 | N |
| ATOM | 133 | N | ALA A | 19 | −29.338 | −34.787 | 3.398 | 1.00 | 25.53 | N |
| ATOM | 134 | CA | ALA A | 19 | −29.039 | −33.357 | 3.353 | 1.00 | 22.29 | C |
| ATOM | 135 | C | ALA A | 19 | −29.709 | −32.827 | 2.087 | 1.00 | 25.38 | C |
| ATOM | 136 | O | ALA A | 19 | −29.680 | −33.497 | 1.065 | 1.00 | 24.09 | O |
| ATOM | 137 | CB | ALA A | 19 | −27.525 | −33.140 | 3.286 | 1.00 | 21.32 | C |
| ATOM | 138 | N | THR A | 20 | −30.352 | −31.669 | 2.166 | 1.00 | 23.31 | N |
| ATOM | 139 | CA | THR A | 20 | −31.007 | −31.035 | 1.021 | 1.00 | 24.50 | C |
| ATOM | 140 | C | THR A | 20 | −30.516 | −29.594 | 1.038 | 1.00 | 27.10 | C |
| ATOM | 141 | O | THR A | 20 | −30.684 | −28.924 | 2.053 | 1.00 | 26.81 | O |
| ATOM | 142 | CB | THR A | 20 | −32.549 | −31.168 | 1.115 | 1.00 | 34.24 | C |
| ATOM | 143 | OG1 | THR A | 20 | −32.903 | −32.529 | 0.864 | 1.00 | 35.83 | O |
| ATOM | 144 | CG2 | THR A | 20 | −33.264 | −30.320 | 0.091 | 1.00 | 34.69 | C |
| ATOM | 145 | N | LEU A | 21 | −29.853 | −29.151 | −0.049 | 1.00 | 21.27 | N |
| ATOM | 146 | CA | LEU A | 21 | −29.261 | −27.818 | −0.164 | 1.00 | 19.66 | C |
| ATOM | 147 | C | LEU A | 21 | −29.961 | −27.122 | −1.275 | 1.00 | 25.80 | C |
| ATOM | 148 | O | LEU A | 21 | −30.175 | −27.725 | −2.305 | 1.00 | 27.08 | O |
| ATOM | 149 | CB | LEU A | 21 | −27.756 | −27.906 | −0.468 | 1.00 | 18.12 | C |
| ATOM | 150 | CG | LEU A | 21 | −26.886 | −28.324 | 0.715 | 1.00 | 20.32 | C |
| ATOM | 151 | CD1 | LEU A | 21 | −26.866 | −29.837 | 0.875 | 1.00 | 19.96 | C |
| ATOM | 152 | CD2 | LEU A | 21 | −25.466 | −27.856 | 0.510 | 1.00 | 22.67 | C |
| ATOM | 153 | N | SER A | 22 | −30.305 | −25.857 | −1.083 | 1.00 | 22.29 | N |
| ATOM | 154 | CA | SER A | 22 | −31.093 | −25.094 | −2.021 | 1.00 | 22.63 | C |
| ATOM | 155 | C | SER A | 22 | −30.252 | −24.026 | −2.687 | 1.00 | 26.66 | C |
| ATOM | 156 | O | SER A | 22 | −29.350 | −23.470 | −2.055 | 1.00 | 24.85 | O |
| ATOM | 157 | CB | SER A | 22 | −32.287 | −24.469 | −1.294 | 1.00 | 26.43 | C |
| ATOM | 158 | OG | SER A | 22 | −32.902 | −23.434 | −2.041 | 1.00 | 36.29 | O |
| ATOM | 159 | N | CYS A | 23 | −30.550 | −23.747 | −3.974 | 1.00 | 22.70 | N |
| ATOM | 160 | CA | CYS A | 23 | −29.874 | −22.703 | −4.731 | 1.00 | 22.38 | C |
| ATOM | 161 | C | CYS A | 23 | −30.905 | −22.058 | −5.604 | 1.00 | 25.64 | C |
| ATOM | 162 | O | CYS A | 23 | −31.574 | −22.745 | −6.386 | 1.00 | 24.65 | O |
| ATOM | 163 | CB | CYS A | 23 | −28.711 | −23.257 | −5.548 | 1.00 | 23.26 | C |
| ATOM | 164 | SG | CYS A | 23 | −27.906 | −22.048 | −6.635 | 1.00 | 28.02 | S |
| ATOM | 165 | N | ARG A | 24 | −31.055 | −20.738 | −5.461 | 1.00 | 21.40 | N |
| ATOM | 166 | CA | ARG A | 24 | −32.017 | −19.996 | −6.246 | 1.00 | 21.42 | C |
| ATOM | 167 | C | ARG A | 24 | −31.386 | −18.852 | −6.999 | 1.00 | 23.15 | C |
| ATOM | 168 | O | ARG A | 24 | −30.670 | −18.046 | −6.411 | 1.00 | 22.28 | O |
| ATOM | 169 | CB | ARG A | 24 | −33.130 | −19.534 | −5.343 | 1.00 | 23.11 | C |
| ATOM | 170 | CG | ARG A | 24 | −33.956 | −20.737 | −4.868 | 1.00 | 27.76 | C |
| ATOM | 171 | CD | ARG A | 24 | −35.045 | −20.268 | −4.000 | 1.00 | 19.74 | C |
| ATOM | 172 | NE | ARG A | 24 | −36.018 | −19.505 | −4.768 | 1.00 | 28.41 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 173 | CZ | ARG A | 24 | −37.068 | −18.900 | −4.238 | 1.00 | 39.47 | C |
| ATOM | 174 | NH1 | ARG A | 24 | −37.283 | −18.955 | −2.928 | 1.00 | 26.42 | N |
| ATOM | 175 | NH2 | ARG A | 24 | −37.902 | −18.219 | −5.005 | 1.00 | 24.70 | N |
| ATOM | 176 | N | ALA A | 25 | −31.618 | −18.816 | −8.312 | 1.00 | 20.64 | N |
| ATOM | 177 | CA | ALA A | 25 | −31.104 | −17.806 | −9.234 | 1.00 | 21.54 | C |
| ATOM | 178 | C | ALA A | 25 | −32.113 | −16.638 | −9.378 | 1.00 | 30.57 | C |
| ATOM | 179 | O | ALA A | 25 | −33.329 | −16.854 | −9.368 | 1.00 | 32.16 | O |
| ATOM | 180 | CB | ALA A | 25 | −30.839 | −18.438 | −10.596 | 1.00 | 22.02 | C |
| ATOM | 181 | N | SER A | 26 | −31.601 | −15.403 | −9.502 | 1.00 | 27.71 | N |
| ATOM | 182 | CA | SER A | 26 | −32.433 | −14.202 | −9.626 | 1.00 | 28.00 | C |
| ATOM | 183 | C | SER A | 26 | −33.156 | −14.148 | −10.996 | 1.00 | 35.55 | C |
| ATOM | 184 | O | SER A | 26 | −34.183 | −13.480 | −11.140 | 1.00 | 37.34 | O |
| ATOM | 185 | CB | SER A | 26 | −31.568 | −12.960 | −9.439 | 1.00 | 27.80 | C |
| ATOM | 186 | OG | SER A | 26 | −30.441 | −12.976 | −10.302 | 1.00 | 30.31 | O |
| ATOM | 187 | N | LYS A | 27 | −32.583 | −14.830 | −11.993 | 1.00 | 30.87 | N |
| ATOM | 188 | CA | LYS A | 27 | −33.055 | −14.915 | −13.369 | 1.00 | 30.99 | C |
| ATOM | 189 | C | LYS A | 27 | −32.820 | −16.378 | −13.751 | 1.00 | 31.07 | C |
| ATOM | 190 | O | LYS A | 27 | −31.935 | −17.000 | −13.192 | 1.00 | 27.71 | O |
| ATOM | 191 | CB | LYS A | 27 | −32.190 | −13.984 | −14.254 | 1.00 | 34.38 | C |
| ATOM | 192 | CG | LYS A | 27 | −32.702 | −13.727 | −15.662 | 1.00 | 57.88 | C |
| ATOM | 193 | CD | LYS A | 27 | −31.560 | −13.464 | −16.703 | 1.00 | 64.53 | C |
| ATOM | 194 | CE | LYS A | 27 | −31.216 | −14.671 | −17.578 | 1.00 | 53.44 | C |
| ATOM | 195 | NZ | LYS A | 27 | −30.228 | −14.336 | −18.665 | 1.00 | 43.38 | N |
| ATOM | 196 | N | GLY A | 28 | −33.637 | −16.923 | −14.642 | 1.00 | 29.23 | N |
| ATOM | 197 | CA | GLY A | 28 | −33.522 | −18.306 | −15.070 | 1.00 | 28.28 | C |
| ATOM | 198 | C | GLY A | 28 | −32.189 | −18.654 | −15.709 | 1.00 | 31.38 | C |
| ATOM | 199 | O | GLY A | 28 | −31.666 | −17.887 | −16.525 | 1.00 | 31.41 | O |
| ATOM | 200 | N | VAL A | 29 | −31.668 | −19.848 | −15.375 | 1.00 | 26.81 | N |
| ATOM | 201 | CA | VAL A | 29 | −30.412 | −20.372 | −15.910 | 1.00 | 26.28 | C |
| ATOM | 202 | C | VAL A | 29 | −30.666 | −21.581 | −16.841 | 1.00 | 33.17 | C |
| ATOM | 203 | O | VAL A | 29 | −29.712 | −22.251 | −17.236 | 1.00 | 32.97 | O |
| ATOM | 204 | CB | VAL A | 29 | −29.341 | −20.663 | −14.796 | 1.00 | 27.72 | C |
| ATOM | 205 | CG1 | VAL A | 29 | −28.899 | −19.371 | −14.108 | 1.00 | 26.87 | C |
| ATOM | 206 | CG2 | VAL A | 29 | −29.836 | −21.657 | −13.760 | 1.00 | 26.39 | C |
| ATOM | 207 | N | SER A | 30 | −31.928 | −21.801 | −17.267 | 1.00 | 32.30 | N |
| ATOM | 208 | CA | SER A | 30 | −32.261 | −22.871 | −18.212 | 1.00 | 33.70 | C |
| ATOM | 209 | C | SER A | 30 | −32.541 | −22.325 | −19.598 | 1.00 | 42.31 | C |
| ATOM | 210 | O | SER A | 30 | −33.175 | −21.285 | −19.722 | 1.00 | 42.53 | O |
| ATOM | 211 | CB | SER A | 30 | −33.473 | −23.669 | −17.739 | 1.00 | 36.36 | C |
| ATOM | 212 | OG | SER A | 30 | −33.311 | −24.127 | −16.406 | 1.00 | 38.88 | O |
| ATOM | 213 | N | THR A | 31 | −32.024 | −23.020 | −20.639 | 1.00 | 42.62 | N |
| ATOM | 214 | CA | THR A | 31 | −32.275 | −22.774 | −22.071 | 1.00 | 43.80 | C |
| ATOM | 215 | C | THR A | 31 | −32.109 | −24.083 | −22.831 | 1.00 | 48.20 | C |
| ATOM | 216 | O | THR A | 31 | −31.103 | −24.784 | −22.625 | 1.00 | 46.56 | O |
| ATOM | 217 | CB | THR A | 31 | −31.274 | −21.811 | −22.791 | 1.00 | 50.67 | C |
| ATOM | 218 | OG1 | THR A | 31 | −30.411 | −21.186 | −21.872 | 1.00 | 49.36 | O |
| ATOM | 219 | CG2 | THR A | 31 | −31.987 | −20.772 | −23.681 | 1.00 | 51.84 | C |
| ATOM | 220 | N | SER A | 32 | −33.010 | −24.329 | −23.799 | 1.00 | 45.02 | N |
| ATOM | 221 | CA | SER A | 32 | −32.894 | −25.433 | −24.742 | 1.00 | 45.24 | C |
| ATOM | 222 | C | SER A | 32 | −32.626 | −26.790 | −24.102 | 1.00 | 48.05 | C |
| ATOM | 223 | O | SER A | 32 | −31.643 | −27.438 | −24.441 | 1.00 | 48.76 | O |
| ATOM | 224 | CB | SER A | 32 | −31.786 | −25.121 | −25.749 | 1.00 | 49.27 | C |
| ATOM | 225 | OG | SER A | 32 | −32.016 | −23.882 | −26.396 | 1.00 | 64.66 | O |
| ATOM | 226 | N | GLY A | 33 | −33.461 | −27.191 | −23.161 | 1.00 | 42.91 | N |
| ATOM | 227 | CA | GLY A | 33 | −33.305 | −28.486 | −22.509 | 1.00 | 41.98 | C |
| ATOM | 228 | C | GLY A | 33 | −32.291 | −28.609 | −21.384 | 1.00 | 42.82 | C |
| ATOM | 229 | O | GLY A | 33 | −32.340 | −29.618 | −20.680 | 1.00 | 43.68 | O |
| ATOM | 230 | N | TYR A | 34 | −31.373 | −27.628 | −21.171 | 1.00 | 36.01 | N |
| ATOM | 231 | CA | TYR A | 34 | −30.388 | −27.708 | −20.073 | 1.00 | 34.20 | C |
| ATOM | 232 | C | TYR A | 34 | −30.411 | −26.520 | −19.152 | 1.00 | 35.74 | C |
| ATOM | 233 | O | TYR A | 34 | −30.677 | −25.411 | −19.600 | 1.00 | 35.40 | O |
| ATOM | 234 | CB | TYR A | 34 | −28.970 | −27.872 | −20.616 | 1.00 | 35.61 | C |
| ATOM | 235 | CG | TYR A | 34 | −28.813 | −29.202 | −21.298 | 1.00 | 40.87 | C |
| ATOM | 236 | CD1 | TYR A | 34 | −28.462 | −30.335 | −20.574 | 1.00 | 42.85 | C |
| ATOM | 237 | CD2 | TYR A | 34 | −29.216 | −29.377 | −22.617 | 1.00 | 44.29 | C |
| ATOM | 238 | CE1 | TYR A | 34 | −28.393 | −31.587 | −21.175 | 1.00 | 44.94 | C |
| ATOM | 239 | CE2 | TYR A | 34 | −29.199 | −30.633 | −23.219 | 1.00 | 47.01 | C |
| ATOM | 240 | CZ | TYR A | 34 | −28.773 | −31.736 | −22.496 | 1.00 | 56.49 | C |
| ATOM | 241 | OH | TYR A | 34 | −28.698 | −32.961 | −23.114 | 1.00 | 60.48 | O |
| ATOM | 242 | N | SER A | 35 | −30.080 | −26.758 | −17.853 | 1.00 | 29.99 | N |
| ATOM | 243 | CA | SER A | 35 | −29.930 | −25.737 | −16.809 | 1.00 | 26.63 | C |
| ATOM | 244 | C | SER A | 35 | −28.430 | −25.612 | −16.541 | 1.00 | 27.11 | C |
| ATOM | 245 | O | SER A | 35 | −27.787 | −26.577 | −16.129 | 1.00 | 25.56 | O |
| ATOM | 246 | CB | SER A | 35 | −30.647 | −26.161 | −15.542 | 1.00 | 26.79 | C |
| ATOM | 247 | OG | SER A | 35 | −32.030 | −26.354 | −15.767 | 1.00 | 34.50 | O |
| ATOM | 248 | N | TYR A | 36 | −27.866 | −24.436 | −16.769 | 1.00 | 22.95 | N |
| ATOM | 249 | CA | TYR A | 36 | −26.429 | −24.208 | −16.606 | 1.00 | 20.73 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 250 | C | TYR A | 36 | −26.142 | −23.859 | −15.150 | 1.00 | 21.52 | C |
| ATOM | 251 | O | TYR A | 36 | −25.884 | −22.709 | −14.825 | 1.00 | 20.34 | O |
| ATOM | 252 | CB | TYR A | 36 | −25.961 | −23.123 | −17.581 | 1.00 | 22.10 | C |
| ATOM | 253 | CG | TYR A | 36 | −26.058 | −23.592 | −19.007 | 1.00 | 23.89 | C |
| ATOM | 254 | CD2 | TYR A | 36 | −24.948 | −24.112 | −19.663 | 1.00 | 25.22 | C |
| ATOM | 255 | CD1 | TYR A | 36 | −27.292 | −23.693 | −19.643 | 1.00 | 25.89 | C |
| ATOM | 256 | CE2 | TYR A | 36 | −25.044 | −24.607 | −20.961 | 1.00 | 26.71 | C |
| ATOM | 257 | CE1 | TYR A | 36 | −27.400 | −24.177 | −20.940 | 1.00 | 26.37 | C |
| ATOM | 258 | CZ | TYR A | 36 | −26.273 | −24.624 | −21.604 | 1.00 | 33.57 | C |
| ATOM | 259 | OH | TYR A | 36 | −26.415 | −25.130 | −22.877 | 1.00 | 39.32 | O |
| ATOM | 260 | N | LEU A | 37 | −26.249 | −24.868 | −14.278 | 1.00 | 17.01 | N |
| ATOM | 261 | CA | LEU A | 37 | −26.095 | −24.756 | −12.836 | 1.00 | 16.38 | C |
| ATOM | 262 | C | LEU A | 37 | −25.281 | −25.939 | −12.343 | 1.00 | 18.22 | C |
| ATOM | 263 | O | LEU A | 37 | −25.672 | −27.059 | −12.615 | 1.00 | 19.01 | O |
| ATOM | 264 | CB | LEU A | 37 | −27.511 | −24.747 | −12.204 | 1.00 | 17.06 | C |
| ATOM | 265 | CG | LEU A | 37 | −27.664 | −24.176 | −10.756 | 1.00 | 19.79 | C |
| ATOM | 266 | CD1 | LEU A | 37 | −27.336 | −25.207 | −9.709 | 1.00 | 16.70 | C |
| ATOM | 267 | CD2 | LEU A | 37 | −26.859 | −22.870 | −10.543 | 1.00 | 20.35 | C |
| ATOM | 268 | N | HIS A | 38 | −24.123 | −25.704 | −11.705 | 1.00 | 13.31 | N |
| ATOM | 269 | CA | HIS A | 38 | −23.196 | −26.758 | −11.248 | 1.00 | 11.46 | C |
| ATOM | 270 | C | HIS A | 38 | −22.871 | −26.625 | −9.745 | 1.00 | 15.73 | C |
| ATOM | 271 | O | HIS A | 38 | −22.851 | −25.512 | −9.205 | 1.00 | 14.16 | O |
| ATOM | 272 | CB | HIS A | 38 | −21.873 | −26.703 | −12.067 | 1.00 | 11.42 | C |
| ATOM | 273 | CG | HIS A | 38 | −22.028 | −26.257 | −13.471 | 1.00 | 13.74 | C |
| ATOM | 274 | ND1 | HIS A | 38 | −22.322 | −27.157 | −14.493 | 1.00 | 16.02 | N |
| ATOM | 275 | CD2 | HIS A | 38 | −21.948 | −25.011 | −13.990 | 1.00 | 15.18 | C |
| ATOM | 276 | CE1 | HIS A | 38 | −22.415 | −26.429 | −15.606 | 1.00 | 15.39 | C |
| ATOM | 277 | NE2 | HIS A | 38 | −22.209 | −25.128 | −15.351 | 1.00 | 15.65 | N |
| ATOM | 278 | N | TRP A | 39 | −22.617 | −27.762 | −9.081 | 1.00 | 13.92 | N |
| ATOM | 279 | CA | TRP A | 39 | −22.321 | −27.829 | −7.645 | 1.00 | 14.12 | C |
| ATOM | 280 | C | TRP A | 39 | −20.915 | −28.314 | −7.343 | 1.00 | 20.19 | C |
| ATOM | 281 | O | TRP A | 39 | −20.457 | −29.298 | −7.908 | 1.00 | 19.88 | O |
| ATOM | 282 | CB | TRP A | 39 | −23.305 | −28.740 | −6.919 | 1.00 | 12.90 | C |
| ATOM | 283 | CG | TRP A | 39 | −24.723 | −28.277 | −7.015 | 1.00 | 15.04 | C |
| ATOM | 284 | CD1 | TRP A | 39 | −25.633 | −28.592 | −7.981 | 1.00 | 18.43 | C |
| ATOM | 285 | CD2 | TRP A | 39 | −25.405 | −27.438 | −6.075 | 1.00 | 15.42 | C |
| ATOM | 286 | NE1 | TRP A | 39 | −26.857 | −28.042 | −7.675 | 1.00 | 18.60 | N |
| ATOM | 287 | CE2 | TRP A | 39 | −26.747 | −27.327 | −6.511 | 1.00 | 19.58 | C |
| ATOM | 288 | CE3 | TRP A | 39 | −25.046 | −26.880 | −4.825 | 1.00 | 17.22 | C |
| ATOM | 289 | CZ2 | TRP A | 39 | −27.729 | −26.667 | −5.758 | 1.00 | 19.64 | C |
| ATOM | 290 | CZ3 | TRP A | 39 | −26.024 | −26.240 | −4.073 | 1.00 | 18.82 | C |
| ATOM | 291 | CH2 | TRP A | 39 | −27.356 | −26.167 | −4.525 | 1.00 | 19.75 | C |
| ATOM | 292 | N | TYR A | 40 | −20.272 | −27.664 | −6.380 | 1.00 | 18.13 | N |
| ATOM | 293 | CA | TYR A | 40 | −18.926 | −27.961 | −5.939 | 1.00 | 17.80 | C |
| ATOM | 294 | C | TYR A | 40 | −18.924 | −28.197 | −4.431 | 1.00 | 23.71 | C |
| ATOM | 295 | O | TYR A | 40 | −19.750 | −27.619 | −3.741 | 1.00 | 24.47 | O |
| ATOM | 296 | CB | TYR A | 40 | −18.030 | −26.749 | −6.235 | 1.00 | 17.12 | C |
| ATOM | 297 | CG | TYR A | 40 | −18.026 | −26.391 | −7.698 | 1.00 | 17.74 | C |
| ATOM | 298 | CD1 | TYR A | 40 | −18.960 | −25.495 | −8.222 | 1.00 | 18.99 | C |
| ATOM | 299 | CD2 | TYR A | 40 | −17.154 | −27.015 | −8.583 | 1.00 | 16.45 | C |
| ATOM | 300 | CE1 | TYR A | 40 | −19.046 | −25.263 | −9.589 | 1.00 | 18.23 | C |
| ATOM | 301 | CE2 | TYR A | 40 | −17.229 | −26.785 | −9.948 | 1.00 | 17.30 | C |
| ATOM | 302 | CZ | TYR A | 40 | −18.142 | −25.870 | −10.450 | 1.00 | 24.55 | C |
| ATOM | 303 | OH | TYR A | 40 | −18.129 | −25.586 | −11.808 | 1.00 | 19.91 | O |
| ATOM | 304 | N | GLN A | 41 | −17.961 | −28.982 | −3.929 | 1.00 | 18.99 | N |
| ATOM | 305 | CA | GLN A | 41 | −17.697 | −29.212 | −2.503 | 1.00 | 17.04 | C |
| ATOM | 306 | C | GLN A | 41 | −16.321 | −28.600 | −2.224 | 1.00 | 19.63 | C |
| ATOM | 307 | O | GLN A | 41 | −15.407 | −28.757 | −3.044 | 1.00 | 16.69 | O |
| ATOM | 308 | CB | GLN A | 41 | −17.609 | −30.701 | −2.178 | 1.00 | 18.53 | C |
| ATOM | 309 | CG | GLN A | 41 | −17.398 | −31.037 | −0.687 | 1.00 | 11.47 | C |
| ATOM | 310 | CD | GLN A | 41 | −17.150 | −32.509 | −0.514 | 1.00 | 20.11 | C |
| ATOM | 311 | OE1 | GLN A | 41 | −17.965 | −33.253 | 0.019 | 1.00 | 19.65 | O |
| ATOM | 312 | NE2 | GLN A | 41 | −16.006 | −32.961 | −0.939 | 1.00 | 16.03 | N |
| ATOM | 313 | N | GLN A | 42 | −16.188 | −27.878 | −1.097 | 1.00 | 18.33 | N |
| ATOM | 314 | CA | GLN A | 42 | −14.916 | −27.316 | −0.662 | 1.00 | 18.37 | C |
| ATOM | 315 | C | GLN A | 42 | −14.696 | −27.669 | 0.798 | 1.00 | 24.93 | C |
| ATOM | 316 | O | GLN A | 42 | −15.551 | −27.422 | 1.637 | 1.00 | 25.45 | O |
| ATOM | 317 | CB | GLN A | 42 | −14.814 | −25.791 | −0.861 | 1.00 | 18.08 | C |
| ATOM | 318 | CG | GLN A | 42 | −13.346 | −25.302 | −0.752 | 1.00 | 5.59 | C |
| ATOM | 319 | CD | GLN A | 42 | −13.185 | −23.836 | −1.094 | 1.00 | 22.04 | C |
| ATOM | 320 | OE1 | GLN A | 42 | −14.117 | −23.041 | −0.921 | 1.00 | 16.98 | O |
| ATOM | 321 | NE2 | GLN A | 42 | −11.994 | −23.429 | −1.595 | 1.00 | 9.30 | N |
| ATOM | 322 | N | LYS A | 43 | −13.541 | −28.252 | 1.077 | 1.00 | 24.08 | N |
| ATOM | 323 | CA | LYS A | 43 | −13.055 | −28.584 | 2.401 | 1.00 | 24.86 | C |
| ATOM | 324 | C | LYS A | 43 | −12.002 | −27.532 | 2.769 | 1.00 | 30.30 | C |
| ATOM | 325 | O | LYS A | 43 | −11.346 | −27.014 | 1.861 | 1.00 | 27.97 | O |
| ATOM | 326 | CB | LYS A | 43 | −12.446 | −29.987 | 2.393 | 1.00 | 27.26 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 327 | CG | LYS A | 43 | −13.507 | −31.027 | 2.123 | 1.00 | 27.79 | C |
| ATOM | 328 | CD | LYS A | 43 | −12.980 | −32.419 | 2.314 | 1.00 | 33.92 | C |
| ATOM | 329 | CE | LYS A | 43 | −14.077 | −33.452 | 2.267 | 1.00 | 38.68 | C |
| ATOM | 330 | NZ | LYS A | 43 | −13.760 | −34.617 | 3.139 | 1.00 | 58.80 | N |
| ATOM | 331 | N | PRO A | 44 | −11.836 | −27.174 | 4.074 | 1.00 | 30.23 | N |
| ATOM | 332 | CA | PRO A | 44 | −10.838 | −26.142 | 4.447 | 1.00 | 29.06 | C |
| ATOM | 333 | C | PRO A | 44 | −9.433 | −26.410 | 3.912 | 1.00 | 29.53 | C |
| ATOM | 334 | O | PRO A | 44 | −8.952 | −27.537 | 3.971 | 1.00 | 28.05 | O |
| ATOM | 335 | CB | PRO A | 44 | −10.855 | −26.168 | 5.979 | 1.00 | 30.75 | C |
| ATOM | 336 | CG | PRO A | 44 | −12.189 | −26.666 | 6.334 | 1.00 | 35.46 | C |
| ATOM | 337 | CD | PRO A | 44 | −12.547 | −27.673 | 5.271 | 1.00 | 32.02 | C |
| ATOM | 338 | N | GLY A | 45 | −8.848 | −25.387 | 3.302 | 1.00 | 26.73 | N |
| ATOM | 339 | CA | GLY A | 45 | −7.526 | −25.459 | 2.698 | 1.00 | 27.32 | C |
| ATOM | 340 | C | GLY A | 45 | −7.444 | −26.242 | 1.414 | 1.00 | 32.23 | C |
| ATOM | 341 | O | GLY A | 45 | −6.338 | −26.459 | 0.924 | 1.00 | 34.62 | O |
| ATOM | 342 | N | GLN A | 46 | −8.584 | −26.681 | 0.847 | 1.00 | 27.27 | N |
| ATOM | 343 | CA | GLN A | 46 | −8.579 | −27.467 | −0.391 | 1.00 | 26.62 | C |
| ATOM | 344 | C | GLN A | 46 | −9.314 | −26.735 | −1.500 | 1.00 | 26.20 | C |
| ATOM | 345 | O | GLN A | 46 | −10.155 | −25.864 | −1.241 | 1.00 | 25.35 | O |
| ATOM | 346 | CB | GLN A | 46 | −9.219 | −28.843 | −0.169 | 1.00 | 27.85 | C |
| ATOM | 347 | CG | GLN A | 46 | −8.533 | −29.677 | 0.912 | 1.00 | 27.24 | C |
| ATOM | 348 | CD | GLN A | 46 | −9.032 | −31.103 | 0.921 | 1.00 | 46.53 | C |
| ATOM | 349 | OE1 | GLN A | 46 | −9.404 | −31.678 | −0.122 | 1.00 | 40.60 | O |
| ATOM | 350 | NE2 | GLN A | 46 | −8.978 | −31.749 | 2.082 | 1.00 | 46.34 | N |
| ATOM | 351 | N | ALA A | 47 | −8.980 | −27.061 | −2.733 | 1.00 | 21.33 | N |
| ATOM | 352 | CA | ALA A | 47 | −9.647 | −26.434 | −3.861 | 1.00 | 21.01 | C |
| ATOM | 353 | C | ALA A | 47 | −11.044 | −27.067 | −4.027 | 1.00 | 22.34 | C |
| ATOM | 354 | O | ALA A | 47 | −11.222 | −28.256 | −3.694 | 1.00 | 20.67 | O |
| ATOM | 355 | CB | ALA A | 47 | −8.837 | −26.641 | −5.122 | 1.00 | 22.89 | C |
| ATOM | 356 | N | PRO A | 48 | −12.028 | −26.318 | −4.567 | 1.00 | 16.53 | N |
| ATOM | 357 | CA | PRO A | 48 | −13.347 | −26.916 | −4.813 | 1.00 | 16.24 | C |
| ATOM | 358 | C | PRO A | 48 | −13.291 | −28.182 | −5.679 | 1.00 | 21.15 | C |
| ATOM | 359 | O | PRO A | 48 | −12.294 | −28.468 | −6.372 | 1.00 | 19.77 | O |
| ATOM | 360 | CB | PRO A | 48 | −14.128 | −25.790 | −5.497 | 1.00 | 16.80 | C |
| ATOM | 361 | CG | PRO A | 48 | −13.455 | −24.581 | −5.106 | 1.00 | 20.20 | C |
| ATOM | 362 | CD | PRO A | 48 | −12.014 | −24.908 | −4.975 | 1.00 | 16.90 | C |
| ATOM | 363 | N | ARG A | 49 | −14.334 | −28.993 | −5.572 | 1.00 | 18.58 | N |
| ATOM | 364 | CA | ARG A | 49 | −14.412 | −30.251 | −6.318 | 1.00 | 17.71 | C |
| ATOM | 365 | C | ARG A | 49 | −15.760 | −30.279 | −6.981 | 1.00 | 20.27 | C |
| ATOM | 366 | O | ARG A | 49 | −16.750 | −30.155 | −6.276 | 1.00 | 19.59 | O |
| ATOM | 367 | CB | ARG A | 49 | −14.275 | −31.439 | −5.331 | 1.00 | 18.33 | C |
| ATOM | 368 | CG | ARG A | 49 | −14.156 | −32.787 | −6.007 | 1.00 | 28.43 | C |
| ATOM | 369 | CD | ARG A | 49 | −14.329 | −33.967 | −5.083 | 1.00 | 39.64 | C |
| ATOM | 370 | NE | ARG A | 49 | −14.411 | −35.214 | −5.856 | 1.00 | 50.07 | N |
| ATOM | 371 | CZ | ARG A | 49 | −14.630 | −36.425 | −5.345 | 1.00 | 60.94 | C |
| ATOM | 372 | NH1 | ARG A | 49 | −14.784 | −36.585 | −4.033 | 1.00 | 50.54 | N |
| ATOM | 373 | NH2 | ARG A | 49 | −14.688 | −37.487 | −6.140 | 1.00 | 45.46 | N |
| ATOM | 374 | N | LEU A | 50 | −15.822 | −30.477 | −8.323 | 1.00 | 16.13 | N |
| ATOM | 375 | CA | LEU A | 50 | −17.099 | −30.569 | −9.042 | 1.00 | 14.02 | C |
| ATOM | 376 | C | LEU A | 50 | −17.872 | −31.820 | −8.620 | 1.00 | 20.31 | C |
| ATOM | 377 | O | LEU A | 50 | −17.327 | −32.933 | −8.626 | 1.00 | 19.70 | O |
| ATOM | 378 | CB | LEU A | 50 | −16.857 | −30.584 | −10.563 | 1.00 | 13.15 | C |
| ATOM | 379 | CG | LEU A | 50 | −18.076 | −30.726 | −11.492 | 1.00 | 17.02 | C |
| ATOM | 380 | CD1 | LEU A | 50 | −19.054 | −29.534 | −11.358 | 1.00 | 15.71 | C |
| ATOM | 381 | CD2 | LEU A | 50 | −17.639 | −30.866 | −12.941 | 1.00 | 17.64 | C |
| ATOM | 382 | N | LEU A | 51 | −19.140 | −31.626 | −8.213 | 1.00 | 17.60 | N |
| ATOM | 383 | CA | LEU A | 51 | −20.020 | −32.732 | −7.799 | 1.00 | 16.26 | C |
| ATOM | 384 | C | LEU A | 51 | −21.068 | −33.036 | −8.863 | 1.00 | 19.39 | C |
| ATOM | 385 | O | LEU A | 51 | −21.224 | −34.189 | −9.278 | 1.00 | 18.88 | O |
| ATOM | 386 | CB | LEU A | 51 | −20.759 | −32.403 | −6.513 | 1.00 | 14.79 | C |
| ATOM | 387 | CG | LEU A | 51 | −19.939 | −32.080 | −5.298 | 1.00 | 19.25 | C |
| ATOM | 388 | CD1 | LEU A | 51 | −20.850 | −31.539 | −4.216 | 1.00 | 19.34 | C |
| ATOM | 389 | CD2 | LEU A | 51 | −19.202 | −33.297 | −4.788 | 1.00 | 22.47 | C |
| ATOM | 390 | N | ILE A | 52 | −21.824 | −31.996 | −9.245 | 1.00 | 13.94 | N |
| ATOM | 391 | CA | ILE A | 52 | −22.933 | −32.084 | −10.174 | 1.00 | 13.91 | C |
| ATOM | 392 | C | ILE A | 52 | −22.771 | −30.997 | −11.238 | 1.00 | 17.67 | C |
| ATOM | 393 | O | ILE A | 52 | −22.442 | −29.868 | −10.895 | 1.00 | 16.47 | O |
| ATOM | 394 | CB | ILE A | 52 | −24.287 | −31.936 | −9.410 | 1.00 | 16.12 | C |
| ATOM | 395 | CG1 | ILE A | 52 | −24.468 | −33.030 | −8.308 | 1.00 | 17.54 | C |
| ATOM | 396 | CG2 | ILE A | 52 | −25.459 | −31.909 | −10.354 | 1.00 | 14.92 | C |
| ATOM | 397 | CD1 | ILE A | 52 | −24.552 | −34.457 | −8.776 | 1.00 | 13.14 | C |
| ATOM | 398 | N | TYR A | 53 | −22.957 | −31.353 | −12.527 | 1.00 | 14.20 | N |
| ATOM | 399 | CA | TYR A | 53 | −22.918 | −30.380 | −13.611 | 1.00 | 15.48 | C |
| ATOM | 400 | C | TYR A | 53 | −24.268 | −30.408 | −14.308 | 1.00 | 20.26 | C |
| ATOM | 401 | O | TYR A | 53 | −24.965 | −31.420 | −14.291 | 1.00 | 20.21 | O |
| ATOM | 402 | CB | TYR A | 53 | −21.759 | −30.629 | −14.605 | 1.00 | 16.83 | C |
| ATOM | 403 | CG | TYR A | 53 | −21.860 | −31.943 | −15.342 | 1.00 | 18.18 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 404 | CD2 | TYR A | 53 | −22.404 | −32.009 | −16.615 | 1.00 | 19.02 | C |
| ATOM | 405 | CD1 | TYR A | 53 | −21.321 | −33.106 | −14.807 | 1.00 | 20.60 | C |
| ATOM | 406 | CE2 | TYR A | 53 | −22.540 | −33.222 | −17.276 | 1.00 | 20.61 | C |
| ATOM | 407 | CE1 | TYR A | 53 | −21.396 | −34.318 | −15.484 | 1.00 | 19.80 | C |
| ATOM | 408 | CZ | TYR A | 53 | −22.018 | −34.376 | −16.712 | 1.00 | 24.37 | C |
| ATOM | 409 | OH | TYR A | 53 | −22.095 | −35.589 | −17.343 | 1.00 | 21.51 | O |
| ATOM | 410 | N | LEU A | 54 | −24.627 | −29.290 | −14.904 | 1.00 | 18.67 | N |
| ATOM | 411 | CA | LEU A | 54 | −25.859 | −29.116 | −15.666 | 1.00 | 19.81 | C |
| ATOM | 412 | C | LEU A | 54 | −27.089 | −29.579 | −14.858 | 1.00 | 26.60 | C |
| ATOM | 413 | O | LEU A | 54 | −27.875 | −30.419 | −15.305 | 1.00 | 26.06 | O |
| ATOM | 414 | CB | LEU A | 54 | −25.757 | −29.776 | −17.065 | 1.00 | 19.95 | C |
| ATOM | 415 | CG | LEU A | 54 | −24.735 | −29.159 | −18.021 | 1.00 | 23.95 | C |
| ATOM | 416 | CD1 | LEU A | 54 | −24.519 | −30.040 | −19.219 | 1.00 | 25.21 | C |
| ATOM | 417 | CD2 | LEU A | 54 | −25.151 | −27.725 | −18.488 | 1.00 | 23.82 | C |
| ATOM | 418 | N | ALA A | 55 | −27.181 | −29.055 | −13.604 | 1.00 | 24.46 | N |
| ATOM | 419 | CA | ALA A | 55 | −28.255 | −29.257 | −12.622 | 1.00 | 22.95 | C |
| ATOM | 420 | C | ALA A | 55 | −28.411 | −30.675 | −12.075 | 1.00 | 25.44 | C |
| ATOM | 421 | O | ALA A | 55 | −28.662 | −30.804 | −10.894 | 1.00 | 25.15 | O |
| ATOM | 422 | CB | ALA A | 55 | −29.588 | −28.783 | −13.192 | 1.00 | 24.18 | C |
| ATOM | 423 | N | SER A | 56 | −28.322 | −31.726 | −12.896 | 1.00 | 21.72 | N |
| ATOM | 424 | CA | SER A | 56 | −28.584 | −33.076 | −12.422 | 1.00 | 21.56 | C |
| ATOM | 425 | C | SER A | 56 | −27.593 | −34.160 | −12.882 | 1.00 | 26.88 | C |
| ATOM | 426 | O | SER A | 56 | −27.873 | −35.316 | −12.630 | 1.00 | 27.47 | O |
| ATOM | 427 | CB | SER A | 56 | −30.010 | −33.462 | −12.825 | 1.00 | 24.12 | C |
| ATOM | 428 | OG | SER A | 56 | −30.228 | −33.280 | −14.213 | 1.00 | 31.90 | O |
| ATOM | 429 | N | TYR A | 57 | −26.418 | −33.833 | −13.453 | 1.00 | 23.91 | N |
| ATOM | 430 | CA | TYR A | 57 | −25.509 | −34.897 | −13.912 | 1.00 | 23.54 | C |
| ATOM | 431 | C | TYR A | 57 | −24.359 | −35.122 | −12.948 | 1.00 | 28.42 | C |
| ATOM | 432 | O | TYR A | 57 | −23.644 | −34.184 | −12.602 | 1.00 | 28.27 | O |
| ATOM | 433 | CB | TYR A | 57 | −25.001 | −34.636 | −15.331 | 1.00 | 23.60 | C |
| ATOM | 434 | CG | TYR A | 57 | −26.129 | −34.574 | −16.333 | 1.00 | 25.28 | C |
| ATOM | 435 | CD1 | TYR A | 57 | −26.628 | −35.730 | −16.924 | 1.00 | 27.25 | C |
| ATOM | 436 | CD2 | TYR A | 57 | −26.785 | −33.379 | −16.597 | 1.00 | 25.35 | C |
| ATOM | 437 | CE1 | TYR A | 57 | −27.745 | −35.695 | −17.750 | 1.00 | 26.29 | C |
| ATOM | 438 | CE2 | TYR A | 57 | −27.923 | −33.337 | −17.387 | 1.00 | 26.48 | C |
| ATOM | 439 | CZ | TYR A | 57 | −28.369 | −34.485 | −18.015 | 1.00 | 36.59 | C |
| ATOM | 440 | OH | TYR A | 57 | −29.425 | −34.426 | −18.918 | 1.00 | 39.87 | O |
| ATOM | 441 | N | LEU A | 58 | −24.171 | −36.379 | −12.529 | 1.00 | 23.95 | N |
| ATOM | 442 | CA | LEU A | 58 | −23.111 | −36.735 | −11.592 | 1.00 | 23.46 | C |
| ATOM | 443 | C | LEU A | 58 | −21.728 | −36.702 | −12.263 | 1.00 | 26.25 | C |
| ATOM | 444 | O | LEU A | 58 | −21.478 | −37.444 | −13.214 | 1.00 | 25.54 | O |
| ATOM | 445 | CB | LEU A | 58 | −23.413 | −38.125 | −11.013 | 1.00 | 24.43 | C |
| ATOM | 446 | CG | LEU A | 58 | −22.514 | −38.654 | −9.915 | 1.00 | 28.12 | C |
| ATOM | 447 | CD1 | LEU A | 58 | −22.636 | −37.817 | −8.645 | 1.00 | 26.26 | C |
| ATOM | 448 | CD2 | LEU A | 58 | −22.836 | −40.116 | −9.658 | 1.00 | 30.59 | C |
| ATOM | 449 | N | GLU A | 59 | −20.814 | −35.869 | −11.734 | 1.00 | 23.31 | N |
| ATOM | 450 | CA | GLU A | 59 | −19.456 | −35.793 | −12.274 | 1.00 | 22.86 | C |
| ATOM | 451 | C | GLU A | 59 | −18.779 | −37.168 | −12.069 | 1.00 | 29.61 | C |
| ATOM | 452 | O | GLU A | 59 | −19.040 | −37.829 | −11.078 | 1.00 | 30.56 | O |
| ATOM | 453 | CB | GLU A | 59 | −18.678 | −34.587 | −11.696 | 1.00 | 21.79 | C |
| ATOM | 454 | CG | GLU A | 59 | −17.155 | −34.659 | −11.718 | 1.00 | 23.30 | C |
| ATOM | 455 | CD | GLU A | 59 | −16.459 | −34.515 | −13.060 | 1.00 | 39.05 | C |
| ATOM | 456 | OE1 | GLU A | 59 | −15.205 | −34.517 | −13.084 | 1.00 | 53.34 | O |
| ATOM | 457 | OE2 | GLU A | 59 | −17.161 | −34.353 | −14.080 | 1.00 | 20.44 | O |
| ATOM | 458 | N | SER A | 60 | −18.013 | −37.631 | −13.065 | 1.00 | 27.69 | N |
| ATOM | 459 | CA | SER A | 60 | −17.333 | −38.929 | −13.035 | 1.00 | 28.60 | C |
| ATOM | 460 | C | SER A | 60 | −16.442 | −39.002 | −11.805 | 1.00 | 32.41 | C |
| ATOM | 461 | O | SER A | 60 | −15.705 | −38.037 | −11.524 | 1.00 | 31.43 | O |
| ATOM | 462 | CB | SER A | 60 | −16.506 | −39.129 | −14.309 | 1.00 | 33.87 | C |
| ATOM | 463 | OG | SER A | 60 | −15.620 | −40.234 | −14.248 | 1.00 | 45.05 | O |
| ATOM | 464 | N | GLY A | 61 | −16.568 | −40.115 | −11.069 | 1.00 | 28.04 | N |
| ATOM | 465 | CA | GLY A | 61 | −15.834 | −40.368 | −9.838 | 1.00 | 27.55 | C |
| ATOM | 466 | C | GLY A | 61 | −16.514 | −39.908 | −8.559 | 1.00 | 32.04 | C |
| ATOM | 467 | O | GLY A | 61 | −16.048 | −40.253 | −7.472 | 1.00 | 33.61 | O |
| ATOM | 468 | N | VAL A | 62 | −17.592 | −39.103 | −8.652 | 1.00 | 27.32 | N |
| ATOM | 469 | CA | VAL A | 62 | −18.292 | −38.607 | −7.463 | 1.00 | 25.33 | C |
| ATOM | 470 | C | VAL A | 62 | −19.227 | −39.721 | −6.939 | 1.00 | 28.44 | C |
| ATOM | 471 | O | VAL A | 62 | −19.869 | −40.400 | −7.735 | 1.00 | 28.90 | O |
| ATOM | 472 | CB | VAL A | 62 | −19.052 | −37.283 | −7.754 | 1.00 | 26.70 | C |
| ATOM | 473 | CG1 | VAL A | 62 | −19.803 | −36.769 | −6.509 | 1.00 | 25.06 | C |
| ATOM | 474 | CG2 | VAL A | 62 | −18.089 | −36.221 | −8.276 | 1.00 | 25.23 | C |
| ATOM | 475 | N | PRO A | 63 | −19.348 | −39.911 | −5.616 | 1.00 | 25.92 | N |
| ATOM | 476 | CA | PRO A | 63 | −20.218 | −40.978 | −5.109 | 1.00 | 26.31 | C |
| ATOM | 477 | C | PRO A | 63 | −21.713 | −40.851 | −5.455 | 1.00 | 30.94 | C |
| ATOM | 478 | O | PRO A | 63 | −22.249 | −39.756 | −5.509 | 1.00 | 30.31 | O |
| ATOM | 479 | CB | PRO A | 63 | −19.971 | −40.907 | −3.601 | 1.00 | 27.77 | C |
| ATOM | 480 | CG | PRO A | 63 | −18.657 | −40.263 | −3.448 | 1.00 | 30.40 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 481 | CD | PRO A | 63 | −18.645 | −39.238 | −4.497 | 1.00 | 26.00 | C |
| ATOM | 482 | N | ALA A | 64 | −22.382 | −41.993 | −5.666 | 1.00 | 29.01 | N |
| ATOM | 483 | CA | ALA A | 64 | −23.797 | −42.081 | −6.031 | 1.00 | 29.33 | C |
| ATOM | 484 | C | ALA A | 64 | −24.752 | −41.329 | −5.093 | 1.00 | 32.30 | C |
| ATOM | 485 | O | ALA A | 64 | −25.824 | −40.911 | −5.529 | 1.00 | 34.05 | O |
| ATOM | 486 | CB | ALA A | 64 | −24.214 | −43.539 | −6.097 | 1.00 | 31.62 | C |
| ATOM | 487 | N | ARG A | 65 | −24.408 | −41.210 | −3.811 | 1.00 | 25.22 | N |
| ATOM | 488 | CA | ARG A | 65 | −25.253 | −40.494 | −2.857 | 1.00 | 24.16 | C |
| ATOM | 489 | C | ARG A | 65 | −25.471 | −38.983 | −3.214 | 1.00 | 27.79 | C |
| ATOM | 490 | O | ARG A | 65 | −26.365 | −38.361 | −2.650 | 1.00 | 28.29 | O |
| ATOM | 491 | CB | ARG A | 65 | −24.707 | −40.654 | −1.415 | 1.00 | 24.19 | C |
| ATOM | 492 | CG | ARG A | 65 | −23.279 | −40.121 | −1.169 | 1.00 | 23.41 | C |
| ATOM | 493 | CD | ARG A | 65 | −22.844 | −40.297 | 0.282 | 1.00 | 19.17 | C |
| ATOM | 494 | NE | ARG A | 65 | −21.558 | −39.633 | 0.507 | 1.00 | 23.18 | N |
| ATOM | 495 | CZ | ARG A | 65 | −20.357 | −40.144 | 0.236 | 1.00 | 28.71 | C |
| ATOM | 496 | NH1 | ARG A | 65 | −20.239 | −41.382 | −0.228 | 1.00 | 16.52 | N |
| ATOM | 497 | NH2 | ARG A | 65 | −19.264 | −39.437 | 0.466 | 1.00 | 13.32 | N |
| ATOM | 498 | N | PHE A | 66 | −24.669 | −38.410 | −4.133 | 1.00 | 23.35 | N |
| ATOM | 499 | CA | PHE A | 66 | −24.823 | −37.028 | −4.603 | 1.00 | 22.26 | C |
| ATOM | 500 | C | PHE A | 66 | −25.759 | −36.972 | −5.825 | 1.00 | 25.14 | C |
| ATOM | 501 | O | PHE A | 66 | −25.562 | −37.694 | −6.791 | 1.00 | 25.10 | O |
| ATOM | 502 | CB | PHE A | 66 | −23.467 | −36.417 | −4.962 | 1.00 | 23.16 | C |
| ATOM | 503 | CG | PHE A | 66 | −22.623 | −36.136 | −3.751 | 1.00 | 24.34 | C |
| ATOM | 504 | CD1 | PHE A | 66 | −22.776 | −34.958 | −3.039 | 1.00 | 25.78 | C |
| ATOM | 505 | CD2 | PHE A | 66 | −21.756 | −37.095 | −3.249 | 1.00 | 26.98 | C |
| ATOM | 506 | CE1 | PHE A | 66 | −22.027 | −34.716 | −1.900 | 1.00 | 25.88 | C |
| ATOM | 507 | CE2 | PHE A | 66 | −20.995 | −36.838 | −2.110 | 1.00 | 28.21 | C |
| ATOM | 508 | CZ | PHE A | 66 | −21.155 | −35.664 | −1.434 | 1.00 | 24.98 | C |
| ATOM | 509 | N | SER A | 67 | −26.806 | −36.152 | −5.749 | 1.00 | 20.81 | N |
| ATOM | 510 | CA | SER A | 67 | −27.742 | −35.988 | −6.832 | 1.00 | 21.08 | C |
| ATOM | 511 | C | SER A | 67 | −28.209 | −34.523 | −6.853 | 1.00 | 27.42 | C |
| ATOM | 512 | O | SER A | 67 | −28.316 | −33.908 | −5.795 | 1.00 | 25.09 | O |
| ATOM | 513 | CB | SER A | 67 | −28.907 | −36.964 | −6.690 | 1.00 | 23.83 | C |
| ATOM | 514 | OG | SER A | 67 | −29.911 | −36.521 | −5.795 | 1.00 | 27.21 | O |
| ATOM | 515 | N | GLY A | 68 | −28.452 | −33.992 | −8.061 | 1.00 | 25.41 | N |
| ATOM | 516 | CA | GLY A | 68 | −28.972 | −32.649 | −8.267 | 1.00 | 23.89 | C |
| ATOM | 517 | C | GLY A | 68 | −30.309 | −32.678 | −8.968 | 1.00 | 26.18 | C |
| ATOM | 518 | O | GLY A | 68 | −30.669 | −33.673 | −9.593 | 1.00 | 26.92 | O |
| ATOM | 519 | N | SER A | 69 | −31.065 | −31.611 | −8.856 | 1.00 | 23.97 | N |
| ATOM | 520 | CA | SER A | 69 | −32.355 | −31.484 | −9.557 | 1.00 | 25.47 | C |
| ATOM | 521 | C | SER A | 69 | −32.791 | −30.008 | −9.630 | 1.00 | 26.85 | C |
| ATOM | 522 | O | SER A | 69 | −32.104 | −29.156 | −9.118 | 1.00 | 23.22 | O |
| ATOM | 523 | CB | SER A | 69 | −33.442 | −32.340 | −8.896 | 1.00 | 30.29 | C |
| ATOM | 524 | OG | SER A | 69 | −33.893 | −31.789 | −7.672 | 1.00 | 41.65 | O |
| ATOM | 525 | N | GLY A | 70 | −33.913 | −29.743 | −10.291 | 1.00 | 27.97 | N |
| ATOM | 526 | CA | GLY A | 70 | −34.477 | −28.409 | −10.458 | 1.00 | 27.35 | C |
| ATOM | 527 | C | GLY A | 70 | −34.304 | −27.897 | −11.868 | 1.00 | 32.89 | C |
| ATOM | 528 | O | GLY A | 70 | −33.673 | −28.545 | −12.706 | 1.00 | 32.95 | O |
| ATOM | 529 | N | SER A | 71 | −34.886 | −26.734 | −12.135 | 1.00 | 30.33 | N |
| ATOM | 530 | CA | SER A | 71 | −34.791 | −26.056 | −13.424 | 1.00 | 30.04 | C |
| ATOM | 531 | C | SER A | 71 | −35.111 | −24.568 | −13.203 | 1.00 | 31.64 | C |
| ATOM | 532 | O | SER A | 71 | −35.472 | −24.190 | −12.084 | 1.00 | 31.25 | O |
| ATOM | 533 | CB | SER A | 71 | −35.761 | −26.676 | −14.431 | 1.00 | 36.74 | C |
| ATOM | 534 | OG | SER A | 71 | −37.064 | −26.780 | −13.879 | 1.00 | 46.84 | O |
| ATOM | 535 | N | GLY A | 72 | −34.985 | −23.757 | −14.261 | 1.00 | 26.02 | N |
| ATOM | 536 | CA | GLY A | 72 | −35.277 | −22.330 | −14.236 | 1.00 | 24.41 | C |
| ATOM | 537 | C | GLY A | 72 | −34.457 | −21.564 | −13.236 | 1.00 | 30.19 | C |
| ATOM | 538 | O | GLY A | 72 | −33.249 | −21.347 | −13.450 | 1.00 | 32.07 | O |
| ATOM | 539 | N | THR A | 73 | −35.092 | −21.229 | −12.095 | 1.00 | 24.91 | N |
| ATOM | 540 | CA | THR A | 73 | −34.488 | −20.474 | −11.005 | 1.00 | 23.58 | C |
| ATOM | 541 | C | THR A | 73 | −34.291 | −21.238 | −9.684 | 1.00 | 28.92 | C |
| ATOM | 542 | O | THR A | 73 | −33.612 | −20.706 | −8.826 | 1.00 | 28.52 | O |
| ATOM | 543 | CB | THR A | 73 | −35.337 | −19.216 | −10.748 | 1.00 | 30.42 | C |
| ATOM | 544 | OG1 | THR A | 73 | −36.715 | −19.576 | −10.594 | 1.00 | 32.62 | O |
| ATOM | 545 | CG2 | THR A | 73 | −35.230 | −18.218 | −11.876 | 1.00 | 25.17 | C |
| ATOM | 546 | N | ASP A | 74 | −34.820 | −22.461 | −9.508 | 1.00 | 26.09 | N |
| ATOM | 547 | CA | ASP A | 74 | −34.767 | −23.188 | −8.213 | 1.00 | 24.45 | C |
| ATOM | 548 | C | ASP A | 74 | −34.066 | −24.515 | −8.372 | 1.00 | 26.52 | C |
| ATOM | 549 | O | ASP A | 74 | −34.441 | −25.296 | −9.233 | 1.00 | 27.52 | O |
| ATOM | 550 | CB | ASP A | 74 | −36.209 | −23.396 | −7.663 | 1.00 | 27.31 | C |
| ATOM | 551 | CG | ASP A | 74 | −37.011 | −22.100 | −7.547 | 1.00 | 43.48 | C |
| ATOM | 552 | OD1 | ASP A | 74 | −37.002 | −21.491 | −6.466 | 1.00 | 48.19 | O |
| ATOM | 553 | OD2 | ASP A | 74 | −37.590 | −21.667 | −8.557 | 1.00 | 50.36 | O |
| ATOM | 554 | N | PHE A | 75 | −33.013 | −24.756 | −7.573 | 1.00 | 21.72 | N |
| ATOM | 555 | CA | PHE A | 75 | −32.184 | −25.939 | −7.703 | 1.00 | 19.42 | C |
| ATOM | 556 | C | PHE A | 75 | −31.896 | −26.534 | −6.386 | 1.00 | 26.14 | C |
| ATOM | 557 | O | PHE A | 75 | −31.781 | −25.815 | −5.397 | 1.00 | 27.28 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 558 | CB | PHE A | 75 | −30.870 | −25.592 | −8.386 | 1.00 | 18.90 | C |
| ATOM | 559 | CG | PHE A | 75 | −31.068 | −25.154 | −9.801 | 1.00 | 20.22 | C |
| ATOM | 560 | CD2 | PHE A | 75 | −31.229 | −23.809 | −10.111 | 1.00 | 20.27 | C |
| ATOM | 561 | CD1 | PHE A | 75 | −31.229 | −26.088 | −10.815 | 1.00 | 22.77 | C |
| ATOM | 562 | CE2 | PHE A | 75 | −31.513 | −23.413 | −11.403 | 1.00 | 22.87 | C |
| ATOM | 563 | CE1 | PHE A | 75 | −31.448 | −25.681 | −12.122 | 1.00 | 22.40 | C |
| ATOM | 564 | CZ | PHE A | 75 | −31.615 | −24.346 | −12.404 | 1.00 | 21.28 | C |
| ATOM | 565 | N | THR A | 76 | −31.723 | −27.858 | −6.371 | 1.00 | 23.71 | N |
| ATOM | 566 | CA | THR A | 76 | −31.449 | −28.583 | −5.142 | 1.00 | 23.88 | C |
| ATOM | 567 | C | THR A | 76 | −30.316 | −29.552 | −5.336 | 1.00 | 25.76 | C |
| ATOM | 568 | O | THR A | 76 | −30.214 | −30.177 | −6.390 | 1.00 | 26.37 | O |
| ATOM | 569 | CB | THR A | 76 | −32.716 | −29.336 | −4.724 | 1.00 | 35.30 | C |
| ATOM | 570 | OG1 | THR A | 76 | −33.776 | −28.396 | −4.606 | 1.00 | 37.61 | O |
| ATOM | 571 | CG2 | THR A | 76 | −32.569 | −30.020 | −3.400 | 1.00 | 37.52 | C |
| ATOM | 572 | N | LEU A | 77 | −29.482 | −29.688 | −4.319 | 1.00 | 20.28 | N |
| ATOM | 573 | CA | LEU A | 77 | −28.434 | −30.713 | −4.252 | 1.00 | 20.39 | C |
| ATOM | 574 | C | LEU A | 77 | −28.887 | −31.595 | −3.098 | 1.00 | 24.46 | C |
| ATOM | 575 | O | LEU A | 77 | −29.315 | −31.055 | −2.087 | 1.00 | 24.23 | O |
| ATOM | 576 | CB | LEU A | 77 | −27.020 | −30.123 | −3.988 | 1.00 | 19.24 | C |
| ATOM | 577 | CG | LEU A | 77 | −25.903 | −31.113 | −3.608 | 1.00 | 22.67 | C |
| ATOM | 578 | CD1 | LEU A | 77 | −25.451 | −31.933 | −4.822 | 1.00 | 22.85 | C |
| ATOM | 579 | CD2 | LEU A | 77 | −24.719 | −30.385 | −3.037 | 1.00 | 20.78 | C |
| ATOM | 580 | N | THR A | 78 | −28.893 | −32.932 | −3.270 | 1.00 | 22.08 | N |
| ATOM | 581 | CA | THR A | 78 | −29.259 | −33.851 | −2.190 | 1.00 | 22.09 | C |
| ATOM | 582 | C | THR A | 78 | −28.108 | −34.801 | −1.934 | 1.00 | 27.43 | C |
| ATOM | 583 | O | THR A | 78 | −27.467 | −35.273 | −2.878 | 1.00 | 28.18 | O |
| ATOM | 584 | CB | THR A | 78 | −30.546 | −34.639 | −2.482 | 1.00 | 24.98 | C |
| ATOM | 585 | OG1 | THR A | 78 | −31.630 | −33.738 | −2.695 | 1.00 | 29.33 | O |
| ATOM | 586 | CG2 | THR A | 78 | −30.945 | −35.570 | −1.339 | 1.00 | 20.77 | C |
| ATOM | 587 | N | ILE A | 79 | −27.849 | −35.085 | −0.650 | 1.00 | 23.16 | N |
| ATOM | 588 | CA | ILE A | 79 | −26.888 | −36.105 | −0.224 | 1.00 | 23.03 | C |
| ATOM | 589 | C | ILE A | 79 | −27.808 | −37.125 | 0.429 | 1.00 | 27.93 | C |
| ATOM | 590 | O | ILE A | 79 | −28.375 | −36.811 | 1.456 | 1.00 | 28.06 | O |
| ATOM | 591 | CB | ILE A | 79 | −25.822 | −35.536 | 0.733 | 1.00 | 25.12 | C |
| ATOM | 592 | CG1 | ILE A | 79 | −25.130 | −34.320 | 0.053 | 1.00 | 24.27 | C |
| ATOM | 593 | CG2 | ILE A | 79 | −24.833 | −36.645 | 1.130 | 1.00 | 24.36 | C |
| ATOM | 594 | CD1 | ILE A | 79 | −24.075 | −33.645 | 0.869 | 1.00 | 27.13 | C |
| ATOM | 595 | N | SER A | 80 | −28.071 | −38.269 | −0.208 | 1.00 | 26.03 | N |
| ATOM | 596 | CA | SER A | 80 | −29.054 | −39.238 | 0.321 | 1.00 | 27.98 | C |
| ATOM | 597 | C | SER A | 80 | −28.792 | −39.753 | 1.746 | 1.00 | 31.87 | C |
| ATOM | 598 | O | SER A | 80 | −29.748 | −40.110 | 2.438 | 1.00 | 32.75 | O |
| ATOM | 599 | CB | SER A | 80 | −29.204 | −40.426 | −0.628 | 1.00 | 30.90 | C |
| ATOM | 600 | OG | SER A | 80 | −27.932 | −41.005 | −0.850 | 1.00 | 39.48 | O |
| ATOM | 601 | N | SER A | 81 | −27.520 | −39.830 | 2.153 | 1.00 | 27.18 | N |
| ATOM | 602 | CA | SER A | 81 | −27.110 | −40.320 | 3.472 | 1.00 | 27.53 | C |
| ATOM | 603 | C | SER A | 81 | −25.731 | −39.737 | 3.730 | 1.00 | 29.39 | C |
| ATOM | 604 | O | SER A | 81 | −24.804 | −40.074 | 3.001 | 1.00 | 30.15 | O |
| ATOM | 605 | CB | SER A | 81 | −27.062 | −41.849 | 3.469 | 1.00 | 32.71 | C |
| ATOM | 606 | OG | SER A | 81 | −26.548 | −42.404 | 4.670 | 1.00 | 44.68 | O |
| ATOM | 607 | N | LEU A | 82 | −25.610 | −38.786 | 4.666 | 1.00 | 23.28 | N |
| ATOM | 608 | CA | LEU A | 82 | −24.326 | −38.124 | 4.909 | 1.00 | 21.44 | C |
| ATOM | 609 | C | LEU A | 82 | −23.247 | −39.093 | 5.417 | 1.00 | 26.81 | C |
| ATOM | 610 | O | LEU A | 82 | −23.526 | −39.946 | 6.258 | 1.00 | 26.66 | O |
| ATOM | 611 | CB | LEU A | 82 | −24.476 | −36.979 | 5.913 | 1.00 | 19.96 | C |
| ATOM | 612 | CG | LEU A | 82 | −25.023 | −35.676 | 5.367 | 1.00 | 22.85 | C |
| ATOM | 613 | CD1 | LEU A | 82 | −25.666 | −34.859 | 6.452 | 1.00 | 21.48 | C |
| ATOM | 614 | CD2 | LEU A | 82 | −23.937 | −34.864 | 4.688 | 1.00 | 24.82 | C |
| ATOM | 615 | N | GLU A | 83 | −22.031 | −38.965 | 4.883 | 1.00 | 23.34 | N |
| ATOM | 616 | CA | GLU A | 83 | −20.864 | −39.721 | 5.338 | 1.00 | 22.77 | C |
| ATOM | 617 | C | GLU A | 83 | −20.010 | −38.716 | 6.105 | 1.00 | 28.76 | C |
| ATOM | 618 | O | GLU A | 83 | −20.044 | −37.525 | 5.773 | 1.00 | 30.84 | O |
| ATOM | 619 | CB | GLU A | 83 | −20.044 | −40.295 | 4.155 | 1.00 | 22.75 | C |
| ATOM | 620 | CG | GLU A | 83 | −20.652 | −41.499 | 3.464 | 1.00 | 25.17 | C |
| ATOM | 621 | CD | GLU A | 83 | −21.143 | −42.656 | 4.322 | 1.00 | 48.64 | C |
| ATOM | 622 | OE1 | GLU A | 83 | −22.279 | −43.113 | 4.059 | 1.00 | 44.04 | O |
| ATOM | 623 | OE2 | GLU A | 83 | −20.424 | −43.092 | 5.258 | 1.00 | 41.54 | O |
| ATOM | 624 | N | PRO A | 84 | −19.189 | −39.137 | 7.075 | 1.00 | 24.97 | N |
| ATOM | 625 | CA | PRO A | 84 | −18.316 | −38.171 | 7.779 | 1.00 | 23.47 | C |
| ATOM | 626 | C | PRO A | 84 | −17.511 | −37.209 | 6.874 | 1.00 | 28.20 | C |
| ATOM | 627 | O | PRO A | 84 | −17.304 | −36.042 | 7.194 | 1.00 | 27.40 | O |
| ATOM | 628 | CB | PRO A | 84 | −17.406 | −39.098 | 8.583 | 1.00 | 25.15 | C |
| ATOM | 629 | CG | PRO A | 84 | −18.294 | −40.256 | 8.902 | 1.00 | 29.91 | C |
| ATOM | 630 | CD | PRO A | 84 | −19.017 | −40.498 | 7.622 | 1.00 | 26.61 | C |
| ATOM | 631 | N | GLU A | 85 | −17.093 | −37.701 | 5.723 | 1.00 | 27.32 | N |
| ATOM | 632 | CA | GLU A | 85 | −16.367 | −36.920 | 4.720 | 1.00 | 27.34 | C |
| ATOM | 633 | C | GLU A | 85 | −17.205 | −35.811 | 4.031 | 1.00 | 31.42 | C |
| ATOM | 634 | O | GLU A | 85 | −16.611 | −34.931 | 3.421 | 1.00 | 30.97 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 635 | CB | GLU A | 85 | −15.720 | −37.849 | 3.665 | 1.00 | 29.96 | C |
| ATOM | 636 | CG | GLU A | 85 | −16.627 | −38.903 | 3.025 | 1.00 | 39.08 | C |
| ATOM | 637 | CD | GLU A | 85 | −16.617 | −40.248 | 3.726 | 1.00 | 63.10 | C |
| ATOM | 638 | OE1 | GLU A | 85 | −16.679 | −41.283 | 3.020 | 1.00 | 69.81 | O |
| ATOM | 639 | OE2 | GLU A | 85 | −16.576 | −40.268 | 4.983 | 1.00 | 42.17 | O |
| ATOM | 640 | N | ASP A | 86 | −18.550 | −35.800 | 4.166 | 1.00 | 27.85 | N |
| ATOM | 641 | CA | ASP A | 86 | −19.404 | −34.800 | 3.504 | 1.00 | 26.14 | C |
| ATOM | 642 | C | ASP A | 86 | −19.628 | −33.506 | 4.293 | 1.00 | 26.96 | C |
| ATOM | 643 | O | ASP A | 86 | −20.300 | −32.608 | 3.797 | 1.00 | 25.67 | O |
| ATOM | 644 | CB | ASP A | 86 | −20.765 | −35.432 | 3.209 | 1.00 | 29.13 | C |
| ATOM | 645 | CG | ASP A | 86 | −20.712 | −36.671 | 2.353 | 1.00 | 35.80 | C |
| ATOM | 646 | OD1 | ASP A | 86 | −19.720 | −36.844 | 1.613 | 1.00 | 34.06 | O |
| ATOM | 647 | OD2 | ASP A | 86 | −21.656 | −37.480 | 2.431 | 1.00 | 42.71 | O |
| ATOM | 648 | N | PHE A | 87 | −19.140 | −33.412 | 5.518 | 1.00 | 21.54 | N |
| ATOM | 649 | CA | PHE A | 87 | −19.331 | −32.195 | 6.296 | 1.00 | 19.48 | C |
| ATOM | 650 | C | PHE A | 87 | −18.304 | −31.206 | 5.746 | 1.00 | 25.31 | C |
| ATOM | 651 | O | PHE A | 87 | −17.104 | −31.343 | 5.983 | 1.00 | 27.57 | O |
| ATOM | 652 | CB | PHE A | 87 | −19.202 | −32.485 | 7.800 | 1.00 | 20.00 | C |
| ATOM | 653 | CG | PHE A | 87 | −20.397 | −33.304 | 8.231 | 1.00 | 21.77 | C |
| ATOM | 654 | CD1 | PHE A | 87 | −21.592 | −32.689 | 8.573 | 1.00 | 22.53 | C |
| ATOM | 655 | CD2 | PHE A | 87 | −20.374 | −34.696 | 8.162 | 1.00 | 25.18 | C |
| ATOM | 656 | CE1 | PHE A | 87 | −22.712 | −33.448 | 8.933 | 1.00 | 22.86 | C |
| ATOM | 657 | CE2 | PHE A | 87 | −21.515 | −35.446 | 8.451 | 1.00 | 27.40 | C |
| ATOM | 658 | CZ | PHE A | 87 | −22.673 | −34.814 | 8.838 | 1.00 | 24.00 | C |
| ATOM | 659 | N | ALA A | 88 | −18.776 | −30.301 | 4.900 | 1.00 | 20.77 | N |
| ATOM | 660 | CA | ALA A | 88 | −17.934 | −29.384 | 4.138 | 1.00 | 19.68 | C |
| ATOM | 661 | C | ALA A | 88 | −18.770 | −28.190 | 3.690 | 1.00 | 21.33 | C |
| ATOM | 662 | O | ALA A | 88 | −19.940 | −28.098 | 4.066 | 1.00 | 20.90 | O |
| ATOM | 663 | CB | ALA A | 88 | −17.411 | −30.131 | 2.897 | 1.00 | 20.02 | C |
| ATOM | 664 | N | VAL A | 89 | −18.198 | −27.304 | 2.863 | 1.00 | 16.30 | N |
| ATOM | 665 | CA | VAL A | 89 | −18.955 | −26.190 | 2.278 | 1.00 | 15.67 | C |
| ATOM | 666 | C | VAL A | 89 | −19.307 | −26.563 | 0.812 | 1.00 | 20.13 | C |
| ATOM | 667 | O | VAL A | 89 | −18.499 | −27.213 | 0.135 | 1.00 | 17.99 | O |
| ATOM | 668 | CB | VAL A | 89 | −18.219 | −24.841 | 2.381 | 1.00 | 18.67 | C |
| ATOM | 669 | CG1 | VAL A | 89 | −19.011 | −23.731 | 1.661 | 1.00 | 18.80 | C |
| ATOM | 670 | CG2 | VAL A | 89 | −17.999 | −24.476 | 3.850 | 1.00 | 17.07 | C |
| ATOM | 671 | N | TYR A | 90 | −20.551 | −26.193 | 0.367 | 1.00 | 18.05 | N |
| ATOM | 672 | CA | TYR A | 90 | −21.077 | −26.447 | −0.967 | 1.00 | 17.24 | C |
| ATOM | 673 | C | TYR A | 90 | −21.467 | −25.140 | −1.646 | 1.00 | 22.84 | C |
| ATOM | 674 | O | TYR A | 90 | −22.154 | −24.307 | −1.067 | 1.00 | 21.62 | O |
| ATOM | 675 | CB | TYR A | 90 | −22.252 | −27.419 | −0.911 | 1.00 | 18.72 | C |
| ATOM | 676 | CG | TYR A | 90 | −21.872 | −28.788 | −0.368 | 1.00 | 20.10 | C |
| ATOM | 677 | CD1 | TYR A | 90 | −21.743 | −29.008 | 0.998 | 1.00 | 20.89 | C |
| ATOM | 678 | CD2 | TYR A | 90 | −21.583 | −29.841 | −1.223 | 1.00 | 20.71 | C |
| ATOM | 679 | CE1 | TYR A | 90 | −21.397 | −30.260 | 1.500 | 1.00 | 19.44 | C |
| ATOM | 680 | CE2 | TYR A | 90 | −21.205 | −31.089 | −0.734 | 1.00 | 21.31 | C |
| ATOM | 681 | CZ | TYR A | 90 | −21.138 | −31.306 | 0.630 | 1.00 | 27.25 | C |
| ATOM | 682 | OH | TYR A | 90 | −20.771 | −32.553 | 1.103 | 1.00 | 25.67 | O |
| ATOM | 683 | N | TYR A | 91 | −21.010 | −24.959 | −2.891 | 1.00 | 21.18 | N |
| ATOM | 684 | CA | TYR A | 91 | −21.281 | −23.777 | −3.705 | 1.00 | 19.95 | C |
| ATOM | 685 | C | TYR A | 91 | −22.030 | −24.168 | −4.957 | 1.00 | 22.95 | C |
| ATOM | 686 | O | TYR A | 91 | −21.772 | −25.230 | −5.512 | 1.00 | 22.18 | O |
| ATOM | 687 | CB | TYR A | 91 | −19.965 | −23.165 | −4.164 | 1.00 | 19.22 | C |
| ATOM | 688 | CG | TYR A | 91 | −19.208 | −22.518 | −3.039 | 1.00 | 19.37 | C |
| ATOM | 689 | CD1 | TYR A | 91 | −19.528 | −21.241 | −2.608 | 1.00 | 21.05 | C |
| ATOM | 690 | CD2 | TYR A | 91 | −18.166 | −23.184 | −2.396 | 1.00 | 18.66 | C |
| ATOM | 691 | CE1 | TYR A | 91 | −18.850 | −20.647 | −1.552 | 1.00 | 20.29 | C |
| ATOM | 692 | CE2 | TYR A | 91 | −17.415 | −22.559 | −1.404 | 1.00 | 17.17 | C |
| ATOM | 693 | CZ | TYR A | 91 | −17.758 | −21.284 | −0.991 | 1.00 | 21.77 | C |
| ATOM | 694 | OH | TYR A | 91 | −17.079 | −20.691 | 0.041 | 1.00 | 24.68 | O |
| ATOM | 695 | N | CYS A | 92 | −22.934 | −23.310 | −5.412 | 1.00 | 20.08 | N |
| ATOM | 696 | CA | CYS A | 92 | −23.560 | −23.486 | −6.709 | 1.00 | 20.31 | C |
| ATOM | 697 | C | CYS A | 92 | −22.913 | −22.445 | −7.623 | 1.00 | 18.05 | C |
| ATOM | 698 | O | CYS A | 92 | −22.284 | −21.507 | −7.152 | 1.00 | 14.62 | O |
| ATOM | 699 | CB | CYS A | 92 | −25.103 | −23.453 | −6.709 | 1.00 | 21.53 | C |
| ATOM | 700 | SG | CYS A | 92 | −25.900 | −21.985 | −5.986 | 1.00 | 26.48 | S |
| ATOM | 701 | N | GLN A | 93 | −22.928 | −22.702 | −8.901 | 1.00 | 13.10 | N |
| ATOM | 702 | CA | GLN A | 93 | −22.395 | −21.781 | −9.877 | 1.00 | 11.51 | C |
| ATOM | 703 | C | GLN A | 93 | −23.180 | −21.915 | −11.163 | 1.00 | 16.98 | C |
| ATOM | 704 | O | GLN A | 93 | −23.508 | −23.035 | −11.542 | 1.00 | 17.25 | O |
| ATOM | 705 | CB | GLN A | 93 | −20.946 | −22.139 | −10.137 | 1.00 | 11.86 | C |
| ATOM | 706 | CG | GLN A | 93 | −20.257 | −21.280 | −11.198 | 1.00 | 11.91 | C |
| ATOM | 707 | CD | GLN A | 93 | −19.888 | −22.114 | −12.387 | 1.00 | 26.46 | C |
| ATOM | 708 | OE1 | GLN A | 93 | −19.445 | −23.255 | −12.248 | 1.00 | 17.78 | O |
| ATOM | 709 | NE2 | GLN A | 93 | −20.022 | −21.563 | −13.580 | 1.00 | 24.96 | N |
| ATOM | 710 | N | HIS A | 94 | −23.464 | −20.790 | −11.840 | 1.00 | 14.01 | N |
| ATOM | 711 | CA | HIS A | 94 | −24.144 | −20.797 | −13.111 | 1.00 | 14.84 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 712 | C | HIS A | 94 | −23.176 | −20.417 | −14.208 | 1.00 | 19.01 | C |
| ATOM | 713 | O | HIS A | 94 | −22.128 | −19.802 | −13.980 | 1.00 | 14.83 | O |
| ATOM | 714 | CB | HIS A | 94 | −25.366 | −19.846 | −13.174 | 1.00 | 16.29 | C |
| ATOM | 715 | CG | HIS A | 94 | −25.010 | −18.414 | −13.456 | 1.00 | 20.20 | C |
| ATOM | 716 | ND1 | HIS A | 94 | −24.927 | −17.932 | −14.749 | 1.00 | 22.75 | N |
| ATOM | 717 | CD2 | HIS A | 94 | −24.722 | −17.406 | −12.601 | 1.00 | 21.58 | C |
| ATOM | 718 | CE1 | HIS A | 94 | −24.548 | −16.668 | −14.643 | 1.00 | 22.27 | C |
| ATOM | 719 | NE2 | HIS A | 94 | −24.425 | −16.304 | −13.372 | 1.00 | 22.08 | N |
| ATOM | 720 | N | SER A | 95 | −23.600 | −20.746 | −15.431 | 1.00 | 18.91 | N |
| ATOM | 721 | CA | SER A | 95 | −22.911 | −20.393 | −16.658 | 1.00 | 18.97 | C |
| ATOM | 722 | C | SER A | 95 | −23.945 | −20.142 | −17.774 | 1.00 | 25.03 | C |
| ATOM | 723 | O | SER A | 95 | −23.661 | −20.396 | −18.930 | 1.00 | 27.45 | O |
| ATOM | 724 | CB | SER A | 95 | −21.860 | −21.449 | −17.006 | 1.00 | 20.22 | C |
| ATOM | 725 | OG | SER A | 95 | −22.393 | −22.761 | −17.009 | 1.00 | 25.52 | O |
| ATOM | 726 | N | ARG A | 96 | −25.124 | −19.565 | −17.428 | 1.00 | 22.02 | N |
| ATOM | 727 | CA | ARG A | 96 | −26.168 | −19.201 | −18.407 | 1.00 | 22.73 | C |
| ATOM | 728 | C | ARG A | 96 | −25.660 | −18.042 | −19.265 | 1.00 | 29.87 | C |
| ATOM | 729 | O | ARG A | 96 | −25.954 | −17.977 | −20.462 | 1.00 | 31.59 | O |
| ATOM | 730 | CB | ARG A | 96 | −27.468 | −18.772 | −17.689 | 1.00 | 19.94 | C |
| ATOM | 731 | CG | ARG A | 96 | −28.580 | −18.154 | −18.587 | 1.00 | 16.73 | C |
| ATOM | 732 | CD | ARG A | 96 | −29.120 | −19.205 | −19.513 | 1.00 | 27.19 | C |
| ATOM | 733 | NE | ARG A | 96 | −30.075 | −18.670 | −20.475 | 1.00 | 38.43 | N |
| ATOM | 734 | CZ | ARG A | 96 | −29.774 | −18.127 | −21.655 | 1.00 | 48.85 | C |
| ATOM | 735 | NH1 | ARG A | 96 | −28.503 | −18.006 | −22.043 | 1.00 | 30.58 | N |
| ATOM | 736 | NH2 | ARG A | 96 | −30.739 | −17.694 | −22.453 | 1.00 | 36.61 | N |
| ATOM | 737 | N | ASP A | 97 | −24.960 | −17.090 | −18.636 | 1.00 | 24.92 | N |
| ATOM | 738 | CA | ASP A | 97 | −24.368 | −15.965 | −19.356 | 1.00 | 24.53 | C |
| ATOM | 739 | C | ASP A | 97 | −23.144 | −15.487 | −18.571 | 1.00 | 25.81 | C |
| ATOM | 740 | O | ASP A | 97 | −22.750 | −16.152 | −17.609 | 1.00 | 21.39 | O |
| ATOM | 741 | CB | ASP A | 97 | −25.411 | −14.852 | −19.532 | 1.00 | 27.34 | C |
| ATOM | 742 | CG | ASP A | 97 | −26.024 | −14.305 | −18.246 | 1.00 | 47.19 | C |
| ATOM | 743 | OD1 | ASP A | 97 | −27.174 | −13.812 | −18.300 | 1.00 | 53.92 | O |
| ATOM | 744 | OD2 | ASP A | 97 | −25.343 | −14.338 | −17.192 | 1.00 | 48.60 | O |
| ATOM | 745 | N | LEU A | 98 | −22.545 | −14.368 | −18.992 | 1.00 | 23.61 | N |
| ATOM | 746 | CA | LEU A | 98 | −21.464 | −13.727 | −18.271 | 1.00 | 24.12 | C |
| ATOM | 747 | C | LEU A | 98 | −22.031 | −12.483 | −17.570 | 1.00 | 31.33 | C |
| ATOM | 748 | O | LEU A | 98 | −22.891 | −11.797 | −18.123 | 1.00 | 32.69 | O |
| ATOM | 749 | CB | LEU A | 98 | −20.330 | −13.302 | −19.208 | 1.00 | 24.87 | C |
| ATOM | 750 | CG | LEU A | 98 | −19.644 | −14.416 | −19.972 | 1.00 | 30.55 | C |
| ATOM | 751 | CD1 | LEU A | 98 | −18.537 | −13.851 | −20.848 | 1.00 | 32.34 | C |
| ATOM | 752 | CD2 | LEU A | 98 | −19.094 | −15.508 | −19.029 | 1.00 | 28.18 | C |
| ATOM | 753 | N | PRO A | 99 | −21.532 | −12.120 | −16.385 | 1.00 | 29.31 | N |
| ATOM | 754 | CA | PRO A | 99 | −20.492 | −12.799 | −15.601 | 1.00 | 27.81 | C |
| ATOM | 755 | C | PRO A | 99 | −20.944 | −14.104 | −14.947 | 1.00 | 29.44 | C |
| ATOM | 756 | O | PRO A | 99 | −22.106 | −14.254 | −14.582 | 1.00 | 29.04 | O |
| ATOM | 757 | CB | PRO A | 99 | −20.128 | −11.746 | −14.540 | 1.00 | 29.62 | C |
| ATOM | 758 | CG | PRO A | 99 | −21.413 | −11.021 | −14.299 | 1.00 | 34.05 | C |
| ATOM | 759 | CD | PRO A | 99 | −22.020 | −10.909 | −15.693 | 1.00 | 31.52 | C |
| ATOM | 760 | N | LEU A | 100 | −20.009 | −15.049 | −14.817 | 1.00 | 24.23 | N |
| ATOM | 761 | CA | LEU A | 100 | −20.237 | −16.314 | −14.133 | 1.00 | 23.19 | C |
| ATOM | 762 | C | LEU A | 100 | −20.259 | −15.948 | −12.646 | 1.00 | 25.80 | C |
| ATOM | 763 | O | LEU A | 100 | −19.457 | −15.112 | −12.219 | 1.00 | 24.99 | O |
| ATOM | 764 | CB | LEU A | 100 | −19.095 | −17.317 | −14.400 | 1.00 | 22.90 | C |
| ATOM | 765 | CG | LEU A | 100 | −18.819 | −17.671 | −15.851 | 1.00 | 27.43 | C |
| ATOM | 766 | CD1 | LEU A | 100 | −17.620 | −18.551 | −15.966 | 1.00 | 26.83 | C |
| ATOM | 767 | CD2 | LEU A | 100 | −19.984 | −18.377 | −16.459 | 1.00 | 30.67 | C |
| ATOM | 768 | N | THR A | 101 | −21.192 | −16.553 | −11.875 | 1.00 | 20.13 | N |
| ATOM | 769 | CA | THR A | 101 | −21.436 | −16.236 | −10.474 | 1.00 | 18.47 | C |
| ATOM | 770 | C | THR A | 101 | −21.573 | −17.513 | −9.667 | 1.00 | 21.91 | C |
| ATOM | 771 | O | THR A | 101 | −21.992 | −18.547 | −10.192 | 1.00 | 20.13 | O |
| ATOM | 772 | CB | THR A | 101 | −22.700 | −15.319 | −10.396 | 1.00 | 29.15 | C |
| ATOM | 773 | OG1 | THR A | 101 | −22.361 | −13.982 | −10.780 | 1.00 | 25.90 | O |
| ATOM | 774 | CG2 | THR A | 101 | −23.317 | −15.278 | −9.059 | 1.00 | 35.88 | C |
| ATOM | 775 | N | PHE A | 102 | −21.179 | −17.435 | −8.381 | 1.00 | 17.52 | N |
| ATOM | 776 | CA | PHE A | 102 | −21.322 | −18.512 | −7.432 | 1.00 | 15.76 | C |
| ATOM | 777 | C | PHE A | 102 | −22.256 | −18.039 | −6.358 | 1.00 | 21.19 | C |
| ATOM | 778 | O | PHE A | 102 | −22.350 | −16.833 | −6.094 | 1.00 | 22.05 | O |
| ATOM | 779 | CB | PHE A | 102 | −19.968 | −18.832 | −6.769 | 1.00 | 15.98 | C |
| ATOM | 780 | CG | PHE A | 102 | −18.948 | −19.450 | −7.682 | 1.00 | 15.33 | C |
| ATOM | 781 | CD1 | PHE A | 102 | −18.155 | −18.658 | −8.497 | 1.00 | 17.15 | C |
| ATOM | 782 | CD2 | PHE A | 102 | −18.744 | −20.822 | −7.691 | 1.00 | 14.75 | C |
| ATOM | 783 | CE1 | PHE A | 102 | −17.153 | −19.225 | −9.298 | 1.00 | 16.72 | C |
| ATOM | 784 | CE2 | PHE A | 102 | −17.758 | −21.387 | −8.499 | 1.00 | 17.57 | C |
| ATOM | 785 | CZ | PHE A | 102 | −16.945 | −20.577 | −9.268 | 1.00 | 15.90 | C |
| ATOM | 786 | N | GLY A | 103 | −22.849 | −18.982 | −5.657 | 1.00 | 17.92 | N |
| ATOM | 787 | CA | GLY A | 103 | −23.668 | −18.663 | −4.495 | 1.00 | 16.99 | C |
| ATOM | 788 | C | GLY A | 103 | −22.743 | −18.422 | −3.318 | 1.00 | 18.11 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 789 | O | GLY A | 103 | −21.549 | −18.683 | −3.407 | 1.00 | 18.24 | O |
| ATOM | 790 | N | GLY A | 104 | −23.279 | −17.930 | −2.213 | 1.00 | 13.41 | N |
| ATOM | 791 | CA | GLY A | 104 | −22.491 | −17.647 | −1.028 | 1.00 | 11.86 | C |
| ATOM | 792 | C | GLY A | 104 | −22.028 | −18.839 | −0.218 | 1.00 | 16.99 | C |
| ATOM | 793 | O | GLY A | 104 | −21.346 | −18.651 | 0.788 | 1.00 | 17.35 | O |
| ATOM | 794 | N | GLY A | 105 | −22.401 | −20.054 | −0.634 | 1.00 | 13.85 | N |
| ATOM | 795 | CA | GLY A | 105 | −22.034 | −21.288 | 0.032 | 1.00 | 12.15 | C |
| ATOM | 796 | C | GLY A | 105 | −23.005 | −21.689 | 1.123 | 1.00 | 18.51 | C |
| ATOM | 797 | O | GLY A | 105 | −23.693 | −20.855 | 1.725 | 1.00 | 17.82 | O |
| ATOM | 798 | N | THR A | 106 | −23.065 | −22.993 | 1.387 | 1.00 | 18.17 | N |
| ATOM | 799 | CA | THR A | 106 | −23.844 | −23.567 | 2.469 | 1.00 | 18.20 | C |
| ATOM | 800 | C | THR A | 106 | −22.934 | −24.488 | 3.224 | 1.00 | 23.79 | C |
| ATOM | 801 | O | THR A | 106 | −22.463 | −25.451 | 2.626 | 1.00 | 24.26 | O |
| ATOM | 802 | CB | THR A | 106 | −25.071 | −24.320 | 1.965 | 1.00 | 20.85 | C |
| ATOM | 803 | OG1 | THR A | 106 | −26.021 | −23.365 | 1.551 | 1.00 | 26.25 | O |
| ATOM | 804 | CG2 | THR A | 106 | −25.727 | −25.189 | 3.057 | 1.00 | 17.54 | C |
| ATOM | 805 | N | LYS A | 107 | −22.754 | −24.260 | 4.546 | 1.00 | 21.53 | N |
| ATOM | 806 | CA | LYS A | 107 | −21.918 | −25.136 | 5.377 | 1.00 | 21.32 | C |
| ATOM | 807 | C | LYS A | 107 | −22.739 | −26.298 | 5.904 | 1.00 | 23.67 | C |
| ATOM | 808 | O | LYS A | 107 | −23.739 | −26.069 | 6.559 | 1.00 | 22.70 | O |
| ATOM | 809 | CB | LYS A | 107 | −21.310 | −24.376 | 6.573 | 1.00 | 24.25 | C |
| ATOM | 810 | CG | LYS A | 107 | −20.229 | −25.169 | 7.330 | 1.00 | 29.20 | C |
| ATOM | 811 | CD | LYS A | 107 | −20.024 | −24.581 | 8.716 | 1.00 | 37.05 | C |
| ATOM | 812 | CE | LYS A | 107 | −18.869 | −25.192 | 9.494 | 1.00 | 45.69 | C |
| ATOM | 813 | NZ | LYS A | 107 | −18.613 | −24.477 | 10.782 | 1.00 | 55.09 | N |
| ATOM | 814 | N | VAL A | 108 | −22.349 | −27.535 | 5.580 | 1.00 | 21.80 | N |
| ATOM | 815 | CA | VAL A | 108 | −22.988 | −28.712 | 6.139 | 1.00 | 23.56 | C |
| ATOM | 816 | C | VAL A | 108 | −22.114 | −29.033 | 7.386 | 1.00 | 28.41 | C |
| ATOM | 817 | O | VAL A | 108 | −20.903 | −29.260 | 7.274 | 1.00 | 26.74 | O |
| ATOM | 818 | CB | VAL A | 108 | −23.144 | −29.880 | 5.147 | 1.00 | 27.92 | C |
| ATOM | 819 | CG1 | VAL A | 108 | −23.814 | −31.072 | 5.834 | 1.00 | 28.62 | C |
| ATOM | 820 | CG2 | VAL A | 108 | −23.965 | −29.440 | 3.952 | 1.00 | 27.50 | C |
| ATOM | 821 | N | GLU A | 109 | −22.737 | −28.940 | 8.575 | 1.00 | 25.04 | N |
| ATOM | 822 | CA | GLU A | 109 | −22.082 | −29.033 | 9.870 | 1.00 | 24.22 | C |
| ATOM | 823 | C | GLU A | 109 | −22.615 | −30.194 | 10.709 | 1.00 | 29.60 | C |
| ATOM | 824 | O | GLU A | 109 | −23.767 | −30.597 | 10.556 | 1.00 | 30.63 | O |
| ATOM | 825 | CB | GLU A | 109 | −22.359 | −27.695 | 10.546 | 1.00 | 24.96 | C |
| ATOM | 826 | CG | GLU A | 109 | −21.804 | −27.491 | 11.930 | 1.00 | 31.56 | C |
| ATOM | 827 | CD | GLU A | 109 | −22.753 | −26.760 | 12.847 | 1.00 | 46.33 | C |
| ATOM | 828 | OE1 | GLU A | 109 | −22.335 | −25.781 | 13.503 | 1.00 | 49.87 | O |
| ATOM | 829 | OE2 | GLU A | 109 | −23.917 | −27.199 | 12.938 | 1.00 | 48.48 | O |
| ATOM | 830 | N | ILE A | 110 | −21.776 | −30.742 | 11.592 | 1.00 | 26.82 | N |
| ATOM | 831 | CA | ILE A | 110 | −22.197 | −31.825 | 12.483 | 1.00 | 27.48 | C |
| ATOM | 832 | C | ILE A | 110 | −23.111 | −31.280 | 13.611 | 1.00 | 28.55 | C |
| ATOM | 833 | O | ILE A | 110 | −22.677 | −30.412 | 14.370 | 1.00 | 26.63 | O |
| ATOM | 834 | CB | ILE A | 110 | −20.970 | −32.575 | 13.057 | 1.00 | 31.12 | C |
| ATOM | 835 | CG1 | ILE A | 110 | −20.244 | −33.322 | 11.940 | 1.00 | 31.71 | C |
| ATOM | 836 | CG2 | ILE A | 110 | −21.413 | −33.566 | 14.158 | 1.00 | 32.61 | C |
| ATOM | 837 | CD1 | ILE A | 110 | −18.790 | −33.629 | 12.228 | 1.00 | 44.80 | C |
| ATOM | 838 | N | LYS A | 111 | −24.350 | −31.801 | 13.730 | 1.00 | 24.22 | N |
| ATOM | 839 | CA | LYS A | 111 | −25.273 | −31.389 | 14.791 | 1.00 | 24.11 | C |
| ATOM | 840 | C | LYS A | 111 | −24.922 | −32.101 | 16.087 | 1.00 | 30.47 | C |
| ATOM | 841 | O | LYS A | 111 | −24.525 | −33.270 | 16.062 | 1.00 | 33.17 | O |
| ATOM | 842 | CB | LYS A | 111 | −26.725 | −31.748 | 14.465 | 1.00 | 26.19 | C |
| ATOM | 843 | CG | LYS A | 111 | −27.746 | −31.061 | 15.372 | 1.00 | 33.13 | C |
| ATOM | 844 | CD | LYS A | 111 | −29.154 | −31.393 | 14.956 | 1.00 | 43.94 | C |
| ATOM | 845 | CE | LYS A | 111 | −30.170 | −30.578 | 15.720 | 1.00 | 60.07 | C |
| ATOM | 846 | NZ | LYS A | 111 | −31.556 | −30.880 | 15.261 | 1.00 | 73.90 | N |
| ATOM | 847 | N | ARG A | 112 | −25.135 | −31.425 | 17.220 | 1.00 | 24.42 | N |
| ATOM | 848 | CA | ARG A | 112 | −24.943 | −32.023 | 18.542 | 1.00 | 23.86 | C |
| ATOM | 849 | C | ARG A | 112 | −25.768 | −31.267 | 19.562 | 1.00 | 28.53 | C |
| ATOM | 850 | O | ARG A | 112 | −26.313 | −30.203 | 19.249 | 1.00 | 28.55 | O |
| ATOM | 851 | CB | ARG A | 112 | −23.446 | −32.058 | 18.936 | 1.00 | 21.06 | C |
| ATOM | 852 | CG | ARG A | 112 | −22.791 | −30.703 | 19.064 | 1.00 | 19.03 | C |
| ATOM | 853 | CD | ARG A | 112 | −21.678 | −30.748 | 20.061 | 1.00 | 22.53 | C |
| ATOM | 854 | NE | ARG A | 112 | −22.164 | −30.819 | 21.446 | 1.00 | 28.38 | N |
| ATOM | 855 | CZ | ARG A | 112 | −21.430 | −31.206 | 22.486 | 1.00 | 33.15 | C |
| ATOM | 856 | NH1 | ARG A | 112 | −20.155 | −31.551 | 22.322 | 1.00 | 28.32 | N |
| ATOM | 857 | NH2 | ARG A | 112 | −21.962 | −31.256 | 23.696 | 1.00 | 22.94 | N |
| ATOM | 858 | N | THR A | 113 | −25.802 | −31.781 | 20.800 | 1.00 | 25.97 | N |
| ATOM | 859 | CA | THR A | 113 | −26.524 | −31.181 | 21.917 | 1.00 | 24.25 | C |
| ATOM | 860 | C | THR A | 113 | −25.930 | −29.830 | 22.233 | 1.00 | 26.86 | C |
| ATOM | 861 | O | THR A | 113 | −24.717 | −29.629 | 22.077 | 1.00 | 24.02 | O |
| ATOM | 862 | CB | THR A | 113 | −26.497 | −32.112 | 23.145 | 1.00 | 26.93 | C |
| ATOM | 863 | OG1 | THR A | 113 | −25.147 | −32.499 | 23.417 | 1.00 | 25.52 | O |
| ATOM | 864 | CG2 | THR A | 113 | −27.372 | −33.337 | 22.957 | 1.00 | 18.12 | C |
| ATOM | 865 | N | VAL A | 114 | −26.792 | −28.897 | 22.696 | 1.00 | 25.09 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 866 | CA | VAL A | 114 | −26.382 | −27.527 | 23.029 | 1.00 | 23.53 | C |
| ATOM | 867 | C | VAL A | 114 | −25.371 | −27.638 | 24.157 | 1.00 | 30.00 | C |
| ATOM | 868 | O | VAL A | 114 | −25.541 | −28.438 | 25.072 | 1.00 | 32.23 | O |
| ATOM | 869 | CB | VAL A | 114 | −27.585 | −26.618 | 23.438 | 1.00 | 25.78 | C |
| ATOM | 870 | CG1 | VAL A | 114 | −27.119 | −25.259 | 23.957 | 1.00 | 24.89 | C |
| ATOM | 871 | CG2 | VAL A | 114 | −28.560 | −26.444 | 22.288 | 1.00 | 24.89 | C |
| ATOM | 872 | N | ALA A | 115 | −24.313 | −26.876 | 24.061 | 1.00 | 25.28 | N |
| ATOM | 873 | CA | ALA A | 115 | −23.264 | −26.838 | 25.046 | 1.00 | 24.30 | C |
| ATOM | 874 | C | ALA A | 115 | −22.926 | −25.356 | 25.272 | 1.00 | 26.14 | C |
| ATOM | 875 | O | ALA A | 115 | −22.507 | −24.670 | 24.344 | 1.00 | 21.54 | O |
| ATOM | 876 | CB | ALA A | 115 | −22.048 | −27.597 | 24.535 | 1.00 | 24.52 | C |
| ATOM | 877 | N | ALA A | 116 | −23.145 | −24.866 | 26.502 | 1.00 | 25.37 | N |
| ATOM | 878 | CA | ALA A | 116 | −22.837 | −23.488 | 26.874 | 1.00 | 24.14 | C |
| ATOM | 879 | C | ALA A | 116 | −21.315 | −23.283 | 26.899 | 1.00 | 27.23 | C |
| ATOM | 880 | O | ALA A | 116 | −20.571 | −24.201 | 27.269 | 1.00 | 26.75 | O |
| ATOM | 881 | CB | ALA A | 116 | −23.402 | −23.184 | 28.258 | 1.00 | 24.85 | C |
| ATOM | 882 | N | PRO A | 117 | −20.820 | −22.087 | 26.550 | 1.00 | 22.97 | N |
| ATOM | 883 | CA | PRO A | 117 | −19.369 | −21.858 | 26.662 | 1.00 | 23.47 | C |
| ATOM | 884 | C | PRO A | 117 | −18.894 | −21.708 | 28.109 | 1.00 | 29.68 | C |
| ATOM | 885 | O | PRO A | 117 | −19.628 | −21.240 | 28.989 | 1.00 | 26.52 | O |
| ATOM | 886 | CB | PRO A | 117 | −19.159 | −20.539 | 25.921 | 1.00 | 24.20 | C |
| ATOM | 887 | CG | PRO A | 117 | −20.487 | −19.855 | 26.011 | 1.00 | 27.97 | C |
| ATOM | 888 | CD | PRO A | 117 | −21.531 | −20.900 | 26.050 | 1.00 | 22.98 | C |
| ATOM | 889 | N | SER A | 118 | −17.638 | −22.119 | 28.339 | 1.00 | 28.35 | N |
| ATOM | 890 | CA | SER A | 118 | −16.922 | −21.847 | 29.576 | 1.00 | 27.38 | C |
| ATOM | 891 | C | SER A | 118 | −16.256 | −20.540 | 29.204 | 1.00 | 27.71 | C |
| ATOM | 892 | O | SER A | 118 | −15.581 | −20.485 | 28.179 | 1.00 | 25.79 | O |
| ATOM | 893 | CB | SER A | 118 | −15.856 | −22.896 | 29.867 | 1.00 | 29.46 | C |
| ATOM | 894 | OG | SER A | 118 | −16.471 | −24.140 | 30.131 | 1.00 | 40.36 | O |
| ATOM | 895 | N | VAL A | 119 | −16.518 | −19.479 | 29.962 | 1.00 | 23.94 | N |
| ATOM | 896 | CA | VAL A | 119 | −15.979 | −18.155 | 29.669 | 1.00 | 21.58 | C |
| ATOM | 897 | C | VAL A | 119 | −14.806 | −17.853 | 30.637 | 1.00 | 25.33 | C |
| ATOM | 898 | O | VAL A | 119 | −14.900 | −18.053 | 31.856 | 1.00 | 23.18 | O |
| ATOM | 899 | CB | VAL A | 119 | −17.087 | −17.070 | 29.712 | 1.00 | 23.07 | C |
| ATOM | 900 | CG1 | VAL A | 119 | −16.560 | −15.716 | 29.224 | 1.00 | 22.24 | C |
| ATOM | 901 | CG2 | VAL A | 119 | −18.309 | −17.508 | 28.893 | 1.00 | 21.48 | C |
| ATOM | 902 | N | PHE A | 120 | −13.711 | −17.351 | 30.069 | 1.00 | 22.51 | N |
| ATOM | 903 | CA | PHE A | 120 | −12.530 | −16.962 | 30.817 | 1.00 | 21.99 | C |
| ATOM | 904 | C | PHE A | 120 | −12.075 | −15.581 | 30.346 | 1.00 | 26.86 | C |
| ATOM | 905 | O | PHE A | 120 | −12.169 | −15.274 | 29.161 | 1.00 | 26.33 | O |
| ATOM | 906 | CB | PHE A | 120 | −11.422 | −17.994 | 30.596 | 1.00 | 22.73 | C |
| ATOM | 907 | CG | PHE A | 120 | −11.794 | −19.408 | 30.970 | 1.00 | 22.55 | C |
| ATOM | 908 | CD2 | PHE A | 120 | −12.246 | −20.307 | 30.003 | 1.00 | 22.58 | C |
| ATOM | 909 | CD1 | PHE A | 120 | −11.647 | −19.860 | 32.281 | 1.00 | 22.95 | C |
| ATOM | 910 | CE2 | PHE A | 120 | −12.533 | −21.641 | 30.339 | 1.00 | 24.58 | C |
| ATOM | 911 | CE1 | PHE A | 120 | −11.895 | −21.203 | 32.608 | 1.00 | 23.86 | C |
| ATOM | 912 | CZ | PHE A | 120 | −12.348 | −22.083 | 31.635 | 1.00 | 22.34 | C |
| ATOM | 913 | N | ILE A | 121 | −11.571 | −14.765 | 31.256 | 1.00 | 24.39 | N |
| ATOM | 914 | CA | ILE A | 121 | −11.031 | −13.453 | 30.911 | 1.00 | 25.26 | C |
| ATOM | 915 | C | ILE A | 121 | −9.543 | −13.490 | 31.333 | 1.00 | 28.99 | C |
| ATOM | 916 | O | ILE A | 121 | −9.208 | −14.147 | 32.322 | 1.00 | 30.21 | O |
| ATOM | 917 | CB | ILE A | 121 | −11.858 | −12.269 | 31.508 | 1.00 | 28.79 | C |
| ATOM | 918 | CG1 | ILE A | 121 | −11.354 | −10.918 | 30.913 | 1.00 | 29.78 | C |
| ATOM | 919 | CG2 | ILE A | 121 | −11.825 | −12.254 | 33.061 | 1.00 | 28.06 | C |
| ATOM | 920 | CD1 | ILE A | 121 | −12.139 | −9.721 | 31.254 | 1.00 | 27.63 | C |
| ATOM | 921 | N | PHE A | 122 | −8.651 | −12.897 | 30.535 | 1.00 | 25.40 | N |
| ATOM | 922 | CA | PHE A | 122 | −7.202 | −12.904 | 30.821 | 1.00 | 26.64 | C |
| ATOM | 923 | C | PHE A | 122 | −6.692 | −11.498 | 30.813 | 1.00 | 33.42 | C |
| ATOM | 924 | O | PHE A | 122 | −6.697 | −10.876 | 29.759 | 1.00 | 34.86 | O |
| ATOM | 925 | CB | PHE A | 122 | −6.432 | −13.677 | 29.753 | 1.00 | 27.97 | C |
| ATOM | 926 | CG | PHE A | 122 | −6.731 | −15.148 | 29.725 | 1.00 | 29.00 | C |
| ATOM | 927 | CD1 | PHE A | 122 | −6.269 | −15.980 | 30.728 | 1.00 | 31.10 | C |
| ATOM | 928 | CD2 | PHE A | 122 | −7.487 | −15.702 | 28.701 | 1.00 | 30.27 | C |
| ATOM | 929 | CE1 | PHE A | 122 | −6.521 | −17.350 | 30.690 | 1.00 | 31.48 | C |
| ATOM | 930 | CE2 | PHE A | 122 | −7.780 | −17.062 | 28.691 | 1.00 | 32.42 | C |
| ATOM | 931 | CZ | PHE A | 122 | −7.297 | −17.877 | 29.689 | 1.00 | 30.68 | C |
| ATOM | 932 | N | PRO A | 123 | −6.214 | −10.945 | 31.927 | 1.00 | 32.42 | N |
| ATOM | 933 | CA | PRO A | 123 | −5.677 | −9.585 | 31.863 | 1.00 | 32.99 | C |
| ATOM | 934 | C | PRO A | 123 | −4.335 | −9.575 | 31.100 | 1.00 | 36.94 | C |
| ATOM | 935 | O | PRO A | 123 | −3.705 | −10.637 | 30.897 | 1.00 | 33.15 | O |
| ATOM | 936 | CB | PRO A | 123 | −5.518 | −9.224 | 33.352 | 1.00 | 35.29 | C |
| ATOM | 937 | CG | PRO A | 123 | −5.236 | −10.465 | 33.995 | 1.00 | 39.57 | C |
| ATOM | 938 | CD | PRO A | 123 | −6.090 | −11.492 | 33.295 | 1.00 | 34.05 | C |
| ATOM | 939 | N | PRO A | 124 | −3.879 | −8.385 | 30.653 | 1.00 | 37.08 | N |
| ATOM | 940 | CA | PRO A | 124 | −2.574 | −8.313 | 29.970 | 1.00 | 37.83 | C |
| ATOM | 941 | C | PRO A | 124 | −1.435 | −8.666 | 30.921 | 1.00 | 42.79 | C |
| ATOM | 942 | O | PRO A | 124 | −1.567 | −8.490 | 32.127 | 1.00 | 43.55 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 943 | CB | PRO A | 124 | −2.488 | −6.848 | 29.527 | 1.00 | 40.31 | C |
| ATOM | 944 | CG | PRO A | 124 | −3.338 | −6.120 | 30.495 | 1.00 | 45.02 | C |
| ATOM | 945 | CD | PRO A | 124 | −4.467 | −7.042 | 30.825 | 1.00 | 39.44 | C |
| ATOM | 946 | N | SER A | 125 | −0.329 | −9.165 | 30.377 | 1.00 | 39.09 | N |
| ATOM | 947 | CA | SER A | 125 | 0.866 | −9.561 | 31.142 | 1.00 | 38.74 | C |
| ATOM | 948 | C | SER A | 125 | 1.715 | −8.339 | 31.537 | 1.00 | 45.83 | C |
| ATOM | 949 | O | SER A | 125 | 1.620 | −7.311 | 30.883 | 1.00 | 44.59 | O |
| ATOM | 950 | CB | SER A | 125 | 1.712 | −10.524 | 30.308 | 1.00 | 38.91 | C |
| ATOM | 951 | OG | SER A | 125 | 2.194 | −9.915 | 29.117 | 1.00 | 41.14 | O |
| ATOM | 952 | N | ASP A | 126 | 2.558 | −8.453 | 32.595 | 1.00 | 47.31 | N |
| ATOM | 953 | CA | ASP A | 126 | 3.488 | −7.376 | 32.963 | 1.00 | 50.61 | C |
| ATOM | 954 | C | ASP A | 126 | 4.520 | −7.208 | 31.856 | 1.00 | 55.14 | C |
| ATOM | 955 | O | ASP A | 126 | 4.979 | −6.093 | 31.635 | 1.00 | 56.70 | O |
| ATOM | 956 | CB | ASP A | 126 | 4.193 | −7.615 | 34.325 | 1.00 | 55.30 | C |
| ATOM | 957 | CG | ASP A | 126 | 3.349 | −7.272 | 35.546 | 1.00 | 76.19 | C |
| ATOM | 958 | OD1 | ASP A | 126 | 2.119 | −7.027 | 35.379 | 1.00 | 77.51 | O |
| ATOM | 959 | OD2 | ASP A | 126 | 3.905 | −7.270 | 36.671 | 1.00 | 85.72 | O |
| ATOM | 960 | N | GLU A | 127 | 4.843 | −8.290 | 31.120 | 1.00 | 51.30 | N |
| ATOM | 961 | CA | GLU A | 127 | 5.748 | −8.199 | 29.970 | 1.00 | 51.87 | C |
| ATOM | 962 | C | GLU A | 127 | 5.148 | −7.267 | 28.901 | 1.00 | 53.22 | C |
| ATOM | 963 | O | GLU A | 127 | 5.800 | −6.290 | 28.543 | 1.00 | 53.26 | O |
| ATOM | 964 | CB | GLU A | 127 | 6.045 | −9.593 | 29.360 | 1.00 | 53.07 | C |
| ATOM | 965 | CG | GLU A | 127 | 7.490 | −9.772 | 28.914 | 1.00 | 66.53 | C |
| ATOM | 966 | CD | GLU A | 127 | 7.964 | −8.883 | 27.779 | 1.00 | 97.60 | C |
| ATOM | 967 | OE1 | GLU A | 127 | 8.013 | −9.367 | 26.625 | 1.00 | 99.65 | O |
| ATOM | 968 | OE2 | GLU A | 127 | 8.358 | −7.728 | 28.055 | 1.00 | 97.10 | O |
| ATOM | 969 | N | GLN A | 128 | 3.901 | −7.543 | 28.410 | 1.00 | 47.51 | N |
| ATOM | 970 | CA | GLN A | 128 | 3.289 | −6.700 | 27.370 | 1.00 | 46.16 | C |
| ATOM | 971 | C | GLN A | 128 | 3.156 | −5.233 | 27.796 | 1.00 | 51.13 | C |
| ATOM | 972 | O | GLN A | 128 | 3.329 | −4.342 | 26.960 | 1.00 | 51.27 | O |
| ATOM | 973 | CB | GLN A | 128 | 1.921 | −7.230 | 26.924 | 1.00 | 45.49 | C |
| ATOM | 974 | CG | GLN A | 128 | 1.446 | −6.576 | 25.616 | 1.00 | 43.31 | C |
| ATOM | 975 | CD | GLN A | 128 | 0.045 | −6.929 | 25.180 | 1.00 | 50.68 | C |
| ATOM | 976 | OE1 | GLN A | 128 | −0.822 | −7.349 | 25.972 | 1.00 | 28.10 | O |
| ATOM | 977 | NE2 | GLN A | 128 | −0.241 | −6.610 | 23.918 | 1.00 | 50.28 | N |
| ATOM | 978 | N | LEU A | 129 | 2.855 | −4.984 | 29.077 | 1.00 | 47.90 | N |
| ATOM | 979 | CA | LEU A | 129 | 2.687 | −3.629 | 29.607 | 1.00 | 48.86 | C |
| ATOM | 980 | C | LEU A | 129 | 3.964 | −2.787 | 29.631 | 1.00 | 56.45 | C |
| ATOM | 981 | O | LEU A | 129 | 3.831 | −1.568 | 29.659 | 1.00 | 58.09 | O |
| ATOM | 982 | CB | LEU A | 129 | 2.044 | −3.656 | 30.994 | 1.00 | 48.33 | C |
| ATOM | 983 | CG | LEU A | 129 | 0.608 | −4.165 | 31.039 | 1.00 | 50.15 | C |
| ATOM | 984 | CD1 | LEU A | 129 | 0.245 | −4.619 | 32.442 | 1.00 | 50.08 | C |
| ATOM | 985 | CD2 | LEU A | 129 | −0.359 | −3.116 | 30.549 | 1.00 | 51.46 | C |
| ATOM | 986 | N | LYS A | 130 | 5.181 | −3.390 | 29.572 | 1.00 | 54.25 | N |
| ATOM | 987 | CA | LYS A | 130 | 6.441 | −2.614 | 29.479 | 1.00 | 56.30 | C |
| ATOM | 988 | C | LYS A | 130 | 6.459 | −1.840 | 28.142 | 1.00 | 62.82 | C |
| ATOM | 989 | O | LYS A | 130 | 6.946 | −0.704 | 28.094 | 1.00 | 65.59 | O |
| ATOM | 990 | CB | LYS A | 130 | 7.680 | −3.519 | 29.560 | 1.00 | 58.66 | C |
| ATOM | 991 | CG | LYS A | 130 | 7.925 | −4.143 | 30.928 | 1.00 | 67.83 | C |
| ATOM | 992 | CD | LYS A | 130 | 8.806 | −5.379 | 30.806 | 1.00 | 77.94 | C |
| ATOM | 993 | CE | LYS A | 130 | 9.047 | −6.090 | 32.112 | 1.00 | 88.47 | C |
| ATOM | 994 | NZ | LYS A | 130 | 9.675 | −7.422 | 31.891 | 1.00 | 95.88 | N |
| ATOM | 995 | N | SER A | 131 | 5.943 | −2.477 | 27.054 | 1.00 | 57.00 | N |
| ATOM | 996 | CA | SER A | 131 | 5.740 | −1.839 | 25.751 | 1.00 | 56.34 | C |
| ATOM | 997 | C | SER A | 131 | 4.388 | −1.115 | 25.898 | 1.00 | 60.73 | C |
| ATOM | 998 | O | SER A | 131 | 3.610 | −1.449 | 26.797 | 1.00 | 59.51 | O |
| ATOM | 999 | CB | SER A | 131 | 5.739 | −2.864 | 24.616 | 1.00 | 58.20 | C |
| ATOM | 1000 | OG | SER A | 131 | 4.540 | −3.617 | 24.489 | 1.00 | 67.98 | O |
| ATOM | 1001 | N | GLY A | 132 | 4.114 | −0.122 | 25.069 | 1.00 | 58.19 | N |
| ATOM | 1002 | CA | GLY A | 132 | 2.912 | 0.694 | 25.238 | 1.00 | 57.66 | C |
| ATOM | 1003 | C | GLY A | 132 | 1.589 | 0.087 | 24.824 | 1.00 | 59.44 | C |
| ATOM | 1004 | O | GLY A | 132 | 0.791 | 0.781 | 24.190 | 1.00 | 60.39 | O |
| ATOM | 1005 | N | THR A | 133 | 1.312 | −1.184 | 25.189 | 1.00 | 52.51 | N |
| ATOM | 1006 | CA | THR A | 133 | 0.090 | −1.877 | 24.756 | 1.00 | 49.06 | C |
| ATOM | 1007 | C | THR A | 133 | −0.468 | −2.779 | 25.843 | 1.00 | 48.42 | C |
| ATOM | 1008 | O | THR A | 133 | 0.256 | −3.192 | 26.754 | 1.00 | 48.22 | O |
| ATOM | 1009 | CB | THR A | 133 | 0.382 | −2.711 | 23.495 | 1.00 | 56.81 | C |
| ATOM | 1010 | OG1 | THR A | 133 | 1.158 | −1.937 | 22.584 | 1.00 | 57.37 | O |
| ATOM | 1011 | CG2 | THR A | 133 | −0.903 | −3.229 | 22.789 | 1.00 | 52.53 | C |
| ATOM | 1012 | N | ALA A | 134 | −1.776 | −3.040 | 25.754 | 1.00 | 40.78 | N |
| ATOM | 1013 | CA | ALA A | 134 | −2.494 | −3.922 | 26.651 | 1.00 | 38.71 | C |
| ATOM | 1014 | C | ALA A | 134 | −3.508 | −4.737 | 25.822 | 1.00 | 42.01 | C |
| ATOM | 1015 | O | ALA A | 134 | −4.340 | −4.150 | 25.129 | 1.00 | 42.61 | O |
| ATOM | 1016 | CB | ALA A | 134 | −3.214 | −3.100 | 27.699 | 1.00 | 39.56 | C |
| ATOM | 1017 | N | SER A | 135 | −3.393 | −6.071 | 25.831 | 1.00 | 35.44 | N |
| ATOM | 1018 | CA | SER A | 135 | −4.342 | −6.934 | 25.150 | 1.00 | 33.11 | C |
| ATOM | 1019 | C | SER A | 135 | −5.087 | −7.687 | 26.218 | 1.00 | 35.93 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1020 | O | SER A | 135 | −4.453 | −8.341 | 27.042 | 1.00 | 35.40 | O |
| ATOM | 1021 | CB | SER A | 135 | −3.627 | −7.930 | 24.242 | 1.00 | 35.94 | C |
| ATOM | 1022 | OG | SER A | 135 | −2.766 | −7.273 | 23.334 | 1.00 | 42.21 | O |
| ATOM | 1023 | N | VAL A | 136 | −6.416 | −7.574 | 26.239 | 1.00 | 33.58 | N |
| ATOM | 1024 | CA | VAL A | 136 | −7.271 | −8.297 | 27.189 | 1.00 | 33.33 | C |
| ATOM | 1025 | C | VAL A | 136 | −7.928 | −9.389 | 26.341 | 1.00 | 34.87 | C |
| ATOM | 1026 | O | VAL A | 136 | −8.509 | −9.070 | 25.311 | 1.00 | 33.21 | O |
| ATOM | 1027 | CB | VAL A | 136 | −8.329 | −7.387 | 27.868 | 1.00 | 37.91 | C |
| ATOM | 1028 | CG1 | VAL A | 136 | −8.935 | −8.082 | 29.083 | 1.00 | 37.04 | C |
| ATOM | 1029 | CG2 | VAL A | 136 | −7.732 | −6.031 | 28.251 | 1.00 | 39.00 | C |
| ATOM | 1030 | N | VAL A | 137 | −7.753 | −10.665 | 26.717 | 1.00 | 30.86 | N |
| ATOM | 1031 | CA | VAL A | 137 | −8.261 | −11.797 | 25.948 | 1.00 | 29.37 | C |
| ATOM | 1032 | C | VAL A | 137 | −9.448 | −12.402 | 26.646 | 1.00 | 35.23 | C |
| ATOM | 1033 | O | VAL A | 137 | −9.384 | −12.643 | 27.845 | 1.00 | 34.54 | O |
| ATOM | 1034 | CB | VAL A | 137 | −7.169 | −12.868 | 25.718 | 1.00 | 32.15 | C |
| ATOM | 1035 | CG1 | VAL A | 137 | −7.739 | −14.087 | 25.000 | 1.00 | 31.36 | C |
| ATOM | 1036 | CG2 | VAL A | 137 | −5.987 | −12.293 | 24.952 | 1.00 | 32.26 | C |
| ATOM | 1037 | N | CYS A | 138 | −10.524 | −12.665 | 25.898 | 1.00 | 34.27 | N |
| ATOM | 1038 | CA | CYS A | 138 | −11.683 | −13.367 | 26.416 | 1.00 | 35.00 | C |
| ATOM | 1039 | C | CYS A | 138 | −11.815 | −14.640 | 25.631 | 1.00 | 31.89 | C |
| ATOM | 1040 | O | CYS A | 138 | −11.825 | −14.582 | 24.410 | 1.00 | 31.01 | O |
| ATOM | 1041 | CB | CYS A | 138 | −12.944 | −12.541 | 26.297 | 1.00 | 38.28 | C |
| ATOM | 1042 | SG | CYS A | 138 | −14.355 | −13.262 | 27.173 | 1.00 | 44.32 | S |
| ATOM | 1043 | N | LEU A | 139 | −11.924 | −15.778 | 26.314 | 1.00 | 24.63 | N |
| ATOM | 1044 | CA | LEU A | 139 | −12.077 | −17.090 | 25.685 | 1.00 | 22.30 | C |
| ATOM | 1045 | C | LEU A | 139 | −13.485 | −17.620 | 26.002 | 1.00 | 24.67 | C |
| ATOM | 1046 | O | LEU A | 139 | −13.910 | −17.498 | 27.134 | 1.00 | 24.07 | O |
| ATOM | 1047 | CB | LEU A | 139 | −10.992 | −18.035 | 26.233 | 1.00 | 21.89 | C |
| ATOM | 1048 | CG | LEU A | 139 | −11.145 | −19.532 | 25.964 | 1.00 | 25.23 | C |
| ATOM | 1049 | CD1 | LEU A | 139 | −11.042 | −19.845 | 24.462 | 1.00 | 23.85 | C |
| ATOM | 1050 | CD2 | LEU A | 139 | −10.120 | −20.331 | 26.795 | 1.00 | 24.04 | C |
| ATOM | 1051 | N | LEU A | 140 | −14.226 | −18.089 | 24.978 | 1.00 | 20.65 | N |
| ATOM | 1052 | CA | LEU A | 140 | −15.491 | −18.816 | 25.062 | 1.00 | 20.23 | C |
| ATOM | 1053 | C | LEU A | 140 | −15.064 | −20.209 | 24.597 | 1.00 | 22.46 | C |
| ATOM | 1054 | O | LEU A | 140 | −14.665 | −20.339 | 23.437 | 1.00 | 21.71 | O |
| ATOM | 1055 | CB | LEU A | 140 | −16.535 | −18.313 | 24.076 | 1.00 | 20.46 | C |
| ATOM | 1056 | CG | LEU A | 140 | −17.345 | −17.112 | 24.433 | 1.00 | 25.35 | C |
| ATOM | 1057 | CD1 | LEU A | 140 | −16.428 | −15.877 | 24.661 | 1.00 | 25.77 | C |
| ATOM | 1058 | CD2 | LEU A | 140 | −18.366 | −16.857 | 23.303 | 1.00 | 22.11 | C |
| ATOM | 1059 | N | ASN A | 141 | −15.088 | −21.225 | 25.482 | 1.00 | 18.57 | N |
| ATOM | 1060 | CA | ASN A | 141 | −14.555 | −22.554 | 25.176 | 1.00 | 18.25 | C |
| ATOM | 1061 | C | ASN A | 141 | −15.562 | −23.671 | 25.043 | 1.00 | 23.28 | C |
| ATOM | 1062 | O | ASN A | 141 | −16.420 | −23.825 | 25.896 | 1.00 | 23.43 | O |
| ATOM | 1063 | CB | ASN A | 141 | −13.571 | −22.922 | 26.279 | 1.00 | 21.86 | C |
| ATOM | 1064 | CG | ASN A | 141 | −12.669 | −24.064 | 25.943 | 1.00 | 43.72 | C |
| ATOM | 1065 | OD1 | ASN A | 141 | −11.881 | −23.972 | 25.015 | 1.00 | 42.73 | O |
| ATOM | 1066 | ND2 | ASN A | 141 | −12.762 | −25.166 | 26.673 | 1.00 | 36.95 | N |
| ATOM | 1067 | N | ASN A | 142 | −15.410 | −24.490 | 23.990 | 1.00 | 22.16 | N |
| ATOM | 1068 | CA | ASN A | 142 | −16.181 | −25.709 | 23.739 | 1.00 | 21.52 | C |
| ATOM | 1069 | C | ASN A | 142 | −17.703 | −25.551 | 23.832 | 1.00 | 23.81 | C |
| ATOM | 1070 | O | ASN A | 142 | −18.363 | −26.298 | 24.538 | 1.00 | 24.20 | O |
| ATOM | 1071 | CB | ASN A | 142 | −15.704 | −26.816 | 24.677 | 1.00 | 18.26 | C |
| ATOM | 1072 | CG | ASN A | 142 | −14.244 | −27.134 | 24.588 | 1.00 | 44.43 | C |
| ATOM | 1073 | OD1 | ASN A | 142 | −13.549 | −26.747 | 23.646 | 1.00 | 32.89 | O |
| ATOM | 1074 | ND2 | ASN A | 142 | −13.748 | −27.891 | 25.556 | 1.00 | 47.68 | N |
| ATOM | 1075 | N | PHE A | 143 | −18.245 | −24.665 | 23.020 | 1.00 | 18.77 | N |
| ATOM | 1076 | CA | PHE A | 143 | −19.681 | −24.420 | 22.929 | 1.00 | 17.43 | C |
| ATOM | 1077 | C | PHE A | 143 | −20.257 | −24.864 | 21.574 | 1.00 | 20.92 | C |
| ATOM | 1078 | O | PHE A | 143 | −19.555 | −24.995 | 20.591 | 1.00 | 19.30 | O |
| ATOM | 1079 | CB | PHE A | 143 | −19.978 | −22.935 | 23.122 | 1.00 | 18.46 | C |
| ATOM | 1080 | CG | PHE A | 143 | −19.325 | −21.995 | 22.136 | 1.00 | 18.41 | C |
| ATOM | 1081 | CD2 | PHE A | 143 | −20.024 | −21.532 | 21.031 | 1.00 | 17.94 | C |
| ATOM | 1082 | CD1 | PHE A | 143 | −18.023 | −21.537 | 22.337 | 1.00 | 20.21 | C |
| ATOM | 1083 | CE2 | PHE A | 143 | −19.439 | −20.648 | 20.136 | 1.00 | 19.69 | C |
| ATOM | 1084 | CE1 | PHE A | 143 | −17.425 | −20.674 | 21.415 | 1.00 | 20.72 | C |
| ATOM | 1085 | CZ | PHE A | 143 | −18.147 | −20.215 | 20.330 | 1.00 | 17.72 | C |
| ATOM | 1086 | N | TYR A | 144 | −21.550 | −25.083 | 21.559 | 1.00 | 19.63 | N |
| ATOM | 1087 | CA | TYR A | 144 | −22.331 | −25.441 | 20.402 | 1.00 | 18.65 | C |
| ATOM | 1088 | C | TYR A | 144 | −23.764 | −24.927 | 20.642 | 1.00 | 24.96 | C |
| ATOM | 1089 | O | TYR A | 144 | −24.299 | −25.138 | 21.726 | 1.00 | 22.69 | O |
| ATOM | 1090 | CB | TYR A | 144 | −22.375 | −26.974 | 20.186 | 1.00 | 18.76 | C |
| ATOM | 1091 | CG | TYR A | 144 | −23.138 | −27.314 | 18.919 | 1.00 | 16.82 | C |
| ATOM | 1092 | CD1 | TYR A | 144 | −22.494 | −27.340 | 17.684 | 1.00 | 15.32 | C |
| ATOM | 1093 | CD2 | TYR A | 144 | −24.528 | −27.455 | 18.934 | 1.00 | 18.10 | C |
| ATOM | 1094 | CE1 | TYR A | 144 | −23.203 | −27.528 | 16.501 | 1.00 | 14.83 | C |
| ATOM | 1095 | CE2 | TYR A | 144 | −25.251 | −27.635 | 17.755 | 1.00 | 19.00 | C |
| ATOM | 1096 | CZ | TYR A | 144 | −24.586 | −27.661 | 16.537 | 1.00 | 27.03 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1097 | OH | TYR A | 144 | −25.319 | −27.794 | 15.378 | 1.00 | 31.16 | O |
| ATOM | 1098 | N | PRO A | 145 | −24.457 | −24.358 | 19.634 | 1.00 | 25.50 | N |
| ATOM | 1099 | CA | PRO A | 145 | −24.003 | −24.033 | 18.262 | 1.00 | 24.06 | C |
| ATOM | 1100 | C | PRO A | 145 | −22.976 | −22.894 | 18.174 | 1.00 | 28.06 | C |
| ATOM | 1101 | O | PRO A | 145 | −22.656 | −22.258 | 19.174 | 1.00 | 27.25 | O |
| ATOM | 1102 | CB | PRO A | 145 | −25.326 | −23.708 | 17.550 | 1.00 | 24.66 | C |
| ATOM | 1103 | CG | PRO A | 145 | −26.148 | −23.103 | 18.586 | 1.00 | 30.56 | C |
| ATOM | 1104 | CD | PRO A | 145 | −25.854 | −23.918 | 19.837 | 1.00 | 27.07 | C |
| ATOM | 1105 | N | ARG A | 146 | −22.463 | −22.651 | 16.952 | 1.00 | 24.74 | N |
| ATOM | 1106 | CA | ARG A | 146 | −21.464 | −21.618 | 16.589 | 1.00 | 24.60 | C |
| ATOM | 1107 | C | ARG A | 146 | −21.835 | −20.178 | 16.995 | 1.00 | 27.83 | C |
| ATOM | 1108 | O | ARG A | 146 | −20.946 | −19.361 | 17.231 | 1.00 | 24.88 | O |
| ATOM | 1109 | CB | ARG A | 146 | −21.268 | −21.688 | 15.039 | 1.00 | 31.21 | C |
| ATOM | 1110 | CG | ARG A | 146 | −20.519 | −20.557 | 14.321 | 1.00 | 42.97 | C |
| ATOM | 1111 | CD | ARG A | 146 | −19.098 | −20.882 | 13.960 | 1.00 | 55.77 | C |
| ATOM | 1112 | NE | ARG A | 146 | −18.541 | −19.824 | 13.114 | 1.00 | 66.15 | N |
| ATOM | 1113 | CZ | ARG A | 146 | −17.394 | −19.899 | 12.444 | 1.00 | 82.85 | C |
| ATOM | 1114 | NH1 | ARG A | 146 | −16.638 | −20.997 | 12.517 | 1.00 | 73.06 | N |
| ATOM | 1115 | NH2 | ARG A | 146 | −16.988 | −18.879 | 11.697 | 1.00 | 69.67 | N |
| ATOM | 1116 | N | GLU A | 147 | −23.135 | −19.855 | 17.019 | 1.00 | 27.13 | N |
| ATOM | 1117 | CA | GLU A | 147 | −23.611 | −18.497 | 17.261 | 1.00 | 27.67 | C |
| ATOM | 1118 | C | GLU A | 147 | −23.315 | −18.045 | 18.662 | 1.00 | 32.33 | C |
| ATOM | 1119 | O | GLU A | 147 | −23.618 | −18.757 | 19.605 | 1.00 | 33.19 | O |
| ATOM | 1120 | CB | GLU A | 147 | −25.126 | −18.376 | 16.996 | 1.00 | 30.27 | C |
| ATOM | 1121 | CG | GLU A | 147 | −25.494 | −18.326 | 15.520 | 1.00 | 45.45 | C |
| ATOM | 1122 | CD | GLU A | 147 | −25.104 | −19.544 | 14.700 | 1.00 | 64.83 | C |
| ATOM | 1123 | OE1 | GLU A | 147 | −24.401 | −19.369 | 13.676 | 1.00 | 71.85 | O |
| ATOM | 1124 | OE2 | GLU A | 147 | −25.461 | −20.676 | 15.107 | 1.00 | 35.92 | O |
| ATOM | 1125 | N | ALA A | 148 | −22.759 | −16.848 | 18.800 | 1.00 | 28.08 | N |
| ATOM | 1126 | CA | ALA A | 148 | −22.413 | −16.285 | 20.083 | 1.00 | 28.76 | C |
| ATOM | 1127 | C | ALA A | 148 | −22.157 | −14.809 | 19.918 | 1.00 | 33.90 | C |
| ATOM | 1128 | O | ALA A | 148 | −21.637 | −14.410 | 18.877 | 1.00 | 35.43 | O |
| ATOM | 1129 | CB | ALA A | 148 | −21.140 | −16.954 | 20.609 | 1.00 | 29.44 | C |
| ATOM | 1130 | N | LYS A | 149 | −22.458 | −14.005 | 20.951 | 1.00 | 29.36 | N |
| ATOM | 1131 | CA | LYS A | 149 | −22.141 | −12.587 | 20.970 | 1.00 | 28.73 | C |
| ATOM | 1132 | C | LYS A | 149 | −21.222 | −12.361 | 22.166 | 1.00 | 33.63 | C |
| ATOM | 1133 | O | LYS A | 149 | −21.409 | −12.987 | 23.206 | 1.00 | 34.64 | O |
| ATOM | 1134 | CB | LYS A | 149 | −23.400 | −11.720 | 21.069 | 1.00 | 32.17 | C |
| ATOM | 1135 | CG | LYS A | 149 | −23.135 | −10.242 | 20.755 | 1.00 | 55.45 | C |
| ATOM | 1136 | CD | LYS A | 149 | −24.415 | −9.397 | 20.657 | 1.00 | 66.16 | C |
| ATOM | 1137 | CE | LYS A | 149 | −25.008 | −9.066 | 21.997 | 1.00 | 77.91 | C |
| ATOM | 1138 | NZ | LYS A | 149 | −26.151 | −8.132 | 21.869 | 1.00 | 87.45 | N |
| ATOM | 1139 | N | VAL A | 150 | −20.200 | −11.515 | 22.000 | 1.00 | 30.02 | N |
| ATOM | 1140 | CA | VAL A | 150 | −19.254 | −11.147 | 23.056 | 1.00 | 29.50 | C |
| ATOM | 1141 | C | VAL A | 150 | −19.178 | −9.642 | 23.076 | 1.00 | 30.50 | C |
| ATOM | 1142 | O | VAL A | 150 | −18.958 | −9.046 | 22.027 | 1.00 | 29.10 | O |
| ATOM | 1143 | CB | VAL A | 150 | −17.849 | −11.746 | 22.825 | 1.00 | 33.08 | C |
| ATOM | 1144 | CG1 | VAL A | 150 | −16.958 | −11.519 | 24.048 | 1.00 | 33.00 | C |
| ATOM | 1145 | CG2 | VAL A | 150 | −17.949 | −13.229 | 22.484 | 1.00 | 32.22 | C |
| ATOM | 1146 | N | GLN A | 151 | −19.359 | −9.022 | 24.239 | 1.00 | 27.02 | N |
| ATOM | 1147 | CA | GLN A | 151 | −19.256 | −7.571 | 24.365 | 1.00 | 27.79 | C |
| ATOM | 1148 | C | GLN A | 151 | −18.257 | −7.242 | 25.442 | 1.00 | 32.34 | C |
| ATOM | 1149 | O | GLN A | 151 | −18.164 | −7.963 | 26.435 | 1.00 | 30.17 | O |
| ATOM | 1150 | CB | GLN A | 151 | −20.613 | −6.933 | 24.700 | 1.00 | 29.74 | C |
| ATOM | 1151 | CG | GLN A | 151 | −21.545 | −6.922 | 23.506 | 1.00 | 47.82 | C |
| ATOM | 1152 | CD | GLN A | 151 | −22.817 | −6.168 | 23.759 | 1.00 | 71.87 | C |
| ATOM | 1153 | OE1 | GLN A | 151 | −23.131 | −5.211 | 23.048 | 1.00 | 71.50 | O |
| ATOM | 1154 | NE2 | GLN A | 151 | −23.615 | −6.619 | 24.726 | 1.00 | 62.77 | N |
| ATOM | 1155 | N | TRP A | 152 | −17.530 | −6.134 | 25.254 | 1.00 | 31.10 | N |
| ATOM | 1156 | CA | TRP A | 152 | −16.567 | −5.639 | 26.228 | 1.00 | 32.06 | C |
| ATOM | 1157 | C | TRP A | 152 | −17.133 | −4.404 | 26.915 | 1.00 | 38.81 | C |
| ATOM | 1158 | O | TRP A | 152 | −17.690 | −3.530 | 26.245 | 1.00 | 39.08 | O |
| ATOM | 1159 | CB | TRP A | 152 | −15.255 | −5.276 | 25.553 | 1.00 | 30.95 | C |
| ATOM | 1160 | CG | TRP A | 152 | −14.478 | −6.467 | 25.117 | 1.00 | 31.09 | C |
| ATOM | 1161 | CD1 | TRP A | 152 | −14.455 | −7.030 | 23.874 | 1.00 | 33.01 | C |
| ATOM | 1162 | CD2 | TRP A | 152 | −13.583 | −7.232 | 25.925 | 1.00 | 31.01 | C |
| ATOM | 1163 | NE1 | TRP A | 152 | −13.560 | −8.069 | 23.844 | 1.00 | 32.20 | N |
| ATOM | 1164 | CE2 | TRP A | 152 | −12.997 | −8.210 | 25.089 | 1.00 | 33.68 | C |
| ATOM | 1165 | CE3 | TRP A | 152 | −13.162 | −7.144 | 27.267 | 1.00 | 32.59 | C |
| ATOM | 1166 | CZ2 | TRP A | 152 | −12.050 | −9.120 | 25.558 | 1.00 | 31.67 | C |
| ATOM | 1167 | CZ3 | TRP A | 152 | −12.252 | −8.072 | 27.738 | 1.00 | 33.47 | C |
| ATOM | 1168 | CH2 | TRP A | 152 | −11.709 | −9.047 | 26.887 | 1.00 | 33.10 | C |
| ATOM | 1169 | N | LYS A | 153 | −16.981 | −4.335 | 28.247 | 1.00 | 36.33 | N |
| ATOM | 1170 | CA | LYS A | 153 | −17.410 | −3.207 | 29.060 | 1.00 | 37.78 | C |
| ATOM | 1171 | C | LYS A | 153 | −16.200 | −2.756 | 29.825 | 1.00 | 43.20 | C |
| ATOM | 1172 | O | LYS A | 153 | −15.596 | −3.582 | 30.495 | 1.00 | 42.82 | O |
| ATOM | 1173 | CB | LYS A | 153 | −18.504 | −3.630 | 30.053 | 1.00 | 40.82 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1174 | CG | LYS A | 153 | −19.909 | −3.190 | 29.684 | 1.00 | 51.13 | C |
| ATOM | 1175 | CD | LYS A | 153 | −20.496 | −4.017 | 28.561 | 1.00 | 55.08 | C |
| ATOM | 1176 | CE | LYS A | 153 | −21.987 | −3.802 | 28.439 | 1.00 | 61.32 | C |
| ATOM | 1177 | NZ | LYS A | 153 | −22.763 | −4.496 | 29.505 | 1.00 | 63.53 | N |
| ATOM | 1178 | N | VAL A | 154 | −15.801 | −1.488 | 29.699 | 1.00 | 42.00 | N |
| ATOM | 1179 | CA | VAL A | 154 | −14.678 | −0.932 | 30.471 | 1.00 | 43.22 | C |
| ATOM | 1180 | C | VAL A | 154 | −15.318 | 0.137 | 31.384 | 1.00 | 49.73 | C |
| ATOM | 1181 | O | VAL A | 154 | −15.739 | 1.188 | 30.894 | 1.00 | 49.81 | O |
| ATOM | 1182 | CB | VAL A | 154 | −13.543 | −0.404 | 29.563 | 1.00 | 46.61 | C |
| ATOM | 1183 | CG1 | VAL A | 154 | −12.424 | 0.214 | 30.386 | 1.00 | 46.81 | C |
| ATOM | 1184 | CG2 | VAL A | 154 | −12.999 | −1.528 | 28.691 | 1.00 | 45.11 | C |
| ATOM | 1185 | N | ASP A | 155 | −15.507 | −0.204 | 32.676 | 1.00 | 48.66 | N |
| ATOM | 1186 | CA | ASP A | 155 | −16.221 | 0.614 | 33.672 | 1.00 | 51.57 | C |
| ATOM | 1187 | C | ASP A | 155 | −17.699 | 0.786 | 33.232 | 1.00 | 60.54 | C |
| ATOM | 1188 | O | ASP A | 155 | −18.235 | 1.905 | 33.232 | 1.00 | 63.73 | O |
| ATOM | 1189 | CB | ASP A | 155 | −15.529 | 1.974 | 33.948 | 1.00 | 54.32 | C |
| ATOM | 1190 | CG | ASP A | 155 | −14.196 | 1.871 | 34.669 | 1.00 | 66.60 | C |
| ATOM | 1191 | OD1 | ASP A | 155 | −14.060 | 0.988 | 35.549 | 1.00 | 68.08 | O |
| ATOM | 1192 | OD2 | ASP A | 155 | −13.334 | 2.743 | 34.441 | 1.00 | 73.21 | O |
| ATOM | 1193 | N | ASN A | 156 | −18.336 | −0.346 | 32.826 | 1.00 | 55.30 | N |
| ATOM | 1194 | CA | ASN A | 156 | −19.729 | −0.423 | 32.344 | 1.00 | 55.00 | C |
| ATOM | 1195 | C | ASN A | 156 | −19.971 | 0.323 | 31.022 | 1.00 | 58.75 | C |
| ATOM | 1196 | O | ASN A | 156 | −21.129 | 0.398 | 30.605 | 1.00 | 60.44 | O |
| ATOM | 1197 | CB | ASN A | 156 | −20.755 | 0.033 | 33.409 | 1.00 | 58.30 | C |
| ATOM | 1198 | CG | ASN A | 156 | −20.473 | −0.457 | 34.818 | 1.00 | 80.39 | C |
| ATOM | 1199 | OD1 | ASN A | 156 | −19.932 | −1.547 | 35.027 | 1.00 | 74.34 | O |
| ATOM | 1200 | ND2 | ASN A | 156 | −20.821 | 0.339 | 35.825 | 1.00 | 72.44 | N |
| ATOM | 1201 | N | ALA A | 157 | −18.909 | 0.820 | 30.332 | 1.00 | 52.63 | N |
| ATOM | 1202 | CA | ALA A | 157 | −19.046 | 1.491 | 29.032 | 1.00 | 51.44 | C |
| ATOM | 1203 | C | ALA A | 157 | −18.861 | 0.466 | 27.908 | 1.00 | 51.19 | C |
| ATOM | 1204 | O | ALA A | 157 | −17.796 | −0.152 | 27.803 | 1.00 | 49.11 | O |
| ATOM | 1205 | CB | ALA A | 157 | −18.002 | 2.588 | 28.891 | 1.00 | 53.20 | C |
| ATOM | 1206 | N | LEU A | 158 | −19.873 | 0.306 | 27.052 | 1.00 | 46.65 | N |
| ATOM | 1207 | CA | LEU A | 158 | −19.791 | −0.626 | 25.926 | 1.00 | 44.52 | C |
| ATOM | 1208 | C | LEU A | 158 | −18.709 | −0.176 | 24.925 | 1.00 | 45.80 | C |
| ATOM | 1209 | O | LEU A | 158 | −18.676 | 0.998 | 24.571 | 1.00 | 46.51 | O |
| ATOM | 1210 | CB | LEU A | 158 | −21.156 | −0.732 | 25.222 | 1.00 | 44.51 | C |
| ATOM | 1211 | CG | LEU A | 158 | −21.228 | −1.666 | 24.014 | 1.00 | 48.42 | C |
| ATOM | 1212 | CD1 | LEU A | 158 | −20.897 | −3.112 | 24.409 | 1.00 | 47.41 | C |
| ATOM | 1213 | CD2 | LEU A | 158 | −22.600 | −1.595 | 23.371 | 1.00 | 51.37 | C |
| ATOM | 1214 | N | GLN A | 159 | −17.832 | −1.105 | 24.479 | 1.00 | 39.19 | N |
| ATOM | 1215 | CA | GLN A | 159 | −16.762 | −0.798 | 23.524 | 1.00 | 37.87 | C |
| ATOM | 1216 | C | GLN A | 159 | −17.151 | −1.184 | 22.107 | 1.00 | 42.19 | C |
| ATOM | 1217 | O | GLN A | 159 | −18.025 | −2.030 | 21.903 | 1.00 | 42.19 | O |
| ATOM | 1218 | CB | GLN A | 159 | −15.489 | −1.572 | 23.864 | 1.00 | 37.44 | C |
| ATOM | 1219 | CG | GLN A | 159 | −15.040 | −1.457 | 25.284 | 1.00 | 36.73 | C |
| ATOM | 1220 | CD | GLN A | 159 | −14.431 | −0.114 | 25.548 | 1.00 | 53.47 | C |
| ATOM | 1221 | OE1 | GLN A | 159 | −13.231 | 0.086 | 25.331 | 1.00 | 44.75 | O |
| ATOM | 1222 | NE2 | GLN A | 159 | −15.229 | 0.826 | 26.041 | 1.00 | 45.27 | N |
| ATOM | 1223 | N | SER A | 160 | −16.444 | −0.614 | 21.131 | 1.00 | 39.14 | N |
| ATOM | 1224 | CA | SER A | 160 | −16.615 | −0.940 | 19.709 | 1.00 | 38.38 | C |
| ATOM | 1225 | C | SER A | 160 | −15.403 | −0.476 | 18.906 | 1.00 | 39.39 | C |
| ATOM | 1226 | O | SER A | 160 | −14.784 | 0.514 | 19.262 | 1.00 | 40.70 | O |
| ATOM | 1227 | CB | SER A | 160 | −17.920 | −0.372 | 19.134 | 1.00 | 43.16 | C |
| ATOM | 1228 | OG | SER A | 160 | −18.129 | 1.002 | 19.408 | 1.00 | 54.50 | O |
| ATOM | 1229 | N | GLY A | 161 | −15.033 | −1.246 | 17.893 | 1.00 | 33.11 | N |
| ATOM | 1230 | CA | GLY A | 161 | −13.899 | −0.950 | 17.031 | 1.00 | 32.65 | C |
| ATOM | 1231 | C | GLY A | 161 | −12.528 | −1.369 | 17.534 | 1.00 | 35.65 | C |
| ATOM | 1232 | O | GLY A | 161 | −11.618 | −1.518 | 16.722 | 1.00 | 35.45 | O |
| ATOM | 1233 | N | ASN A | 162 | −12.351 | −1.578 | 18.853 | 1.00 | 31.77 | N |
| ATOM | 1234 | CA | ASN A | 162 | −11.043 | −1.932 | 19.450 | 1.00 | 31.03 | C |
| ATOM | 1235 | C | ASN A | 162 | −10.910 | −3.438 | 19.820 | 1.00 | 34.09 | C |
| ATOM | 1236 | O | ASN A | 162 | −10.029 | −3.786 | 20.612 | 1.00 | 34.89 | O |
| ATOM | 1237 | CB | ASN A | 162 | −10.784 | −1.060 | 20.698 | 1.00 | 30.36 | C |
| ATOM | 1238 | CG | ASN A | 162 | −11.898 | −1.098 | 21.718 | 1.00 | 41.48 | C |
| ATOM | 1239 | OD1 | ASN A | 162 | −12.856 | −1.865 | 21.585 | 1.00 | 29.18 | O |
| ATOM | 1240 | ND2 | ASN A | 162 | −11.817 | −0.253 | 22.737 | 1.00 | 38.02 | N |
| ATOM | 1241 | N | SER A | 163 | −11.755 | −4.320 | 19.250 | 1.00 | 28.84 | N |
| ATOM | 1242 | CA | SER A | 163 | −11.693 | −5.758 | 19.522 | 1.00 | 27.99 | C |
| ATOM | 1243 | C | SER A | 163 | −11.767 | −6.568 | 18.248 | 1.00 | 32.39 | C |
| ATOM | 1244 | O | SER A | 163 | −12.324 | −6.094 | 17.265 | 1.00 | 33.90 | O |
| ATOM | 1245 | CB | SER A | 163 | −12.779 | −6.196 | 20.509 | 1.00 | 29.57 | C |
| ATOM | 1246 | OG | SER A | 163 | −14.091 | −6.196 | 19.971 | 1.00 | 32.98 | O |
| ATOM | 1247 | N | GLN A | 164 | −11.177 | −7.775 | 18.258 | 1.00 | 27.95 | N |
| ATOM | 1248 | CA | GLN A | 164 | −11.200 | −8.703 | 17.121 | 1.00 | 26.97 | C |
| ATOM | 1249 | C | GLN A | 164 | −11.536 | −10.097 | 17.605 | 1.00 | 28.50 | C |
| ATOM | 1250 | O | GLN A | 164 | −11.010 | −10.515 | 18.619 | 1.00 | 27.82 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1251 | CB | GLN A | 164 | −9.838 | −8.740 | 16.409 | 1.00 | 28.72 | C |
| ATOM | 1252 | CG | GLN A | 164 | −9.451 | −7.401 | 15.808 | 1.00 | 44.57 | C |
| ATOM | 1253 | CD | GLN A | 164 | −8.188 | −7.499 | 14.986 | 1.00 | 51.85 | C |
| ATOM | 1254 | OE1 | GLN A | 164 | −7.083 | −7.456 | 15.528 | 1.00 | 51.17 | O |
| ATOM | 1255 | NE2 | GLN A | 164 | −8.320 | −7.624 | 13.664 | 1.00 | 30.00 | N |
| ATOM | 1256 | N | GLU A | 165 | −12.361 | −10.830 | 16.868 | 1.00 | 25.16 | N |
| ATOM | 1257 | CA | GLU A | 165 | −12.726 | −12.213 | 17.209 | 1.00 | 23.32 | C |
| ATOM | 1258 | C | GLU A | 165 | −11.991 | −13.194 | 16.299 | 1.00 | 26.23 | C |
| ATOM | 1259 | O | GLU A | 165 | −11.640 | −12.870 | 15.168 | 1.00 | 27.81 | O |
| ATOM | 1260 | CB | GLU A | 165 | −14.260 | −12.460 | 17.077 | 1.00 | 23.24 | C |
| ATOM | 1261 | CG | GLU A | 165 | −15.108 | −11.730 | 18.108 | 1.00 | 36.87 | C |
| ATOM | 1262 | CD | GLU A | 165 | −16.599 | −12.052 | 18.098 | 1.00 | 64.29 | C |
| ATOM | 1263 | OE1 | GLU A | 165 | −17.322 | −11.497 | 18.955 | 1.00 | 51.97 | O |
| ATOM | 1264 | OE2 | GLU A | 165 | −17.053 | −12.836 | 17.231 | 1.00 | 63.85 | O |
| ATOM | 1265 | N | SER A | 166 | −11.892 | −14.433 | 16.756 | 1.00 | 20.80 | N |
| ATOM | 1266 | CA | SER A | 166 | −11.316 | −15.540 | 16.007 | 1.00 | 19.22 | C |
| ATOM | 1267 | C | SER A | 166 | −12.019 | −16.778 | 16.493 | 1.00 | 24.12 | C |
| ATOM | 1268 | O | SER A | 166 | −12.145 | −16.958 | 17.711 | 1.00 | 24.30 | O |
| ATOM | 1269 | CB | SER A | 166 | −9.821 | −15.651 | 16.271 | 1.00 | 21.26 | C |
| ATOM | 1270 | OG | SER A | 166 | −9.267 | −16.590 | 15.371 | 1.00 | 27.85 | O |
| ATOM | 1271 | N | VAL A | 167 | −12.505 | −17.613 | 15.564 | 1.00 | 20.77 | N |
| ATOM | 1272 | CA | VAL A | 167 | −13.245 | −18.823 | 15.895 | 1.00 | 21.02 | C |
| ATOM | 1273 | C | VAL A | 167 | −12.515 | −20.018 | 15.328 | 1.00 | 25.27 | C |
| ATOM | 1274 | O | VAL A | 167 | −11.931 | −19.918 | 14.252 | 1.00 | 24.77 | O |
| ATOM | 1275 | CB | VAL A | 167 | −14.716 | −18.736 | 15.368 | 1.00 | 25.62 | C |
| ATOM | 1276 | CG1 | VAL A | 167 | −15.583 | −19.854 | 15.964 | 1.00 | 25.50 | C |
| ATOM | 1277 | CG2 | VAL A | 167 | −15.321 | −17.376 | 15.706 | 1.00 | 25.27 | C |
| ATOM | 1278 | N | THR A | 168 | −12.535 | −21.155 | 16.051 | 1.00 | 22.14 | N |
| ATOM | 1279 | CA | THR A | 168 | −11.902 | −22.388 | 15.555 | 1.00 | 21.63 | C |
| ATOM | 1280 | C | THR A | 168 | −12.859 | −23.114 | 14.618 | 1.00 | 25.09 | C |
| ATOM | 1281 | O | THR A | 168 | −14.040 | −22.801 | 14.591 | 1.00 | 24.71 | O |
| ATOM | 1282 | CB | THR A | 168 | −11.541 | −23.354 | 16.712 | 1.00 | 25.87 | C |
| ATOM | 1283 | OG1 | THR A | 168 | −12.698 | −23.606 | 17.510 | 1.00 | 21.57 | O |
| ATOM | 1284 | CG2 | THR A | 168 | −10.412 | −22.848 | 17.570 | 1.00 | 23.21 | C |
| ATOM | 1285 | N | GLU A | 169 | −12.349 | −24.121 | 13.885 | 1.00 | 22.90 | N |
| ATOM | 1286 | CA | GLU A | 169 | −13.176 | −25.024 | 13.069 | 1.00 | 21.71 | C |
| ATOM | 1287 | C | GLU A | 169 | −13.870 | −25.993 | 14.021 | 1.00 | 26.31 | C |
| ATOM | 1288 | O | GLU A | 169 | −13.379 | −26.249 | 15.118 | 1.00 | 25.92 | O |
| ATOM | 1289 | CB | GLU A | 169 | −12.360 | −25.825 | 12.023 | 1.00 | 22.27 | C |
| ATOM | 1290 | CG | GLU A | 169 | −12.296 | −25.120 | 10.667 | 1.00 | 38.52 | C |
| ATOM | 1291 | CD | GLU A | 169 | −13.600 | −24.946 | 9.897 | 1.00 | 69.06 | C |
| ATOM | 1292 | OE1 | GLU A | 169 | −13.579 | −24.186 | 8.901 | 1.00 | 56.58 | O |
| ATOM | 1293 | OE2 | GLU A | 169 | −14.639 | −25.529 | 10.297 | 1.00 | 68.88 | O |
| ATOM | 1294 | N | GLN A | 170 | −15.015 | −26.533 | 13.609 | 1.00 | 24.06 | N |
| ATOM | 1295 | CA | GLN A | 170 | −15.728 | −27.488 | 14.443 | 1.00 | 23.32 | C |
| ATOM | 1296 | C | GLN A | 170 | −14.753 | −28.604 | 14.846 | 1.00 | 28.92 | C |
| ATOM | 1297 | O | GLN A | 170 | −13.976 | −29.070 | 14.017 | 1.00 | 27.94 | O |
| ATOM | 1298 | CB | GLN A | 170 | −16.916 | −28.041 | 13.697 | 1.00 | 23.80 | C |
| ATOM | 1299 | CG | GLN A | 170 | −17.778 | −28.889 | 14.550 | 1.00 | 23.77 | C |
| ATOM | 1300 | CD | GLN A | 170 | −19.139 | −29.099 | 13.956 | 1.00 | 32.44 | C |
| ATOM | 1301 | OE1 | GLN A | 170 | −19.273 | −29.286 | 12.758 | 1.00 | 35.21 | O |
| ATOM | 1302 | NE2 | GLN A | 170 | −20.162 | −29.188 | 14.787 | 1.00 | 23.42 | N |
| ATOM | 1303 | N | ASP A | 171 | −14.731 | −28.950 | 16.137 | 1.00 | 26.94 | N |
| ATOM | 1304 | CA | ASP A | 171 | −13.792 | −29.918 | 16.669 | 1.00 | 27.64 | C |
| ATOM | 1305 | C | ASP A | 171 | −14.076 | −31.325 | 16.163 | 1.00 | 35.11 | C |
| ATOM | 1306 | O | ASP A | 171 | −15.200 | −31.806 | 16.279 | 1.00 | 34.61 | O |
| ATOM | 1307 | CB | ASP A | 171 | −13.801 | −29.895 | 18.198 | 1.00 | 28.52 | C |
| ATOM | 1308 | CG | ASP A | 171 | −12.654 | −30.667 | 18.801 | 1.00 | 39.98 | C |
| ATOM | 1309 | OD1 | ASP A | 171 | −11.515 | −30.188 | 18.717 | 1.00 | 42.69 | O |
| ATOM | 1310 | OD2 | ASP A | 171 | −12.895 | −31.766 | 19.334 | 1.00 | 48.47 | O |
| ATOM | 1311 | N | SER A | 172 | −13.031 | −31.990 | 15.642 | 1.00 | 34.36 | N |
| ATOM | 1312 | CA | SER A | 172 | −13.105 | −33.348 | 15.102 | 1.00 | 35.56 | C |
| ATOM | 1313 | C | SER A | 172 | −13.567 | −34.398 | 16.138 | 1.00 | 38.99 | C |
| ATOM | 1314 | O | SER A | 172 | −14.204 | −35.377 | 15.739 | 1.00 | 39.53 | O |
| ATOM | 1315 | CB | SER A | 172 | −11.756 | −33.757 | 14.515 | 1.00 | 40.62 | C |
| ATOM | 1316 | OG | SER A | 172 | −10.744 | −33.688 | 15.506 | 1.00 | 54.61 | O |
| ATOM | 1317 | N | LYS A | 173 | −13.259 | −34.202 | 17.447 | 1.00 | 34.23 | N |
| ATOM | 1318 | CA | LYS A | 173 | −13.656 | −35.152 | 18.494 | 1.00 | 33.36 | C |
| ATOM | 1319 | C | LYS A | 173 | −15.030 | −34.845 | 19.117 | 1.00 | 37.05 | C |
| ATOM | 1320 | O | LYS A | 173 | −15.830 | −35.770 | 19.254 | 1.00 | 37.37 | O |
| ATOM | 1321 | CB | LYS A | 173 | −12.608 | −35.226 | 19.600 | 1.00 | 34.84 | C |
| ATOM | 1322 | CG | LYS A | 173 | −11.284 | −35.814 | 19.161 | 1.00 | 47.79 | C |
| ATOM | 1323 | CD | LYS A | 173 | −10.341 | −35.895 | 20.346 | 1.00 | 62.80 | C |
| ATOM | 1324 | CE | LYS A | 173 | −8.933 | −36.288 | 19.971 | 1.00 | 84.90 | C |
| ATOM | 1325 | NZ | LYS A | 173 | −8.035 | −36.312 | 21.160 | 1.00 | 98.24 | N |
| ATOM | 1326 | N | ASP A | 174 | −15.309 | −33.572 | 19.509 | 1.00 | 31.74 | N |
| ATOM | 1327 | CA | ASP A | 174 | −16.550 | −33.243 | 20.214 | 1.00 | 30.38 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1328 | C | ASP A | 174 | −17.510 | −32.316 | 19.469 | 1.00 | 30.71 | C |
| ATOM | 1329 | O | ASP A | 174 | −18.538 | −31.954 | 20.032 | 1.00 | 29.77 | O |
| ATOM | 1330 | CB | ASP A | 174 | −16.246 | −32.702 | 21.629 | 1.00 | 32.84 | C |
| ATOM | 1331 | CG | ASP A | 174 | −15.524 | −31.383 | 21.759 | 1.00 | 50.02 | C |
| ATOM | 1332 | OD1 | ASP A | 174 | −15.559 | −30.592 | 20.793 | 1.00 | 51.85 | O |
| ATOM | 1333 | OD2 | ASP A | 174 | −15.008 | −31.089 | 22.877 | 1.00 | 54.26 | O |
| ATOM | 1334 | N | SER A | 175 | −17.217 | −31.969 | 18.221 | 1.00 | 25.91 | N |
| ATOM | 1335 | CA | SER A | 175 | −18.091 | −31.149 | 17.382 | 1.00 | 24.60 | C |
| ATOM | 1336 | C | SER A | 175 | −18.435 | −29.751 | 17.964 | 1.00 | 25.62 | C |
| ATOM | 1337 | O | SER A | 175 | −19.429 | −29.141 | 17.539 | 1.00 | 23.51 | O |
| ATOM | 1338 | CB | SER A | 175 | −19.359 | −31.927 | 17.030 | 1.00 | 27.29 | C |
| ATOM | 1339 | OG | SER A | 175 | −19.010 | −33.183 | 16.474 | 1.00 | 32.91 | O |
| ATOM | 1340 | N | THR A | 176 | −17.571 | −29.200 | 18.844 | 1.00 | 21.48 | N |
| ATOM | 1341 | CA | THR A | 176 | −17.823 | −27.872 | 19.416 | 1.00 | 20.88 | C |
| ATOM | 1342 | C | THR A | 176 | −16.983 | −26.786 | 18.759 | 1.00 | 25.41 | C |
| ATOM | 1343 | O | THR A | 176 | −16.086 | −27.058 | 17.953 | 1.00 | 23.30 | O |
| ATOM | 1344 | CB | THR A | 176 | −17.604 | −27.873 | 20.928 | 1.00 | 26.13 | C |
| ATOM | 1345 | OG1 | THR A | 176 | −16.218 | −28.071 | 21.248 | 1.00 | 27.26 | O |
| ATOM | 1346 | CG2 | THR A | 176 | −18.495 | −28.849 | 21.644 | 1.00 | 18.20 | C |
| ATOM | 1347 | N | TYR A | 177 | −17.275 | −25.543 | 19.145 | 1.00 | 23.39 | N |
| ATOM | 1348 | CA | TYR A | 177 | −16.538 | −24.365 | 18.730 | 1.00 | 22.14 | C |
| ATOM | 1349 | C | TYR A | 177 | −15.941 | −23.731 | 19.936 | 1.00 | 27.66 | C |
| ATOM | 1350 | O | TYR A | 177 | −16.450 | −23.881 | 21.049 | 1.00 | 28.79 | O |
| ATOM | 1351 | CB | TYR A | 177 | −17.475 | −23.349 | 18.097 | 1.00 | 22.63 | C |
| ATOM | 1352 | CG | TYR A | 177 | −18.054 | −23.850 | 16.803 | 1.00 | 22.62 | C |
| ATOM | 1353 | CD1 | TYR A | 177 | −17.349 | −23.725 | 15.611 | 1.00 | 23.59 | C |
| ATOM | 1354 | CD2 | TYR A | 177 | −19.255 | −24.550 | 16.781 | 1.00 | 22.81 | C |
| ATOM | 1355 | CE1 | TYR A | 177 | −17.832 | −24.261 | 14.430 | 1.00 | 23.44 | C |
| ATOM | 1356 | CE2 | TYR A | 177 | −19.726 | −25.131 | 15.613 | 1.00 | 23.05 | C |
| ATOM | 1357 | CZ | TYR A | 177 | −19.025 | −24.957 | 14.433 | 1.00 | 31.00 | C |
| ATOM | 1358 | OH | TYR A | 177 | −19.505 | −25.476 | 13.265 | 1.00 | 34.41 | O |
| ATOM | 1359 | N | SER A | 178 | −14.856 | −23.016 | 19.704 | 1.00 | 24.04 | N |
| ATOM | 1360 | CA | SER A | 178 | −14.180 | −22.182 | 20.669 | 1.00 | 23.59 | C |
| ATOM | 1361 | C | SER A | 178 | −13.980 | −20.827 | 19.993 | 1.00 | 25.80 | C |
| ATOM | 1362 | O | SER A | 178 | −13.895 | −20.751 | 18.770 | 1.00 | 24.12 | O |
| ATOM | 1363 | CB | SER A | 178 | −12.870 | −22.816 | 21.111 | 1.00 | 26.31 | C |
| ATOM | 1364 | OG | SER A | 178 | −13.187 | −23.878 | 21.995 | 1.00 | 33.80 | O |
| ATOM | 1365 | N | LEU A | 179 | −13.966 | −19.766 | 20.764 | 1.00 | 23.48 | N |
| ATOM | 1366 | CA | LEU A | 179 | −13.849 | −18.412 | 20.229 | 1.00 | 23.36 | C |
| ATOM | 1367 | C | LEU A | 179 | −12.963 | −17.558 | 21.132 | 1.00 | 26.42 | C |
| ATOM | 1368 | O | LEU A | 179 | −12.975 | −17.737 | 22.330 | 1.00 | 26.16 | O |
| ATOM | 1369 | CB | LEU A | 179 | −15.257 | −17.816 | 20.144 | 1.00 | 22.89 | C |
| ATOM | 1370 | CG | LEU A | 179 | −15.394 | −16.434 | 19.511 | 1.00 | 26.35 | C |
| ATOM | 1371 | CD1 | LEU A | 179 | −16.701 | −16.348 | 18.713 | 1.00 | 27.28 | C |
| ATOM | 1372 | CD2 | LEU A | 179 | −15.434 | −15.309 | 20.583 | 1.00 | 21.38 | C |
| ATOM | 1373 | N | SER A | 180 | −12.232 | −16.627 | 20.572 | 1.00 | 23.23 | N |
| ATOM | 1374 | CA | SER A | 180 | −11.434 | −15.719 | 21.368 | 1.00 | 25.25 | C |
| ATOM | 1375 | C | SER A | 180 | −11.779 | −14.296 | 20.936 | 1.00 | 31.24 | C |
| ATOM | 1376 | O | SER A | 180 | −12.003 | −14.073 | 19.752 | 1.00 | 30.51 | O |
| ATOM | 1377 | CB | SER A | 180 | −9.937 | −16.006 | 21.193 | 1.00 | 29.66 | C |
| ATOM | 1378 | OG | SER A | 180 | −9.370 | −15.359 | 20.064 | 1.00 | 40.32 | O |
| ATOM | 1379 | N | SER A | 181 | −11.884 | −13.347 | 21.888 | 1.00 | 28.72 | N |
| ATOM | 1380 | CA | SER A | 181 | −12.079 | −11.924 | 21.556 | 1.00 | 26.96 | C |
| ATOM | 1381 | C | SER A | 181 | −10.963 | −11.215 | 22.242 | 1.00 | 28.18 | C |
| ATOM | 1382 | O | SER A | 181 | −10.670 | −11.550 | 23.369 | 1.00 | 29.39 | O |
| ATOM | 1383 | CB | SER A | 181 | −13.413 | −11.373 | 22.024 | 1.00 | 28.60 | C |
| ATOM | 1384 | OG | SER A | 181 | −13.501 | −10.032 | 21.557 | 1.00 | 31.47 | O |
| ATOM | 1385 | N | THR A | 182 | −10.293 | −10.313 | 21.560 | 1.00 | 25.14 | N |
| ATOM | 1386 | CA | THR A | 182 | −9.142 | −9.603 | 22.100 | 1.00 | 26.55 | C |
| ATOM | 1387 | C | THR A | 182 | −9.372 | −8.089 | 22.007 | 1.00 | 30.56 | C |
| ATOM | 1388 | O | THR A | 182 | −9.390 | −7.550 | 20.904 | 1.00 | 27.87 | O |
| ATOM | 1389 | CB | THR A | 182 | −7.852 | −10.063 | 21.383 | 1.00 | 29.38 | C |
| ATOM | 1390 | OG1 | THR A | 182 | −7.679 | −11.471 | 21.605 | 1.00 | 32.88 | O |
| ATOM | 1391 | CG2 | THR A | 182 | −6.605 | −9.315 | 21.864 | 1.00 | 16.97 | C |
| ATOM | 1392 | N | LEU A | 183 | −9.519 | −7.417 | 23.181 | 1.00 | 26.92 | N |
| ATOM | 1393 | CA | LEU A | 183 | −9.671 | −5.966 | 23.274 | 1.00 | 26.91 | C |
| ATOM | 1394 | C | LEU A | 183 | −8.260 | −5.372 | 23.329 | 1.00 | 33.74 | C |
| ATOM | 1395 | O | LEU A | 183 | −7.480 | −5.804 | 24.171 | 1.00 | 34.42 | O |
| ATOM | 1396 | CB | LEU A | 183 | −10.436 | −5.621 | 24.539 | 1.00 | 26.40 | C |
| ATOM | 1397 | CG | LEU A | 183 | −10.622 | −4.152 | 24.865 | 1.00 | 29.70 | C |
| ATOM | 1398 | CD1 | LEU A | 183 | −11.689 | −3.549 | 23.981 | 1.00 | 28.57 | C |
| ATOM | 1399 | CD2 | LEU A | 183 | −10.980 | −3.979 | 26.353 | 1.00 | 28.52 | C |
| ATOM | 1400 | N | THR A | 184 | −7.907 | −4.439 | 22.421 | 1.00 | 31.60 | N |
| ATOM | 1401 | CA | THR A | 184 | −6.561 | −3.846 | 22.391 | 1.00 | 33.26 | C |
| ATOM | 1402 | C | THR A | 184 | −6.627 | −2.370 | 22.800 | 1.00 | 41.11 | C |
| ATOM | 1403 | O | THR A | 184 | −7.537 | −1.636 | 22.399 | 1.00 | 41.00 | O |
| ATOM | 1404 | CB | THR A | 184 | −5.885 | −4.080 | 21.030 | 1.00 | 40.80 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1405 | OG1 | THR A | 184 | −5.772 | −5.481 | 20.839 | 1.00 | 40.38 | O |
| ATOM | 1406 | CG2 | THR A | 184 | −4.475 | −3.479 | 20.938 | 1.00 | 39.64 | C |
| ATOM | 1407 | N | LEU A | 185 | −5.686 | −1.959 | 23.655 | 1.00 | 40.02 | N |
| ATOM | 1408 | CA | LEU A | 185 | −5.613 | −0.593 | 24.148 | 1.00 | 42.28 | C |
| ATOM | 1409 | C | LEU A | 185 | −4.186 | −0.207 | 24.274 | 1.00 | 48.01 | C |
| ATOM | 1410 | O | LEU A | 185 | −3.309 | −1.074 | 24.294 | 1.00 | 48.14 | O |
| ATOM | 1411 | CB | LEU A | 185 | −6.272 | −0.471 | 25.532 | 1.00 | 42.84 | C |
| ATOM | 1412 | CG | LEU A | 185 | −7.766 | −0.777 | 25.587 | 1.00 | 47.65 | C |
| ATOM | 1413 | CD1 | LEU A | 185 | −8.218 | −0.939 | 26.991 | 1.00 | 47.78 | C |
| ATOM | 1414 | CD2 | LEU A | 185 | −8.574 | 0.313 | 24.914 | 1.00 | 52.42 | C |
| ATOM | 1415 | N | SER A | 186 | −3.949 | 1.098 | 24.395 | 1.00 | 44.82 | N |
| ATOM | 1416 | CA | SER A | 186 | −2.628 | 1.624 | 24.659 | 1.00 | 45.43 | C |
| ATOM | 1417 | C | SER A | 186 | −2.446 | 1.515 | 26.188 | 1.00 | 50.37 | C |
| ATOM | 1418 | O | SER A | 186 | −3.442 | 1.405 | 26.904 | 1.00 | 48.85 | O |
| ATOM | 1419 | CB | SER A | 186 | −2.535 | 3.070 | 24.185 | 1.00 | 49.88 | C |
| ATOM | 1420 | OG | SER A | 186 | −3.402 | 3.931 | 24.905 | 1.00 | 57.50 | O |
| ATOM | 1421 | N | LYS A | 187 | −1.200 | 1.535 | 26.692 | 1.00 | 49.53 | N |
| ATOM | 1422 | CA | LYS A | 187 | −0.958 | 1.464 | 28.146 | 1.00 | 50.01 | C |
| ATOM | 1423 | C | LYS A | 187 | −1.618 | 2.668 | 28.827 | 1.00 | 56.93 | C |
| ATOM | 1424 | O | LYS A | 187 | −2.229 | 2.502 | 29.879 | 1.00 | 56.71 | O |
| ATOM | 1425 | CB | LYS A | 187 | 0.551 | 1.439 | 28.468 | 1.00 | 53.12 | C |
| ATOM | 1426 | CG | LYS A | 187 | 0.882 | 0.877 | 29.851 | 1.00 | 58.59 | C |
| ATOM | 1427 | CD | LYS A | 187 | 2.135 | 1.504 | 30.439 | 1.00 | 72.56 | C |
| ATOM | 1428 | CE | LYS A | 187 | 2.446 | 0.947 | 31.806 | 1.00 | 88.72 | C |
| ATOM | 1429 | NZ | LYS A | 187 | 3.395 | 1.814 | 32.558 | 1.00 | 102.55 | N |
| ATOM | 1430 | N | ALA A | 188 | −1.519 | 3.871 | 28.201 | 1.00 | 55.81 | N |
| ATOM | 1431 | CA | ALA A | 188 | −2.111 | 5.120 | 28.696 | 1.00 | 57.28 | C |
| ATOM | 1432 | C | ALA A | 188 | −3.615 | 4.968 | 28.879 | 1.00 | 62.75 | C |
| ATOM | 1433 | O | ALA A | 188 | −4.119 | 5.218 | 29.978 | 1.00 | 63.02 | O |
| ATOM | 1434 | CB | ALA A | 188 | −1.825 | 6.246 | 27.723 | 1.00 | 59.30 | C |
| ATOM | 1435 | N | ASP A | 189 | −4.317 | 4.490 | 27.819 | 1.00 | 58.91 | N |
| ATOM | 1436 | CA | ASP A | 189 | −5.768 | 4.238 | 27.849 | 1.00 | 57.29 | C |
| ATOM | 1437 | C | ASP A | 189 | −6.122 | 3.074 | 28.778 | 1.00 | 59.42 | C |
| ATOM | 1438 | O | ASP A | 189 | −7.181 | 3.121 | 29.404 | 1.00 | 60.46 | O |
| ATOM | 1439 | CB | ASP A | 189 | −6.338 | 3.968 | 26.437 | 1.00 | 58.07 | C |
| ATOM | 1440 | CG | ASP A | 189 | −6.495 | 5.179 | 25.518 | 1.00 | 71.06 | C |
| ATOM | 1441 | OD1 | ASP A | 189 | −6.119 | 6.300 | 25.932 | 1.00 | 74.53 | O |
| ATOM | 1442 | OD2 | ASP A | 189 | −7.034 | 5.009 | 24.400 | 1.00 | 74.69 | O |
| ATOM | 1443 | N | TYR A | 190 | −5.259 | 2.039 | 28.882 | 1.00 | 52.65 | N |
| ATOM | 1444 | CA | TYR A | 190 | −5.513 | 0.913 | 29.793 | 1.00 | 50.08 | C |
| ATOM | 1445 | C | TYR A | 190 | −5.475 | 1.369 | 31.264 | 1.00 | 58.59 | C |
| ATOM | 1446 | O | TYR A | 190 | −6.254 | 0.870 | 32.078 | 1.00 | 58.49 | O |
| ATOM | 1447 | CB | TYR A | 190 | −4.519 | −0.241 | 29.550 | 1.00 | 48.19 | C |
| ATOM | 1448 | CG | TYR A | 190 | −4.620 | −1.372 | 30.556 | 1.00 | 45.32 | C |
| ATOM | 1449 | CD1 | TYR A | 190 | −5.747 | −2.188 | 30.608 | 1.00 | 44.28 | C |
| ATOM | 1450 | CD2 | TYR A | 190 | −3.564 | −1.664 | 31.417 | 1.00 | 45.66 | C |
| ATOM | 1451 | CE1 | TYR A | 190 | −5.847 | −3.229 | 31.531 | 1.00 | 41.91 | C |
| ATOM | 1452 | CE2 | TYR A | 190 | −3.639 | −2.725 | 32.319 | 1.00 | 45.10 | C |
| ATOM | 1453 | CZ | TYR A | 190 | −4.793 | −3.491 | 32.390 | 1.00 | 48.55 | C |
| ATOM | 1454 | OH | TYR A | 190 | −4.883 | −4.541 | 33.275 | 1.00 | 49.95 | O |
| ATOM | 1455 | N | GLU A | 191 | −4.578 | 2.325 | 31.592 | 1.00 | 58.25 | N |
| ATOM | 1456 | CA | GLU A | 191 | −4.426 | 2.865 | 32.949 | 1.00 | 59.61 | C |
| ATOM | 1457 | C | GLU A | 191 | −5.535 | 3.872 | 33.357 | 1.00 | 64.72 | C |
| ATOM | 1458 | O | GLU A | 191 | −5.662 | 4.166 | 34.548 | 1.00 | 64.98 | O |
| ATOM | 1459 | CB | GLU A | 191 | −3.037 | 3.498 | 33.118 | 1.00 | 62.82 | C |
| ATOM | 1460 | CG | GLU A | 191 | −1.908 | 2.478 | 33.133 | 1.00 | 74.97 | C |
| ATOM | 1461 | CD | GLU A | 191 | −0.511 | 3.063 | 33.000 | 1.00 | 106.28 | C |
| ATOM | 1462 | OE1 | GLU A | 191 | 0.350 | 2.740 | 33.851 | 1.00 | 105.30 | O |
| ATOM | 1463 | OE2 | GLU A | 191 | −0.277 | 3.852 | 32.055 | 1.00 | 102.29 | O |
| ATOM | 1464 | N | LYS A | 192 | −6.325 | 4.402 | 32.391 | 1.00 | 61.21 | N |
| ATOM | 1465 | CA | LYS A | 192 | −7.429 | 5.335 | 32.687 | 1.00 | 61.01 | C |
| ATOM | 1466 | C | LYS A | 192 | −8.652 | 4.668 | 33.393 | 1.00 | 63.12 | C |
| ATOM | 1467 | O | LYS A | 192 | −9.398 | 5.378 | 34.063 | 1.00 | 63.27 | O |
| ATOM | 1468 | CB | LYS A | 192 | −7.918 | 6.040 | 31.402 | 1.00 | 62.82 | C |
| ATOM | 1469 | CG | LYS A | 192 | −6.987 | 7.131 | 30.890 | 1.00 | 75.76 | C |
| ATOM | 1470 | CD | LYS A | 192 | −7.444 | 7.711 | 29.534 | 1.00 | 82.21 | C |
| ATOM | 1471 | CE | LYS A | 192 | −6.411 | 8.643 | 28.929 | 1.00 | 91.81 | C |
| ATOM | 1472 | NZ | LYS A | 192 | −6.857 | 9.241 | 27.638 | 1.00 | 94.84 | N |
| ATOM | 1473 | N | HIS A | 193 | −8.882 | 3.337 | 33.207 | 1.00 | 57.29 | N |
| ATOM | 1474 | CA | HIS A | 193 | −10.041 | 2.604 | 33.762 | 1.00 | 55.51 | C |
| ATOM | 1475 | C | HIS A | 193 | −9.635 | 1.436 | 34.657 | 1.00 | 54.42 | C |
| ATOM | 1476 | O | HIS A | 193 | −8.473 | 1.041 | 34.597 | 1.00 | 53.71 | O |
| ATOM | 1477 | CB | HIS A | 193 | −10.855 | 2.087 | 32.601 | 1.00 | 55.74 | C |
| ATOM | 1478 | CG | HIS A | 193 | −11.117 | 3.153 | 31.593 | 1.00 | 61.02 | C |
| ATOM | 1479 | ND1 | HIS A | 193 | −10.428 | 3.189 | 30.386 | 1.00 | 63.26 | N |
| ATOM | 1480 | CD2 | HIS A | 193 | −11.931 | 4.228 | 31.666 | 1.00 | 64.38 | C |
| ATOM | 1481 | CE1 | HIS A | 193 | −10.877 | 4.257 | 29.749 | 1.00 | 63.80 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1482 | NE2 | HIS A | 193 | −11.778 | 4.916 | 30.483 | 1.00 | 64.99 | N |
| ATOM | 1483 | N | LYS A | 194 | −10.560 | 0.883 | 35.503 | 1.00 | 47.55 | N |
| ATOM | 1484 | CA | LYS A | 194 | −10.164 | −0.233 | 36.384 | 1.00 | 45.76 | C |
| ATOM | 1485 | C | LYS A | 194 | −10.954 | −1.539 | 36.177 | 1.00 | 44.78 | C |
| ATOM | 1486 | O | LYS A | 194 | −10.337 | −2.600 | 36.262 | 1.00 | 42.91 | O |
| ATOM | 1487 | CB | LYS A | 194 | −10.147 | 0.170 | 37.874 | 1.00 | 49.98 | C |
| ATOM | 1488 | CG | LYS A | 194 | −11.488 | 0.297 | 38.595 | 1.00 | 60.76 | C |
| ATOM | 1489 | CD | LYS A | 194 | −11.692 | −0.810 | 39.633 | 1.00 | 61.00 | C |
| ATOM | 1490 | CE | LYS A | 194 | −12.943 | −0.609 | 40.450 | 1.00 | 59.79 | C |
| ATOM | 1491 | NZ | LYS A | 194 | −12.678 | 0.219 | 41.654 | 1.00 | 75.13 | N |
| ATOM | 1492 | N | VAL A | 195 | −12.251 | −1.494 | 35.869 | 1.00 | 39.59 | N |
| ATOM | 1493 | CA | VAL A | 195 | −13.035 | −2.725 | 35.660 | 1.00 | 37.88 | C |
| ATOM | 1494 | C | VAL A | 195 | −13.032 | −3.109 | 34.147 | 1.00 | 40.85 | C |
| ATOM | 1495 | O | VAL A | 195 | −13.469 | −2.316 | 33.311 | 1.00 | 40.60 | O |
| ATOM | 1496 | CB | VAL A | 195 | −14.492 | −2.587 | 36.208 | 1.00 | 41.12 | C |
| ATOM | 1497 | CG1 | VAL A | 195 | −15.177 | −3.952 | 36.278 | 1.00 | 39.21 | C |
| ATOM | 1498 | CG2 | VAL A | 195 | −14.515 | −1.908 | 37.580 | 1.00 | 41.86 | C |
| ATOM | 1499 | N | TYR A | 196 | −12.520 | −4.310 | 33.814 | 1.00 | 34.69 | N |
| ATOM | 1500 | CA | TYR A | 196 | −12.473 | −4.832 | 32.444 | 1.00 | 33.44 | C |
| ATOM | 1501 | C | TYR A | 196 | −13.392 | −6.035 | 32.400 | 1.00 | 33.74 | C |
| ATOM | 1502 | O | TYR A | 196 | −13.151 | −7.001 | 33.106 | 1.00 | 32.46 | O |
| ATOM | 1503 | CB | TYR A | 196 | −11.021 | −5.184 | 32.034 | 1.00 | 34.64 | C |
| ATOM | 1504 | CG | TYR A | 196 | −10.251 | −3.931 | 31.695 | 1.00 | 36.14 | C |
| ATOM | 1505 | CD1 | TYR A | 196 | −9.728 | −3.124 | 32.701 | 1.00 | 40.16 | C |
| ATOM | 1506 | CD2 | TYR A | 196 | −10.237 | −3.433 | 30.397 | 1.00 | 35.29 | C |
| ATOM | 1507 | CE1 | TYR A | 196 | −9.152 | −1.886 | 32.415 | 1.00 | 43.46 | C |
| ATOM | 1508 | CE2 | TYR A | 196 | −9.615 | −2.229 | 30.091 | 1.00 | 37.04 | C |
| ATOM | 1509 | CZ | TYR A | 196 | −9.102 | −1.436 | 31.104 | 1.00 | 46.55 | C |
| ATOM | 1510 | OH | TYR A | 196 | −8.515 | −0.225 | 30.788 | 1.00 | 44.19 | O |
| ATOM | 1511 | N | ALA A | 197 | −14.488 | −5.943 | 31.650 | 1.00 | 29.84 | N |
| ATOM | 1512 | CA | ALA A | 197 | −15.490 | −6.989 | 31.654 | 1.00 | 29.47 | C |
| ATOM | 1513 | C | ALA A | 197 | −15.785 | −7.558 | 30.271 | 1.00 | 34.07 | C |
| ATOM | 1514 | O | ALA A | 197 | −15.822 | −6.851 | 29.278 | 1.00 | 30.77 | O |
| ATOM | 1515 | CB | ALA A | 197 | −16.771 | −6.487 | 32.313 | 1.00 | 30.16 | C |
| ATOM | 1516 | N | CYS A | 198 | −16.016 | −8.856 | 30.245 | 1.00 | 35.22 | N |
| ATOM | 1517 | CA | CYS A | 198 | −16.347 | −9.616 | 29.068 | 1.00 | 37.04 | C |
| ATOM | 1518 | C | CYS A | 198 | −17.784 | −10.155 | 29.284 | 1.00 | 37.76 | C |
| ATOM | 1519 | O | CYS A | 198 | −17.991 | −10.946 | 30.195 | 1.00 | 36.39 | O |
| ATOM | 1520 | CB | CYS A | 198 | −15.337 | −10.749 | 28.895 | 1.00 | 39.90 | C |
| ATOM | 1521 | SG | CYS A | 198 | −15.555 | −11.640 | 27.355 | 1.00 | 45.28 | S |
| ATOM | 1522 | N | GLU A | 199 | −18.774 | −9.703 | 28.491 | 1.00 | 33.62 | N |
| ATOM | 1523 | CA | GLU A | 199 | −20.177 | −10.154 | 28.600 | 1.00 | 32.34 | C |
| ATOM | 1524 | C | GLU A | 199 | −20.480 | −11.077 | 27.399 | 1.00 | 32.33 | C |
| ATOM | 1525 | O | GLU A | 199 | −20.295 | −10.668 | 26.251 | 1.00 | 30.20 | O |
| ATOM | 1526 | CB | GLU A | 199 | −21.125 | −8.947 | 28.641 | 1.00 | 34.68 | C |
| ATOM | 1527 | CG | GLU A | 199 | −22.561 | −9.287 | 29.025 | 1.00 | 46.80 | C |
| ATOM | 1528 | CD | GLU A | 199 | −23.349 | −8.220 | 29.772 | 1.00 | 79.83 | C |
| ATOM | 1529 | OE1 | GLU A | 199 | −22.760 | −7.184 | 30.163 | 1.00 | 74.94 | O |
| ATOM | 1530 | OE2 | GLU A | 199 | −24.557 | −8.449 | 30.013 | 1.00 | 79.65 | O |
| ATOM | 1531 | N | VAL A | 200 | −20.887 | −12.339 | 27.673 | 1.00 | 26.67 | N |
| ATOM | 1532 | CA | VAL A | 200 | −21.136 | −13.363 | 26.647 | 1.00 | 23.74 | C |
| ATOM | 1533 | C | VAL A | 200 | −22.604 | −13.764 | 26.609 | 1.00 | 27.42 | C |
| ATOM | 1534 | O | VAL A | 200 | −23.199 | −13.950 | 27.670 | 1.00 | 26.49 | O |
| ATOM | 1535 | CB | VAL A | 200 | −20.264 | −14.599 | 26.946 | 1.00 | 25.05 | C |
| ATOM | 1536 | CG1 | VAL A | 200 | −20.605 | −15.757 | 26.021 | 1.00 | 23.66 | C |
| ATOM | 1537 | CG2 | VAL A | 200 | −18.784 | −14.245 | 26.871 | 1.00 | 24.87 | C |
| ATOM | 1538 | N | THR A | 201 | −23.164 | −13.970 | 25.388 | 1.00 | 23.77 | N |
| ATOM | 1539 | CA | THR A | 201 | −24.522 | −14.462 | 25.205 | 1.00 | 24.08 | C |
| ATOM | 1540 | C | THR A | 201 | −24.502 | −15.629 | 24.230 | 1.00 | 28.57 | C |
| ATOM | 1541 | O | THR A | 201 | −23.826 | −15.604 | 23.205 | 1.00 | 29.10 | O |
| ATOM | 1542 | CB | THR A | 201 | −25.529 | −13.375 | 24.830 | 1.00 | 34.02 | C |
| ATOM | 1543 | OG1 | THR A | 201 | −25.192 | −12.801 | 23.591 | 1.00 | 40.29 | O |
| ATOM | 1544 | CG2 | THR A | 201 | −25.640 | −12.323 | 25.867 | 1.00 | 33.42 | C |
| ATOM | 1545 | N | HIS A | 202 | −25.234 | −16.659 | 24.570 | 1.00 | 24.72 | N |
| ATOM | 1546 | CA | HIS A | 202 | −25.275 | −17.885 | 23.800 | 1.00 | 23.29 | C |
| ATOM | 1547 | C | HIS A | 202 | −26.605 | −18.577 | 24.117 | 1.00 | 27.03 | C |
| ATOM | 1548 | O | HIS A | 202 | −27.192 | −18.339 | 25.171 | 1.00 | 26.50 | O |
| ATOM | 1549 | CB | HIS A | 202 | −24.056 | −18.765 | 24.178 | 1.00 | 22.61 | C |
| ATOM | 1550 | CG | HIS A | 202 | −23.957 | −20.024 | 23.381 | 1.00 | 25.58 | C |
| ATOM | 1551 | ND1 | HIS A | 202 | −24.618 | −21.172 | 23.771 | 1.00 | 27.78 | N |
| ATOM | 1552 | CD2 | HIS A | 202 | −23.279 | −20.283 | 22.238 | 1.00 | 26.54 | C |
| ATOM | 1553 | CE1 | HIS A | 202 | −24.347 | −22.083 | 22.848 | 1.00 | 26.22 | C |
| ATOM | 1554 | NE2 | HIS A | 202 | −23.569 | −21.588 | 21.893 | 1.00 | 26.01 | N |
| ATOM | 1555 | N | GLN A | 203 | −27.087 | −19.408 | 23.200 | 1.00 | 25.16 | N |
| ATOM | 1556 | CA | GLN A | 203 | −28.330 | −20.172 | 23.406 | 1.00 | 26.39 | C |
| ATOM | 1557 | C | GLN A | 203 | −28.286 | −21.022 | 24.720 | 1.00 | 30.36 | C |
| ATOM | 1558 | O | GLN A | 203 | −29.299 | −21.164 | 25.408 | 1.00 | 32.38 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1559 | CB | GLN A | 203 | −28.563 | −21.091 | 22.187 | 1.00 | 26.97 | C |
| ATOM | 1560 | CG | GLN A | 203 | −29.737 | −22.059 | 22.328 | 1.00 | 34.31 | C |
| ATOM | 1561 | CD | GLN A | 203 | −29.814 | −23.013 | 21.172 | 1.00 | 41.63 | C |
| ATOM | 1562 | OE1 | GLN A | 203 | −28.868 | −23.187 | 20.391 | 1.00 | 34.04 | O |
| ATOM | 1563 | NE2 | GLN A | 203 | −30.938 | −23.677 | 21.054 | 1.00 | 27.64 | N |
| ATOM | 1564 | N | GLY A | 204 | −27.122 | −21.579 | 25.032 | 1.00 | 23.66 | N |
| ATOM | 1565 | CA | GLY A | 204 | −26.929 | −22.400 | 26.212 | 1.00 | 23.23 | C |
| ATOM | 1566 | C | GLY A | 204 | −26.918 | −21.659 | 27.536 | 1.00 | 28.33 | C |
| ATOM | 1567 | O | GLY A | 204 | −26.849 | −22.323 | 28.575 | 1.00 | 29.45 | O |
| ATOM | 1568 | N | LEU A | 205 | −26.960 | −20.290 | 27.533 | 1.00 | 23.24 | N |
| ATOM | 1569 | CA | LEU A | 205 | −26.955 | −19.476 | 28.737 | 1.00 | 23.19 | C |
| ATOM | 1570 | C | LEU A | 205 | −28.330 | −18.798 | 28.893 | 1.00 | 30.33 | C |
| ATOM | 1571 | O | LEU A | 205 | −28.766 | −18.082 | 27.982 | 1.00 | 30.87 | O |
| ATOM | 1572 | CB | LEU A | 205 | −25.851 | −18.427 | 28.615 | 1.00 | 22.39 | C |
| ATOM | 1573 | CG | LEU A | 205 | −24.439 | −18.930 | 28.348 | 1.00 | 24.98 | C |
| ATOM | 1574 | CD1 | LEU A | 205 | −23.519 | −17.766 | 27.997 | 1.00 | 24.16 | C |
| ATOM | 1575 | CD2 | LEU A | 205 | −23.896 | −19.696 | 29.543 | 1.00 | 24.19 | C |
| ATOM | 1576 | N | SER A | 206 | −29.016 | −19.018 | 30.034 | 1.00 | 28.81 | N |
| ATOM | 1577 | CA | SER A | 206 | −30.353 | −18.428 | 30.287 | 1.00 | 29.87 | C |
| ATOM | 1578 | C | SER A | 206 | −30.299 | −16.902 | 30.474 | 1.00 | 37.21 | C |
| ATOM | 1579 | O | SER A | 206 | −31.314 | −16.232 | 30.331 | 1.00 | 38.62 | O |
| ATOM | 1580 | CB | SER A | 206 | −31.001 | −19.071 | 31.504 | 1.00 | 31.50 | C |
| ATOM | 1581 | OG | SER A | 206 | −30.073 | −19.086 | 32.573 | 1.00 | 41.30 | O |
| ATOM | 1582 | N | SER A | 207 | −29.126 | −16.370 | 30.845 | 1.00 | 34.51 | N |
| ATOM | 1583 | CA | SER A | 207 | −28.865 | −14.947 | 31.025 | 1.00 | 34.77 | C |
| ATOM | 1584 | C | SER A | 207 | −27.410 | −14.748 | 30.592 | 1.00 | 38.01 | C |
| ATOM | 1585 | O | SER A | 207 | −26.649 | −15.714 | 30.629 | 1.00 | 35.38 | O |
| ATOM | 1586 | CB | SER A | 207 | −29.021 | −14.547 | 32.492 | 1.00 | 41.41 | C |
| ATOM | 1587 | OG | SER A | 207 | −30.197 | −15.086 | 33.075 | 1.00 | 58.80 | O |
| ATOM | 1588 | N | PRO A | 208 | −26.989 | −13.533 | 30.187 | 1.00 | 36.60 | N |
| ATOM | 1589 | CA | PRO A | 208 | −25.583 | −13.338 | 29.793 | 1.00 | 35.80 | C |
| ATOM | 1590 | C | PRO A | 208 | −24.583 | −13.667 | 30.906 | 1.00 | 38.44 | C |
| ATOM | 1591 | O | PRO A | 208 | −24.913 | −13.497 | 32.077 | 1.00 | 40.85 | O |
| ATOM | 1592 | CB | PRO A | 208 | −25.519 | −11.846 | 29.436 | 1.00 | 38.57 | C |
| ATOM | 1593 | CG | PRO A | 208 | −26.928 | −11.441 | 29.173 | 1.00 | 43.67 | C |
| ATOM | 1594 | CD | PRO A | 208 | −27.760 | −12.280 | 30.080 | 1.00 | 39.55 | C |
| ATOM | 1595 | N | VAL A | 209 | −23.381 | −14.139 | 30.548 | 1.00 | 31.11 | N |
| ATOM | 1596 | CA | VAL A | 209 | −22.317 | −14.457 | 31.506 | 1.00 | 29.87 | C |
| ATOM | 1597 | C | VAL A | 209 | −21.278 | −13.366 | 31.407 | 1.00 | 34.05 | C |
| ATOM | 1598 | O | VAL A | 209 | −20.730 | −13.180 | 30.328 | 1.00 | 35.32 | O |
| ATOM | 1599 | CB | VAL A | 209 | −21.705 | −15.853 | 31.224 | 1.00 | 32.20 | C |
| ATOM | 1600 | CG1 | VAL A | 209 | −20.329 | −16.016 | 31.870 | 1.00 | 32.06 | C |
| ATOM | 1601 | CG2 | VAL A | 209 | −22.642 | −16.937 | 31.718 | 1.00 | 32.18 | C |
| ATOM | 1602 | N | THR A | 210 | −20.978 | −12.676 | 32.508 | 1.00 | 31.31 | N |
| ATOM | 1603 | CA | THR A | 210 | −19.970 | −11.610 | 32.534 | 1.00 | 32.52 | C |
| ATOM | 1604 | C | THR A | 210 | −18.754 | −12.007 | 33.364 | 1.00 | 38.49 | C |
| ATOM | 1605 | O | THR A | 210 | −18.916 | −12.294 | 34.544 | 1.00 | 40.54 | O |
| ATOM | 1606 | CB | THR A | 210 | −20.559 | −10.314 | 33.118 | 1.00 | 40.14 | C |
| ATOM | 1607 | OG1 | THR A | 210 | −21.757 | −9.990 | 32.403 | 1.00 | 40.45 | O |
| ATOM | 1608 | CG2 | THR A | 210 | −19.555 | −9.132 | 33.079 | 1.00 | 32.87 | C |
| ATOM | 1609 | N | LYS A | 211 | −17.557 | −12.012 | 32.772 | 1.00 | 33.29 | N |
| ATOM | 1610 | CA | LYS A | 211 | −16.305 | −12.276 | 33.492 | 1.00 | 32.64 | C |
| ATOM | 1611 | C | LYS A | 211 | −15.560 | −10.958 | 33.547 | 1.00 | 37.50 | C |
| ATOM | 1612 | O | LYS A | 211 | −15.485 | −10.260 | 32.540 | 1.00 | 37.97 | O |
| ATOM | 1613 | CB | LYS A | 211 | −15.434 | −13.328 | 32.777 | 1.00 | 32.95 | C |
| ATOM | 1614 | CG | LYS A | 211 | −16.015 | −14.733 | 32.812 | 1.00 | 34.32 | C |
| ATOM | 1615 | CD | LYS A | 211 | −15.932 | −15.399 | 34.185 | 1.00 | 32.20 | C |
| ATOM | 1616 | CE | LYS A | 211 | −16.918 | −16.543 | 34.297 | 1.00 | 45.25 | C |
| ATOM | 1617 | NZ | LYS A | 211 | −16.558 | −17.484 | 35.395 | 1.00 | 58.75 | N |
| ATOM | 1618 | N | SER A | 212 | −15.020 | −10.604 | 34.702 | 1.00 | 34.06 | N |
| ATOM | 1619 | CA | SER A | 212 | −14.281 | −9.354 | 34.842 | 1.00 | 34.12 | C |
| ATOM | 1620 | C | SER A | 212 | −13.109 | −9.474 | 35.819 | 1.00 | 37.64 | C |
| ATOM | 1621 | O | SER A | 212 | −12.889 | −10.522 | 36.428 | 1.00 | 35.48 | O |
| ATOM | 1622 | CB | SER A | 212 | −15.220 | −8.244 | 35.296 | 1.00 | 36.70 | C |
| ATOM | 1623 | OG | SER A | 212 | −15.830 | −8.613 | 36.519 | 1.00 | 39.13 | O |
| ATOM | 1624 | N | PHE A | 213 | −12.307 | −8.414 | 35.873 | 1.00 | 35.31 | N |
| ATOM | 1625 | CA | PHE A | 213 | −11.198 | −8.283 | 36.801 | 1.00 | 35.94 | C |
| ATOM | 1626 | C | PHE A | 213 | −10.969 | −6.795 | 37.034 | 1.00 | 41.58 | C |
| ATOM | 1627 | O | PHE A | 213 | −11.409 | −5.983 | 36.221 | 1.00 | 40.85 | O |
| ATOM | 1628 | CB | PHE A | 213 | −9.916 | −8.973 | 36.287 | 1.00 | 37.15 | C |
| ATOM | 1629 | CG | PHE A | 213 | −9.260 | −8.287 | 35.116 | 1.00 | 38.36 | C |
| ATOM | 1630 | CD1 | PHE A | 213 | −8.333 | −7.261 | 35.316 | 1.00 | 41.36 | C |
| ATOM | 1631 | CD2 | PHE A | 213 | −9.572 | −8.659 | 33.808 | 1.00 | 38.20 | C |
| ATOM | 1632 | CE1 | PHE A | 213 | −7.762 | −6.591 | 34.227 | 1.00 | 42.61 | C |
| ATOM | 1633 | CE2 | PHE A | 213 | −8.964 | −8.030 | 32.721 | 1.00 | 40.56 | C |
| ATOM | 1634 | CZ | PHE A | 213 | −8.054 | −7.005 | 32.930 | 1.00 | 40.59 | C |
| ATOM | 1635 | N | ASN A | 214 | −10.256 | −6.451 | 38.121 | 1.00 | 40.03 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1636 | CA | ASN A | 214 | −9.950 | −5.080 | 38.481 | 1.00 | 41.16 | C |
| ATOM | 1637 | C | ASN A | 214 | −8.479 | −4.830 | 38.201 | 1.00 | 47.21 | C |
| ATOM | 1638 | O | ASN A | 214 | −7.637 | −5.491 | 38.807 | 1.00 | 47.86 | O |
| ATOM | 1639 | CB | ASN A | 214 | −10.293 | −4.847 | 39.964 | 1.00 | 43.41 | C |
| ATOM | 1640 | CG | ASN A | 214 | −11.771 | −4.643 | 40.224 | 1.00 | 55.78 | C |
| ATOM | 1641 | OD1 | ASN A | 214 | −12.552 | −4.327 | 39.328 | 1.00 | 50.62 | O |
| ATOM | 1642 | ND2 | ASN A | 214 | −12.208 | −4.847 | 41.451 | 1.00 | 44.08 | N |
| ATOM | 1643 | N | ARG A | 215 | −8.158 | −3.922 | 37.256 | 1.00 | 45.23 | N |
| ATOM | 1644 | CA | ARG A | 215 | −6.764 | −3.599 | 36.912 | 1.00 | 46.61 | C |
| ATOM | 1645 | C | ARG A | 215 | −6.020 | −3.170 | 38.171 | 1.00 | 57.75 | C |
| ATOM | 1646 | O | ARG A | 215 | −6.484 | −2.269 | 38.880 | 1.00 | 58.97 | O |
| ATOM | 1647 | CB | ARG A | 215 | −6.708 | −2.454 | 35.898 | 1.00 | 44.07 | C |
| ATOM | 1648 | CG | ARG A | 215 | −5.288 | −1.992 | 35.558 | 1.00 | 48.95 | C |
| ATOM | 1649 | CD | ARG A | 215 | −5.279 | −0.804 | 34.617 | 1.00 | 48.91 | C |
| ATOM | 1650 | NE | ARG A | 215 | −5.957 | 0.344 | 35.216 | 1.00 | 59.36 | N |
| ATOM | 1651 | CZ | ARG A | 215 | −5.458 | 1.133 | 36.171 | 1.00 | 83.41 | C |
| ATOM | 1652 | NH1 | ARG A | 215 | −4.225 | 0.932 | 36.640 | 1.00 | 72.51 | N |
| ATOM | 1653 | NH2 | ARG A | 215 | −6.182 | 2.141 | 36.654 | 1.00 | 70.81 | N |
| ATOM | 1654 | N | GLY A | 216 | −4.887 | −3.819 | 38.438 | 1.00 | 57.02 | N |
| ATOM | 1655 | CA | GLY A | 216 | −4.068 | −3.530 | 39.609 | 1.00 | 58.95 | C |
| ATOM | 1656 | C | GLY A | 216 | −4.278 | −4.516 | 40.736 | 1.00 | 64.69 | C |
| ATOM | 1657 | O | GLY A | 216 | −3.338 | −4.764 | 41.502 | 1.00 | 65.56 | O |
| ATOM | 1658 | N | GLU A | 217 | −5.501 | −5.119 | 40.830 | 1.00 | 60.99 | N |
| ATOM | 1659 | CA | GLU A | 217 | −5.853 | −6.101 | 41.869 | 1.00 | 60.87 | C |
| ATOM | 1660 | C | GLU A | 217 | −5.664 | −7.541 | 41.344 | 1.00 | 63.78 | C |
| ATOM | 1661 | O | GLU A | 217 | −6.490 | −8.410 | 41.626 | 1.00 | 63.35 | O |
| ATOM | 1662 | CB | GLU A | 217 | −7.308 | −5.891 | 42.346 | 1.00 | 61.99 | C |
| ATOM | 1663 | CG | GLU A | 217 | −7.676 | −4.453 | 42.703 | 1.00 | 74.84 | C |
| ATOM | 1664 | CD | GLU A | 217 | −9.098 | −4.253 | 43.207 | 1.00 | 95.07 | C |
| ATOM | 1665 | OE1 | GLU A | 217 | −9.873 | −5.238 | 43.220 | 1.00 | 80.05 | O |
| ATOM | 1666 | OE2 | GLU A | 217 | −9.441 | −3.106 | 43.580 | 1.00 | 90.46 | O |
| ATOM | 1667 | N | CYS A | 218 | −4.559 | −7.794 | 40.614 | 1.00 | 59.74 | N |
| ATOM | 1668 | CA | CYS A | 218 | −4.221 | −9.095 | 40.042 | 1.00 | 89.03 | C |
| ATOM | 1669 | C | CYS A | 218 | −2.803 | −9.496 | 40.461 | 1.00 | 123.73 | C |
| ATOM | 1670 | O | CYS A | 218 | −2.376 | −9.212 | 41.578 | 1.00 | 91.59 | O |
| ATOM | 1671 | CB | CYS A | 218 | −4.352 | −9.050 | 38.519 | 1.00 | 88.23 | C |
| ATOM | 1672 | SG | CYS A | 218 | −6.051 | −8.843 | 37.914 | 1.00 | 90.62 | S |
| ATOM | 1673 | N1 | CFF A | 501 | −25.632 | −35.191 | −20.572 | 1.00 | 32.18 | N |
| ATOM | 1674 | C2 | CFF A | 501 | −26.796 | −35.702 | −21.160 | 1.00 | 36.69 | C |
| ATOM | 1675 | C1O | CFF A | 501 | −25.480 | −33.731 | −20.537 | 1.00 | 26.94 | C |
| ATOM | 1676 | C6 | CFF A | 501 | −24.624 | −35.957 | −19.950 | 1.00 | 33.15 | C |
| ATOM | 1677 | N3 | CFF A | 501 | −26.941 | −37.099 | −21.202 | 1.00 | 38.65 | N |
| ATOM | 1678 | O11 | CFF A | 501 | −27.622 | −34.966 | −21.664 | 1.00 | 39.78 | O |
| ATOM | 1679 | C12 | CFF A | 501 | −28.165 | −37.675 | −21.776 | 1.00 | 40.11 | C |
| ATOM | 1680 | C4 | CFF A | 501 | −25.988 | −37.896 | −20.625 | 1.00 | 36.19 | C |
| ATOM | 1681 | C5 | CFF A | 501 | −24.892 | −37.361 | −19.987 | 1.00 | 34.19 | C |
| ATOM | 1682 | N9 | CFF A | 501 | −25.998 | −39.256 | −20.552 | 1.00 | 36.16 | N |
| ATOM | 1683 | O13 | CFF A | 501 | −23.614 | −35.429 | −19.514 | 1.00 | 31.51 | O |
| ATOM | 1684 | N7 | CFF A | 501 | −24.131 | −38.442 | −19.613 | 1.00 | 33.85 | N |
| ATOM | 1685 | C8 | CFF A | 501 | −24.855 | −39.545 | −19.962 | 1.00 | 36.62 | C |
| ATOM | 1686 | C14 | CFF A | 501 | −22.842 | −38.424 | −18.933 | 1.00 | 34.36 | C |
| ATOM | 1687 | N | GLN B | 1 | −4.884 | −38.958 | −15.355 | 1.00 | 52.82 | N |
| ATOM | 1688 | CA | GLN B | 1 | −3.780 | −38.264 | −14.693 | 1.00 | 50.71 | C |
| ATOM | 1689 | C | GLN B | 1 | −3.815 | −36.730 | −15.012 | 1.00 | 48.35 | C |
| ATOM | 1690 | O | GLN B | 1 | −2.776 | −36.113 | −15.284 | 1.00 | 47.01 | O |
| ATOM | 1691 | CB | GLN B | 1 | −2.441 | −38.928 | −15.102 | 1.00 | 52.60 | C |
| ATOM | 1692 | CG | GLN B | 1 | −1.449 | −39.037 | −13.940 | 1.00 | 74.60 | C |
| ATOM | 1693 | CD | GLN B | 1 | −0.031 | −39.386 | −14.356 | 1.00 | 100.05 | C |
| ATOM | 1694 | OE1 | GLN B | 1 | 0.942 | −38.865 | −13.791 | 1.00 | 95.84 | O |
| ATOM | 1695 | NE2 | GLN B | 1 | 0.145 | −40.344 | −15.273 | 1.00 | 92.98 | N |
| ATOM | 1696 | N | VAL B | 2 | −5.020 | −36.114 | −14.941 | 1.00 | 40.36 | N |
| ATOM | 1697 | CA | VAL B | 2 | −5.172 | −34.669 | −15.176 | 1.00 | 37.41 | C |
| ATOM | 1698 | C | VAL B | 2 | −4.620 | −33.914 | −13.936 | 1.00 | 36.02 | C |
| ATOM | 1699 | O | VAL B | 2 | −4.973 | −34.234 | −12.800 | 1.00 | 31.43 | O |
| ATOM | 1700 | CB | VAL B | 2 | −6.646 | −34.277 | −15.465 | 1.00 | 39.81 | C |
| ATOM | 1701 | CG1 | VAL B | 2 | −6.802 | −32.756 | −15.559 | 1.00 | 38.64 | C |
| ATOM | 1702 | CG2 | VAL B | 2 | −7.144 | −34.958 | −16.741 | 1.00 | 40.15 | C |
| ATOM | 1703 | N | GLN B | 3 | −3.743 | −32.932 | −14.169 | 1.00 | 31.67 | N |
| ATOM | 1704 | CA | GLN B | 3 | −3.146 | −32.148 | −13.100 | 1.00 | 29.95 | C |
| ATOM | 1705 | C | GLN B | 3 | −3.115 | −30.681 | −13.481 | 1.00 | 31.01 | C |
| ATOM | 1706 | O | GLN B | 3 | −3.000 | −30.377 | −14.662 | 1.00 | 30.96 | O |
| ATOM | 1707 | CB | GLN B | 3 | −1.729 | −32.648 | −12.841 | 1.00 | 31.56 | C |
| ATOM | 1708 | CG | GLN B | 3 | −1.696 | −34.085 | −12.326 | 1.00 | 45.91 | C |
| ATOM | 1709 | CD | GLN B | 3 | −0.295 | −34.535 | −12.043 | 1.00 | 65.99 | C |
| ATOM | 1710 | OE1 | GLN B | 3 | 0.238 | −34.275 | −10.970 | 1.00 | 61.21 | O |
| ATOM | 1711 | NE2 | GLN B | 3 | 0.350 | −35.182 | −13.009 | 1.00 | 62.64 | N |
| ATOM | 1712 | N | LEU B | 4 | −3.317 | −29.784 | −12.484 | 1.00 | 24.83 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1713 | CA | LEU B | 4 | −3.250 | −28.324 | −12.621 | 1.00 | 22.53 | C |
| ATOM | 1714 | C | LEU B | 4 | −2.406 | −27.915 | −11.434 | 1.00 | 26.30 | C |
| ATOM | 1715 | O | LEU B | 4 | −2.870 | −28.026 | −10.298 | 1.00 | 27.68 | O |
| ATOM | 1716 | CB | LEU B | 4 | −4.628 | −27.616 | −12.556 | 1.00 | 22.01 | C |
| ATOM | 1717 | CG | LEU B | 4 | −5.612 | −27.755 | −13.748 | 1.00 | 26.01 | C |
| ATOM | 1718 | CD1 | LEU B | 4 | −6.784 | −26.787 | −13.597 | 1.00 | 23.83 | C |
| ATOM | 1719 | CD2 | LEU B | 4 | −4.935 | −27.501 | −15.072 | 1.00 | 29.37 | C |
| ATOM | 1720 | N | VAL B | 5 | −1.121 | −27.591 | −11.663 | 1.00 | 22.34 | N |
| ATOM | 1721 | CA | VAL B | 5 | −0.217 | −27.249 | −10.580 | 1.00 | 21.22 | C |
| ATOM | 1722 | C | VAL B | 5 | 0.111 | −25.785 | −10.613 | 1.00 | 23.74 | C |
| ATOM | 1723 | O | VAL B | 5 | 0.788 | −25.325 | −11.514 | 1.00 | 24.44 | O |
| ATOM | 1724 | CB | VAL B | 5 | 1.038 | −28.154 | −10.555 | 1.00 | 25.29 | C |
| ATOM | 1725 | CG1 | VAL B | 5 | 1.923 | −27.814 | −9.335 | 1.00 | 24.61 | C |
| ATOM | 1726 | CG2 | VAL B | 5 | 0.618 | −29.622 | −10.502 | 1.00 | 24.65 | C |
| ATOM | 1727 | N | GLN B | 6 | −0.332 | −25.067 | −9.596 | 1.00 | 20.94 | N |
| ATOM | 1728 | CA | GLN B | 6 | −0.126 | −23.632 | −9.442 | 1.00 | 20.38 | C |
| ATOM | 1729 | C | GLN B | 6 | 1.207 | −23.295 | −8.777 | 1.00 | 22.73 | C |
| ATOM | 1730 | O | GLN B | 6 | 1.780 | −24.144 | −8.118 | 1.00 | 22.26 | O |
| ATOM | 1731 | CB | GLN B | 6 | −1.295 | −23.025 | −8.611 | 1.00 | 20.18 | C |
| ATOM | 1732 | CG | GLN B | 6 | −2.638 | −23.280 | −9.273 | 1.00 | 9.72 | C |
| ATOM | 1733 | CD | GLN B | 6 | −3.767 | −22.492 | −8.724 | 1.00 | 24.33 | C |
| ATOM | 1734 | OE1 | GLN B | 6 | −4.788 | −23.061 | −8.369 | 1.00 | 29.28 | O |
| ATOM | 1735 | NE2 | GLN B | 6 | −3.680 | −21.166 | −8.741 | 1.00 | 17.86 | N |
| ATOM | 1736 | N | SER B | 7 | 1.667 | −22.030 | −8.910 | 1.00 | 21.05 | N |
| ATOM | 1737 | CA | SER B | 7 | 2.900 | −21.543 | −8.265 | 1.00 | 21.34 | C |
| ATOM | 1738 | C | SER B | 7 | 2.589 | −21.248 | −6.764 | 1.00 | 24.61 | C |
| ATOM | 1739 | O | SER B | 7 | 1.403 | −21.169 | −6.401 | 1.00 | 22.84 | O |
| ATOM | 1740 | CB | SER B | 7 | 3.449 | −20.319 | −8.993 | 1.00 | 25.29 | C |
| ATOM | 1741 | OG | SER B | 7 | 2.476 | −19.312 | −9.229 | 1.00 | 34.58 | O |
| ATOM | 1742 | N | GLY B | 8 | 3.647 | −21.136 | −5.933 | 1.00 | 20.55 | N |
| ATOM | 1743 | CA | GLY B | 8 | 3.600 | −21.017 | −4.467 | 1.00 | 18.91 | C |
| ATOM | 1744 | C | GLY B | 8 | 3.252 | −19.663 | −3.884 | 1.00 | 23.33 | C |
| ATOM | 1745 | O | GLY B | 8 | 3.019 | −18.732 | −4.646 | 1.00 | 22.28 | O |
| ATOM | 1746 | N | VAL B | 9 | 3.143 | −19.563 | −2.514 | 1.00 | 21.14 | N |
| ATOM | 1747 | CA | VAL B | 9 | 2.768 | −18.321 | −1.791 | 1.00 | 21.60 | C |
| ATOM | 1748 | C | VAL B | 9 | 3.375 | −17.057 | −2.353 | 1.00 | 26.71 | C |
| ATOM | 1749 | O | VAL B | 9 | 4.567 | −17.056 | −2.649 | 1.00 | 28.56 | O |
| ATOM | 1750 | CB | VAL B | 9 | 3.037 | −18.309 | −0.243 | 1.00 | 24.53 | C |
| ATOM | 1751 | CG1 | VAL B | 9 | 1.869 | −18.872 | 0.531 | 1.00 | 23.45 | C |
| ATOM | 1752 | CG2 | VAL B | 9 | 4.371 | −18.960 | 0.150 | 1.00 | 23.72 | C |
| ATOM | 1753 | N | GLU B | 10 | 2.602 | −15.956 | −2.378 | 1.00 | 21.77 | N |
| ATOM | 1754 | CA | GLU B | 10 | 3.110 | −14.673 | −2.836 | 1.00 | 22.79 | C |
| ATOM | 1755 | C | GLU B | 10 | 2.814 | −13.624 | −1.788 | 1.00 | 29.94 | C |
| ATOM | 1756 | O | GLU B | 10 | 1.681 | −13.522 | −1.297 | 1.00 | 30.49 | O |
| ATOM | 1757 | CB | GLU B | 10 | 2.514 | −14.272 | −4.187 | 1.00 | 24.48 | C |
| ATOM | 1758 | CG | GLU B | 10 | 2.837 | −15.211 | −5.348 | 1.00 | 29.51 | C |
| ATOM | 1759 | CD | GLU B | 10 | 4.173 | −15.021 | −6.047 | 1.00 | 55.10 | C |
| ATOM | 1760 | OE1 | GLU B | 10 | 5.126 | −14.503 | −5.422 | 1.00 | 42.30 | O |
| ATOM | 1761 | OE2 | GLU B | 10 | 4.264 | −15.402 | −7.237 | 1.00 | 59.07 | O |
| ATOM | 1762 | N | VAL B | 11 | 3.852 | −12.897 | −1.383 | 1.00 | 26.59 | N |
| ATOM | 1763 | CA | VAL B | 11 | 3.733 | −11.833 | −0.394 | 1.00 | 26.23 | C |
| ATOM | 1764 | C | VAL B | 11 | 4.185 | −10.620 | −1.152 | 1.00 | 32.16 | C |
| ATOM | 1765 | O | VAL B | 11 | 5.309 | −10.606 | −1.645 | 1.00 | 33.64 | O |
| ATOM | 1766 | CB | VAL B | 11 | 4.580 | −12.104 | 0.862 | 1.00 | 28.66 | C |
| ATOM | 1767 | CG1 | VAL B | 11 | 4.500 | −10.923 | 1.814 | 1.00 | 29.12 | C |
| ATOM | 1768 | CG2 | VAL B | 11 | 4.138 | −13.386 | 1.546 | 1.00 | 26.98 | C |
| ATOM | 1769 | N | LYS B | 12 | 3.293 | −9.660 | −1.350 | 1.00 | 28.02 | N |
| ATOM | 1770 | CA | LYS B | 12 | 3.558 | −8.506 | −2.193 | 1.00 | 28.02 | C |
| ATOM | 1771 | C | LYS B | 12 | 3.197 | −7.250 | −1.487 | 1.00 | 33.53 | C |
| ATOM | 1772 | O | LYS B | 12 | 2.452 | −7.277 | −0.519 | 1.00 | 34.62 | O |
| ATOM | 1773 | CB | LYS B | 12 | 2.728 | −8.621 | −3.502 | 1.00 | 30.74 | C |
| ATOM | 1774 | CG | LYS B | 12 | 3.059 | −9.844 | −4.398 | 1.00 | 25.05 | C |
| ATOM | 1775 | CD | LYS B | 12 | 4.343 | −9.617 | −5.196 | 1.00 | 26.98 | C |
| ATOM | 1776 | CE | LYS B | 12 | 4.907 | −10.893 | −5.761 | 1.00 | 38.28 | C |
| ATOM | 1777 | NZ | LYS B | 12 | 5.837 | −10.625 | −6.900 | 1.00 | 50.70 | N |
| ATOM | 1778 | N | LYS B | 13 | 3.687 | −6.134 | −2.007 | 1.00 | 31.60 | N |
| ATOM | 1779 | CA | LYS B | 13 | 3.461 | −4.809 | −1.440 | 1.00 | 31.27 | C |
| ATOM | 1780 | C | LYS B | 13 | 2.305 | −4.142 | −2.190 | 1.00 | 35.58 | C |
| ATOM | 1781 | O | LYS B | 13 | 2.182 | −4.336 | −3.411 | 1.00 | 35.11 | O |
| ATOM | 1782 | CB | LYS B | 13 | 4.737 | −3.946 | −1.580 | 1.00 | 33.93 | C |
| ATOM | 1783 | CG | LYS B | 13 | 5.316 | −3.455 | −0.267 | 1.00 | 50.57 | C |
| ATOM | 1784 | CD | LYS B | 13 | 6.338 | −4.407 | 0.337 | 1.00 | 55.93 | C |
| ATOM | 1785 | CE | LYS B | 13 | 6.639 | −4.057 | 1.770 | 1.00 | 60.39 | C |
| ATOM | 1786 | NZ | LYS B | 13 | 7.956 | −4.579 | 2.208 | 1.00 | 75.27 | N |
| ATOM | 1787 | N | PRO B | 14 | 1.501 | −3.279 | −1.528 | 1.00 | 31.94 | N |
| ATOM | 1788 | CA | PRO B | 14 | 0.454 | −2.550 | −2.267 | 1.00 | 32.44 | C |
| ATOM | 1789 | C | PRO B | 14 | 1.049 | −1.773 | −3.455 | 1.00 | 40.13 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1790 | O | PRO B | 14 | 2.160 | −1.245 | −3.344 | 1.00 | 40.93 | O |
| ATOM | 1791 | CB | PRO B | 14 | −0.128 | −1.603 | −1.208 | 1.00 | 33.29 | C |
| ATOM | 1792 | CG | PRO B | 14 | 0.226 | −2.212 | 0.069 | 1.00 | 36.57 | C |
| ATOM | 1793 | CD | PRO B | 14 | 1.523 | −2.878 | −0.112 | 1.00 | 32.35 | C |
| ATOM | 1794 | N | GLY B | 15 | 0.362 | −1.791 | −4.597 | 1.00 | 37.74 | N |
| ATOM | 1795 | CA | GLY B | 15 | 0.828 | −1.149 | −5.823 | 1.00 | 36.91 | C |
| ATOM | 1796 | C | GLY B | 15 | 1.634 | −2.046 | −6.737 | 1.00 | 39.29 | C |
| ATOM | 1797 | O | GLY B | 15 | 1.714 | −1.781 | −7.935 | 1.00 | 39.60 | O |
| ATOM | 1798 | N | ALA B | 16 | 2.240 | −3.112 | −6.194 | 1.00 | 35.36 | N |
| ATOM | 1799 | CA | ALA B | 16 | 3.027 | −4.067 | −6.973 | 1.00 | 34.01 | C |
| ATOM | 1800 | C | ALA B | 16 | 2.085 | −4.965 | −7.777 | 1.00 | 38.69 | C |
| ATOM | 1801 | O | ALA B | 16 | 0.856 | −4.902 | −7.617 | 1.00 | 37.69 | O |
| ATOM | 1802 | CB | ALA B | 16 | 3.876 | −4.928 | −6.033 | 1.00 | 33.60 | C |
| ATOM | 1803 | N | SER B | 17 | 2.679 | −5.824 | −8.617 | 1.00 | 35.31 | N |
| ATOM | 1804 | CA | SER B | 17 | 1.949 | −6.803 | −9.396 | 1.00 | 34.86 | C |
| ATOM | 1805 | C | SER B | 17 | 2.373 | −8.228 | −8.989 | 1.00 | 37.12 | C |
| ATOM | 1806 | O | SER B | 17 | 3.489 | −8.442 | −8.511 | 1.00 | 37.72 | O |
| ATOM | 1807 | CB | SER B | 17 | 2.194 | −6.581 | −10.886 | 1.00 | 40.16 | C |
| ATOM | 1808 | OG | SER B | 17 | 3.458 | −7.058 | −11.316 | 1.00 | 50.20 | O |
| ATOM | 1809 | N | VAL B | 18 | 1.483 | −9.204 | −9.222 | 1.00 | 29.66 | N |
| ATOM | 1810 | CA | VAL B | 18 | 1.741 | −10.628 | −8.987 | 1.00 | 25.79 | C |
| ATOM | 1811 | C | VAL B | 18 | 1.415 | −11.334 | −10.283 | 1.00 | 29.72 | C |
| ATOM | 1812 | O | VAL B | 18 | 0.621 | −10.831 | −11.056 | 1.00 | 31.00 | O |
| ATOM | 1813 | CB | VAL B | 18 | 0.918 | −11.208 | −7.819 | 1.00 | 25.87 | C |
| ATOM | 1814 | CG1 | VAL B | 18 | −0.583 | −11.183 | −8.110 | 1.00 | 24.19 | C |
| ATOM | 1815 | CG2 | VAL B | 18 | 1.388 | −12.619 | −7.453 | 1.00 | 25.04 | C |
| ATOM | 1816 | N | LYS B | 19 | 2.048 | −12.467 | −10.528 | 1.00 | 26.32 | N |
| ATOM | 1817 | CA | LYS B | 19 | 1.815 | −13.296 | −11.691 | 1.00 | 26.71 | C |
| ATOM | 1818 | C | LYS B | 19 | 1.814 | −14.736 | −11.189 | 1.00 | 32.30 | C |
| ATOM | 1819 | O | LYS B | 19 | 2.814 | −15.219 | −10.655 | 1.00 | 34.19 | O |
| ATOM | 1820 | CB | LYS B | 19 | 2.880 | −13.070 | −12.762 | 1.00 | 30.28 | C |
| ATOM | 1821 | CG | LYS B | 19 | 2.520 | −13.679 | −14.126 | 1.00 | 30.50 | C |
| ATOM | 1822 | CD | LYS B | 19 | 3.377 | −13.066 | −15.223 | 1.00 | 36.72 | C |
| ATOM | 1823 | CE | LYS B | 19 | 3.228 | −13.814 | −16.522 | 1.00 | 52.11 | C |
| ATOM | 1824 | NZ | LYS B | 19 | 3.790 | −13.058 | −17.670 | 1.00 | 58.49 | N |
| ATOM | 1825 | N | VAL B | 20 | 0.661 | −15.371 | −11.270 | 1.00 | 26.19 | N |
| ATOM | 1826 | CA | VAL B | 20 | 0.450 | −16.723 | −10.809 | 1.00 | 23.92 | C |
| ATOM | 1827 | C | VAL B | 20 | 0.479 | −17.557 | −12.039 | 1.00 | 25.33 | C |
| ATOM | 1828 | O | VAL B | 20 | −0.030 | −17.132 | −13.050 | 1.00 | 24.41 | O |
| ATOM | 1829 | CB | VAL B | 20 | −0.933 | −16.800 | −10.092 | 1.00 | 26.58 | C |
| ATOM | 1830 | CG1 | VAL B | 20 | −1.243 | −18.225 | −9.620 | 1.00 | 25.11 | C |
| ATOM | 1831 | CG2 | VAL B | 20 | −0.983 | −15.808 | −8.932 | 1.00 | 26.18 | C |
| ATOM | 1832 | N | SER B | 21 | 1.015 | −18.749 | −11.968 | 1.00 | 23.76 | N |
| ATOM | 1833 | CA | SER B | 21 | 1.040 | −19.653 | −13.116 | 1.00 | 23.31 | C |
| ATOM | 1834 | C | SER B | 21 | 0.292 | −20.891 | −12.754 | 1.00 | 27.35 | C |
| ATOM | 1835 | O | SER B | 21 | 0.112 | −21.202 | −11.578 | 1.00 | 26.41 | O |
| ATOM | 1836 | CB | SER B | 21 | 2.471 | −19.994 | −13.530 | 1.00 | 25.77 | C |
| ATOM | 1837 | OG | SER B | 21 | 3.131 | −20.831 | −12.597 | 1.00 | 30.32 | O |
| ATOM | 1838 | N | CYS B | 22 | −0.151 | −21.593 | −13.768 | 1.00 | 27.03 | N |
| ATOM | 1839 | CA | CYS B | 22 | −0.913 | −22.802 | −13.622 | 1.00 | 28.41 | C |
| ATOM | 1840 | C | CYS B | 22 | −0.381 | −23.808 | −14.669 | 1.00 | 33.50 | C |
| ATOM | 1841 | O | CYS B | 22 | −0.635 | −23.679 | −15.878 | 1.00 | 32.60 | O |
| ATOM | 1842 | CB | CYS B | 22 | −2.392 | −22.477 | −13.801 | 1.00 | 30.04 | C |
| ATOM | 1843 | SG | CYS B | 22 | −3.488 | −23.912 | −13.731 | 1.00 | 35.19 | S |
| ATOM | 1844 | N | LYS B | 23 | 0.447 | −24.750 | −14.195 | 1.00 | 30.23 | N |
| ATOM | 1845 | CA | LYS B | 23 | 1.070 | −25.763 | −15.050 | 1.00 | 30.17 | C |
| ATOM | 1846 | C | LYS B | 23 | 0.076 | −26.844 | −15.306 | 1.00 | 31.49 | C |
| ATOM | 1847 | O | LYS B | 23 | −0.363 | −27.485 | −14.370 | 1.00 | 30.41 | O |
| ATOM | 1848 | CB | LYS B | 23 | 2.346 | −26.335 | −14.375 | 1.00 | 32.73 | C |
| ATOM | 1849 | CG | LYS B | 23 | 3.047 | −27.499 | −15.087 | 1.00 | 32.51 | C |
| ATOM | 1850 | CD | LYS B | 23 | 3.640 | −27.128 | −16.412 | 1.00 | 31.85 | C |
| ATOM | 1851 | CE | LYS B | 23 | 4.084 | −28.371 | −17.140 | 1.00 | 31.72 | C |
| ATOM | 1852 | NZ | LYS B | 23 | 4.959 | −28.006 | −18.284 | 1.00 | 33.61 | N |
| ATOM | 1853 | N | ALA B | 24 | −0.271 | −27.072 | −16.555 | 1.00 | 30.85 | N |
| ATOM | 1854 | CA | ALA B | 24 | −1.229 | −28.112 | −16.924 | 1.00 | 31.71 | C |
| ATOM | 1855 | C | ALA B | 24 | −0.524 | −29.379 | −17.470 | 1.00 | 35.87 | C |
| ATOM | 1856 | O | ALA B | 24 | 0.518 | −29.277 | −18.137 | 1.00 | 35.76 | O |
| ATOM | 1857 | CB | ALA B | 24 | −2.177 | −27.565 | −17.966 | 1.00 | 33.18 | C |
| ATOM | 1858 | N | SER B | 25 | −1.083 | −30.568 | −17.167 | 1.00 | 31.32 | N |
| ATOM | 1859 | CA | SER B | 25 | −0.562 | −31.842 | −17.702 | 1.00 | 31.13 | C |
| ATOM | 1860 | C | SER B | 25 | −1.632 | −32.945 | −17.703 | 1.00 | 34.66 | C |
| ATOM | 1861 | O | SER B | 25 | −2.638 | −32.818 | −17.009 | 1.00 | 33.41 | O |
| ATOM | 1862 | CB | SER B | 25 | 0.696 | −32.296 | −16.960 | 1.00 | 34.75 | C |
| ATOM | 1863 | OG | SER B | 25 | 0.468 | −32.688 | −15.615 | 1.00 | 42.86 | O |
| ATOM | 1864 | N | GLY B | 26 | −1.427 | −33.969 | −18.540 | 1.00 | 32.21 | N |
| ATOM | 1865 | CA | GLY B | 26 | −2.301 | −35.132 | −18.635 | 1.00 | 31.62 | C |
| ATOM | 1866 | C | GLY B | 26 | −3.531 | −34.983 | −19.499 | 1.00 | 38.46 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1867 | O | GLY B | 26 | −4.449 | −35.812 | −19.423 | 1.00 | 37.63 | O |
| ATOM | 1868 | N | TYR B | 27 | −3.571 | −33.940 | −20.344 | 1.00 | 37.14 | N |
| ATOM | 1869 | CA | TYR B | 27 | −4.711 | −33.724 | −21.238 | 1.00 | 36.49 | C |
| ATOM | 1870 | C | TYR B | 27 | −4.303 | −32.800 | −22.385 | 1.00 | 43.43 | C |
| ATOM | 1871 | O | TYR B | 27 | −3.223 | −32.188 | −22.356 | 1.00 | 41.56 | O |
| ATOM | 1872 | CB | TYR B | 27 | −5.929 | −33.171 | −20.462 | 1.00 | 35.46 | C |
| ATOM | 1873 | CG | TYR B | 27 | −5.774 | −31.747 | −19.973 | 1.00 | 35.83 | C |
| ATOM | 1874 | CD1 | TYR B | 27 | −5.226 | −31.472 | −18.724 | 1.00 | 36.81 | C |
| ATOM | 1875 | CD2 | TYR B | 27 | −6.255 | −30.679 | −20.721 | 1.00 | 36.46 | C |
| ATOM | 1876 | CE1 | TYR B | 27 | −5.105 | −30.163 | −18.259 | 1.00 | 35.88 | C |
| ATOM | 1877 | CE2 | TYR B | 27 | −6.182 | −29.372 | −20.251 | 1.00 | 37.00 | C |
| ATOM | 1878 | CZ | TYR B | 27 | −5.614 | −29.114 | −19.012 | 1.00 | 42.52 | C |
| ATOM | 1879 | OH | TYR B | 27 | −5.524 | −27.817 | −18.546 | 1.00 | 36.84 | O |
| ATOM | 1880 | N | THR B | 28 | −5.176 | −32.708 | −23.392 | 1.00 | 43.63 | N |
| ATOM | 1881 | CA | THR B | 28 | −4.955 | −31.827 | −24.530 | 1.00 | 45.77 | C |
| ATOM | 1882 | C | THR B | 28 | −5.367 | −30.391 | −24.122 | 1.00 | 49.63 | C |
| ATOM | 1883 | O | THR B | 28 | −6.560 | −30.080 | −24.060 | 1.00 | 48.62 | O |
| ATOM | 1884 | CB | THR B | 28 | −5.715 | −32.354 | −25.753 | 1.00 | 62.69 | C |
| ATOM | 1885 | OG1 | THR B | 28 | −5.344 | −33.724 | −25.959 | 1.00 | 70.12 | O |
| ATOM | 1886 | CG2 | THR B | 28 | −5.434 | −31.531 | −27.011 | 1.00 | 57.01 | C |
| ATOM | 1887 | N | PHE B | 29 | −4.364 | −29.558 | −23.796 | 1.00 | 46.12 | N |
| ATOM | 1888 | CA | PHE B | 29 | −4.510 | −28.158 | −23.376 | 1.00 | 45.87 | C |
| ATOM | 1889 | C | PHE B | 29 | −5.536 | −27.385 | −24.234 | 1.00 | 50.97 | C |
| ATOM | 1890 | O | PHE B | 29 | −6.421 | −26.714 | −23.701 | 1.00 | 49.49 | O |
| ATOM | 1891 | CB | PHE B | 29 | −3.128 | −27.481 | −23.442 | 1.00 | 47.70 | C |
| ATOM | 1892 | CG | PHE B | 29 | −2.960 | −26.176 | −22.703 | 1.00 | 49.27 | C |
| ATOM | 1893 | CD1 | PHE B | 29 | −3.263 | −26.083 | −21.345 | 1.00 | 51.30 | C |
| ATOM | 1894 | CD2 | PHE B | 29 | −2.296 | −25.108 | −23.296 | 1.00 | 51.56 | C |
| ATOM | 1895 | CE1 | PHE B | 29 | −3.019 | −24.906 | −20.636 | 1.00 | 51.44 | C |
| ATOM | 1896 | CE2 | PHE B | 29 | −2.030 | −23.942 | −22.577 | 1.00 | 53.70 | C |
| ATOM | 1897 | CZ | PHE B | 29 | −2.418 | −23.839 | −21.259 | 1.00 | 50.74 | C |
| ATOM | 1898 | N | THR B | 30 | −5.434 | −27.556 | −25.559 | 1.00 | 49.73 | N |
| ATOM | 1899 | CA | THR B | 30 | −6.276 | −26.951 | −26.606 | 1.00 | 50.06 | C |
| ATOM | 1900 | C | THR B | 30 | −7.788 | −27.186 | −26.426 | 1.00 | 51.20 | C |
| ATOM | 1901 | O | THR B | 30 | −8.576 | −26.283 | −26.704 | 1.00 | 52.26 | O |
| ATOM | 1902 | CB | THR B | 30 | −5.785 | −27.499 | −27.965 | 1.00 | 67.81 | C |
| ATOM | 1903 | OG1 | THR B | 30 | −4.402 | −27.147 | −28.105 | 1.00 | 71.63 | O |
| ATOM | 1904 | CG2 | THR B | 30 | −6.601 | −26.998 | −29.161 | 1.00 | 69.38 | C |
| ATOM | 1905 | N | ASN B | 31 | −8.189 | −28.373 | −25.959 | 1.00 | 43.80 | N |
| ATOM | 1906 | CA | ASN B | 31 | −9.608 | −28.728 | −25.768 | 1.00 | 42.67 | C |
| ATOM | 1907 | C | ASN B | 31 | −10.345 | −28.039 | −24.604 | 1.00 | 42.98 | C |
| ATOM | 1908 | O | ASN B | 31 | −11.537 | −28.324 | −24.415 | 1.00 | 41.33 | O |
| ATOM | 1909 | CB | ASN B | 31 | −9.751 | −30.269 | −25.591 | 1.00 | 47.35 | C |
| ATOM | 1910 | CG | ASN B | 31 | −10.148 | −31.020 | −26.836 | 1.00 | 74.04 | C |
| ATOM | 1911 | OD1 | ASN B | 31 | −10.984 | −31.928 | −26.780 | 1.00 | 70.30 | O |
| ATOM | 1912 | ND2 | ASN B | 31 | −9.506 | −30.732 | −27.967 | 1.00 | 65.06 | N |
| ATOM | 1913 | N | TYR B | 32 | −9.657 | −27.208 | −23.776 | 1.00 | 37.44 | N |
| ATOM | 1914 | CA | TYR B | 32 | −10.298 | −26.613 | −22.608 | 1.00 | 34.80 | C |
| ATOM | 1915 | C | TYR B | 32 | −9.944 | −25.140 | −22.378 | 1.00 | 33.65 | C |
| ATOM | 1916 | O | TYR B | 32 | −8.805 | −24.725 | −22.565 | 1.00 | 30.21 | O |
| ATOM | 1917 | CB | TYR B | 32 | −9.912 | −27.429 | −21.348 | 1.00 | 34.53 | C |
| ATOM | 1918 | CG | TYR B | 32 | −10.351 | −28.879 | −21.356 | 1.00 | 35.50 | C |
| ATOM | 1919 | CD1 | TYR B | 32 | −9.606 | −29.847 | −22.013 | 1.00 | 36.85 | C |
| ATOM | 1920 | CD2 | TYR B | 32 | −11.414 | −29.310 | −20.569 | 1.00 | 37.03 | C |
| ATOM | 1921 | CE1 | TYR B | 32 | −10.001 | −31.184 | −22.025 | 1.00 | 35.69 | C |
| ATOM | 1922 | CE2 | TYR B | 32 | −11.818 | −30.649 | −20.560 | 1.00 | 37.96 | C |
| ATOM | 1923 | CZ | TYR B | 32 | −11.112 | −31.585 | −21.295 | 1.00 | 45.71 | C |
| ATOM | 1924 | OH | TYR B | 32 | −11.509 | −32.913 | −21.254 | 1.00 | 51.42 | O |
| ATOM | 1925 | N | TYR B | 33 | −10.921 | −24.370 | −21.880 | 1.00 | 30.40 | N |
| ATOM | 1926 | CA | TYR B | 33 | −10.683 | −22.992 | −21.441 | 1.00 | 30.28 | C |
| ATOM | 1927 | C | TYR B | 33 | −9.944 | −23.102 | −20.107 | 1.00 | 31.04 | C |
| ATOM | 1928 | O | TYR B | 33 | −10.086 | −24.117 | −19.416 | 1.00 | 30.10 | O |
| ATOM | 1929 | CB | TYR B | 33 | −11.999 | −22.264 | −21.113 | 1.00 | 32.20 | C |
| ATOM | 1930 | CG | TYR B | 33 | −12.838 | −21.897 | −22.309 | 1.00 | 37.24 | C |
| ATOM | 1931 | CD1 | TYR B | 33 | −12.416 | −20.922 | −23.206 | 1.00 | 40.26 | C |
| ATOM | 1932 | CD2 | TYR B | 33 | −14.110 | −22.431 | −22.482 | 1.00 | 38.49 | C |
| ATOM | 1933 | CE1 | TYR B | 33 | −13.181 | −20.591 | −24.325 | 1.00 | 42.99 | C |
| ATOM | 1934 | CE2 | TYR B | 33 | −14.892 | −22.089 | −23.582 | 1.00 | 40.20 | C |
| ATOM | 1935 | CZ | TYR B | 33 | −14.433 | −21.153 | −24.491 | 1.00 | 47.66 | C |
| ATOM | 1936 | OH | TYR B | 33 | −15.208 | −20.813 | −25.573 | 1.00 | 48.23 | O |
| ATOM | 1937 | N | MET B | 34 | −9.192 | −22.069 | −19.728 | 1.00 | 25.12 | N |
| ATOM | 1938 | CA | MET B | 34 | −8.577 | −22.025 | −18.413 | 1.00 | 23.73 | C |
| ATOM | 1939 | C | MET B | 34 | −9.152 | −20.804 | −17.742 | 1.00 | 24.57 | C |
| ATOM | 1940 | O | MET B | 34 | −9.025 | −19.689 | −18.255 | 1.00 | 23.69 | O |
| ATOM | 1941 | CB | MET B | 34 | −7.053 | −21.983 | −18.442 | 1.00 | 27.25 | C |
| ATOM | 1942 | CG | MET B | 34 | −6.466 | −22.219 | −17.070 | 1.00 | 32.79 | C |
| ATOM | 1943 | SD | MET B | 34 | −6.634 | −23.946 | −16.492 | 1.00 | 38.98 | S |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 1944 | CE | MET B | 34 | −5.262 | −24.688 | −17.486 | 1.00 | 36.13 | C |
| ATOM | 1945 | N | TYR B | 35 | −9.816 | −21.028 | −16.618 | 1.00 | 20.58 | N |
| ATOM | 1946 | CA | TYR B | 35 | −10.506 | −20.013 | −15.844 | 1.00 | 21.77 | C |
| ATOM | 1947 | C | TYR B | 35 | −9.770 | −19.646 | −14.590 | 1.00 | 23.74 | C |
| ATOM | 1948 | O | TYR B | 35 | −9.045 | −20.475 | −14.057 | 1.00 | 20.50 | O |
| ATOM | 1949 | CB | TYR B | 35 | −11.883 | −20.553 | −15.493 | 1.00 | 25.04 | C |
| ATOM | 1950 | CG | TYR B | 35 | −12.858 | −20.343 | −16.618 | 1.00 | 30.81 | C |
| ATOM | 1951 | CD2 | TYR B | 35 | −13.114 | −21.340 | −17.547 | 1.00 | 32.50 | C |
| ATOM | 1952 | CD1 | TYR B | 35 | −13.493 | −19.139 | −16.779 | 1.00 | 34.87 | C |
| ATOM | 1953 | CE2 | TYR B | 35 | −14.071 | −21.163 | −18.553 | 1.00 | 34.04 | C |
| ATOM | 1954 | CE1 | TYR B | 35 | −14.454 | −18.944 | −17.770 | 1.00 | 39.29 | C |
| ATOM | 1955 | CZ | TYR B | 35 | −14.746 | −19.961 | −18.659 | 1.00 | 42.08 | C |
| ATOM | 1956 | OH | TYR B | 35 | −15.721 | −19.728 | −19.611 | 1.00 | 48.31 | O |
| ATOM | 1957 | N | TRP B | 36 | −10.001 | −18.428 | −14.071 | 1.00 | 21.77 | N |
| ATOM | 1958 | CA | TRP B | 36 | −9.377 | −17.971 | −12.817 | 1.00 | 20.91 | C |
| ATOM | 1959 | C | TRP B | 36 | −10.459 | −17.491 | −11.880 | 1.00 | 21.04 | C |
| ATOM | 1960 | O | TRP B | 36 | −11.380 | −16.773 | −12.288 | 1.00 | 20.25 | O |
| ATOM | 1961 | CB | TRP B | 36 | −8.340 | −16.884 | −13.081 | 1.00 | 21.12 | C |
| ATOM | 1962 | CG | TRP B | 36 | −7.163 | −17.404 | −13.858 | 1.00 | 23.05 | C |
| ATOM | 1963 | CD1 | TRP B | 36 | −7.046 | −17.499 | −15.222 | 1.00 | 26.40 | C |
| ATOM | 1964 | CD2 | TRP B | 36 | −5.983 | −18.004 | −13.307 | 1.00 | 22.60 | C |
| ATOM | 1965 | NE1 | TRP B | 36 | −5.811 | −18.003 | −15.551 | 1.00 | 26.83 | N |
| ATOM | 1966 | CE2 | TRP B | 36 | −5.150 | −18.360 | −14.390 | 1.00 | 27.44 | C |
| ATOM | 1967 | CE3 | TRP B | 36 | −5.499 | −18.174 | −11.992 | 1.00 | 23.72 | C |
| ATOM | 1968 | CZ2 | TRP B | 36 | −3.848 | −18.843 | −14.198 | 1.00 | 26.07 | C |
| ATOM | 1969 | CZ3 | TRP B | 36 | −4.217 | −18.673 | −11.806 | 1.00 | 24.71 | C |
| ATOM | 1970 | CH2 | TRP B | 36 | −3.403 | −18.994 | −12.900 | 1.00 | 25.27 | C |
| ATOM | 1971 | N | VAL B | 37 | −10.368 | −17.932 | −10.632 | 1.00 | 16.71 | N |
| ATOM | 1972 | CA | VAL B | 37 | −11.365 | −17.705 | −9.583 | 1.00 | 16.71 | C |
| ATOM | 1973 | C | VAL B | 37 | −10.632 | −17.374 | −8.298 | 1.00 | 23.31 | C |
| ATOM | 1974 | O | VAL B | 37 | −9.657 | −18.064 | −7.965 | 1.00 | 22.48 | O |
| ATOM | 1975 | CB | VAL B | 37 | −12.217 | −19.023 | −9.414 | 1.00 | 19.10 | C |
| ATOM | 1976 | CG1 | VAL B | 37 | −13.153 | −18.970 | −8.206 | 1.00 | 17.44 | C |
| ATOM | 1977 | CG2 | VAL B | 37 | −12.995 | −19.358 | −10.695 | 1.00 | 18.52 | C |
| ATOM | 1978 | N | ARG B | 38 | −11.088 | −16.354 | −7.555 | 1.00 | 22.52 | N |
| ATOM | 1979 | CA | ARG B | 38 | −10.446 | −16.068 | −6.262 | 1.00 | 22.21 | C |
| ATOM | 1980 | C | ARG B | 38 | −11.408 | −16.200 | −5.074 | 1.00 | 24.08 | C |
| ATOM | 1981 | O | ARG B | 38 | −12.623 | −16.098 | −5.219 | 1.00 | 21.55 | O |
| ATOM | 1982 | CB | ARG B | 38 | −9.724 | −14.723 | −6.258 | 1.00 | 22.03 | C |
| ATOM | 1983 | CG | ARG B | 38 | −10.633 | −13.531 | −6.157 | 1.00 | 21.31 | C |
| ATOM | 1984 | CD | ARG B | 38 | −9.807 | −12.296 | −5.961 | 1.00 | 24.56 | C |
| ATOM | 1985 | NE | ARG B | 38 | −10.662 | −11.175 | −5.596 | 1.00 | 36.67 | N |
| ATOM | 1986 | CZ | ARG B | 38 | −10.282 | −9.905 | −5.593 | 1.00 | 42.55 | C |
| ATOM | 1987 | NH1 | ARG B | 38 | −9.042 | −9.572 | −5.931 | 1.00 | 26.77 | N |
| ATOM | 1988 | NH2 | ARG B | 38 | −11.145 | −8.954 | −5.272 | 1.00 | 30.00 | N |
| ATOM | 1989 | N | GLN B | 39 | −10.829 | −16.449 | −3.907 | 1.00 | 22.38 | N |
| ATOM | 1990 | CA | GLN B | 39 | −11.535 | −16.574 | −2.635 | 1.00 | 21.99 | C |
| ATOM | 1991 | C | GLN B | 39 | −10.847 | −15.717 | −1.548 | 1.00 | 27.54 | C |
| ATOM | 1992 | O | GLN B | 39 | −9.750 | −16.052 | −1.099 | 1.00 | 25.75 | O |
| ATOM | 1993 | CB | GLN B | 39 | −11.558 | −18.045 | −2.223 | 1.00 | 21.99 | C |
| ATOM | 1994 | CG | GLN B | 39 | −12.475 | −18.336 | −1.070 | 1.00 | 13.37 | C |
| ATOM | 1995 | CD | GLN B | 39 | −12.743 | −19.809 | −0.981 | 1.00 | 26.33 | C |
| ATOM | 1996 | OE1 | GLN B | 39 | −11.861 | −20.627 | −1.241 | 1.00 | 17.94 | O |
| ATOM | 1997 | NE2 | GLN B | 39 | −13.967 | −20.191 | −0.608 | 1.00 | 15.59 | N |
| ATOM | 1998 | N | ALA B | 40 | −11.463 | −14.587 | −1.157 | 1.00 | 27.75 | N |
| ATOM | 1999 | CA | ALA B | 40 | −10.903 | −13.744 | −0.071 | 1.00 | 28.48 | C |
| ATOM | 2000 | C | ALA B | 40 | −11.084 | −14.420 | 1.311 | 1.00 | 33.86 | C |
| ATOM | 2001 | O | ALA B | 40 | −11.909 | −15.328 | 1.428 | 1.00 | 31.26 | O |
| ATOM | 2002 | CB | ALA B | 40 | −11.531 | −12.357 | −0.090 | 1.00 | 29.51 | C |
| ATOM | 2003 | N | PRO B | 41 | −10.247 | −14.087 | 2.344 | 1.00 | 34.75 | N |
| ATOM | 2004 | CA | PRO B | 41 | −10.368 | −14.783 | 3.648 | 1.00 | 33.84 | C |
| ATOM | 2005 | C | PRO B | 41 | −11.795 | −14.843 | 4.223 | 1.00 | 35.36 | C |
| ATOM | 2006 | O | PRO B | 41 | −12.459 | −13.802 | 4.349 | 1.00 | 34.59 | O |
| ATOM | 2007 | CB | PRO B | 41 | −9.396 | −14.010 | 4.559 | 1.00 | 35.22 | C |
| ATOM | 2008 | CG | PRO B | 41 | −8.426 | −13.388 | 3.649 | 1.00 | 39.83 | C |
| ATOM | 2009 | CD | PRO B | 41 | −9.159 | −13.078 | 2.379 | 1.00 | 36.13 | C |
| ATOM | 2010 | N | GLY B | 42 | −12.244 | −16.066 | 4.536 | 1.00 | 29.63 | N |
| ATOM | 2011 | CA | GLY B | 42 | −13.584 | −16.334 | 5.051 | 1.00 | 29.00 | C |
| ATOM | 2012 | C | GLY B | 42 | −14.728 | −15.978 | 4.109 | 1.00 | 33.50 | C |
| ATOM | 2013 | O | GLY B | 42 | −15.868 | −15.893 | 4.569 | 1.00 | 34.92 | O |
| ATOM | 2014 | N | GLN B | 43 | −14.457 | −15.782 | 2.787 | 1.00 | 28.75 | N |
| ATOM | 2015 | CA | GLN B | 43 | −15.447 | −15.386 | 1.765 | 1.00 | 27.89 | C |
| ATOM | 2016 | C | GLN B | 43 | −15.665 | −16.506 | 0.747 | 1.00 | 29.71 | C |
| ATOM | 2017 | O | GLN B | 43 | −15.018 | −17.559 | 0.827 | 1.00 | 29.44 | O |
| ATOM | 2018 | CB | GLN B | 43 | −14.989 | −14.101 | 1.019 | 1.00 | 29.81 | C |
| ATOM | 2019 | CG | GLN B | 43 | −14.799 | −12.861 | 1.902 | 1.00 | 40.57 | C |
| ATOM | 2020 | CD | GLN B | 43 | −16.062 | −12.516 | 2.647 | 1.00 | 73.24 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2021 | OE1 | GLN B | 43 | −17.065 | −12.110 | 2.034 | 1.00 | 75.37 | O |
| ATOM | 2022 | NE2 | GLN B | 43 | −16.071 | −12.724 | 3.973 | 1.00 | 59.99 | N |
| ATOM | 2023 | N | GLY B | 44 | −16.606 | −16.273 | −0.172 | 1.00 | 24.61 | N |
| ATOM | 2024 | CA | GLY B | 44 | −16.971 | −17.215 | −1.226 | 1.00 | 23.29 | C |
| ATOM | 2025 | C | GLY B | 44 | −16.122 | −17.132 | −2.479 | 1.00 | 26.11 | C |
| ATOM | 2026 | O | GLY B | 44 | −15.056 | −16.519 | −2.486 | 1.00 | 25.76 | O |
| ATOM | 2027 | N | LEU B | 45 | −16.577 | −17.767 | −3.551 | 1.00 | 22.97 | N |
| ATOM | 2028 | CA | LEU B | 45 | −15.835 | −17.840 | −4.813 | 1.00 | 21.51 | C |
| ATOM | 2029 | C | LEU B | 45 | −16.242 | −16.742 | −5.769 | 1.00 | 26.41 | C |
| ATOM | 2030 | O | LEU B | 45 | −17.414 | −16.409 | −5.870 | 1.00 | 27.64 | O |
| ATOM | 2031 | CB | LEU B | 45 | −16.011 | −19.232 | −5.439 | 1.00 | 20.11 | C |
| ATOM | 2032 | CG | LEU B | 45 | −15.495 | −20.386 | −4.584 | 1.00 | 21.13 | C |
| ATOM | 2033 | CD1 | LEU B | 45 | −16.079 | −21.737 | −5.058 | 1.00 | 19.80 | C |
| ATOM | 2034 | CD2 | LEU B | 45 | −13.980 | −20.447 | −4.629 | 1.00 | 20.68 | C |
| ATOM | 2035 | N | GLU B | 46 | −15.269 | −16.156 | −6.445 | 1.00 | 24.40 | N |
| ATOM | 2036 | CA | GLU B | 46 | −15.482 | −15.050 | −7.365 | 1.00 | 25.86 | C |
| ATOM | 2037 | C | GLU B | 46 | −14.767 | −15.325 | −8.694 | 1.00 | 30.09 | C |
| ATOM | 2038 | O | GLU B | 46 | −13.536 | −15.481 | −8.703 | 1.00 | 30.27 | O |
| ATOM | 2039 | CB | GLU B | 46 | −14.905 | −13.806 | −6.692 | 1.00 | 27.63 | C |
| ATOM | 2040 | CG | GLU B | 46 | −14.959 | −12.514 | −7.497 | 1.00 | 38.10 | C |
| ATOM | 2041 | CD | GLU B | 46 | −14.543 | −11.309 | −6.672 | 1.00 | 59.40 | C |
| ATOM | 2042 | OE1 | GLU B | 46 | −13.862 | −11.479 | −5.629 | 1.00 | 62.80 | O |
| ATOM | 2043 | OE2 | GLU B | 46 | −14.928 | −10.186 | −7.063 | 1.00 | 51.53 | O |
| ATOM | 2044 | N | TRP B | 47 | −15.522 | −15.390 | −9.802 | 1.00 | 25.25 | N |
| ATOM | 2045 | CA | TRP B | 47 | −14.934 | −15.621 | −11.126 | 1.00 | 24.93 | C |
| ATOM | 2046 | C | TRP B | 47 | −14.240 | −14.345 | −11.609 | 1.00 | 27.77 | C |
| ATOM | 2047 | O | TRP B | 47 | −14.864 | −13.270 | −11.638 | 1.00 | 26.80 | O |
| ATOM | 2048 | CB | TRP B | 47 | −16.000 | −16.077 | −12.138 | 1.00 | 24.70 | C |
| ATOM | 2049 | CG | TRP B | 47 | −15.554 | −16.036 | −13.575 | 1.00 | 27.08 | C |
| ATOM | 2050 | CD1 | TRP B | 47 | −14.710 | −16.906 | −14.199 | 1.00 | 29.95 | C |
| ATOM | 2051 | CD2 | TRP B | 47 | −15.923 | −15.058 | −14.563 | 1.00 | 28.03 | C |
| ATOM | 2052 | NE1 | TRP B | 47 | −14.539 | −16.534 | −15.512 | 1.00 | 30.51 | N |
| ATOM | 2053 | CE2 | TRP B | 47 | −15.266 | −15.408 | −15.763 | 1.00 | 32.55 | C |
| ATOM | 2054 | CE3 | TRP B | 47 | −16.820 | −13.984 | −14.582 | 1.00 | 29.84 | C |
| ATOM | 2055 | CZ2 | TRP B | 47 | −15.461 | −14.712 | −16.961 | 1.00 | 32.04 | C |
| ATOM | 2056 | CZ3 | TRP B | 47 | −16.961 | −13.254 | −15.756 | 1.00 | 32.15 | C |
| ATOM | 2057 | CH2 | TRP B | 47 | −16.287 | −13.623 | −16.927 | 1.00 | 32.93 | C |
| ATOM | 2058 | N | MET B | 48 | −12.968 | −14.473 | −12.032 | 1.00 | 22.71 | N |
| ATOM | 2059 | CA | MET B | 48 | −12.208 | −13.315 | −12.509 | 1.00 | 23.08 | C |
| ATOM | 2060 | C | MET B | 48 | −12.176 | −13.207 | −14.062 | 1.00 | 26.54 | C |
| ATOM | 2061 | O | MET B | 48 | −12.433 | −12.142 | −14.633 | 1.00 | 22.27 | O |
| ATOM | 2062 | CB | MET B | 48 | −10.795 | −13.381 | −11.961 | 1.00 | 24.76 | C |
| ATOM | 2063 | CG | MET B | 48 | −10.720 | −13.140 | −10.485 | 1.00 | 27.58 | C |
| ATOM | 2064 | SD | MET B | 48 | −9.067 | −13.617 | −9.974 | 1.00 | 32.46 | S |
| ATOM | 2065 | CE | MET B | 48 | −8.074 | −12.283 | −10.702 | 1.00 | 30.32 | C |
| ATOM | 2066 | N | GLY B | 49 | −11.856 | −14.321 | −14.710 | 1.00 | 25.34 | N |
| ATOM | 2067 | CA | GLY B | 49 | −11.766 | −14.360 | −16.158 | 1.00 | 25.42 | C |
| ATOM | 2068 | C | GLY B | 49 | −11.396 | −15.719 | −16.692 | 1.00 | 29.10 | C |
| ATOM | 2069 | O | GLY B | 49 | −11.135 | −16.644 | −15.921 | 1.00 | 27.81 | O |
| ATOM | 2070 | N | GLY B | 50 | −11.444 | −15.837 | −18.014 | 1.00 | 26.96 | N |
| ATOM | 2071 | CA | GLY B | 50 | −11.091 | −17.052 | −18.729 | 1.00 | 26.17 | C |
| ATOM | 2072 | C | GLY B | 50 | −10.379 | −16.738 | −20.022 | 1.00 | 29.94 | C |
| ATOM | 2073 | O | GLY B | 50 | −10.612 | −15.691 | −20.608 | 1.00 | 30.04 | O |
| ATOM | 2074 | N | ILE B | 51 | −9.503 | −17.632 | −20.459 | 1.00 | 27.12 | N |
| ATOM | 2075 | CA | ILE B | 51 | −8.729 | −17.504 | −21.697 | 1.00 | 26.54 | C |
| ATOM | 2076 | C | ILE B | 51 | −8.912 | −18.768 | −22.502 | 1.00 | 30.38 | C |
| ATOM | 2077 | O | ILE B | 51 | −8.995 | −19.860 | −21.937 | 1.00 | 26.82 | O |
| ATOM | 2078 | CB | ILE B | 51 | −7.203 | −17.246 | −21.433 | 1.00 | 28.66 | C |
| ATOM | 2079 | CG1 | ILE B | 51 | −6.442 | −17.004 | −22.748 | 1.00 | 28.71 | C |
| ATOM | 2080 | CG2 | ILE B | 51 | −6.542 | −18.399 | −20.662 | 1.00 | 28.00 | C |
| ATOM | 2081 | CD1 | ILE B | 51 | −5.148 | −16.302 | −22.582 | 1.00 | 32.54 | C |
| ATOM | 2082 | N | ASN B | 52 | −8.929 | −18.609 | −23.820 | 1.00 | 32.31 | N |
| ATOM | 2083 | CA | ASN B | 52 | −8.971 | −19.700 | −24.787 | 1.00 | 34.32 | C |
| ATOM | 2084 | C | ASN B | 52 | −7.491 | −19.920 | −25.173 | 1.00 | 41.59 | C |
| ATOM | 2085 | O | ASN B | 52 | −6.885 | −18.979 | −25.676 | 1.00 | 39.72 | O |
| ATOM | 2086 | CB | ASN B | 52 | −9.796 | −19.271 | −25.992 | 1.00 | 34.45 | C |
| ATOM | 2087 | CG | ASN B | 52 | −9.979 | −20.348 | −27.020 | 1.00 | 54.30 | C |
| ATOM | 2088 | OD1 | ASN B | 52 | −9.270 | −21.363 | −27.031 | 1.00 | 50.48 | O |
| ATOM | 2089 | ND2 | ASN B | 52 | −10.943 | −20.149 | −27.907 | 1.00 | 42.53 | N |
| ATOM | 2090 | N | PRO B | 53 | −6.861 | −21.091 | −24.900 | 1.00 | 43.26 | N |
| ATOM | 2091 | CA | PRO B | 53 | −5.422 | −21.243 | −25.236 | 1.00 | 43.62 | C |
| ATOM | 2092 | C | PRO B | 53 | −5.088 | −21.393 | −26.727 | 1.00 | 48.81 | C |
| ATOM | 2093 | O | PRO B | 53 | −3.917 | −21.222 | −27.079 | 1.00 | 48.57 | O |
| ATOM | 2094 | CB | PRO B | 53 | −4.966 | −22.469 | −24.425 | 1.00 | 44.80 | C |
| ATOM | 2095 | CG | PRO B | 53 | −6.202 | −23.131 | −23.914 | 1.00 | 49.25 | C |
| ATOM | 2096 | CD | PRO B | 53 | −7.416 | −22.315 | −24.282 | 1.00 | 45.42 | C |
| ATOM | 2097 | N | SER B | 54 | −6.079 | −21.673 | −27.606 | 1.00 | 46.66 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2098 | CA | SER B | 54 | −5.814 | −21.824 | −29.052 | 1.00 | 47.73 | C |
| ATOM | 2099 | C | SER B | 54 | −5.622 | −20.462 | −29.763 | 1.00 | 51.08 | C |
| ATOM | 2100 | O | SER B | 54 | −4.626 | −20.285 | −30.461 | 1.00 | 52.05 | O |
| ATOM | 2101 | CB | SER B | 54 | −6.907 | −22.657 | −29.729 | 1.00 | 51.89 | C |
| ATOM | 2102 | OG | SER B | 54 | −8.213 | −22.160 | −29.489 | 1.00 | 61.44 | O |
| ATOM | 2103 | N | ASN B | 55 | −6.538 | −19.500 | −29.543 | 1.00 | 44.67 | N |
| ATOM | 2104 | CA | ASN B | 55 | −6.470 | −18.170 | −30.153 | 1.00 | 43.90 | C |
| ATOM | 2105 | C | ASN B | 55 | −6.086 | −17.008 | −29.166 | 1.00 | 47.96 | C |
| ATOM | 2106 | O | ASN B | 55 | −5.874 | −15.874 | −29.617 | 1.00 | 49.37 | O |
| ATOM | 2107 | CB | ASN B | 55 | −7.797 | −17.866 | −30.867 | 1.00 | 42.32 | C |
| ATOM | 2108 | CG | ASN B | 55 | −9.014 | −17.753 | −29.963 | 1.00 | 57.80 | C |
| ATOM | 2109 | OD1 | ASN B | 55 | −8.914 | −17.450 | −28.770 | 1.00 | 48.80 | O |
| ATOM | 2110 | ND2 | ASN B | 55 | −10.202 | −17.964 | −30.510 | 1.00 | 44.86 | N |
| ATOM | 2111 | N | GLY B | 56 | −6.039 | −17.281 | −27.853 | 1.00 | 40.78 | N |
| ATOM | 2112 | CA | GLY B | 56 | −5.726 | −16.270 | −26.848 | 1.00 | 37.86 | C |
| ATOM | 2113 | C | GLY B | 56 | −6.877 | −15.346 | −26.480 | 1.00 | 38.24 | C |
| ATOM | 2114 | O | GLY B | 56 | −6.659 | −14.374 | −25.752 | 1.00 | 38.67 | O |
| ATOM | 2115 | N | GLY B | 57 | −8.090 | −15.637 | −26.981 | 1.00 | 31.03 | N |
| ATOM | 2116 | CA | GLY B | 57 | −9.302 | −14.883 | −26.703 | 1.00 | 28.52 | C |
| ATOM | 2117 | C | GLY B | 57 | −9.656 | −15.020 | −25.241 | 1.00 | 31.10 | C |
| ATOM | 2118 | O | GLY B | 57 | −9.536 | −16.114 | −24.678 | 1.00 | 28.40 | O |
| ATOM | 2119 | N | THR B | 58 | −10.072 | −13.895 | −24.613 | 1.00 | 28.23 | N |
| ATOM | 2120 | CA | THR B | 58 | −10.389 | −13.811 | −23.200 | 1.00 | 26.58 | C |
| ATOM | 2121 | C | THR B | 58 | −11.786 | −13.282 | −22.912 | 1.00 | 30.91 | C |
| ATOM | 2122 | O | THR B | 58 | −12.406 | −12.673 | −23.770 | 1.00 | 31.83 | O |
| ATOM | 2123 | CB | THR B | 58 | −9.364 | −12.901 | −22.517 | 1.00 | 31.61 | C |
| ATOM | 2124 | OG1 | THR B | 58 | −9.346 | −11.669 | −23.230 | 1.00 | 30.30 | O |
| ATOM | 2125 | CG2 | THR B | 58 | −7.957 | −13.515 | −22.475 | 1.00 | 28.10 | C |
| ATOM | 2126 | N | ASN B | 59 | −12.259 | −13.515 | −21.670 | 1.00 | 27.24 | N |
| ATOM | 2127 | CA | ASN B | 59 | −13.546 | −13.046 | −21.121 | 1.00 | 27.12 | C |
| ATOM | 2128 | C | ASN B | 59 | −13.247 | −12.668 | −19.707 | 1.00 | 32.05 | C |
| ATOM | 2129 | O | ASN B | 59 | −12.548 | −13.401 | −19.025 | 1.00 | 31.81 | O |
| ATOM | 2130 | CB | ASN B | 59 | −14.634 | −14.134 | −21.128 | 1.00 | 26.68 | C |
| ATOM | 2131 | CG | ASN B | 59 | −15.313 | −14.297 | −22.466 | 1.00 | 57.47 | C |
| ATOM | 2132 | OD1 | ASN B | 59 | −15.751 | −13.321 | −23.082 | 1.00 | 48.94 | O |
| ATOM | 2133 | ND2 | ASN B | 59 | −15.438 | −15.533 | −22.954 | 1.00 | 54.06 | N |
| ATOM | 2134 | N | PHE B | 60 | −13.758 | −11.537 | −19.263 | 1.00 | 30.78 | N |
| ATOM | 2135 | CA | PHE B | 60 | −13.505 | −11.028 | −17.936 | 1.00 | 29.76 | C |
| ATOM | 2136 | C | PHE B | 60 | −14.745 | −10.676 | −17.185 | 1.00 | 36.25 | C |
| ATOM | 2137 | O | PHE B | 60 | −15.813 | −10.459 | −17.765 | 1.00 | 37.68 | O |
| ATOM | 2138 | CB | PHE B | 60 | −12.661 | −9.763 | −18.055 | 1.00 | 31.22 | C |
| ATOM | 2139 | CG | PHE B | 60 | −11.226 | −10.065 | −18.347 | 1.00 | 32.38 | C |
| ATOM | 2140 | CD1 | PHE B | 60 | −10.381 | −10.514 | −17.342 | 1.00 | 33.59 | C |
| ATOM | 2141 | CD2 | PHE B | 60 | −10.716 | −9.922 | −19.630 | 1.00 | 34.94 | C |
| ATOM | 2142 | CE1 | PHE B | 60 | −9.054 | −10.824 | −17.617 | 1.00 | 34.79 | C |
| ATOM | 2143 | CE2 | PHE B | 60 | −9.378 | −10.228 | −19.904 | 1.00 | 37.68 | C |
| ATOM | 2144 | CZ | PHE B | 60 | −8.552 | −10.653 | −18.889 | 1.00 | 35.37 | C |
| ATOM | 2145 | N | ASN B | 61 | −14.566 | −10.573 | −15.868 | 1.00 | 32.99 | N |
| ATOM | 2146 | CA | ASN B | 61 | −15.534 | −10.031 | −14.939 | 1.00 | 33.45 | C |
| ATOM | 2147 | C | ASN B | 61 | −15.225 | −8.504 | −14.997 | 1.00 | 39.25 | C |
| ATOM | 2148 | O | ASN B | 61 | −14.046 | −8.135 | −14.984 | 1.00 | 39.04 | O |
| ATOM | 2149 | CB | ASN B | 61 | −15.290 | −10.618 | −13.572 | 1.00 | 30.39 | C |
| ATOM | 2150 | CG | ASN B | 61 | −16.191 | −10.137 | −12.465 | 1.00 | 48.08 | C |
| ATOM | 2151 | OD1 | ASN B | 61 | −16.570 | −8.967 | −12.399 | 1.00 | 42.77 | O |
| ATOM | 2152 | ND2 | ASN B | 61 | −16.454 | −11.004 | −11.493 | 1.00 | 40.42 | N |
| ATOM | 2153 | N | GLU B | 62 | −16.245 | −7.633 | −15.142 | 1.00 | 36.84 | N |
| ATOM | 2154 | CA | GLU B | 62 | −16.002 | −6.182 | −15.284 | 1.00 | 37.31 | C |
| ATOM | 2155 | C | GLU B | 62 | −15.153 | −5.596 | −14.151 | 1.00 | 40.16 | C |
| ATOM | 2156 | O | GLU B | 62 | −14.367 | −4.697 | −14.407 | 1.00 | 39.82 | O |
| ATOM | 2157 | CB | GLU B | 62 | −17.310 | −5.382 | −15.467 | 1.00 | 39.32 | C |
| ATOM | 2158 | N | LYS B | 63 | −15.277 | −6.131 | −12.927 | 1.00 | 36.38 | N |
| ATOM | 2159 | CA | LYS B | 63 | −14.472 | −5.719 | −11.773 | 1.00 | 36.32 | C |
| ATOM | 2160 | C | LYS B | 63 | −12.931 | −5.957 | −12.007 | 1.00 | 41.33 | C |
| ATOM | 2161 | O | LYS B | 63 | −12.112 | −5.230 | −11.448 | 1.00 | 40.92 | O |
| ATOM | 2162 | CB | LYS B | 63 | −14.954 | −6.478 | −10.506 | 1.00 | 37.79 | C |
| ATOM | 2163 | CG | LYS B | 63 | −14.139 | −6.178 | −9.245 | 1.00 | 61.36 | C |
| ATOM | 2164 | CD | LYS B | 63 | −14.722 | −6.795 | −7.980 | 1.00 | 74.59 | C |
| ATOM | 2165 | CE | LYS B | 63 | −13.718 | −6.756 | −6.842 | 1.00 | 83.74 | C |
| ATOM | 2166 | NZ | LYS B | 63 | −14.275 | −7.291 | −5.570 | 1.00 | 90.12 | N |
| ATOM | 2167 | N | PHE B | 64 | −12.559 | −6.972 | −12.800 | 1.00 | 38.34 | N |
| ATOM | 2168 | CA | PHE B | 64 | −11.166 | −7.340 | −13.062 | 1.00 | 38.35 | C |
| ATOM | 2169 | C | PHE B | 64 | −10.696 | −7.093 | −14.503 | 1.00 | 44.69 | C |
| ATOM | 2170 | O | PHE B | 64 | −9.499 | −7.215 | −14.750 | 1.00 | 44.64 | O |
| ATOM | 2171 | CB | PHE B | 64 | −10.973 | −8.840 | −12.748 | 1.00 | 39.00 | C |
| ATOM | 2172 | CG | PHE B | 64 | −11.260 | −9.192 | −11.313 | 1.00 | 39.21 | C |
| ATOM | 2173 | CD1 | PHE B | 64 | −10.330 | −8.939 | −10.324 | 1.00 | 42.15 | C |
| ATOM | 2174 | CD2 | PHE B | 64 | −12.480 | −9.731 | −10.944 | 1.00 | 40.17 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2175 | CE1 | PHE B | 64 | −10.615 | −9.231 | −8.993 | 1.00 | 42.67 | C |
| ATOM | 2176 | CE2 | PHE B | 64 | −12.766 | −10.017 | −9.621 | 1.00 | 41.75 | C |
| ATOM | 2177 | CZ | PHE B | 64 | −11.839 | −9.765 | −8.650 | 1.00 | 40.28 | C |
| ATOM | 2178 | N | LYS B | 65 | −11.583 | −6.714 | −15.435 | 1.00 | 43.43 | N |
| ATOM | 2179 | CA | LYS B | 65 | −11.183 | −6.583 | −16.836 | 1.00 | 45.29 | C |
| ATOM | 2180 | C | LYS B | 65 | −10.078 | −5.560 | −17.112 | 1.00 | 52.96 | C |
| ATOM | 2181 | O | LYS B | 65 | −9.463 | −5.684 | −18.170 | 1.00 | 56.45 | O |
| ATOM | 2182 | CB | LYS B | 65 | −12.389 | −6.340 | −17.779 | 1.00 | 48.10 | C |
| ATOM | 2183 | CG | LYS B | 65 | −12.731 | −4.894 | −18.106 | 1.00 | 64.93 | C |
| ATOM | 2184 | CD | LYS B | 65 | −14.196 | −4.733 | −18.534 | 1.00 | 72.22 | C |
| ATOM | 2185 | CE | LYS B | 65 | −14.402 | −3.683 | −19.592 | 1.00 | 78.93 | C |
| ATOM | 2186 | NZ | LYS B | 65 | −15.755 | −3.086 | −19.491 | 1.00 | 88.22 | N |
| ATOM | 2187 | N | ASN B | 66 | −9.798 | −4.602 | −16.211 | 1.00 | 48.60 | N |
| ATOM | 2188 | CA | ASN B | 66 | −8.779 | −3.569 | −16.452 | 1.00 | 49.00 | C |
| ATOM | 2189 | C | ASN B | 66 | −7.510 | −3.694 | −15.593 | 1.00 | 51.00 | C |
| ATOM | 2190 | O | ASN B | 66 | −6.584 | −2.899 | −15.786 | 1.00 | 50.97 | O |
| ATOM | 2191 | CB | ASN B | 66 | −9.409 | −2.165 | −16.298 | 1.00 | 51.79 | C |
| ATOM | 2192 | CG | ASN B | 66 | −10.533 | −1.924 | −17.295 | 1.00 | 72.41 | C |
| ATOM | 2193 | OD1 | ASN B | 66 | −11.701 | −1.727 | −16.923 | 1.00 | 63.29 | O |
| ATOM | 2194 | ND2 | ASN B | 66 | −10.214 | −1.945 | −18.591 | 1.00 | 59.77 | N |
| ATOM | 2195 | N | ARG B | 67 | −7.441 | −4.681 | −14.675 | 1.00 | 44.57 | N |
| ATOM | 2196 | CA | ARG B | 67 | −6.241 | −4.911 | −13.857 | 1.00 | 41.63 | C |
| ATOM | 2197 | C | ARG B | 67 | −5.629 | −6.287 | −14.086 | 1.00 | 38.37 | C |
| ATOM | 2198 | O | ARG B | 67 | −4.511 | −6.502 | −13.630 | 1.00 | 36.06 | O |
| ATOM | 2199 | CB | ARG B | 67 | −6.553 | −4.704 | −12.367 | 1.00 | 42.52 | C |
| ATOM | 2200 | CG | ARG B | 67 | −6.361 | −3.262 | −11.876 | 1.00 | 50.51 | C |
| ATOM | 2201 | CD | ARG B | 67 | −6.258 | −3.180 | −10.354 | 1.00 | 53.54 | C |
| ATOM | 2202 | NE | ARG B | 67 | −7.292 | −3.984 | −9.679 | 1.00 | 46.11 | N |
| ATOM | 2203 | CZ | ARG B | 67 | −7.121 | −4.718 | −8.577 | 1.00 | 52.14 | C |
| ATOM | 2204 | NH1 | ARG B | 67 | −5.929 | −4.778 | −7.980 | 1.00 | 27.86 | N |
| ATOM | 2205 | NH2 | ARG B | 67 | −8.139 | −5.406 | −8.067 | 1.00 | 34.98 | N |
| ATOM | 2206 | N | VAL B | 68 | −6.325 | −7.202 | −14.809 | 1.00 | 32.59 | N |
| ATOM | 2207 | CA | VAL B | 68 | −5.864 | −8.575 | −15.048 | 1.00 | 30.74 | C |
| ATOM | 2208 | C | VAL B | 68 | −5.503 | −8.810 | −16.511 | 1.00 | 32.32 | C |
| ATOM | 2209 | O | VAL B | 68 | −6.242 | −8.408 | −17.413 | 1.00 | 30.44 | O |
| ATOM | 2210 | CB | VAL B | 68 | −6.906 | −9.626 | −14.562 | 1.00 | 33.96 | C |
| ATOM | 2211 | CG1 | VAL B | 68 | −6.408 | −11.047 | −14.793 | 1.00 | 33.56 | C |
| ATOM | 2212 | CG2 | VAL B | 68 | −7.207 | −9.442 | −13.085 | 1.00 | 33.63 | C |
| ATOM | 2213 | N | THR B | 69 | −4.373 | −9.508 | −16.726 | 1.00 | 28.68 | N |
| ATOM | 2214 | CA | THR B | 69 | −3.894 | −9.926 | −18.032 | 1.00 | 28.20 | C |
| ATOM | 2215 | C | THR B | 69 | −3.769 | −11.454 | −17.978 | 1.00 | 30.40 | C |
| ATOM | 2216 | O | THR B | 69 | −3.084 | −11.980 | −17.087 | 1.00 | 27.70 | O |
| ATOM | 2217 | CB | THR B | 69 | −2.560 | −9.244 | −18.370 | 1.00 | 34.59 | C |
| ATOM | 2218 | OG1 | THR B | 69 | −2.757 | −7.834 | −18.416 | 1.00 | 39.52 | O |
| ATOM | 2219 | CG2 | THR B | 69 | −1.973 | −9.729 | −19.697 | 1.00 | 29.63 | C |
| ATOM | 2220 | N | LEU B | 70 | −4.460 | −12.163 | −18.912 | 1.00 | 26.63 | N |
| ATOM | 2221 | CA | LEU B | 70 | −4.396 | −13.624 | −19.021 | 1.00 | 25.07 | C |
| ATOM | 2222 | C | LEU B | 70 | −3.575 | −13.970 | −20.274 | 1.00 | 31.13 | C |
| ATOM | 2223 | O | LEU B | 70 | −3.766 | −13.390 | −21.347 | 1.00 | 32.18 | O |
| ATOM | 2224 | CB | LEU B | 70 | −5.799 | −14.285 | −19.065 | 1.00 | 24.23 | C |
| ATOM | 2225 | CG | LEU B | 70 | −6.763 | −13.955 | −17.901 | 1.00 | 27.20 | C |
| ATOM | 2226 | CD1 | LEU B | 70 | −8.106 | −14.641 | −18.064 | 1.00 | 26.15 | C |
| ATOM | 2227 | CD2 | LEU B | 70 | −6.176 | −14.357 | −16.558 | 1.00 | 27.70 | C |
| ATOM | 2228 | N | THR B | 71 | −2.602 | −14.847 | −20.104 | 1.00 | 28.24 | N |
| ATOM | 2229 | CA | THR B | 71 | −1.753 | −15.335 | −21.167 | 1.00 | 29.59 | C |
| ATOM | 2230 | C | THR B | 71 | −1.578 | −16.845 | −20.995 | 1.00 | 37.78 | C |
| ATOM | 2231 | O | THR B | 71 | −1.741 | −17.378 | −19.897 | 1.00 | 37.44 | O |
| ATOM | 2232 | CB | THR B | 71 | −0.412 | −14.597 | −21.134 | 1.00 | 33.04 | C |
| ATOM | 2233 | OG1 | THR B | 71 | 0.145 | −14.682 | −19.817 | 1.00 | 27.77 | O |
| ATOM | 2234 | CG2 | THR B | 71 | −0.535 | −13.145 | −21.557 | 1.00 | 24.02 | C |
| ATOM | 2235 | N | THR B | 72 | −1.290 | −17.531 | −22.091 | 1.00 | 38.77 | N |
| ATOM | 2236 | CA | THR B | 72 | −1.022 | −18.969 | −22.120 | 1.00 | 39.84 | C |
| ATOM | 2237 | C | THR B | 72 | 0.261 | −19.187 | −22.915 | 1.00 | 47.81 | C |
| ATOM | 2238 | O | THR B | 72 | 0.513 | −18.472 | −23.886 | 1.00 | 47.88 | O |
| ATOM | 2239 | CB | THR B | 72 | −2.189 | −19.752 | −22.739 | 1.00 | 47.98 | C |
| ATOM | 2240 | OG1 | THR B | 72 | −2.613 | −19.131 | −23.958 | 1.00 | 55.44 | O |
| ATOM | 2241 | CG2 | THR B | 72 | −3.350 | −19.881 | −21.799 | 1.00 | 42.46 | C |
| ATOM | 2242 | N | ASP B | 73 | 1.099 | −20.127 | −22.453 | 1.00 | 46.98 | N |
| ATOM | 2243 | CA | ASP B | 73 | 2.339 | −20.537 | −23.106 | 1.00 | 47.12 | C |
| ATOM | 2244 | C | ASP B | 73 | 2.113 | −21.996 | −23.439 | 1.00 | 52.41 | C |
| ATOM | 2245 | O | ASP B | 73 | 2.240 | −22.852 | −22.574 | 1.00 | 51.96 | O |
| ATOM | 2246 | CB | ASP B | 73 | 3.541 | −20.323 | −22.165 | 1.00 | 48.64 | C |
| ATOM | 2247 | CG | ASP B | 73 | 4.906 | −20.723 | −22.705 | 1.00 | 59.18 | C |
| ATOM | 2248 | OD1 | ASP B | 73 | 5.060 | −20.792 | −23.945 | 1.00 | 61.02 | O |
| ATOM | 2249 | OD2 | ASP B | 73 | 5.844 | −20.875 | −21.889 | 1.00 | 61.82 | O |
| ATOM | 2250 | N | SER B | 74 | 1.653 | −22.264 | −24.659 | 1.00 | 52.29 | N |
| ATOM | 2251 | CA | SER B | 74 | 1.345 | −23.623 | −25.139 | 1.00 | 53.04 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2252 | C | SER B | 74 | 2.572 | −24.536 | −25.208 | 1.00 | 58.11 | C |
| ATOM | 2253 | O | SER B | 74 | 2.402 | −25.761 | −25.154 | 1.00 | 57.51 | O |
| ATOM | 2254 | CB | SER B | 74 | 0.679 | −23.564 | −26.505 | 1.00 | 56.63 | C |
| ATOM | 2255 | OG | SER B | 74 | 1.450 | −22.728 | −27.349 | 1.00 | 71.27 | O |
| ATOM | 2256 | N | SER B | 75 | 3.798 | −23.968 | −25.297 | 1.00 | 55.41 | N |
| ATOM | 2257 | CA | SER B | 75 | 5.005 | −24.792 | −25.303 | 1.00 | 56.04 | C |
| ATOM | 2258 | C | SER B | 75 | 5.099 | −25.495 | −23.959 | 1.00 | 60.69 | C |
| ATOM | 2259 | O | SER B | 75 | 5.082 | −26.735 | −23.935 | 1.00 | 62.94 | O |
| ATOM | 2260 | CB | SER B | 75 | 6.261 | −23.964 | −25.567 | 1.00 | 60.35 | C |
| ATOM | 2261 | OG | SER B | 75 | 6.473 | −22.946 | −24.607 | 1.00 | 70.66 | O |
| ATOM | 2262 | N | THR B | 76 | 5.073 | −24.707 | −22.839 | 1.00 | 52.74 | N |
| ATOM | 2263 | CA | THR B | 76 | 5.114 | −25.242 | −21.475 | 1.00 | 50.43 | C |
| ATOM | 2264 | C | THR B | 76 | 3.712 | −25.530 | −20.878 | 1.00 | 51.31 | C |
| ATOM | 2265 | O | THR B | 76 | 3.630 | −25.725 | −19.667 | 1.00 | 51.61 | O |
| ATOM | 2266 | CB | THR B | 76 | 5.948 | −24.310 | −20.545 | 1.00 | 57.63 | C |
| ATOM | 2267 | OG1 | THR B | 76 | 5.265 | −23.061 | −20.317 | 1.00 | 53.08 | O |
| ATOM | 2268 | CG2 | THR B | 76 | 7.367 | −24.083 | −21.073 | 1.00 | 56.74 | C |
| ATOM | 2269 | N | THR B | 77 | 2.634 | −25.629 | −21.709 | 1.00 | 44.75 | N |
| ATOM | 2270 | CA | THR B | 77 | 1.228 | −25.847 | −21.300 | 1.00 | 42.42 | C |
| ATOM | 2271 | C | THR B | 77 | 0.909 | −25.202 | −19.943 | 1.00 | 39.94 | C |
| ATOM | 2272 | O | THR B | 77 | 0.363 | −25.839 | −19.049 | 1.00 | 37.54 | O |
| ATOM | 2273 | CB | THR B | 77 | 0.861 | −27.327 | −21.357 | 1.00 | 51.97 | C |
| ATOM | 2274 | OG1 | THR B | 77 | 1.830 | −28.056 | −20.613 | 1.00 | 56.43 | O |
| ATOM | 2275 | CG2 | THR B | 77 | 0.777 | −27.852 | −22.779 | 1.00 | 46.43 | C |
| ATOM | 2276 | N | THR B | 78 | 1.295 | −23.930 | −19.804 | 1.00 | 33.54 | N |
| ATOM | 2277 | CA | THR B | 78 | 1.109 | −23.159 | −18.594 | 1.00 | 31.41 | C |
| ATOM | 2278 | C | THR B | 78 | 0.183 | −22.000 | −18.894 | 1.00 | 32.95 | C |
| ATOM | 2279 | O | THR B | 78 | 0.291 | −21.388 | −19.968 | 1.00 | 34.42 | O |
| ATOM | 2280 | CB | THR B | 78 | 2.481 | −22.712 | −18.073 | 1.00 | 37.05 | C |
| ATOM | 2281 | OG1 | THR B | 78 | 3.208 | −23.882 | −17.718 | 1.00 | 45.97 | O |
| ATOM | 2282 | CG2 | THR B | 78 | 2.404 | −21.839 | −16.848 | 1.00 | 30.64 | C |
| ATOM | 2283 | N | ALA B | 79 | −0.740 | −21.713 | −17.954 | 1.00 | 23.79 | N |
| ATOM | 2284 | CA | ALA B | 79 | −1.646 | −20.569 | −18.026 | 1.00 | 21.94 | C |
| ATOM | 2285 | C | ALA B | 79 | −1.138 | −19.566 | −17.001 | 1.00 | 25.21 | C |
| ATOM | 2286 | O | ALA B | 79 | −0.643 | −20.012 | −15.971 | 1.00 | 24.15 | O |
| ATOM | 2287 | CB | ALA B | 79 | −3.059 | −21.001 | −17.679 | 1.00 | 21.93 | C |
| ATOM | 2288 | N | TYR B | 80 | −1.198 | −18.241 | −17.274 | 1.00 | 22.57 | N |
| ATOM | 2289 | CA | TYR B | 80 | −0.748 | −17.224 | −16.317 | 1.00 | 23.23 | C |
| ATOM | 2290 | C | TYR B | 80 | −1.792 | −16.164 | −16.036 | 1.00 | 28.53 | C |
| ATOM | 2291 | O | TYR B | 80 | −2.572 | −15.804 | −16.915 | 1.00 | 27.88 | O |
| ATOM | 2292 | CB | TYR B | 80 | 0.507 | −16.496 | −16.798 | 1.00 | 26.15 | C |
| ATOM | 2293 | CG | TYR B | 80 | 1.672 | −17.395 | −17.132 | 1.00 | 27.36 | C |
| ATOM | 2294 | CD1 | TYR B | 80 | 1.860 | −17.868 | −18.422 | 1.00 | 29.95 | C |
| ATOM | 2295 | CD2 | TYR B | 80 | 2.646 | −17.683 | −16.185 | 1.00 | 28.07 | C |
| ATOM | 2296 | CE1 | TYR B | 80 | 2.964 | −18.646 | −18.753 | 1.00 | 34.56 | C |
| ATOM | 2297 | CE2 | TYR B | 80 | 3.744 | −18.484 | −16.495 | 1.00 | 29.78 | C |
| ATOM | 2298 | CZ | TYR B | 80 | 3.913 | −18.948 | −17.789 | 1.00 | 40.96 | C |
| ATOM | 2299 | OH | TYR B | 80 | 4.983 | −19.745 | −18.128 | 1.00 | 42.92 | O |
| ATOM | 2300 | N | MET B | 81 | −1.738 | −15.606 | −14.815 | 1.00 | 25.46 | N |
| ATOM | 2301 | CA | MET B | 81 | −2.649 | −14.583 | −14.348 | 1.00 | 25.73 | C |
| ATOM | 2302 | C | MET B | 81 | −1.839 | −13.452 | −13.697 | 1.00 | 29.74 | C |
| ATOM | 2303 | O | MET B | 81 | −1.261 | −13.641 | −12.630 | 1.00 | 29.57 | O |
| ATOM | 2304 | CB | MET B | 81 | −3.605 | −15.222 | −13.347 | 1.00 | 28.05 | C |
| ATOM | 2305 | CG | MET B | 81 | −4.859 | −14.447 | −13.096 | 1.00 | 33.11 | C |
| ATOM | 2306 | SD | MET B | 81 | −4.629 | −13.014 | −12.037 | 1.00 | 38.10 | S |
| ATOM | 2307 | CE | MET B | 81 | −4.276 | −13.817 | −10.451 | 1.00 | 33.49 | C |
| ATOM | 2308 | N | GLU B | 82 | −1.809 | −12.281 | −14.341 | 1.00 | 25.50 | N |
| ATOM | 2309 | CA | GLU B | 82 | −1.104 | −11.129 | −13.824 | 1.00 | 25.35 | C |
| ATOM | 2310 | C | GLU B | 82 | −2.103 | −10.126 | −13.261 | 1.00 | 29.53 | C |
| ATOM | 2311 | O | GLU B | 82 | −2.950 | −9.631 | −14.001 | 1.00 | 30.07 | O |
| ATOM | 2312 | CB | GLU B | 82 | −0.283 | −10.503 | −14.926 | 1.00 | 27.20 | C |
| ATOM | 2313 | CG | GLU B | 82 | 0.651 | −9.403 | −14.460 | 1.00 | 38.09 | C |
| ATOM | 2314 | CD | GLU B | 82 | 1.553 | −8.957 | −15.597 | 1.00 | 69.32 | C |
| ATOM | 2315 | OE1 | GLU B | 82 | 2.793 | −9.045 | −15.439 | 1.00 | 50.19 | O |
| ATOM | 2316 | OE2 | GLU B | 82 | 1.021 | −8.590 | −16.673 | 1.00 | 74.25 | O |
| ATOM | 2317 | N | LEU B | 83 | −2.038 | −9.858 | −11.959 | 1.00 | 24.95 | N |
| ATOM | 2318 | CA | LEU B | 83 | −2.905 | −8.883 | −11.322 | 1.00 | 25.06 | C |
| ATOM | 2319 | C | LEU B | 83 | −1.962 | −7.673 | −10.961 | 1.00 | 34.68 | C |
| ATOM | 2320 | O | LEU B | 83 | −0.946 | −7.867 | −10.275 | 1.00 | 35.67 | O |
| ATOM | 2321 | CB | LEU B | 83 | −3.592 | −9.512 | −10.096 | 1.00 | 23.02 | C |
| ATOM | 2322 | CG | LEU B | 83 | −4.535 | −8.625 | −9.266 | 1.00 | 25.55 | C |
| ATOM | 2323 | CD1 | LEU B | 83 | −5.604 | −7.965 | −10.111 | 1.00 | 25.85 | C |
| ATOM | 2324 | CD2 | LEU B | 83 | −5.247 | −9.444 | −8.206 | 1.00 | 24.76 | C |
| ATOM | 2325 | N | LYS B | 84 | −2.241 | −6.475 | −11.528 | 1.00 | 31.07 | N |
| ATOM | 2326 | CA | LYS B | 84 | −1.423 | −5.275 | −11.316 | 1.00 | 32.62 | C |
| ATOM | 2327 | C | LYS B | 84 | −2.048 | −4.308 | −10.311 | 1.00 | 37.70 | C |
| ATOM | 2328 | O | LYS B | 84 | −3.223 | −4.441 | −9.977 | 1.00 | 37.67 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2329 | CB | LYS B | 84 | −1.185 | −4.540 | −12.650 | 1.00 | 36.29 | C |
| ATOM | 2330 | CG | LYS B | 84 | −0.376 | −5.351 | −13.665 | 1.00 | 56.56 | C |
| ATOM | 2331 | CD | LYS B | 84 | 0.717 | −4.511 | −14.328 | 1.00 | 68.57 | C |
| ATOM | 2332 | CE | LYS B | 84 | 1.539 | −5.287 | −15.330 | 1.00 | 79.14 | C |
| ATOM | 2333 | NZ | LYS B | 84 | 0.851 | −5.438 | −16.647 | 1.00 | 84.98 | N |
| ATOM | 2334 | N | SER B | 85 | −1.249 | −3.342 | −9.815 | 1.00 | 34.82 | N |
| ATOM | 2335 | CA | SER B | 85 | −1.718 | −2.321 | −8.873 | 1.00 | 34.66 | C |
| ATOM | 2336 | C | SER B | 85 | −2.425 | −2.970 | −7.707 | 1.00 | 39.24 | C |
| ATOM | 2337 | O | SER B | 85 | −3.615 | −2.725 | −7.486 | 1.00 | 41.13 | O |
| ATOM | 2338 | CB | SER B | 85 | −2.638 | −1.325 | −9.582 | 1.00 | 37.40 | C |
| ATOM | 2339 | OG | SER B | 85 | −2.042 | −0.853 | −10.782 | 1.00 | 45.16 | O |
| ATOM | 2340 | N | LEU B | 86 | −1.706 | −3.822 | −6.975 | 1.00 | 34.83 | N |
| ATOM | 2341 | CA | LEU B | 86 | −2.312 | −4.579 | −5.880 | 1.00 | 34.33 | C |
| ATOM | 2342 | C | LEU B | 86 | −2.822 | −3.740 | −4.710 | 1.00 | 39.59 | C |
| ATOM | 2343 | O | LEU B | 86 | −2.095 | −2.929 | −4.150 | 1.00 | 40.25 | O |
| ATOM | 2344 | CB | LEU B | 86 | −1.362 | −5.663 | −5.360 | 1.00 | 34.01 | C |
| ATOM | 2345 | CG | LEU B | 86 | −1.220 | −6.893 | −6.246 | 1.00 | 37.63 | C |
| ATOM | 2346 | CD1 | LEU B | 86 | 0.028 | −7.650 | −5.889 | 1.00 | 37.07 | C |
| ATOM | 2347 | CD2 | LEU B | 86 | −2.436 | −7.802 | −6.139 | 1.00 | 39.07 | C |
| ATOM | 2348 | N | GLN B | 87 | −4.070 | −3.989 | −4.330 | 1.00 | 36.14 | N |
| ATOM | 2349 | CA | GLN B | 87 | −4.775 | −3.374 | −3.225 | 1.00 | 35.58 | C |
| ATOM | 2350 | C | GLN B | 87 | −4.818 | −4.369 | −2.047 | 1.00 | 40.55 | C |
| ATOM | 2351 | O | GLN B | 87 | −4.601 | −5.566 | −2.233 | 1.00 | 39.12 | O |
| ATOM | 2352 | CB | GLN B | 87 | −6.183 | −2.997 | −3.705 | 1.00 | 37.12 | C |
| ATOM | 2353 | CG | GLN B | 87 | −6.155 | −1.852 | −4.729 | 1.00 | 58.45 | C |
| ATOM | 2354 | CD | GLN B | 87 | −7.089 | −2.009 | −5.915 | 1.00 | 66.38 | C |
| ATOM | 2355 | OE1 | GLN B | 87 | −8.214 | −2.508 | −5.788 | 1.00 | 57.83 | O |
| ATOM | 2356 | NE2 | GLN B | 87 | −6.677 | −1.484 | −7.079 | 1.00 | 49.96 | N |
| ATOM | 2357 | N | PHE B | 88 | −5.071 | −3.884 | −0.835 | 1.00 | 39.90 | N |
| ATOM | 2358 | CA | PHE B | 88 | −5.116 | −4.749 | 0.351 | 1.00 | 40.38 | C |
| ATOM | 2359 | C | PHE B | 88 | −6.225 | −5.792 | 0.256 | 1.00 | 40.93 | C |
| ATOM | 2360 | O | PHE B | 88 | −6.041 | −6.904 | 0.730 | 1.00 | 40.30 | O |
| ATOM | 2361 | CB | PHE B | 88 | −5.287 | −3.923 | 1.640 | 1.00 | 43.98 | C |
| ATOM | 2362 | CG | PHE B | 88 | −4.087 | −3.062 | 1.994 | 1.00 | 47.37 | C |
| ATOM | 2363 | CD1 | PHE B | 88 | −2.911 | −3.637 | 2.472 | 1.00 | 50.61 | C |
| ATOM | 2364 | CD2 | PHE B | 88 | −4.123 | −1.681 | 1.819 | 1.00 | 49.87 | C |
| ATOM | 2365 | CE1 | PHE B | 88 | −1.810 | −2.842 | 2.810 | 1.00 | 51.44 | C |
| ATOM | 2366 | CE2 | PHE B | 88 | −3.012 | −0.893 | 2.140 | 1.00 | 53.16 | C |
| ATOM | 2367 | CZ | PHE B | 88 | −1.872 | −1.478 | 2.658 | 1.00 | 50.86 | C |
| ATOM | 2368 | N | ASP B | 89 | −7.345 | −5.457 | −0.397 | 1.00 | 36.23 | N |
| ATOM | 2369 | CA | ASP B | 89 | −8.463 | −6.389 | −0.576 | 1.00 | 35.34 | C |
| ATOM | 2370 | C | ASP B | 89 | −8.218 | −7.428 | −1.709 | 1.00 | 34.45 | C |
| ATOM | 2371 | O | ASP B | 89 | −9.103 | −8.220 | −1.987 | 1.00 | 32.80 | O |
| ATOM | 2372 | CB | ASP B | 89 | −9.810 | −5.645 | −0.746 | 1.00 | 38.54 | C |
| ATOM | 2373 | CG | ASP B | 89 | −9.928 | −4.658 | −1.898 | 1.00 | 60.29 | C |
| ATOM | 2374 | OD1 | ASP B | 89 | −8.915 | −4.446 | −2.614 | 1.00 | 60.92 | O |
| ATOM | 2375 | OD2 | ASP B | 89 | −11.031 | −4.070 | −2.066 | 1.00 | 72.65 | O |
| ATOM | 2376 | N | ASP B | 90 | −6.998 | −7.471 | −2.302 | 1.00 | 28.48 | N |
| ATOM | 2377 | CA | ASP B | 90 | −6.609 | −8.491 | −3.262 | 1.00 | 26.61 | C |
| ATOM | 2378 | C | ASP B | 90 | −5.999 | −9.689 | −2.541 | 1.00 | 27.35 | C |
| ATOM | 2379 | O | ASP B | 90 | −5.670 | −10.672 | −3.189 | 1.00 | 27.23 | O |
| ATOM | 2380 | CB | ASP B | 90 | −5.660 | −7.937 | −4.326 | 1.00 | 28.18 | C |
| ATOM | 2381 | CG | ASP B | 90 | −6.308 | −6.930 | −5.226 | 1.00 | 35.13 | C |
| ATOM | 2382 | OD1 | ASP B | 90 | −7.407 | −7.210 | −5.739 | 1.00 | 37.56 | O |
| ATOM | 2383 | OD2 | ASP B | 90 | −5.680 | −5.906 | −5.507 | 1.00 | 42.08 | O |
| ATOM | 2384 | N | THR B | 91 | −5.925 | −9.655 | −1.211 | 1.00 | 23.47 | N |
| ATOM | 2385 | CA | THR B | 91 | −5.467 | −10.791 | −0.431 | 1.00 | 23.54 | C |
| ATOM | 2386 | C | THR B | 91 | −6.519 | −11.880 | −0.581 | 1.00 | 27.84 | C |
| ATOM | 2387 | O | THR B | 91 | −7.698 | −11.632 | −0.291 | 1.00 | 28.31 | O |
| ATOM | 2388 | CB | THR B | 91 | −5.250 | −10.382 | 1.019 | 1.00 | 24.48 | C |
| ATOM | 2389 | OG1 | THR B | 91 | −4.204 | −9.411 | 1.038 | 1.00 | 29.00 | O |
| ATOM | 2390 | CG2 | THR B | 91 | −4.933 | −11.557 | 1.921 | 1.00 | 17.33 | C |
| ATOM | 2391 | N | ALA B | 92 | −6.106 | −13.062 | −1.079 | 1.00 | 22.75 | N |
| ATOM | 2392 | CA | ALA B | 92 | −7.035 | −14.168 | −1.368 | 1.00 | 21.04 | C |
| ATOM | 2393 | C | ALA B | 92 | −6.261 | −15.365 | −1.843 | 1.00 | 23.10 | C |
| ATOM | 2394 | O | ALA B | 92 | −5.061 | −15.253 | −2.077 | 1.00 | 21.91 | O |
| ATOM | 2395 | CB | ALA B | 92 | −7.981 | −13.745 | −2.497 | 1.00 | 21.05 | C |
| ATOM | 2396 | N | VAL B | 93 | −6.970 | −16.497 | −2.045 | 1.00 | 18.62 | N |
| ATOM | 2397 | CA | VAL B | 93 | −6.445 | −17.678 | −2.715 | 1.00 | 16.62 | C |
| ATOM | 2398 | C | VAL B | 93 | −6.963 | −17.550 | −4.151 | 1.00 | 22.21 | C |
| ATOM | 2399 | O | VAL B | 93 | −8.134 | −17.186 | −4.365 | 1.00 | 22.91 | O |
| ATOM | 2400 | CB | VAL B | 93 | −6.827 | −19.024 | −2.073 | 1.00 | 17.77 | C |
| ATOM | 2401 | CG1 | VAL B | 93 | −6.296 | −20.205 | −2.904 | 1.00 | 16.06 | C |
| ATOM | 2402 | CG2 | VAL B | 93 | −6.315 | −19.087 | −0.638 | 1.00 | 15.82 | C |
| ATOM | 2403 | N | TYR B | 94 | −6.043 | −17.698 | −5.124 | 1.00 | 18.75 | N |
| ATOM | 2404 | CA | TYR B | 94 | −6.326 | −17.624 | −6.546 | 1.00 | 18.17 | C |
| ATOM | 2405 | C | TYR B | 94 | −6.272 | −19.036 | −7.104 | 1.00 | 23.65 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2406 | O | TYR B | 94 | −5.300 | −19.758 | −6.862 | 1.00 | 22.37 | O |
| ATOM | 2407 | CB | TYR B | 94 | −5.332 | −16.697 | −7.255 | 1.00 | 18.20 | C |
| ATOM | 2408 | CG | TYR B | 94 | −5.574 | −15.252 | −6.875 | 1.00 | 18.69 | C |
| ATOM | 2409 | CD1 | TYR B | 94 | −5.202 | −14.769 | −5.629 | 1.00 | 19.64 | C |
| ATOM | 2410 | CD2 | TYR B | 94 | −6.274 | −14.397 | −7.719 | 1.00 | 19.24 | C |
| ATOM | 2411 | CE1 | TYR B | 94 | −5.421 | −13.439 | −5.277 | 1.00 | 19.98 | C |
| ATOM | 2412 | CE2 | TYR B | 94 | −6.579 | −13.096 | −7.339 | 1.00 | 19.19 | C |
| ATOM | 2413 | CZ | TYR B | 94 | −6.148 | −12.617 | −6.117 | 1.00 | 25.91 | C |
| ATOM | 2414 | OH | TYR B | 94 | −6.439 | −11.317 | −5.754 | 1.00 | 30.34 | O |
| ATOM | 2415 | N | TYR B | 95 | −7.340 | −19.449 | −7.806 | 1.00 | 22.24 | N |
| ATOM | 2416 | CA | TYR B | 95 | −7.402 | −20.768 | −8.437 | 1.00 | 23.26 | C |
| ATOM | 2417 | C | TYR B | 95 | −7.517 | −20.664 | −9.928 | 1.00 | 26.95 | C |
| ATOM | 2418 | O | TYR B | 95 | −8.349 | −19.907 | −10.378 | 1.00 | 27.42 | O |
| ATOM | 2419 | CB | TYR B | 95 | −8.654 | −21.532 | −7.988 | 1.00 | 24.01 | C |
| ATOM | 2420 | CG | TYR B | 95 | −8.698 | −21.846 | −6.514 | 1.00 | 23.66 | C |
| ATOM | 2421 | CD1 | TYR B | 95 | −8.120 | −23.006 | −6.016 | 1.00 | 23.60 | C |
| ATOM | 2422 | CD2 | TYR B | 95 | −9.426 | −21.044 | −5.630 | 1.00 | 23.46 | C |
| ATOM | 2423 | CE1 | TYR B | 95 | −8.203 | −23.333 | −4.668 | 1.00 | 21.26 | C |
| ATOM | 2424 | CE2 | TYR B | 95 | −9.548 | −21.382 | −4.288 | 1.00 | 23.69 | C |
| ATOM | 2425 | CZ | TYR B | 95 | −8.948 | −22.541 | −3.813 | 1.00 | 30.18 | C |
| ATOM | 2426 | OH | TYR B | 95 | −9.056 | −22.883 | −2.484 | 1.00 | 31.11 | O |
| ATOM | 2427 | N | CYS B | 96 | −6.803 | −21.510 | −10.680 | 1.00 | 24.20 | N |
| ATOM | 2428 | CA | CYS B | 96 | −7.031 | −21.700 | −12.091 | 1.00 | 25.10 | C |
| ATOM | 2429 | C | CYS B | 96 | −7.939 | −22.938 | −12.111 | 1.00 | 23.74 | C |
| ATOM | 2430 | O | CYS B | 96 | −7.815 | −23.805 | −11.239 | 1.00 | 21.39 | O |
| ATOM | 2431 | CB | CYS B | 96 | −5.747 | −21.952 | −12.873 | 1.00 | 28.22 | C |
| ATOM | 2432 | SG | CYS B | 96 | −4.864 | −23.416 | −12.326 | 1.00 | 34.05 | S |
| ATOM | 2433 | N | ALA B | 97 | −8.823 | −23.035 | −13.101 | 1.00 | 17.93 | N |
| ATOM | 2434 | CA | ALA B | 97 | −9.713 | −24.184 | −13.242 | 1.00 | 16.25 | C |
| ATOM | 2435 | C | ALA B | 97 | −9.977 | −24.421 | −14.734 | 1.00 | 19.86 | C |
| ATOM | 2436 | O | ALA B | 97 | −10.077 | −23.464 | −15.494 | 1.00 | 16.66 | O |
| ATOM | 2437 | CB | ALA B | 97 | −11.036 | −23.924 | −12.506 | 1.00 | 15.64 | C |
| ATOM | 2438 | N | ARG B | 98 | −10.120 | −25.682 | −15.153 | 1.00 | 20.21 | N |
| ATOM | 2439 | CA | ARG B | 98 | −10.403 | −25.965 | −16.563 | 1.00 | 21.73 | C |
| ATOM | 2440 | C | ARG B | 98 | −11.936 | −26.182 | −16.814 | 1.00 | 25.55 | C |
| ATOM | 2441 | O | ARG B | 98 | −12.660 | −26.668 | −15.947 | 1.00 | 23.39 | O |
| ATOM | 2442 | CB | ARG B | 98 | −9.550 | −27.140 | −17.072 | 1.00 | 22.09 | C |
| ATOM | 2443 | CG | ARG B | 98 | −10.117 | −28.501 | −16.759 | 1.00 | 28.30 | C |
| ATOM | 2444 | CD | ARG B | 98 | −9.391 | −29.598 | −17.487 | 1.00 | 32.03 | C |
| ATOM | 2445 | NE | ARG B | 98 | −10.211 | −30.804 | −17.480 | 1.00 | 30.30 | N |
| ATOM | 2446 | CZ | ARG B | 98 | −9.888 | −31.955 | −18.058 | 1.00 | 42.71 | C |
| ATOM | 2447 | NH1 | ARG B | 98 | −8.743 | −32.076 | −18.721 | 1.00 | 40.98 | N |
| ATOM | 2448 | NH2 | ARG B | 98 | −10.710 | −32.992 | −17.988 | 1.00 | 27.16 | N |
| ATOM | 2449 | N | ARG B | 99 | −12.391 | −25.793 | −18.002 | 1.00 | 21.75 | N |
| ATOM | 2450 | CA | ARG B | 99 | −13.750 | −25.983 | −18.455 | 1.00 | 22.15 | C |
| ATOM | 2451 | C | ARG B | 99 | −13.654 | −26.509 | −19.858 | 1.00 | 30.08 | C |
| ATOM | 2452 | O | ARG B | 99 | −12.875 | −25.973 | −20.664 | 1.00 | 29.74 | O |
| ATOM | 2453 | CB | ARG B | 99 | −14.532 | −24.665 | −18.496 | 1.00 | 19.21 | C |
| ATOM | 2454 | CG | ARG B | 99 | −16.042 | −24.912 | −18.412 | 1.00 | 25.13 | C |
| ATOM | 2455 | CD | ARG B | 99 | −16.818 | −23.953 | −19.281 | 1.00 | 32.60 | C |
| ATOM | 2456 | NE | ARG B | 99 | −16.887 | −24.406 | −20.661 | 1.00 | 35.32 | N |
| ATOM | 2457 | CZ | ARG B | 99 | −17.436 | −23.725 | −21.657 | 1.00 | 41.48 | C |
| ATOM | 2458 | NH1 | ARG B | 99 | −17.978 | −22.536 | −21.438 | 1.00 | 27.12 | N |
| ATOM | 2459 | NH2 | ARG B | 99 | −17.464 | −24.237 | −22.881 | 1.00 | 30.31 | N |
| ATOM | 2460 | N | ASP B | 100 | −14.436 | −27.549 | −20.174 | 1.00 | 28.06 | N |
| ATOM | 2461 | CA | ASP B | 100 | −14.420 | −28.094 | −21.529 | 1.00 | 27.86 | C |
| ATOM | 2462 | C | ASP B | 100 | −14.867 | −27.018 | −22.534 | 1.00 | 32.15 | C |
| ATOM | 2463 | O | ASP B | 100 | −15.908 | −26.368 | −22.358 | 1.00 | 29.17 | O |
| ATOM | 2464 | CB | ASP B | 100 | −15.299 | −29.326 | −21.615 | 1.00 | 29.04 | C |
| ATOM | 2465 | CG | ASP B | 100 | −15.096 | −30.156 | −22.858 | 1.00 | 33.97 | C |
| ATOM | 2466 | OD2 | ASP B | 100 | −14.966 | −29.576 | −23.943 | 1.00 | 36.35 | O |
| ATOM | 2467 | OD1 | ASP B | 100 | −15.046 | −31.388 | −22.735 | 1.00 | 36.50 | O |
| ATOM | 2468 | N | TYR B | 101 | −14.055 | −26.837 | −23.585 | 1.00 | 31.14 | N |
| ATOM | 2469 | CA | TYR B | 101 | −14.320 | −25.867 | −24.641 | 1.00 | 31.67 | C |
| ATOM | 2470 | C | TYR B | 101 | −15.529 | −26.299 | −25.445 | 1.00 | 34.26 | C |
| ATOM | 2471 | O | TYR B | 101 | −16.393 | −25.492 | −25.748 | 1.00 | 34.77 | O |
| ATOM | 2472 | CB | TYR B | 101 | −13.096 | −25.780 | −25.569 | 1.00 | 34.00 | C |
| ATOM | 2473 | CG | TYR B | 101 | −13.321 | −24.894 | −26.765 | 1.00 | 37.51 | C |
| ATOM | 2474 | CD1 | TYR B | 101 | −13.278 | −23.516 | −26.647 | 1.00 | 39.85 | C |
| ATOM | 2475 | CD2 | TYR B | 101 | −13.673 | −25.431 | −27.996 | 1.00 | 39.42 | C |
| ATOM | 2476 | CE1 | TYR B | 101 | −13.528 | −22.688 | −27.735 | 1.00 | 41.60 | C |
| ATOM | 2477 | CE2 | TYR B | 101 | −14.010 | −24.614 | −29.069 | 1.00 | 41.32 | C |
| ATOM | 2478 | CZ | TYR B | 101 | −13.898 | −23.238 | −28.949 | 1.00 | 48.16 | C |
| ATOM | 2479 | OH | TYR B | 101 | −14.144 | −22.398 | −30.019 | 1.00 | 49.85 | O |
| ATOM | 2480 | N | ARG B | 102 | −15.590 | −27.586 | −25.761 | 1.00 | 30.60 | N |
| ATOM | 2481 | CA | ARG B | 102 | −16.612 | −28.170 | −26.625 | 1.00 | 30.80 | C |
| ATOM | 2482 | C | ARG B | 102 | −18.035 | −28.113 | −26.033 | 1.00 | 33.54 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2483 | O | ARG B | 102 | −18.989 | −27.738 | −26.729 | 1.00 | 34.67 | O |
| ATOM | 2484 | CB | ARG B | 102 | −16.244 | −29.629 | −26.958 | 1.00 | 29.59 | C |
| ATOM | 2485 | CG | ARG B | 102 | −14.868 | −29.822 | −27.621 | 1.00 | 28.51 | C |
| ATOM | 2486 | CD | ARG B | 102 | −14.400 | −31.248 | −27.463 | 1.00 | 31.91 | C |
| ATOM | 2487 | NE | ARG B | 102 | −14.062 | −31.578 | −26.073 | 1.00 | 38.86 | N |
| ATOM | 2488 | CZ | ARG B | 102 | −13.807 | −32.805 | −25.624 | 1.00 | 48.31 | C |
| ATOM | 2489 | NH1 | ARG B | 102 | −13.829 | −33.844 | −26.452 | 1.00 | 37.53 | N |
| ATOM | 2490 | NH2 | ARG B | 102 | −13.519 | −33.004 | −24.338 | 1.00 | 32.95 | N |
| ATOM | 2491 | N | PHE B | 103 | −18.178 | −28.555 | −24.790 | 1.00 | 27.40 | N |
| ATOM | 2492 | CA | PHE B | 103 | −19.454 | −28.579 | −24.090 | 1.00 | 26.71 | C |
| ATOM | 2493 | C | PHE B | 103 | −19.231 | −28.259 | −22.594 | 1.00 | 32.79 | C |
| ATOM | 2494 | O | PHE B | 103 | −18.412 | −28.885 | −21.942 | 1.00 | 32.99 | O |
| ATOM | 2495 | CB | PHE B | 103 | −20.103 | −29.954 | −24.292 | 1.00 | 27.91 | C |
| ATOM | 2496 | CG | PHE B | 103 | −21.448 | −30.155 | −23.644 | 1.00 | 29.09 | C |
| ATOM | 2497 | CD1 | PHE B | 103 | −22.495 | −29.283 | −23.894 | 1.00 | 32.06 | C |
| ATOM | 2498 | CD2 | PHE B | 103 | −21.706 | −31.285 | −22.885 | 1.00 | 31.62 | C |
| ATOM | 2499 | CE1 | PHE B | 103 | −23.757 | −29.509 | −23.346 | 1.00 | 33.29 | C |
| ATOM | 2500 | CE2 | PHE B | 103 | −22.972 | −31.526 | −22.363 | 1.00 | 34.25 | C |
| ATOM | 2501 | CZ | PHE B | 103 | −23.989 | −30.635 | −22.589 | 1.00 | 32.66 | C |
| ATOM | 2502 | N | ASP B | 104 | −19.966 | −27.300 | −22.058 | 1.00 | 29.73 | N |
| ATOM | 2503 | CA | ASP B | 104 | −19.832 | −26.873 | −20.667 | 1.00 | 27.91 | C |
| ATOM | 2504 | C | ASP B | 104 | −20.394 | −27.877 | −19.647 | 1.00 | 31.89 | C |
| ATOM | 2505 | O | ASP B | 104 | −21.613 | −27.973 | −19.503 | 1.00 | 31.56 | O |
| ATOM | 2506 | CB | ASP B | 104 | −20.515 | −25.512 | −20.519 | 1.00 | 29.50 | C |
| ATOM | 2507 | CG | ASP B | 104 | −20.447 | −24.867 | −19.172 | 1.00 | 35.44 | C |
| ATOM | 2508 | OD1 | ASP B | 104 | −19.707 | −25.380 | −18.292 | 1.00 | 34.23 | O |
| ATOM | 2509 | OD2 | ASP B | 104 | −21.112 | −23.849 | −18.992 | 1.00 | 45.09 | O |
| ATOM | 2510 | N | MET B | 105 | −19.484 | −28.558 | −18.879 | 1.00 | 27.24 | N |
| ATOM | 2511 | CA | MET B | 105 | −19.825 | −29.532 | −17.830 | 1.00 | 25.58 | C |
| ATOM | 2512 | C | MET B | 105 | −19.143 | −29.090 | −16.504 | 1.00 | 26.27 | C |
| ATOM | 2513 | O | MET B | 105 | −18.721 | −29.924 | −15.693 | 1.00 | 25.24 | O |
| ATOM | 2514 | CB | MET B | 105 | −19.412 | −30.963 | −18.256 | 1.00 | 28.02 | C |
| ATOM | 2515 | CG | MET B | 105 | −20.163 | −31.474 | −19.487 | 1.00 | 33.53 | C |
| ATOM | 2516 | SD | MET B | 105 | −19.474 | −32.987 | −20.276 | 1.00 | 39.41 | S |
| ATOM | 2517 | CE | MET B | 105 | −20.577 | −34.120 | −19.847 | 1.00 | 36.36 | C |
| ATOM | 2518 | N | GLY B | 106 | −19.126 | −27.774 | −16.280 | 1.00 | 19.60 | N |
| ATOM | 2519 | CA | GLY B | 106 | −18.545 | −27.163 | −15.100 | 1.00 | 18.70 | C |
| ATOM | 2520 | C | GLY B | 106 | −17.024 | −27.127 | −15.055 | 1.00 | 24.56 | C |
| ATOM | 2521 | O | GLY B | 106 | −16.328 | −27.566 | −15.979 | 1.00 | 21.52 | O |
| ATOM | 2522 | N | PHE B | 107 | −16.506 | −26.578 | −13.945 | 1.00 | 25.70 | N |
| ATOM | 2523 | CA | PHE B | 107 | −15.068 | −26.509 | −13.651 | 1.00 | 24.87 | C |
| ATOM | 2524 | C | PHE B | 107 | −14.690 | −27.890 | −13.143 | 1.00 | 26.63 | C |
| ATOM | 2525 | O | PHE B | 107 | −14.710 | −28.103 | −11.951 | 1.00 | 23.65 | O |
| ATOM | 2526 | CB | PHE B | 107 | −14.773 | −25.423 | −12.592 | 1.00 | 25.92 | C |
| ATOM | 2527 | CG | PHE B | 107 | −15.106 | −24.032 | −13.059 | 1.00 | 29.76 | C |
| ATOM | 2528 | CD1 | PHE B | 107 | −14.742 | −23.595 | −14.326 | 1.00 | 36.17 | C |
| ATOM | 2529 | CD2 | PHE B | 107 | −15.770 | −23.145 | −12.234 | 1.00 | 33.24 | C |
| ATOM | 2530 | CE1 | PHE B | 107 | −15.082 | −22.308 | −14.761 | 1.00 | 37.70 | C |
| ATOM | 2531 | CE2 | PHE B | 107 | −16.139 | −21.877 | −12.693 | 1.00 | 36.04 | C |
| ATOM | 2532 | CZ | PHE B | 107 | −15.769 | −21.461 | −13.935 | 1.00 | 34.69 | C |
| ATOM | 2533 | N | ASP B | 108 | −14.423 | −28.840 | −14.049 | 1.00 | 24.51 | N |
| ATOM | 2534 | CA | ASP B | 108 | −14.165 | −30.230 | −13.658 | 1.00 | 24.68 | C |
| ATOM | 2535 | C | ASP B | 108 | −12.838 | −30.462 | −12.934 | 1.00 | 30.36 | C |
| ATOM | 2536 | O | ASP B | 108 | −12.718 | −31.468 | −12.228 | 1.00 | 29.91 | O |
| ATOM | 2537 | CB | ASP B | 108 | −14.297 | −31.183 | −14.854 | 1.00 | 27.03 | C |
| ATOM | 2538 | CG | ASP B | 108 | −13.306 | −31.000 | −15.972 | 1.00 | 41.87 | C |
| ATOM | 2539 | OD1 | ASP B | 108 | −12.650 | −29.948 | −16.013 | 1.00 | 42.86 | O |
| ATOM | 2540 | OD2 | ASP B | 108 | −13.247 | −31.877 | −16.866 | 1.00 | 49.98 | O |
| ATOM | 2541 | N | TYR B | 109 | −11.851 | −29.572 | −13.094 | 1.00 | 26.41 | N |
| ATOM | 2542 | CA | TYR B | 109 | −10.594 | −29.730 | −12.387 | 1.00 | 26.21 | C |
| ATOM | 2543 | C | TYR B | 109 | −10.029 | −28.349 | −12.045 | 1.00 | 25.85 | C |
| ATOM | 2544 | O | TYR B | 109 | −10.044 | −27.460 | −12.889 | 1.00 | 24.25 | O |
| ATOM | 2545 | CB | TYR B | 109 | −9.599 | −30.644 | −13.133 | 1.00 | 29.88 | C |
| ATOM | 2546 | CG | TYR B | 109 | −8.466 | −31.127 | −12.236 | 1.00 | 36.71 | C |
| ATOM | 2547 | CD1 | TYR B | 109 | −7.441 | −30.268 | −11.848 | 1.00 | 39.20 | C |
| ATOM | 2548 | CD2 | TYR B | 109 | −8.418 | −32.443 | −11.776 | 1.00 | 38.96 | C |
| ATOM | 2549 | CE1 | TYR B | 109 | −6.412 | −30.692 | −11.001 | 1.00 | 40.16 | C |
| ATOM | 2550 | CE2 | TYR B | 109 | −7.382 | −32.883 | −10.934 | 1.00 | 39.84 | C |
| ATOM | 2551 | CZ | TYR B | 109 | −6.374 | −32.002 | −10.561 | 1.00 | 46.78 | C |
| ATOM | 2552 | OH | TYR B | 109 | −5.313 | −32.372 | −9.768 | 1.00 | 48.82 | O |
| ATOM | 2553 | N | TRP B | 110 | −9.574 | −28.181 | −10.757 | 1.00 | 19.49 | N |
| ATOM | 2554 | CA | TRP B | 110 | −9.007 | −26.957 | −10.196 | 1.00 | 16.54 | C |
| ATOM | 2555 | C | TRP B | 110 | −7.569 | −27.167 | −9.759 | 1.00 | 22.00 | C |
| ATOM | 2556 | O | TRP B | 110 | −7.197 | −28.250 | −9.323 | 1.00 | 23.38 | O |
| ATOM | 2557 | CB | TRP B | 110 | −9.819 | −26.529 | −8.967 | 1.00 | 13.54 | C |
| ATOM | 2558 | CG | TRP B | 110 | −11.263 | −26.212 | −9.219 | 1.00 | 13.58 | C |
| ATOM | 2559 | CD1 | TRP B | 110 | −12.232 | −27.052 | −9.698 | 1.00 | 16.42 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2560 | CD2 | TRP B | 110 | −11.911 | −24.975 | −8.934 | 1.00 | 13.60 | C |
| ATOM | 2561 | NE1 | TRP B | 110 | −13.457 | −26.431 | −9.653 | 1.00 | 15.18 | N |
| ATOM | 2562 | CE2 | TRP B | 110 | −13.277 | −25.132 | −9.247 | 1.00 | 16.85 | C |
| ATOM | 2563 | CE3 | TRP B | 110 | −11.473 | −23.746 | −8.418 | 1.00 | 15.33 | C |
| ATOM | 2564 | CZ2 | TRP B | 110 | −14.194 | −24.094 | −9.097 | 1.00 | 16.97 | C |
| ATOM | 2565 | CZ3 | TRP B | 110 | −12.372 | −22.703 | −8.325 | 1.00 | 17.32 | C |
| ATOM | 2566 | CH2 | TRP B | 110 | −13.723 | −22.886 | −8.642 | 1.00 | 18.09 | C |
| ATOM | 2567 | N | GLY B | 111 | −6.777 | −26.106 | −9.803 | 1.00 | 19.09 | N |
| ATOM | 2568 | CA | GLY B | 111 | −5.415 | −26.136 | −9.286 | 1.00 | 17.96 | C |
| ATOM | 2569 | C | GLY B | 111 | −5.503 | −26.107 | −7.767 | 1.00 | 20.16 | C |
| ATOM | 2570 | O | GLY B | 111 | −6.612 | −25.990 | −7.232 | 1.00 | 18.93 | O |
| ATOM | 2571 | N | GLN B | 112 | −4.364 | −26.241 | −7.044 | 1.00 | 16.35 | N |
| ATOM | 2572 | CA | GLN B | 112 | −4.417 | −26.314 | −5.567 | 1.00 | 16.28 | C |
| ATOM | 2573 | C | GLN B | 112 | −4.674 | −24.991 | −4.850 | 1.00 | 20.57 | C |
| ATOM | 2574 | O | GLN B | 112 | −4.957 | −25.020 | −3.663 | 1.00 | 21.92 | O |
| ATOM | 2575 | CB | GLN B | 112 | −3.163 | −26.994 | −4.967 | 1.00 | 17.39 | C |
| ATOM | 2576 | CG | GLN B | 112 | −1.874 | −26.156 | −4.821 | 1.00 | 18.10 | C |
| ATOM | 2577 | CD | GLN B | 112 | −1.089 | −26.024 | −6.099 | 1.00 | 24.99 | C |
| ATOM | 2578 | OE1 | GLN B | 112 | −1.630 | −26.150 | −7.188 | 1.00 | 21.88 | O |
| ATOM | 2579 | NE2 | GLN B | 112 | 0.198 | −25.677 | −6.002 | 1.00 | 22.03 | N |
| ATOM | 2580 | N | GLY B | 113 | −4.542 | −23.868 | −5.538 | 1.00 | 15.82 | N |
| ATOM | 2581 | CA | GLY B | 113 | −4.694 | −22.556 | −4.935 | 1.00 | 14.88 | C |
| ATOM | 2582 | C | GLY B | 113 | −3.344 | −21.878 | −4.778 | 1.00 | 20.21 | C |
| ATOM | 2583 | O | GLY B | 113 | −2.321 | −22.549 | −4.579 | 1.00 | 18.95 | O |
| ATOM | 2584 | N | THR B | 114 | −3.325 | −20.552 | −4.932 | 1.00 | 18.60 | N |
| ATOM | 2585 | CA | THR B | 114 | −2.138 | −19.734 | −4.722 | 1.00 | 20.62 | C |
| ATOM | 2586 | C | THR B | 114 | −2.548 | −18.600 | −3.788 | 1.00 | 28.23 | C |
| ATOM | 2587 | O | THR B | 114 | −3.331 | −17.731 | −4.179 | 1.00 | 27.74 | O |
| ATOM | 2588 | CB | THR B | 114 | −1.548 | −19.181 | −6.031 | 1.00 | 22.85 | C |
| ATOM | 2589 | OG1 | THR B | 114 | −1.160 | −20.282 | −6.853 | 1.00 | 22.17 | O |
| ATOM | 2590 | CG2 | THR B | 114 | −0.333 | −18.286 | −5.780 | 1.00 | 16.74 | C |
| ATOM | 2591 | N | THR B | 115 | −1.994 | −18.597 | −2.577 | 1.00 | 25.38 | N |
| ATOM | 2592 | CA | THR B | 115 | −2.275 | −17.562 | −1.600 | 1.00 | 25.21 | C |
| ATOM | 2593 | C | THR B | 115 | −1.449 | −16.334 | −1.979 | 1.00 | 28.36 | C |
| ATOM | 2594 | O | THR B | 115 | −0.233 | −16.461 | −2.145 | 1.00 | 26.97 | O |
| ATOM | 2595 | CB | THR B | 115 | −1.933 | −18.074 | −0.173 | 1.00 | 28.81 | C |
| ATOM | 2596 | OG1 | THR B | 115 | −2.788 | −19.175 | 0.154 | 1.00 | 28.05 | O |
| ATOM | 2597 | CG2 | THR B | 115 | −2.049 | −16.979 | 0.897 | 1.00 | 22.97 | C |
| ATOM | 2598 | N | VAL B | 116 | −2.112 | −15.167 | −2.160 | 1.00 | 24.10 | N |
| ATOM | 2599 | CA | VAL B | 116 | −1.446 | −13.893 | −2.424 | 1.00 | 23.73 | C |
| ATOM | 2600 | C | VAL B | 116 | −1.814 | −13.016 | −1.234 | 1.00 | 26.83 | C |
| ATOM | 2601 | O | VAL B | 116 | −2.987 | −12.924 | −0.896 | 1.00 | 25.67 | O |
| ATOM | 2602 | CB | VAL B | 116 | −1.847 | −13.224 | −3.766 | 1.00 | 27.78 | C |
| ATOM | 2603 | CG1 | VAL B | 116 | −1.039 | −11.938 | −4.007 | 1.00 | 26.88 | C |
| ATOM | 2604 | CG2 | VAL B | 116 | −1.688 | −14.190 | −4.943 | 1.00 | 27.29 | C |
| ATOM | 2605 | N | THR B | 117 | −0.818 | −12.436 | −0.550 | 1.00 | 24.91 | N |
| ATOM | 2606 | CA | THR B | 117 | −1.047 | −11.559 | 0.606 | 1.00 | 23.78 | C |
| ATOM | 2607 | C | THR B | 117 | −0.519 | −10.196 | 0.245 | 1.00 | 27.63 | C |
| ATOM | 2608 | O | THR B | 117 | 0.644 | −10.089 | −0.131 | 1.00 | 27.64 | O |
| ATOM | 2609 | CB | THR B | 117 | −0.359 | −12.123 | 1.837 | 1.00 | 29.81 | C |
| ATOM | 2610 | OG1 | THR B | 117 | −0.922 | −13.410 | 2.134 | 1.00 | 33.58 | O |
| ATOM | 2611 | CG2 | THR B | 117 | −0.499 | −11.215 | 3.051 | 1.00 | 29.06 | C |
| ATOM | 2612 | N | VAL B | 118 | −1.371 | −9.168 | 0.284 | 1.00 | 26.06 | N |
| ATOM | 2613 | CA | VAL B | 118 | −0.949 | −7.800 | −0.009 | 1.00 | 27.70 | C |
| ATOM | 2614 | C | VAL B | 118 | −0.686 | −7.118 | 1.312 | 1.00 | 33.29 | C |
| ATOM | 2615 | O | VAL B | 118 | −1.580 | −7.050 | 2.160 | 1.00 | 32.29 | O |
| ATOM | 2616 | CB | VAL B | 118 | −1.961 | −7.058 | −0.895 | 1.00 | 32.17 | C |
| ATOM | 2617 | CG1 | VAL B | 118 | −1.470 | −5.644 | −1.198 | 1.00 | 32.77 | C |
| ATOM | 2618 | CG2 | VAL B | 118 | −2.184 | −7.840 | −2.186 | 1.00 | 31.83 | C |
| ATOM | 2619 | N | SER B | 119 | 0.573 | −6.724 | 1.546 | 1.00 | 31.91 | N |
| ATOM | 2620 | CA | SER B | 119 | 0.955 | −6.115 | 2.820 | 1.00 | 32.11 | C |
| ATOM | 2621 | C | SER B | 119 | 2.208 | −5.268 | 2.709 | 1.00 | 39.10 | C |
| ATOM | 2622 | O | SER B | 119 | 3.223 | −5.715 | 2.160 | 1.00 | 39.86 | O |
| ATOM | 2623 | CB | SER B | 119 | 1.230 | −7.191 | 3.863 | 1.00 | 34.14 | C |
| ATOM | 2624 | OG | SER B | 119 | 1.549 | −6.626 | 5.128 | 1.00 | 43.94 | O |
| ATOM | 2625 | N | SER B | 120 | 2.170 | −4.104 | 3.368 | 1.00 | 34.85 | N |
| ATOM | 2626 | CA | SER B | 120 | 3.317 | −3.210 | 3.494 | 1.00 | 34.48 | C |
| ATOM | 2627 | C | SER B | 120 | 4.311 | −3.736 | 4.587 | 1.00 | 37.65 | C |
| ATOM | 2628 | O | SER B | 120 | 5.401 | −3.183 | 4.709 | 1.00 | 38.37 | O |
| ATOM | 2629 | CB | SER B | 120 | 2.844 | −1.802 | 3.839 | 1.00 | 36.78 | C |
| ATOM | 2630 | OG | SER B | 120 | 1.958 | −1.869 | 4.945 | 1.00 | 49.93 | O |
| ATOM | 2631 | N | ALA B | 121 | 3.950 | −4.802 | 5.361 | 1.00 | 32.19 | N |
| ATOM | 2632 | CA | ALA B | 121 | 4.833 | −5.392 | 6.379 | 1.00 | 31.26 | C |
| ATOM | 2633 | C | ALA B | 121 | 6.009 | −6.185 | 5.796 | 1.00 | 36.12 | C |
| ATOM | 2634 | O | ALA B | 121 | 5.958 | −6.710 | 4.677 | 1.00 | 35.66 | O |
| ATOM | 2635 | CB | ALA B | 121 | 4.030 | −6.306 | 7.305 | 1.00 | 31.02 | C |
| ATOM | 2636 | N | SER B | 122 | 7.055 | −6.324 | 6.611 | 1.00 | 34.00 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2637 | CA | SER B | 122 | 8.244 | −7.107 | 6.278 | 1.00 | 34.09 | C |
| ATOM | 2638 | C | SER B | 122 | 8.343 | −8.209 | 7.322 | 1.00 | 35.57 | C |
| ATOM | 2639 | O | SER B | 122 | 7.632 | −8.138 | 8.328 | 1.00 | 34.38 | O |
| ATOM | 2640 | CB | SER B | 122 | 9.492 | −6.224 | 6.247 | 1.00 | 40.77 | C |
| ATOM | 2641 | OG | SER B | 122 | 9.408 | −5.144 | 7.166 | 1.00 | 58.00 | O |
| ATOM | 2642 | N | THR B | 123 | 9.177 | −9.253 | 7.077 | 1.00 | 31.42 | N |
| ATOM | 2643 | CA | THR B | 123 | 9.314 | −10.365 | 8.025 | 1.00 | 30.37 | C |
| ATOM | 2644 | C | THR B | 123 | 9.560 | −9.868 | 9.455 | 1.00 | 34.36 | C |
| ATOM | 2645 | O | THR B | 123 | 10.400 | −8.999 | 9.670 | 1.00 | 34.79 | O |
| ATOM | 2646 | CB | THR B | 123 | 10.354 | −11.386 | 7.566 | 1.00 | 32.74 | C |
| ATOM | 2647 | OG1 | THR B | 123 | 9.898 | −11.935 | 6.344 | 1.00 | 36.94 | O |
| ATOM | 2648 | CG2 | THR B | 123 | 10.528 | −12.541 | 8.544 | 1.00 | 28.08 | C |
| ATOM | 2649 | N | LYS B | 124 | 8.781 | −10.388 | 10.412 | 1.00 | 30.13 | N |
| ATOM | 2650 | CA | LYS B | 124 | 8.884 | −10.018 | 11.826 | 1.00 | 29.03 | C |
| ATOM | 2651 | C | LYS B | 124 | 8.455 | −11.192 | 12.693 | 1.00 | 31.85 | C |
| ATOM | 2652 | O | LYS B | 124 | 7.415 | −11.796 | 12.443 | 1.00 | 29.29 | O |
| ATOM | 2653 | CB | LYS B | 124 | 8.000 | −8.798 | 12.143 | 1.00 | 29.80 | C |
| ATOM | 2654 | CG | LYS B | 124 | 8.135 | −8.329 | 13.588 | 1.00 | 41.38 | C |
| ATOM | 2655 | CD | LYS B | 124 | 7.743 | −6.866 | 13.784 | 1.00 | 49.53 | C |
| ATOM | 2656 | CE | LYS B | 124 | 7.091 | −6.609 | 15.118 | 1.00 | 62.98 | C |
| ATOM | 2657 | NZ | LYS B | 124 | 7.895 | −7.109 | 16.262 | 1.00 | 78.30 | N |
| ATOM | 2658 | N | GLY B | 125 | 9.247 | −11.469 | 13.714 | 1.00 | 30.95 | N |
| ATOM | 2659 | CA | GLY B | 125 | 8.989 | −12.532 | 14.673 | 1.00 | 31.41 | C |
| ATOM | 2660 | C | GLY B | 125 | 8.012 | −12.089 | 15.743 | 1.00 | 35.64 | C |
| ATOM | 2661 | O | GLY B | 125 | 7.943 | −10.890 | 16.065 | 1.00 | 35.41 | O |
| ATOM | 2662 | N | PRO B | 126 | 7.205 | −13.028 | 16.292 | 1.00 | 31.20 | N |
| ATOM | 2663 | CA | PRO B | 126 | 6.240 | −12.624 | 17.322 | 1.00 | 31.29 | C |
| ATOM | 2664 | C | PRO B | 126 | 6.886 | −12.388 | 18.689 | 1.00 | 36.68 | C |
| ATOM | 2665 | O | PRO B | 126 | 8.013 | −12.799 | 18.982 | 1.00 | 36.65 | O |
| ATOM | 2666 | CB | PRO B | 126 | 5.285 | −13.831 | 17.413 | 1.00 | 32.62 | C |
| ATOM | 2667 | CG | PRO B | 126 | 6.162 | −15.012 | 17.060 | 1.00 | 36.75 | C |
| ATOM | 2668 | CD | PRO B | 126 | 7.161 | −14.488 | 16.041 | 1.00 | 32.21 | C |
| ATOM | 2669 | N | SER B | 127 | 6.113 | −11.739 | 19.531 | 1.00 | 32.88 | N |
| ATOM | 2670 | CA | SER B | 127 | 6.376 | −11.558 | 20.934 | 1.00 | 32.44 | C |
| ATOM | 2671 | C | SER B | 127 | 5.396 | −12.604 | 21.521 | 1.00 | 31.89 | C |
| ATOM | 2672 | O | SER B | 127 | 4.332 | −12.840 | 20.931 | 1.00 | 28.69 | O |
| ATOM | 2673 | CB | SER B | 127 | 6.024 | −10.132 | 21.352 | 1.00 | 36.80 | C |
| ATOM | 2674 | OG | SER B | 127 | 6.671 | −9.185 | 20.515 | 1.00 | 43.15 | O |
| ATOM | 2675 | N | VAL B | 128 | 5.790 | −13.305 | 22.582 | 1.00 | 27.31 | N |
| ATOM | 2676 | CA | VAL B | 128 | 4.930 | −14.339 | 23.158 | 1.00 | 26.37 | C |
| ATOM | 2677 | C | VAL B | 128 | 4.596 | −13.931 | 24.602 | 1.00 | 31.69 | C |
| ATOM | 2678 | O | VAL B | 128 | 5.490 | −13.703 | 25.396 | 1.00 | 32.87 | O |
| ATOM | 2679 | CB | VAL B | 128 | 5.565 | −15.740 | 23.028 | 1.00 | 28.37 | C |
| ATOM | 2680 | CG1 | VAL B | 128 | 4.620 | −16.822 | 23.555 | 1.00 | 27.01 | C |
| ATOM | 2681 | CG2 | VAL B | 128 | 5.944 | −16.008 | 21.567 | 1.00 | 27.67 | C |
| ATOM | 2682 | N | PHE B | 129 | 3.309 | −13.775 | 24.906 | 1.00 | 27.55 | N |
| ATOM | 2683 | CA | PHE B | 129 | 2.840 | −13.338 | 26.216 | 1.00 | 26.74 | C |
| ATOM | 2684 | C | PHE B | 129 | 1.996 | −14.405 | 26.871 | 1.00 | 29.95 | C |
| ATOM | 2685 | O | PHE B | 129 | 1.181 | −15.001 | 26.198 | 1.00 | 29.92 | O |
| ATOM | 2686 | CB | PHE B | 129 | 2.020 | −12.067 | 26.055 | 1.00 | 27.08 | C |
| ATOM | 2687 | CG | PHE B | 129 | 2.767 | −10.978 | 25.336 | 1.00 | 28.02 | C |
| ATOM | 2688 | CD1 | PHE B | 129 | 3.997 | −10.529 | 25.805 | 1.00 | 31.83 | C |
| ATOM | 2689 | CD2 | PHE B | 129 | 2.208 | −10.341 | 24.238 | 1.00 | 28.81 | C |
| ATOM | 2690 | CE1 | PHE B | 129 | 4.644 | −9.457 | 25.194 | 1.00 | 33.54 | C |
| ATOM | 2691 | CE2 | PHE B | 129 | 2.857 | −9.267 | 23.627 | 1.00 | 31.99 | C |
| ATOM | 2692 | CZ | PHE B | 129 | 4.078 | −8.844 | 24.091 | 1.00 | 31.18 | C |
| ATOM | 2693 | N | PRO B | 130 | 2.132 | −14.659 | 28.175 | 1.00 | 27.95 | N |
| ATOM | 2694 | CA | PRO B | 130 | 1.279 | −15.686 | 28.794 | 1.00 | 27.70 | C |
| ATOM | 2695 | C | PRO B | 130 | −0.148 | −15.189 | 29.027 | 1.00 | 30.64 | C |
| ATOM | 2696 | O | PRO B | 130 | −0.376 | −13.998 | 29.232 | 1.00 | 29.40 | O |
| ATOM | 2697 | CB | PRO B | 130 | 1.988 | −15.983 | 30.114 | 1.00 | 29.61 | C |
| ATOM | 2698 | CG | PRO B | 130 | 2.674 | −14.702 | 30.465 | 1.00 | 34.14 | C |
| ATOM | 2699 | CD | PRO B | 130 | 3.005 | −14.001 | 29.174 | 1.00 | 29.79 | C |
| ATOM | 2700 | N | LEU B | 131 | −1.100 | −16.111 | 28.960 | 1.00 | 27.71 | N |
| ATOM | 2701 | CA | LEU B | 131 | −2.513 | −15.857 | 29.237 | 1.00 | 27.00 | C |
| ATOM | 2702 | C | LEU B | 131 | −2.834 | −16.707 | 30.459 | 1.00 | 31.90 | C |
| ATOM | 2703 | O | LEU B | 131 | −2.919 | −17.939 | 30.376 | 1.00 | 30.45 | O |
| ATOM | 2704 | CB | LEU B | 131 | −3.421 | −16.234 | 28.059 | 1.00 | 25.45 | C |
| ATOM | 2705 | CG | LEU B | 131 | −3.261 | −15.413 | 26.769 | 1.00 | 26.82 | C |
| ATOM | 2706 | CD1 | LEU B | 131 | −4.053 | −16.056 | 25.637 | 1.00 | 24.13 | C |
| ATOM | 2707 | CD2 | LEU B | 131 | −3.725 | −14.005 | 26.974 | 1.00 | 27.41 | C |
| ATOM | 2708 | N | ALA B | 132 | −2.906 | −16.044 | 31.603 | 1.00 | 29.58 | N |
| ATOM | 2709 | CA | ALA B | 132 | −3.159 | −16.686 | 32.886 | 1.00 | 30.56 | C |
| ATOM | 2710 | C | ALA B | 132 | −4.235 | −15.887 | 33.653 | 1.00 | 35.82 | C |
| ATOM | 2711 | O | ALA B | 132 | −4.257 | −14.640 | 33.571 | 1.00 | 34.51 | O |
| ATOM | 2712 | CB | ALA B | 132 | −1.860 | −16.750 | 33.695 | 1.00 | 31.30 | C |
| ATOM | 2713 | N | PRO B | 133 | −5.156 | −16.588 | 34.353 | 1.00 | 33.07 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2714 | CA | PRO B | 133 | −6.195 | −15.875 | 35.134 | 1.00 | 34.03 | C |
| ATOM | 2715 | C | PRO B | 133 | −5.685 | −14.899 | 36.211 | 1.00 | 41.24 | C |
| ATOM | 2716 | O | PRO B | 133 | −4.562 | −15.043 | 36.719 | 1.00 | 41.46 | O |
| ATOM | 2717 | CB | PRO B | 133 | −6.977 | −17.015 | 35.802 | 1.00 | 35.67 | C |
| ATOM | 2718 | CG | PRO B | 133 | −6.034 | −18.179 | 35.810 | 1.00 | 39.58 | C |
| ATOM | 2719 | CD | PRO B | 133 | −5.243 | −18.049 | 34.550 | 1.00 | 34.19 | C |
| ATOM | 2720 | N | CYS B | 134 | −6.543 | −13.927 | 36.578 | 1.00 | 38.82 | N |
| ATOM | 2721 | CA | CYS B | 134 | −6.257 | −12.907 | 37.588 | 1.00 | 77.23 | C |
| ATOM | 2722 | C | CYS B | 134 | −6.464 | −13.492 | 38.990 | 1.00 | 88.64 | C |
| ATOM | 2723 | O | CYS B | 134 | −5.810 | −14.461 | 39.373 | 1.00 | 52.37 | O |
| ATOM | 2724 | CB | CYS B | 134 | −7.140 | −11.679 | 37.361 | 1.00 | 78.04 | C |
| ATOM | 2725 | SG | CYS B | 134 | −7.051 | −10.438 | 38.680 | 1.00 | 83.30 | S |
| ATOM | 2726 | N | GLU B | 140 | −14.136 | −23.795 | 40.927 | 1.00 | 57.83 | N |
| ATOM | 2727 | CA | GLU B | 140 | −14.070 | −23.996 | 39.461 | 1.00 | 56.17 | C |
| ATOM | 2728 | C | GLU B | 140 | −13.166 | −25.205 | 39.100 | 1.00 | 54.96 | C |
| ATOM | 2729 | O | GLU B | 140 | −11.950 | −25.096 | 39.196 | 1.00 | 53.94 | O |
| ATOM | 2730 | CB | GLU B | 140 | −13.578 | −22.712 | 38.777 | 1.00 | 57.72 | C |
| ATOM | 2731 | CG | GLU B | 140 | −14.090 | −22.567 | 37.356 | 1.00 | 73.73 | C |
| ATOM | 2732 | CD | GLU B | 140 | −15.439 | −21.884 | 37.249 | 1.00 | 95.44 | C |
| ATOM | 2733 | OE1 | GLU B | 140 | −16.461 | −22.603 | 37.156 | 1.00 | 96.05 | O |
| ATOM | 2734 | OE2 | GLU B | 140 | −15.473 | −20.631 | 37.263 | 1.00 | 81.66 | O |
| ATOM | 2735 | N | SER B | 141 | −13.757 | −26.356 | 38.708 | 1.00 | 49.14 | N |
| ATOM | 2736 | CA | SER B | 141 | −13.000 | −27.593 | 38.430 | 1.00 | 47.85 | C |
| ATOM | 2737 | C | SER B | 141 | −12.049 | −27.552 | 37.207 | 1.00 | 48.19 | C |
| ATOM | 2738 | O | SER B | 141 | −11.121 | −28.363 | 37.140 | 1.00 | 48.93 | O |
| ATOM | 2739 | CB | SER B | 141 | −13.951 | −28.782 | 38.291 | 1.00 | 50.78 | C |
| ATOM | 2740 | OG | SER B | 141 | −14.791 | −28.631 | 37.158 | 1.00 | 61.90 | O |
| ATOM | 2741 | N | THR B | 142 | −12.288 | −26.654 | 36.245 | 1.00 | 40.89 | N |
| ATOM | 2742 | CA | THR B | 142 | −11.473 | −26.527 | 35.020 | 1.00 | 38.45 | C |
| ATOM | 2743 | C | THR B | 142 | −10.868 | −25.117 | 34.923 | 1.00 | 37.37 | C |
| ATOM | 2744 | O | THR B | 142 | −11.574 | −24.118 | 35.124 | 1.00 | 37.14 | O |
| ATOM | 2745 | CB | THR B | 142 | −12.329 | −26.823 | 33.772 | 1.00 | 45.30 | C |
| ATOM | 2746 | OG1 | THR B | 142 | −13.170 | −27.969 | 34.006 | 1.00 | 44.53 | O |
| ATOM | 2747 | CG2 | THR B | 142 | −11.484 | −27.043 | 32.539 | 1.00 | 41.46 | C |
| ATOM | 2748 | N | ALA B | 143 | −9.549 | −25.050 | 34.659 | 1.00 | 29.55 | N |
| ATOM | 2749 | CA | ALA B | 143 | −8.807 | −23.806 | 34.488 | 1.00 | 26.97 | C |
| ATOM | 2750 | C | ALA B | 143 | −8.462 | −23.626 | 33.006 | 1.00 | 29.03 | C |
| ATOM | 2751 | O | ALA B | 143 | −8.270 | −24.610 | 32.297 | 1.00 | 25.75 | O |
| ATOM | 2752 | CB | ALA B | 143 | −7.524 | −23.872 | 35.281 | 1.00 | 27.78 | C |
| ATOM | 2753 | N | ALA B | 144 | −8.365 | −22.380 | 32.544 | 1.00 | 28.58 | N |
| ATOM | 2754 | CA | ALA B | 144 | −7.909 | −22.077 | 31.184 | 1.00 | 28.62 | C |
| ATOM | 2755 | C | ALA B | 144 | −6.574 | −21.304 | 31.257 | 1.00 | 33.48 | C |
| ATOM | 2756 | O | ALA B | 144 | −6.366 | −20.475 | 32.146 | 1.00 | 31.11 | O |
| ATOM | 2757 | CB | ALA B | 144 | −8.949 | −21.274 | 30.426 | 1.00 | 28.65 | C |
| ATOM | 2758 | N | LEU B | 145 | −5.661 | −21.620 | 30.351 | 1.00 | 34.09 | N |
| ATOM | 2759 | CA | LEU B | 145 | −4.395 | −20.899 | 30.236 | 1.00 | 36.57 | C |
| ATOM | 2760 | C | LEU B | 145 | −3.952 | −20.898 | 28.799 | 1.00 | 39.68 | C |
| ATOM | 2761 | O | LEU B | 145 | −4.388 | −21.748 | 28.027 | 1.00 | 39.79 | O |
| ATOM | 2762 | CB | LEU B | 145 | −3.312 | −21.408 | 31.195 | 1.00 | 38.16 | C |
| ATOM | 2763 | CG | LEU B | 145 | −2.945 | −22.875 | 31.110 | 1.00 | 43.97 | C |
| ATOM | 2764 | CD1 | LEU B | 145 | −1.742 | −23.080 | 30.192 | 1.00 | 45.62 | C |
| ATOM | 2765 | CD2 | LEU B | 145 | −2.601 | −23.422 | 32.482 | 1.00 | 45.10 | C |
| ATOM | 2766 | N | GLY B | 146 | −3.162 | −19.912 | 28.418 | 1.00 | 35.24 | N |
| ATOM | 2767 | CA | GLY B | 146 | −2.749 | −19.823 | 27.034 | 1.00 | 33.89 | C |
| ATOM | 2768 | C | GLY B | 146 | −1.533 | −18.987 | 26.745 | 1.00 | 36.62 | C |
| ATOM | 2769 | O | GLY B | 146 | −0.803 | −18.586 | 27.648 | 1.00 | 33.77 | O |
| ATOM | 2770 | N | CYS B | 147 | −1.350 | −18.696 | 25.458 | 1.00 | 35.09 | N |
| ATOM | 2771 | CA | CYS B | 147 | −0.270 | −17.882 | 24.953 | 1.00 | 35.84 | C |
| ATOM | 2772 | C | CYS B | 147 | −0.811 | −16.899 | 23.915 | 1.00 | 32.97 | C |
| ATOM | 2773 | O | CYS B | 147 | −1.465 | −17.325 | 22.968 | 1.00 | 29.99 | O |
| ATOM | 2774 | CB | CYS B | 147 | 0.820 | −18.771 | 24.358 | 1.00 | 38.55 | C |
| ATOM | 2775 | SG | CYS B | 147 | 2.098 | −19.250 | 25.550 | 1.00 | 45.13 | S |
| ATOM | 2776 | N | LEU B | 148 | −0.549 | −15.600 | 24.096 | 1.00 | 26.74 | N |
| ATOM | 2777 | CA | LEU B | 148 | −0.869 | −14.590 | 23.097 | 1.00 | 25.12 | C |
| ATOM | 2778 | C | LEU B | 148 | 0.435 | −14.425 | 22.258 | 1.00 | 30.22 | C |
| ATOM | 2779 | O | LEU B | 148 | 1.472 | −14.017 | 22.796 | 1.00 | 29.46 | O |
| ATOM | 2780 | CB | LEU B | 148 | −1.300 | −13.282 | 23.760 | 1.00 | 24.76 | C |
| ATOM | 2781 | CG | LEU B | 148 | −1.366 | −12.021 | 22.886 | 1.00 | 28.54 | C |
| ATOM | 2782 | CD1 | LEU B | 148 | −2.480 | −12.136 | 21.834 | 1.00 | 28.22 | C |
| ATOM | 2783 | CD2 | LEU B | 148 | −1.596 | −10.779 | 23.749 | 1.00 | 26.23 | C |
| ATOM | 2784 | N | VAL B | 149 | 0.380 | −14.834 | 20.957 | 1.00 | 25.84 | N |
| ATOM | 2785 | CA | VAL B | 149 | 1.479 | −14.764 | 19.974 | 1.00 | 23.09 | C |
| ATOM | 2786 | C | VAL B | 149 | 1.164 | −13.515 | 19.121 | 1.00 | 28.50 | C |
| ATOM | 2787 | O | VAL B | 149 | 0.333 | −13.583 | 18.234 | 1.00 | 28.56 | O |
| ATOM | 2788 | CB | VAL B | 149 | 1.511 | −16.079 | 19.158 | 1.00 | 22.55 | C |
| ATOM | 2789 | CG1 | VAL B | 149 | 2.666 | −16.090 | 18.162 | 1.00 | 22.69 | C |
| ATOM | 2790 | CG2 | VAL B | 149 | 1.571 | −17.289 | 20.079 | 1.00 | 21.13 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2791 | N | LYS B | 150 | 1.724 | −12.362 | 19.474 | 1.00 | 26.40 | N |
| ATOM | 2792 | CA | LYS B | 150 | 1.356 | −11.074 | 18.870 | 1.00 | 26.44 | C |
| ATOM | 2793 | C | LYS B | 150 | 2.416 | −10.428 | 17.925 | 1.00 | 32.78 | C |
| ATOM | 2794 | O | LYS B | 150 | 3.623 | −10.503 | 18.189 | 1.00 | 31.58 | O |
| ATOM | 2795 | CB | LYS B | 150 | 1.004 | −10.112 | 20.029 | 1.00 | 28.18 | C |
| ATOM | 2796 | CG | LYS B | 150 | 0.635 | −8.716 | 19.588 | 1.00 | 39.63 | C |
| ATOM | 2797 | CD | LYS B | 150 | −0.281 | −8.007 | 20.543 | 1.00 | 41.69 | C |
| ATOM | 2798 | CE | LYS B | 150 | −0.232 | −6.503 | 20.355 | 1.00 | 51.97 | C |
| ATOM | 2799 | NZ | LYS B | 150 | −0.761 | −6.031 | 19.054 | 1.00 | 55.29 | N |
| ATOM | 2800 | N | ASP B | 151 | 1.925 | −9.772 | 16.820 | 1.00 | 30.07 | N |
| ATOM | 2801 | CA | ASP B | 151 | 2.723 | −9.002 | 15.845 | 1.00 | 29.64 | C |
| ATOM | 2802 | C | ASP B | 151 | 3.802 | −9.785 | 15.105 | 1.00 | 31.27 | C |
| ATOM | 2803 | O | ASP B | 151 | 5.003 | −9.508 | 15.241 | 1.00 | 31.92 | O |
| ATOM | 2804 | CB | ASP B | 151 | 3.357 | −7.749 | 16.515 | 1.00 | 31.71 | C |
| ATOM | 2805 | CG | ASP B | 151 | 2.339 | −6.804 | 17.118 | 1.00 | 42.14 | C |
| ATOM | 2806 | OD1 | ASP B | 151 | 1.179 | −6.797 | 16.640 | 1.00 | 42.71 | O |
| ATOM | 2807 | OD2 | ASP B | 151 | 2.689 | −6.093 | 18.090 | 1.00 | 48.64 | O |
| ATOM | 2808 | N | TYR B | 152 | 3.378 | −10.704 | 14.265 | 1.00 | 25.13 | N |
| ATOM | 2809 | CA | TYR B | 152 | 4.319 | −11.454 | 13.444 | 1.00 | 23.73 | C |
| ATOM | 2810 | C | TYR B | 152 | 3.907 | −11.320 | 11.981 | 1.00 | 27.85 | C |
| ATOM | 2811 | O | TYR B | 152 | 2.768 | −10.977 | 11.680 | 1.00 | 25.67 | O |
| ATOM | 2812 | CB | TYR B | 152 | 4.450 | −12.922 | 13.891 | 1.00 | 22.85 | C |
| ATOM | 2813 | CG | TYR B | 152 | 3.193 | −13.738 | 13.727 | 1.00 | 22.76 | C |
| ATOM | 2814 | CD2 | TYR B | 152 | 2.951 | −14.454 | 12.555 | 1.00 | 22.42 | C |
| ATOM | 2815 | CD1 | TYR B | 152 | 2.206 | −13.746 | 14.713 | 1.00 | 24.56 | C |
| ATOM | 2816 | CE2 | TYR B | 152 | 1.754 | −15.141 | 12.358 | 1.00 | 21.85 | C |
| ATOM | 2817 | CE1 | TYR B | 152 | 1.016 | −14.458 | 14.541 | 1.00 | 24.71 | C |
| ATOM | 2818 | CZ | TYR B | 152 | 0.795 | −15.156 | 13.359 | 1.00 | 29.45 | C |
| ATOM | 2819 | OH | TYR B | 152 | −0.378 | −15.842 | 13.161 | 1.00 | 29.29 | O |
| ATOM | 2820 | N | PHE B | 153 | 4.880 | −11.494 | 11.086 | 1.00 | 25.58 | N |
| ATOM | 2821 | CA | PHE B | 153 | 4.650 | −11.440 | 9.653 | 1.00 | 24.84 | C |
| ATOM | 2822 | C | PHE B | 153 | 5.746 | −12.227 | 8.950 | 1.00 | 28.41 | C |
| ATOM | 2823 | O | PHE B | 153 | 6.897 | −12.040 | 9.315 | 1.00 | 27.83 | O |
| ATOM | 2824 | CB | PHE B | 153 | 4.634 | −9.985 | 9.132 | 1.00 | 26.15 | C |
| ATOM | 2825 | CG | PHE B | 153 | 4.164 | −9.928 | 7.690 | 1.00 | 26.63 | C |
| ATOM | 2826 | CD1 | PHE B | 153 | 2.810 | −10.044 | 7.379 | 1.00 | 26.95 | C |
| ATOM | 2827 | CD2 | PHE B | 153 | 5.080 | −9.922 | 6.644 | 1.00 | 27.61 | C |
| ATOM | 2828 | CE1 | PHE B | 153 | 2.382 | −10.094 | 6.059 | 1.00 | 26.83 | C |
| ATOM | 2829 | CE2 | PHE B | 153 | 4.655 | −9.980 | 5.326 | 1.00 | 29.60 | C |
| ATOM | 2830 | CZ | PHE B | 153 | 3.304 | −10.057 | 5.038 | 1.00 | 27.63 | C |
| ATOM | 2831 | N | PRO B | 154 | 5.465 | −13.046 | 7.909 | 1.00 | 25.98 | N |
| ATOM | 2832 | CA | PRO B | 154 | 4.163 | −13.468 | 7.371 | 1.00 | 25.98 | C |
| ATOM | 2833 | C | PRO B | 154 | 3.627 | −14.674 | 8.155 | 1.00 | 32.05 | C |
| ATOM | 2834 | O | PRO B | 154 | 4.221 | −15.079 | 9.147 | 1.00 | 33.49 | O |
| ATOM | 2835 | CB | PRO B | 154 | 4.542 | −13.894 | 5.943 | 1.00 | 27.25 | C |
| ATOM | 2836 | CG | PRO B | 154 | 5.866 | −14.571 | 6.135 | 1.00 | 30.35 | C |
| ATOM | 2837 | CD | PRO B | 154 | 6.557 | −13.786 | 7.241 | 1.00 | 26.88 | C |
| ATOM | 2838 | N | GLU B | 155 | 2.554 | −15.285 | 7.682 | 1.00 | 28.35 | N |
| ATOM | 2839 | CA | GLU B | 155 | 2.051 | −16.508 | 8.289 | 1.00 | 27.47 | C |
| ATOM | 2840 | C | GLU B | 155 | 2.909 | −17.669 | 7.808 | 1.00 | 31.86 | C |
| ATOM | 2841 | O | GLU B | 155 | 3.567 | −17.553 | 6.774 | 1.00 | 31.12 | O |
| ATOM | 2842 | CB | GLU B | 155 | 0.589 | −16.776 | 7.870 | 1.00 | 28.04 | C |
| ATOM | 2843 | CG | GLU B | 155 | −0.416 | −15.881 | 8.559 | 1.00 | 35.02 | C |
| ATOM | 2844 | CD | GLU B | 155 | −1.732 | −16.585 | 8.803 | 1.00 | 59.74 | C |
| ATOM | 2845 | OE1 | GLU B | 155 | −2.629 | −16.502 | 7.930 | 1.00 | 53.85 | O |
| ATOM | 2846 | OE2 | GLU B | 155 | −1.841 | −17.274 | 9.842 | 1.00 | 56.39 | O |
| ATOM | 2847 | N | PRO B | 156 | 2.886 | −18.820 | 8.505 | 1.00 | 30.50 | N |
| ATOM | 2848 | CA | PRO B | 156 | 2.144 | −19.132 | 9.749 | 1.00 | 29.71 | C |
| ATOM | 2849 | C | PRO B | 156 | 3.059 | −19.256 | 10.973 | 1.00 | 32.47 | C |
| ATOM | 2850 | O | PRO B | 156 | 4.287 | −19.317 | 10.856 | 1.00 | 30.42 | O |
| ATOM | 2851 | CB | PRO B | 156 | 1.590 | −20.528 | 9.423 | 1.00 | 30.52 | C |
| ATOM | 2852 | CG | PRO B | 156 | 2.795 | −21.196 | 8.684 | 1.00 | 34.51 | C |
| ATOM | 2853 | CD | PRO B | 156 | 3.586 | −20.035 | 8.021 | 1.00 | 31.13 | C |
| ATOM | 2854 | N | VAL B | 157 | 2.429 | −19.393 | 12.151 | 1.00 | 30.74 | N |
| ATOM | 2855 | CA | VAL B | 157 | 3.107 | −19.775 | 13.396 | 1.00 | 30.27 | C |
| ATOM | 2856 | C | VAL B | 157 | 2.430 | −21.071 | 13.801 | 1.00 | 32.93 | C |
| ATOM | 2857 | O | VAL B | 157 | 1.223 | −21.211 | 13.566 | 1.00 | 33.86 | O |
| ATOM | 2858 | CB | VAL B | 157 | 3.086 | −18.755 | 14.558 | 1.00 | 33.65 | C |
| ATOM | 2859 | CG1 | VAL B | 157 | 3.707 | −17.443 | 14.140 | 1.00 | 33.24 | C |
| ATOM | 2860 | CG2 | VAL B | 157 | 1.685 | −18.550 | 15.110 | 1.00 | 33.47 | C |
| ATOM | 2861 | N | THR B | 158 | 3.181 | −22.019 | 14.379 | 1.00 | 25.94 | N |
| ATOM | 2862 | CA | THR B | 158 | 2.598 | −23.241 | 14.917 | 1.00 | 24.36 | C |
| ATOM | 2863 | C | THR B | 158 | 2.803 | −23.170 | 16.463 | 1.00 | 28.16 | C |
| ATOM | 2864 | O | THR B | 158 | 3.793 | −22.599 | 16.952 | 1.00 | 25.21 | O |
| ATOM | 2865 | CB | THR B | 158 | 3.192 | −24.501 | 14.284 | 1.00 | 31.69 | C |
| ATOM | 2866 | OG1 | THR B | 158 | 4.586 | −24.547 | 14.597 | 1.00 | 42.63 | O |
| ATOM | 2867 | CG2 | THR B | 158 | 2.975 | −24.563 | 12.759 | 1.00 | 23.18 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2868 | N | VAL B | 159 | 1.823 | −23.696 | 17.218 | 1.00 | 23.87 | N |
| ATOM | 2869 | CA | VAL B | 159 | 1.900 | −23.711 | 18.662 | 1.00 | 22.64 | C |
| ATOM | 2870 | C | VAL B | 159 | 1.661 | −25.118 | 19.159 | 1.00 | 27.93 | C |
| ATOM | 2871 | O | VAL B | 159 | 0.709 | −25.774 | 18.726 | 1.00 | 27.38 | O |
| ATOM | 2872 | CB | VAL B | 159 | 0.938 | −22.712 | 19.321 | 1.00 | 24.11 | C |
| ATOM | 2873 | CG1 | VAL B | 159 | 1.232 | −22.598 | 20.818 | 1.00 | 23.83 | C |
| ATOM | 2874 | CG2 | VAL B | 159 | 1.007 | −21.344 | 18.628 | 1.00 | 22.88 | C |
| ATOM | 2875 | N | SER B | 160 | 2.554 | −25.597 | 20.045 | 1.00 | 24.23 | N |
| ATOM | 2876 | CA | SER B | 160 | 2.387 | −26.882 | 20.709 | 1.00 | 23.24 | C |
| ATOM | 2877 | C | SER B | 160 | 2.472 | −26.613 | 22.223 | 1.00 | 28.83 | C |
| ATOM | 2878 | O | SER B | 160 | 2.784 | −25.488 | 22.662 | 1.00 | 28.08 | O |
| ATOM | 2879 | CB | SER B | 160 | 3.394 | −27.918 | 20.214 | 1.00 | 25.22 | C |
| ATOM | 2880 | OG | SER B | 160 | 4.731 | −27.661 | 20.605 | 1.00 | 38.38 | O |
| ATOM | 2881 | N | TRP B | 161 | 2.106 | −27.609 | 23.014 | 1.00 | 25.53 | N |
| ATOM | 2882 | CA | TRP B | 161 | 2.114 | −27.470 | 24.452 | 1.00 | 25.13 | C |
| ATOM | 2883 | C | TRP B | 161 | 2.906 | −28.603 | 25.021 | 1.00 | 28.27 | C |
| ATOM | 2884 | O | TRP B | 161 | 2.734 | −29.742 | 24.575 | 1.00 | 26.86 | O |
| ATOM | 2885 | CB | TRP B | 161 | 0.658 | −27.446 | 24.991 | 1.00 | 23.61 | C |
| ATOM | 2886 | CG | TRP B | 161 | −0.004 | −26.116 | 24.818 | 1.00 | 23.34 | C |
| ATOM | 2887 | CD1 | TRP B | 161 | −0.653 | −25.663 | 23.708 | 1.00 | 25.72 | C |
| ATOM | 2888 | CD2 | TRP B | 161 | 0.128 | −24.995 | 25.690 | 1.00 | 22.80 | C |
| ATOM | 2889 | NE1 | TRP B | 161 | −1.006 | −24.345 | 23.872 | 1.00 | 24.50 | N |
| ATOM | 2890 | CE2 | TRP B | 161 | −0.553 | −23.911 | 25.084 | 1.00 | 25.97 | C |
| ATOM | 2891 | CE3 | TRP B | 161 | 0.642 | −24.832 | 26.994 | 1.00 | 23.72 | C |
| ATOM | 2892 | CZ2 | TRP B | 161 | −0.748 | −22.688 | 25.738 | 1.00 | 25.64 | C |
| ATOM | 2893 | CZ3 | TRP B | 161 | 0.473 | −23.605 | 27.635 | 1.00 | 24.95 | C |
| ATOM | 2894 | CH2 | TRP B | 161 | −0.206 | −22.547 | 27.007 | 1.00 | 25.57 | C |
| ATOM | 2895 | N | ASN B | 162 | 3.815 | −28.286 | 25.973 | 1.00 | 26.95 | N |
| ATOM | 2896 | CA | ASN B | 162 | 4.665 | −29.262 | 26.664 | 1.00 | 27.38 | C |
| ATOM | 2897 | C | ASN B | 162 | 5.353 | −30.194 | 25.673 | 1.00 | 32.89 | C |
| ATOM | 2898 | O | ASN B | 162 | 5.332 | −31.416 | 25.868 | 1.00 | 32.87 | O |
| ATOM | 2899 | CB | ASN B | 162 | 3.822 | −30.065 | 27.681 | 1.00 | 26.95 | C |
| ATOM | 2900 | CG | ASN B | 162 | 3.340 | −29.246 | 28.854 | 1.00 | 40.46 | C |
| ATOM | 2901 | OD1 | ASN B | 162 | 3.691 | −28.076 | 29.021 | 1.00 | 36.14 | O |
| ATOM | 2902 | ND2 | ASN B | 162 | 2.564 | −29.862 | 29.723 | 1.00 | 26.40 | N |
| ATOM | 2903 | N | SER B | 163 | 5.855 | −29.621 | 24.542 | 1.00 | 29.90 | N |
| ATOM | 2904 | CA | SER B | 163 | 6.570 | −30.346 | 23.475 | 1.00 | 28.77 | C |
| ATOM | 2905 | C | SER B | 163 | 5.746 | −31.462 | 22.826 | 1.00 | 31.04 | C |
| ATOM | 2906 | O | SER B | 163 | 6.318 | −32.464 | 22.422 | 1.00 | 28.95 | O |
| ATOM | 2907 | CB | SER B | 163 | 7.876 | −30.934 | 24.024 | 1.00 | 30.82 | C |
| ATOM | 2908 | OG | SER B | 163 | 8.576 | −30.027 | 24.863 | 1.00 | 33.59 | O |
| ATOM | 2909 | N | GLY B | 164 | 4.428 | −31.291 | 22.749 | 1.00 | 29.39 | N |
| ATOM | 2910 | CA | GLY B | 164 | 3.534 | −32.281 | 22.166 | 1.00 | 29.34 | C |
| ATOM | 2911 | C | GLY B | 164 | 2.960 | −33.278 | 23.150 | 1.00 | 37.61 | C |
| ATOM | 2912 | O | GLY B | 164 | 2.154 | −34.117 | 22.747 | 1.00 | 40.36 | O |
| ATOM | 2913 | N | ALA B | 165 | 3.364 | −33.235 | 24.435 | 1.00 | 35.06 | N |
| ATOM | 2914 | CA | ALA B | 165 | 2.822 | −34.132 | 25.474 | 1.00 | 34.93 | C |
| ATOM | 2915 | C | ALA B | 165 | 1.352 | −33.754 | 25.794 | 1.00 | 40.39 | C |
| ATOM | 2916 | O | ALA B | 165 | 0.524 | −34.634 | 26.047 | 1.00 | 39.86 | O |
| ATOM | 2917 | CB | ALA B | 165 | 3.661 | −34.047 | 26.737 | 1.00 | 35.51 | C |
| ATOM | 2918 | N | LEU B | 166 | 1.042 | −32.444 | 25.744 | 1.00 | 37.26 | N |
| ATOM | 2919 | CA | LEU B | 166 | −0.288 | −31.915 | 25.981 | 1.00 | 36.54 | C |
| ATOM | 2920 | C | LEU B | 166 | −0.938 | −31.588 | 24.651 | 1.00 | 41.28 | C |
| ATOM | 2921 | O | LEU B | 166 | −0.520 | −30.650 | 23.981 | 1.00 | 40.67 | O |
| ATOM | 2922 | CB | LEU B | 166 | −0.185 | −30.664 | 26.865 | 1.00 | 36.67 | C |
| ATOM | 2923 | CG | LEU B | 166 | −1.487 | −30.072 | 27.400 | 1.00 | 41.39 | C |
| ATOM | 2924 | CD1 | LEU B | 166 | −2.376 | −31.144 | 28.062 | 1.00 | 41.63 | C |
| ATOM | 2925 | CD2 | LEU B | 166 | −1.191 | −28.968 | 28.397 | 1.00 | 43.73 | C |
| ATOM | 2926 | N | THR B | 167 | −1.903 | −32.425 | 24.232 | 1.00 | 38.24 | N |
| ATOM | 2927 | CA | THR B | 167 | −2.675 | −32.242 | 23.001 | 1.00 | 37.11 | C |
| ATOM | 2928 | C | THR B | 167 | −4.167 | −32.094 | 23.318 | 1.00 | 41.57 | C |
| ATOM | 2929 | O | THR B | 167 | −4.829 | −31.292 | 22.675 | 1.00 | 42.15 | O |
| ATOM | 2930 | CB | THR B | 167 | −2.367 | −33.359 | 21.984 | 1.00 | 42.77 | C |
| ATOM | 2931 | OG1 | THR B | 167 | −2.633 | −34.633 | 22.576 | 1.00 | 50.73 | O |
| ATOM | 2932 | CG2 | THR B | 167 | −0.925 | −33.309 | 21.481 | 1.00 | 34.42 | C |
| ATOM | 2933 | N | SER B | 168 | −4.705 | −32.839 | 24.296 | 1.00 | 38.18 | N |
| ATOM | 2934 | CA | SER B | 168 | −6.118 | −32.713 | 24.680 | 1.00 | 37.70 | C |
| ATOM | 2935 | C | SER B | 168 | −6.443 | −31.338 | 25.324 | 1.00 | 36.91 | C |
| ATOM | 2936 | O | SER B | 168 | −5.698 | −30.864 | 26.191 | 1.00 | 35.50 | O |
| ATOM | 2937 | CB | SER B | 168 | −6.508 | −33.827 | 25.643 | 1.00 | 43.31 | C |
| ATOM | 2938 | OG | SER B | 168 | −6.335 | −35.079 | 24.995 | 1.00 | 62.11 | O |
| ATOM | 2939 | N | GLY B | 169 | −7.558 | −30.743 | 24.891 | 1.00 | 28.76 | N |
| ATOM | 2940 | CA | GLY B | 169 | −8.017 | −29.448 | 25.372 | 1.00 | 27.62 | C |
| ATOM | 2941 | C | GLY B | 169 | −7.316 | −28.241 | 24.763 | 1.00 | 29.34 | C |
| ATOM | 2942 | O | GLY B | 169 | −7.564 | −27.117 | 25.209 | 1.00 | 27.71 | O |
| ATOM | 2943 | N | VAL B | 170 | −6.461 | −28.445 | 23.721 | 1.00 | 24.66 | N |
| ATOM | 2944 | CA | VAL B | 170 | −5.707 | −27.364 | 23.091 | 1.00 | 23.89 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 2945 | C | VAL B | 170 | −6.481 | −26.787 | 21.901 | 1.00 | 30.56 | C |
| ATOM | 2946 | O | VAL B | 170 | −6.882 | −27.556 | 21.032 | 1.00 | 32.45 | O |
| ATOM | 2947 | CB | VAL B | 170 | −4.294 | −27.831 | 22.642 | 1.00 | 24.97 | C |
| ATOM | 2948 | CG1 | VAL B | 170 | −3.601 | −26.763 | 21.782 | 1.00 | 24.03 | C |
| ATOM | 2949 | CG2 | VAL B | 170 | −3.439 | −28.203 | 23.837 | 1.00 | 24.68 | C |
| ATOM | 2950 | N | HIS B | 171 | −6.617 | −25.440 | 21.827 | 1.00 | 25.23 | N |
| ATOM | 2951 | CA | HIS B | 171 | −7.225 | −24.746 | 20.692 | 1.00 | 23.85 | C |
| ATOM | 2952 | C | HIS B | 171 | −6.284 | −23.677 | 20.233 | 1.00 | 25.81 | C |
| ATOM | 2953 | O | HIS B | 171 | −6.105 | −22.694 | 20.950 | 1.00 | 22.81 | O |
| ATOM | 2954 | CB | HIS B | 171 | −8.550 | −24.061 | 21.060 | 1.00 | 25.22 | C |
| ATOM | 2955 | CG | HIS B | 171 | −9.590 | −25.006 | 21.539 | 1.00 | 29.10 | C |
| ATOM | 2956 | ND1 | HIS B | 171 | −10.119 | −25.980 | 20.710 | 1.00 | 31.02 | N |
| ATOM | 2957 | CD2 | HIS B | 171 | −10.120 | −25.140 | 22.772 | 1.00 | 30.38 | C |
| ATOM | 2958 | CE1 | HIS B | 171 | −10.971 | −26.659 | 21.458 | 1.00 | 30.12 | C |
| ATOM | 2959 | NE2 | HIS B | 171 | −11.031 | −26.164 | 22.696 | 1.00 | 30.23 | N |
| ATOM | 2960 | N | THR B | 172 | −5.659 | −23.844 | 19.052 | 1.00 | 24.62 | N |
| ATOM | 2961 | CA | THR B | 172 | −4.823 | −22.775 | 18.520 | 1.00 | 24.89 | C |
| ATOM | 2962 | C | THR B | 172 | −5.728 | −22.027 | 17.556 | 1.00 | 25.73 | C |
| ATOM | 2963 | O | THR B | 172 | −6.150 | −22.581 | 16.555 | 1.00 | 26.38 | O |
| ATOM | 2964 | CB | THR B | 172 | −3.479 | −23.250 | 17.940 | 1.00 | 31.32 | C |
| ATOM | 2965 | OG1 | THR B | 172 | −2.729 | −23.895 | 18.977 | 1.00 | 27.41 | O |
| ATOM | 2966 | CG2 | THR B | 172 | −2.653 | −22.067 | 17.390 | 1.00 | 25.66 | C |
| ATOM | 2967 | N | PHE B | 173 | −6.062 | −20.787 | 17.885 | 1.00 | 20.61 | N |
| ATOM | 2968 | CA | PHE B | 173 | −6.943 | −19.984 | 17.050 | 1.00 | 18.78 | C |
| ATOM | 2969 | C | PHE B | 173 | −6.328 | −19.568 | 15.718 | 1.00 | 25.32 | C |
| ATOM | 2970 | O | PHE B | 173 | −5.114 | −19.319 | 15.657 | 1.00 | 25.83 | O |
| ATOM | 2971 | CB | PHE B | 173 | −7.396 | −18.745 | 17.830 | 1.00 | 18.75 | C |
| ATOM | 2972 | CG | PHE B | 173 | −8.409 | −19.120 | 18.880 | 1.00 | 17.96 | C |
| ATOM | 2973 | CD2 | PHE B | 173 | −8.016 | −19.397 | 20.186 | 1.00 | 17.45 | C |
| ATOM | 2974 | CD1 | PHE B | 173 | −9.742 | −19.291 | 18.544 | 1.00 | 19.57 | C |
| ATOM | 2975 | CE2 | PHE B | 173 | −8.947 | −19.830 | 21.134 | 1.00 | 19.55 | C |
| ATOM | 2976 | CE1 | PHE B | 173 | −10.676 | −19.662 | 19.507 | 1.00 | 19.59 | C |
| ATOM | 2977 | CZ | PHE B | 173 | −10.273 | −19.965 | 20.785 | 1.00 | 17.09 | C |
| ATOM | 2978 | N | PRO B | 174 | −7.149 | −19.442 | 14.641 | 1.00 | 24.07 | N |
| ATOM | 2979 | CA | PRO B | 174 | −6.602 | −18.914 | 13.373 | 1.00 | 24.51 | C |
| ATOM | 2980 | C | PRO B | 174 | −6.151 | −17.446 | 13.581 | 1.00 | 30.28 | C |
| ATOM | 2981 | O | PRO B | 174 | −6.747 | −16.741 | 14.380 | 1.00 | 32.72 | O |
| ATOM | 2982 | CB | PRO B | 174 | −7.775 | −19.042 | 12.368 | 1.00 | 25.66 | C |
| ATOM | 2983 | CG | PRO B | 174 | −8.983 | −19.206 | 13.174 | 1.00 | 30.40 | C |
| ATOM | 2984 | CD | PRO B | 174 | −8.605 | −19.703 | 14.549 | 1.00 | 25.91 | C |
| ATOM | 2985 | N | ALA B | 175 | −5.098 | −17.005 | 12.913 | 1.00 | 24.63 | N |
| ATOM | 2986 | CA | ALA B | 175 | −4.593 | −15.659 | 13.106 | 1.00 | 24.42 | C |
| ATOM | 2987 | C | ALA B | 175 | −5.515 | −14.564 | 12.608 | 1.00 | 28.44 | C |
| ATOM | 2988 | O | ALA B | 175 | −6.265 | −14.775 | 11.668 | 1.00 | 25.95 | O |
| ATOM | 2989 | CB | ALA B | 175 | −3.237 | −15.512 | 12.433 | 1.00 | 25.38 | C |
| ATOM | 2990 | N | VAL B | 176 | −5.405 | −13.364 | 13.234 | 1.00 | 28.05 | N |
| ATOM | 2991 | CA | VAL B | 176 | −6.146 | −12.153 | 12.849 | 1.00 | 27.83 | C |
| ATOM | 2992 | C | VAL B | 176 | −5.138 | −11.155 | 12.294 | 1.00 | 31.50 | C |
| ATOM | 2993 | O | VAL B | 176 | −4.089 | −10.951 | 12.901 | 1.00 | 30.60 | O |
| ATOM | 2994 | CB | VAL B | 176 | −7.023 | −11.497 | 13.975 | 1.00 | 30.92 | C |
| ATOM | 2995 | CG1 | VAL B | 176 | −8.152 | −12.419 | 14.413 | 1.00 | 30.22 | C |
| ATOM | 2996 | CG2 | VAL B | 176 | −6.200 | −11.026 | 15.178 | 1.00 | 30.70 | C |
| ATOM | 2997 | N | LEU B | 177 | −5.440 | −10.564 | 11.132 | 1.00 | 29.89 | N |
| ATOM | 2998 | CA | LEU B | 177 | −4.629 | −9.497 | 10.556 | 1.00 | 31.22 | C |
| ATOM | 2999 | C | LEU B | 177 | −5.017 | −8.239 | 11.313 | 1.00 | 35.58 | C |
| ATOM | 3000 | O | LEU B | 177 | −6.193 | −7.883 | 11.328 | 1.00 | 33.53 | O |
| ATOM | 3001 | CB | LEU B | 177 | −4.924 | −9.285 | 9.062 | 1.00 | 31.78 | C |
| ATOM | 3002 | CG | LEU B | 177 | −4.009 | −8.271 | 8.358 | 1.00 | 37.00 | C |
| ATOM | 3003 | CD1 | LEU B | 177 | −2.654 | −8.870 | 8.072 | 1.00 | 36.57 | C |
| ATOM | 3004 | CD2 | LEU B | 177 | −4.642 | −7.777 | 7.060 | 1.00 | 42.08 | C |
| ATOM | 3005 | N | GLN B | 178 | −4.052 | −7.578 | 11.962 | 1.00 | 34.53 | N |
| ATOM | 3006 | CA | GLN B | 178 | −4.358 | −6.363 | 12.710 | 1.00 | 35.09 | C |
| ATOM | 3007 | C | GLN B | 178 | −4.292 | −5.101 | 11.803 | 1.00 | 39.93 | C |
| ATOM | 3008 | O | GLN B | 178 | −3.883 | −5.173 | 10.635 | 1.00 | 38.04 | O |
| ATOM | 3009 | CB | GLN B | 178 | −3.390 | −6.232 | 13.886 | 1.00 | 36.46 | C |
| ATOM | 3010 | CG | GLN B | 178 | −3.410 | −7.417 | 14.859 | 1.00 | 34.06 | C |
| ATOM | 3011 | CD | GLN B | 178 | −2.140 | −7.482 | 15.687 | 1.00 | 44.98 | C |
| ATOM | 3012 | OE1 | GLN B | 178 | −2.164 | −7.382 | 16.911 | 1.00 | 43.06 | O |
| ATOM | 3013 | NE2 | GLN B | 178 | −0.991 | −7.655 | 15.047 | 1.00 | 29.12 | N |
| ATOM | 3014 | N | SER B | 179 | −4.698 | −3.942 | 12.357 | 1.00 | 38.70 | N |
| ATOM | 3015 | CA | SER B | 179 | −4.633 | −2.641 | 11.660 | 1.00 | 39.47 | C |
| ATOM | 3016 | C | SER B | 179 | −3.180 | −2.375 | 11.162 | 1.00 | 42.83 | C |
| ATOM | 3017 | O | SER B | 179 | −2.980 | −1.897 | 10.041 | 1.00 | 43.33 | O |
| ATOM | 3018 | CB | SER B | 179 | −5.053 | −1.510 | 12.604 | 1.00 | 44.01 | C |
| ATOM | 3019 | OG | SER B | 179 | −5.866 | −1.971 | 13.674 | 1.00 | 56.26 | O |
| ATOM | 3020 | N | SER B | 180 | −2.178 | −2.726 | 12.007 | 1.00 | 36.55 | N |
| ATOM | 3021 | CA | SER B | 180 | −0.748 | −2.563 | 11.734 | 1.00 | 35.81 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3022 | C | SER B | 180 | −0.205 | −3.373 | 10.563 | 1.00 | 39.87 | C |
| ATOM | 3023 | O | SER B | 180 | 0.922 | −3.122 | 10.129 | 1.00 | 41.63 | O |
| ATOM | 3024 | CB | SER B | 180 | 0.050 | −2.936 | 12.977 | 1.00 | 38.85 | C |
| ATOM | 3025 | OG | SER B | 180 | −0.168 | −4.296 | 13.311 | 1.00 | 46.47 | O |
| ATOM | 3026 | N | GLY B | 181 | −0.951 | −4.367 | 10.099 | 1.00 | 33.84 | N |
| ATOM | 3027 | CA | GLY B | 181 | −0.507 | −5.228 | 9.010 | 1.00 | 31.94 | C |
| ATOM | 3028 | C | GLY B | 181 | 0.294 | −6.429 | 9.483 | 1.00 | 30.23 | C |
| ATOM | 3029 | O | GLY B | 181 | 0.906 | −7.123 | 8.677 | 1.00 | 29.75 | O |
| ATOM | 3030 | N | LEU B | 182 | 0.288 | −6.693 | 10.783 | 1.00 | 23.76 | N |
| ATOM | 3031 | CA | LEU B | 182 | 0.967 | −7.833 | 11.353 | 1.00 | 21.88 | C |
| ATOM | 3032 | C | LEU B | 182 | −0.092 | −8.753 | 11.899 | 1.00 | 24.72 | C |
| ATOM | 3033 | O | LEU B | 182 | −1.135 | −8.290 | 12.370 | 1.00 | 23.62 | O |
| ATOM | 3034 | CB | LEU B | 182 | 1.897 | −7.382 | 12.486 | 1.00 | 21.60 | C |
| ATOM | 3035 | CG | LEU B | 182 | 2.940 | −6.357 | 12.110 | 1.00 | 24.81 | C |
| ATOM | 3036 | CD1 | LEU B | 182 | 3.644 | −5.850 | 13.313 | 1.00 | 24.51 | C |
| ATOM | 3037 | CD2 | LEU B | 182 | 3.947 | −6.929 | 11.128 | 1.00 | 23.16 | C |
| ATOM | 3038 | N | TYR B | 183 | 0.205 | −10.044 | 11.913 | 1.00 | 22.40 | N |
| ATOM | 3039 | CA | TYR B | 183 | −0.695 | −11.053 | 12.450 | 1.00 | 22.55 | C |
| ATOM | 3040 | C | TYR B | 183 | −0.563 | −11.193 | 13.953 | 1.00 | 28.88 | C |
| ATOM | 3041 | O | TYR B | 183 | 0.421 | −10.786 | 14.563 | 1.00 | 30.48 | O |
| ATOM | 3042 | CB | TYR B | 183 | −0.446 | −12.404 | 11.788 | 1.00 | 24.33 | C |
| ATOM | 3043 | CG | TYR B | 183 | −0.866 | −12.415 | 10.337 | 1.00 | 28.66 | C |
| ATOM | 3044 | CD1 | TYR B | 183 | −2.206 | −12.545 | 9.981 | 1.00 | 30.63 | C |
| ATOM | 3045 | CD2 | TYR B | 183 | 0.068 | −12.233 | 9.318 | 1.00 | 30.03 | C |
| ATOM | 3046 | CE1 | TYR B | 183 | −2.606 | −12.512 | 8.646 | 1.00 | 32.52 | C |
| ATOM | 3047 | CE2 | TYR B | 183 | −0.319 | −12.213 | 7.977 | 1.00 | 31.34 | C |
| ATOM | 3048 | CZ | TYR B | 183 | −1.655 | −12.388 | 7.643 | 1.00 | 41.26 | C |
| ATOM | 3049 | OH | TYR B | 183 | −2.065 | −12.411 | 6.327 | 1.00 | 42.36 | O |
| ATOM | 3050 | N | SER B | 184 | −1.574 | −11.791 | 14.544 | 1.00 | 25.99 | N |
| ATOM | 3051 | CA | SER B | 184 | −1.627 | −12.071 | 15.961 | 1.00 | 25.28 | C |
| ATOM | 3052 | C | SER B | 184 | −2.553 | −13.277 | 16.211 | 1.00 | 28.05 | C |
| ATOM | 3053 | O | SER B | 184 | −3.559 | −13.444 | 15.527 | 1.00 | 25.02 | O |
| ATOM | 3054 | CB | SER B | 184 | −2.129 | −10.837 | 16.701 | 1.00 | 28.59 | C |
| ATOM | 3055 | OG | SER B | 184 | −2.315 | −11.091 | 18.082 | 1.00 | 43.19 | O |
| ATOM | 3056 | N | LEU B | 185 | −2.192 | −14.141 | 17.152 | 1.00 | 26.92 | N |
| ATOM | 3057 | CA | LEU B | 185 | −3.063 | −15.254 | 17.513 | 1.00 | 26.39 | C |
| ATOM | 3058 | C | LEU B | 185 | −2.912 | −15.645 | 18.967 | 1.00 | 31.71 | C |
| ATOM | 3059 | O | LEU B | 185 | −1.976 | −15.212 | 19.653 | 1.00 | 31.23 | O |
| ATOM | 3060 | CB | LEU B | 185 | −2.871 | −16.463 | 16.588 | 1.00 | 25.81 | C |
| ATOM | 3061 | CG | LEU B | 185 | −1.596 | −17.316 | 16.651 | 1.00 | 29.59 | C |
| ATOM | 3062 | CD1 | LEU B | 185 | −1.543 | −18.206 | 17.917 | 1.00 | 28.61 | C |
| ATOM | 3063 | CD2 | LEU B | 185 | −1.546 | −18.218 | 15.404 | 1.00 | 31.62 | C |
| ATOM | 3064 | N | SER B | 186 | −3.818 | −16.519 | 19.412 | 1.00 | 27.88 | N |
| ATOM | 3065 | CA | SER B | 186 | −3.795 | −17.077 | 20.747 | 1.00 | 26.94 | C |
| ATOM | 3066 | C | SER B | 186 | −3.955 | −18.589 | 20.695 | 1.00 | 28.93 | C |
| ATOM | 3067 | O | SER B | 186 | −4.567 | −19.146 | 19.775 | 1.00 | 27.69 | O |
| ATOM | 3068 | CB | SER B | 186 | −4.878 | −16.457 | 21.618 | 1.00 | 30.93 | C |
| ATOM | 3069 | OG | SER B | 186 | −4.424 | −15.209 | 22.111 | 1.00 | 43.85 | O |
| ATOM | 3070 | N | SER B | 187 | −3.301 | −19.245 | 21.642 | 1.00 | 25.50 | N |
| ATOM | 3071 | CA | SER B | 187 | −3.374 | −20.683 | 21.829 | 1.00 | 24.93 | C |
| ATOM | 3072 | C | SER B | 187 | −3.742 | −20.863 | 23.269 | 1.00 | 28.82 | C |
| ATOM | 3073 | O | SER B | 187 | −3.119 | −20.230 | 24.132 | 1.00 | 29.22 | O |
| ATOM | 3074 | CB | SER B | 187 | −2.043 | −21.365 | 21.545 | 1.00 | 27.40 | C |
| ATOM | 3075 | OG | SER B | 187 | −2.299 | −22.759 | 21.553 | 1.00 | 35.29 | O |
| ATOM | 3076 | N | VAL B | 188 | −4.786 | −21.640 | 23.527 | 1.00 | 22.29 | N |
| ATOM | 3077 | CA | VAL B | 188 | −5.246 | −21.890 | 24.873 | 1.00 | 21.87 | C |
| ATOM | 3078 | C | VAL B | 188 | −5.294 | −23.396 | 25.096 | 1.00 | 29.12 | C |
| ATOM | 3079 | O | VAL B | 188 | −5.266 | −24.189 | 24.153 | 1.00 | 29.37 | O |
| ATOM | 3080 | CB | VAL B | 188 | −6.608 | −21.185 | 25.164 | 1.00 | 24.31 | C |
| ATOM | 3081 | CG1 | VAL B | 188 | −6.559 | −19.719 | 24.720 | 1.00 | 24.02 | C |
| ATOM | 3082 | CG2 | VAL B | 188 | −7.776 | −21.901 | 24.486 | 1.00 | 23.32 | C |
| ATOM | 3083 | N | VAL B | 189 | −5.357 | −23.772 | 26.352 | 1.00 | 26.51 | N |
| ATOM | 3084 | CA | VAL B | 189 | −5.506 | −25.144 | 26.790 | 1.00 | 25.45 | C |
| ATOM | 3085 | C | VAL B | 189 | −6.386 | −25.134 | 28.062 | 1.00 | 28.65 | C |
| ATOM | 3086 | O | VAL B | 189 | −6.230 | −24.238 | 28.897 | 1.00 | 26.50 | O |
| ATOM | 3087 | CB | VAL B | 189 | −4.129 | −25.843 | 27.010 | 1.00 | 27.47 | C |
| ATOM | 3088 | CG1 | VAL B | 189 | −3.306 | −25.164 | 28.085 | 1.00 | 26.16 | C |
| ATOM | 3089 | CG2 | VAL B | 189 | −4.323 | −27.317 | 27.335 | 1.00 | 27.34 | C |
| ATOM | 3090 | N | THR B | 190 | −7.336 | −26.057 | 28.181 | 1.00 | 25.11 | N |
| ATOM | 3091 | CA | THR B | 190 | −8.100 | −26.142 | 29.430 | 1.00 | 26.50 | C |
| ATOM | 3092 | C | THR B | 190 | −7.521 | −27.320 | 30.193 | 1.00 | 31.88 | C |
| ATOM | 3093 | O | THR B | 190 | −7.144 | −28.314 | 29.564 | 1.00 | 30.52 | O |
| ATOM | 3094 | CB | THR B | 190 | −9.626 | −26.240 | 29.246 | 1.00 | 27.64 | C |
| ATOM | 3095 | OG1 | THR B | 190 | −9.936 | −27.202 | 28.248 | 1.00 | 32.89 | O |
| ATOM | 3096 | CG2 | THR B | 190 | −10.249 | −24.906 | 28.928 | 1.00 | 18.98 | C |
| ATOM | 3097 | N | VAL B | 191 | −7.387 | −27.191 | 31.530 | 1.00 | 29.24 | N |
| ATOM | 3098 | CA | VAL B | 191 | −6.790 | −28.241 | 32.368 | 1.00 | 29.50 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3099 | C | VAL B | 191 | −7.515 | −28.329 | 33.700 | 1.00 | 37.50 | C |
| ATOM | 3100 | O | VAL B | 191 | −8.119 | −27.328 | 34.123 | 1.00 | 34.43 | O |
| ATOM | 3101 | CB | VAL B | 191 | −5.268 | −27.991 | 32.598 | 1.00 | 32.29 | C |
| ATOM | 3102 | CG1 | VAL B | 191 | −4.511 | −27.924 | 31.277 | 1.00 | 31.48 | C |
| ATOM | 3103 | CG2 | VAL B | 191 | −5.017 | −26.729 | 33.414 | 1.00 | 32.28 | C |
| ATOM | 3104 | N | PRO B | 192 | −7.410 | −29.490 | 34.413 | 1.00 | 39.62 | N |
| ATOM | 3105 | CA | PRO B | 192 | −8.019 | −29.580 | 35.757 | 1.00 | 40.45 | C |
| ATOM | 3106 | C | PRO B | 192 | −7.392 | −28.559 | 36.699 | 1.00 | 46.74 | C |
| ATOM | 3107 | O | PRO B | 192 | −6.165 | −28.505 | 36.772 | 1.00 | 47.00 | O |
| ATOM | 3108 | CB | PRO B | 192 | −7.686 | −31.012 | 36.223 | 1.00 | 42.09 | C |
| ATOM | 3109 | CG | PRO B | 192 | −7.222 | −31.737 | 35.034 | 1.00 | 46.85 | C |
| ATOM | 3110 | CD | PRO B | 192 | −6.690 | −30.738 | 34.066 | 1.00 | 42.31 | C |
| ATOM | 3111 | N | SER B | 193 | −8.207 | −27.747 | 37.401 | 1.00 | 44.32 | N |
| ATOM | 3112 | CA | SER B | 193 | −7.685 | −26.760 | 38.355 | 1.00 | 45.16 | C |
| ATOM | 3113 | C | SER B | 193 | −6.727 | −27.393 | 39.389 | 1.00 | 50.26 | C |
| ATOM | 3114 | O | SER B | 193 | −5.706 | −26.781 | 39.699 | 1.00 | 50.03 | O |
| ATOM | 3115 | CB | SER B | 193 | −8.824 | −26.037 | 39.060 | 1.00 | 47.74 | C |
| ATOM | 3116 | OG | SER B | 193 | −9.455 | −25.162 | 38.144 | 1.00 | 52.58 | O |
| ATOM | 3117 | N | SER B | 194 | −7.008 | −28.641 | 39.837 | 1.00 | 47.26 | N |
| ATOM | 3118 | CA | SER B | 194 | −6.149 | −29.368 | 40.773 | 1.00 | 49.01 | C |
| ATOM | 3119 | C | SER B | 194 | −4.690 | −29.520 | 40.280 | 1.00 | 58.67 | C |
| ATOM | 3120 | O | SER B | 194 | −3.775 | −29.530 | 41.100 | 1.00 | 60.91 | O |
| ATOM | 3121 | CB | SER B | 194 | −6.743 | −30.735 | 41.118 | 1.00 | 51.29 | C |
| ATOM | 3122 | OG | SER B | 194 | −6.806 | −31.633 | 40.019 | 1.00 | 57.13 | O |
| ATOM | 3123 | N | SER B | 195 | −4.470 | −29.614 | 38.963 | 1.00 | 56.56 | N |
| ATOM | 3124 | CA | SER B | 195 | −3.119 | −29.744 | 38.409 | 1.00 | 57.10 | C |
| ATOM | 3125 | C | SER B | 195 | −2.266 | −28.491 | 38.596 | 1.00 | 61.22 | C |
| ATOM | 3126 | O | SER B | 195 | −1.056 | −28.619 | 38.761 | 1.00 | 61.99 | O |
| ATOM | 3127 | CB | SER B | 195 | −3.173 | −30.067 | 36.914 | 1.00 | 59.73 | C |
| ATOM | 3128 | OG | SER B | 195 | −3.719 | −31.354 | 36.682 | 1.00 | 70.35 | O |
| ATOM | 3129 | N | LEU B | 196 | −2.873 | −27.293 | 38.576 | 1.00 | 56.22 | N |
| ATOM | 3130 | CA | LEU B | 196 | −2.139 | −26.023 | 38.611 | 1.00 | 55.99 | C |
| ATOM | 3131 | C | LEU B | 196 | −0.968 | −25.989 | 39.611 | 1.00 | 62.86 | C |
| ATOM | 3132 | O | LEU B | 196 | 0.081 | −25.416 | 39.296 | 1.00 | 63.59 | O |
| ATOM | 3133 | CB | LEU B | 196 | −3.086 | −24.832 | 38.834 | 1.00 | 55.43 | C |
| ATOM | 3134 | CG | LEU B | 196 | −4.097 | −24.523 | 37.705 | 1.00 | 58.35 | C |
| ATOM | 3135 | CD1 | LEU B | 196 | −5.011 | −23.388 | 38.107 | 1.00 | 58.38 | C |
| ATOM | 3136 | CD2 | LEU B | 196 | −3.400 | −24.168 | 36.396 | 1.00 | 58.09 | C |
| ATOM | 3137 | N | GLY B | 197 | −1.125 | −26.638 | 40.759 | 1.00 | 59.51 | N |
| ATOM | 3138 | CA | GLY B | 197 | −0.060 | −26.730 | 41.750 | 1.00 | 60.07 | C |
| ATOM | 3139 | C | GLY B | 197 | 1.006 | −27.737 | 41.366 | 1.00 | 63.00 | C |
| ATOM | 3140 | O | GLY B | 197 | 2.198 | −27.425 | 41.385 | 1.00 | 62.89 | O |
| ATOM | 3141 | N | THR B | 198 | 0.570 | −28.948 | 40.992 | 1.00 | 58.32 | N |
| ATOM | 3142 | CA | THR B | 198 | 1.451 | −30.055 | 40.613 | 1.00 | 57.68 | C |
| ATOM | 3143 | C | THR B | 198 | 2.165 | −29.890 | 39.243 | 1.00 | 57.66 | C |
| ATOM | 3144 | O | THR B | 198 | 3.391 | −29.982 | 39.191 | 1.00 | 58.33 | O |
| ATOM | 3145 | CB | THR B | 198 | 0.645 | −31.376 | 40.648 | 1.00 | 71.67 | C |
| ATOM | 3146 | OG1 | THR B | 198 | 0.154 | −31.578 | 41.980 | 1.00 | 73.17 | O |
| ATOM | 3147 | CG2 | THR B | 198 | 1.476 | −32.598 | 40.207 | 1.00 | 73.41 | C |
| ATOM | 3148 | N | LYS B | 199 | 1.392 | −29.702 | 38.147 | 1.00 | 49.33 | N |
| ATOM | 3149 | CA | LYS B | 199 | 1.879 | −29.646 | 36.750 | 1.00 | 45.56 | C |
| ATOM | 3150 | C | LYS B | 199 | 2.303 | −28.259 | 36.262 | 1.00 | 45.11 | C |
| ATOM | 3151 | O | LYS B | 199 | 1.761 | −27.250 | 36.697 | 1.00 | 44.44 | O |
| ATOM | 3152 | CB | LYS B | 199 | 0.798 | −30.168 | 35.786 | 1.00 | 45.24 | C |
| ATOM | 3153 | CG | LYS B | 199 | 0.167 | −31.517 | 36.139 | 1.00 | 52.08 | C |
| ATOM | 3154 | CD | LYS B | 199 | 1.076 | −32.692 | 35.901 | 1.00 | 58.21 | C |
| ATOM | 3155 | CE | LYS B | 199 | 0.550 | −33.968 | 36.520 | 1.00 | 69.86 | C |
| ATOM | 3156 | NZ | LYS B | 199 | 0.837 | −35.153 | 35.665 | 1.00 | 86.48 | N |
| ATOM | 3157 | N | THR B | 200 | 3.246 | −28.233 | 35.306 | 1.00 | 39.77 | N |
| ATOM | 3158 | CA | THR B | 200 | 3.730 | −27.025 | 34.623 | 1.00 | 38.11 | C |
| ATOM | 3159 | C | THR B | 200 | 3.164 | −27.025 | 33.191 | 1.00 | 37.87 | C |
| ATOM | 3160 | O | THR B | 200 | 2.913 | −28.095 | 32.615 | 1.00 | 36.83 | O |
| ATOM | 3161 | CB | THR B | 200 | 5.275 | −26.974 | 34.619 | 1.00 | 49.18 | C |
| ATOM | 3162 | OG1 | THR B | 200 | 5.796 | −27.983 | 33.748 | 1.00 | 50.44 | O |
| ATOM | 3163 | CG2 | THR B | 200 | 5.864 | −27.141 | 36.012 | 1.00 | 48.65 | C |
| ATOM | 3164 | N | TYR B | 201 | 2.946 | −25.832 | 32.624 | 1.00 | 32.62 | N |
| ATOM | 3165 | CA | TYR B | 201 | 2.404 | −25.691 | 31.274 | 1.00 | 31.25 | C |
| ATOM | 3166 | C | TYR B | 201 | 3.263 | −24.749 | 30.492 | 1.00 | 32.57 | C |
| ATOM | 3167 | O | TYR B | 201 | 3.453 | −23.607 | 30.894 | 1.00 | 30.61 | O |
| ATOM | 3168 | CB | TYR B | 201 | 0.942 | −25.219 | 31.305 | 1.00 | 32.36 | C |
| ATOM | 3169 | CG | TYR B | 201 | 0.059 | −26.252 | 31.961 | 1.00 | 33.29 | C |
| ATOM | 3170 | CD1 | TYR B | 201 | −0.266 | −27.426 | 31.301 | 1.00 | 36.37 | C |
| ATOM | 3171 | CD2 | TYR B | 201 | −0.269 | −26.159 | 33.307 | 1.00 | 33.14 | C |
| ATOM | 3172 | CE1 | TYR B | 201 | −0.939 | −28.461 | 31.946 | 1.00 | 39.07 | C |
| ATOM | 3173 | CE2 | TYR B | 201 | −1.022 | −27.145 | 33.940 | 1.00 | 33.91 | C |
| ATOM | 3174 | CZ | TYR B | 201 | −1.354 | −28.300 | 33.257 | 1.00 | 42.76 | C |
| ATOM | 3175 | OH | TYR B | 201 | −2.095 | −29.278 | 33.875 | 1.00 | 43.29 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3176 | N | THR B | 202 | 3.784 | −25.235 | 29.362 | 1.00 | 29.87 | N |
| ATOM | 3177 | CA | THR B | 202 | 4.664 | −24.469 | 28.497 | 1.00 | 29.79 | C |
| ATOM | 3178 | C | THR B | 202 | 4.175 | −24.506 | 27.065 | 1.00 | 32.31 | C |
| ATOM | 3179 | O | THR B | 202 | 3.950 | −25.590 | 26.536 | 1.00 | 28.50 | O |
| ATOM | 3180 | CB | THR B | 202 | 6.073 | −25.054 | 28.607 | 1.00 | 31.80 | C |
| ATOM | 3181 | OG1 | THR B | 202 | 6.505 | −24.910 | 29.962 | 1.00 | 32.64 | O |
| ATOM | 3182 | CG2 | THR B | 202 | 7.048 | −24.423 | 27.635 | 1.00 | 23.56 | C |
| ATOM | 3183 | N | CYS B | 203 | 4.066 | −23.328 | 26.429 | 1.00 | 33.66 | N |
| ATOM | 3184 | CA | CYS B | 203 | 3.710 | −23.222 | 25.016 | 1.00 | 36.05 | C |
| ATOM | 3185 | C | CYS B | 203 | 4.983 | −23.003 | 24.168 | 1.00 | 38.10 | C |
| ATOM | 3186 | O | CYS B | 203 | 5.824 | −22.132 | 24.468 | 1.00 | 36.04 | O |
| ATOM | 3187 | CB | CYS B | 203 | 2.651 | −22.149 | 24.777 | 1.00 | 38.66 | C |
| ATOM | 3188 | SG | CYS B | 203 | 3.292 | −20.491 | 24.453 | 1.00 | 44.80 | S |
| ATOM | 3189 | N | ASN B | 204 | 5.104 | −23.824 | 23.106 | 1.00 | 33.84 | N |
| ATOM | 3190 | CA | ASN B | 204 | 6.239 | −23.842 | 22.173 | 1.00 | 32.22 | C |
| ATOM | 3191 | C | ASN B | 204 | 5.795 | −23.169 | 20.885 | 1.00 | 32.21 | C |
| ATOM | 3192 | O | ASN B | 204 | 4.952 | −23.719 | 20.178 | 1.00 | 31.00 | O |
| ATOM | 3193 | CB | ASN B | 204 | 6.634 | −25.277 | 21.896 | 1.00 | 30.17 | C |
| ATOM | 3194 | CG | ASN B | 204 | 6.520 | −26.128 | 23.111 | 1.00 | 38.12 | C |
| ATOM | 3195 | OD1 | ASN B | 204 | 5.602 | −26.927 | 23.253 | 1.00 | 37.16 | O |
| ATOM | 3196 | ND2 | ASN B | 204 | 7.392 | −25.898 | 24.045 | 1.00 | 28.87 | N |
| ATOM | 3197 | N | VAL B | 205 | 6.270 | −21.951 | 20.637 | 1.00 | 27.66 | N |
| ATOM | 3198 | CA | VAL B | 205 | 5.886 | −21.144 | 19.475 | 1.00 | 27.22 | C |
| ATOM | 3199 | C | VAL B | 205 | 7.004 | −21.201 | 18.440 | 1.00 | 31.49 | C |
| ATOM | 3200 | O | VAL B | 205 | 8.160 | −20.961 | 18.783 | 1.00 | 31.04 | O |
| ATOM | 3201 | CB | VAL B | 205 | 5.568 | −19.682 | 19.902 | 1.00 | 31.28 | C |
| ATOM | 3202 | CG1 | VAL B | 205 | 5.283 | −18.804 | 18.690 | 1.00 | 30.22 | C |
| ATOM | 3203 | CG2 | VAL B | 205 | 4.392 | −19.643 | 20.888 | 1.00 | 30.90 | C |
| ATOM | 3204 | N | ASP B | 206 | 6.641 | −21.477 | 17.173 | 1.00 | 28.61 | N |
| ATOM | 3205 | CA | ASP B | 206 | 7.574 | −21.585 | 16.065 | 1.00 | 30.16 | C |
| ATOM | 3206 | C | ASP B | 206 | 7.090 | −20.738 | 14.910 | 1.00 | 34.78 | C |
| ATOM | 3207 | O | ASP B | 206 | 5.972 | −20.947 | 14.446 | 1.00 | 36.24 | O |
| ATOM | 3208 | CB | ASP B | 206 | 7.660 | −23.062 | 15.625 | 1.00 | 33.28 | C |
| ATOM | 3209 | CG | ASP B | 206 | 8.698 | −23.342 | 14.562 | 1.00 | 52.13 | C |
| ATOM | 3210 | OD1 | ASP B | 206 | 9.832 | −22.835 | 14.692 | 1.00 | 57.75 | O |
| ATOM | 3211 | OD2 | ASP B | 206 | 8.379 | −24.068 | 13.600 | 1.00 | 60.83 | O |
| ATOM | 3212 | N | HIS B | 207 | 7.902 | −19.765 | 14.472 | 1.00 | 30.23 | N |
| ATOM | 3213 | CA | HIS B | 207 | 7.620 | −18.888 | 13.324 | 1.00 | 28.47 | C |
| ATOM | 3214 | C | HIS B | 207 | 8.801 | −19.074 | 12.391 | 1.00 | 33.31 | C |
| ATOM | 3215 | O | HIS B | 207 | 9.825 | −18.399 | 12.543 | 1.00 | 32.79 | O |
| ATOM | 3216 | CB | HIS B | 207 | 7.460 | −17.401 | 13.748 | 1.00 | 27.76 | C |
| ATOM | 3217 | CG | HIS B | 207 | 7.115 | −16.485 | 12.610 | 1.00 | 29.22 | C |
| ATOM | 3218 | ND1 | HIS B | 207 | 7.845 | −15.344 | 12.359 | 1.00 | 30.66 | N |
| ATOM | 3219 | CD2 | HIS B | 207 | 6.135 | −16.576 | 11.689 | 1.00 | 29.34 | C |
| ATOM | 3220 | CE1 | HIS B | 207 | 7.320 | −14.808 | 11.272 | 1.00 | 29.35 | C |
| ATOM | 3221 | NE2 | HIS B | 207 | 6.298 | −15.523 | 10.827 | 1.00 | 29.00 | N |
| ATOM | 3222 | N | LYS B | 208 | 8.689 | −20.070 | 11.486 | 1.00 | 32.24 | N |
| ATOM | 3223 | CA | LYS B | 208 | 9.742 | −20.420 | 10.514 | 1.00 | 32.61 | C |
| ATOM | 3224 | C | LYS B | 208 | 10.241 | −19.224 | 9.686 | 1.00 | 34.27 | C |
| ATOM | 3225 | O | LYS B | 208 | 11.465 | −19.032 | 9.650 | 1.00 | 35.56 | O |
| ATOM | 3226 | CB | LYS B | 208 | 9.321 | −21.585 | 9.598 | 1.00 | 34.93 | C |
| ATOM | 3227 | CG | LYS B | 208 | 9.346 | −22.944 | 10.279 | 1.00 | 57.95 | C |
| ATOM | 3228 | CD | LYS B | 208 | 9.159 | −24.081 | 9.256 | 1.00 | 68.97 | C |
| ATOM | 3229 | CE | LYS B | 208 | 8.739 | −25.405 | 9.856 | 1.00 | 69.44 | C |
| ATOM | 3230 | NZ | LYS B | 208 | 7.263 | −25.468 | 10.066 | 1.00 | 80.47 | N |
| ATOM | 3231 | N | PRO B | 209 | 9.360 | −18.362 | 9.118 | 1.00 | 27.30 | N |
| ATOM | 3232 | CA | PRO B | 209 | 9.851 | −17.202 | 8.323 | 1.00 | 26.84 | C |
| ATOM | 3233 | C | PRO B | 209 | 10.906 | −16.284 | 8.973 | 1.00 | 32.64 | C |
| ATOM | 3234 | O | PRO B | 209 | 11.754 | −15.751 | 8.273 | 1.00 | 32.54 | O |
| ATOM | 3235 | CB | PRO B | 209 | 8.577 | −16.422 | 8.032 | 1.00 | 28.01 | C |
| ATOM | 3236 | CG | PRO B | 209 | 7.479 | −17.446 | 8.039 | 1.00 | 31.40 | C |
| ATOM | 3237 | CD | PRO B | 209 | 7.882 | −18.456 | 9.072 | 1.00 | 27.72 | C |
| ATOM | 3238 | N | SER B | 210 | 10.863 | −16.102 | 10.303 | 1.00 | 30.97 | N |
| ATOM | 3239 | CA | SER B | 210 | 11.851 | −15.301 | 11.035 | 1.00 | 31.12 | C |
| ATOM | 3240 | C | SER B | 210 | 12.828 | −16.208 | 11.831 | 1.00 | 33.71 | C |
| ATOM | 3241 | O | SER B | 210 | 13.680 | −15.694 | 12.561 | 1.00 | 31.57 | O |
| ATOM | 3242 | CB | SER B | 210 | 11.141 | −14.335 | 11.978 | 1.00 | 32.52 | C |
| ATOM | 3243 | OG | SER B | 210 | 10.427 | −15.074 | 12.949 | 1.00 | 36.43 | O |
| ATOM | 3244 | N | ASN B | 211 | 12.700 | −17.551 | 11.684 | 1.00 | 31.38 | N |
| ATOM | 3245 | CA | ASN B | 211 | 13.505 | −18.525 | 12.412 | 1.00 | 32.35 | C |
| ATOM | 3246 | C | ASN B | 211 | 13.372 | −18.293 | 13.946 | 1.00 | 38.88 | C |
| ATOM | 3247 | O | ASN B | 211 | 14.356 | −18.393 | 14.688 | 1.00 | 40.11 | O |
| ATOM | 3248 | CB | ASN B | 211 | 14.972 | −18.456 | 11.938 | 1.00 | 32.75 | C |
| ATOM | 3249 | CG | ASN B | 211 | 15.744 | −19.737 | 12.136 | 1.00 | 60.03 | C |
| ATOM | 3250 | OD1 | ASN B | 211 | 15.179 | −20.825 | 12.352 | 1.00 | 49.83 | O |
| ATOM | 3251 | ND2 | ASN B | 211 | 17.064 | −19.645 | 12.023 | 1.00 | 55.41 | N |
| ATOM | 3252 | N | THR B | 212 | 12.151 | −17.940 | 14.410 | 1.00 | 35.29 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3253 | CA | THR B | 212 | 11.895 | −17.660 | 15.829 | 1.00 | 34.73 | C |
| ATOM | 3254 | C | THR B | 212 | 11.282 | −18.872 | 16.484 | 1.00 | 36.26 | C |
| ATOM | 3255 | O | THR B | 212 | 10.338 | −19.430 | 15.954 | 1.00 | 35.26 | O |
| ATOM | 3256 | CB | THR B | 212 | 10.998 | −16.414 | 16.010 | 1.00 | 39.25 | C |
| ATOM | 3257 | OG1 | THR B | 212 | 11.601 | −15.318 | 15.326 | 1.00 | 41.08 | O |
| ATOM | 3258 | CG2 | THR B | 212 | 10.803 | −16.029 | 17.484 | 1.00 | 34.63 | C |
| ATOM | 3259 | N | LYS B | 213 | 11.813 | −19.255 | 17.649 | 1.00 | 33.39 | N |
| ATOM | 3260 | CA | LYS B | 213 | 11.321 | −20.363 | 18.460 | 1.00 | 31.98 | C |
| ATOM | 3261 | C | LYS B | 213 | 11.266 | −19.895 | 19.923 | 1.00 | 31.72 | C |
| ATOM | 3262 | O | LYS B | 213 | 12.285 | −19.450 | 20.449 | 1.00 | 28.77 | O |
| ATOM | 3263 | CB | LYS B | 213 | 12.215 | −21.607 | 18.289 | 1.00 | 34.83 | C |
| ATOM | 3264 | CG | LYS B | 213 | 11.842 | −22.463 | 17.088 | 1.00 | 39.85 | C |
| ATOM | 3265 | CD | LYS B | 213 | 12.832 | −23.615 | 16.880 | 1.00 | 48.55 | C |
| ATOM | 3266 | CE | LYS B | 213 | 13.783 | −23.400 | 15.724 | 1.00 | 65.77 | C |
| ATOM | 3267 | NZ | LYS B | 213 | 13.297 | −24.045 | 14.479 | 1.00 | 81.18 | N |
| ATOM | 3268 | N | VAL B | 214 | 10.062 | −19.927 | 20.553 | 1.00 | 28.13 | N |
| ATOM | 3269 | CA | VAL B | 214 | 9.891 | −19.487 | 21.946 | 1.00 | 27.74 | C |
| ATOM | 3270 | C | VAL B | 214 | 9.174 | −20.557 | 22.722 | 1.00 | 30.49 | C |
| ATOM | 3271 | O | VAL B | 214 | 8.161 | −21.055 | 22.266 | 1.00 | 29.76 | O |
| ATOM | 3272 | CB | VAL B | 214 | 9.123 | −18.149 | 22.054 | 1.00 | 32.19 | C |
| ATOM | 3273 | CG1 | VAL B | 214 | 9.131 | −17.631 | 23.488 | 1.00 | 32.93 | C |
| ATOM | 3274 | CG2 | VAL B | 214 | 9.699 | −17.098 | 21.102 | 1.00 | 32.27 | C |
| ATOM | 3275 | N | ASP B | 215 | 9.690 | −20.895 | 23.903 | 1.00 | 27.85 | N |
| ATOM | 3276 | CA | ASP B | 215 | 9.105 | −21.849 | 24.836 | 1.00 | 27.00 | C |
| ATOM | 3277 | C | ASP B | 215 | 8.792 | −20.977 | 26.058 | 1.00 | 32.99 | C |
| ATOM | 3278 | O | ASP B | 215 | 9.717 | −20.496 | 26.689 | 1.00 | 32.38 | O |
| ATOM | 3279 | CB | ASP B | 215 | 10.101 | −22.973 | 25.156 | 1.00 | 28.80 | C |
| ATOM | 3280 | CG | ASP B | 215 | 10.472 | −23.818 | 23.938 | 1.00 | 42.50 | C |
| ATOM | 3281 | OD1 | ASP B | 215 | 9.538 | −24.257 | 23.201 | 1.00 | 43.67 | O |
| ATOM | 3282 | OD2 | ASP B | 215 | 11.695 | −24.069 | 23.731 | 1.00 | 42.54 | O |
| ATOM | 3283 | N | LYS B | 216 | 7.505 | −20.661 | 26.306 | 1.00 | 31.21 | N |
| ATOM | 3284 | CA | LYS B | 216 | 7.098 | −19.746 | 27.376 | 1.00 | 31.07 | C |
| ATOM | 3285 | C | LYS B | 216 | 6.338 | −20.496 | 28.427 | 1.00 | 36.27 | C |
| ATOM | 3286 | O | LYS B | 216 | 5.364 | −21.166 | 28.113 | 1.00 | 34.25 | O |
| ATOM | 3287 | CB | LYS B | 216 | 6.228 | −18.600 | 26.792 | 1.00 | 32.61 | C |
| ATOM | 3288 | CG | LYS B | 216 | 6.360 | −17.249 | 27.505 | 1.00 | 35.81 | C |
| ATOM | 3289 | CD | LYS B | 216 | 7.763 | −16.659 | 27.396 | 1.00 | 49.25 | C |
| ATOM | 3290 | CE | LYS B | 216 | 7.808 | −15.154 | 27.477 | 1.00 | 67.19 | C |
| ATOM | 3291 | NZ | LYS B | 216 | 7.258 | −14.614 | 28.753 | 1.00 | 79.78 | N |
| ATOM | 3292 | N | ARG B | 217 | 6.802 | −20.415 | 29.679 | 1.00 | 36.33 | N |
| ATOM | 3293 | CA | ARG B | 217 | 6.145 | −21.050 | 30.810 | 1.00 | 36.43 | C |
| ATOM | 3294 | C | ARG B | 217 | 4.984 | −20.150 | 31.204 | 1.00 | 38.52 | C |
| ATOM | 3295 | O | ARG B | 217 | 5.190 | −18.959 | 31.455 | 1.00 | 38.62 | O |
| ATOM | 3296 | CB | ARG B | 217 | 7.130 | −21.191 | 31.986 | 1.00 | 41.88 | C |
| ATOM | 3297 | CG | ARG B | 217 | 6.570 | −21.882 | 33.246 | 1.00 | 57.95 | C |
| ATOM | 3298 | CD | ARG B | 217 | 6.369 | −23.379 | 33.105 | 1.00 | 68.93 | C |
| ATOM | 3299 | NE | ARG B | 217 | 7.642 | −24.071 | 32.888 | 1.00 | 88.74 | N |
| ATOM | 3300 | CZ | ARG B | 217 | 8.554 | −24.337 | 33.825 | 1.00 | 102.94 | C |
| ATOM | 3301 | NH1 | ARG B | 217 | 8.345 | −23.984 | 35.093 | 1.00 | 88.20 | N |
| ATOM | 3302 | NH2 | ARG B | 217 | 9.682 | −24.964 | 33.503 | 1.00 | 85.65 | N |
| ATOM | 3303 | N | VAL B | 218 | 3.779 | −20.711 | 31.265 | 1.00 | 34.05 | N |
| ATOM | 3304 | CA | VAL B | 218 | 2.587 | −19.970 | 31.666 | 1.00 | 34.14 | C |
| ATOM | 3305 | C | VAL B | 218 | 2.279 | −20.326 | 33.143 | 1.00 | 39.76 | C |
| ATOM | 3306 | O | VAL B | 218 | 2.022 | −21.485 | 33.445 | 1.00 | 38.45 | O |
| ATOM | 3307 | CB | VAL B | 218 | 1.429 | −20.278 | 30.696 | 1.00 | 36.40 | C |
| ATOM | 3308 | CG1 | VAL B | 218 | 0.196 | −19.452 | 31.037 | 1.00 | 36.23 | C |
| ATOM | 3309 | CG2 | VAL B | 218 | 1.866 | −20.008 | 29.265 | 1.00 | 35.40 | C |
| ATOM | 3310 | N | GLU B | 219 | 2.366 | −19.347 | 34.071 | 1.00 | 38.36 | N |
| ATOM | 3311 | CA | GLU B | 219 | 2.122 | −19.611 | 35.504 | 1.00 | 60.90 | C |
| ATOM | 3312 | C | GLU B | 219 | 0.977 | −18.775 | 36.061 | 1.00 | 84.72 | C |
| ATOM | 3313 | O | GLU B | 219 | 0.847 | −17.607 | 35.713 | 1.00 | 55.25 | O |
| ATOM | 3314 | CB | GLU B | 219 | 3.415 | −19.380 | 36.302 | 1.00 | 62.96 | C |
| ATOM | 3315 | CG | GLU B | 219 | 4.388 | −20.548 | 36.199 | 1.00 | 72.73 | C |
| ATOM | 3316 | CD | GLU B | 219 | 5.874 | −20.224 | 36.185 | 1.00 | 88.62 | C |
| ATOM | 3317 | OE1 | GLU B | 219 | 6.648 | −21.018 | 36.767 | 1.00 | 81.43 | O |
| ATOM | 3318 | OE2 | GLU B | 219 | 6.274 | −19.216 | 35.555 | 1.00 | 74.99 | O |
| ATOM | 3319 | N | GLY B | 236 | −26.030 | −36.040 | 41.275 | 1.00 | 64.72 | N |
| ATOM | 3320 | CA | GLY B | 236 | −25.369 | −34.819 | 40.821 | 1.00 | 63.86 | C |
| ATOM | 3321 | C | GLY B | 236 | −24.920 | −34.952 | 39.381 | 1.00 | 65.78 | C |
| ATOM | 3322 | O | GLY B | 236 | −23.784 | −35.364 | 39.121 | 1.00 | 66.11 | O |
| ATOM | 3323 | N | GLY B | 237 | −25.837 | −34.650 | 38.455 | 1.00 | 58.41 | N |
| ATOM | 3324 | CA | GLY B | 237 | −25.621 | −34.793 | 37.019 | 1.00 | 55.65 | C |
| ATOM | 3325 | C | GLY B | 237 | −25.966 | −36.201 | 36.558 | 1.00 | 54.52 | C |
| ATOM | 3326 | O | GLY B | 237 | −26.042 | −37.112 | 37.390 | 1.00 | 54.29 | O |
| ATOM | 3327 | N | PRO B | 238 | −26.192 | −36.447 | 35.244 | 1.00 | 46.98 | N |
| ATOM | 3328 | CA | PRO B | 238 | −26.535 | −37.821 | 34.804 | 1.00 | 44.68 | C |
| ATOM | 3329 | C | PRO B | 238 | −25.394 | −38.828 | 34.962 | 1.00 | 41.97 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3330 | O | PRO B | 238 | −24.231 | −38.430 | 35.016 | 1.00 | 41.24 | O |
| ATOM | 3331 | CB | PRO B | 238 | −26.965 | −37.651 | 33.337 | 1.00 | 46.17 | C |
| ATOM | 3332 | CG | PRO B | 238 | −26.938 | −36.205 | 33.051 | 1.00 | 50.81 | C |
| ATOM | 3333 | CD | PRO B | 238 | −26.145 | −35.512 | 34.108 | 1.00 | 47.22 | C |
| ATOM | 3334 | N | SER B | 239 | −25.731 | −40.117 | 35.092 | 1.00 | 34.73 | N |
| ATOM | 3335 | CA | SER B | 239 | −24.737 | −41.202 | 35.245 | 1.00 | 33.16 | C |
| ATOM | 3336 | C | SER B | 239 | −24.936 | −42.250 | 34.140 | 1.00 | 31.96 | C |
| ATOM | 3337 | O | SER B | 239 | −26.076 | −42.572 | 33.797 | 1.00 | 27.44 | O |
| ATOM | 3338 | CB | SER B | 239 | −24.854 | −41.869 | 36.613 | 1.00 | 37.09 | C |
| ATOM | 3339 | OG | SER B | 239 | −24.150 | −41.114 | 37.583 | 1.00 | 51.67 | O |
| ATOM | 3340 | N | VAL B | 240 | −23.818 | −42.789 | 33.614 | 1.00 | 29.19 | N |
| ATOM | 3341 | CA | VAL B | 240 | −23.831 | −43.761 | 32.520 | 1.00 | 29.79 | C |
| ATOM | 3342 | C | VAL B | 240 | −23.363 | −45.177 | 32.968 | 1.00 | 34.22 | C |
| ATOM | 3343 | O | VAL B | 240 | −22.344 | −45.295 | 33.643 | 1.00 | 35.54 | O |
| ATOM | 3344 | CB | VAL B | 240 | −22.949 | −43.213 | 31.365 | 1.00 | 32.68 | C |
| ATOM | 3345 | CG1 | VAL B | 240 | −23.011 | −44.115 | 30.140 | 1.00 | 31.19 | C |
| ATOM | 3346 | CG2 | VAL B | 240 | −23.349 | −41.778 | 31.016 | 1.00 | 32.46 | C |
| ATOM | 3347 | N | PHE B | 241 | −24.091 | −46.233 | 32.552 | 1.00 | 29.06 | N |
| ATOM | 3348 | CA | PHE B | 241 | −23.738 | −47.643 | 32.786 | 1.00 | 27.76 | C |
| ATOM | 3349 | C | PHE B | 241 | −23.639 | −48.324 | 31.414 | 1.00 | 30.49 | C |
| ATOM | 3350 | O | PHE B | 241 | −24.539 | −48.184 | 30.600 | 1.00 | 31.40 | O |
| ATOM | 3351 | CB | PHE B | 241 | −24.738 | −48.342 | 33.738 | 1.00 | 29.59 | C |
| ATOM | 3352 | CG | PHE B | 241 | −24.764 | −47.629 | 35.069 | 1.00 | 31.58 | C |
| ATOM | 3353 | CD1 | PHE B | 241 | −23.730 | −47.798 | 35.981 | 1.00 | 34.37 | C |
| ATOM | 3354 | CD2 | PHE B | 241 | −25.686 | −46.622 | 35.313 | 1.00 | 33.90 | C |
| ATOM | 3355 | CE1 | PHE B | 241 | −23.655 | −47.020 | 37.130 | 1.00 | 34.97 | C |
| ATOM | 3356 | CE2 | PHE B | 241 | −25.598 | −45.835 | 36.458 | 1.00 | 36.33 | C |
| ATOM | 3357 | CZ | PHE B | 241 | −24.575 | −46.030 | 37.351 | 1.00 | 34.23 | C |
| ATOM | 3358 | N | LEU B | 242 | −22.522 | −48.990 | 31.134 | 1.00 | 25.45 | N |
| ATOM | 3359 | CA | LEU B | 242 | −22.272 | −49.659 | 29.863 | 1.00 | 24.34 | C |
| ATOM | 3360 | C | LEU B | 242 | −22.296 | −51.187 | 30.143 | 1.00 | 27.71 | C |
| ATOM | 3361 | O | LEU B | 242 | −21.559 | −51.641 | 31.004 | 1.00 | 26.80 | O |
| ATOM | 3362 | CB | LEU B | 242 | −20.918 | −49.148 | 29.280 | 1.00 | 22.97 | C |
| ATOM | 3363 | CG | LEU B | 242 | −20.493 | −49.721 | 27.927 | 1.00 | 27.67 | C |
| ATOM | 3364 | CD1 | LEU B | 242 | −21.530 | −49.446 | 26.842 | 1.00 | 28.34 | C |
| ATOM | 3365 | CD2 | LEU B | 242 | −19.175 | −49.182 | 27.512 | 1.00 | 28.21 | C |
| ATOM | 3366 | N | PHE B | 243 | −23.167 | −51.967 | 29.452 | 1.00 | 25.31 | N |
| ATOM | 3367 | CA | PHE B | 243 | −23.336 | −53.421 | 29.718 | 1.00 | 25.22 | C |
| ATOM | 3368 | C | PHE B | 243 | −22.802 | −54.290 | 28.580 | 1.00 | 29.94 | C |
| ATOM | 3369 | O | PHE B | 243 | −23.078 | −54.001 | 27.426 | 1.00 | 28.50 | O |
| ATOM | 3370 | CB | PHE B | 243 | −24.816 | −53.768 | 29.970 | 1.00 | 25.88 | C |
| ATOM | 3371 | CG | PHE B | 243 | −25.390 | −53.069 | 31.175 | 1.00 | 26.37 | C |
| ATOM | 3372 | CD2 | PHE B | 243 | −25.349 | −53.669 | 32.436 | 1.00 | 27.05 | C |
| ATOM | 3373 | CD1 | PHE B | 243 | −25.914 | −51.785 | 31.073 | 1.00 | 27.20 | C |
| ATOM | 3374 | CE2 | PHE B | 243 | −25.809 | −52.992 | 33.567 | 1.00 | 28.65 | C |
| ATOM | 3375 | CE1 | PHE B | 243 | −26.375 | −51.108 | 32.213 | 1.00 | 27.20 | C |
| ATOM | 3376 | CZ | PHE B | 243 | −26.345 | −51.726 | 33.447 | 1.00 | 26.04 | C |
| ATOM | 3377 | N | PRO B | 244 | −22.091 | −55.405 | 28.878 | 1.00 | 26.74 | N |
| ATOM | 3378 | CA | PRO B | 244 | −21.574 | −56.251 | 27.781 | 1.00 | 25.98 | C |
| ATOM | 3379 | C | PRO B | 244 | −22.683 | −57.065 | 27.136 | 1.00 | 28.76 | C |
| ATOM | 3380 | O | PRO B | 244 | −23.796 | −57.090 | 27.665 | 1.00 | 29.19 | O |
| ATOM | 3381 | CB | PRO B | 244 | −20.577 | −57.166 | 28.505 | 1.00 | 27.66 | C |
| ATOM | 3382 | CG | PRO B | 244 | −21.138 | −57.296 | 29.893 | 1.00 | 30.11 | C |
| ATOM | 3383 | CD | PRO B | 244 | −21.751 | −55.966 | 30.206 | 1.00 | 25.88 | C |
| ATOM | 3384 | N | PRO B | 245 | −22.407 | −57.797 | 26.039 | 1.00 | 23.95 | N |
| ATOM | 3385 | CA | PRO B | 245 | −23.453 | −58.682 | 25.485 | 1.00 | 23.27 | C |
| ATOM | 3386 | C | PRO B | 245 | −23.730 | −59.875 | 26.411 | 1.00 | 29.52 | C |
| ATOM | 3387 | O | PRO B | 245 | −22.905 | −60.184 | 27.272 | 1.00 | 28.91 | O |
| ATOM | 3388 | CB | PRO B | 245 | −22.862 | −59.152 | 24.156 | 1.00 | 23.80 | C |
| ATOM | 3389 | CG | PRO B | 245 | −21.514 | −58.566 | 24.045 | 1.00 | 26.17 | C |
| ATOM | 3390 | CD | PRO B | 245 | −21.131 | −57.923 | 25.305 | 1.00 | 22.74 | C |
| ATOM | 3391 | N | LYS B | 246 | −24.877 | −60.560 | 26.230 | 1.00 | 27.64 | N |
| ATOM | 3392 | CA | LYS B | 246 | −25.178 | −61.790 | 26.981 | 1.00 | 26.75 | C |
| ATOM | 3393 | C | LYS B | 246 | −24.169 | −62.860 | 26.482 | 1.00 | 32.49 | C |
| ATOM | 3394 | O | LYS B | 246 | −23.898 | −62.891 | 25.290 | 1.00 | 32.14 | O |
| ATOM | 3395 | CB | LYS B | 246 | −26.622 | −62.260 | 26.735 | 1.00 | 28.07 | C |
| ATOM | 3396 | CG | LYS B | 246 | −27.649 | −61.442 | 27.516 | 1.00 | 48.97 | C |
| ATOM | 3397 | CD | LYS B | 246 | −29.095 | −61.520 | 26.968 | 1.00 | 63.12 | C |
| ATOM | 3398 | CE | LYS B | 246 | −29.910 | −62.707 | 27.442 | 1.00 | 78.95 | C |
| ATOM | 3399 | NZ | LYS B | 246 | −31.276 | −62.308 | 27.900 | 1.00 | 87.11 | N |
| ATOM | 3400 | N | PRO B | 247 | −23.553 | −63.705 | 27.343 | 1.00 | 31.53 | N |
| ATOM | 3401 | CA | PRO B | 247 | −22.555 | −64.686 | 26.839 | 1.00 | 31.16 | C |
| ATOM | 3402 | C | PRO B | 247 | −23.021 | −65.657 | 25.741 | 1.00 | 33.51 | C |
| ATOM | 3403 | O | PRO B | 247 | −22.227 | −65.978 | 24.881 | 1.00 | 32.71 | O |
| ATOM | 3404 | CB | PRO B | 247 | −22.138 | −65.438 | 28.105 | 1.00 | 32.75 | C |
| ATOM | 3405 | CG | PRO B | 247 | −22.393 | −64.461 | 29.198 | 1.00 | 36.45 | C |
| ATOM | 3406 | CD | PRO B | 247 | −23.677 | −63.795 | 28.811 | 1.00 | 31.87 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3407 | N | LYS B | 248 | −24.288 | −66.101 | 25.755 | 1.00 | 29.87 | N |
| ATOM | 3408 | CA | LYS B | 248 | −24.837 | −67.015 | 24.728 | 1.00 | 28.90 | C |
| ATOM | 3409 | C | LYS B | 248 | −24.872 | −66.347 | 23.341 | 1.00 | 29.14 | C |
| ATOM | 3410 | O | LYS B | 248 | −24.677 | −67.007 | 22.320 | 1.00 | 27.16 | O |
| ATOM | 3411 | CB | LYS B | 248 | −26.284 | −67.475 | 25.105 | 1.00 | 31.80 | C |
| ATOM | 3412 | CG | LYS B | 248 | −26.490 | −68.987 | 25.065 | 1.00 | 45.97 | C |
| ATOM | 3413 | CD | LYS B | 248 | −27.923 | −69.397 | 24.748 | 1.00 | 51.61 | C |
| ATOM | 3414 | CE | LYS B | 248 | −28.920 | −68.988 | 25.790 | 1.00 | 67.04 | C |
| ATOM | 3415 | NZ | LYS B | 248 | −30.210 | −69.722 | 25.628 | 1.00 | 75.30 | N |
| ATOM | 3416 | N | ASP B | 249 | −25.131 | −65.030 | 23.324 | 1.00 | 25.74 | N |
| ATOM | 3417 | CA | ASP B | 249 | −25.299 | −64.236 | 22.115 | 1.00 | 24.58 | C |
| ATOM | 3418 | C | ASP B | 249 | −24.054 | −64.103 | 21.290 | 1.00 | 28.91 | C |
| ATOM | 3419 | O | ASP B | 249 | −24.143 | −64.104 | 20.066 | 1.00 | 28.42 | O |
| ATOM | 3420 | CB | ASP B | 249 | −25.854 | −62.842 | 22.449 | 1.00 | 25.45 | C |
| ATOM | 3421 | CG | ASP B | 249 | −27.276 | −62.798 | 22.958 | 1.00 | 36.96 | C |
| ATOM | 3422 | OD1 | ASP B | 249 | −27.971 | −63.836 | 22.880 | 1.00 | 37.71 | O |
| ATOM | 3423 | OD2 | ASP B | 249 | −27.720 | −61.707 | 23.382 | 1.00 | 46.77 | O |
| ATOM | 3424 | N | THR B | 250 | −22.899 | −63.999 | 21.934 | 1.00 | 26.17 | N |
| ATOM | 3425 | CA | THR B | 250 | −21.626 | −63.855 | 21.220 | 1.00 | 26.06 | C |
| ATOM | 3426 | C | THR B | 250 | −21.075 | −65.210 | 20.714 | 1.00 | 31.06 | C |
| ATOM | 3427 | O | THR B | 250 | −20.043 | −65.210 | 20.062 | 1.00 | 31.98 | O |
| ATOM | 3428 | CB | THR B | 250 | −20.582 | −63.262 | 22.172 | 1.00 | 33.31 | C |
| ATOM | 3429 | OG1 | THR B | 250 | −20.354 | −64.223 | 23.193 | 1.00 | 33.52 | O |
| ATOM | 3430 | CG2 | THR B | 250 | −21.032 | −61.945 | 22.814 | 1.00 | 31.34 | C |
| ATOM | 3431 | N | LEU B | 251 | −21.677 | −66.351 | 21.118 | 1.00 | 25.98 | N |
| ATOM | 3432 | CA | LEU B | 251 | −21.196 | −67.698 | 20.837 | 1.00 | 24.03 | C |
| ATOM | 3433 | C | LEU B | 251 | −22.037 | −68.433 | 19.820 | 1.00 | 28.69 | C |
| ATOM | 3434 | O | LEU B | 251 | −21.600 | −69.476 | 19.344 | 1.00 | 26.29 | O |
| ATOM | 3435 | CB | LEU B | 251 | −21.212 | −68.497 | 22.173 | 1.00 | 23.88 | C |
| ATOM | 3436 | CG | LEU B | 251 | −20.280 | −67.999 | 23.307 | 1.00 | 24.62 | C |
| ATOM | 3437 | CD1 | LEU B | 251 | −20.559 | −68.740 | 24.573 | 1.00 | 24.75 | C |
| ATOM | 3438 | CD2 | LEU B | 251 | −18.790 | −68.125 | 22.939 | 1.00 | 19.03 | C |
| ATOM | 3439 | N | MET B | 252 | −23.248 | −67.937 | 19.514 | 1.00 | 29.47 | N |
| ATOM | 3440 | CA | MET B | 252 | −24.172 | −68.545 | 18.554 | 1.00 | 31.08 | C |
| ATOM | 3441 | C | MET B | 252 | −24.440 | −67.528 | 17.424 | 1.00 | 38.81 | C |
| ATOM | 3442 | O | MET B | 252 | −24.989 | −66.462 | 17.698 | 1.00 | 38.28 | O |
| ATOM | 3443 | CB | MET B | 252 | −25.498 | −68.885 | 19.259 | 1.00 | 33.40 | C |
| ATOM | 3444 | CG | MET B | 252 | −25.371 | −69.924 | 20.313 | 1.00 | 36.88 | C |
| ATOM | 3445 | SD | MET B | 252 | −26.982 | −70.399 | 21.047 | 1.00 | 42.27 | S |
| ATOM | 3446 | CE | MET B | 252 | −27.812 | −71.071 | 19.627 | 1.00 | 39.53 | C |
| ATOM | 3447 | N | ILE B | 253 | −24.096 | −67.873 | 16.150 | 1.00 | 38.76 | N |
| ATOM | 3448 | CA | ILE B | 253 | −24.316 | −66.986 | 14.991 | 1.00 | 38.46 | C |
| ATOM | 3449 | C | ILE B | 253 | −25.822 | −66.669 | 14.807 | 1.00 | 41.81 | C |
| ATOM | 3450 | O | ILE B | 253 | −26.154 | −65.659 | 14.198 | 1.00 | 42.04 | O |
| ATOM | 3451 | CB | ILE B | 253 | −23.671 | −67.582 | 13.683 | 1.00 | 42.08 | C |
| ATOM | 3452 | CG1 | ILE B | 253 | −23.439 | −66.503 | 12.591 | 1.00 | 42.60 | C |
| ATOM | 3453 | CG2 | ILE B | 253 | −24.517 | −68.743 | 13.101 | 1.00 | 42.03 | C |
| ATOM | 3454 | CD1 | ILE B | 253 | −22.448 | −65.319 | 12.955 | 1.00 | 48.00 | C |
| ATOM | 3455 | N | SER B | 254 | −26.720 | −67.532 | 15.311 | 1.00 | 37.82 | N |
| ATOM | 3456 | CA | SER B | 254 | −28.156 | −67.313 | 15.196 | 1.00 | 37.85 | C |
| ATOM | 3457 | C | SER B | 254 | −28.653 | −66.165 | 16.079 | 1.00 | 41.99 | C |
| ATOM | 3458 | O | SER B | 254 | −29.621 | −65.501 | 15.709 | 1.00 | 43.30 | O |
| ATOM | 3459 | CB | SER B | 254 | −28.919 | −68.595 | 15.516 | 1.00 | 41.18 | C |
| ATOM | 3460 | OG | SER B | 254 | −28.641 | −69.083 | 16.818 | 1.00 | 49.30 | O |
| ATOM | 3461 | N | ARG B | 255 | −28.001 | −65.925 | 17.231 | 1.00 | 36.23 | N |
| ATOM | 3462 | CA | ARG B | 255 | −28.395 | −64.861 | 18.157 | 1.00 | 34.30 | C |
| ATOM | 3463 | C | ARG B | 255 | −27.673 | −63.541 | 17.843 | 1.00 | 35.47 | C |
| ATOM | 3464 | O | ARG B | 255 | −26.661 | −63.547 | 17.140 | 1.00 | 34.37 | O |
| ATOM | 3465 | CB | ARG B | 255 | −28.100 | −65.298 | 19.592 | 1.00 | 34.01 | C |
| ATOM | 3466 | CG | ARG B | 255 | −28.726 | −66.624 | 19.998 | 1.00 | 35.47 | C |
| ATOM | 3467 | CD | ARG B | 255 | −28.504 | −66.893 | 21.480 | 1.00 | 43.94 | C |
| ATOM | 3468 | NE | ARG B | 255 | −29.705 | −66.638 | 22.278 | 1.00 | 54.46 | N |
| ATOM | 3469 | CZ | ARG B | 255 | −30.711 | −67.497 | 22.446 | 1.00 | 73.44 | C |
| ATOM | 3470 | NH1 | ARG B | 255 | −30.683 | −68.697 | 21.865 | 1.00 | 52.24 | N |
| ATOM | 3471 | NH2 | ARG B | 255 | −31.758 | −67.162 | 23.193 | 1.00 | 71.38 | N |
| ATOM | 3472 | N | THR B | 256 | −28.181 | −62.409 | 18.379 | 1.00 | 32.38 | N |
| ATOM | 3473 | CA | THR B | 256 | −27.598 | −61.073 | 18.131 | 1.00 | 32.01 | C |
| ATOM | 3474 | C | THR B | 256 | −26.924 | −60.460 | 19.404 | 1.00 | 31.75 | C |
| ATOM | 3475 | O | THR B | 256 | −27.621 | −59.985 | 20.302 | 1.00 | 28.53 | O |
| ATOM | 3476 | CB | THR B | 256 | −28.688 | −60.125 | 17.566 | 1.00 | 49.27 | C |
| ATOM | 3477 | OG1 | THR B | 256 | −29.279 | −60.718 | 16.399 | 1.00 | 49.23 | O |
| ATOM | 3478 | CG2 | THR B | 256 | −28.129 | −58.726 | 17.214 | 1.00 | 48.98 | C |
| ATOM | 3479 | N | PRO B | 257 | −25.571 | −60.389 | 19.457 | 1.00 | 25.90 | N |
| ATOM | 3480 | CA | PRO B | 257 | −24.915 | −59.788 | 20.637 | 1.00 | 25.21 | C |
| ATOM | 3481 | C | PRO B | 257 | −24.953 | −58.254 | 20.608 | 1.00 | 29.92 | C |
| ATOM | 3482 | O | PRO B | 257 | −24.811 | −57.651 | 19.543 | 1.00 | 31.24 | O |
| ATOM | 3483 | CB | PRO B | 257 | −23.497 | −60.353 | 20.552 | 1.00 | 26.06 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3484 | CG | PRO B | 257 | −23.279 | −60.671 | 19.147 | 1.00 | 27.05 | C |
| ATOM | 3485 | CD | PRO B | 257 | −24.584 | −60.880 | 18.480 | 1.00 | 23.23 | C |
| ATOM | 3486 | N | GLU B | 258 | −25.223 | −57.620 | 21.750 | 1.00 | 26.71 | N |
| ATOM | 3487 | CA | GLU B | 258 | −25.324 | −56.155 | 21.833 | 1.00 | 25.92 | C |
| ATOM | 3488 | C | GLU B | 258 | −24.646 | −55.580 | 23.061 | 1.00 | 29.92 | C |
| ATOM | 3489 | O | GLU B | 258 | −24.820 | −56.112 | 24.153 | 1.00 | 31.14 | O |
| ATOM | 3490 | CB | GLU B | 258 | −26.804 | −55.719 | 21.928 | 1.00 | 26.69 | C |
| ATOM | 3491 | CG | GLU B | 258 | −27.725 | −56.326 | 20.891 | 1.00 | 34.25 | C |
| ATOM | 3492 | CD | GLU B | 258 | −29.185 | −55.997 | 21.103 | 1.00 | 60.20 | C |
| ATOM | 3493 | OE1 | GLU B | 258 | −29.658 | −56.113 | 22.258 | 1.00 | 62.25 | O |
| ATOM | 3494 | OE2 | GLU B | 258 | −29.859 | −55.623 | 20.115 | 1.00 | 55.92 | O |
| ATOM | 3495 | N | VAL B | 259 | −24.024 | −54.417 | 22.916 | 1.00 | 24.24 | N |
| ATOM | 3496 | CA | VAL B | 259 | −23.504 | −53.655 | 24.042 | 1.00 | 23.58 | C |
| ATOM | 3497 | C | VAL B | 259 | −24.597 | −52.609 | 24.298 | 1.00 | 26.40 | C |
| ATOM | 3498 | O | VAL B | 259 | −25.216 | −52.179 | 23.334 | 1.00 | 26.52 | O |
| ATOM | 3499 | CB | VAL B | 259 | −22.114 | −53.061 | 23.743 | 1.00 | 28.01 | C |
| ATOM | 3500 | CG1 | VAL B | 259 | −21.703 | −52.084 | 24.819 | 1.00 | 29.30 | C |
| ATOM | 3501 | CG2 | VAL B | 259 | −21.084 | −54.172 | 23.663 | 1.00 | 27.75 | C |
| ATOM | 3502 | N | THR B | 260 | −24.908 | −52.292 | 25.579 | 1.00 | 23.51 | N |
| ATOM | 3503 | CA | THR B | 260 | −25.985 | −51.366 | 25.998 | 1.00 | 23.51 | C |
| ATOM | 3504 | C | THR B | 260 | −25.478 | −50.223 | 26.886 | 1.00 | 27.80 | C |
| ATOM | 3505 | O | THR B | 260 | −24.898 | −50.469 | 27.931 | 1.00 | 24.65 | O |
| ATOM | 3506 | CB | THR B | 260 | −27.096 | −52.125 | 26.774 | 1.00 | 27.39 | C |
| ATOM | 3507 | OG1 | THR B | 260 | −27.404 | −53.324 | 26.083 | 1.00 | 28.09 | O |
| ATOM | 3508 | CG2 | THR B | 260 | −28.360 | −51.316 | 26.927 | 1.00 | 19.06 | C |
| ATOM | 3509 | N | CYS B | 261 | −25.725 | −48.980 | 26.471 | 1.00 | 29.15 | N |
| ATOM | 3510 | CA | CYS B | 261 | −25.375 | −47.776 | 27.213 | 1.00 | 31.15 | C |
| ATOM | 3511 | C | CYS B | 261 | −26.653 | −47.247 | 27.830 | 1.00 | 36.66 | C |
| ATOM | 3512 | O | CYS B | 261 | −27.598 | −46.987 | 27.083 | 1.00 | 36.09 | O |
| ATOM | 3513 | CB | CYS B | 261 | −24.781 | −46.754 | 26.267 | 1.00 | 32.44 | C |
| ATOM | 3514 | SG | CYS B | 261 | −23.728 | −45.517 | 27.054 | 1.00 | 37.46 | S |
| ATOM | 3515 | N | VAL B | 262 | −26.713 | −47.104 | 29.169 | 1.00 | 33.94 | N |
| ATOM | 3516 | CA | VAL B | 262 | −27.911 | −46.575 | 29.812 | 1.00 | 34.71 | C |
| ATOM | 3517 | C | VAL B | 262 | −27.518 | −45.337 | 30.598 | 1.00 | 37.76 | C |
| ATOM | 3518 | O | VAL B | 262 | −26.551 | −45.386 | 31.359 | 1.00 | 37.26 | O |
| ATOM | 3519 | CB | VAL B | 262 | −28.738 | −47.639 | 30.616 | 1.00 | 39.84 | C |
| ATOM | 3520 | CG1 | VAL B | 262 | −28.614 | −49.023 | 29.991 | 1.00 | 39.15 | C |
| ATOM | 3521 | CG2 | VAL B | 262 | −28.382 | −47.688 | 32.084 | 1.00 | 40.75 | C |
| ATOM | 3522 | N | VAL B | 263 | −28.202 | −44.197 | 30.344 | 1.00 | 33.29 | N |
| ATOM | 3523 | CA | VAL B | 263 | −27.945 | −42.967 | 31.090 | 1.00 | 32.52 | C |
| ATOM | 3524 | C | VAL B | 263 | −29.198 | −42.710 | 31.954 | 1.00 | 36.83 | C |
| ATOM | 3525 | O | VAL B | 263 | −30.344 | −42.787 | 31.464 | 1.00 | 35.66 | O |
| ATOM | 3526 | CB | VAL B | 263 | −27.427 | −41.745 | 30.258 | 1.00 | 36.39 | C |
| ATOM | 3527 | CG1 | VAL B | 263 | −28.358 | −41.373 | 29.142 | 1.00 | 36.83 | C |
| ATOM | 3528 | CG2 | VAL B | 263 | −27.169 | −40.523 | 31.130 | 1.00 | 36.11 | C |
| ATOM | 3529 | N | VAL B | 264 | −28.948 | −42.536 | 33.275 | 1.00 | 33.00 | N |
| ATOM | 3530 | CA | VAL B | 264 | −29.950 | −42.259 | 34.299 | 1.00 | 33.38 | C |
| ATOM | 3531 | C | VAL B | 264 | −29.624 | −40.882 | 34.865 | 1.00 | 35.85 | C |
| ATOM | 3532 | O | VAL B | 264 | −28.497 | −40.389 | 34.700 | 1.00 | 32.37 | O |
| ATOM | 3533 | CB | VAL B | 264 | −30.021 | −43.336 | 35.436 | 1.00 | 37.51 | C |
| ATOM | 3534 | CG1 | VAL B | 264 | −30.426 | −44.690 | 34.886 | 1.00 | 37.27 | C |
| ATOM | 3535 | CG2 | VAL B | 264 | −28.708 | −43.450 | 36.215 | 1.00 | 37.06 | C |
| ATOM | 3536 | N | ASP B | 265 | −30.602 | −40.309 | 35.583 | 1.00 | 35.17 | N |
| ATOM | 3537 | CA | ASP B | 265 | −30.533 | −38.992 | 36.217 | 1.00 | 36.30 | C |
| ATOM | 3538 | C | ASP B | 265 | −30.374 | −37.877 | 35.199 | 1.00 | 42.46 | C |
| ATOM | 3539 | O | ASP B | 265 | −29.646 | −36.913 | 35.435 | 1.00 | 42.49 | O |
| ATOM | 3540 | CB | ASP B | 265 | −29.456 | −38.934 | 37.321 | 1.00 | 38.37 | C |
| ATOM | 3541 | CG | ASP B | 265 | −29.784 | −39.800 | 38.506 | 1.00 | 50.75 | C |
| ATOM | 3542 | OD1 | ASP B | 265 | −30.990 | −40.028 | 38.757 | 1.00 | 49.38 | O |
| ATOM | 3543 | OD2 | ASP B | 265 | −28.838 | −40.205 | 39.220 | 1.00 | 59.48 | O |
| ATOM | 3544 | N | VAL B | 266 | −31.108 | −37.994 | 34.079 | 1.00 | 38.92 | N |
| ATOM | 3545 | CA | VAL B | 266 | −31.154 | −36.967 | 33.046 | 1.00 | 38.67 | C |
| ATOM | 3546 | C | VAL B | 266 | −32.220 | −35.977 | 33.554 | 1.00 | 42.97 | C |
| ATOM | 3547 | O | VAL B | 266 | −33.346 | −36.409 | 33.831 | 1.00 | 41.34 | O |
| ATOM | 3548 | CB | VAL B | 266 | −31.523 | −37.616 | 31.679 | 1.00 | 42.36 | C |
| ATOM | 3549 | CG1 | VAL B | 266 | −31.801 | −36.566 | 30.597 | 1.00 | 41.28 | C |
| ATOM | 3550 | CG2 | VAL B | 266 | −30.434 | −38.591 | 31.236 | 1.00 | 41.65 | C |
| ATOM | 3551 | N | SER B | 267 | −31.870 | −34.673 | 33.717 | 1.00 | 41.52 | N |
| ATOM | 3552 | CA | SER B | 267 | −32.824 | −33.671 | 34.254 | 1.00 | 42.87 | C |
| ATOM | 3553 | C | SER B | 267 | −34.106 | −33.564 | 33.453 | 1.00 | 49.65 | C |
| ATOM | 3554 | O | SER B | 267 | −34.123 | −33.807 | 32.247 | 1.00 | 49.10 | O |
| ATOM | 3555 | CB | SER B | 267 | −32.229 | −32.259 | 34.309 | 1.00 | 44.58 | C |
| ATOM | 3556 | OG | SER B | 267 | −30.859 | −32.223 | 34.650 | 1.00 | 57.59 | O |
| ATOM | 3557 | N | GLN B | 268 | −35.149 | −33.073 | 34.119 | 1.00 | 48.37 | N |
| ATOM | 3558 | CA | GLN B | 268 | −36.421 | −32.752 | 33.480 | 1.00 | 48.81 | C |
| ATOM | 3559 | C | GLN B | 268 | −36.181 | −31.520 | 32.563 | 1.00 | 51.13 | C |
| ATOM | 3560 | O | GLN B | 268 | −36.858 | −31.365 | 31.546 | 1.00 | 49.85 | O |

TABLE 7-continued

Three-dimensional crystal coordinates for caffeine-pembrolizumab complex.
Atomic Coordinates of Caffeine/Pembrolizumab Crystal Complex

| | | | | | | | | | | | |
|---|---|---|---|---|---|---|---|---|---|---|---|
| ATOM | 3561 | CB | GLN | B | 268 | −37.495 | −32.427 | 34.544 | 1.00 | 51.27 | C |
| ATOM | 3562 | N | GLU | B | 269 | −35.185 | −30.671 | 32.932 | 1.00 | 47.53 | N |
| ATOM | 3563 | CA | GLU | B | 269 | −34.797 | −29.448 | 32.223 | 1.00 | 46.62 | C |
| ATOM | 3564 | C | GLU | B | 269 | −33.930 | −29.691 | 30.975 | 1.00 | 47.53 | C |
| ATOM | 3565 | O | GLU | B | 269 | −33.868 | −28.799 | 30.131 | 1.00 | 47.43 | O |
| ATOM | 3566 | CB | GLU | B | 269 | −34.030 | −28.501 | 33.175 | 1.00 | 47.99 | C |
| ATOM | 3567 | CG | GLU | B | 269 | −34.759 | −28.163 | 34.473 | 1.00 | 63.96 | C |
| ATOM | 3568 | CD | GLU | B | 269 | −33.942 | −28.260 | 35.752 | 1.00 | 94.97 | C |
| ATOM | 3569 | OE1 | GLU | B | 269 | −34.144 | −27.404 | 36.645 | 1.00 | 88.99 | O |
| ATOM | 3570 | OE2 | GLU | B | 269 | −33.139 | −29.213 | 35.887 | 1.00 | 93.30 | O |
| ATOM | 3571 | N | ASP | B | 270 | −33.275 | −30.867 | 30.843 | 1.00 | 41.92 | N |
| ATOM | 3572 | CA | ASP | B | 270 | −32.367 | −31.184 | 29.727 | 1.00 | 41.04 | C |
| ATOM | 3573 | C | ASP | B | 270 | −32.604 | −32.609 | 29.144 | 1.00 | 41.42 | C |
| ATOM | 3574 | O | ASP | B | 270 | −31.760 | −33.501 | 29.299 | 1.00 | 38.81 | O |
| ATOM | 3575 | CB | ASP | B | 270 | −30.897 | −31.016 | 30.178 | 1.00 | 42.90 | C |
| ATOM | 3576 | CG | ASP | B | 270 | −30.570 | −29.608 | 30.637 | 1.00 | 60.50 | C |
| ATOM | 3577 | OD1 | ASP | B | 270 | −30.801 | −28.661 | 29.855 | 1.00 | 63.43 | O |
| ATOM | 3578 | OD2 | ASP | B | 270 | −30.138 | −29.447 | 31.801 | 1.00 | 69.61 | O |
| ATOM | 3579 | N | PRO | B | 271 | −33.728 | −32.796 | 28.414 | 1.00 | 37.59 | N |
| ATOM | 3580 | CA | PRO | B | 271 | −34.006 | −34.105 | 27.788 | 1.00 | 37.40 | C |
| ATOM | 3581 | C | PRO | B | 271 | −33.039 | −34.548 | 26.672 | 1.00 | 41.08 | C |
| ATOM | 3582 | O | PRO | B | 271 | −33.119 | −35.698 | 26.272 | 1.00 | 39.83 | O |
| ATOM | 3583 | CB | PRO | B | 271 | −35.446 | −33.964 | 27.270 | 1.00 | 39.34 | C |
| ATOM | 3584 | CG | PRO | B | 271 | −35.934 | −32.676 | 27.736 | 1.00 | 43.51 | C |
| ATOM | 3585 | CD | PRO | B | 271 | −34.808 | −31.827 | 28.138 | 1.00 | 38.69 | C |
| ATOM | 3586 | N | GLU | B | 272 | −32.198 | −33.625 | 26.143 | 1.00 | 40.74 | N |
| ATOM | 3587 | CA | GLU | B | 272 | −31.041 | −33.765 | 25.201 | 1.00 | 41.02 | C |
| ATOM | 3588 | C | GLU | B | 272 | −30.424 | −35.185 | 25.104 | 1.00 | 42.27 | C |
| ATOM | 3589 | O | GLU | B | 272 | −29.309 | −35.413 | 25.554 | 1.00 | 40.34 | O |
| ATOM | 3590 | CB | GLU | B | 272 | −29.890 | −32.762 | 25.646 | 1.00 | 42.70 | C |
| ATOM | 3591 | CG | GLU | B | 272 | −30.121 | −31.270 | 25.391 | 1.00 | 57.53 | C |
| ATOM | 3592 | CD | GLU | B | 272 | −29.851 | −30.742 | 23.987 | 1.00 | 86.05 | C |
| ATOM | 3593 | OE1 | GLU | B | 272 | −29.162 | −29.701 | 23.867 | 1.00 | 45.07 | O |
| ATOM | 3594 | OE2 | GLU | B | 272 | −30.394 | −31.318 | 23.014 | 1.00 | 97.95 | O |
| ATOM | 3595 | N | VAL | B | 273 | −31.138 | −36.107 | 24.463 | 1.00 | 40.45 | N |
| ATOM | 3596 | CA | VAL | B | 273 | −30.737 | −37.525 | 24.262 | 1.00 | 40.05 | C |
| ATOM | 3597 | C | VAL | B | 273 | −29.471 | −37.765 | 23.293 | 1.00 | 38.34 | C |
| ATOM | 3598 | O | VAL | B | 273 | −29.729 | −38.186 | 22.158 | 1.00 | 39.55 | O |
| ATOM | 3599 | CB | VAL | B | 273 | −32.010 | −38.381 | 23.753 | 1.00 | 45.21 | C |
| ATOM | 3600 | CG1 | VAL | B | 273 | −33.063 | −38.565 | 24.845 | 1.00 | 45.87 | C |
| ATOM | 3601 | CG2 | VAL | B | 273 | −32.687 | −37.805 | 22.490 | 1.00 | 45.09 | C |
| ATOM | 3602 | N | GLN | B | 274 | −28.139 | −37.620 | 23.699 | 1.00 | 29.31 | N |
| ATOM | 3603 | CA | GLN | B | 274 | −27.065 | −37.917 | 22.673 | 1.00 | 27.07 | C |
| ATOM | 3604 | C | GLN | B | 274 | −25.974 | −39.009 | 22.967 | 1.00 | 29.49 | C |
| ATOM | 3605 | O | GLN | B | 274 | −25.199 | −38.860 | 23.889 | 1.00 | 30.49 | O |
| ATOM | 3606 | CB | GLN | B | 274 | −26.310 | −36.669 | 22.238 | 1.00 | 27.24 | C |
| ATOM | 3607 | CG | GLN | B | 274 | −25.511 | −36.926 | 20.930 | 1.00 | 35.22 | C |
| ATOM | 3608 | CD | GLN | B | 274 | −24.748 | −35.747 | 20.385 | 1.00 | 56.56 | C |
| ATOM | 3609 | OE1 | GLN | B | 274 | −25.113 | −34.585 | 20.583 | 1.00 | 51.71 | O |
| ATOM | 3610 | NE2 | GLN | B | 274 | −23.682 | −36.026 | 19.635 | 1.00 | 45.60 | N |
| ATOM | 3611 | N | PHE | B | 275 | −25.782 | −39.973 | 22.018 | 1.00 | 24.31 | N |
| ATOM | 3612 | CA | PHE | B | 275 | −24.756 | −41.033 | 22.112 | 1.00 | 22.82 | C |
| ATOM | 3613 | C | PHE | B | 275 | −23.800 | −41.054 | 20.938 | 1.00 | 25.93 | C |
| ATOM | 3614 | O | PHE | B | 275 | −24.243 | −40.945 | 19.822 | 1.00 | 24.46 | O |
| ATOM | 3615 | CB | PHE | B | 275 | −25.429 | −42.418 | 22.129 | 1.00 | 23.70 | C |
| ATOM | 3616 | CG | PHE | B | 275 | −26.357 | −42.608 | 23.292 | 1.00 | 23.52 | C |
| ATOM | 3617 | CD2 | PHE | B | 275 | −25.896 | −43.141 | 24.487 | 1.00 | 23.23 | C |
| ATOM | 3618 | CD1 | PHE | B | 275 | −27.691 | −42.236 | 23.202 | 1.00 | 24.28 | C |
| ATOM | 3619 | CE2 | PHE | B | 275 | −26.760 | −43.311 | 25.573 | 1.00 | 25.80 | C |
| ATOM | 3620 | CE1 | PHE | B | 275 | −28.542 | −42.381 | 24.289 | 1.00 | 24.32 | C |
| ATOM | 3621 | CZ | PHE | B | 275 | −28.078 | −42.933 | 25.464 | 1.00 | 23.71 | C |
| ATOM | 3622 | N | ASN | B | 276 | −22.509 | −41.286 | 21.174 | 1.00 | 24.67 | N |
| ATOM | 3623 | CA | ASN | B | 276 | −21.501 | −41.491 | 20.113 | 1.00 | 24.25 | C |
| ATOM | 3624 | C | ASN | B | 276 | −20.821 | −42.840 | 20.462 | 1.00 | 28.91 | C |
| ATOM | 3625 | O | ASN | B | 276 | −20.593 | −43.106 | 21.640 | 1.00 | 29.29 | O |
| ATOM | 3626 | CB | ASN | B | 276 | −20.514 | −40.326 | 20.037 | 1.00 | 21.79 | C |
| ATOM | 3627 | CG | ASN | B | 276 | −21.152 | −39.101 | 19.405 | 1.00 | 37.82 | C |
| ATOM | 3628 | OD1 | ASN | B | 276 | −21.808 | −38.294 | 20.075 | 1.00 | 28.36 | O |
| ATOM | 3629 | ND2 | ASN | B | 276 | −21.108 | −39.007 | 18.084 | 1.00 | 22.58 | N |
| ATOM | 3630 | N | TRP | B | 277 | −20.641 | −43.729 | 19.480 | 1.00 | 24.34 | N |
| ATOM | 3631 | CA | TRP | B | 277 | −20.101 | −45.069 | 19.710 | 1.00 | 24.47 | C |
| ATOM | 3632 | C | TRP | B | 277 | −18.827 | −45.287 | 18.943 | 1.00 | 28.75 | C |
| ATOM | 3633 | O | TRP | B | 277 | −18.792 | −44.959 | 17.773 | 1.00 | 27.72 | O |
| ATOM | 3634 | CB | TRP | B | 277 | −21.115 | −46.112 | 19.260 | 1.00 | 23.26 | C |
| ATOM | 3635 | CG | TRP | B | 277 | −22.262 | −46.286 | 20.191 | 1.00 | 24.98 | C |
| ATOM | 3636 | CD1 | TRP | B | 277 | −23.501 | −45.735 | 20.082 | 1.00 | 27.80 | C |
| ATOM | 3637 | CD2 | TRP | B | 277 | −22.304 | −47.154 | 21.334 | 1.00 | 25.58 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3638 | NE1 | TRP B | 277 | −24.335 | −46.251 | 21.050 | 1.00 | 27.92 | N |
| ATOM | 3639 | CE2 | TRP B | 277 | −23.615 | −47.099 | 21.853 | 1.00 | 29.39 | C |
| ATOM | 3640 | CE3 | TRP B | 277 | −21.361 | −47.990 | 21.957 | 1.00 | 26.85 | C |
| ATOM | 3641 | CZ2 | TRP B | 277 | −24.012 | −47.857 | 22.950 | 1.00 | 28.85 | C |
| ATOM | 3642 | CZ3 | TRP B | 277 | −21.761 | −48.751 | 23.038 | 1.00 | 28.43 | C |
| ATOM | 3643 | CH2 | TRP B | 277 | −23.082 | −48.698 | 23.505 | 1.00 | 29.49 | C |
| ATOM | 3644 | N | TYR B | 278 | −17.798 | −45.873 | 19.570 | 1.00 | 26.90 | N |
| ATOM | 3645 | CA | TYR B | 278 | −16.524 | −46.159 | 18.890 | 1.00 | 26.15 | C |
| ATOM | 3646 | C | TYR B | 278 | −16.142 | −47.602 | 19.128 | 1.00 | 32.42 | C |
| ATOM | 3647 | O | TYR B | 278 | −16.330 | −48.094 | 20.238 | 1.00 | 33.83 | O |
| ATOM | 3648 | CB | TYR B | 278 | −15.407 | −45.251 | 19.406 | 1.00 | 25.46 | C |
| ATOM | 3649 | CG | TYR B | 278 | −15.819 | −43.804 | 19.493 | 1.00 | 24.01 | C |
| ATOM | 3650 | CD1 | TYR B | 278 | −16.606 | −43.343 | 20.547 | 1.00 | 26.48 | C |
| ATOM | 3651 | CD2 | TYR B | 278 | −15.432 | −42.891 | 18.523 | 1.00 | 22.26 | C |
| ATOM | 3652 | CE1 | TYR B | 278 | −17.038 | −42.024 | 20.603 | 1.00 | 25.19 | C |
| ATOM | 3653 | CE2 | TYR B | 278 | −15.869 | −41.573 | 18.560 | 1.00 | 22.12 | C |
| ATOM | 3654 | CZ | TYR B | 278 | −16.682 | −41.144 | 19.593 | 1.00 | 29.56 | C |
| ATOM | 3655 | OH | TYR B | 278 | −17.083 | −39.829 | 19.606 | 1.00 | 32.82 | O |
| ATOM | 3656 | N | VAL B | 279 | −15.591 | −48.266 | 18.108 | 1.00 | 29.16 | N |
| ATOM | 3657 | CA | VAL B | 279 | −15.095 | −49.653 | 18.160 | 1.00 | 28.52 | C |
| ATOM | 3658 | C | VAL B | 279 | −13.587 | −49.528 | 17.908 | 1.00 | 34.63 | C |
| ATOM | 3659 | O | VAL B | 279 | −13.197 | −49.097 | 16.829 | 1.00 | 33.44 | O |
| ATOM | 3660 | CB | VAL B | 279 | −15.807 | −50.533 | 17.103 | 1.00 | 30.74 | C |
| ATOM | 3661 | CG1 | VAL B | 279 | −15.242 | −51.950 | 17.091 | 1.00 | 30.84 | C |
| ATOM | 3662 | CG2 | VAL B | 279 | −17.312 | −50.557 | 17.359 | 1.00 | 30.09 | C |
| ATOM | 3663 | N | ASP B | 280 | −12.747 | −49.820 | 18.915 | 1.00 | 34.98 | N |
| ATOM | 3664 | CA | ASP B | 280 | −11.281 | −49.629 | 18.849 | 1.00 | 36.10 | C |
| ATOM | 3665 | C | ASP B | 280 | −10.905 | −48.186 | 18.429 | 1.00 | 42.91 | C |
| ATOM | 3666 | O | ASP B | 280 | −9.971 | −47.976 | 17.643 | 1.00 | 43.61 | O |
| ATOM | 3667 | CB | ASP B | 280 | −10.571 | −50.699 | 17.979 | 1.00 | 37.49 | C |
| ATOM | 3668 | CG | ASP B | 280 | −10.319 | −52.036 | 18.659 | 1.00 | 47.91 | C |
| ATOM | 3669 | OD1 | ASP B | 280 | −10.311 | −52.084 | 19.917 | 1.00 | 48.99 | O |
| ATOM | 3670 | OD2 | ASP B | 280 | −10.051 | −53.017 | 17.944 | 1.00 | 55.96 | O |
| ATOM | 3671 | N | GLY B | 281 | −11.649 | −47.213 | 18.981 | 1.00 | 40.02 | N |
| ATOM | 3672 | CA | GLY B | 281 | −11.445 | −45.786 | 18.745 | 1.00 | 38.87 | C |
| ATOM | 3673 | C | GLY B | 281 | −12.038 | −45.227 | 17.467 | 1.00 | 42.37 | C |
| ATOM | 3674 | O | GLY B | 281 | −11.947 | −44.013 | 17.259 | 1.00 | 44.09 | O |
| ATOM | 3675 | N | VAL B | 282 | −12.671 | −46.084 | 16.610 | 1.00 | 34.52 | N |
| ATOM | 3676 | CA | VAL B | 282 | −13.279 | −45.667 | 15.349 | 1.00 | 32.60 | C |
| ATOM | 3677 | C | VAL B | 282 | −14.785 | −45.492 | 15.522 | 1.00 | 35.45 | C |
| ATOM | 3678 | O | VAL B | 282 | −15.464 | −46.442 | 15.913 | 1.00 | 37.01 | O |
| ATOM | 3679 | CB | VAL B | 282 | −12.984 | −46.706 | 14.235 | 1.00 | 35.48 | C |
| ATOM | 3680 | CG1 | VAL B | 282 | −13.697 | −46.330 | 12.949 | 1.00 | 34.37 | C |
| ATOM | 3681 | CG2 | VAL B | 282 | −11.474 | −46.853 | 14.006 | 1.00 | 35.33 | C |
| ATOM | 3682 | N | GLU B | 283 | −15.324 | −44.331 | 15.152 | 1.00 | 28.48 | N |
| ATOM | 3683 | CA | GLU B | 283 | −16.759 | −44.110 | 15.276 | 1.00 | 27.31 | C |
| ATOM | 3684 | C | GLU B | 283 | −17.628 | −44.999 | 14.376 | 1.00 | 29.45 | C |
| ATOM | 3685 | O | GLU B | 283 | −17.284 | −45.215 | 13.221 | 1.00 | 32.56 | O |
| ATOM | 3686 | CB | GLU B | 283 | −17.104 | −42.640 | 15.054 | 1.00 | 28.57 | C |
| ATOM | 3687 | CG | GLU B | 283 | −18.514 | −42.306 | 15.534 | 1.00 | 39.82 | C |
| ATOM | 3688 | CD | GLU B | 283 | −18.865 | −40.839 | 15.684 | 1.00 | 52.12 | C |
| ATOM | 3689 | OE1 | GLU B | 283 | −18.009 | −39.966 | 15.406 | 1.00 | 38.64 | O |
| ATOM | 3690 | OE2 | GLU B | 283 | −20.010 | −40.568 | 16.111 | 1.00 | 40.60 | O |
| ATOM | 3691 | N | VAL B | 284 | −18.757 | −45.499 | 14.896 | 1.00 | 21.93 | N |
| ATOM | 3692 | CA | VAL B | 284 | −19.706 | −46.329 | 14.122 | 1.00 | 21.11 | C |
| ATOM | 3693 | C | VAL B | 284 | −21.081 | −45.667 | 14.312 | 1.00 | 26.50 | C |
| ATOM | 3694 | O | VAL B | 284 | −21.308 | −45.067 | 15.357 | 1.00 | 24.68 | O |
| ATOM | 3695 | CB | VAL B | 284 | −19.695 | −47.849 | 14.517 | 1.00 | 23.56 | C |
| ATOM | 3696 | CG1 | VAL B | 284 | −18.316 | −48.464 | 14.331 | 1.00 | 21.40 | C |
| ATOM | 3697 | CG2 | VAL B | 284 | −20.172 | −48.062 | 15.947 | 1.00 | 23.89 | C |
| ATOM | 3698 | N | HIS B | 285 | −21.971 | −45.765 | 13.313 | 1.00 | 27.03 | N |
| ATOM | 3699 | CA | HIS B | 285 | −23.276 | −45.074 | 13.284 | 1.00 | 28.90 | C |
| ATOM | 3700 | C | HIS B | 285 | −24.511 | −45.985 | 13.243 | 1.00 | 33.86 | C |
| ATOM | 3701 | O | HIS B | 285 | −25.629 | −45.484 | 13.131 | 1.00 | 33.38 | O |
| ATOM | 3702 | CB | HIS B | 285 | −23.280 | −44.099 | 12.065 | 1.00 | 30.37 | C |
| ATOM | 3703 | CG | HIS B | 285 | −22.074 | −43.200 | 12.063 | 1.00 | 32.83 | C |
| ATOM | 3704 | ND1 | HIS B | 285 | −21.963 | −42.143 | 12.959 | 1.00 | 34.34 | N |
| ATOM | 3705 | CD2 | HIS B | 285 | −20.902 | −43.332 | 11.401 | 1.00 | 34.26 | C |
| ATOM | 3706 | CE1 | HIS B | 285 | −20.759 | −41.626 | 12.765 | 1.00 | 33.60 | C |
| ATOM | 3707 | NE2 | HIS B | 285 | −20.072 | −42.319 | 11.855 | 1.00 | 33.88 | N |
| ATOM | 3708 | N | ASN B | 286 | −24.339 | −47.287 | 13.463 | 1.00 | 32.13 | N |
| ATOM | 3709 | CA | ASN B | 286 | −25.459 | −48.228 | 13.426 | 1.00 | 33.34 | C |
| ATOM | 3710 | C | ASN B | 286 | −26.163 | −48.481 | 14.803 | 1.00 | 39.63 | C |
| ATOM | 3711 | O | ASN B | 286 | −27.008 | −49.378 | 14.870 | 1.00 | 41.88 | O |
| ATOM | 3712 | CB | ASN B | 286 | −24.998 | −49.550 | 12.789 | 1.00 | 33.69 | C |
| ATOM | 3713 | CG | ASN B | 286 | −23.914 | −50.245 | 13.564 | 1.00 | 45.72 | C |
| ATOM | 3714 | OD1 | ASN B | 286 | −22.958 | −49.606 | 14.012 | 1.00 | 39.87 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3715 | ND2 | ASN B | 286 | −24.052 | −51.544 | 13.786 | 1.00 | 38.98 | N |
| ATOM | 3716 | N | ALA B | 287 | −25.875 | −47.704 | 15.873 | 1.00 | 34.57 | N |
| ATOM | 3717 | CA | ALA B | 287 | −26.570 | −47.915 | 17.147 | 1.00 | 34.60 | C |
| ATOM | 3718 | C | ALA B | 287 | −27.999 | −47.392 | 17.060 | 1.00 | 40.56 | C |
| ATOM | 3719 | O | ALA B | 287 | −28.270 | −46.455 | 16.307 | 1.00 | 42.63 | O |
| ATOM | 3720 | CB | ALA B | 287 | −25.845 | −47.214 | 18.282 | 1.00 | 34.88 | C |
| ATOM | 3721 | N | LYS B | 288 | −28.896 | −47.958 | 17.865 | 1.00 | 35.35 | N |
| ATOM | 3722 | CA | LYS B | 288 | −30.306 | −47.586 | 17.889 | 1.00 | 34.92 | C |
| ATOM | 3723 | C | LYS B | 288 | −30.665 | −47.053 | 19.286 | 1.00 | 38.04 | C |
| ATOM | 3724 | O | LYS B | 288 | −30.572 | −47.782 | 20.268 | 1.00 | 37.72 | O |
| ATOM | 3725 | CB | LYS B | 288 | −31.171 | −48.808 | 17.493 | 1.00 | 38.04 | C |
| ATOM | 3726 | CG | LYS B | 288 | −32.086 | −48.587 | 16.280 | 1.00 | 65.77 | C |
| ATOM | 3727 | CD | LYS B | 288 | −33.530 | −48.190 | 16.656 | 1.00 | 83.06 | C |
| ATOM | 3728 | CE | LYS B | 288 | −33.678 | −46.723 | 17.008 | 1.00 | 96.73 | C |
| ATOM | 3729 | NZ | LYS B | 288 | −34.921 | −46.426 | 17.780 | 1.00 | 107.33 | N |
| ATOM | 3730 | N | THR B | 289 | −31.035 | −45.763 | 19.367 | 1.00 | 35.19 | N |
| ATOM | 3731 | CA | THR B | 289 | −31.402 | −45.094 | 20.606 | 1.00 | 35.19 | C |
| ATOM | 3732 | C | THR B | 289 | −32.879 | −45.306 | 20.865 | 1.00 | 42.15 | C |
| ATOM | 3733 | O | THR B | 289 | −33.684 | −45.176 | 19.953 | 1.00 | 43.88 | O |
| ATOM | 3734 | CB | THR B | 289 | −30.960 | −43.645 | 20.582 | 1.00 | 35.60 | C |
| ATOM | 3735 | OG1 | THR B | 289 | −29.550 | −43.640 | 20.330 | 1.00 | 42.58 | O |
| ATOM | 3736 | CG2 | THR B | 289 | −31.235 | −42.941 | 21.885 | 1.00 | 30.26 | C |
| ATOM | 3737 | N | LYS B | 290 | −33.219 | −45.728 | 22.078 | 1.00 | 39.01 | N |
| ATOM | 3738 | CA | LYS B | 290 | −34.585 | −46.029 | 22.438 | 1.00 | 40.76 | C |
| ATOM | 3739 | C | LYS B | 290 | −35.280 | −44.734 | 22.799 | 1.00 | 51.32 | C |
| ATOM | 3740 | O | LYS B | 290 | −34.596 | −43.738 | 23.083 | 1.00 | 52.41 | O |
| ATOM | 3741 | CB | LYS B | 290 | −34.601 | −47.008 | 23.622 | 1.00 | 42.69 | C |
| ATOM | 3742 | CG | LYS B | 290 | −34.121 | −48.393 | 23.247 | 1.00 | 46.01 | C |
| ATOM | 3743 | CD | LYS B | 290 | −34.475 | −49.425 | 24.318 | 1.00 | 49.92 | C |
| ATOM | 3744 | CE | LYS B | 290 | −33.981 | −50.803 | 23.932 | 1.00 | 70.78 | C |
| ATOM | 3745 | NZ | LYS B | 290 | −33.650 | −51.650 | 25.116 | 1.00 | 83.95 | N |
| ATOM | 3746 | N | PRO B | 291 | −36.631 | −44.689 | 22.792 | 1.00 | 50.35 | N |
| ATOM | 3747 | CA | PRO B | 291 | −37.302 | −43.450 | 23.201 | 1.00 | 50.59 | C |
| ATOM | 3748 | C | PRO B | 291 | −37.107 | −43.192 | 24.698 | 1.00 | 53.02 | C |
| ATOM | 3749 | O | PRO B | 291 | −37.080 | −44.130 | 25.499 | 1.00 | 51.54 | O |
| ATOM | 3750 | CB | PRO B | 291 | −38.777 | −43.719 | 22.874 | 1.00 | 53.19 | C |
| ATOM | 3751 | CG | PRO B | 291 | −38.919 | −45.187 | 23.016 | 1.00 | 57.91 | C |
| ATOM | 3752 | CD | PRO B | 291 | −37.615 | −45.749 | 22.492 | 1.00 | 52.87 | C |
| ATOM | 3753 | N | ARG B | 292 | −36.976 | −41.904 | 25.046 | 1.00 | 48.75 | N |
| ATOM | 3754 | CA | ARG B | 292 | −36.831 | −41.358 | 26.406 | 1.00 | 47.78 | C |
| ATOM | 3755 | C | ARG B | 292 | −37.880 | −41.947 | 27.351 | 1.00 | 52.43 | C |
| ATOM | 3756 | O | ARG B | 292 | −39.042 | −41.988 | 26.958 | 1.00 | 53.26 | O |
| ATOM | 3757 | CB | ARG B | 292 | −37.060 | −39.836 | 26.315 | 1.00 | 46.70 | C |
| ATOM | 3758 | CG | ARG B | 292 | −36.405 | −39.031 | 27.370 | 1.00 | 50.36 | C |
| ATOM | 3759 | CD | ARG B | 292 | −36.770 | −37.575 | 27.209 | 1.00 | 47.41 | C |
| ATOM | 3760 | NE | ARG B | 292 | −36.024 | −36.924 | 26.125 | 1.00 | 45.04 | N |
| ATOM | 3761 | CZ | ARG B | 292 | −36.533 | −36.419 | 25.000 | 1.00 | 44.02 | C |
| ATOM | 3762 | NH1 | ARG B | 292 | −37.836 | −36.506 | 24.748 | 1.00 | 38.66 | N |
| ATOM | 3763 | NH2 | ARG B | 292 | −35.744 | −35.818 | 24.121 | 1.00 | 29.31 | N |
| ATOM | 3764 | N | GLU B | 293 | −37.497 | −42.380 | 28.579 | 1.00 | 48.94 | N |
| ATOM | 3765 | CA | GLU B | 293 | −38.433 | −42.943 | 29.571 | 1.00 | 49.75 | C |
| ATOM | 3766 | C | GLU B | 293 | −38.417 | −42.157 | 30.887 | 1.00 | 55.29 | C |
| ATOM | 3767 | O | GLU B | 293 | −37.406 | −42.168 | 31.579 | 1.00 | 53.21 | O |
| ATOM | 3768 | CB | GLU B | 293 | −38.089 | −44.409 | 29.877 | 1.00 | 51.42 | C |
| ATOM | 3769 | CG | GLU B | 293 | −38.473 | −45.387 | 28.778 | 1.00 | 67.43 | C |
| ATOM | 3770 | CD | GLU B | 293 | −37.392 | −46.341 | 28.292 | 1.00 | 107.86 | C |
| ATOM | 3771 | OE1 | GLU B | 293 | −37.578 | −46.914 | 27.192 | 1.00 | 116.66 | O |
| ATOM | 3772 | OE2 | GLU B | 293 | −36.352 | −46.497 | 28.977 | 1.00 | 100.43 | O |
| ATOM | 3773 | N | GLU B | 294 | −39.567 | −41.558 | 31.276 | 1.00 | 55.74 | N |
| ATOM | 3774 | CA | GLU B | 294 | −39.707 | −40.803 | 32.533 | 1.00 | 56.51 | C |
| ATOM | 3775 | C | GLU B | 294 | −39.695 | −41.771 | 33.709 | 1.00 | 60.20 | C |
| ATOM | 3776 | O | GLU B | 294 | −40.387 | −42.788 | 33.673 | 1.00 | 59.43 | O |
| ATOM | 3777 | CB | GLU B | 294 | −41.039 | −40.037 | 32.588 | 1.00 | 59.02 | C |
| ATOM | 3778 | CG | GLU B | 294 | −41.254 | −39.011 | 31.491 | 1.00 | 74.70 | C |
| ATOM | 3779 | CD | GLU B | 294 | −42.709 | −38.834 | 31.096 | 1.00 | 111.06 | C |
| ATOM | 3780 | OE1 | GLU B | 294 | −43.563 | −38.725 | 32.007 | 1.00 | 114.12 | O |
| ATOM | 3781 | OE2 | GLU B | 294 | −42.996 | −38.807 | 29.876 | 1.00 | 107.02 | O |
| ATOM | 3782 | N | GLN B | 295 | −38.937 | −41.445 | 34.755 | 1.00 | 57.84 | N |
| ATOM | 3783 | CA | GLN B | 295 | −38.820 | −42.278 | 35.956 | 1.00 | 58.48 | C |
| ATOM | 3784 | C | GLN B | 295 | −39.672 | −41.720 | 37.101 | 1.00 | 65.79 | C |
| ATOM | 3785 | O | GLN B | 295 | −40.004 | −40.532 | 37.099 | 1.00 | 66.52 | O |
| ATOM | 3786 | CB | GLN B | 295 | −37.343 | −42.356 | 36.386 | 1.00 | 58.47 | C |
| ATOM | 3787 | CG | GLN B | 295 | −36.411 | −42.859 | 35.297 | 1.00 | 51.75 | C |
| ATOM | 3788 | CD | GLN B | 295 | −36.757 | −44.267 | 34.908 | 1.00 | 63.65 | C |
| ATOM | 3789 | OE1 | GLN B | 295 | −36.547 | −45.203 | 35.679 | 1.00 | 60.02 | O |
| ATOM | 3790 | NE2 | GLN B | 295 | −37.345 | −44.458 | 33.736 | 1.00 | 56.66 | N |
| ATOM | 3791 | N | PHE B | 296 | −39.943 | −42.553 | 38.125 | 1.00 | 63.65 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3792 | CA | PHE B | 296 | −40.751 | −42.157 | 39.292 | 1.00 | 64.61 | C |
| ATOM | 3793 | C | PHE B | 296 | −40.063 | −41.120 | 40.219 | 1.00 | 67.02 | C |
| ATOM | 3794 | O | PHE B | 296 | −40.690 | −40.691 | 41.192 | 1.00 | 68.05 | O |
| ATOM | 3795 | CB | PHE B | 296 | −41.166 | −43.394 | 40.112 | 1.00 | 67.74 | C |
| ATOM | 3796 | CG | PHE B | 296 | −42.264 | −44.232 | 39.496 | 1.00 | 71.12 | C |
| ATOM | 3797 | CD1 | PHE B | 296 | −41.998 | −45.083 | 38.428 | 1.00 | 74.62 | C |
| ATOM | 3798 | CD2 | PHE B | 296 | −43.538 | −44.252 | 40.048 | 1.00 | 75.40 | C |
| ATOM | 3799 | CE1 | PHE B | 296 | −43.003 | −45.888 | 37.884 | 1.00 | 76.31 | C |
| ATOM | 3800 | CE2 | PHE B | 296 | −44.539 | −45.072 | 39.512 | 1.00 | 79.22 | C |
| ATOM | 3801 | CZ | PHE B | 296 | −44.266 | −45.877 | 38.427 | 1.00 | 76.72 | C |
| ATOM | 3802 | N | ASN B | 297 | −38.799 | −40.715 | 39.925 | 1.00 | 60.68 | N |
| ATOM | 3803 | CA | ASN B | 297 | −38.031 | −39.744 | 40.714 | 1.00 | 59.62 | C |
| ATOM | 3804 | C | ASN B | 297 | −37.783 | −38.426 | 39.943 | 1.00 | 61.40 | C |
| ATOM | 3805 | O | ASN B | 297 | −36.766 | −37.757 | 40.163 | 1.00 | 59.75 | O |
| ATOM | 3806 | CB | ASN B | 297 | −36.713 | −40.389 | 41.221 | 1.00 | 60.66 | C |
| ATOM | 3807 | CG | ASN B | 297 | −35.820 | −41.017 | 40.160 | 1.00 | 78.53 | C |
| ATOM | 3808 | OD1 | ASN B | 297 | −35.920 | −40.723 | 38.962 | 1.00 | 74.87 | O |
| ATOM | 3809 | ND2 | ASN B | 297 | −34.945 | −41.916 | 40.594 | 1.00 | 61.06 | N |
| ATOM | 3810 | N | SER B | 298 | −38.739 | −38.037 | 39.071 | 1.00 | 58.09 | N |
| ATOM | 3811 | CA | SER B | 298 | −38.685 | −36.803 | 38.268 | 1.00 | 57.44 | C |
| ATOM | 3812 | C | SER B | 298 | −37.451 | −36.677 | 37.312 | 1.00 | 57.12 | C |
| ATOM | 3813 | O | SER B | 298 | −37.056 | −35.551 | 36.971 | 1.00 | 56.63 | O |
| ATOM | 3814 | CB | SER B | 298 | −38.792 | −35.575 | 39.175 | 1.00 | 63.15 | C |
| ATOM | 3815 | OG | SER B | 298 | −37.537 | −35.144 | 39.685 | 1.00 | 74.81 | O |
| ATOM | 3816 | N | THR B | 299 | −36.879 | −37.809 | 36.854 | 1.00 | 50.25 | N |
| ATOM | 3817 | CA | THR B | 299 | −35.750 | −37.793 | 35.903 | 1.00 | 47.82 | C |
| ATOM | 3818 | C | THR B | 299 | −36.049 | −38.710 | 34.725 | 1.00 | 48.09 | C |
| ATOM | 3819 | O | THR B | 299 | −36.957 | −39.540 | 34.804 | 1.00 | 46.91 | O |
| ATOM | 3820 | CB | THR B | 299 | −34.427 | −38.206 | 36.566 | 1.00 | 50.94 | C |
| ATOM | 3821 | OG1 | THR B | 299 | −34.511 | −39.565 | 36.987 | 1.00 | 49.97 | O |
| ATOM | 3822 | CG2 | THR B | 299 | −34.037 | −37.302 | 37.722 | 1.00 | 48.53 | C |
| ATOM | 3823 | N | TYR B | 300 | −35.281 | −38.567 | 33.631 | 1.00 | 43.53 | N |
| ATOM | 3824 | CA | TYR B | 300 | −35.445 | −39.451 | 32.461 | 1.00 | 42.54 | C |
| ATOM | 3825 | C | TYR B | 300 | −34.382 | −40.543 | 32.502 | 1.00 | 42.49 | C |
| ATOM | 3826 | O | TYR B | 300 | −33.369 | −40.412 | 33.189 | 1.00 | 41.97 | O |
| ATOM | 3827 | CB | TYR B | 300 | −35.350 | −38.694 | 31.121 | 1.00 | 42.93 | C |
| ATOM | 3828 | CG | TYR B | 300 | −36.396 | −37.623 | 30.916 | 1.00 | 44.87 | C |
| ATOM | 3829 | CD1 | TYR B | 300 | −37.708 | −37.957 | 30.597 | 1.00 | 46.94 | C |
| ATOM | 3830 | CD2 | TYR B | 300 | −36.047 | −36.274 | 30.900 | 1.00 | 45.81 | C |
| ATOM | 3831 | CE1 | TYR B | 300 | −38.656 | −36.975 | 30.297 | 1.00 | 47.53 | C |
| ATOM | 3832 | CE2 | TYR B | 300 | −36.989 | −35.282 | 30.620 | 1.00 | 47.08 | C |
| ATOM | 3833 | CZ | TYR B | 300 | −38.296 | −35.639 | 30.311 | 1.00 | 52.42 | C |
| ATOM | 3834 | OH | TYR B | 300 | −39.255 | −34.694 | 30.020 | 1.00 | 50.44 | O |
| ATOM | 3835 | N | ARG B | 301 | −34.644 | −41.624 | 31.777 | 1.00 | 36.46 | N |
| ATOM | 3836 | CA | ARG B | 301 | −33.737 | −42.750 | 31.596 | 1.00 | 34.26 | C |
| ATOM | 3837 | C | ARG B | 301 | −33.705 | −42.996 | 30.086 | 1.00 | 35.84 | C |
| ATOM | 3838 | O | ARG B | 301 | −34.778 | −43.091 | 29.480 | 1.00 | 33.42 | O |
| ATOM | 3839 | CB | ARG B | 301 | −34.254 | −43.988 | 32.343 | 1.00 | 32.79 | C |
| ATOM | 3840 | CG | ARG B | 301 | −33.461 | −45.269 | 32.073 | 1.00 | 39.66 | C |
| ATOM | 3841 | CD | ARG B | 301 | −33.932 | −46.373 | 32.971 | 1.00 | 42.67 | C |
| ATOM | 3842 | NE | ARG B | 301 | −33.153 | −47.597 | 32.804 | 1.00 | 43.23 | N |
| ATOM | 3843 | CZ | ARG B | 301 | −33.351 | −48.526 | 31.876 | 1.00 | 53.81 | C |
| ATOM | 3844 | NH1 | ARG B | 301 | −34.318 | −48.383 | 30.971 | 1.00 | 50.49 | N |
| ATOM | 3845 | NH2 | ARG B | 301 | −32.584 | −49.610 | 31.844 | 1.00 | 37.59 | N |
| ATOM | 3846 | N | VAL B | 302 | −32.496 | −43.076 | 29.470 | 1.00 | 32.53 | N |
| ATOM | 3847 | CA | VAL B | 302 | −32.397 | −43.287 | 28.020 | 1.00 | 32.29 | C |
| ATOM | 3848 | C | VAL B | 302 | −31.274 | −44.306 | 27.692 | 1.00 | 36.41 | C |
| ATOM | 3849 | O | VAL B | 302 | −30.165 | −44.228 | 28.209 | 1.00 | 36.45 | O |
| ATOM | 3850 | CB | VAL B | 302 | −32.327 | −41.950 | 27.217 | 1.00 | 36.13 | C |
| ATOM | 3851 | CG1 | VAL B | 302 | −31.413 | −40.918 | 27.843 | 1.00 | 35.38 | C |
| ATOM | 3852 | CG2 | VAL B | 302 | −31.975 | −42.175 | 25.755 | 1.00 | 36.04 | C |
| ATOM | 3853 | N | VAL B | 303 | −31.620 | −45.296 | 26.853 | 1.00 | 33.65 | N |
| ATOM | 3854 | CA | VAL B | 303 | −30.772 | −46.426 | 26.463 | 1.00 | 32.65 | C |
| ATOM | 3855 | C | VAL B | 303 | −30.425 | −46.390 | 24.970 | 1.00 | 34.36 | C |
| ATOM | 3856 | O | VAL B | 303 | −31.313 | −46.153 | 24.141 | 1.00 | 32.81 | O |
| ATOM | 3857 | CB | VAL B | 303 | −31.520 | −47.755 | 26.777 | 1.00 | 36.82 | C |
| ATOM | 3858 | CG1 | VAL B | 303 | −30.672 | −48.979 | 26.413 | 1.00 | 36.66 | C |
| ATOM | 3859 | CG2 | VAL B | 303 | −31.985 | −47.815 | 28.229 | 1.00 | 36.53 | C |
| ATOM | 3860 | N | SER B | 304 | −29.143 | −46.694 | 24.623 | 1.00 | 30.40 | N |
| ATOM | 3861 | CA | SER B | 304 | −28.684 | −46.838 | 23.234 | 1.00 | 28.85 | C |
| ATOM | 3862 | C | SER B | 304 | −28.112 | −48.232 | 23.094 | 1.00 | 32.88 | C |
| ATOM | 3863 | O | SER B | 304 | −27.418 | −48.680 | 24.002 | 1.00 | 31.36 | O |
| ATOM | 3864 | CB | SER B | 304 | −27.647 | −45.793 | 22.880 | 1.00 | 30.00 | C |
| ATOM | 3865 | OG | SER B | 304 | −27.213 | −45.933 | 21.535 | 1.00 | 29.66 | O |
| ATOM | 3866 | N | VAL B | 305 | −28.435 | −48.942 | 21.989 | 1.00 | 30.22 | N |
| ATOM | 3867 | CA | VAL B | 305 | −28.027 | −50.333 | 21.803 | 1.00 | 29.44 | C |
| ATOM | 3868 | C | VAL B | 305 | −27.199 | −50.526 | 20.541 | 1.00 | 32.88 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3869 | O | VAL B | 305 | −27.734 | −50.473 | 19.433 | 1.00 | 34.43 | O |
| ATOM | 3870 | CB | VAL B | 305 | −29.257 | −51.266 | 21.813 | 1.00 | 34.16 | C |
| ATOM | 3871 | CG1 | VAL B | 305 | −28.826 | −52.720 | 21.852 | 1.00 | 34.26 | C |
| ATOM | 3872 | CG2 | VAL B | 305 | −30.175 | −50.968 | 22.997 | 1.00 | 34.50 | C |
| ATOM | 3873 | N | LEU B | 306 | −25.907 | −50.826 | 20.716 | 1.00 | 26.04 | N |
| ATOM | 3874 | CA | LEU B | 306 | −24.998 | −51.120 | 19.632 | 1.00 | 24.02 | C |
| ATOM | 3875 | C | LEU B | 306 | −24.921 | −52.638 | 19.452 | 1.00 | 29.88 | C |
| ATOM | 3876 | O | LEU B | 306 | −24.506 | −53.341 | 20.358 | 1.00 | 29.77 | O |
| ATOM | 3877 | CB | LEU B | 306 | −23.596 | −50.590 | 19.961 | 1.00 | 23.14 | C |
| ATOM | 3878 | CG | LEU B | 306 | −22.549 | −50.786 | 18.868 | 1.00 | 26.58 | C |
| ATOM | 3879 | CD1 | LEU B | 306 | −22.890 | −49.948 | 17.631 | 1.00 | 25.47 | C |
| ATOM | 3880 | CD2 | LEU B | 306 | −21.179 | −50.464 | 19.380 | 1.00 | 26.09 | C |
| ATOM | 3881 | N | THR B | 307 | −25.311 | −53.128 | 18.284 | 1.00 | 28.68 | N |
| ATOM | 3882 | CA | THR B | 307 | −25.222 | −54.530 | 17.885 | 1.00 | 28.63 | C |
| ATOM | 3883 | C | THR B | 307 | −23.755 | −54.752 | 17.545 | 1.00 | 32.50 | C |
| ATOM | 3884 | O | THR B | 307 | −23.138 | −53.902 | 16.896 | 1.00 | 30.97 | O |
| ATOM | 3885 | CB | THR B | 307 | −26.110 | −54.791 | 16.651 | 1.00 | 34.72 | C |
| ATOM | 3886 | OG1 | THR B | 307 | −27.473 | −54.777 | 17.060 | 1.00 | 36.84 | O |
| ATOM | 3887 | CG2 | THR B | 307 | −25.817 | −56.116 | 15.993 | 1.00 | 36.81 | C |
| ATOM | 3888 | N | VAL B | 308 | −23.186 | −55.868 | 17.985 | 1.00 | 29.22 | N |
| ATOM | 3889 | CA | VAL B | 308 | −21.766 | −56.106 | 17.750 | 1.00 | 27.92 | C |
| ATOM | 3890 | C | VAL B | 308 | −21.557 | −57.352 | 16.913 | 1.00 | 32.97 | C |
| ATOM | 3891 | O | VAL B | 308 | −22.440 | −58.217 | 16.811 | 1.00 | 31.01 | O |
| ATOM | 3892 | CB | VAL B | 308 | −20.958 | −56.113 | 19.099 | 1.00 | 29.73 | C |
| ATOM | 3893 | CG1 | VAL B | 308 | −21.229 | −54.830 | 19.909 | 1.00 | 28.25 | C |
| ATOM | 3894 | CG2 | VAL B | 308 | −21.240 | −57.357 | 19.946 | 1.00 | 29.34 | C |
| ATOM | 3895 | N | LEU B | 309 | −20.384 | −57.421 | 16.280 | 1.00 | 30.85 | N |
| ATOM | 3896 | CA | LEU B | 309 | −19.999 | −58.602 | 15.502 | 1.00 | 29.79 | C |
| ATOM | 3897 | C | LEU B | 309 | −19.521 | −59.648 | 16.512 | 1.00 | 29.56 | C |
| ATOM | 3898 | O | LEU B | 309 | −18.703 | −59.317 | 17.360 | 1.00 | 28.30 | O |
| ATOM | 3899 | CB | LEU B | 309 | −18.875 | −58.249 | 14.516 | 1.00 | 29.88 | C |
| ATOM | 3900 | CG | LEU B | 309 | −19.282 | −58.020 | 13.071 | 1.00 | 36.72 | C |
| ATOM | 3901 | CD1 | LEU B | 309 | −20.497 | −57.098 | 12.949 | 1.00 | 37.02 | C |
| ATOM | 3902 | CD2 | LEU B | 309 | −18.106 | −57.465 | 12.285 | 1.00 | 39.30 | C |
| ATOM | 3903 | N | HIS B | 310 | −19.982 | −60.902 | 16.406 | 1.00 | 25.79 | N |
| ATOM | 3904 | CA | HIS B | 310 | −19.588 | −61.991 | 17.339 | 1.00 | 24.67 | C |
| ATOM | 3905 | C | HIS B | 310 | −18.063 | −62.085 | 17.515 | 1.00 | 32.43 | C |
| ATOM | 3906 | O | HIS B | 310 | −17.555 | −62.097 | 18.651 | 1.00 | 31.68 | O |
| ATOM | 3907 | CB | HIS B | 310 | −20.106 | −63.346 | 16.848 | 1.00 | 23.75 | C |
| ATOM | 3908 | CG | HIS B | 310 | −21.584 | −63.394 | 16.702 | 1.00 | 26.41 | C |
| ATOM | 3909 | ND1 | HIS B | 310 | −22.233 | −62.623 | 15.763 | 1.00 | 27.93 | N |
| ATOM | 3910 | CD2 | HIS B | 310 | −22.495 | −64.150 | 17.354 | 1.00 | 28.56 | C |
| ATOM | 3911 | CE1 | HIS B | 310 | −23.517 | −62.903 | 15.897 | 1.00 | 27.97 | C |
| ATOM | 3912 | NE2 | HIS B | 310 | −23.720 | −63.818 | 16.848 | 1.00 | 28.41 | N |
| ATOM | 3913 | N | GLN B | 311 | −17.343 | −62.110 | 16.385 | 1.00 | 31.08 | N |
| ATOM | 3914 | CA | GLN B | 311 | −15.889 | −62.226 | 16.387 | 1.00 | 32.91 | C |
| ATOM | 3915 | C | GLN B | 311 | −15.187 | −60.967 | 16.885 | 1.00 | 38.18 | C |
| ATOM | 3916 | O | GLN B | 311 | −14.091 | −61.080 | 17.446 | 1.00 | 37.78 | O |
| ATOM | 3917 | CB | GLN B | 311 | −15.360 | −62.640 | 14.991 | 1.00 | 35.54 | C |
| ATOM | 3918 | CG | GLN B | 311 | −14.017 | −63.385 | 15.041 | 1.00 | 58.10 | C |
| ATOM | 3919 | CD | GLN B | 311 | −14.065 | −64.642 | 15.895 | 1.00 | 70.82 | C |
| ATOM | 3920 | OE1 | GLN B | 311 | −15.010 | −65.430 | 15.806 | 1.00 | 66.34 | O |
| ATOM | 3921 | NE2 | GLN B | 311 | −13.090 | −64.825 | 16.799 | 1.00 | 53.69 | N |
| ATOM | 3922 | N | ASP B | 312 | −15.807 | −59.771 | 16.717 | 1.00 | 33.86 | N |
| ATOM | 3923 | CA | ASP B | 312 | −15.206 | −58.534 | 17.227 | 1.00 | 32.24 | C |
| ATOM | 3924 | C | ASP B | 312 | −15.217 | −58.541 | 18.765 | 1.00 | 32.36 | C |
| ATOM | 3925 | O | ASP B | 312 | −14.210 | −58.190 | 19.379 | 1.00 | 33.76 | O |
| ATOM | 3926 | CB | ASP B | 312 | −15.913 | −57.273 | 16.666 | 1.00 | 34.57 | C |
| ATOM | 3927 | CG | ASP B | 312 | −15.554 | −56.857 | 15.244 | 1.00 | 49.71 | C |
| ATOM | 3928 | OD1 | ASP B | 312 | −14.626 | −57.464 | 14.657 | 1.00 | 51.59 | O |
| ATOM | 3929 | OD2 | ASP B | 312 | −16.151 | −55.878 | 14.746 | 1.00 | 56.94 | O |
| ATOM | 3930 | N | TRP B | 313 | −16.329 | −58.965 | 19.395 | 1.00 | 23.45 | N |
| ATOM | 3931 | CA | TRP B | 313 | −16.349 | −59.074 | 20.842 | 1.00 | 21.17 | C |
| ATOM | 3932 | C | TRP B | 313 | −15.282 | −60.123 | 21.267 | 1.00 | 25.61 | C |
| ATOM | 3933 | O | TRP B | 313 | −14.453 | −59.815 | 22.107 | 1.00 | 26.86 | O |
| ATOM | 3934 | CB | TRP B | 313 | −17.767 | −59.443 | 21.386 | 1.00 | 17.68 | C |
| ATOM | 3935 | CG | TRP B | 313 | −17.781 | −59.583 | 22.874 | 1.00 | 16.63 | C |
| ATOM | 3936 | CD1 | TRP B | 313 | −17.551 | −60.721 | 23.589 | 1.00 | 19.40 | C |
| ATOM | 3937 | CD2 | TRP B | 313 | −17.756 | −58.506 | 23.823 | 1.00 | 15.63 | C |
| ATOM | 3938 | NE1 | TRP B | 313 | −17.541 | −60.433 | 24.941 | 1.00 | 17.98 | N |
| ATOM | 3939 | CE2 | TRP B | 313 | −17.626 | −59.078 | 25.105 | 1.00 | 18.88 | C |
| ATOM | 3940 | CE3 | TRP B | 313 | −17.900 | −57.121 | 23.717 | 1.00 | 16.37 | C |
| ATOM | 3941 | CZ2 | TRP B | 313 | −17.545 | −58.302 | 26.259 | 1.00 | 19.00 | C |
| ATOM | 3942 | CZ3 | TRP B | 313 | −17.865 | −56.354 | 24.864 | 1.00 | 17.78 | C |
| ATOM | 3943 | CH2 | TRP B | 313 | −17.722 | −56.946 | 26.121 | 1.00 | 18.95 | C |
| ATOM | 3944 | N | LEU B | 314 | −15.270 | −61.307 | 20.648 | 1.00 | 21.94 | N |
| ATOM | 3945 | CA | LEU B | 314 | −14.318 | −62.368 | 21.000 | 1.00 | 23.01 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 3946 | C | LEU B | 314 | −12.843 | −62.029 | 20.687 | 1.00 | 30.27 | C |
| ATOM | 3947 | O | LEU B | 314 | −11.959 | −62.501 | 21.411 | 1.00 | 29.40 | O |
| ATOM | 3948 | CB | LEU B | 314 | −14.718 | −63.716 | 20.383 | 1.00 | 22.76 | C |
| ATOM | 3949 | CG | LEU B | 314 | −16.061 | −64.253 | 20.897 | 1.00 | 26.96 | C |
| ATOM | 3950 | CD1 | LEU B | 314 | −16.581 | −65.339 | 20.011 | 1.00 | 26.47 | C |
| ATOM | 3951 | CD2 | LEU B | 314 | −15.946 | −64.742 | 22.346 | 1.00 | 29.01 | C |
| ATOM | 3952 | N | ASN B | 315 | −12.570 | −61.159 | 19.707 | 1.00 | 28.45 | N |
| ATOM | 3953 | CA | ASN B | 315 | −11.187 | −60.729 | 19.430 | 1.00 | 28.88 | C |
| ATOM | 3954 | C | ASN B | 315 | −10.657 | −59.622 | 20.392 | 1.00 | 33.13 | C |
| ATOM | 3955 | O | ASN B | 315 | −9.483 | −59.266 | 20.304 | 1.00 | 33.35 | O |
| ATOM | 3956 | CB | ASN B | 315 | −11.010 | −60.309 | 17.960 | 1.00 | 27.97 | C |
| ATOM | 3957 | CG | ASN B | 315 | −10.988 | −61.467 | 17.006 | 1.00 | 44.35 | C |
| ATOM | 3958 | OD1 | ASN B | 315 | −10.807 | −62.619 | 17.390 | 1.00 | 45.25 | O |
| ATOM | 3959 | ND2 | ASN B | 315 | −11.167 | −61.192 | 15.732 | 1.00 | 41.34 | N |
| ATOM | 3960 | N | GLY B | 316 | −11.472 | −59.153 | 21.330 | 1.00 | 29.08 | N |
| ATOM | 3961 | CA | GLY B | 316 | −11.035 | −58.172 | 22.317 | 1.00 | 28.60 | C |
| ATOM | 3962 | C | GLY B | 316 | −11.202 | −56.714 | 21.941 | 1.00 | 31.49 | C |
| ATOM | 3963 | O | GLY B | 316 | −10.610 | −55.856 | 22.594 | 1.00 | 30.44 | O |
| ATOM | 3964 | N | LYS B | 317 | −12.054 | −56.408 | 20.927 | 1.00 | 27.87 | N |
| ATOM | 3965 | CA | LYS B | 317 | −12.342 | −55.028 | 20.533 | 1.00 | 26.28 | C |
| ATOM | 3966 | C | LYS B | 317 | −13.032 | −54.293 | 21.678 | 1.00 | 29.75 | C |
| ATOM | 3967 | O | LYS B | 317 | −13.862 | −54.888 | 22.392 | 1.00 | 28.00 | O |
| ATOM | 3968 | CB | LYS B | 317 | −13.209 | −54.963 | 19.259 | 1.00 | 27.73 | C |
| ATOM | 3969 | CG | LYS B | 317 | −12.492 | −55.486 | 18.013 | 1.00 | 32.01 | C |
| ATOM | 3970 | CD | LYS B | 317 | −12.796 | −54.697 | 16.763 | 1.00 | 39.00 | C |
| ATOM | 3971 | CE | LYS B | 317 | −12.029 | −55.229 | 15.567 | 1.00 | 52.98 | C |
| ATOM | 3972 | NZ | LYS B | 317 | −12.453 | −54.581 | 14.287 | 1.00 | 63.09 | N |
| ATOM | 3973 | N | GLU B | 318 | −12.629 | −53.008 | 21.888 | 1.00 | 26.82 | N |
| ATOM | 3974 | CA | GLU B | 318 | −13.170 | −52.144 | 22.936 | 1.00 | 25.94 | C |
| ATOM | 3975 | C | GLU B | 318 | −14.320 | −51.364 | 22.398 | 1.00 | 27.57 | C |
| ATOM | 3976 | O | GLU B | 318 | −14.174 | −50.720 | 21.375 | 1.00 | 28.30 | O |
| ATOM | 3977 | CB | GLU B | 318 | −12.113 | −51.174 | 23.454 | 1.00 | 27.93 | C |
| ATOM | 3978 | CG | GLU B | 318 | −10.861 | −51.867 | 23.982 | 1.00 | 51.66 | C |
| ATOM | 3979 | CD | GLU B | 318 | −10.050 | −51.141 | 25.048 | 1.00 | 87.34 | C |
| ATOM | 3980 | OE1 | GLU B | 318 | −10.230 | −49.912 | 25.216 | 1.00 | 96.27 | O |
| ATOM | 3981 | OE2 | GLU B | 318 | −9.212 | −51.806 | 25.702 | 1.00 | 77.28 | O |
| ATOM | 3982 | N | TYR B | 319 | −15.458 | −51.389 | 23.099 | 1.00 | 22.98 | N |
| ATOM | 3983 | CA | TYR B | 319 | −16.658 | −50.660 | 22.728 | 1.00 | 22.26 | C |
| ATOM | 3984 | C | TYR B | 319 | −16.792 | −49.471 | 23.670 | 1.00 | 28.61 | C |
| ATOM | 3985 | O | TYR B | 319 | −16.913 | −49.665 | 24.865 | 1.00 | 29.99 | O |
| ATOM | 3986 | CB | TYR B | 319 | −17.882 | −51.577 | 22.815 | 1.00 | 22.10 | C |
| ATOM | 3987 | CG | TYR B | 319 | −17.809 | −52.683 | 21.789 | 1.00 | 22.76 | C |
| ATOM | 3988 | CD1 | TYR B | 319 | −17.127 | −53.866 | 22.062 | 1.00 | 24.11 | C |
| ATOM | 3989 | CD2 | TYR B | 319 | −18.242 | −52.476 | 20.486 | 1.00 | 23.21 | C |
| ATOM | 3990 | CE1 | TYR B | 319 | −16.928 | −54.826 | 21.082 | 1.00 | 21.37 | C |
| ATOM | 3991 | CE2 | TYR B | 319 | −18.155 | −53.484 | 19.531 | 1.00 | 23.77 | C |
| ATOM | 3992 | CZ | TYR B | 319 | −17.502 | −54.662 | 19.842 | 1.00 | 26.19 | C |
| ATOM | 3993 | OH | TYR B | 319 | −17.325 | −55.647 | 18.927 | 1.00 | 29.87 | O |
| ATOM | 3994 | N | LYS B | 320 | −16.744 | −48.257 | 23.137 | 1.00 | 25.26 | N |
| ATOM | 3995 | CA | LYS B | 320 | −16.815 | −47.022 | 23.909 | 1.00 | 24.58 | C |
| ATOM | 3996 | C | LYS B | 320 | −18.127 | −46.320 | 23.648 | 1.00 | 30.89 | C |
| ATOM | 3997 | O | LYS B | 320 | −18.556 | −46.211 | 22.514 | 1.00 | 31.23 | O |
| ATOM | 3998 | CB | LYS B | 320 | −15.645 | −46.128 | 23.519 | 1.00 | 24.63 | C |
| ATOM | 3999 | CG | LYS B | 320 | −15.405 | −44.843 | 24.317 | 1.00 | 18.93 | C |
| ATOM | 4000 | CD | LYS B | 320 | −13.981 | −44.401 | 23.933 | 1.00 | 35.48 | C |
| ATOM | 4001 | CE | LYS B | 320 | −13.371 | −43.263 | 24.672 | 1.00 | 45.94 | C |
| ATOM | 4002 | NZ | LYS B | 320 | −11.868 | −43.307 | 24.645 | 1.00 | 53.09 | N |
| ATOM | 4003 | N | CYS B | 321 | −18.757 | −45.854 | 24.705 | 1.00 | 30.09 | N |
| ATOM | 4004 | CA | CYS B | 321 | −19.995 | −45.124 | 24.657 | 1.00 | 30.45 | C |
| ATOM | 4005 | C | CYS B | 321 | −19.729 | −43.726 | 25.245 | 1.00 | 32.29 | C |
| ATOM | 4006 | O | CYS B | 321 | −19.385 | −43.644 | 26.413 | 1.00 | 32.69 | O |
| ATOM | 4007 | CB | CYS B | 321 | −21.058 | −45.855 | 25.460 | 1.00 | 32.36 | C |
| ATOM | 4008 | SG | CYS B | 321 | −22.665 | −45.043 | 25.367 | 1.00 | 37.75 | S |
| ATOM | 4009 | N | LYS B | 322 | −19.907 | −42.648 | 24.460 | 1.00 | 26.76 | N |
| ATOM | 4010 | CA | LYS B | 322 | −19.719 | −41.256 | 24.900 | 1.00 | 24.65 | C |
| ATOM | 4011 | C | LYS B | 322 | −21.102 | −40.610 | 24.984 | 1.00 | 27.71 | C |
| ATOM | 4012 | O | LYS B | 322 | −21.775 | −40.495 | 23.961 | 1.00 | 26.11 | O |
| ATOM | 4013 | CB | LYS B | 322 | −18.817 | −40.490 | 23.928 | 1.00 | 25.44 | C |
| ATOM | 4014 | CG | LYS B | 322 | −18.702 | −38.980 | 24.237 | 1.00 | 45.09 | C |
| ATOM | 4015 | CD | LYS B | 322 | −18.249 | −38.122 | 23.028 | 1.00 | 52.25 | C |
| ATOM | 4016 | CE | LYS B | 322 | −16.761 | −38.185 | 22.779 | 1.00 | 54.96 | C |
| ATOM | 4017 | NZ | LYS B | 322 | −16.318 | −37.171 | 21.787 | 1.00 | 56.18 | N |
| ATOM | 4018 | N | VAL B | 323 | −21.503 | −40.130 | 26.185 | 1.00 | 24.97 | N |
| ATOM | 4019 | CA | VAL B | 323 | −22.816 | −39.510 | 26.385 | 1.00 | 24.75 | C |
| ATOM | 4020 | C | VAL B | 323 | −22.710 | −37.994 | 26.505 | 1.00 | 27.27 | C |
| ATOM | 4021 | O | VAL B | 323 | −21.892 | −37.498 | 27.278 | 1.00 | 23.90 | O |
| ATOM | 4022 | CB | VAL B | 323 | −23.530 | −40.140 | 27.591 | 1.00 | 28.83 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 4023 | CG1 | VAL B | 323 | −24.868 | −39.444 | 27.866 | 1.00 | 28.94 | C |
| ATOM | 4024 | CG2 | VAL B | 323 | −23.728 | −41.635 | 27.352 | 1.00 | 28.43 | C |
| ATOM | 4025 | N | SER B | 324 | −23.567 | −37.262 | 25.738 | 1.00 | 25.19 | N |
| ATOM | 4026 | CA | SER B | 324 | −23.591 | −35.794 | 25.710 | 1.00 | 24.41 | C |
| ATOM | 4027 | C | SER B | 324 | −24.975 | −35.308 | 26.076 | 1.00 | 29.81 | C |
| ATOM | 4028 | O | SER B | 324 | −25.982 | −35.925 | 25.710 | 1.00 | 29.06 | O |
| ATOM | 4029 | CB | SER B | 324 | −23.111 | −35.260 | 24.355 | 1.00 | 26.95 | C |
| ATOM | 4030 | OG | SER B | 324 | −21.703 | −35.429 | 24.191 | 1.00 | 30.94 | O |
| ATOM | 4031 | N | ASN B | 325 | −25.018 | −34.256 | 26.908 | 1.00 | 29.30 | N |
| ATOM | 4032 | CA | ASN B | 325 | −26.257 | −33.676 | 27.430 | 1.00 | 30.03 | C |
| ATOM | 4033 | C | ASN B | 325 | −25.943 | −32.252 | 27.829 | 1.00 | 35.53 | C |
| ATOM | 4034 | O | ASN B | 325 | −24.801 | −32.014 | 28.193 | 1.00 | 35.17 | O |
| ATOM | 4035 | CB | ASN B | 325 | −26.721 | −34.481 | 28.656 | 1.00 | 28.82 | C |
| ATOM | 4036 | CG | ASN B | 325 | −28.032 | −34.039 | 29.227 | 1.00 | 44.00 | C |
| ATOM | 4037 | OD1 | ASN B | 325 | −28.089 | −33.390 | 30.286 | 1.00 | 46.66 | O |
| ATOM | 4038 | ND2 | ASN B | 325 | −29.114 | −34.371 | 28.538 | 1.00 | 30.03 | N |
| ATOM | 4039 | N | LYS B | 326 | −26.916 | −31.308 | 27.773 | 1.00 | 33.88 | N |
| ATOM | 4040 | CA | LYS B | 326 | −26.649 | −29.905 | 28.159 | 1.00 | 34.74 | C |
| ATOM | 4041 | C | LYS B | 326 | −26.332 | −29.780 | 29.672 | 1.00 | 42.09 | C |
| ATOM | 4042 | O | LYS B | 326 | −25.578 | −28.885 | 30.070 | 1.00 | 40.27 | O |
| ATOM | 4043 | CB | LYS B | 326 | −27.816 | −28.977 | 27.789 | 1.00 | 36.60 | C |
| ATOM | 4044 | CG | LYS B | 326 | −27.420 | −27.505 | 27.721 | 1.00 | 38.50 | C |
| ATOM | 4045 | CD | LYS B | 326 | −28.424 | −26.574 | 28.370 | 1.00 | 46.29 | C |
| ATOM | 4046 | CE | LYS B | 326 | −27.822 | −25.222 | 28.640 | 1.00 | 52.67 | C |
| ATOM | 4047 | NZ | LYS B | 326 | −27.038 | −25.204 | 29.911 | 1.00 | 67.27 | N |
| ATOM | 4048 | N | GLY B | 327 | −26.882 | −30.702 | 30.477 | 1.00 | 41.26 | N |
| ATOM | 4049 | CA | GLY B | 327 | −26.620 | −30.798 | 31.909 | 1.00 | 41.08 | C |
| ATOM | 4050 | C | GLY B | 327 | −25.324 | −31.515 | 32.280 | 1.00 | 43.39 | C |
| ATOM | 4051 | O | GLY B | 327 | −25.112 | −31.814 | 33.457 | 1.00 | 44.86 | O |
| ATOM | 4052 | N | LEU B | 328 | −24.448 | −31.807 | 31.311 | 1.00 | 37.18 | N |
| ATOM | 4053 | CA | LEU B | 328 | −23.163 | −32.429 | 31.579 | 1.00 | 37.32 | C |
| ATOM | 4054 | C | LEU B | 328 | −22.088 | −31.431 | 31.173 | 1.00 | 44.05 | C |
| ATOM | 4055 | O | LEU B | 328 | −21.925 | −31.264 | 29.968 | 1.00 | 44.23 | O |
| ATOM | 4056 | CB | LEU B | 328 | −22.981 | −33.740 | 30.761 | 1.00 | 36.71 | C |
| ATOM | 4057 | CG | LEU B | 328 | −23.423 | −35.028 | 31.437 | 1.00 | 39.94 | C |
| ATOM | 4058 | CD1 | LEU B | 328 | −23.499 | −36.170 | 30.440 | 1.00 | 38.30 | C |
| ATOM | 4059 | CD2 | LEU B | 328 | −22.525 | −35.369 | 32.615 | 1.00 | 40.87 | C |
| ATOM | 4060 | N | PRO B | 329 | −21.338 | −30.762 | 32.104 | 1.00 | 41.94 | N |
| ATOM | 4061 | CA | PRO B | 329 | −20.250 | −29.841 | 31.673 | 1.00 | 41.44 | C |
| ATOM | 4062 | C | PRO B | 329 | −19.309 | −30.402 | 30.599 | 1.00 | 43.11 | C |
| ATOM | 4063 | O | PRO B | 329 | −18.829 | −29.639 | 29.754 | 1.00 | 42.90 | O |
| ATOM | 4064 | CB | PRO B | 329 | −19.478 | −29.548 | 32.974 | 1.00 | 43.91 | C |
| ATOM | 4065 | CG | PRO B | 329 | −20.002 | −30.526 | 33.986 | 1.00 | 49.01 | C |
| ATOM | 4066 | CD | PRO B | 329 | −21.407 | −30.834 | 33.576 | 1.00 | 44.20 | C |
| ATOM | 4067 | N | SER B | 330 | −19.035 | −31.725 | 30.646 | 1.00 | 37.79 | N |
| ATOM | 4068 | CA | SER B | 330 | −18.254 | −32.432 | 29.628 | 1.00 | 37.20 | C |
| ATOM | 4069 | C | SER B | 330 | −18.847 | −33.857 | 29.412 | 1.00 | 40.74 | C |
| ATOM | 4070 | O | SER B | 330 | −19.639 | −34.334 | 30.224 | 1.00 | 40.95 | O |
| ATOM | 4071 | CB | SER B | 330 | −16.757 | −32.431 | 29.956 | 1.00 | 40.33 | C |
| ATOM | 4072 | OG | SER B | 330 | −16.332 | −33.520 | 30.756 | 1.00 | 49.62 | O |
| ATOM | 4073 | N | SER B | 331 | −18.544 | −34.482 | 28.281 | 1.00 | 37.11 | N |
| ATOM | 4074 | CA | SER B | 331 | −19.123 | −35.790 | 27.950 | 1.00 | 36.75 | C |
| ATOM | 4075 | C | SER B | 331 | −18.675 | −36.908 | 28.899 | 1.00 | 38.43 | C |
| ATOM | 4076 | O | SER B | 331 | −17.542 | −36.885 | 29.383 | 1.00 | 38.16 | O |
| ATOM | 4077 | CB | SER B | 331 | −18.789 | −36.179 | 26.507 | 1.00 | 38.78 | C |
| ATOM | 4078 | OG | SER B | 331 | −19.097 | −35.142 | 25.587 | 1.00 | 46.23 | O |
| ATOM | 4079 | N | ILE B | 332 | −19.567 | −37.869 | 29.157 | 1.00 | 33.55 | N |
| ATOM | 4080 | CA | ILE B | 332 | −19.278 | −39.053 | 29.970 | 1.00 | 33.48 | C |
| ATOM | 4081 | C | ILE B | 332 | −18.923 | −40.197 | 29.004 | 1.00 | 36.47 | C |
| ATOM | 4082 | O | ILE B | 332 | −19.791 | −40.688 | 28.279 | 1.00 | 35.59 | O |
| ATOM | 4083 | CB | ILE B | 332 | −20.469 | −39.483 | 30.889 | 1.00 | 37.01 | C |
| ATOM | 4084 | CG1 | ILE B | 332 | −20.930 | −38.349 | 31.858 | 1.00 | 37.90 | C |
| ATOM | 4085 | CG2 | ILE B | 332 | −20.127 | −40.763 | 31.668 | 1.00 | 36.71 | C |
| ATOM | 4086 | CD1 | ILE B | 332 | −19.930 | −37.860 | 32.843 | 1.00 | 51.36 | C |
| ATOM | 4087 | N | GLU B | 333 | −17.661 | −40.625 | 29.016 | 1.00 | 31.90 | N |
| ATOM | 4088 | CA | GLU B | 333 | −17.205 | −41.762 | 28.240 | 1.00 | 30.26 | C |
| ATOM | 4089 | C | GLU B | 333 | −17.178 | −43.009 | 29.146 | 1.00 | 32.57 | C |
| ATOM | 4090 | O | GLU B | 333 | −16.920 | −42.900 | 30.342 | 1.00 | 32.63 | O |
| ATOM | 4091 | CB | GLU B | 333 | −15.811 | −41.484 | 27.673 | 1.00 | 31.30 | C |
| ATOM | 4092 | CG | GLU B | 333 | −15.794 | −40.346 | 26.671 | 1.00 | 33.53 | C |
| ATOM | 4093 | CD | GLU B | 333 | −14.529 | −40.291 | 25.839 | 1.00 | 55.95 | C |
| ATOM | 4094 | OE1 | GLU B | 333 | −13.481 | −40.779 | 26.319 | 1.00 | 41.50 | O |
| ATOM | 4095 | OE2 | GLU B | 333 | −14.593 | −39.806 | 24.686 | 1.00 | 61.12 | O |
| ATOM | 4096 | N | LYS B | 334 | −17.497 | −44.175 | 28.580 | 1.00 | 28.02 | N |
| ATOM | 4097 | CA | LYS B | 334 | −17.461 | −45.483 | 29.262 | 1.00 | 27.23 | C |
| ATOM | 4098 | C | LYS B | 334 | −17.010 | −46.528 | 28.235 | 1.00 | 30.37 | C |
| ATOM | 4099 | O | LYS B | 334 | −17.467 | −46.482 | 27.090 | 1.00 | 29.34 | O |

TABLE 7-continued

Three-dimensional crystal coordinates for caffeine-pembrolizumab complex.
Atomic Coordinates of Caffeine/Pembrolizumab Crystal Complex

| | | | | | | | | | | | |
|---|---|---|---|---|---|---|---|---|---|---|---|
| ATOM | 4100 | CB | LYS | B | 334 | −18.832 | −45.868 | 29.861 | 1.00 | 29.17 | C |
| ATOM | 4101 | CG | LYS | B | 334 | −19.283 | −45.029 | 31.064 | 1.00 | 36.18 | C |
| ATOM | 4102 | CD | LYS | B | 334 | −18.418 | −45.192 | 32.314 | 1.00 | 37.46 | C |
| ATOM | 4103 | CE | LYS | B | 334 | −18.859 | −44.212 | 33.381 | 1.00 | 46.86 | C |
| ATOM | 4104 | NZ | LYS | B | 334 | −18.168 | −44.413 | 34.677 | 1.00 | 49.97 | N |
| ATOM | 4105 | N | THR | B | 335 | −16.069 | −47.406 | 28.607 | 1.00 | 27.45 | N |
| ATOM | 4106 | CA | THR | B | 335 | −15.515 | −48.419 | 27.689 | 1.00 | 28.01 | C |
| ATOM | 4107 | C | THR | B | 335 | −15.785 | −49.818 | 28.240 | 1.00 | 32.11 | C |
| ATOM | 4108 | O | THR | B | 335 | −15.953 | −49.989 | 29.437 | 1.00 | 32.51 | O |
| ATOM | 4109 | CB | THR | B | 335 | −13.993 | −48.164 | 27.479 | 1.00 | 39.31 | C |
| ATOM | 4110 | OG1 | THR | B | 335 | −13.787 | −46.799 | 27.147 | 1.00 | 40.77 | O |
| ATOM | 4111 | CG2 | THR | B | 335 | −13.402 | −48.994 | 26.362 | 1.00 | 40.43 | C |
| ATOM | 4112 | N | ILE | B | 336 | −15.858 | −50.807 | 27.368 | 1.00 | 29.15 | N |
| ATOM | 4113 | CA | ILE | B | 336 | −16.082 | −52.198 | 27.779 | 1.00 | 28.22 | C |
| ATOM | 4114 | C | ILE | B | 336 | −15.535 | −53.144 | 26.708 | 1.00 | 29.19 | C |
| ATOM | 4115 | O | ILE | B | 336 | −15.760 | −52.949 | 25.519 | 1.00 | 27.60 | O |
| ATOM | 4116 | CB | ILE | B | 336 | −17.586 | −52.493 | 28.142 | 1.00 | 31.78 | C |
| ATOM | 4117 | CG1 | ILE | B | 336 | −17.673 | −53.643 | 29.127 | 1.00 | 33.88 | C |
| ATOM | 4118 | CG2 | ILE | B | 336 | −18.465 | −52.783 | 26.915 | 1.00 | 32.12 | C |
| ATOM | 4119 | CD1 | ILE | B | 336 | −18.969 | −53.831 | 29.695 | 1.00 | 51.19 | C |
| ATOM | 4120 | N | SER | B | 337 | −14.806 | −54.157 | 27.147 | 1.00 | 25.37 | N |
| ATOM | 4121 | CA | SER | B | 337 | −14.269 | −55.187 | 26.295 | 1.00 | 24.50 | C |
| ATOM | 4122 | C | SER | B | 337 | −14.340 | −56.506 | 27.019 | 1.00 | 28.97 | C |
| ATOM | 4123 | O | SER | B | 337 | −14.664 | −56.559 | 28.209 | 1.00 | 28.78 | O |
| ATOM | 4124 | CB | SER | B | 337 | −12.829 | −54.872 | 25.911 | 1.00 | 27.86 | C |
| ATOM | 4125 | OG | SER | B | 337 | −12.103 | −54.259 | 26.954 | 1.00 | 36.70 | O |
| ATOM | 4126 | N | LYS | B | 338 | −14.076 | −57.576 | 26.283 | 1.00 | 25.55 | N |
| ATOM | 4127 | CA | LYS | B | 338 | −14.010 | −58.906 | 26.834 | 1.00 | 26.20 | C |
| ATOM | 4128 | C | LYS | B | 338 | −12.686 | −58.973 | 27.633 | 1.00 | 32.89 | C |
| ATOM | 4129 | O | LYS | B | 338 | −11.676 | −58.406 | 27.189 | 1.00 | 32.48 | O |
| ATOM | 4130 | CB | LYS | B | 338 | −13.996 | −59.945 | 25.705 | 1.00 | 28.22 | C |
| ATOM | 4131 | CG | LYS | B | 338 | −14.185 | −61.377 | 26.185 | 1.00 | 31.76 | C |
| ATOM | 4132 | CD | LYS | B | 338 | −13.766 | −62.339 | 25.125 | 1.00 | 33.83 | C |
| ATOM | 4133 | CE | LYS | B | 338 | −12.295 | −62.624 | 25.211 | 1.00 | 33.92 | C |
| ATOM | 4134 | NZ | LYS | B | 338 | −11.791 | −63.215 | 23.960 | 1.00 | 35.45 | N |
| ATOM | 4135 | N | ALA | B | 339 | −12.711 | −59.655 | 28.808 | 1.00 | 29.26 | N |
| ATOM | 4136 | CA | ALA | B | 339 | −11.553 | −59.802 | 29.679 | 1.00 | 28.90 | C |
| ATOM | 4137 | C | ALA | B | 339 | −10.322 | −60.356 | 28.948 | 1.00 | 33.24 | C |
| ATOM | 4138 | O | ALA | B | 339 | −10.438 | −61.286 | 28.140 | 1.00 | 32.81 | O |
| ATOM | 4139 | CB | ALA | B | 339 | −11.911 | −60.684 | 30.858 | 1.00 | 30.04 | C |
| ATOM | 4140 | N | LYS | B | 340 | −9.151 | −59.758 | 29.203 | 1.00 | 31.20 | N |
| ATOM | 4141 | CA | LYS | B | 340 | −7.903 | −60.180 | 28.564 | 1.00 | 31.65 | C |
| ATOM | 4142 | C | LYS | B | 340 | −7.327 | −61.342 | 29.323 | 1.00 | 37.51 | C |
| ATOM | 4143 | O | LYS | B | 340 | −7.619 | −61.531 | 30.511 | 1.00 | 38.72 | O |
| ATOM | 4144 | CB | LYS | B | 340 | −6.888 | −59.032 | 28.520 | 1.00 | 34.70 | C |
| ATOM | 4145 | CG | LYS | B | 340 | −7.359 | −57.809 | 27.743 | 1.00 | 42.75 | C |
| ATOM | 4146 | CD | LYS | B | 340 | −6.277 | −56.723 | 27.731 | 1.00 | 56.21 | C |
| ATOM | 4147 | CE | LYS | B | 340 | −6.779 | −55.361 | 27.283 | 1.00 | 71.84 | C |
| ATOM | 4148 | NZ | LYS | B | 340 | −6.149 | −54.920 | 26.005 | 1.00 | 80.10 | N |
| ATOM | 4149 | N | GLY | B | 341 | −6.507 | −62.115 | 28.639 | 1.00 | 34.20 | N |
| ATOM | 4150 | CA | GLY | B | 341 | −5.890 | −63.313 | 29.198 | 1.00 | 34.19 | C |
| ATOM | 4151 | C | GLY | B | 341 | −6.218 | −64.513 | 28.338 | 1.00 | 38.79 | C |
| ATOM | 4152 | O | GLY | B | 341 | −7.214 | −64.506 | 27.606 | 1.00 | 37.73 | O |
| ATOM | 4153 | N | GLN | B | 342 | −5.348 | −65.539 | 28.398 | 1.00 | 36.50 | N |
| ATOM | 4154 | CA | GLN | B | 342 | −5.462 | −66.772 | 27.613 | 1.00 | 35.59 | C |
| ATOM | 4155 | C | GLN | B | 342 | −6.805 | −67.478 | 27.863 | 1.00 | 37.71 | C |
| ATOM | 4156 | O | GLN | B | 342 | −7.024 | −67.953 | 28.979 | 1.00 | 38.52 | O |
| ATOM | 4157 | CB | GLN | B | 342 | −4.304 | −67.726 | 27.995 | 1.00 | 37.37 | C |
| ATOM | 4158 | CG | GLN | B | 342 | −4.280 | −69.077 | 27.270 | 1.00 | 47.55 | C |
| ATOM | 4159 | CD | GLN | B | 342 | −4.246 | −68.929 | 25.773 | 1.00 | 76.49 | C |
| ATOM | 4160 | OE1 | GLN | B | 342 | −3.537 | −68.071 | 25.238 | 1.00 | 78.45 | O |
| ATOM | 4161 | NE2 | GLN | B | 342 | −4.991 | −69.768 | 25.054 | 1.00 | 67.08 | N |
| ATOM | 4162 | N | PRO | B | 343 | −7.693 | −67.635 | 26.860 | 1.00 | 32.19 | N |
| ATOM | 4163 | CA | PRO | B | 343 | −8.934 | −68.385 | 27.116 | 1.00 | 31.75 | C |
| ATOM | 4164 | C | PRO | B | 343 | −8.651 | −69.820 | 27.542 | 1.00 | 36.38 | C |
| ATOM | 4165 | O | PRO | B | 343 | −7.785 | −70.463 | 26.964 | 1.00 | 37.72 | O |
| ATOM | 4166 | CB | PRO | B | 343 | −9.684 | −68.332 | 25.775 | 1.00 | 32.10 | C |
| ATOM | 4167 | CG | PRO | B | 343 | −9.100 | −67.204 | 25.059 | 1.00 | 35.16 | C |
| ATOM | 4168 | CD | PRO | B | 343 | −7.655 | −67.145 | 25.472 | 1.00 | 31.39 | C |
| ATOM | 4169 | N | ARG | B | 344 | −9.319 | −70.274 | 28.599 | 1.00 | 32.25 | N |
| ATOM | 4170 | CA | ARG | B | 344 | −9.212 | −71.623 | 29.139 | 1.00 | 32.43 | C |
| ATOM | 4171 | C | ARG | B | 344 | −10.594 | −72.298 | 29.066 | 1.00 | 34.75 | C |
| ATOM | 4172 | O | ARG | B | 344 | −11.638 | −71.676 | 29.254 | 1.00 | 33.44 | O |
| ATOM | 4173 | CB | ARG | B | 344 | −8.656 | −71.592 | 30.568 | 1.00 | 33.49 | C |
| ATOM | 4174 | CG | ARG | B | 344 | −7.183 | −71.292 | 30.553 | 1.00 | 42.74 | C |
| ATOM | 4175 | CD | ARG | B | 344 | −6.607 | −70.893 | 31.890 | 1.00 | 57.56 | C |
| ATOM | 4176 | NE | ARG | B | 344 | −5.404 | −71.665 | 32.215 | 1.00 | 78.37 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 4177 | CZ | ARG B | 344 | −4.221 | −71.578 | 31.597 | 1.00 | 94.52 | C |
| ATOM | 4178 | NH1 | ARG B | 344 | −4.050 | −70.735 | 30.577 | 1.00 | 74.27 | N |
| ATOM | 4179 | NH2 | ARG B | 344 | −3.203 | −72.338 | 31.988 | 1.00 | 85.56 | N |
| ATOM | 4180 | N | GLU B | 345 | −10.572 | −73.570 | 28.765 | 1.00 | 30.92 | N |
| ATOM | 4181 | CA | GLU B | 345 | −11.743 | −74.370 | 28.504 | 1.00 | 30.49 | C |
| ATOM | 4182 | C | GLU B | 345 | −12.388 | −74.902 | 29.775 | 1.00 | 34.95 | C |
| ATOM | 4183 | O | GLU B | 345 | −11.686 | −75.491 | 30.611 | 1.00 | 35.53 | O |
| ATOM | 4184 | CB | GLU B | 345 | −11.271 | −75.530 | 27.624 | 1.00 | 32.27 | C |
| ATOM | 4185 | CG | GLU B | 345 | −12.310 | −76.499 | 27.130 | 1.00 | 42.28 | C |
| ATOM | 4186 | CD | GLU B | 345 | −11.692 | −77.494 | 26.173 | 1.00 | 60.19 | C |
| ATOM | 4187 | OE1 | GLU B | 345 | −10.582 | −77.993 | 26.461 | 1.00 | 70.03 | O |
| ATOM | 4188 | OE2 | GLU B | 345 | −12.300 | −77.749 | 25.112 | 1.00 | 59.53 | O |
| ATOM | 4189 | N | PRO B | 346 | −13.731 | −74.811 | 29.902 | 1.00 | 30.15 | N |
| ATOM | 4190 | CA | PRO B | 346 | −14.388 | −75.391 | 31.077 | 1.00 | 29.41 | C |
| ATOM | 4191 | C | PRO B | 346 | −14.303 | −76.913 | 31.124 | 1.00 | 32.53 | C |
| ATOM | 4192 | O | PRO B | 346 | −14.269 | −77.561 | 30.087 | 1.00 | 30.00 | O |
| ATOM | 4193 | CB | PRO B | 346 | −15.858 | −74.959 | 30.915 | 1.00 | 30.77 | C |
| ATOM | 4194 | CG | PRO B | 346 | −16.032 | −74.677 | 29.488 | 1.00 | 34.69 | C |
| ATOM | 4195 | CD | PRO B | 346 | −14.710 | −74.189 | 28.988 | 1.00 | 30.75 | C |
| ATOM | 4196 | N | GLN B | 347 | −14.293 | −77.472 | 32.345 | 1.00 | 29.71 | N |
| ATOM | 4197 | CA | GLN B | 347 | −14.370 | −78.904 | 32.595 | 1.00 | 28.31 | C |
| ATOM | 4198 | C | GLN B | 347 | −15.742 | −79.061 | 33.215 | 1.00 | 30.00 | C |
| ATOM | 4199 | O | GLN B | 347 | −16.065 | −78.294 | 34.118 | 1.00 | 29.06 | O |
| ATOM | 4200 | CB | GLN B | 347 | −13.302 | −79.361 | 33.565 | 1.00 | 29.66 | C |
| ATOM | 4201 | CG | GLN B | 347 | −11.875 | −79.142 | 33.071 | 1.00 | 45.33 | C |
| ATOM | 4202 | CD | GLN B | 347 | −10.916 | −79.282 | 34.233 | 1.00 | 70.38 | C |
| ATOM | 4203 | OE1 | GLN B | 347 | −10.806 | −80.355 | 34.846 | 1.00 | 66.34 | O |
| ATOM | 4204 | NE2 | GLN B | 347 | −10.233 | −78.197 | 34.599 | 1.00 | 61.00 | N |
| ATOM | 4205 | N | VAL B | 348 | −16.573 | −79.983 | 32.695 | 1.00 | 25.69 | N |
| ATOM | 4206 | CA | VAL B | 348 | −17.936 | −80.192 | 33.171 | 1.00 | 25.68 | C |
| ATOM | 4207 | C | VAL B | 348 | −18.085 | −81.543 | 33.847 | 1.00 | 30.61 | C |
| ATOM | 4208 | O | VAL B | 348 | −17.794 | −82.569 | 33.230 | 1.00 | 31.66 | O |
| ATOM | 4209 | CB | VAL B | 348 | −18.937 | −80.004 | 32.013 | 1.00 | 28.56 | C |
| ATOM | 4210 | CG1 | VAL B | 348 | −20.379 | −80.018 | 32.522 | 1.00 | 28.70 | C |
| ATOM | 4211 | CG2 | VAL B | 348 | −18.652 | −78.694 | 31.305 | 1.00 | 27.18 | C |
| ATOM | 4212 | N | TYR B | 349 | −18.529 | −81.555 | 35.114 | 1.00 | 26.68 | N |
| ATOM | 4213 | CA | TYR B | 349 | −18.748 | −82.793 | 35.876 | 1.00 | 26.90 | C |
| ATOM | 4214 | C | TYR B | 349 | −20.134 | −82.771 | 36.443 | 1.00 | 33.26 | C |
| ATOM | 4215 | O | TYR B | 349 | −20.519 | −81.764 | 37.017 | 1.00 | 33.71 | O |
| ATOM | 4216 | CB | TYR B | 349 | −17.738 | −82.917 | 37.010 | 1.00 | 28.33 | C |
| ATOM | 4217 | CG | TYR B | 349 | −16.307 | −82.886 | 36.531 | 1.00 | 31.20 | C |
| ATOM | 4218 | CD1 | TYR B | 349 | −15.677 | −84.038 | 36.086 | 1.00 | 34.51 | C |
| ATOM | 4219 | CD2 | TYR B | 349 | −15.580 | −81.705 | 36.526 | 1.00 | 31.97 | C |
| ATOM | 4220 | CE1 | TYR B | 349 | −14.389 | −83.999 | 35.557 | 1.00 | 37.92 | C |
| ATOM | 4221 | CE2 | TYR B | 349 | −14.264 | −81.667 | 36.068 | 1.00 | 33.03 | C |
| ATOM | 4222 | CZ | TYR B | 349 | −13.679 | −82.812 | 35.555 | 1.00 | 39.42 | C |
| ATOM | 4223 | OH | TYR B | 349 | −12.379 | −82.812 | 35.104 | 1.00 | 35.57 | O |
| ATOM | 4224 | N | THR B | 350 | −20.908 | −83.830 | 36.257 | 1.00 | 33.30 | N |
| ATOM | 4225 | CA | THR B | 350 | −22.268 | −83.898 | 36.799 | 1.00 | 34.86 | C |
| ATOM | 4226 | C | THR B | 350 | −22.215 | −84.809 | 37.989 | 1.00 | 42.54 | C |
| ATOM | 4227 | O | THR B | 350 | −21.641 | −85.891 | 37.876 | 1.00 | 45.29 | O |
| ATOM | 4228 | CB | THR B | 350 | −23.273 | −84.396 | 35.774 | 1.00 | 36.28 | C |
| ATOM | 4229 | OG1 | THR B | 350 | −22.764 | −85.567 | 35.140 | 1.00 | 38.58 | O |
| ATOM | 4230 | CG2 | THR B | 350 | −23.610 | −83.339 | 34.762 | 1.00 | 32.51 | C |
| ATOM | 4231 | N | LEU B | 351 | −22.802 | −84.397 | 39.110 | 1.00 | 38.77 | N |
| ATOM | 4232 | CA | LEU B | 351 | −22.785 | −85.173 | 40.349 | 1.00 | 40.04 | C |
| ATOM | 4233 | C | LEU B | 351 | −24.231 | −85.568 | 40.729 | 1.00 | 44.78 | C |
| ATOM | 4234 | O | LEU B | 351 | −25.123 | −84.715 | 40.710 | 1.00 | 42.11 | O |
| ATOM | 4235 | CB | LEU B | 351 | −22.110 | −84.357 | 41.464 | 1.00 | 39.80 | C |
| ATOM | 4236 | CG | LEU B | 351 | −20.811 | −83.618 | 41.077 | 1.00 | 44.05 | C |
| ATOM | 4237 | CD1 | LEU B | 351 | −20.305 | −82.801 | 42.219 | 1.00 | 45.72 | C |
| ATOM | 4238 | CD2 | LEU B | 351 | −19.714 | −84.565 | 40.669 | 1.00 | 46.25 | C |
| ATOM | 4239 | N | PRO B | 352 | −24.495 | −86.869 | 41.012 | 1.00 | 43.41 | N |
| ATOM | 4240 | CA | PRO B | 352 | −25.875 | −87.290 | 41.331 | 1.00 | 43.38 | C |
| ATOM | 4241 | C | PRO B | 352 | −26.358 | −86.828 | 42.702 | 1.00 | 45.01 | C |
| ATOM | 4242 | O | PRO B | 352 | −25.528 | −86.395 | 43.510 | 1.00 | 43.42 | O |
| ATOM | 4243 | CB | PRO B | 352 | −25.795 | −88.827 | 41.259 | 1.00 | 45.70 | C |
| ATOM | 4244 | CG | PRO B | 352 | −24.396 | −89.141 | 41.605 | 1.00 | 49.87 | C |
| ATOM | 4245 | CD | PRO B | 352 | −23.561 | −88.014 | 41.067 | 1.00 | 44.92 | C |
| ATOM | 4246 | N | PRO B | 353 | −27.682 | −86.945 | 43.008 | 1.00 | 41.74 | N |
| ATOM | 4247 | CA | PRO B | 353 | −28.152 | −86.561 | 44.353 | 1.00 | 42.07 | C |
| ATOM | 4248 | C | PRO B | 353 | −27.557 | −87.417 | 45.440 | 1.00 | 48.90 | C |
| ATOM | 4249 | O | PRO B | 353 | −27.313 | −88.610 | 45.233 | 1.00 | 49.79 | O |
| ATOM | 4250 | CB | PRO B | 353 | −29.674 | −86.768 | 44.309 | 1.00 | 43.91 | C |
| ATOM | 4251 | CG | PRO B | 353 | −30.017 | −87.186 | 42.934 | 1.00 | 47.39 | C |
| ATOM | 4252 | CD | PRO B | 353 | −28.771 | −87.497 | 42.182 | 1.00 | 42.98 | C |
| ATOM | 4253 | N | SER B | 354 | −27.331 | −86.805 | 46.599 | 1.00 | 47.94 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 4254 | CA | SER B | 354 | −26.828 | −87.496 | 47.796 | 1.00 | 48.42 | C |
| ATOM | 4255 | C | SER B | 354 | −27.850 | −88.533 | 48.206 | 1.00 | 52.73 | C |
| ATOM | 4256 | O | SER B | 354 | −29.044 | −88.240 | 48.120 | 1.00 | 52.17 | O |
| ATOM | 4257 | CB | SER B | 354 | −26.646 | −86.499 | 48.937 | 1.00 | 50.47 | C |
| ATOM | 4258 | OG | SER B | 354 | −26.481 | −87.147 | 50.185 | 1.00 | 60.90 | O |
| ATOM | 4259 | N | GLN B | 355 | −27.414 | −89.722 | 48.665 | 1.00 | 50.99 | N |
| ATOM | 4260 | CA | GLN B | 355 | −28.360 | −90.745 | 49.153 | 1.00 | 52.55 | C |
| ATOM | 4261 | C | GLN B | 355 | −29.191 | −90.227 | 50.328 | 1.00 | 56.08 | C |
| ATOM | 4262 | O | GLN B | 355 | −30.352 | −90.598 | 50.430 | 1.00 | 55.98 | O |
| ATOM | 4263 | CB | GLN B | 355 | −27.659 | −92.061 | 49.551 | 1.00 | 55.14 | C |
| ATOM | 4264 | CG | GLN B | 355 | −27.218 | −92.900 | 48.353 | 1.00 | 76.02 | C |
| ATOM | 4265 | CD | GLN B | 355 | −28.387 | −93.335 | 47.492 | 1.00 | 93.96 | C |
| ATOM | 4266 | OE1 | GLN B | 355 | −29.457 | −93.723 | 47.995 | 1.00 | 86.14 | O |
| ATOM | 4267 | NE2 | GLN B | 355 | −28.232 | −93.235 | 46.173 | 1.00 | 85.05 | N |
| ATOM | 4268 | N | GLU B | 356 | −28.627 | −89.295 | 51.146 | 1.00 | 52.99 | N |
| ATOM | 4269 | CA | GLU B | 356 | −29.306 | −88.663 | 52.280 | 1.00 | 53.04 | C |
| ATOM | 4270 | C | GLU B | 356 | −30.471 | −87.738 | 51.853 | 1.00 | 58.39 | C |
| ATOM | 4271 | O | GLU B | 356 | −31.299 | −87.402 | 52.694 | 1.00 | 59.40 | O |
| ATOM | 4272 | CB | GLU B | 356 | −28.305 | −87.869 | 53.139 | 1.00 | 54.09 | C |
| ATOM | 4273 | CG | GLU B | 356 | −27.174 | −88.687 | 53.760 | 1.00 | 66.58 | C |
| ATOM | 4274 | CD | GLU B | 356 | −27.516 | −89.698 | 54.845 | 1.00 | 81.58 | C |
| ATOM | 4275 | OE1 | GLU B | 356 | −28.686 | −89.751 | 55.288 | 1.00 | 56.78 | O |
| ATOM | 4276 | OE2 | GLU B | 356 | −26.590 | −90.423 | 55.277 | 1.00 | 78.25 | O |
| ATOM | 4277 | N | GLU B | 357 | −30.533 | −87.314 | 50.583 | 1.00 | 55.41 | N |
| ATOM | 4278 | CA | GLU B | 357 | −31.613 | −86.471 | 50.048 | 1.00 | 55.98 | C |
| ATOM | 4279 | C | GLU B | 357 | −32.762 | −87.326 | 49.432 | 1.00 | 64.03 | C |
| ATOM | 4280 | O | GLU B | 357 | −33.771 | −86.761 | 49.007 | 1.00 | 63.73 | O |
| ATOM | 4281 | CB | GLU B | 357 | −31.033 | −85.521 | 48.969 | 1.00 | 55.96 | C |
| ATOM | 4282 | CG | GLU B | 357 | −31.848 | −84.260 | 48.691 | 1.00 | 59.88 | C |
| ATOM | 4283 | CD | GLU B | 357 | −31.241 | −83.321 | 47.664 | 1.00 | 68.32 | C |
| ATOM | 4284 | OE1 | GLU B | 357 | −30.331 | −83.756 | 46.923 | 1.00 | 54.17 | O |
| ATOM | 4285 | OE2 | GLU B | 357 | −31.694 | −82.155 | 47.575 | 1.00 | 63.63 | O |
| ATOM | 4286 | N | MET B | 358 | −32.632 | −88.678 | 49.403 | 1.00 | 63.45 | N |
| ATOM | 4287 | CA | MET B | 358 | −33.644 | −89.543 | 48.780 | 1.00 | 64.45 | C |
| ATOM | 4288 | C | MET B | 358 | −34.901 | −89.722 | 49.638 | 1.00 | 70.11 | C |
| ATOM | 4289 | O | MET B | 358 | −35.888 | −90.268 | 49.143 | 1.00 | 70.77 | O |
| ATOM | 4290 | CB | MET B | 358 | −33.043 | −90.896 | 48.372 | 1.00 | 67.48 | C |
| ATOM | 4291 | CG | MET B | 358 | −31.868 | −90.794 | 47.388 | 1.00 | 70.92 | C |
| ATOM | 4292 | SD | MET B | 358 | −32.135 | −89.936 | 45.798 | 1.00 | 75.16 | S |
| ATOM | 4293 | CE | MET B | 358 | −33.633 | −90.702 | 45.268 | 1.00 | 73.11 | C |
| ATOM | 4294 | N | THR B | 359 | −34.908 | −89.192 | 50.878 | 1.00 | 66.23 | N |
| ATOM | 4295 | CA | THR B | 359 | −36.072 | −89.188 | 51.748 | 1.00 | 66.62 | C |
| ATOM | 4296 | C | THR B | 359 | −36.819 | −87.834 | 51.567 | 1.00 | 71.33 | C |
| ATOM | 4297 | O | THR B | 359 | −37.211 | −87.216 | 52.563 | 1.00 | 72.52 | O |
| ATOM | 4298 | CB | THR B | 359 | −35.612 | −89.438 | 53.200 | 1.00 | 74.49 | C |
| ATOM | 4299 | OG1 | THR B | 359 | −34.701 | −88.407 | 53.591 | 1.00 | 71.22 | O |
| ATOM | 4300 | CG2 | THR B | 359 | −34.940 | −90.801 | 53.372 | 1.00 | 74.02 | C |
| ATOM | 4301 | N | LYS B | 360 | −37.000 | −87.372 | 50.294 | 1.00 | 66.06 | N |
| ATOM | 4302 | CA | LYS B | 360 | −37.680 | −86.114 | 49.939 | 1.00 | 64.31 | C |
| ATOM | 4303 | C | LYS B | 360 | −38.407 | −86.269 | 48.590 | 1.00 | 67.08 | C |
| ATOM | 4304 | O | LYS B | 360 | −37.986 | −87.081 | 47.772 | 1.00 | 66.69 | O |
| ATOM | 4305 | CB | LYS B | 360 | −36.683 | −84.951 | 49.849 | 1.00 | 65.23 | C |
| ATOM | 4306 | CG | LYS B | 360 | −36.050 | −84.574 | 51.181 | 1.00 | 79.85 | C |
| ATOM | 4307 | CD | LYS B | 360 | −35.346 | −83.219 | 51.125 | 1.00 | 90.59 | C |
| ATOM | 4308 | CE | LYS B | 360 | −36.277 | −82.035 | 51.276 | 1.00 | 105.16 | C |
| ATOM | 4309 | NZ | LYS B | 360 | −36.619 | −81.759 | 52.701 | 1.00 | 117.82 | N |
| ATOM | 4310 | N | ASN B | 361 | −39.480 | −85.477 | 48.353 | 1.00 | 62.48 | N |
| ATOM | 4311 | CA | ASN B | 361 | −40.288 | −85.529 | 47.116 | 1.00 | 61.17 | C |
| ATOM | 4312 | C | ASN B | 361 | −39.526 | −84.939 | 45.923 | 1.00 | 59.69 | C |
| ATOM | 4313 | O | ASN B | 361 | −39.875 | −85.218 | 44.777 | 1.00 | 57.65 | O |
| ATOM | 4314 | CB | ASN B | 361 | −41.654 | −84.803 | 47.318 | 1.00 | 64.43 | C |
| ATOM | 4315 | CG | ASN B | 361 | −42.682 | −84.974 | 46.201 | 1.00 | 82.48 | C |
| ATOM | 4316 | OD1 | ASN B | 361 | −43.172 | −83.993 | 45.616 | 1.00 | 77.01 | O |
| ATOM | 4317 | ND2 | ASN B | 361 | −43.087 | −86.210 | 45.923 | 1.00 | 68.04 | N |
| ATOM | 4318 | N | GLN B | 362 | −38.489 | −84.128 | 46.194 | 1.00 | 53.68 | N |
| ATOM | 4319 | CA | GLN B | 362 | −37.640 | −83.527 | 45.178 | 1.00 | 50.64 | C |
| ATOM | 4320 | C | GLN B | 362 | −36.147 | −83.744 | 45.512 | 1.00 | 50.31 | C |
| ATOM | 4321 | O | GLN B | 362 | −35.788 | −83.774 | 46.694 | 1.00 | 49.18 | O |
| ATOM | 4322 | CB | GLN B | 362 | −37.985 | −82.045 | 45.047 | 1.00 | 50.96 | C |
| ATOM | 4323 | CG | GLN B | 362 | −39.394 | −81.806 | 44.511 | 1.00 | 60.42 | C |
| ATOM | 4324 | CD | GLN B | 362 | −39.474 | −80.527 | 43.714 | 1.00 | 82.95 | C |
| ATOM | 4325 | OE1 | GLN B | 362 | −39.505 | −79.428 | 44.280 | 1.00 | 81.76 | O |
| ATOM | 4326 | NE2 | GLN B | 362 | −39.460 | −80.621 | 42.388 | 1.00 | 71.80 | N |
| ATOM | 4327 | N | VAL B | 363 | −35.293 | −83.936 | 44.465 | 1.00 | 44.24 | N |
| ATOM | 4328 | CA | VAL B | 363 | −33.840 | −84.163 | 44.605 | 1.00 | 42.42 | C |
| ATOM | 4329 | C | VAL B | 363 | −33.030 | −83.161 | 43.771 | 1.00 | 43.31 | C |
| ATOM | 4330 | O | VAL B | 363 | −33.534 | −82.587 | 42.798 | 1.00 | 41.73 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 4331 | CB | VAL B | 363 | −33.424 | −85.640 | 44.344 | 1.00 | 46.60 | C |
| ATOM | 4332 | CG1 | VAL B | 363 | −34.219 | −86.582 | 45.237 | 1.00 | 47.79 | C |
| ATOM | 4333 | CG2 | VAL B | 363 | −33.570 | −86.046 | 42.883 | 1.00 | 45.78 | C |
| ATOM | 4334 | N | SER B | 364 | −31.765 | −82.955 | 44.168 | 1.00 | 39.07 | N |
| ATOM | 4335 | CA | SER B | 364 | −30.867 | −81.981 | 43.545 | 1.00 | 37.68 | C |
| ATOM | 4336 | C | SER B | 364 | −29.797 | −82.609 | 42.638 | 1.00 | 39.73 | C |
| ATOM | 4337 | O | SER B | 364 | −28.916 | −83.334 | 43.112 | 1.00 | 37.84 | O |
| ATOM | 4338 | CB | SER B | 364 | −30.187 | −81.140 | 44.626 | 1.00 | 42.03 | C |
| ATOM | 4339 | OG | SER B | 364 | −31.126 | −80.370 | 45.363 | 1.00 | 53.53 | O |
| ATOM | 4340 | N | LEU B | 365 | −29.861 | −82.304 | 41.327 | 1.00 | 36.81 | N |
| ATOM | 4341 | CA | LEU B | 365 | −28.844 | −82.738 | 40.365 | 1.00 | 35.09 | C |
| ATOM | 4342 | C | LEU B | 365 | −27.850 | −81.580 | 40.273 | 1.00 | 35.44 | C |
| ATOM | 4343 | O | LEU B | 365 | −28.258 | −80.434 | 40.092 | 1.00 | 33.10 | O |
| ATOM | 4344 | CB | LEU B | 365 | −29.461 | −83.023 | 38.995 | 1.00 | 35.21 | C |
| ATOM | 4345 | CG | LEU B | 365 | −30.610 | −84.036 | 38.940 | 1.00 | 41.34 | C |
| ATOM | 4346 | CD1 | LEU B | 365 | −30.889 | −84.456 | 37.502 | 1.00 | 41.80 | C |
| ATOM | 4347 | CD2 | LEU B | 365 | −30.314 | −85.262 | 39.734 | 1.00 | 43.23 | C |
| ATOM | 4348 | N | THR B | 366 | −26.566 | −81.868 | 40.444 | 1.00 | 32.21 | N |
| ATOM | 4349 | CA | THR B | 366 | −25.524 | −80.861 | 40.433 | 1.00 | 31.37 | C |
| ATOM | 4350 | C | THR B | 366 | −24.677 | −80.947 | 39.187 | 1.00 | 38.34 | C |
| ATOM | 4351 | O | THR B | 366 | −24.398 | −82.043 | 38.687 | 1.00 | 35.99 | O |
| ATOM | 4352 | CB | THR B | 366 | −24.666 | −81.013 | 41.673 | 1.00 | 34.46 | C |
| ATOM | 4353 | OG1 | THR B | 366 | −25.507 | −80.843 | 42.811 | 1.00 | 34.50 | O |
| ATOM | 4354 | CG2 | THR B | 366 | −23.528 | −80.001 | 41.735 | 1.00 | 32.27 | C |
| ATOM | 4355 | N | CYS B | 367 | −24.214 | −79.766 | 38.723 | 1.00 | 37.12 | N |
| ATOM | 4356 | CA | CYS B | 367 | −23.301 | −79.664 | 37.604 | 1.00 | 36.60 | C |
| ATOM | 4357 | C | CYS B | 367 | −22.156 | −78.755 | 38.008 | 1.00 | 37.20 | C |
| ATOM | 4358 | O | CYS B | 367 | −22.379 | −77.576 | 38.264 | 1.00 | 36.50 | O |
| ATOM | 4359 | CB | CYS B | 367 | −24.002 | −79.148 | 36.357 | 1.00 | 37.57 | C |
| ATOM | 4360 | SG | CYS B | 367 | −22.955 | −79.167 | 34.884 | 1.00 | 42.43 | S |
| ATOM | 4361 | N | LEU B | 368 | −20.942 | −79.299 | 38.070 | 1.00 | 31.27 | N |
| ATOM | 4362 | CA | LEU B | 368 | −19.739 | −78.537 | 38.398 | 1.00 | 29.03 | C |
| ATOM | 4363 | C | LEU B | 368 | −19.027 | −78.141 | 37.062 | 1.00 | 32.54 | C |
| ATOM | 4364 | O | LEU B | 368 | −18.653 | −79.014 | 36.294 | 1.00 | 32.00 | O |
| ATOM | 4365 | CB | LEU B | 368 | −18.830 | −79.422 | 39.254 | 1.00 | 28.10 | C |
| ATOM | 4366 | CG | LEU B | 368 | −17.381 | −79.001 | 39.394 | 1.00 | 30.21 | C |
| ATOM | 4367 | CD1 | LEU B | 368 | −17.261 | −77.553 | 39.955 | 1.00 | 26.51 | C |
| ATOM | 4368 | CD2 | LEU B | 368 | −16.635 | −80.034 | 40.214 | 1.00 | 33.88 | C |
| ATOM | 4369 | N | VAL B | 369 | −18.875 | −76.837 | 36.799 | 1.00 | 27.75 | N |
| ATOM | 4370 | CA | VAL B | 369 | −18.180 | −76.295 | 35.637 | 1.00 | 26.47 | C |
| ATOM | 4371 | C | VAL B | 369 | −16.978 | −75.548 | 36.207 | 1.00 | 30.64 | C |
| ATOM | 4372 | O | VAL B | 369 | −17.160 | −74.728 | 37.086 | 1.00 | 30.98 | O |
| ATOM | 4373 | CB | VAL B | 369 | −19.091 | −75.383 | 34.801 | 1.00 | 29.30 | C |
| ATOM | 4374 | CG1 | VAL B | 369 | −18.396 | −74.949 | 33.514 | 1.00 | 28.94 | C |
| ATOM | 4375 | CG2 | VAL B | 369 | −20.413 | −76.086 | 34.498 | 1.00 | 28.76 | C |
| ATOM | 4376 | N | LYS B | 370 | −15.753 | −75.907 | 35.813 | 1.00 | 27.23 | N |
| ATOM | 4377 | CA | LYS B | 370 | −14.547 | −75.331 | 36.404 | 1.00 | 25.78 | C |
| ATOM | 4378 | C | LYS B | 370 | −13.397 | −75.232 | 35.431 | 1.00 | 30.05 | C |
| ATOM | 4379 | O | LYS B | 370 | −13.431 | −75.791 | 34.334 | 1.00 | 30.04 | O |
| ATOM | 4380 | CB | LYS B | 370 | −14.125 | −76.147 | 37.648 | 1.00 | 27.86 | C |
| ATOM | 4381 | CG | LYS B | 370 | −13.884 | −77.646 | 37.362 | 1.00 | 33.09 | C |
| ATOM | 4382 | CD | LYS B | 370 | −12.937 | −78.303 | 38.355 | 1.00 | 39.87 | C |
| ATOM | 4383 | CE | LYS B | 370 | −11.664 | −78.781 | 37.704 | 1.00 | 50.91 | C |
| ATOM | 4384 | NZ | LYS B | 370 | −10.656 | −79.220 | 38.700 | 1.00 | 68.01 | N |
| ATOM | 4385 | N | GLY B | 371 | −12.399 | −74.471 | 35.831 | 1.00 | 27.43 | N |
| ATOM | 4386 | CA | GLY B | 371 | −11.188 | −74.262 | 35.050 | 1.00 | 26.71 | C |
| ATOM | 4387 | C | GLY B | 371 | −11.329 | −73.425 | 33.800 | 1.00 | 26.79 | C |
| ATOM | 4388 | O | GLY B | 371 | −10.464 | −73.513 | 32.923 | 1.00 | 25.52 | O |
| ATOM | 4389 | N | PHE B | 372 | −12.383 | −72.565 | 33.730 | 1.00 | 20.58 | N |
| ATOM | 4390 | CA | PHE B | 372 | −12.638 | −71.743 | 32.538 | 1.00 | 17.84 | C |
| ATOM | 4391 | C | PHE B | 372 | −12.202 | −70.293 | 32.717 | 1.00 | 21.59 | C |
| ATOM | 4392 | O | PHE B | 372 | −12.003 | −69.820 | 33.831 | 1.00 | 18.43 | O |
| ATOM | 4393 | CB | PHE B | 372 | −14.107 | −71.809 | 32.080 | 1.00 | 18.65 | C |
| ATOM | 4394 | CG | PHE B | 372 | −15.153 | −71.376 | 33.086 | 1.00 | 20.74 | C |
| ATOM | 4395 | CD1 | PHE B | 372 | −15.656 | −72.267 | 34.021 | 1.00 | 21.62 | C |
| ATOM | 4396 | CD2 | PHE B | 372 | −15.585 | −70.057 | 33.141 | 1.00 | 22.67 | C |
| ATOM | 4397 | CE1 | PHE B | 372 | −16.637 | −71.875 | 34.922 | 1.00 | 21.50 | C |
| ATOM | 4398 | CE2 | PHE B | 372 | −16.546 | −69.662 | 34.066 | 1.00 | 24.03 | C |
| ATOM | 4399 | CZ | PHE B | 372 | −17.093 | −70.583 | 34.929 | 1.00 | 21.13 | C |
| ATOM | 4400 | N | TYR B | 373 | −11.953 | −69.630 | 31.581 | 1.00 | 21.07 | N |
| ATOM | 4401 | CA | TYR B | 373 | −11.520 | −68.246 | 31.530 | 1.00 | 19.78 | C |
| ATOM | 4402 | C | TYR B | 373 | −11.754 | −67.767 | 30.095 | 1.00 | 23.96 | C |
| ATOM | 4403 | O | TYR B | 373 | −11.417 | −68.493 | 29.143 | 1.00 | 22.19 | O |
| ATOM | 4404 | CB | TYR B | 373 | −10.017 | −68.071 | 31.925 | 1.00 | 21.52 | C |
| ATOM | 4405 | CG | TYR B | 373 | −9.651 | −66.603 | 32.088 | 1.00 | 24.86 | C |
| ATOM | 4406 | CD1 | TYR B | 373 | −9.306 | −65.818 | 30.983 | 1.00 | 26.72 | C |
| ATOM | 4407 | CD2 | TYR B | 373 | −9.800 | −65.961 | 33.314 | 1.00 | 25.12 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 4408 | CE1 | TYR B | 373 | −9.168 | −64.432 | 31.090 | 1.00 | 26.02 | C |
| ATOM | 4409 | CE2 | TYR B | 373 | −9.557 | −64.597 | 33.452 | 1.00 | 25.69 | C |
| ATOM | 4410 | CZ | TYR B | 373 | −9.284 | −63.825 | 32.333 | 1.00 | 36.79 | C |
| ATOM | 4411 | OH | TYR B | 373 | −9.119 | −62.464 | 32.503 | 1.00 | 37.61 | O |
| ATOM | 4412 | N | PRO B | 374 | −12.296 | −66.547 | 29.900 | 1.00 | 21.33 | N |
| ATOM | 4413 | CA | PRO B | 374 | −12.838 | −65.629 | 30.918 | 1.00 | 21.43 | C |
| ATOM | 4414 | C | PRO B | 374 | −14.127 | −66.187 | 31.588 | 1.00 | 25.41 | C |
| ATOM | 4415 | O | PRO B | 374 | −14.640 | −67.221 | 31.178 | 1.00 | 24.21 | O |
| ATOM | 4416 | CB | PRO B | 374 | −13.069 | −64.340 | 30.105 | 1.00 | 22.35 | C |
| ATOM | 4417 | CG | PRO B | 374 | −13.384 | −64.811 | 28.752 | 1.00 | 25.44 | C |
| ATOM | 4418 | CD | PRO B | 374 | −12.515 | −66.023 | 28.534 | 1.00 | 21.04 | C |
| ATOM | 4419 | N | SER B | 375 | −14.662 | −65.487 | 32.592 | 1.00 | 23.61 | N |
| ATOM | 4420 | CA | SER B | 375 | −15.851 | −65.902 | 33.342 | 1.00 | 24.61 | C |
| ATOM | 4421 | C | SER B | 375 | −17.214 | −65.846 | 32.561 | 1.00 | 31.04 | C |
| ATOM | 4422 | O | SER B | 375 | −18.248 | −66.225 | 33.128 | 1.00 | 32.64 | O |
| ATOM | 4423 | CB | SER B | 375 | −15.956 | −65.091 | 34.636 | 1.00 | 27.16 | C |
| ATOM | 4424 | OG | SER B | 375 | −16.169 | −63.709 | 34.388 | 1.00 | 31.70 | O |
| ATOM | 4425 | N | ASP B | 376 | −17.228 | −65.397 | 31.298 | 1.00 | 27.30 | N |
| ATOM | 4426 | CA | ASP B | 376 | −18.461 | −65.312 | 30.483 | 1.00 | 27.31 | C |
| ATOM | 4427 | C | ASP B | 376 | −18.844 | −66.729 | 30.045 | 1.00 | 29.50 | C |
| ATOM | 4428 | O | ASP B | 376 | −18.076 | −67.383 | 29.353 | 1.00 | 28.03 | O |
| ATOM | 4429 | CB | ASP B | 376 | −18.279 | −64.405 | 29.240 | 1.00 | 28.28 | C |
| ATOM | 4430 | CG | ASP B | 376 | −17.705 | −63.042 | 29.540 | 1.00 | 45.58 | C |
| ATOM | 4431 | OD1 | ASP B | 376 | −17.938 | −62.535 | 30.661 | 1.00 | 48.11 | O |
| ATOM | 4432 | OD2 | ASP B | 376 | −17.010 | −62.484 | 28.660 | 1.00 | 56.30 | O |
| ATOM | 4433 | N | ILE B | 377 | −19.994 | −67.218 | 30.506 | 1.00 | 25.84 | N |
| ATOM | 4434 | CA | ILE B | 377 | −20.413 | −68.584 | 30.246 | 1.00 | 25.53 | C |
| ATOM | 4435 | C | ILE B | 377 | −21.927 | −68.617 | 30.333 | 1.00 | 30.59 | C |
| ATOM | 4436 | O | ILE B | 377 | −22.533 | −67.701 | 30.897 | 1.00 | 30.24 | O |
| ATOM | 4437 | CB | ILE B | 377 | −19.715 | −69.529 | 31.312 | 1.00 | 28.33 | C |
| ATOM | 4438 | CG1 | ILE B | 377 | −19.724 | −71.021 | 30.887 | 1.00 | 29.35 | C |
| ATOM | 4439 | CG2 | ILE B | 377 | −20.304 | −69.353 | 32.718 | 1.00 | 26.16 | C |
| ATOM | 4440 | CD1 | ILE B | 377 | −18.676 | −71.901 | 31.628 | 1.00 | 30.50 | C |
| ATOM | 4441 | N | ALA B | 378 | −22.524 | −69.638 | 29.718 | 1.00 | 26.08 | N |
| ATOM | 4442 | CA | ALA B | 378 | −23.956 | −69.906 | 29.759 | 1.00 | 25.17 | C |
| ATOM | 4443 | C | ALA B | 378 | −24.080 | −71.389 | 30.118 | 1.00 | 32.28 | C |
| ATOM | 4444 | O | ALA B | 378 | −23.343 | −72.220 | 29.564 | 1.00 | 31.99 | O |
| ATOM | 4445 | CB | ALA B | 378 | −24.604 | −69.616 | 28.411 | 1.00 | 24.37 | C |
| ATOM | 4446 | N | VAL B | 379 | −24.943 | −71.707 | 31.104 | 1.00 | 28.87 | N |
| ATOM | 4447 | CA | VAL B | 379 | −25.151 | −73.073 | 31.561 | 1.00 | 29.27 | C |
| ATOM | 4448 | C | VAL B | 379 | −26.674 | −73.311 | 31.618 | 1.00 | 34.55 | C |
| ATOM | 4449 | O | VAL B | 379 | −27.409 | −72.468 | 32.150 | 1.00 | 33.91 | O |
| ATOM | 4450 | CB | VAL B | 379 | −24.438 | −73.286 | 32.938 | 1.00 | 32.92 | C |
| ATOM | 4451 | CG1 | VAL B | 379 | −24.827 | −74.617 | 33.585 | 1.00 | 33.51 | C |
| ATOM | 4452 | CG2 | VAL B | 379 | −22.923 | −73.186 | 32.779 | 1.00 | 32.10 | C |
| ATOM | 4453 | N | GLU B | 380 | −27.146 | −74.452 | 31.071 | 1.00 | 29.51 | N |
| ATOM | 4454 | CA | GLU B | 380 | −28.570 | −74.767 | 31.056 | 1.00 | 28.26 | C |
| ATOM | 4455 | C | GLU B | 380 | −28.791 | −76.227 | 31.300 | 1.00 | 31.45 | C |
| ATOM | 4456 | O | GLU B | 380 | −27.837 | −77.000 | 31.300 | 1.00 | 31.63 | O |
| ATOM | 4457 | CB | GLU B | 380 | −29.149 | −74.406 | 29.697 | 1.00 | 29.88 | C |
| ATOM | 4458 | CG | GLU B | 380 | −29.464 | −72.942 | 29.489 | 1.00 | 37.07 | C |
| ATOM | 4459 | CD | GLU B | 380 | −29.754 | −72.614 | 28.041 | 1.00 | 54.35 | C |
| ATOM | 4460 | OE1 | GLU B | 380 | −30.248 | −73.499 | 27.303 | 1.00 | 53.40 | O |
| ATOM | 4461 | OE2 | GLU B | 380 | −29.474 | −71.465 | 27.639 | 1.00 | 53.88 | O |
| ATOM | 4462 | N | TRP B | 381 | −30.056 | −76.627 | 31.481 | 1.00 | 27.13 | N |
| ATOM | 4463 | CA | TRP B | 381 | −30.387 | −78.024 | 31.689 | 1.00 | 27.26 | C |
| ATOM | 4464 | C | TRP B | 381 | −31.509 | −78.470 | 30.763 | 1.00 | 35.94 | C |
| ATOM | 4465 | O | TRP B | 381 | −32.381 | −77.680 | 30.409 | 1.00 | 36.48 | O |
| ATOM | 4466 | CB | TRP B | 381 | −30.792 | −78.290 | 33.139 | 1.00 | 25.12 | C |
| ATOM | 4467 | CG | TRP B | 381 | −29.691 | −78.241 | 34.165 | 1.00 | 24.66 | C |
| ATOM | 4468 | CD1 | TRP B | 381 | −29.341 | −77.165 | 34.930 | 1.00 | 26.82 | C |
| ATOM | 4469 | CD2 | TRP B | 381 | −29.036 | −79.377 | 34.754 | 1.00 | 24.16 | C |
| ATOM | 4470 | NE1 | TRP B | 381 | −28.453 | −77.549 | 35.916 | 1.00 | 25.19 | N |
| ATOM | 4471 | CE2 | TRP B | 381 | −28.281 | −78.904 | 35.856 | 1.00 | 26.07 | C |
| ATOM | 4472 | CE3 | TRP B | 381 | −29.005 | −80.749 | 34.448 | 1.00 | 25.53 | C |
| ATOM | 4473 | CZ2 | TRP B | 381 | −27.482 | −79.742 | 36.624 | 1.00 | 24.91 | C |
| ATOM | 4474 | CZ3 | TRP B | 381 | −28.200 | −81.584 | 35.206 | 1.00 | 26.84 | C |
| ATOM | 4475 | CH2 | TRP B | 381 | −27.434 | −81.076 | 36.266 | 1.00 | 27.33 | C |
| ATOM | 4476 | N | GLU B | 382 | −31.500 | −79.745 | 30.393 | 1.00 | 35.33 | N |
| ATOM | 4477 | CA | GLU B | 382 | −32.541 | −80.310 | 29.551 | 1.00 | 36.37 | C |
| ATOM | 4478 | C | GLU B | 382 | −32.689 | −81.792 | 29.793 | 1.00 | 42.19 | C |
| ATOM | 4479 | O | GLU B | 382 | −31.847 | −82.444 | 30.424 | 1.00 | 41.77 | O |
| ATOM | 4480 | CB | GLU B | 382 | −32.286 | −80.044 | 28.067 | 1.00 | 37.58 | C |
| ATOM | 4481 | CG | GLU B | 382 | −30.986 | −80.623 | 27.539 | 1.00 | 53.33 | C |
| ATOM | 4482 | CD | GLU B | 382 | −30.808 | −80.558 | 26.033 | 1.00 | 79.08 | C |
| ATOM | 4483 | OE1 | GLU B | 382 | −31.815 | −80.404 | 25.302 | 1.00 | 84.65 | O |
| ATOM | 4484 | OE2 | GLU B | 382 | −29.659 | −80.769 | 25.584 | 1.00 | 61.75 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 4485 | N | SER B | 383 | −33.807 | −82.299 | 29.328 | 1.00 | 39.91 | N |
| ATOM | 4486 | CA | SER B | 383 | −34.124 | −83.707 | 29.403 | 1.00 | 40.87 | C |
| ATOM | 4487 | C | SER B | 383 | −34.938 | −84.029 | 28.164 | 1.00 | 47.57 | C |
| ATOM | 4488 | O | SER B | 383 | −35.841 | −83.260 | 27.822 | 1.00 | 48.22 | O |
| ATOM | 4489 | CB | SER B | 383 | −34.934 | −84.015 | 30.653 | 1.00 | 41.92 | C |
| ATOM | 4490 | OG | SER B | 383 | −35.132 | −85.415 | 30.773 | 1.00 | 46.33 | O |
| ATOM | 4491 | N | ASN B | 384 | −34.589 | −85.110 | 27.457 | 1.00 | 44.36 | N |
| ATOM | 4492 | CA | ASN B | 384 | −35.347 | −85.524 | 26.293 | 1.00 | 45.16 | C |
| ATOM | 4493 | C | ASN B | 384 | −35.532 | −84.391 | 25.231 | 1.00 | 51.70 | C |
| ATOM | 4494 | O | ASN B | 384 | −36.556 | −84.330 | 24.552 | 1.00 | 52.10 | O |
| ATOM | 4495 | CB | ASN B | 384 | −36.686 | −86.126 | 26.775 | 1.00 | 42.00 | C |
| ATOM | 4496 | CG | ASN B | 384 | −36.499 | −87.374 | 27.629 | 1.00 | 58.26 | C |
| ATOM | 4497 | OD1 | ASN B | 384 | −35.513 | −88.117 | 27.513 | 1.00 | 57.30 | O |
| ATOM | 4498 | ND2 | ASN B | 384 | −37.477 | −87.696 | 28.447 | 1.00 | 47.76 | N |
| ATOM | 4499 | N | GLY B | 385 | −34.526 | −83.530 | 25.086 | 1.00 | 49.31 | N |
| ATOM | 4500 | CA | GLY B | 385 | −34.559 | −82.455 | 24.099 | 1.00 | 50.04 | C |
| ATOM | 4501 | C | GLY B | 385 | −35.549 | −81.329 | 24.344 | 1.00 | 55.55 | C |
| ATOM | 4502 | O | GLY B | 385 | −36.009 | −80.683 | 23.398 | 1.00 | 56.43 | O |
| ATOM | 4503 | N | GLN B | 386 | −35.873 | −81.079 | 25.605 | 1.00 | 50.90 | N |
| ATOM | 4504 | CA | GLN B | 386 | −36.763 | −80.003 | 26.016 | 1.00 | 50.11 | C |
| ATOM | 4505 | C | GLN B | 386 | −36.097 | −79.319 | 27.218 | 1.00 | 50.95 | C |
| ATOM | 4506 | O | GLN B | 386 | −35.497 | −80.016 | 28.044 | 1.00 | 50.38 | O |
| ATOM | 4507 | CB | GLN B | 386 | −38.129 | −80.580 | 26.412 | 1.00 | 52.71 | C |
| ATOM | 4508 | CG | GLN B | 386 | −39.016 | −80.959 | 25.231 | 1.00 | 75.81 | C |
| ATOM | 4509 | CD | GLN B | 386 | −39.815 | −79.789 | 24.707 | 1.00 | 100.94 | C |
| ATOM | 4510 | OE1 | GLN B | 386 | −40.943 | −79.536 | 25.157 | 1.00 | 98.74 | O |
| ATOM | 4511 | NE2 | GLN B | 386 | −39.267 | −79.064 | 23.732 | 1.00 | 89.83 | N |
| ATOM | 4512 | N | PRO B | 387 | −36.166 | −77.982 | 27.345 | 1.00 | 45.99 | N |
| ATOM | 4513 | CA | PRO B | 387 | −35.520 | −77.326 | 28.501 | 1.00 | 45.37 | C |
| ATOM | 4514 | C | PRO B | 387 | −36.118 | −77.662 | 29.871 | 1.00 | 50.23 | C |
| ATOM | 4515 | O | PRO B | 387 | −37.336 | −77.712 | 30.022 | 1.00 | 51.48 | O |
| ATOM | 4516 | CB | PRO B | 387 | −35.656 | −75.823 | 28.193 | 1.00 | 46.11 | C |
| ATOM | 4517 | CG | PRO B | 387 | −36.782 | −75.718 | 27.252 | 1.00 | 50.89 | C |
| ATOM | 4518 | CD | PRO B | 387 | −36.809 | −77.000 | 26.454 | 1.00 | 47.23 | C |
| ATOM | 4519 | N | GLU B | 388 | −35.240 | −77.862 | 30.872 | 1.00 | 46.00 | N |
| ATOM | 4520 | CA | GLU B | 388 | −35.597 | −78.076 | 32.279 | 1.00 | 45.58 | C |
| ATOM | 4521 | C | GLU B | 388 | −35.312 | −76.732 | 32.935 | 1.00 | 49.81 | C |
| ATOM | 4522 | O | GLU B | 388 | −34.150 | −76.373 | 33.073 | 1.00 | 49.86 | O |
| ATOM | 4523 | CB | GLU B | 388 | −34.738 | −79.185 | 32.915 | 1.00 | 46.64 | C |
| ATOM | 4524 | CG | GLU B | 388 | −35.130 | −80.582 | 32.492 | 1.00 | 55.24 | C |
| ATOM | 4525 | CD | GLU B | 388 | −36.576 | −80.952 | 32.770 | 1.00 | 79.39 | C |
| ATOM | 4526 | OE1 | GLU B | 388 | −37.176 | −81.641 | 31.913 | 1.00 | 84.45 | O |
| ATOM | 4527 | OE2 | GLU B | 388 | −37.130 | −80.497 | 33.801 | 1.00 | 60.80 | O |
| ATOM | 4528 | N | ASN B | 389 | −36.355 | −75.953 | 33.257 | 1.00 | 46.44 | N |
| ATOM | 4529 | CA | ASN B | 389 | −36.209 | −74.577 | 33.758 | 1.00 | 45.13 | C |
| ATOM | 4530 | C | ASN B | 389 | −36.142 | −74.401 | 35.297 | 1.00 | 45.92 | C |
| ATOM | 4531 | O | ASN B | 389 | −35.904 | −73.275 | 35.750 | 1.00 | 44.99 | O |
| ATOM | 4532 | CB | ASN B | 389 | −37.345 | −73.724 | 33.187 | 1.00 | 47.07 | C |
| ATOM | 4533 | CG | ASN B | 389 | −37.327 | −73.708 | 31.685 | 1.00 | 74.31 | C |
| ATOM | 4534 | OD1 | ASN B | 389 | −36.296 | −73.427 | 31.071 | 1.00 | 64.18 | O |
| ATOM | 4535 | ND2 | ASN B | 389 | −38.443 | −74.051 | 31.055 | 1.00 | 73.99 | N |
| ATOM | 4536 | N | ASN B | 390 | −36.269 | −75.487 | 36.081 | 1.00 | 40.32 | N |
| ATOM | 4537 | CA | ASN B | 390 | −36.224 | −75.428 | 37.541 | 1.00 | 39.09 | C |
| ATOM | 4538 | C | ASN B | 390 | −34.793 | −75.570 | 38.113 | 1.00 | 39.64 | C |
| ATOM | 4539 | O | ASN B | 390 | −34.510 | −76.494 | 38.869 | 1.00 | 40.05 | O |
| ATOM | 4540 | CB | ASN B | 390 | −37.164 | −76.500 | 38.123 | 1.00 | 40.67 | C |
| ATOM | 4541 | CG | ASN B | 390 | −37.588 | −76.195 | 39.529 | 1.00 | 51.98 | C |
| ATOM | 4542 | OD1 | ASN B | 390 | −37.754 | −75.036 | 39.892 | 1.00 | 47.45 | O |
| ATOM | 4543 | ND2 | ASN B | 390 | −37.769 | −77.212 | 40.361 | 1.00 | 41.33 | N |
| ATOM | 4544 | N | TYR B | 391 | −33.896 | −74.638 | 37.770 | 1.00 | 33.77 | N |
| ATOM | 4545 | CA | TYR B | 391 | −32.505 | −74.675 | 38.234 | 1.00 | 32.47 | C |
| ATOM | 4546 | C | TYR B | 391 | −32.035 | −73.313 | 38.635 | 1.00 | 34.34 | C |
| ATOM | 4547 | O | TYR B | 391 | −32.719 | −72.329 | 38.389 | 1.00 | 35.01 | O |
| ATOM | 4548 | CB | TYR B | 391 | −31.556 | −75.232 | 37.151 | 1.00 | 32.65 | C |
| ATOM | 4549 | CG | TYR B | 391 | −31.461 | −74.377 | 35.905 | 1.00 | 33.06 | C |
| ATOM | 4550 | CD2 | TYR B | 391 | −30.385 | −73.520 | 35.705 | 1.00 | 32.58 | C |
| ATOM | 4551 | CD1 | TYR B | 391 | −32.378 | −74.516 | 34.870 | 1.00 | 35.32 | C |
| ATOM | 4552 | CE2 | TYR B | 391 | −30.291 | −72.728 | 34.558 | 1.00 | 32.03 | C |
| ATOM | 4553 | CE1 | TYR B | 391 | −32.278 | −73.755 | 33.702 | 1.00 | 35.16 | C |
| ATOM | 4554 | CZ | TYR B | 391 | −31.241 | −72.847 | 33.557 | 1.00 | 36.64 | C |
| ATOM | 4555 | OH | TYR B | 391 | −31.141 | −72.107 | 32.400 | 1.00 | 33.65 | O |
| ATOM | 4556 | N | LYS B | 392 | −30.881 | −73.264 | 39.295 | 1.00 | 28.03 | N |
| ATOM | 4557 | CA | LYS B | 392 | −30.228 | −72.013 | 39.679 | 1.00 | 25.67 | C |
| ATOM | 4558 | C | LYS B | 392 | −28.751 | −72.275 | 39.549 | 1.00 | 27.29 | C |
| ATOM | 4559 | O | LYS B | 392 | −28.296 | −73.366 | 39.827 | 1.00 | 28.14 | O |
| ATOM | 4560 | CB | LYS B | 392 | −30.570 | −71.579 | 41.109 | 1.00 | 26.54 | C |
| ATOM | 4561 | CG | LYS B | 392 | −32.012 | −71.202 | 41.381 | 1.00 | 27.78 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 4562 | CD | LYS B | 392 | −32.416 | −69.787 | 40.942 | 1.00 | 28.42 | C |
| ATOM | 4563 | CE | LYS B | 392 | −33.850 | −69.505 | 41.382 | 1.00 | 30.15 | C |
| ATOM | 4564 | NZ | LYS B | 392 | −34.113 | −68.052 | 41.568 | 1.00 | 55.33 | N |
| ATOM | 4565 | N | THR B | 393 | −28.023 | −71.310 | 39.101 | 1.00 | 24.29 | N |
| ATOM | 4566 | CA | THR B | 393 | −26.580 | −71.400 | 38.868 | 1.00 | 23.97 | C |
| ATOM | 4567 | C | THR B | 393 | −25.942 | −70.331 | 39.737 | 1.00 | 29.04 | C |
| ATOM | 4568 | O | THR B | 393 | −26.509 | −69.260 | 39.934 | 1.00 | 27.95 | O |
| ATOM | 4569 | CB | THR B | 393 | −26.331 | −71.197 | 37.361 | 1.00 | 27.31 | C |
| ATOM | 4570 | OG1 | THR B | 393 | −27.049 | −72.211 | 36.679 | 1.00 | 27.35 | O |
| ATOM | 4571 | CG2 | THR B | 393 | −24.855 | −71.259 | 36.957 | 1.00 | 22.98 | C |
| ATOM | 4572 | N | THR B | 394 | −24.772 | −70.621 | 40.263 | 1.00 | 27.37 | N |
| ATOM | 4573 | CA | THR B | 394 | −24.091 | −69.691 | 41.147 | 1.00 | 25.91 | C |
| ATOM | 4574 | C | THR B | 394 | −23.360 | −68.760 | 40.253 | 1.00 | 28.49 | C |
| ATOM | 4575 | O | THR B | 394 | −23.068 | −69.154 | 39.138 | 1.00 | 28.18 | O |
| ATOM | 4576 | CB | THR B | 394 | −23.081 | −70.419 | 42.053 | 1.00 | 27.24 | C |
| ATOM | 4577 | OG1 | THR B | 394 | −21.966 | −70.865 | 41.264 | 1.00 | 29.84 | O |
| ATOM | 4578 | CG2 | THR B | 394 | −23.708 | −71.566 | 42.808 | 1.00 | 23.30 | C |
| ATOM | 4579 | N | PRO B | 395 | −22.998 | −67.548 | 40.691 | 1.00 | 24.89 | N |
| ATOM | 4580 | CA | PRO B | 395 | −22.133 | −66.723 | 39.846 | 1.00 | 24.48 | C |
| ATOM | 4581 | C | PRO B | 395 | −20.736 | −67.366 | 39.742 | 1.00 | 28.52 | C |
| ATOM | 4582 | O | PRO B | 395 | −20.372 | −68.114 | 40.644 | 1.00 | 29.66 | O |
| ATOM | 4583 | CB | PRO B | 395 | −22.071 | −65.391 | 40.607 | 1.00 | 25.48 | C |
| ATOM | 4584 | CG | PRO B | 395 | −23.062 | −65.496 | 41.719 | 1.00 | 30.12 | C |
| ATOM | 4585 | CD | PRO B | 395 | −23.196 | −66.928 | 42.014 | 1.00 | 26.60 | C |
| ATOM | 4586 | N | PRO B | 396 | −19.906 | −67.071 | 38.725 | 1.00 | 24.77 | N |
| ATOM | 4587 | CA | PRO B | 396 | −18.550 | −67.653 | 38.695 | 1.00 | 24.89 | C |
| ATOM | 4588 | C | PRO B | 396 | −17.682 | −67.203 | 39.871 | 1.00 | 28.75 | C |
| ATOM | 4589 | O | PRO B | 396 | −17.826 | −66.091 | 40.364 | 1.00 | 29.44 | O |
| ATOM | 4590 | CB | PRO B | 396 | −17.987 | −67.188 | 37.333 | 1.00 | 25.97 | C |
| ATOM | 4591 | CG | PRO B | 396 | −19.204 | −66.807 | 36.525 | 1.00 | 29.19 | C |
| ATOM | 4592 | CD | PRO B | 396 | −20.138 | −66.221 | 37.542 | 1.00 | 25.38 | C |
| ATOM | 4593 | N | VAL B | 397 | −16.823 | −68.071 | 40.351 | 1.00 | 24.78 | N |
| ATOM | 4594 | CA | VAL B | 397 | −15.965 | −67.749 | 41.495 | 1.00 | 25.71 | C |
| ATOM | 4595 | C | VAL B | 397 | −14.507 | −67.919 | 41.094 | 1.00 | 30.51 | C |
| ATOM | 4596 | O | VAL B | 397 | −14.134 | −68.969 | 40.579 | 1.00 | 29.64 | O |
| ATOM | 4597 | CB | VAL B | 397 | −16.331 | −68.663 | 42.700 | 1.00 | 29.92 | C |
| ATOM | 4598 | CG1 | VAL B | 397 | −15.430 | −68.397 | 43.918 | 1.00 | 29.66 | C |
| ATOM | 4599 | CG2 | VAL B | 397 | −17.794 | −68.506 | 43.070 | 1.00 | 29.61 | C |
| ATOM | 4600 | N | LEU B | 398 | −13.675 | −66.925 | 41.390 | 1.00 | 29.41 | N |
| ATOM | 4601 | CA | LEU B | 398 | −12.251 | −67.000 | 41.049 | 1.00 | 31.50 | C |
| ATOM | 4602 | C | LEU B | 398 | −11.513 | −68.061 | 41.833 | 1.00 | 37.44 | C |
| ATOM | 4603 | O | LEU B | 398 | −11.695 | −68.157 | 43.039 | 1.00 | 38.10 | O |
| ATOM | 4604 | CB | LEU B | 398 | −11.576 | −65.645 | 41.309 | 1.00 | 32.09 | C |
| ATOM | 4605 | CG | LEU B | 398 | −10.161 | −65.451 | 40.769 | 1.00 | 36.05 | C |
| ATOM | 4606 | CD1 | LEU B | 398 | −10.132 | −65.501 | 39.244 | 1.00 | 34.01 | C |
| ATOM | 4607 | CD2 | LEU B | 398 | −9.612 | −64.122 | 41.244 | 1.00 | 37.20 | C |
| ATOM | 4608 | N | ASP B | 399 | −10.661 | −68.839 | 41.152 | 1.00 | 36.03 | N |
| ATOM | 4609 | CA | ASP B | 399 | −9.814 | −69.855 | 41.795 | 1.00 | 36.88 | C |
| ATOM | 4610 | C | ASP B | 399 | −8.393 | −69.316 | 41.910 | 1.00 | 40.03 | C |
| ATOM | 4611 | O | ASP B | 399 | −8.010 | −68.405 | 41.172 | 1.00 | 40.95 | O |
| ATOM | 4612 | CB | ASP B | 399 | −9.785 | −71.187 | 40.996 | 1.00 | 39.09 | C |
| ATOM | 4613 | CG | ASP B | 399 | −10.790 | −72.214 | 41.457 | 1.00 | 47.13 | C |
| ATOM | 4614 | OD1 | ASP B | 399 | −10.919 | −72.411 | 42.678 | 1.00 | 49.80 | O |
| ATOM | 4615 | OD2 | ASP B | 399 | −11.387 | −72.868 | 40.604 | 1.00 | 50.45 | O |
| ATOM | 4616 | N | SER B | 400 | −7.602 | −69.928 | 42.785 | 1.00 | 35.95 | N |
| ATOM | 4617 | CA | SER B | 400 | −6.215 | −69.546 | 43.012 | 1.00 | 36.84 | C |
| ATOM | 4618 | C | SER B | 400 | −5.331 | −69.631 | 41.752 | 1.00 | 42.73 | C |
| ATOM | 4619 | O | SER B | 400 | −4.375 | −68.880 | 41.659 | 1.00 | 44.73 | O |
| ATOM | 4620 | CB | SER B | 400 | −5.624 | −70.353 | 44.168 | 1.00 | 42.95 | C |
| ATOM | 4621 | OG | SER B | 400 | −5.857 | −71.743 | 44.010 | 1.00 | 58.41 | O |
| ATOM | 4622 | N | ASP B | 401 | −5.679 | −70.469 | 40.760 | 1.00 | 39.78 | N |
| ATOM | 4623 | CA | ASP B | 401 | −4.937 | −70.561 | 39.487 | 1.00 | 38.73 | C |
| ATOM | 4624 | C | ASP B | 401 | −5.328 | −69.473 | 38.441 | 1.00 | 40.47 | C |
| ATOM | 4625 | O | ASP B | 401 | −4.760 | −69.463 | 37.347 | 1.00 | 39.27 | O |
| ATOM | 4626 | CB | ASP B | 401 | −5.068 | −71.976 | 38.875 | 1.00 | 40.60 | C |
| ATOM | 4627 | CG | ASP B | 401 | −6.458 | −72.389 | 38.402 | 1.00 | 49.38 | C |
| ATOM | 4628 | OD1 | ASP B | 401 | −7.445 | −71.687 | 38.750 | 1.00 | 47.10 | O |
| ATOM | 4629 | OD2 | ASP B | 401 | −6.568 | −73.445 | 37.729 | 1.00 | 55.50 | O |
| ATOM | 4630 | N | GLY B | 402 | −6.293 | −68.602 | 38.765 | 1.00 | 35.68 | N |
| ATOM | 4631 | CA | GLY B | 402 | −6.753 | −67.552 | 37.856 | 1.00 | 33.65 | C |
| ATOM | 4632 | C | GLY B | 402 | −7.986 | −67.893 | 37.037 | 1.00 | 32.64 | C |
| ATOM | 4633 | O | GLY B | 402 | −8.543 | −67.018 | 36.377 | 1.00 | 31.52 | O |
| ATOM | 4634 | N | SER B | 403 | −8.402 | −69.156 | 37.041 | 1.00 | 27.32 | N |
| ATOM | 4635 | CA | SER B | 403 | −9.586 | −69.627 | 36.319 | 1.00 | 26.90 | C |
| ATOM | 4636 | C | SER B | 403 | −10.864 | −69.559 | 37.204 | 1.00 | 27.29 | C |
| ATOM | 4637 | O | SER B | 403 | −10.773 | −69.377 | 38.426 | 1.00 | 25.87 | O |
| ATOM | 4638 | CB | SER B | 403 | −9.364 | −71.060 | 35.842 | 1.00 | 32.43 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 4639 | OG | SER B | 403 | −9.372 | −72.014 | 36.900 | 1.00 | 44.67 | O |
| ATOM | 4640 | N | PHE B | 404 | −12.044 | −69.715 | 36.588 | 1.00 | 21.49 | N |
| ATOM | 4641 | CA | PHE B | 404 | −13.284 | −69.655 | 37.359 | 1.00 | 22.11 | C |
| ATOM | 4642 | C | PHE B | 404 | −13.949 | −71.013 | 37.508 | 1.00 | 29.56 | C |
| ATOM | 4643 | O | PHE B | 404 | −13.550 | −72.016 | 36.900 | 1.00 | 30.24 | O |
| ATOM | 4644 | CB | PHE B | 404 | −14.262 | −68.635 | 36.758 | 1.00 | 22.81 | C |
| ATOM | 4645 | CG | PHE B | 404 | −13.764 | −67.210 | 36.816 | 1.00 | 23.73 | C |
| ATOM | 4646 | CD1 | PHE B | 404 | −12.906 | −66.713 | 35.836 | 1.00 | 26.68 | C |
| ATOM | 4647 | CD2 | PHE B | 404 | −14.150 | −66.363 | 37.848 | 1.00 | 25.03 | C |
| ATOM | 4648 | CE1 | PHE B | 404 | −12.431 | −65.394 | 35.902 | 1.00 | 27.05 | C |
| ATOM | 4649 | CE2 | PHE B | 404 | −13.692 | −65.041 | 37.903 | 1.00 | 26.56 | C |
| ATOM | 4650 | CZ | PHE B | 404 | −12.820 | −64.572 | 36.937 | 1.00 | 24.18 | C |
| ATOM | 4651 | N | PHE B | 405 | −14.930 | −71.052 | 38.392 | 1.00 | 26.18 | N |
| ATOM | 4652 | CA | PHE B | 405 | −15.741 | −72.229 | 38.552 | 1.00 | 26.28 | C |
| ATOM | 4653 | C | PHE B | 405 | −17.108 | −71.825 | 38.969 | 1.00 | 28.84 | C |
| ATOM | 4654 | O | PHE B | 405 | −17.320 | −70.688 | 39.407 | 1.00 | 26.85 | O |
| ATOM | 4655 | CB | PHE B | 405 | −15.129 | −73.236 | 39.541 | 1.00 | 29.47 | C |
| ATOM | 4656 | CG | PHE B | 405 | −15.269 | −72.890 | 41.003 | 1.00 | 32.15 | C |
| ATOM | 4657 | CD1 | PHE B | 405 | −14.377 | −72.023 | 41.616 | 1.00 | 34.85 | C |
| ATOM | 4658 | CD2 | PHE B | 405 | −16.303 | −73.429 | 41.767 | 1.00 | 34.37 | C |
| ATOM | 4659 | CE1 | PHE B | 405 | −14.500 | −71.720 | 42.967 | 1.00 | 36.21 | C |
| ATOM | 4660 | CE2 | PHE B | 405 | −16.431 | −73.110 | 43.108 | 1.00 | 37.32 | C |
| ATOM | 4661 | CZ | PHE B | 405 | −15.545 | −72.240 | 43.698 | 1.00 | 35.46 | C |
| ATOM | 4662 | N | LEU B | 406 | −18.041 | −72.764 | 38.825 | 1.00 | 25.40 | N |
| ATOM | 4663 | CA | LEU B | 406 | −19.412 | −72.580 | 39.265 | 1.00 | 24.53 | C |
| ATOM | 4664 | C | LEU B | 406 | −20.125 | −73.924 | 39.368 | 1.00 | 27.64 | C |
| ATOM | 4665 | O | LEU B | 406 | −19.675 | −74.931 | 38.814 | 1.00 | 27.26 | O |
| ATOM | 4666 | CB | LEU B | 406 | −20.184 | −71.592 | 38.360 | 1.00 | 22.95 | C |
| ATOM | 4667 | CG | LEU B | 406 | −20.380 | −71.955 | 36.895 | 1.00 | 26.28 | C |
| ATOM | 4668 | CD1 | LEU B | 406 | −21.434 | −73.098 | 36.711 | 1.00 | 25.51 | C |
| ATOM | 4669 | CD2 | LEU B | 406 | −20.840 | −70.719 | 36.117 | 1.00 | 26.71 | C |
| ATOM | 4670 | N | TYR B | 407 | −21.221 | −73.932 | 40.107 | 1.00 | 23.69 | N |
| ATOM | 4671 | CA | TYR B | 407 | −22.090 | −75.091 | 40.232 | 1.00 | 22.83 | C |
| ATOM | 4672 | C | TYR B | 407 | −23.487 | −74.687 | 39.762 | 1.00 | 27.85 | C |
| ATOM | 4673 | O | TYR B | 407 | −23.919 | −73.542 | 39.970 | 1.00 | 28.26 | O |
| ATOM | 4674 | CB | TYR B | 407 | −22.171 | −75.576 | 41.672 | 1.00 | 22.69 | C |
| ATOM | 4675 | CG | TYR B | 407 | −20.953 | −76.309 | 42.167 | 1.00 | 21.88 | C |
| ATOM | 4676 | CD1 | TYR B | 407 | −19.912 | −75.626 | 42.781 | 1.00 | 23.64 | C |
| ATOM | 4677 | CD2 | TYR B | 407 | −20.896 | −77.698 | 42.144 | 1.00 | 22.25 | C |
| ATOM | 4678 | CE1 | TYR B | 407 | −18.863 | −76.304 | 43.394 | 1.00 | 23.59 | C |
| ATOM | 4679 | CE2 | TYR B | 407 | −19.811 | −78.387 | 42.682 | 1.00 | 23.07 | C |
| ATOM | 4680 | CZ | TYR B | 407 | −18.798 | −77.684 | 43.317 | 1.00 | 33.55 | C |
| ATOM | 4681 | OH | TYR B | 407 | −17.733 | −78.329 | 43.900 | 1.00 | 40.27 | O |
| ATOM | 4682 | N | SER B | 408 | −24.179 | −75.606 | 39.123 | 1.00 | 23.26 | N |
| ATOM | 4683 | CA | SER B | 408 | −25.556 | −75.383 | 38.730 | 1.00 | 23.80 | C |
| ATOM | 4684 | C | SER B | 408 | −26.341 | −76.502 | 39.386 | 1.00 | 28.73 | C |
| ATOM | 4685 | O | SER B | 408 | −25.874 | −77.650 | 39.417 | 1.00 | 27.48 | O |
| ATOM | 4686 | CB | SER B | 408 | −25.705 | −75.391 | 37.210 | 1.00 | 28.09 | C |
| ATOM | 4687 | OG | SER B | 408 | −26.996 | −74.940 | 36.820 | 1.00 | 38.44 | O |
| ATOM | 4688 | N | ARG B | 409 | −27.479 | −76.165 | 39.983 | 1.00 | 27.88 | N |
| ATOM | 4689 | CA | ARG B | 409 | −28.313 | −77.130 | 40.710 | 1.00 | 28.71 | C |
| ATOM | 4690 | C | ARG B | 409 | −29.667 | −77.251 | 40.031 | 1.00 | 33.24 | C |
| ATOM | 4691 | O | ARG B | 409 | −30.378 | −76.258 | 39.945 | 1.00 | 32.38 | O |
| ATOM | 4692 | CB | ARG B | 409 | −28.533 | −76.656 | 42.165 | 1.00 | 27.80 | C |
| ATOM | 4693 | CG | ARG B | 409 | −29.285 | −77.686 | 43.028 | 1.00 | 32.89 | C |
| ATOM | 4694 | CD | ARG B | 409 | −29.174 | −77.489 | 44.536 | 1.00 | 44.05 | C |
| ATOM | 4695 | NE | ARG B | 409 | −30.478 | −77.232 | 45.165 | 1.00 | 48.64 | N |
| ATOM | 4696 | CZ | ARG B | 409 | −31.089 | −76.044 | 45.206 | 1.00 | 63.86 | C |
| ATOM | 4697 | NH1 | ARG B | 409 | −30.528 | −74.974 | 44.643 | 1.00 | 57.24 | N |
| ATOM | 4698 | NH2 | ARG B | 409 | −32.272 | −75.918 | 45.797 | 1.00 | 39.12 | N |
| ATOM | 4699 | N | LEU B | 410 | −30.042 | −78.436 | 39.575 | 1.00 | 30.58 | N |
| ATOM | 4700 | CA | LEU B | 410 | −31.376 | −78.628 | 38.996 | 1.00 | 31.46 | C |
| ATOM | 4701 | C | LEU B | 410 | −32.240 | −79.400 | 40.019 | 1.00 | 36.97 | C |
| ATOM | 4702 | O | LEU B | 410 | −31.807 | −80.452 | 40.515 | 1.00 | 37.30 | O |
| ATOM | 4703 | CB | LEU B | 410 | −31.330 | −79.369 | 37.630 | 1.00 | 30.34 | C |
| ATOM | 4704 | CG | LEU B | 410 | −32.699 | −79.776 | 37.043 | 1.00 | 34.64 | C |
| ATOM | 4705 | CD1 | LEU B | 410 | −33.423 | −78.585 | 36.474 | 1.00 | 32.94 | C |
| ATOM | 4706 | CD2 | LEU B | 410 | −32.546 | −80.829 | 35.954 | 1.00 | 39.27 | C |
| ATOM | 4707 | N | THR B | 411 | −33.460 | −78.885 | 40.314 | 1.00 | 32.28 | N |
| ATOM | 4708 | CA | THR B | 411 | −34.390 | −79.548 | 41.224 | 1.00 | 32.23 | C |
| ATOM | 4709 | C | THR B | 411 | −35.342 | −80.404 | 40.397 | 1.00 | 35.66 | C |
| ATOM | 4710 | O | THR B | 411 | −36.026 | −79.882 | 39.512 | 1.00 | 34.08 | O |
| ATOM | 4711 | CB | THR B | 411 | −35.117 | −78.533 | 42.123 | 1.00 | 39.06 | C |
| ATOM | 4712 | OG1 | THR B | 411 | −34.137 | −77.759 | 42.811 | 1.00 | 44.01 | O |
| ATOM | 4713 | CG2 | THR B | 411 | −36.039 | −79.223 | 43.160 | 1.00 | 29.75 | C |
| ATOM | 4714 | N | VAL B | 412 | −35.352 | −81.724 | 40.650 | 1.00 | 34.73 | N |
| ATOM | 4715 | CA | VAL B | 412 | −36.210 | −82.661 | 39.919 | 1.00 | 36.57 | C |

TABLE 7-continued

Three-dimensional crystal coordinates for caffeine-pembrolizumab complex.
Atomic Coordinates of Caffeine/Pembrolizumab Crystal Complex

| | | | | | | | | | | | |
|---|---|---|---|---|---|---|---|---|---|---|---|
| ATOM | 4716 | C | VAL | B | 412 | −37.085 | −83.367 | 40.919 | 1.00 | 46.53 | C |
| ATOM | 4717 | O | VAL | B | 412 | −36.660 | −83.581 | 42.045 | 1.00 | 47.15 | O |
| ATOM | 4718 | CB | VAL | B | 412 | −35.420 | −83.700 | 39.045 | 1.00 | 39.78 | C |
| ATOM | 4719 | CG1 | VAL | B | 412 | −34.358 | −83.024 | 38.186 | 1.00 | 38.06 | C |
| ATOM | 4720 | CG2 | VAL | B | 412 | −34.795 | −84.816 | 39.888 | 1.00 | 40.05 | C |
| ATOM | 4721 | N | ASP | B | 413 | −38.277 | −83.791 | 40.504 | 1.00 | 47.09 | N |
| ATOM | 4722 | CA | ASP | B | 413 | −39.127 | −84.608 | 41.368 | 1.00 | 49.13 | C |
| ATOM | 4723 | C | ASP | B | 413 | −38.407 | −85.969 | 41.493 | 1.00 | 55.75 | C |
| ATOM | 4724 | O | ASP | B | 413 | −37.976 | −86.486 | 40.474 | 1.00 | 54.69 | O |
| ATOM | 4725 | CB | ASP | B | 413 | −40.520 | −84.819 | 40.738 | 1.00 | 51.55 | C |
| ATOM | 4726 | CG | ASP | B | 413 | −41.346 | −83.559 | 40.599 | 1.00 | 64.21 | C |
| ATOM | 4727 | OD1 | ASP | B | 413 | −41.430 | −82.784 | 41.592 | 1.00 | 68.49 | O |
| ATOM | 4728 | OD2 | ASP | B | 413 | −41.939 | −83.360 | 39.518 | 1.00 | 65.72 | O |
| ATOM | 4729 | N | LYS | B | 414 | −38.238 | −86.518 | 42.716 | 1.00 | 54.96 | N |
| ATOM | 4730 | CA | LYS | B | 414 | −37.571 | −87.814 | 42.961 | 1.00 | 55.72 | C |
| ATOM | 4731 | C | LYS | B | 414 | −38.078 | −88.896 | 41.994 | 1.00 | 61.99 | C |
| ATOM | 4732 | O | LYS | B | 414 | −37.286 | −89.699 | 41.502 | 1.00 | 61.62 | O |
| ATOM | 4733 | CB | LYS | B | 414 | −37.785 | −88.257 | 44.422 | 1.00 | 58.01 | C |
| ATOM | 4734 | CG | LYS | B | 414 | −37.150 | −89.603 | 44.750 | 1.00 | 65.77 | C |
| ATOM | 4735 | CD | LYS | B | 414 | −37.199 | −89.940 | 46.228 | 1.00 | 71.38 | C |
| ATOM | 4736 | CE | LYS | B | 414 | −38.607 | −90.126 | 46.746 | 1.00 | 78.90 | C |
| ATOM | 4737 | NZ | LYS | B | 414 | −38.615 | −90.635 | 48.140 | 1.00 | 96.92 | N |
| ATOM | 4738 | N | SER | B | 415 | −39.406 | −88.907 | 41.741 | 1.00 | 59.97 | N |
| ATOM | 4739 | CA | SER | B | 415 | −40.094 | −89.795 | 40.784 | 1.00 | 59.70 | C |
| ATOM | 4740 | C | SER | B | 415 | −39.355 | −89.820 | 39.421 | 1.00 | 61.51 | C |
| ATOM | 4741 | O | SER | B | 415 | −38.937 | −90.882 | 38.971 | 1.00 | 62.74 | O |
| ATOM | 4742 | CB | SER | B | 415 | −41.537 | −89.312 | 40.593 | 1.00 | 63.09 | C |
| ATOM | 4743 | OG | SER | B | 415 | −42.187 | −89.862 | 39.460 | 1.00 | 73.11 | O |
| ATOM | 4744 | N | ARG | B | 416 | −39.199 | −88.641 | 38.789 | 1.00 | 55.22 | N |
| ATOM | 4745 | CA | ARG | B | 416 | −38.518 | −88.442 | 37.503 | 1.00 | 53.42 | C |
| ATOM | 4746 | C | ARG | B | 416 | −37.133 | −89.121 | 37.467 | 1.00 | 56.64 | C |
| ATOM | 4747 | O | ARG | B | 416 | −36.804 | −89.781 | 36.488 | 1.00 | 57.91 | O |
| ATOM | 4748 | CB | ARG | B | 416 | −38.348 | −86.935 | 37.202 | 1.00 | 52.94 | C |
| ATOM | 4749 | CG | ARG | B | 416 | −39.421 | −86.272 | 36.332 | 1.00 | 67.22 | C |
| ATOM | 4750 | CD | ARG | B | 416 | −38.769 | −85.187 | 35.463 | 1.00 | 82.66 | C |
| ATOM | 4751 | NE | ARG | B | 416 | −39.725 | −84.301 | 34.799 | 1.00 | 96.38 | N |
| ATOM | 4752 | CZ | ARG | B | 416 | −40.392 | −84.580 | 33.679 | 1.00 | 116.66 | C |
| ATOM | 4753 | NH1 | ARG | B | 416 | −40.230 | −85.755 | 33.069 | 1.00 | 106.42 | N |
| ATOM | 4754 | NH2 | ARG | B | 416 | −41.238 | −83.693 | 33.166 | 1.00 | 104.83 | N |
| ATOM | 4755 | N | TRP | B | 417 | −36.339 | −88.957 | 38.529 | 1.00 | 51.34 | N |
| ATOM | 4756 | CA | TRP | B | 417 | −34.998 | −89.539 | 38.660 | 1.00 | 50.72 | C |
| ATOM | 4757 | C | TRP | B | 417 | −35.003 | −91.079 | 38.795 | 1.00 | 58.23 | C |
| ATOM | 4758 | O | TRP | B | 417 | −34.157 | −91.748 | 38.200 | 1.00 | 58.30 | O |
| ATOM | 4759 | CB | TRP | B | 417 | −34.321 | −88.922 | 39.888 | 1.00 | 48.70 | C |
| ATOM | 4760 | CG | TRP | B | 417 | −32.951 | −89.433 | 40.187 | 1.00 | 49.36 | C |
| ATOM | 4761 | CD1 | TRP | B | 417 | −32.579 | −90.190 | 41.256 | 1.00 | 52.91 | C |
| ATOM | 4762 | CD2 | TRP | B | 417 | −31.751 | −89.150 | 39.454 | 1.00 | 48.35 | C |
| ATOM | 4763 | NE1 | TRP | B | 417 | −31.215 | −90.374 | 41.255 | 1.00 | 52.29 | N |
| ATOM | 4764 | CE2 | TRP | B | 417 | −30.685 | −89.759 | 40.148 | 1.00 | 52.52 | C |
| ATOM | 4765 | CE3 | TRP | B | 417 | −31.470 | −88.426 | 38.284 | 1.00 | 48.85 | C |
| ATOM | 4766 | CZ2 | TRP | B | 417 | −29.368 | −89.693 | 39.697 | 1.00 | 51.03 | C |
| ATOM | 4767 | CZ3 | TRP | B | 417 | −30.153 | −88.320 | 37.868 | 1.00 | 49.62 | C |
| ATOM | 4768 | CH2 | TRP | B | 417 | −29.122 | −88.955 | 38.572 | 1.00 | 50.48 | C |
| ATOM | 4769 | N | GLN | B | 418 | −35.920 | −91.627 | 39.621 | 1.00 | 56.68 | N |
| ATOM | 4770 | CA | GLN | B | 418 | −36.048 | −93.071 | 39.864 | 1.00 | 56.69 | C |
| ATOM | 4771 | C | GLN | B | 418 | −36.485 | −93.855 | 38.625 | 1.00 | 61.03 | C |
| ATOM | 4772 | O | GLN | B | 418 | −36.149 | −95.032 | 38.505 | 1.00 | 61.20 | O |
| ATOM | 4773 | CB | GLN | B | 418 | −37.002 | −93.337 | 41.037 | 1.00 | 58.60 | C |
| ATOM | 4774 | CG | GLN | B | 418 | −36.379 | −92.989 | 42.379 | 1.00 | 66.27 | C |
| ATOM | 4775 | CD | GLN | B | 418 | −37.351 | −93.030 | 43.536 | 1.00 | 90.63 | C |
| ATOM | 4776 | OE1 | GLN | B | 418 | −38.574 | −92.915 | 43.373 | 1.00 | 86.37 | O |
| ATOM | 4777 | NE2 | GLN | B | 418 | −36.815 | −93.081 | 44.752 | 1.00 | 83.47 | N |
| ATOM | 4778 | N | GLN | B | 419 | −37.174 | −93.200 | 37.676 | 1.00 | 57.55 | N |
| ATOM | 4779 | CA | GLN | B | 419 | −37.601 | −93.847 | 36.431 | 1.00 | 57.44 | C |
| ATOM | 4780 | C | GLN | B | 419 | −36.484 | −93.921 | 35.355 | 1.00 | 60.82 | C |
| ATOM | 4781 | O | GLN | B | 419 | −36.744 | −94.412 | 34.253 | 1.00 | 60.34 | O |
| ATOM | 4782 | CB | GLN | B | 419 | −38.865 | −93.162 | 35.876 | 1.00 | 58.86 | C |
| ATOM | 4783 | CG | GLN | B | 419 | −40.095 | −93.359 | 36.767 | 1.00 | 68.32 | C |
| ATOM | 4784 | CD | GLN | B | 419 | −41.265 | −92.493 | 36.355 | 1.00 | 93.40 | C |
| ATOM | 4785 | OE1 | GLN | B | 419 | −41.325 | −91.963 | 35.230 | 1.00 | 88.97 | O |
| ATOM | 4786 | NE2 | GLN | B | 419 | −42.233 | −92.337 | 37.257 | 1.00 | 86.55 | N |
| ATOM | 4787 | N | GLY | B | 420 | −35.262 | −93.468 | 35.680 | 1.00 | 56.66 | N |
| ATOM | 4788 | CA | GLY | B | 420 | −34.119 | −93.552 | 34.779 | 1.00 | 55.29 | C |
| ATOM | 4789 | C | GLY | B | 420 | −34.179 | −92.597 | 33.610 | 1.00 | 59.15 | C |
| ATOM | 4790 | O | GLY | B | 420 | −33.707 | −92.928 | 32.508 | 1.00 | 58.96 | O |
| ATOM | 4791 | N | ASN | B | 421 | −34.757 | −91.396 | 33.836 | 1.00 | 54.69 | N |
| ATOM | 4792 | CA | ASN | B | 421 | −34.843 | −90.366 | 32.788 | 1.00 | 52.34 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 4793 | C | ASN B | 421 | −33.482 | −89.664 | 32.792 | 1.00 | 51.05 | C |
| ATOM | 4794 | O | ASN B | 421 | −32.892 | −89.496 | 33.859 | 1.00 | 50.55 | O |
| ATOM | 4795 | CB | ASN B | 421 | −35.999 | −89.383 | 33.055 | 1.00 | 54.95 | C |
| ATOM | 4796 | CG | ASN B | 421 | −37.344 | −90.052 | 33.271 | 1.00 | 90.05 | C |
| ATOM | 4797 | OD1 | ASN B | 421 | −37.583 | −91.180 | 32.830 | 1.00 | 94.55 | O |
| ATOM | 4798 | ND2 | ASN B | 421 | −38.253 | −89.386 | 33.972 | 1.00 | 80.76 | N |
| ATOM | 4799 | N | VAL B | 422 | −32.949 | −89.343 | 31.610 | 1.00 | 44.02 | N |
| ATOM | 4800 | CA | VAL B | 422 | −31.636 | −88.724 | 31.466 | 1.00 | 41.23 | C |
| ATOM | 4801 | C | VAL B | 422 | −31.775 | −87.206 | 31.520 | 1.00 | 41.12 | C |
| ATOM | 4802 | O | VAL B | 422 | −32.635 | −86.645 | 30.839 | 1.00 | 40.14 | O |
| ATOM | 4803 | CB | VAL B | 422 | −30.963 | −89.192 | 30.136 | 1.00 | 44.85 | C |
| ATOM | 4804 | CG1 | VAL B | 422 | −29.626 | −88.486 | 29.896 | 1.00 | 43.05 | C |
| ATOM | 4805 | CG2 | VAL B | 422 | −30.769 | −90.708 | 30.129 | 1.00 | 45.29 | C |
| ATOM | 4806 | N | PHE B | 423 | −30.907 | −86.550 | 32.312 | 1.00 | 35.64 | N |
| ATOM | 4807 | CA | PHE B | 423 | −30.824 | −85.087 | 32.454 | 1.00 | 33.85 | C |
| ATOM | 4808 | C | PHE B | 423 | −29.485 | −84.619 | 31.866 | 1.00 | 39.47 | C |
| ATOM | 4809 | O | PHE B | 423 | −28.513 | −85.369 | 31.891 | 1.00 | 39.65 | O |
| ATOM | 4810 | CB | PHE B | 423 | −30.934 | −84.686 | 33.943 | 1.00 | 33.95 | C |
| ATOM | 4811 | CG | PHE B | 423 | −32.340 | −84.909 | 34.425 | 1.00 | 33.71 | C |
| ATOM | 4812 | CD1 | PHE B | 423 | −32.721 | −86.142 | 34.938 | 1.00 | 37.18 | C |
| ATOM | 4813 | CD2 | PHE B | 423 | −33.332 | −83.986 | 34.147 | 1.00 | 33.41 | C |
| ATOM | 4814 | CE1 | PHE B | 423 | −34.047 | −86.405 | 35.271 | 1.00 | 38.21 | C |
| ATOM | 4815 | CE2 | PHE B | 423 | −34.663 | −84.261 | 34.436 | 1.00 | 37.87 | C |
| ATOM | 4816 | CZ | PHE B | 423 | −35.009 | −85.460 | 35.031 | 1.00 | 37.33 | C |
| ATOM | 4817 | N | SER B | 424 | −29.429 | −83.416 | 31.329 | 1.00 | 36.06 | N |
| ATOM | 4818 | CA | SER B | 424 | −28.187 | −82.936 | 30.733 | 1.00 | 36.07 | C |
| ATOM | 4819 | C | SER B | 424 | −27.903 | −81.531 | 31.134 | 1.00 | 39.49 | C |
| ATOM | 4820 | O | SER B | 424 | −28.754 | −80.673 | 30.972 | 1.00 | 37.95 | O |
| ATOM | 4821 | CB | SER B | 424 | −28.247 | −82.991 | 29.209 | 1.00 | 39.42 | C |
| ATOM | 4822 | OG | SER B | 424 | −27.901 | −84.278 | 28.727 | 1.00 | 55.05 | O |
| ATOM | 4823 | N | CYS B | 425 | −26.669 | −81.299 | 31.569 | 1.00 | 36.54 | N |
| ATOM | 4824 | CA | CYS B | 425 | −26.125 | −80.000 | 31.888 | 1.00 | 36.28 | C |
| ATOM | 4825 | C | CYS B | 425 | −25.343 | −79.557 | 30.630 | 1.00 | 38.04 | C |
| ATOM | 4826 | O | CYS B | 425 | −24.335 | −80.182 | 30.288 | 1.00 | 35.60 | O |
| ATOM | 4827 | CB | CYS B | 425 | −25.206 | −80.103 | 33.096 | 1.00 | 37.95 | C |
| ATOM | 4828 | SG | CYS B | 425 | −24.217 | −78.621 | 33.383 | 1.00 | 42.39 | S |
| ATOM | 4829 | N | SER B | 426 | −25.831 | −78.530 | 29.933 | 1.00 | 33.63 | N |
| ATOM | 4830 | CA | SER B | 426 | −25.193 | −78.011 | 28.744 | 1.00 | 33.53 | C |
| ATOM | 4831 | C | SER B | 426 | −24.410 | −76.740 | 29.080 | 1.00 | 35.47 | C |
| ATOM | 4832 | O | SER B | 426 | −24.881 | −75.919 | 29.848 | 1.00 | 35.07 | O |
| ATOM | 4833 | CB | SER B | 426 | −26.228 | −77.741 | 27.663 | 1.00 | 39.87 | C |
| ATOM | 4834 | OG | SER B | 426 | −27.153 | −76.739 | 28.043 | 1.00 | 53.30 | O |
| ATOM | 4835 | N | VAL B | 427 | −23.200 | −76.595 | 28.511 | 1.00 | 30.46 | N |
| ATOM | 4836 | CA | VAL B | 427 | −22.328 | −75.461 | 28.763 | 1.00 | 27.57 | C |
| ATOM | 4837 | C | VAL B | 427 | −21.880 | −74.851 | 27.435 | 1.00 | 31.29 | C |
| ATOM | 4838 | O | VAL B | 427 | −21.532 | −75.579 | 26.509 | 1.00 | 28.84 | O |
| ATOM | 4839 | CB | VAL B | 427 | −21.127 | −75.892 | 29.632 | 1.00 | 29.35 | C |
| ATOM | 4840 | CG1 | VAL B | 427 | −20.169 | −74.732 | 29.874 | 1.00 | 28.38 | C |
| ATOM | 4841 | CG2 | VAL B | 427 | −21.594 | −76.496 | 30.957 | 1.00 | 28.61 | C |
| ATOM | 4842 | N | MET B | 428 | −21.867 | −73.504 | 27.375 | 1.00 | 29.34 | N |
| ATOM | 4843 | CA | MET B | 428 | −21.430 | −72.734 | 26.224 | 1.00 | 29.61 | C |
| ATOM | 4844 | C | MET B | 428 | −20.349 | −71.737 | 26.620 | 1.00 | 29.79 | C |
| ATOM | 4845 | O | MET B | 428 | −20.548 | −70.926 | 27.520 | 1.00 | 29.19 | O |
| ATOM | 4846 | CB | MET B | 428 | −22.613 | −72.032 | 25.601 | 1.00 | 33.24 | C |
| ATOM | 4847 | CG | MET B | 428 | −23.467 | −72.984 | 24.890 | 1.00 | 40.55 | C |
| ATOM | 4848 | SD | MET B | 428 | −24.669 | −72.163 | 23.855 | 1.00 | 48.18 | S |
| ATOM | 4849 | CE | MET B | 428 | −26.189 | −72.594 | 24.757 | 1.00 | 46.22 | C |
| ATOM | 4850 | N | HIS B | 429 | −19.185 | −71.842 | 25.990 | 1.00 | 23.42 | N |
| ATOM | 4851 | CA | HIS B | 429 | −18.034 | −71.003 | 26.322 | 1.00 | 20.76 | C |
| ATOM | 4852 | C | HIS B | 429 | −17.165 | −70.892 | 25.078 | 1.00 | 24.07 | C |
| ATOM | 4853 | O | HIS B | 429 | −17.023 | −71.877 | 24.369 | 1.00 | 23.26 | O |
| ATOM | 4854 | CB | HIS B | 429 | −17.252 | −71.650 | 27.487 | 1.00 | 20.39 | C |
| ATOM | 4855 | CG | HIS B | 429 | −16.193 | −70.770 | 28.073 | 1.00 | 22.48 | C |
| ATOM | 4856 | ND1 | HIS B | 429 | −14.893 | −70.803 | 27.614 | 1.00 | 23.65 | N |
| ATOM | 4857 | CD2 | HIS B | 429 | −16.288 | −69.839 | 29.042 | 1.00 | 23.79 | C |
| ATOM | 4858 | CE1 | HIS B | 429 | −14.241 | −69.885 | 28.293 | 1.00 | 22.48 | C |
| ATOM | 4859 | NE2 | HIS B | 429 | −15.040 | −69.285 | 29.181 | 1.00 | 23.30 | N |
| ATOM | 4860 | N | GLU B | 430 | −16.555 | −69.723 | 24.844 | 1.00 | 21.84 | N |
| ATOM | 4861 | CA | GLU B | 430 | −15.711 | −69.473 | 23.679 | 1.00 | 22.25 | C |
| ATOM | 4862 | C | GLU B | 430 | −14.561 | −70.477 | 23.492 | 1.00 | 25.28 | C |
| ATOM | 4863 | O | GLU B | 430 | −14.216 | −70.790 | 22.344 | 1.00 | 26.40 | O |
| ATOM | 4864 | CB | GLU B | 430 | −15.153 | −68.026 | 23.656 | 1.00 | 23.59 | C |
| ATOM | 4865 | CG | GLU B | 430 | −13.923 | −67.769 | 24.534 | 1.00 | 39.27 | C |
| ATOM | 4866 | CD | GLU B | 430 | −13.058 | −66.599 | 24.109 | 1.00 | 57.04 | C |
| ATOM | 4867 | OE1 | GLU B | 430 | −12.892 | −65.674 | 24.934 | 1.00 | 46.22 | O |
| ATOM | 4868 | OE2 | GLU B | 430 | −12.512 | −66.621 | 22.979 | 1.00 | 48.67 | O |
| ATOM | 4869 | N | ALA B | 431 | −13.959 | −70.940 | 24.598 | 1.00 | 18.41 | N |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 4870 | CA | ALA B | 431 | −12.803 | −71.819 | 24.543 | 1.00 | 18.24 | C |
| ATOM | 4871 | C | ALA B | 431 | −13.142 | −73.291 | 24.160 | 1.00 | 23.61 | C |
| ATOM | 4872 | O | ALA B | 431 | −12.220 | −74.064 | 23.832 | 1.00 | 21.93 | O |
| ATOM | 4873 | CB | ALA B | 431 | −12.030 | −71.749 | 25.860 | 1.00 | 18.24 | C |
| ATOM | 4874 | N | LEU B | 432 | −14.455 | −73.664 | 24.178 | 1.00 | 20.63 | N |
| ATOM | 4875 | CA | LEU B | 432 | −14.916 | −74.989 | 23.762 | 1.00 | 20.78 | C |
| ATOM | 4876 | C | LEU B | 432 | −14.978 | −75.069 | 22.218 | 1.00 | 23.99 | C |
| ATOM | 4877 | O | LEU B | 432 | −15.293 | −74.095 | 21.548 | 1.00 | 22.10 | O |
| ATOM | 4878 | CB | LEU B | 432 | −16.338 | −75.312 | 24.322 | 1.00 | 20.83 | C |
| ATOM | 4879 | CG | LEU B | 432 | −16.474 | −75.672 | 25.795 | 1.00 | 25.49 | C |
| ATOM | 4880 | CD1 | LEU B | 432 | −17.926 | −75.690 | 26.223 | 1.00 | 25.33 | C |
| ATOM | 4881 | CD2 | LEU B | 432 | −15.850 | −77.009 | 26.102 | 1.00 | 28.01 | C |
| ATOM | 4882 | N | HIS B | 433 | −14.761 | −76.258 | 21.671 | 1.00 | 22.90 | N |
| ATOM | 4883 | CA | HIS B | 433 | −14.932 | −76.493 | 20.234 | 1.00 | 22.97 | C |
| ATOM | 4884 | C | HIS B | 433 | −16.449 | −76.454 | 19.931 | 1.00 | 28.46 | C |
| ATOM | 4885 | O | HIS B | 433 | −17.222 | −77.116 | 20.615 | 1.00 | 29.61 | O |
| ATOM | 4886 | CB | HIS B | 433 | −14.363 | −77.854 | 19.824 | 1.00 | 23.90 | C |
| ATOM | 4887 | CG | HIS B | 433 | −14.346 | −78.019 | 18.339 | 1.00 | 28.11 | C |
| ATOM | 4888 | ND1 | HIS B | 433 | −14.791 | −79.170 | 17.735 | 1.00 | 30.87 | N |
| ATOM | 4889 | CD2 | HIS B | 433 | −13.998 | −77.138 | 17.382 | 1.00 | 29.31 | C |
| ATOM | 4890 | CE1 | HIS B | 433 | −14.634 | −78.984 | 16.444 | 1.00 | 29.62 | C |
| ATOM | 4891 | NE2 | HIS B | 433 | −14.175 | −77.770 | 16.188 | 1.00 | 29.41 | N |
| ATOM | 4892 | N | ASN B | 434 | −16.867 | −75.618 | 18.972 | 1.00 | 25.91 | N |
| ATOM | 4893 | CA | ASN B | 434 | −18.272 | −75.373 | 18.624 | 1.00 | 25.43 | C |
| ATOM | 4894 | C | ASN B | 434 | −18.934 | −74.614 | 19.745 | 1.00 | 28.76 | C |
| ATOM | 4895 | O | ASN B | 434 | −20.150 | −74.605 | 19.830 | 1.00 | 29.46 | O |
| ATOM | 4896 | CB | ASN B | 434 | −19.039 | −76.673 | 18.294 | 1.00 | 28.37 | C |
| ATOM | 4897 | CG | ASN B | 434 | −18.529 | −77.348 | 17.035 | 1.00 | 36.25 | C |
| ATOM | 4898 | OD1 | ASN B | 434 | −18.372 | −76.687 | 16.006 | 1.00 | 23.01 | O |
| ATOM | 4899 | ND2 | ASN B | 434 | −18.235 | −78.654 | 17.075 | 1.00 | 20.88 | N |
| ATOM | 4900 | N | HIS B | 435 | −18.141 | −73.966 | 20.612 | 1.00 | 24.55 | N |
| ATOM | 4901 | CA | HIS B | 435 | −18.620 | −73.232 | 21.773 | 1.00 | 24.13 | C |
| ATOM | 4902 | C | HIS B | 435 | −19.620 | −74.013 | 22.637 | 1.00 | 25.23 | C |
| ATOM | 4903 | O | HIS B | 435 | −20.392 | −73.409 | 23.376 | 1.00 | 25.75 | O |
| ATOM | 4904 | CB | HIS B | 435 | −19.236 | −71.893 | 21.320 | 1.00 | 25.22 | C |
| ATOM | 4905 | CG | HIS B | 435 | −18.293 | −71.013 | 20.554 | 1.00 | 28.69 | C |
| ATOM | 4906 | ND1 | HIS B | 435 | −18.755 | −70.080 | 19.637 | 1.00 | 30.22 | N |
| ATOM | 4907 | CD2 | HIS B | 435 | −16.946 | −70.944 | 20.602 | 1.00 | 30.46 | C |
| ATOM | 4908 | CE1 | HIS B | 435 | −17.686 | −69.456 | 19.179 | 1.00 | 29.25 | C |
| ATOM | 4909 | NE2 | HIS B | 435 | −16.571 | −69.942 | 19.735 | 1.00 | 30.08 | N |
| ATOM | 4910 | N | TYR B | 436 | −19.581 | −75.323 | 22.604 | 1.00 | 19.79 | N |
| ATOM | 4911 | CA | TYR B | 436 | −20.598 | −76.094 | 23.283 | 1.00 | 20.91 | C |
| ATOM | 4912 | C | TYR B | 436 | −20.098 | −77.446 | 23.747 | 1.00 | 26.08 | C |
| ATOM | 4913 | O | TYR B | 436 | −19.308 | −78.075 | 23.058 | 1.00 | 24.85 | O |
| ATOM | 4914 | CB | TYR B | 436 | −21.810 | −76.283 | 22.313 | 1.00 | 22.66 | C |
| ATOM | 4915 | CG | TYR B | 436 | −23.000 | −76.980 | 22.925 | 1.00 | 24.00 | C |
| ATOM | 4916 | CD1 | TYR B | 436 | −23.066 | −78.368 | 22.985 | 1.00 | 25.58 | C |
| ATOM | 4917 | CD2 | TYR B | 436 | −24.060 | −76.256 | 23.449 | 1.00 | 25.19 | C |
| ATOM | 4918 | CE1 | TYR B | 436 | −24.149 | −79.014 | 23.578 | 1.00 | 25.03 | C |
| ATOM | 4919 | CE2 | TYR B | 436 | −25.111 | −76.887 | 24.108 | 1.00 | 27.26 | C |
| ATOM | 4920 | CZ | TYR B | 436 | −25.167 | −78.271 | 24.149 | 1.00 | 36.44 | C |
| ATOM | 4921 | OH | TYR B | 436 | −26.220 | −78.911 | 24.772 | 1.00 | 44.37 | O |
| ATOM | 4922 | N | THR B | 437 | −20.536 | −77.852 | 24.967 | 1.00 | 24.92 | N |
| ATOM | 4923 | CA | THR B | 437 | −20.341 | −79.186 | 25.520 | 1.00 | 24.40 | C |
| ATOM | 4924 | C | THR B | 437 | −21.516 | −79.544 | 26.385 | 1.00 | 26.54 | C |
| ATOM | 4925 | O | THR B | 437 | −22.276 | −78.685 | 26.842 | 1.00 | 24.28 | O |
| ATOM | 4926 | CB | THR B | 437 | −19.007 | −79.397 | 26.238 | 1.00 | 32.39 | C |
| ATOM | 4927 | OG1 | THR B | 437 | −18.810 | −80.814 | 26.356 | 1.00 | 33.32 | O |
| ATOM | 4928 | CG2 | THR B | 437 | −18.953 | −78.754 | 27.641 | 1.00 | 29.43 | C |
| ATOM | 4929 | N | GLN B | 438 | −21.614 | −80.822 | 26.682 | 1.00 | 27.13 | N |
| ATOM | 4930 | CA | GLN B | 438 | −22.691 | −81.339 | 27.519 | 1.00 | 28.63 | C |
| ATOM | 4931 | C | GLN B | 438 | −22.242 | −82.533 | 28.354 | 1.00 | 32.62 | C |
| ATOM | 4932 | O | GLN B | 438 | −21.309 | −83.236 | 27.969 | 1.00 | 31.29 | O |
| ATOM | 4933 | CB | GLN B | 438 | −23.819 | −81.751 | 26.574 | 1.00 | 30.73 | C |
| ATOM | 4934 | CG | GLN B | 438 | −25.059 | −82.313 | 27.224 | 1.00 | 47.79 | C |
| ATOM | 4935 | CD | GLN B | 438 | −26.024 | −82.698 | 26.151 | 1.00 | 57.77 | C |
| ATOM | 4936 | OE1 | GLN B | 438 | −26.275 | −83.890 | 25.921 | 1.00 | 48.13 | O |
| ATOM | 4937 | NE2 | GLN B | 438 | −26.552 | −81.694 | 25.446 | 1.00 | 42.52 | N |
| ATOM | 4938 | N | LYS B | 439 | −22.900 | −82.743 | 29.506 | 1.00 | 31.17 | N |
| ATOM | 4939 | CA | LYS B | 439 | −22.710 | −83.925 | 30.344 | 1.00 | 31.81 | C |
| ATOM | 4940 | C | LYS B | 439 | −24.085 | −84.399 | 30.779 | 1.00 | 38.97 | C |
| ATOM | 4941 | O | LYS B | 439 | −24.881 | −83.602 | 31.292 | 1.00 | 37.73 | O |
| ATOM | 4942 | CB | LYS B | 439 | −21.831 | −83.641 | 31.557 | 1.00 | 34.08 | C |
| ATOM | 4943 | CG | LYS B | 439 | −20.385 | −83.973 | 31.319 | 1.00 | 56.58 | C |
| ATOM | 4944 | CD | LYS B | 439 | −20.073 | −85.449 | 31.492 | 1.00 | 68.38 | C |
| ATOM | 4945 | CE | LYS B | 439 | −19.529 | −85.753 | 32.861 | 1.00 | 79.30 | C |
| ATOM | 4946 | NZ | LYS B | 439 | −18.093 | −85.362 | 33.040 | 1.00 | 83.28 | N |

TABLE 7-continued

Three-dimensional crystal coordinates for caffeine-pembrolizumab complex.
Atomic Coordinates of Caffeine/Pembrolizumab Crystal Complex

| | | | | | | | | | | | |
|---|---|---|---|---|---|---|---|---|---|---|---|
| ATOM | 4947 | N | SER | B | 440 | −24.364 | −85.691 | 30.564 | 1.00 | 39.10 | N |
| ATOM | 4948 | CA | SER | B | 440 | −25.625 | −86.314 | 30.959 | 1.00 | 40.39 | C |
| ATOM | 4949 | C | SER | B | 440 | −25.542 | −86.899 | 32.356 | 1.00 | 45.78 | C |
| ATOM | 4950 | O | SER | B | 440 | −24.445 | −87.113 | 32.893 | 1.00 | 45.92 | O |
| ATOM | 4951 | CB | SER | B | 440 | −26.068 | −87.371 | 29.957 | 1.00 | 45.30 | C |
| ATOM | 4952 | OG | SER | B | 440 | −26.734 | −86.730 | 28.882 | 1.00 | 57.38 | O |
| ATOM | 4953 | N | LEU | B | 441 | −26.717 | −87.113 | 32.956 | 1.00 | 42.70 | N |
| ATOM | 4954 | CA | LEU | B | 441 | −26.823 | −87.617 | 34.318 | 1.00 | 44.09 | C |
| ATOM | 4955 | C | LEU | B | 441 | −28.034 | −88.529 | 34.428 | 1.00 | 48.61 | C |
| ATOM | 4956 | O | LEU | B | 441 | −29.107 | −88.207 | 33.913 | 1.00 | 47.47 | O |
| ATOM | 4957 | CB | LEU | B | 441 | −26.930 | −86.409 | 35.282 | 1.00 | 43.72 | C |
| ATOM | 4958 | CG | LEU | B | 441 | −26.744 | −86.675 | 36.755 | 1.00 | 47.86 | C |
| ATOM | 4959 | CD1 | LEU | B | 441 | −25.437 | −87.368 | 37.046 | 1.00 | 47.31 | C |
| ATOM | 4960 | CD2 | LEU | B | 441 | −26.876 | −85.414 | 37.540 | 1.00 | 51.49 | C |
| ATOM | 4961 | N | SER | B | 442 | −27.841 | −89.685 | 35.063 | 1.00 | 46.70 | N |
| ATOM | 4962 | CA | SER | B | 442 | −28.879 | −90.696 | 35.180 | 1.00 | 47.47 | C |
| ATOM | 4963 | C | SER | B | 442 | −28.664 | −91.604 | 36.370 | 1.00 | 53.20 | C |
| ATOM | 4964 | O | SER | B | 442 | −27.551 | −91.704 | 36.892 | 1.00 | 51.73 | O |
| ATOM | 4965 | CB | SER | B | 442 | −28.890 | −91.548 | 33.915 | 1.00 | 51.21 | C |
| ATOM | 4966 | OG | SER | B | 442 | −30.126 | −91.388 | 33.246 | 1.00 | 64.71 | O |
| ATOM | 4967 | N | LEU | B | 443 | −29.744 | −92.291 | 36.780 | 1.00 | 52.92 | N |
| ATOM | 4968 | CA | LEU | B | 443 | −29.698 | −93.300 | 37.838 | 1.00 | 54.44 | C |
| ATOM | 4969 | C | LEU | B | 443 | −29.172 | −94.574 | 37.155 | 1.00 | 61.47 | C |
| ATOM | 4970 | O | LEU | B | 443 | −29.725 | −94.984 | 36.126 | 1.00 | 60.91 | O |
| ATOM | 4971 | CB | LEU | B | 443 | −31.104 | −93.541 | 38.429 | 1.00 | 55.24 | C |
| ATOM | 4972 | CG | LEU | B | 443 | −31.239 | −94.685 | 39.466 | 1.00 | 60.40 | C |
| ATOM | 4973 | CD1 | LEU | B | 443 | −30.373 | −94.444 | 40.684 | 1.00 | 59.82 | C |
| ATOM | 4974 | CD2 | LEU | B | 443 | −32.662 | −94.850 | 39.910 | 1.00 | 62.95 | C |
| ATOM | 4975 | N | SER | B | 444 | −28.091 | −95.178 | 37.697 | 1.00 | 60.00 | N |
| ATOM | 4976 | CA | SER | B | 444 | −27.490 | −96.403 | 37.126 | 1.00 | 103.48 | C |
| ATOM | 4977 | C | SER | B | 444 | −28.486 | −97.578 | 37.055 | 1.00 | 131.18 | C |
| ATOM | 4978 | O | SER | B | 444 | −29.015 | −97.889 | 35.987 | 1.00 | 91.12 | O |
| ATOM | 4979 | CB | SER | B | 444 | −26.273 | −96.829 | 37.946 | 1.00 | 107.82 | C |
| ATOM | 4980 | OG | SER | B | 444 | −25.353 | −95.763 | 38.116 | 1.00 | 116.71 | O |
| ATOM | 4981 | C1 | NAG | B | 505 | −34.024 | −42.592 | 39.731 | 1.00 | 57.69 | C |
| ATOM | 4982 | C2 | NAG | B | 505 | −32.673 | −42.755 | 40.425 | 1.00 | 56.35 | C |
| ATOM | 4983 | C3 | NAG | B | 505 | −31.757 | −43.516 | 39.470 | 1.00 | 53.12 | C |
| ATOM | 4984 | C4 | NAG | B | 505 | −32.359 | −44.882 | 39.141 | 1.00 | 53.20 | C |
| ATOM | 4985 | C5 | NAG | B | 505 | −33.750 | −44.698 | 38.528 | 1.00 | 56.40 | C |
| ATOM | 4986 | C6 | NAG | B | 505 | −34.502 | −45.999 | 38.261 | 1.00 | 53.67 | C |
| ATOM | 4987 | C7 | NAG | B | 505 | −32.154 | −40.894 | 41.969 | 1.00 | 60.17 | C |
| ATOM | 4988 | C8 | NAG | B | 505 | −31.573 | −39.515 | 42.080 | 1.00 | 57.61 | C |
| ATOM | 4989 | N2 | NAG | B | 505 | −32.118 | −41.449 | 40.747 | 1.00 | 58.95 | N |
| ATOM | 4990 | O3 | NAG | B | 505 | −30.468 | −43.631 | 40.067 | 1.00 | 52.14 | O |
| ATOM | 4991 | O4 | NAG | B | 505 | −31.520 | −45.631 | 38.263 | 1.00 | 50.19 | O |
| ATOM | 4992 | O5 | NAG | B | 505 | −34.576 | −43.874 | 39.385 | 1.00 | 59.37 | O |
| ATOM | 4993 | O6 | NAG | B | 505 | −34.977 | −46.659 | 39.435 | 1.00 | 51.58 | O |
| ATOM | 4994 | O7 | NAG | B | 505 | −32.629 | −41.480 | 42.939 | 1.00 | 62.50 | O |
| ATOM | 4995 | C1 | NAG | B | 506 | −30.579 | −46.535 | 38.842 | 1.00 | 49.95 | C |
| ATOM | 4996 | C2 | NAG | B | 506 | −30.292 | −47.655 | 37.843 | 1.00 | 48.05 | C |
| ATOM | 4997 | C3 | NAG | B | 506 | −29.246 | −48.586 | 38.460 | 1.00 | 45.53 | C |
| ATOM | 4998 | C4 | NAG | B | 506 | −27.972 | −47.815 | 38.804 | 1.00 | 46.08 | C |
| ATOM | 4999 | C5 | NAG | B | 506 | −28.315 | −46.650 | 39.733 | 1.00 | 48.72 | C |
| ATOM | 5000 | C6 | NAG | B | 506 | −27.155 | −45.722 | 39.991 | 1.00 | 47.54 | C |
| ATOM | 5001 | C7 | NAG | B | 506 | −32.038 | −48.501 | 36.305 | 1.00 | 51.68 | C |
| ATOM | 5002 | C8 | NAG | B | 506 | −33.317 | −49.278 | 36.203 | 1.00 | 51.16 | C |
| ATOM | 5003 | N2 | NAG | B | 506 | −31.519 | −48.379 | 37.545 | 1.00 | 51.51 | N |
| ATOM | 5004 | O3 | NAG | B | 506 | −28.947 | −49.639 | 37.552 | 1.00 | 44.28 | O |
| ATOM | 5005 | O4 | NAG | B | 506 | −27.037 | −48.652 | 39.481 | 1.00 | 46.62 | O |
| ATOM | 5006 | O5 | NAG | B | 506 | −29.361 | −45.846 | 39.157 | 1.00 | 50.29 | O |
| ATOM | 5007 | O6 | NAG | B | 506 | −27.577 | −44.612 | 40.767 | 1.00 | 49.27 | O |
| ATOM | 5008 | O7 | NAG | B | 506 | −31.494 | −48.016 | 35.315 | 1.00 | 50.95 | O |
| ATOM | 5009 | C1 | BMA | B | 507 | −26.031 | −49.333 | 38.741 | 1.00 | 48.36 | C |
| ATOM | 5010 | C2 | BMA | B | 507 | −24.774 | −49.480 | 39.620 | 1.00 | 47.94 | C |
| ATOM | 5011 | C3 | BMA | B | 507 | −23.745 | −50.389 | 38.941 | 1.00 | 46.93 | C |
| ATOM | 5012 | C4 | BMA | B | 507 | −24.362 | −51.724 | 38.521 | 1.00 | 46.34 | C |
| ATOM | 5013 | C5 | BMA | B | 507 | −25.616 | −51.493 | 37.678 | 1.00 | 46.33 | C |
| ATOM | 5014 | C6 | BMA | B | 507 | −26.385 | −52.757 | 37.394 | 1.00 | 47.40 | C |
| ATOM | 5015 | O2 | BMA | B | 507 | −25.127 | −49.984 | 40.906 | 1.00 | 49.58 | O |
| ATOM | 5016 | O3 | BMA | B | 507 | −22.596 | −50.597 | 39.766 | 1.00 | 49.13 | O |
| ATOM | 5017 | O4 | BMA | B | 507 | −23.430 | −52.472 | 37.747 | 1.00 | 46.64 | O |
| ATOM | 5018 | O5 | BMA | B | 507 | −26.531 | −50.625 | 38.370 | 1.00 | 48.31 | O |
| ATOM | 5019 | O6 | BMA | B | 507 | −27.671 | −52.441 | 36.878 | 1.00 | 49.23 | O |
| ATOM | 5020 | C1 | MAN | B | 508 | −28.370 | −53.535 | 36.372 | 1.00 | 53.31 | C |
| ATOM | 5021 | C2 | MAN | B | 508 | −29.363 | −53.026 | 35.317 | 1.00 | 58.52 | C |
| ATOM | 5022 | C3 | MAN | B | 508 | −30.508 | −52.264 | 35.982 | 1.00 | 57.29 | C |
| ATOM | 5023 | C4 | MAN | B | 508 | −31.179 | −53.115 | 37.059 | 1.00 | 58.11 | C |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 5024 | C5 | MAN B | 508 | −30.132 | −53.583 | 38.069 | 1.00 | 58.39 | C |
| ATOM | 5025 | C6 | MAN B | 508 | −30.676 | −54.549 | 39.101 | 1.00 | 63.56 | C |
| ATOM | 5026 | O2 | MAN B | 508 | −29.887 | −54.121 | 34.560 | 1.00 | 63.33 | O |
| ATOM | 5027 | O3 | MAN B | 508 | −31.454 | −51.850 | 35.004 | 1.00 | 56.70 | O |
| ATOM | 5028 | O4 | MAN B | 508 | −32.225 | −52.387 | 37.704 | 1.00 | 58.23 | O |
| ATOM | 5029 | O5 | MAN B | 508 | −29.058 | −54.269 | 37.391 | 1.00 | 54.48 | O |
| ATOM | 5030 | O6 | MAN B | 508 | −29.673 | −54.944 | 40.032 | 1.00 | 65.61 | O |
| ATOM | 5031 | C1 | MAN B | 509 | −21.373 | −49.928 | 39.424 | 1.00 | 56.87 | C |
| ATOM | 5032 | C2 | MAN B | 509 | −20.167 | −50.648 | 40.059 | 1.00 | 66.01 | C |
| ATOM | 5033 | C3 | MAN B | 509 | −20.252 | −50.535 | 41.582 | 1.00 | 64.19 | C |
| ATOM | 5034 | C4 | MAN B | 509 | −20.373 | −49.073 | 42.016 | 1.00 | 63.60 | C |
| ATOM | 5035 | C5 | MAN B | 509 | −21.516 | −48.377 | 41.274 | 1.00 | 62.77 | C |
| ATOM | 5036 | C6 | MAN B | 509 | −21.570 | −46.886 | 41.500 | 1.00 | 65.31 | C |
| ATOM | 5037 | O2 | MAN B | 509 | −18.946 | −50.014 | 39.653 | 1.00 | 75.96 | O |
| ATOM | 5038 | O3 | MAN B | 509 | −19.102 | −51.130 | 42.178 | 1.00 | 62.04 | O |
| ATOM | 5039 | O4 | MAN B | 509 | −20.579 | −48.986 | 43.419 | 1.00 | 63.40 | O |
| ATOM | 5040 | O5 | MAN B | 509 | −21.382 | −48.562 | 39.852 | 1.00 | 58.22 | O |
| ATOM | 5041 | O6 | MAN B | 509 | −22.661 | −46.310 | 40.794 | 1.00 | 66.63 | O |
| ATOM | 5042 | C1 | NAG B | 510 | −18.410 | −50.350 | 38.379 | 1.00 | 83.99 | C |
| ATOM | 5043 | C2 | NAG B | 510 | −17.889 | −49.055 | 37.747 | 1.00 | 87.69 | C |
| ATOM | 5044 | C3 | NAG B | 510 | −17.246 | −49.396 | 36.400 | 1.00 | 91.11 | C |
| ATOM | 5045 | C4 | NAG B | 510 | −16.135 | −50.430 | 36.576 | 1.00 | 92.06 | C |
| ATOM | 5046 | C5 | NAG B | 510 | −16.669 | −51.667 | 37.301 | 1.00 | 90.74 | C |
| ATOM | 5047 | C6 | NAG B | 510 | −15.583 | −52.649 | 37.683 | 1.00 | 91.13 | C |
| ATOM | 5048 | C7 | NAG B | 510 | −18.847 | −46.789 | 38.022 | 1.00 | 89.72 | C |
| ATOM | 5049 | C8 | NAG B | 510 | −19.974 | −45.878 | 37.630 | 1.00 | 90.11 | C |
| ATOM | 5050 | N2 | NAG B | 510 | −18.935 | −48.057 | 37.576 | 1.00 | 88.26 | N |
| ATOM | 5051 | O3 | NAG B | 510 | −16.750 | −48.216 | 35.768 | 1.00 | 91.68 | O |
| ATOM | 5052 | O4 | NAG B | 510 | −15.610 | −50.804 | 35.303 | 1.00 | 92.28 | O |
| ATOM | 5053 | O5 | NAG B | 510 | −17.330 | −51.284 | 38.525 | 1.00 | 88.10 | O |
| ATOM | 5054 | O6 | NAG B | 510 | −16.118 | −53.775 | 38.367 | 1.00 | 91.85 | O |
| ATOM | 5055 | O7 | NAG B | 510 | −17.904 | −46.399 | 38.706 | 1.00 | 90.20 | O |
| ATOM | 5056 | C1 | NAG B | 511 | −29.124 | −54.548 | 33.436 | 1.00 | 62.47 | C |
| ATOM | 5057 | C2 | NAG B | 511 | −29.368 | −56.049 | 33.274 | 1.00 | 64.25 | C |
| ATOM | 5058 | C3 | NAG B | 511 | −28.668 | −56.562 | 32.016 | 1.00 | 65.21 | C |
| ATOM | 5059 | C4 | NAG B | 511 | −29.082 | −55.740 | 30.795 | 1.00 | 64.87 | C |
| ATOM | 5060 | C5 | NAG B | 511 | −28.801 | −54.259 | 31.058 | 1.00 | 62.55 | C |
| ATOM | 5061 | C6 | NAG B | 511 | −29.193 | −53.324 | 29.927 | 1.00 | 62.23 | C |
| ATOM | 5062 | C7 | NAG B | 511 | −29.743 | −57.329 | 35.351 | 1.00 | 67.73 | C |
| ATOM | 5063 | C8 | NAG B | 511 | −29.084 | −58.047 | 36.491 | 1.00 | 66.79 | C |
| ATOM | 5064 | N2 | NAG B | 511 | −28.915 | −56.783 | 34.445 | 1.00 | 65.81 | N |
| ATOM | 5065 | O3 | NAG B | 511 | −28.987 | −57.937 | 31.842 | 1.00 | 66.68 | O |
| ATOM | 5066 | O4 | NAG B | 511 | −28.370 | −56.190 | 29.644 | 1.00 | 65.69 | O |
| ATOM | 5067 | O5 | NAG B | 511 | −29.488 | −53.825 | 32.248 | 1.00 | 61.17 | O |
| ATOM | 5068 | O6 | NAG B | 511 | −30.579 | −52.994 | 29.899 | 1.00 | 61.74 | O |
| ATOM | 5069 | O7 | NAG B | 511 | −30.967 | −57.244 | 35.256 | 1.00 | 69.63 | O |
| ATOM | 5070 | C1 | SUC B | 512 | 5.120 | −49.460 | 9.099 | 1.00 | 193.80 | C |
| ATOM | 5071 | C2 | SUC B | 512 | 3.831 | −48.665 | 9.318 | 1.00 | 193.55 | C |
| ATOM | 5072 | C3 | SUC B | 512 | 3.057 | −49.188 | 10.526 | 1.00 | 193.20 | C |
| ATOM | 5073 | C4 | SUC B | 512 | 2.853 | −50.697 | 10.433 | 1.00 | 193.48 | C |
| ATOM | 5074 | C5 | SUC B | 512 | 4.199 | −51.394 | 10.234 | 1.00 | 193.82 | C |
| ATOM | 5075 | C6 | SUC B | 512 | 4.075 | −52.889 | 10.025 | 1.00 | 193.14 | C |
| ATOM | 5076 | O1 | SUC B | 512 | 6.127 | −49.096 | 10.076 | 1.00 | 192.89 | O |
| ATOM | 5077 | O2 | SUC B | 512 | 4.122 | −47.280 | 9.482 | 1.00 | 193.59 | O |
| ATOM | 5078 | O3 | SUC B | 512 | 1.797 | −48.533 | 10.623 | 1.00 | 192.38 | O |
| ATOM | 5079 | O4 | SUC B | 512 | 2.226 | −51.171 | 11.621 | 1.00 | 193.40 | O |
| ATOM | 5080 | O5 | SUC B | 512 | 4.865 | −50.862 | 9.069 | 1.00 | 194.36 | O |
| ATOM | 5081 | O6 | SUC B | 512 | 5.336 | −53.540 | 10.099 | 1.00 | 192.94 | O |
| ATOM | 5082 | C1' | SUC B | 512 | 7.656 | −47.302 | 10.612 | 1.00 | 190.91 | C |
| ATOM | 5083 | C2' | SUC B | 512 | 7.376 | −48.494 | 9.688 | 1.00 | 191.41 | C |
| ATOM | 5084 | C3' | SUC B | 512 | 8.504 | −49.619 | 9.707 | 1.00 | 191.52 | C |
| ATOM | 5085 | C4' | SUC B | 512 | 8.816 | −49.828 | 8.225 | 1.00 | 190.83 | C |
| ATOM | 5086 | C5' | SUC B | 512 | 8.504 | −48.460 | 7.629 | 1.00 | 190.13 | C |
| ATOM | 5087 | C6' | SUC B | 512 | 8.210 | −48.445 | 6.146 | 1.00 | 189.44 | C |
| ATOM | 5088 | O1' | SUC B | 512 | 7.706 | −47.690 | 11.978 | 1.00 | 190.86 | O |
| ATOM | 5089 | O2' | SUC B | 512 | 7.352 | −47.999 | 8.351 | 1.00 | 190.26 | O |
| ATOM | 5090 | O3' | SUC B | 512 | 8.202 | −50.820 | 10.410 | 1.00 | 191.71 | O |
| ATOM | 5091 | O4' | SUC B | 512 | 10.175 | −50.184 | 7.999 | 1.00 | 190.94 | O |
| ATOM | 5092 | O6' | SUC B | 512 | 7.011 | −49.143 | 5.833 | 1.00 | 188.79 | O |
| ATOM | 5093 | C1 | SUC B | 513 | 11.964 | −46.921 | −7.792 | 1.00 | 190.43 | C |
| ATOM | 5094 | C2 | SUC B | 513 | 11.179 | −47.770 | −6.791 | 1.00 | 190.49 | C |
| ATOM | 5095 | C3 | SUC B | 513 | 11.270 | −47.193 | −5.380 | 1.00 | 189.88 | C |
| ATOM | 5096 | C4 | SUC B | 513 | 12.719 | −46.929 | −4.981 | 1.00 | 190.13 | C |
| ATOM | 5097 | C5 | SUC B | 513 | 13.407 | −46.070 | −6.041 | 1.00 | 190.20 | C |
| ATOM | 5098 | C6 | SUC B | 513 | 14.886 | −45.857 | −5.786 | 1.00 | 190.03 | C |
| ATOM | 5099 | O1 | SUC B | 513 | 11.250 | −45.697 | −8.112 | 1.00 | 188.94 | O |
| ATOM | 5100 | O2 | SUC B | 513 | 9.817 | −47.872 | −7.194 | 1.00 | 190.30 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 5101 | O3 | SUC B | 513 | 10.672 | −48.091 | −4.451 | 1.00 | 189.35 | O |
| ATOM | 5102 | O4 | SUC B | 513 | 12.755 | −46.270 | −3.718 | 1.00 | 189.63 | O |
| ATOM | 5103 | O5 | SUC B | 513 | 13.294 | −46.689 | −7.340 | 1.00 | 190.89 | O |
| ATOM | 5104 | O6 | SUC B | 513 | 15.638 | −47.056 | −5.934 | 1.00 | 190.19 | O |
| ATOM | 5105 | C1' | SUC B | 513 | 10.185 | −46.203 | −10.251 | 1.00 | 187.13 | C |
| ATOM | 5106 | C2' | SUC B | 513 | 11.128 | −45.263 | −9.479 | 1.00 | 187.76 | C |
| ATOM | 5107 | C3' | SUC B | 513 | 10.656 | −43.771 | −9.448 | 1.00 | 186.66 | C |
| ATOM | 5108 | C4' | SUC B | 513 | 11.958 | −42.999 | −9.620 | 1.00 | 186.96 | C |
| ATOM | 5109 | C5' | SUC B | 513 | 12.746 | −43.919 | −10.546 | 1.00 | 187.84 | C |
| ATOM | 5110 | C6' | SUC B | 513 | 14.250 | −43.750 | −10.519 | 1.00 | 188.25 | C |
| ATOM | 5111 | O1' | SUC B | 513 | 10.112 | −45.861 | −11.628 | 1.00 | 187.10 | O |
| ATOM | 5112 | O2' | SUC B | 513 | 12.390 | −45.250 | −10.143 | 1.00 | 188.26 | O |
| ATOM | 5113 | O3' | SUC B | 513 | 9.866 | −43.372 | −8.333 | 1.00 | 185.69 | O |
| ATOM | 5114 | O4' | SUC B | 513 | 11.749 | −41.732 | −10.232 | 1.00 | 186.64 | O |
| ATOM | 5115 | O6' | SUC B | 513 | 14.807 | −44.058 | −9.246 | 1.00 | 188.18 | O |
| ATOM | 5116 | OW | WAT W | 1 | 2.920 | −23.751 | 34.384 | 1.00 | 33.07 | O |
| ATOM | 5117 | OW | WAT W | 2 | −25.763 | −73.452 | 27.499 | 1.00 | 29.99 | O |
| ATOM | 5118 | OW | WAT W | 3 | −27.003 | −24.341 | −0.941 | 1.00 | 22.34 | O |
| ATOM | 5119 | OW | WAT W | 4 | −38.407 | −24.017 | −10.386 | 1.00 | 33.24 | O |
| ATOM | 5120 | OW | WAT W | 5 | −16.450 | −28.291 | 28.960 | 1.00 | 44.69 | O |
| ATOM | 5121 | OW | WAT W | 6 | −29.904 | −77.537 | 27.995 | 1.00 | 50.73 | O |
| ATOM | 5122 | OW | WAT W | 7 | −22.601 | 1.699 | 27.086 | 1.00 | 50.39 | O |
| ATOM | 5123 | OW | WAT W | 8 | −18.625 | −82.177 | 28.715 | 1.00 | 34.37 | O |
| ATOM | 5124 | OW | WAT W | 9 | −35.506 | −19.442 | −0.632 | 1.00 | 43.97 | O |
| ATOM | 5125 | OW | WAT W | 10 | −3.912 | −7.994 | 3.681 | 1.00 | 33.92 | O |
| ATOM | 5126 | OW | WAT W | 11 | −28.123 | −34.331 | 18.759 | 1.00 | 37.32 | O |
| ATOM | 5127 | OW | WAT W | 12 | −12.073 | −42.317 | 28.322 | 1.00 | 53.42 | O |
| ATOM | 5128 | OW | WAT W | 13 | 5.803 | −6.425 | −8.720 | 1.00 | 45.55 | O |
| ATOM | 5129 | OW | WAT W | 14 | −2.848 | −31.640 | 32.447 | 1.00 | 50.59 | O |
| ATOM | 5130 | OW | WAT W | 15 | −13.388 | −33.988 | −29.130 | 1.00 | 31.11 | O |
| ATOM | 5131 | OW | WAT W | 16 | −16.737 | −42.814 | 11.116 | 1.00 | 45.20 | O |
| ATOM | 5132 | OW | WAT W | 17 | 12.327 | −10.193 | 13.635 | 1.00 | 39.15 | O |
| ATOM | 5133 | OW | WAT W | 18 | −18.153 | −29.228 | 10.328 | 1.00 | 39.30 | O |
| ATOM | 5134 | OW | WAT W | 19 | −13.886 | −9.167 | −21.584 | 1.00 | 44.49 | O |
| ATOM | 5135 | OW | WAT W | 20 | −5.774 | −12.896 | 20.082 | 1.00 | 36.26 | O |
| ATOM | 5136 | OW | WAT W | 21 | −27.880 | −91.570 | 44.028 | 1.00 | 44.60 | O |
| ATOM | 5137 | OW | WAT W | 22 | −2.011 | −26.480 | 18.462 | 1.00 | 30.26 | O |
| ATOM | 5138 | OW | WAT W | 23 | −36.940 | −92.707 | 49.876 | 1.00 | 51.54 | O |
| ATOM | 5139 | OW | WAT W | 24 | 12.335 | −22.487 | 9.387 | 1.00 | 44.58 | O |
| ATOM | 5140 | OW | WAT W | 25 | −5.792 | −28.477 | 18.701 | 1.00 | 41.25 | O |
| ATOM | 5141 | OW | WAT W | 26 | −17.957 | −17.372 | 3.613 | 1.00 | 39.38 | O |
| ATOM | 5142 | OW | WAT W | 27 | −7.946 | −64.377 | 36.479 | 1.00 | 34.00 | O |
| ATOM | 5143 | OW | WAT W | 28 | −9.708 | −62.465 | 36.914 | 1.00 | 29.67 | O |
| ATOM | 5144 | OW | WAT W | 29 | −31.518 | −19.713 | 24.848 | 1.00 | 28.09 | O |
| ATOM | 5145 | OW | WAT W | 30 | −18.532 | −28.019 | 7.935 | 1.00 | 39.20 | O |
| ATOM | 5146 | OW | WAT W | 31 | −4.928 | −22.730 | 13.543 | 1.00 | 36.05 | O |
| ATOM | 5147 | OW | WAT W | 32 | −21.838 | −88.045 | 29.807 | 1.00 | 39.51 | O |
| ATOM | 5148 | OW | WAT W | 33 | −16.251 | −85.930 | 30.744 | 1.00 | 38.59 | O |
| ATOM | 5149 | OW | WAT W | 34 | −32.595 | −34.979 | 7.095 | 1.00 | 43.91 | O |
| ATOM | 5150 | OW | WAT W | 35 | −4.618 | −26.664 | −1.290 | 1.00 | 47.91 | O |
| ATOM | 5151 | OW | WAT W | 36 | 4.648 | −23.806 | 36.505 | 1.00 | 48.40 | O |
| ATOM | 5152 | OW | WAT W | 37 | −13.864 | −42.143 | 13.953 | 1.00 | 41.23 | O |
| ATOM | 5153 | OW | WAT W | 38 | −1.430 | −32.963 | −8.936 | 1.00 | 40.84 | O |
| ATOM | 5154 | OW | WAT W | 39 | −3.527 | −13.484 | −24.541 | 1.00 | 36.24 | O |
| ATOM | 5155 | OW | WAT W | 40 | −24.915 | −57.414 | 30.170 | 1.00 | 45.24 | O |
| ATOM | 5156 | OW | WAT W | 41 | −15.540 | −65.635 | 26.381 | 1.00 | 40.06 | O |
| ATOM | 5157 | OW | WAT W | 42 | 10.724 | −12.629 | 17.905 | 1.00 | 48.59 | O |
| ATOM | 5158 | OW | WAT W | 43 | −10.430 | −11.470 | −26.651 | 1.00 | 56.27 | O |
| ATOM | 5159 | OW | WAT W | 44 | −17.456 | −36.242 | 0.092 | 1.00 | 22.74 | O |
| ATOM | 5160 | OW | WAT W | 45 | −19.089 | −23.565 | −16.091 | 1.00 | 27.59 | O |
| ATOM | 5161 | OW | WAT W | 46 | −13.926 | −39.702 | 21.706 | 1.00 | 32.93 | O |
| ATOM | 5162 | OW | WAT W | 47 | −13.924 | −26.380 | 20.598 | 1.00 | 22.63 | O |
| ATOM | 5163 | OW | WAT W | 48 | −22.687 | −29.379 | 27.884 | 1.00 | 32.13 | O |
| ATOM | 5164 | OW | WAT W | 49 | −14.195 | −13.868 | −2.543 | 1.00 | 17.58 | O |
| ATOM | 5165 | OW | WAT W | 50 | −31.526 | −32.922 | −5.427 | 1.00 | 35.15 | O |
| ATOM | 5166 | OW | WAT W | 51 | −15.633 | −38.121 | 17.671 | 1.00 | 40.23 | O |
| ATOM | 5167 | OW | WAT W | 52 | −19.474 | −15.053 | −7.588 | 1.00 | 25.53 | O |
| ATOM | 5168 | OW | WAT W | 53 | −26.232 | −55.647 | 26.584 | 1.00 | 34.84 | O |
| ATOM | 5169 | OW | WAT W | 54 | −24.684 | −85.894 | 26.823 | 1.00 | 31.52 | O |
| ATOM | 5170 | OW | WAT W | 55 | −28.479 | −36.115 | −10.253 | 1.00 | 22.28 | O |
| ATOM | 5171 | OW | WAT W | 56 | −31.961 | −20.532 | −1.580 | 1.00 | 33.75 | O |
| ATOM | 5172 | OW | WAT W | 57 | −19.218 | −17.017 | −3.492 | 1.00 | 23.75 | O |
| ATOM | 5173 | OW | WAT W | 58 | −17.248 | −32.284 | −16.153 | 1.00 | 15.25 | O |
| ATOM | 5174 | OW | WAT W | 59 | −32.086 | −31.769 | 5.071 | 1.00 | 37.47 | O |
| ATOM | 5175 | OW | WAT W | 60 | −13.553 | −47.738 | 21.065 | 1.00 | 18.06 | O |
| ATOM | 5176 | OW | WAT W | 61 | −14.865 | −3.870 | 21.102 | 1.00 | 38.80 | O |
| ATOM | 5177 | OW | WAT W | 62 | −18.648 | −19.085 | 1.505 | 1.00 | 36.01 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 5178 | OW | WAT W | 63 | −6.531 | −15.439 | 17.291 | 1.00 | 34.45 | O |
| ATOM | 5179 | OW | WAT W | 64 | 5.715 | −25.500 | 17.653 | 1.00 | 42.41 | O |
| ATOM | 5180 | OW | WAT W | 65 | −27.575 | −15.831 | 26.493 | 1.00 | 24.57 | O |
| ATOM | 5181 | OW | WAT W | 66 | −29.706 | −29.658 | −17.197 | 1.00 | 21.69 | O |
| ATOM | 5182 | OW | WAT W | 67 | −29.259 | −28.928 | −9.040 | 1.00 | 11.49 | O |
| ATOM | 5183 | OW | WAT W | 68 | −26.006 | −38.526 | −13.434 | 1.00 | 21.57 | O |
| ATOM | 5184 | OW | WAT W | 69 | −29.088 | −38.211 | −3.745 | 1.00 | 23.90 | O |
| ATOM | 5185 | OW | WAT W | 70 | 6.613 | −13.681 | −2.725 | 1.00 | 38.73 | O |
| ATOM | 5186 | OW | WAT W | 71 | −18.526 | −55.204 | 16.553 | 1.00 | 26.39 | O |
| ATOM | 5187 | OW | WAT W | 72 | −17.413 | −4.772 | 22.313 | 1.00 | 28.03 | O |
| ATOM | 5188 | OW | WAT W | 73 | −16.360 | −10.098 | −21.683 | 1.00 | 37.56 | O |
| ATOM | 5189 | OW | WAT W | 74 | −6.110 | −26.121 | 17.352 | 1.00 | 29.55 | O |
| ATOM | 5190 | OW | WAT W | 75 | −15.775 | −33.673 | 6.499 | 1.00 | 39.01 | O |
| ATOM | 5191 | OW | WAT W | 76 | −10.766 | −30.437 | −8.265 | 1.00 | 31.67 | O |
| ATOM | 5192 | OW | WAT W | 77 | −30.679 | −15.090 | −6.086 | 1.00 | 25.05 | O |
| ATOM | 5193 | OW | WAT W | 78 | −2.834 | −13.145 | 31.482 | 1.00 | 26.98 | O |
| ATOM | 5194 | OW | WAT W | 79 | −1.816 | −15.695 | −24.745 | 1.00 | 36.11 | O |
| ATOM | 5195 | OW | WAT W | 80 | −5.982 | −67.40 | 731.695 | 1.00 | 36.19 | O |
| ATOM | 5196 | OW | WAT W | 81 | −4.249 | −17.658 | −18.124 | 1.00 | 25.61 | O |
| ATOM | 5197 | OW | WAT W | 82 | −28.071 | −51.738 | 17.043 | 1.00 | 31.70 | O |
| ATOM | 5198 | OW | WAT W | 83 | −14.709 | −32.724 | −20.418 | 1.00 | 33.32 | O |
| ATOM | 5199 | OW | WAT W | 84 | −19.912 | −10.864 | 18.661 | 1.00 | 39.87 | O |
| ATOM | 5200 | OW | WAT W | 85 | −9.542 | −9.432 | 1.179 | 1.00 | 30.56 | O |
| ATOM | 5201 | OW | WAT W | 86 | −13.721 | −19.231 | 2.812 | 1.00 | 41.95 | O |
| ATOM | 5202 | OW | WAT W | 87 | −21.443 | −42.803 | 16.781 | 1.00 | 29.22 | O |
| ATOM | 5203 | OW | WAT W | 88 | −18.503 | −64.951 | 42.936 | 1.00 | 34.68 | O |
| ATOM | 5204 | OW | WAT W | 89 | −24.086 | −14.861 | −6.480 | 1.00 | 37.61 | O |
| ATOM | 5205 | OW | WAT W | 90 | −24.692 | −13.062 | −14.959 | 1.00 | 19.77 | O |
| ATOM | 5206 | OW | WAT W | 91 | −3.914 | −10.929 | 27.681 | 1.00 | 27.74 | O |
| ATOM | 5207 | OW | WAT W | 92 | −35.736 | −27.254 | −6.747 | 1.00 | 41.71 | O |
| ATOM | 5208 | OW | WAT W | 93 | −25.158 | −18.147 | 1.613 | 1.00 | 32.06 | O |
| ATOM | 5209 | OW | WAT W | 94 | −20.247 | −61.606 | 26.904 | 1.00 | 36.68 | O |
| ATOM | 5210 | OW | WAT W | 95 | −6.042 | −30.768 | 28.828 | 1.00 | 35.42 | O |
| ATOM | 5211 | OW | WAT W | 96 | −35.001 | −20.618 | −17.398 | 1.00 | 30.61 | O |
| ATOM | 5212 | OW | WAT W | 97 | 6.518 | −6.457 | −3.445 | 1.00 | 28.37 | O |
| ATOM | 5213 | OW | WAT W | 98 | 1.054 | −14.054 | 5.429 | 1.00 | 35.48 | O |
| ATOM | 5214 | OW | WAT W | 99 | −21.129 | −65.208 | 32.897 | 1.00 | 37.67 | O |
| ATOM | 5215 | OW | WAT W | 100 | −9.178 | −20.499 | −0.375 | 1.00 | 36.08 | O |
| ATOM | 5216 | OW | WAT W | 101 | −10.032 | −6.252 | −5.248 | 1.00 | 36.73 | O |
| ATOM | 5217 | OW | WAT W | 102 | −10.013 | −79.878 | 24.001 | 1.00 | 33.28 | O |
| ATOM | 5218 | OW | WAT W | 103 | −32.324 | −90.976 | 36.058 | 1.00 | 46.96 | O |
| ATOM | 5219 | OW | WAT W | 104 | −21.744 | −37.785 | 22.712 | 1.00 | 27.00 | O |
| ATOM | 5220 | OW | WAT W | 105 | −34.770 | −45.788 | 26.803 | 1.00 | 41.79 | O |
| ATOM | 5221 | OW | WAT W | 106 | −32.630 | −38.102 | 6.956 | 1.00 | 38.49 | O |
| ATOM | 5222 | OW | WAT W | 107 | 0.715 | −29.693 | 21.769 | 1.00 | 27.07 | O |
| ATOM | 5223 | OW | WAT W | 108 | −25.745 | −17.673 | −1.054 | 1.00 | 18.79 | O |
| ATOM | 5224 | OW | WAT W | 109 | 3.892 | −22.440 | −1.723 | 1.00 | 29.70 | O |
| ATOM | 5225 | OW | WAT W | 110 | −11.783 | −16.744 | 12.573 | 1.00 | 29.91 | O |
| ATOM | 5226 | OW | WAT W | 111 | −23.836 | −45.768 | 16.495 | 1.00 | 33.62 | O |
| ATOM | 5227 | OW | WAT W | 112 | −18.548 | −10.448 | −17.721 | 1.00 | 39.04 | O |
| ATOM | 5228 | OW | WAT W | 113 | −21.242 | −41.746 | 35.152 | 1.00 | 36.72 | O |
| ATOM | 5229 | OW | WAT W | 114 | −29.572 | −68.801 | 38.073 | 1.00 | 31.81 | O |
| ATOM | 5230 | OW | WAT W | 115 | −5.372 | −66.393 | 41.165 | 1.00 | 38.54 | O |
| ATOM | 5231 | OW | WAT W | 116 | −13.069 | −9.551 | 14.367 | 1.00 | 28.20 | O |
| ATOM | 5232 | OW | WAT W | 117 | −14.513 | −25.162 | 3.281 | 1.00 | 30.80 | O |
| ATOM | 5233 | OW | WAT W | 118 | −12.782 | −29.464 | 22.369 | 1.00 | 39.95 | O |
| ATOM | 5234 | OW | WAT W | 119 | −17.185 | −47.225 | 11.008 | 1.00 | 33.45 | O |
| ATOM | 5235 | OW | WAT W | 120 | −4.044 | −25.287 | 1.870 | 1.00 | 41.81 | O |
| ATOM | 5236 | OW | WAT W | 121 | −8.941 | −12.624 | 18.995 | 1.00 | 39.82 | O |
| ATOM | 5237 | OW | WAT W | 122 | −13.467 | −31.217 | −9.573 | 1.00 | 25.37 | O |
| ATOM | 5238 | OW | WAT W | 123 | −0.318 | −24.455 | 15.675 | 1.00 | 31.54 | O |
| ATOM | 5239 | OW | WAT W | 124 | 10.565 | −21.575 | 29.393 | 1.00 | 49.03 | O |
| ATOM | 5240 | OW | WAT W | 125 | −29.344 | −23.581 | 10.555 | 1.00 | 58.87 | O |
| ATOM | 5241 | OW | WAT W | 126 | −26.296 | −59.482 | 24.034 | 1.00 | 23.15 | O |
| ATOM | 5242 | OW | WAT W | 127 | −34.263 | −24.257 | −4.434 | 1.00 | 25.93 | O |
| ATOM | 5243 | OW | WAT W | 128 | −27.189 | −70.635 | 34.495 | 1.00 | 34.43 | O |
| ATOM | 5244 | OW | WAT W | 129 | −6.072 | −29.413 | −6.972 | 1.00 | 29.07 | O |
| ATOM | 5245 | OW | WAT W | 130 | −0.279 | −13.026 | −17.706 | 1.00 | 26.10 | O |
| ATOM | 5246 | OW | WAT W | 131 | −0.103 | −3.615 | 5.427 | 1.00 | 44.91 | O |
| ATOM | 5247 | OW | WAT W | 132 | −14.768 | −34.094 | −9.088 | 1.00 | 28.19 | O |
| ATOM | 5248 | OW | WAT W | 133 | −30.641 | −36.157 | −14.973 | 1.00 | 38.16 | O |
| ATOM | 5249 | OW | WAT W | 134 | −19.499 | −41.310 | −11.008 | 1.00 | 39.90 | O |
| ATOM | 5250 | OW | WAT W | 135 | −28.524 | −40.725 | −5.113 | 1.00 | 29.95 | O |
| ATOM | 5251 | OW | WAT W | 136 | −12.801 | −17.200 | −23.652 | 1.00 | 38.80 | O |
| ATOM | 5252 | OW | WAT W | 137 | −27.996 | −40.210 | 19.923 | 1.00 | 25.18 | O |
| ATOM | 5253 | OW | WAT W | 138 | −15.704 | −31.566 | −18.269 | 1.00 | 24.31 | O |
| ATOM | 5254 | OW | WAT W | 139 | −28.185 | −20.489 | 18.727 | 1.00 | 30.68 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 5255 | OW | WAT W | 140 | −34.637 | −31.867 | −12.612 | 1.00 | 42.75 | O |
| ATOM | 5256 | OW | WAT W | 141 | −39.298 | −77.031 | 32.857 | 1.00 | 41.76 | O |
| ATOM | 5257 | OW | WAT W | 142 | −25.339 | −19.223 | 9.103 | 1.00 | 36.65 | O |
| ATOM | 5258 | OW | WAT W | 143 | −15.374 | −20.459 | 33.431 | 1.00 | 46.30 | O |
| ATOM | 5259 | OW | WAT W | 144 | −9.773 | −8.695 | 39.838 | 1.00 | 31.82 | O |
| ATOM | 5260 | OW | WAT W | 145 | −14.733 | −47.375 | 31.497 | 1.00 | 31.50 | O |
| ATOM | 5261 | OW | WAT W | 146 | −32.442 | −39.431 | −3.894 | 1.00 | 42.22 | O |
| ATOM | 5262 | OW | WAT W | 147 | −26.274 | −70.353 | 16.002 | 1.00 | 38.85 | O |
| ATOM | 5263 | OW | WAT W | 148 | −14.635 | −4.149 | 17.219 | 1.00 | 44.03 | O |
| ATOM | 5264 | OW | WAT W | 149 | −24.103 | −30.912 | 25.379 | 1.00 | 43.81 | O |
| ATOM | 5265 | OW | WAT W | 150 | −28.274 | −20.668 | 8.520 | 1.00 | 45.38 | O |
| ATOM | 5266 | OW | WAT W | 151 | −24.893 | −66.388 | 31.102 | 1.00 | 35.38 | O |
| ATOM | 5267 | OW | WAT W | 152 | −8.262 | −75.072 | 27.278 | 1.00 | 35.53 | O |
| ATOM | 5268 | OW | WAT W | 153 | −5.215 | −12.474 | 5.922 | 1.00 | 38.89 | O |
| ATOM | 5269 | OW | WAT W | 154 | −10.988 | −5.626 | −8.066 | 1.00 | 41.95 | O |
| ATOM | 5270 | OW | WAT W | 155 | −24.480 | −86.596 | 51.835 | 1.00 | 42.41 | O |
| ATOM | 5271 | OW | WAT W | 156 | −2.845 | −34.410 | 26.011 | 1.00 | 31.61 | O |
| ATOM | 5272 | OW | WAT W | 157 | −22.429 | −25.725 | −23.601 | 1.00 | 36.47 | O |
| ATOM | 5273 | OW | WAT W | 158 | −16.962 | −22.862 | −26.263 | 1.00 | 42.15 | O |
| ATOM | 5274 | OW | WAT W | 159 | −20.873 | −40.178 | −13.025 | 1.00 | 43.07 | O |
| ATOM | 5275 | OW | WAT W | 160 | −26.854 | −62.555 | 13.774 | 1.00 | 51.12 | O |
| ATOM | 5276 | OW | WAT W | 161 | −6.581 | −25.464 | −20.773 | 1.00 | 51.36 | O |
| ATOM | 5277 | OW | WAT W | 162 | 0.839 | −30.423 | −14.094 | 1.00 | 33.23 | O |
| ATOM | 5278 | OW | WAT W | 163 | −30.535 | −62.890 | 19.770 | 1.00 | 47.72 | O |
| ATOM | 5279 | OW | WAT W | 164 | −28.775 | −29.065 | 19.148 | 1.00 | 26.60 | O |
| ATOM | 5280 | OW | WAT W | 165 | −16.471 | −64.994 | 44.642 | 1.00 | 32.77 | O |
| ATOM | 5281 | OW | WAT W | 166 | 3.384 | −24.109 | −12.016 | 1.00 | 49.90 | O |
| ATOM | 5282 | OW | WAT W | 167 | −28.006 | −31.938 | 34.812 | 1.00 | 44.43 | O |
| ATOM | 5283 | OW | WAT W | 168 | 9.564 | −23.704 | 20.536 | 1.00 | 35.72 | O |
| ATOM | 5284 | OW | WAT W | 169 | −24.451 | −35.873 | 15.193 | 1.00 | 37.59 | O |
| ATOM | 5285 | OW | WAT W | 170 | −33.176 | −41.619 | 35.847 | 1.00 | 33.71 | O |
| ATOM | 5286 | OW | WAT W | 171 | −20.433 | −49.114 | 33.291 | 1.00 | 35.51 | O |
| ATOM | 5287 | OW | WAT W | 172 | −10.681 | −21.868 | −30.632 | 1.00 | 44.34 | O |
| ATOM | 5288 | OW | WAT W | 173 | −23.855 | −67.701 | 36.923 | 1.00 | 43.22 | O |
| ATOM | 5289 | OW | WAT W | 174 | −31.323 | −44.049 | 16.914 | 1.00 | 43.90 | O |
| ATOM | 5290 | OW | WAT W | 175 | −23.313 | −12.426 | −7.119 | 1.00 | 33.40 | O |
| ATOM | 5291 | OW | WAT W | 176 | −15.842 | −39.731 | 31.168 | 1.00 | 39.19 | O |
| ATOM | 5292 | OW | WAT W | 177 | −38.026 | −35.342 | 22.078 | 1.00 | 30.49 | O |
| ATOM | 5293 | OW | WAT W | 178 | −18.905 | −62.999 | 34.021 | 1.00 | 44.47 | O |
| ATOM | 5294 | OW | WAT W | 179 | −16.392 | −17.236 | 7.412 | 1.00 | 45.04 | O |
| ATOM | 5295 | OW | WAT W | 180 | −31.040 | −94.049 | 33.700 | 1.00 | 36.31 | O |
| ATOM | 5296 | OW | WAT W | 181 | 1.114 | −24.432 | 36.537 | 1.00 | 34.37 | O |
| ATOM | 5297 | OW | WAT W | 182 | −37.769 | −77.843 | 35.173 | 1.00 | 38.34 | O |
| ATOM | 5298 | OW | WAT W | 183 | −15.991 | −35.140 | 24.035 | 1.00 | 49.87 | O |
| ATOM | 5299 | OW | WAT W | 184 | −13.223 | −50.764 | 14.571 | 1.00 | 36.16 | O |
| ATOM | 5300 | OW | WAT W | 185 | −13.709 | −44.772 | 29.833 | 1.00 | 47.64 | O |
| ATOM | 5301 | OW | WAT W | 186 | −17.439 | −67.504 | 26.441 | 1.00 | 27.75 | O |
| ATOM | 5302 | OW | WAT W | 187 | 9.318 | −5.529 | 10.461 | 1.00 | 44.08 | O |
| ATOM | 5303 | OW | WAT W | 188 | 3.390 | −14.946 | −19.646 | 1.00 | 46.47 | O |
| ATOM | 5304 | OW | WAT W | 189 | −3.405 | −20.470 | 13.476 | 1.00 | 36.22 | O |
| ATOM | 5305 | OW | WAT W | 190 | −3.147 | −66.815 | 39.675 | 1.00 | 60.12 | O |
| ATOM | 5306 | OW | WAT W | 191 | −15.375 | −22.392 | 1.952 | 1.00 | 36.59 | O |
| ATOM | 5307 | OW | WAT W | 192 | 6.155 | −23.661 | 12.072 | 1.00 | 50.58 | O |
| ATOM | 5308 | OW | WAT W | 193 | −30.419 | −27.957 | 25.653 | 1.00 | 32.61 | O |
| ATOM | 5309 | OW | WAT W | 194 | 0.206 | 4.424 | 26.005 | 1.00 | 44.19 | O |
| ATOM | 5310 | OW | WAT W | 195 | −33.008 | −18.322 | −19.846 | 1.00 | 55.96 | O |
| ATOM | 5311 | OW | WAT W | 196 | −30.690 | −41.378 | 4.915 | 1.00 | 54.52 | O |
| ATOM | 5312 | OW | WAT W | 197 | 9.384 | −24.880 | 30.131 | 1.00 | 43.23 | O |
| ATOM | 5313 | OW | WAT W | 198 | −20.463 | −14.625 | −2.704 | 1.00 | 42.66 | O |
| ATOM | 5314 | OW | WAT W | 199 | −30.131 | −19.496 | 6.060 | 1.00 | 36.23 | O |
| ATOM | 5315 | OW | WAT W | 200 | −13.929 | −18.153 | 34.513 | 1.00 | 39.81 | O |
| ATOM | 5316 | OW | WAT W | 201 | −8.970 | −57.831 | 31.296 | 1.00 | 37.66 | O |
| ATOM | 5317 | OW | WAT W | 202 | −24.345 | −10.494 | 33.073 | 1.00 | 41.09 | O |
| ATOM | 5318 | OW | WAT W | 203 | −9.518 | −29.841 | 39.384 | 1.00 | 51.84 | O |
| ATOM | 5319 | OW | WAT W | 204 | −41.540 | −87.450 | 43.193 | 1.00 | 52.05 | O |
| ATOM | 5320 | OW | WAT W | 205 | −31.769 | −36.270 | −9.657 | 1.00 | 54.13 | O |
| ATOM | 5321 | OW | WAT W | 206 | 4.889 | −18.462 | −11.979 | 1.00 | 40.40 | O |
| ATOM | 5322 | OW | WAT W | 207 | −20.895 | −62.146 | 13.347 | 1.00 | 42.00 | O |
| ATOM | 5323 | OW | WAT W | 208 | −19.165 | −34.536 | 33.464 | 1.00 | 44.58 | O |
| ATOM | 5324 | OW | WAT W | 209 | −27.951 | −20.874 | 15.887 | 1.00 | 34.97 | O |
| ATOM | 5325 | OW | WAT W | 210 | −24.976 | −72.212 | 17.467 | 1.00 | 32.09 | O |
| ATOM | 5326 | OW | WAT W | 211 | −23.097 | −41.678 | −13.352 | 1.00 | 37.19 | O |
| ATOM | 5327 | OW | WAT W | 212 | 0.386 | −22.533 | −4.258 | 1.00 | 22.03 | O |
| ATOM | 5328 | OW | WAT W | 213 | −17.295 | −36.709 | 15.855 | 1.00 | 38.14 | O |
| ATOM | 5329 | OW | WAT W | 214 | −18.217 | −14.426 | −9.789 | 1.00 | 28.07 | O |
| ATOM | 5330 | OW | WAT W | 215 | −0.357 | −9.492 | 27.438 | 1.00 | 34.84 | O |
| ATOM | 5331 | OW | WAT W | 216 | −14.288 | −57.310 | 23.542 | 1.00 | 30.04 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 5332 | OW | WAT W | 217 | −13.272 | −26.273 | 17.977 | 1.00 | 31.09 | O |
| ATOM | 5333 | OW | WAT W | 218 | −26.105 | −19.366 | 20.322 | 1.00 | 23.98 | O |
| ATOM | 5334 | OW | WAT W | 219 | −3.088 | −17.841 | −26.286 | 1.00 | 50.44 | O |
| ATOM | 5335 | OW | WAT W | 220 | −9.312 | −24.165 | 13.986 | 1.00 | 26.22 | O |
| ATOM | 5336 | OW | WAT W | 221 | −14.657 | −36.384 | 0.422 | 1.00 | 41.25 | O |
| ATOM | 5337 | OW | WAT W | 222 | −16.335 | −28.954 | −18.320 | 1.00 | 27.94 | O |
| ATOM | 5338 | OW | WAT W | 223 | −31.299 | −40.047 | 19.854 | 1.00 | 59.75 | O |
| ATOM | 5339 | OW | WAT W | 224 | −22.055 | −85.923 | 27.235 | 1.00 | 38.86 | O |
| ATOM | 5340 | OW | WAT W | 225 | −14.482 | −36.959 | −9.362 | 1.00 | 28.10 | O |
| ATOM | 5341 | OW | WAT W | 226 | −23.732 | −26.837 | 28.478 | 1.00 | 35.95 | O |
| ATOM | 5342 | OW | WAT W | 227 | −2.631 | −64.957 | 29.568 | 1.00 | 50.39 | O |
| ATOM | 5343 | OW | WAT W | 228 | 7.986 | −27.818 | 26.256 | 1.00 | 39.54 | O |
| ATOM | 5344 | OW | WAT W | 229 | −37.158 | −18.578 | −7.649 | 1.00 | 34.33 | O |
| ATOM | 5345 | OW | WAT W | 230 | −24.983 | −38.744 | 17.366 | 1.00 | 40.78 | O |
| ATOM | 5346 | OW | WAT W | 231 | −27.628 | −83.794 | 46.664 | 1.00 | 41.21 | O |
| ATOM | 5347 | OW | WAT W | 232 | −9.148 | −26.794 | 17.873 | 1.00 | 43.89 | O |
| ATOM | 5348 | OW | WAT W | 233 | −7.992 | −5.913 | 18.960 | 1.00 | 36.39 | O |
| ATOM | 5349 | OW | WAT W | 234 | −30.434 | −21.994 | 27.775 | 1.00 | 54.37 | O |
| ATOM | 5350 | OW | WAT W | 235 | −15.459 | −39.949 | 14.512 | 1.00 | 47.99 | O |
| ATOM | 5351 | OW | WAT W | 236 | −28.290 | −74.951 | 25.362 | 1.00 | 37.45 | O |
| ATOM | 5352 | OW | WAT W | 237 | 0.340 | −4.346 | 15.875 | 1.00 | 39.62 | O |
| ATOM | 5353 | OW | WAT W | 238 | −29.459 | −33.575 | 32.739 | 1.00 | 38.35 | O |
| ATOM | 5354 | OW | WAT W | 239 | −10.426 | −35.272 | −19.592 | 1.00 | 41.76 | O |
| ATOM | 5355 | OW | WAT W | 240 | −7.440 | −34.453 | −23.285 | 1.00 | 40.14 | O |
| ATOM | 5356 | OW | WAT W | 241 | −16.918 | −25.855 | 28.001 | 1.00 | 36.95 | O |
| ATOM | 5357 | OW | WAT W | 242 | −18.095 | −19.788 | 32.193 | 1.00 | 33.78 | O |
| ATOM | 5358 | OW | WAT W | 243 | 4.893 | −12.814 | −9.471 | 1.00 | 50.14 | O |
| ATOM | 5359 | OW | WAT W | 244 | 6.066 | −27.423 | 30.988 | 1.00 | 27.40 | O |
| ATOM | 5360 | OW | WAT W | 245 | −7.635 | 0.408 | 14.216 | 1.00 | 54.01 | O |
| ATOM | 5361 | OW | WAT W | 246 | −14.606 | −64.412 | 42.789 | 1.00 | 38.46 | O |
| ATOM | 5362 | OW | WAT W | 247 | −4.020 | −18.856 | 11.018 | 1.00 | 34.46 | O |
| ATOM | 5363 | OW | WAT W | 248 | −15.746 | −9.446 | 20.227 | 1.00 | 39.34 | O |
| ATOM | 5364 | OW | WAT W | 249 | −4.367 | −8.678 | 18.641 | 1.00 | 31.67 | O |
| ATOM | 5365 | OW | WAT W | 250 | −17.267 | −81.223 | 24.144 | 1.00 | 39.75 | O |
| ATOM | 5366 | OW | WAT W | 251 | −18.235 | −62.022 | 13.619 | 1.00 | 38.84 | O |
| ATOM | 5367 | OW | WAT W | 252 | −11.152 | −75.589 | 21.346 | 1.00 | 38.99 | O |
| ATOM | 5368 | OW | WAT W | 253 | −22.270 | −13.755 | 35.083 | 1.00 | 41.80 | O |
| ATOM | 5369 | OW | WAT W | 254 | −14.870 | −39.907 | −4.336 | 1.00 | 54.88 | O |
| ATOM | 5370 | OW | WAT W | 255 | 0.194 | −20.709 | −2.019 | 1.00 | 17.75 | O |
| ATOM | 5371 | OW | WAT W | 256 | −9.244 | −30.208 | 4.351 | 1.00 | 38.01 | O |
| ATOM | 5372 | OW | WAT W | 257 | −1.364 | −11.882 | 27.450 | 1.00 | 38.18 | O |
| ATOM | 5373 | OW | WAT W | 258 | −15.260 | −7.852 | 17.188 | 1.00 | 39.85 | O |
| ATOM | 5374 | OW | WAT W | 259 | −0.928 | −9.121 | 34.634 | 1.00 | 40.62 | O |
| ATOM | 5375 | OW | WAT W | 260 | 12.642 | −8.300 | 7.954 | 1.00 | 52.01 | O |
| ATOM | 5376 | OW | WAT W | 261 | −20.094 | −15.171 | 35.791 | 1.00 | 47.96 | O |
| ATOM | 5377 | OW | WAT W | 262 | −26.772 | −38.511 | −9.369 | 1.00 | 55.40 | O |
| ATOM | 5378 | OW | WAT W | 263 | −18.703 | −8.354 | −16.047 | 1.00 | 60.45 | O |
| ATOM | 5379 | OW | WAT W | 264 | 9.028 | −0.748 | 26.222 | 1.00 | 51.43 | O |
| ATOM | 5380 | OW | WAT W | 265 | 1.925 | −5.683 | 22.487 | 1.00 | 49.16 | O |
| ATOM | 5381 | OW | WAT W | 266 | −13.447 | −63.026 | 33.074 | 1.00 | 25.86 | O |
| ATOM | 5382 | OW | WAT W | 267 | −10.149 | −30.802 | −4.027 | 1.00 | 28.50 | O |
| ATOM | 5383 | OW | WAT W | 268 | −27.810 | −86.476 | 26.408 | 1.00 | 43.28 | O |
| ATOM | 5384 | OW | WAT W | 269 | −5.783 | −10.662 | −20.823 | 1.00 | 38.87 | O |
| ATOM | 5385 | OW | WAT W | 270 | −14.299 | 3.235 | 29.807 | 1.00 | 47.68 | O |
| ATOM | 5386 | OW | WAT W | 271 | −10.712 | −39.694 | 25.453 | 1.00 | 52.10 | O |
| ATOM | 5387 | OW | WAT W | 272 | −22.290 | −32.444 | 27.471 | 1.00 | 25.90 | O |
| ATOM | 5388 | OW | WAT W | 273 | −20.739 | −47.558 | 11.058 | 1.00 | 46.12 | O |
| ATOM | 5389 | OW | WAT W | 274 | −20.261 | −30.710 | 26.451 | 1.00 | 36.48 | O |
| ATOM | 5390 | OW | WAT W | 275 | −3.704 | −7.228 | 20.852 | 1.00 | 37.99 | O |
| ATOM | 5391 | OW | WAT W | 276 | −7.106 | −12.035 | 8.550 | 1.00 | 49.42 | O |
| ATOM | 5392 | OW | WAT W | 277 | −15.200 | −60.614 | 29.548 | 1.00 | 42.93 | O |
| ATOM | 5393 | OW | WAT W | 278 | −21.279 | −23.237 | 11.432 | 1.00 | 38.64 | O |
| ATOM | 5394 | OW | WAT W | 279 | −12.447 | −59.095 | 14.411 | 1.00 | 36.28 | O |
| ATOM | 5395 | OW | WAT W | 280 | −17.042 | −36.220 | −2.508 | 1.00 | 41.97 | O |
| ATOM | 5396 | OW | WAT W | 281 | −9.561 | −63.530 | 26.640 | 1.00 | 40.30 | O |
| ATOM | 5397 | OW | WAT W | 282 | −12.254 | −11.118 | 3.585 | 1.00 | 46.66 | O |
| ATOM | 5398 | OW | WAT W | 283 | −8.903 | −17.257 | 1.197 | 1.00 | 33.78 | O |
| ATOM | 5399 | OW | WAT W | 284 | −0.732 | −19.668 | 11.874 | 1.00 | 46.78 | O |
| ATOM | 5400 | OW | WAT W | 285 | −30.025 | −17.530 | 1.952 | 1.00 | 42.37 | O |
| ATOM | 5401 | OW | WAT W | 286 | −1.815 | −3.989 | 17.527 | 1.00 | 52.97 | O |
| ATOM | 5402 | OW | WAT W | 287 | −29.761 | −36.153 | 20.371 | 1.00 | 46.78 | O |
| ATOM | 5403 | OW | WAT W | 288 | −24.713 | −90.413 | 49.503 | 1.00 | 48.67 | O |
| ATOM | 5404 | OW | WAT W | 289 | −30.239 | −27.201 | 10.046 | 1.00 | 32.48 | O |
| ATOM | 5405 | OW | WAT W | 290 | −8.461 | −45.438 | 16.365 | 1.00 | 50.94 | O |
| ATOM | 5406 | OW | WAT W | 291 | −26.660 | −67.558 | 36.851 | 1.00 | 58.30 | O |
| ATOM | 5407 | OW | WAT W | 292 | −10.159 | −26.924 | 25.610 | 1.00 | 31.40 | O |
| ATOM | 5408 | OW | WAT W | 293 | −13.797 | −78.452 | 23.046 | 1.00 | 40.66 | O |

TABLE 7-continued

Three-dimensional crystal coordinates for caffeine-pembrolizumab complex.
Atomic Coordinates of Caffeine/Pembrolizumab Crystal Complex

| | | | | | | | | | | |
|---|---|---|---|---|---|---|---|---|---|---|
| ATOM | 5409 | OW | WAT W | 294 | −15.223 | −26.255 | 35.866 | 1.00 | 46.18 | O |
| ATOM | 5410 | OW | WAT W | 295 | −14.787 | −73.556 | 17.778 | 1.00 | 27.97 | O |
| ATOM | 5411 | OW | WAT W | 296 | 8.789 | −13.349 | 23.443 | 1.00 | 43.11 | O |
| ATOM | 5412 | OW | WAT W | 297 | −24.690 | −39.080 | −15.710 | 1.00 | 32.14 | O |
| ATOM | 5413 | OW | WAT W | 298 | −23.103 | −86.967 | 44.414 | 1.00 | 32.90 | O |
| ATOM | 5414 | OW | WAT W | 299 | 6.175 | −21.205 | 10.886 | 1.00 | 38.60 | O |
| ATOM | 5415 | OW | WAT W | 300 | −11.612 | −73.499 | 38.127 | 1.00 | 38.35 | O |

The crystal has a distinct quaternary structure compared to the pembrolizumab crystals prepared using the high salt process previously described. See WO 2016/137850. The caffeine binding site found in the pembrolizumab crystal is novel compared to the pembrolizumab antibody structure determined from crystals grown using the previous high salt process.

Example 11

Batch Crystallization Process (175 mL scale)

A 42.7 mg/mL solution of pembrolizumab in 20 mM histidine buffer pH 5.4 (0.2 micron filtered) was prepared using sterile non pyrogenic water solution. A solution of 10.18% PEG 3350 (50% solution Rigaku Item #108058), 50 mM HEPES (1 M solution, pH 7.4 Hampton Research HR2-941-27), pH 7.0 solution (400 mL) was prepared by adding 20 mL of 1M HEPES, pH 7.4 and 81.6 mL of 50% PEG 3350 to 298.4 mL sterile water for injection (Hospira RI-4469). The resulting solution was 0.2 micron filtered and stored at room temperature.

A solution of 2.5% caffeine (Sigma Lot #SLBK4804V), 20 mM histidine (Sigma H-8000), pH 5.4 was prepared by adding 1.25 g caffeine to 50 mL of 20 mM histidine, pH 5.4. The solution was heated to 60° C. until the caffeine went into solution. The solution was allowed to cool to room temperature before usage.

In a 50 mL polypropylene centrifuge tube (Fisherbrand™ Sterile cat #05-539-8), 13.32 mL of pembrolizumab (42.7 mg/mL) solution in 20 mM histidine buffer, pH 5.4 was added, along with 26.4 mL of a solution comprising 10.18% PEG 3350, 50 mM HEPES, pH 7.0 at room temperature. 4 mL of a solution comprising 2.5% caffeine, 20 mM histidine buffer, pH 5.4 was then added. The process was repeated for a total of four 50 mL centrifuge tubes.

Figure 7A:
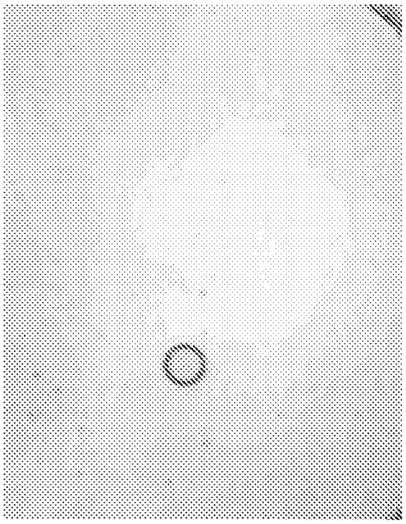
FIGS. 7A-7C shows crystal images produced using the visible (FIG. 7A), UV-TPEF (FIG. 7B) and SHG (FIG. 7C) modes of the SONICC™ imaging system using batch crystallization (175 mL scale) and the conditions described in EXAMPLE 11.
Figure 7B:
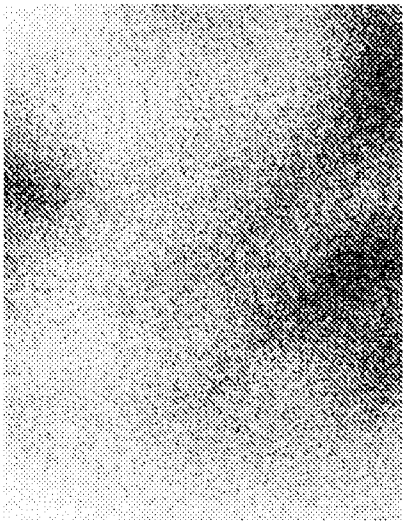
Figure 7C:
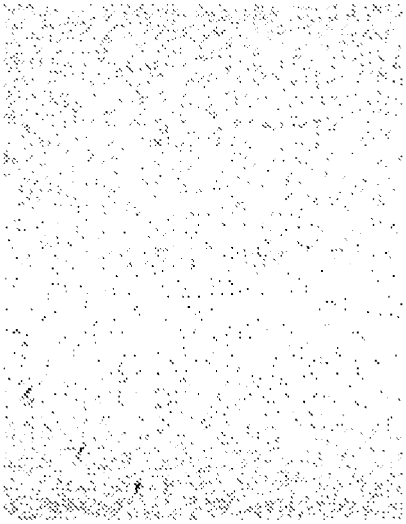

The tubes (in solution) were placed on the Labnet rotisserie (cat #H5600) and rotated at room temperature. Visible turbidity was observed after 15 minutes. Rotation of the batch continued for 2 hours at room temperature. Crystallinity was verified by Formulatrix SONICC™ analyses on each tube analyzed in a Whatman Fast Frame 4 slide well plate at a 1:10 dilution in 10% PEG 3350, 50 mM HEPES, pH 7.0 solutions. Representative analyses using the SONICC™ imaging system are shown in FIG. 7.

The 50 mL tubes were centrifuged in a Beckman Coulter Allegra X-15R centrifuge at 2300 RPM at room temperature for 10 minutes. The resulting mother liquors were decanted off. The resulting pellets in each 50 mL conical tube were re-suspended with 40 mL of 10% PEG 3350, 50 mM HEPES, and pH 7.0 buffer. This process was repeated. The resulting pellet was checked for crystallinity by SONICC™ analyses. The pembrolizumab concentration was measured by dissolution in cold phosphate buffered saline solution (PBS); weight:volume, 100 mg suspension: 1 mL PBS measurement. Using a nano drop UV spectrometer, the measured A280 readings for the resulting 19.5 mg in 10 mL of PBS solution was 195 mg/mL final concentration (9.4 mL) with an overall 84% yield. Further dilutions were made to prepare 175 and 150 mg/mL suspensions using 10% PEG 3350, 50 mM HEPES, and pH 7.0 buffer.

This experiment shows that the crystallization process is scaleable and reproducible, resulting in crystalline suspensions within 2 hours at room temperature in high yield. Results also demonstrate that pembrolizumab crystalline suspensions can be concentrated to high concentrations.

Example 12

Characterization of Pembrolizumab Crystal Suspension

The pembrolizumab crystal suspension prepared in EXAMPLE 11 was characterized by measuring particle size, dynamic viscosity, and injectability, as described below.

Particle Size Analyses

A Horiba LA-960 was used to measure average mean particle size. The Horiba LA-960 combines a modern sizing technique with refinements that allow measurement of suspension samples from 10 nanometers to 5 millimeters. The central theory in laser diffraction is that a particle will scatter light at an angle determined by that particle's size. Larger particles will scatter at small angles and smaller particles scatter at wide angles. A collection of particles will produce a pattern of scattered light defined by intensity and angle that can be transformed into a particle size distribution result. Samples were diluted 1:10 with 10% PEG 3350, 50 mM HEPES, pH 7.0 buffer. The average mean particle size was 4.4 microns.

Dynamic Viscosity Measurement

Figure 8A:
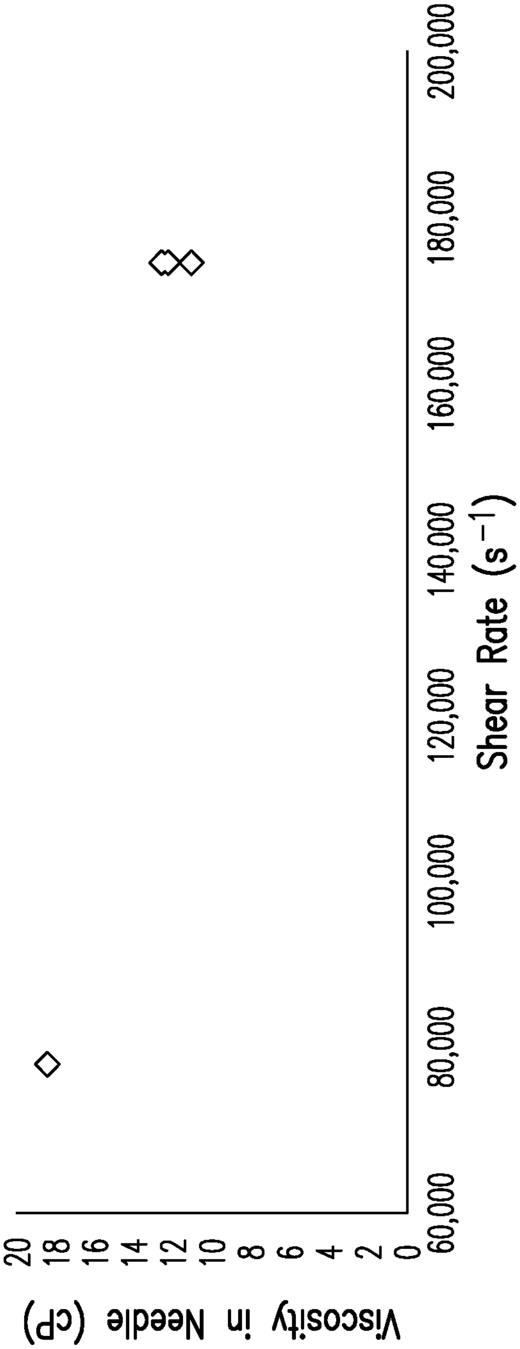
FIG. 8A shows the viscosity (cP) of a 200 mg/mL crystalline pembrolizumab suspension v. shear rate ($s^{-1}$) with BD Hypak 1 mL PFS with 27 G RW and 29 G TW×½" needle. See EXAMPLE 12.

A Rheosense m-VROC instrument derives viscosity from pressure drop using Hagen-Poiseuille equation. Shear sweeps were performed from 1,500-95,000 (1/s) to measure dynamic viscosity. The viscosity of a 200 mg/mL formula was measured and plotted vs different shear rates using a BD Hypak 1 ml pre-filled syringe with either a 27 gauge regular wall (RW) or a 29 gauge thin wall (TW) with a ½" needle. Viscosity versus shear rate data is provided in FIG. 8A. For the 200 mg/mL crystalline suspension sample, the viscosity at room temperature was 26 cP at a shear rate of about 2000 $sec^{-1}$. As the shear rate was increased further to 80,000 $sec^{-1}$ and 180000 $sec^{-1}$, a concomitant decrease in viscosity was observed. The viscosity decreases from 18 cP to 12 cP which is within the acceptable range for high concentration injection products such as monoclonal antibodies. The unexpected shear thinning behavior in this crystalline suspension formulation can be leveraged to ease injection of the drug product from a device such as a syringe or an auto-injector.

Injectability Measurements

Preliminary injection force feasibility testing was run on 200 mg/mL crystalline pembrolizumab suspensions, in a variety of 1 mL plastic and glass syringes and needles. See Table 8.

TABLE 8

| Injection Force of 200 mg/mL Crystalline Pembrolizumab Suspensions | | | | |
|---|---|---|---|---|
| ID | Syringe Type | Needle Type | Injection Rate at Plunger (mm/min) | Average Injection Force (N) |
| 1 | BD Disposable 1 mL syringe, Luer-Lok (mfg. #309628) | BD General Use 27 G × ½", Luer-Lok (mfg. #305109) | 300 | 8.46 |
| 2 | BD Hypak 1 mL PFS | 29 G TW × ½" | 133.86 | 12.11 |
| 3 | BD Hypak 1 mL PFS | 29 G TW × ½" | 300 | 16.20 |
| 4 | BD Hypak 1 mL PFS | 29 G × ½" | 133.86 | 12.01 |
| 5 | BD Hypak 1 mL PFS | 29 G × ½" | 300 | 18.41 |
| 6 | BD Hypak 1 mL PFS | 29 G TW × ½" | 300 | 17.98 |
| 7 | BD Safety-Lok I mL Insulin Syringe (mfg. #329464) | BD Ultra-Fine 29 G × ½" (mfg. #329464) | 300 | 6.37 |

Figure 8B:
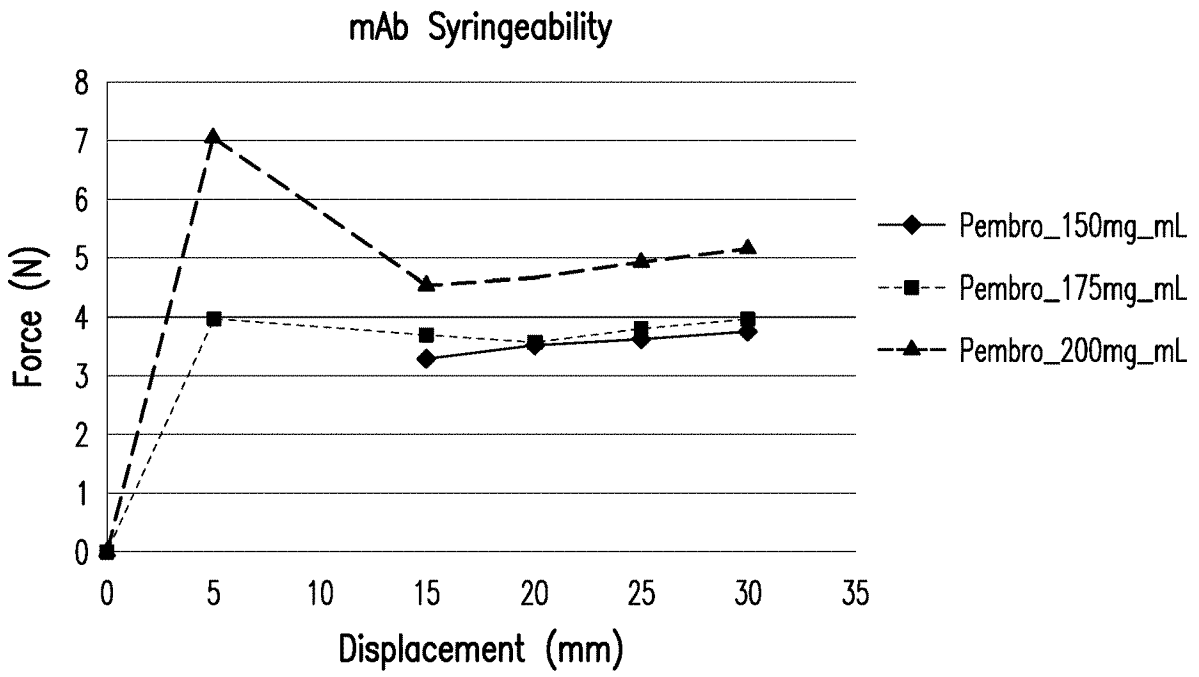
FIG. 8B shows the syringe injection force (N) v. displacement (mm) of 200 (triangles), 175 (squares) and 150 (diamonds) mg/mL pembrolizumab crystalline suspensions, produced as described in EXAMPLE 11.
Figure 9:
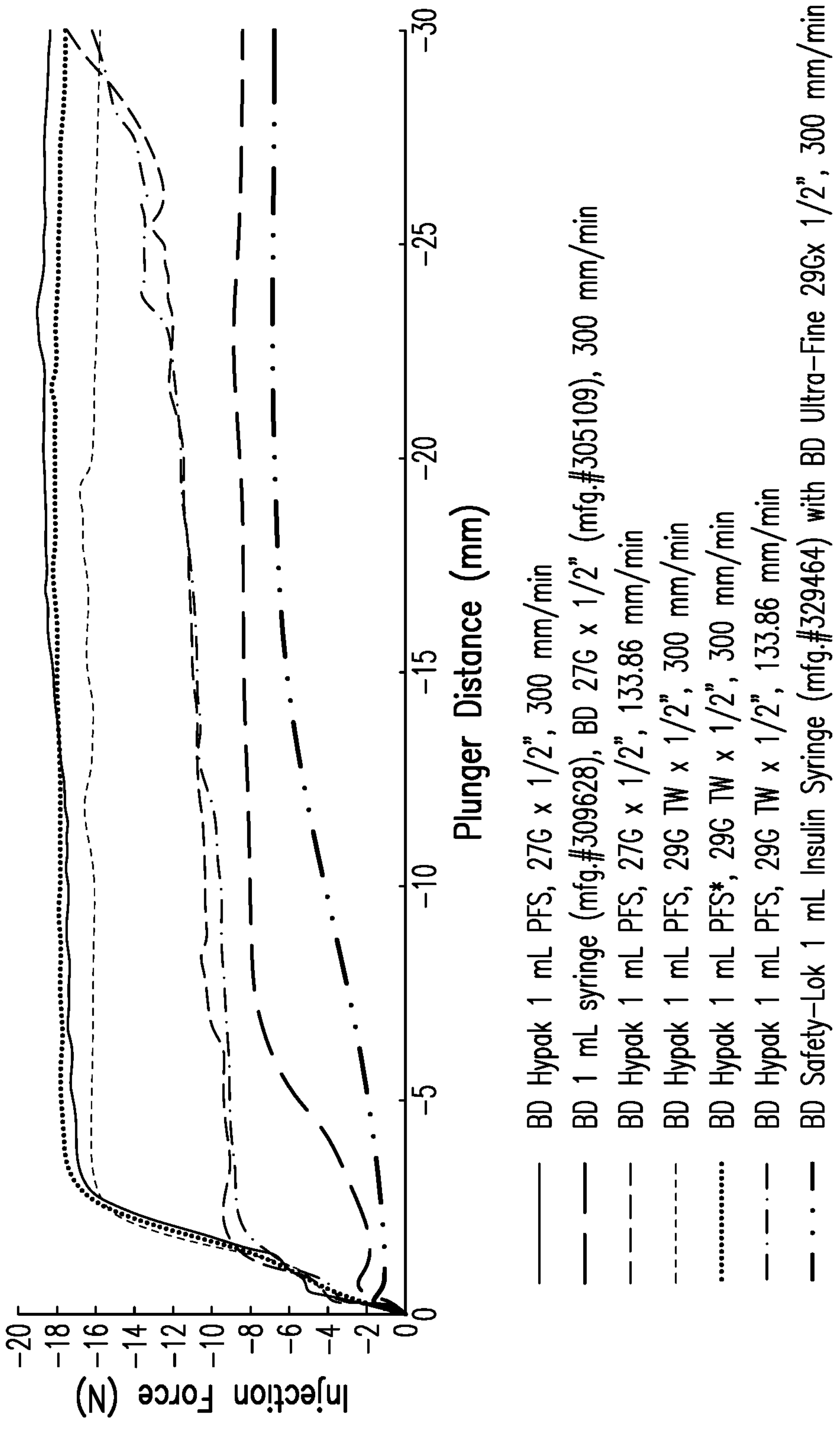
FIG. 9 provides the injection force (N) required over distance (mm) for a 200 mg/mL crystalline pembrolizumab suspension in a variety of 1 mL plastic and glass syringes. See EXAMPLE 12. The crystalline suspension was produced under the conditions described in EXAMPLE 11.

Syringe injection force is the force required to dispense contents of a syringe at a fixed rate. This force is often measured using a tensile/compression tester (i.e. INSTRON). A tensile/compression tester (INSTRON, Norwood, MA) was used to measure pembrolizumab crystalline suspensions filled in 1-mL polycarbonate syringes at 200, 175 and 150 mg/mL at an injection rate of 120 mm/min (175 mg/mL and 200 mg/mL) or 225 mm/min (150 mg/mL). Injection force of the pembrolizumab suspensions at the three different concentrations are provided in FIG. 8B and the injection forces for the samples filled in glass syringes are shown in FIG. 9.

Results indicate that the break-loose and the gliding forces were higher (7.08 N and 4.52-5.12N, respectively) for the 200 mg/mL suspension while the lower concentration (175 and 150 mg/mL) samples showed lower break-loose and gliding forces (3.96 N and 3.57-3.97 N respectively). See FIG. 8B. Injection forces varied according to material type of the syringe barrel (plastic or glass), injection rate, needle size (27 or 29 G) and needle thickness (thin wall or regular wall). FIG. 9. The injection forces were lower for the plastic syringes (<8.5 N) compared to the glass syringes (>12 N). See FIG. 8B.

For the 200 mg/mL suspension, higher injection rates required higher injection forces. See Table 8 and FIG. 9. For example, in the BD Hypak 1 mL glass syringe, for an injection rate of 133.86 mm/min, the injection force was 12.1 N compared to 16.2 N for an injection rate of 300 mm/min. The injection forces observed (6.36-18.41 N) were within the acceptable range for a subcutaneous injection of 200 mg/mL crystalline suspension of pembrolizumab. Overall, these data suggest that for injection of a 200 mg/mL crystalline suspension of pembrolizumab, syringes made of polycarbonate plastic or glass, thin or regular wall 27 or 29 G stainless steel needle can be used at an injection rate 133.86 to 300 mm/min with injection forces that are acceptable for subcutaneous injection.

Example 13

High Performance Ion-Exchange Chromatography Analyses Materials

A 44 mg/mL solution of pembrolizumab in 20 mM histidine buffer, pH 5.4 (0.2 micron filtered) was prepared using sterile non pyrogenic water solution.

A solution of 10.18% PEG 3350, 50 mM HEPES, pH 7.4 was prepared by adding 2.5 mL of 1M HEPES (Hampton Research HR2-941-27), pH 7.4 and 10.2 mL of 50% PEG 3350 (50% solution; Rigaku Item #108058) to 37.3 mL sterile water for injection (Hospira RI-4469). The resulting solution was 0.2 micron filtered.

A solution of 2.5% caffeine, 20 mM histidine, pH 5.4 was prepared by adding 1.25 g caffeine (Sigma; Lot #SLBK4804V) to 50 mL 20 mM histidine (Sigma; H-8000), pH 5.4. The solution was heated to 60° C. until the caffeine went into solution. The solution was allowed to cool to room temperature before usage.

Batch Crystallization Process (1 mL)

To 333 µl of pembrolizumab (44 mg/mL) in 20 M histidine buffer, pH 5.4 was added 666 µl 10.18% PEG 3350, 50 mM HEPES, pH 7.2 at room temperature. To the resulting solution was added 100 µl of 2.5% caffeine, 20 mM histidine buffer, pH 5.4. The mixture (in solution) was placed on the Labnet rotisserie at room temperature. Visible turbidity was observed after 15 minutes. The batch continued to be rotated for 2 hours at room temperature. Crystals were observed based on microscopic inspection.

The crystalline suspension was centrifuged at 3000 RPM for 3 minutes in a microfuge at room temperature. The mother liquor was pipetted off. The pellet was re-suspended in 1 mL of 10.18% PEG 3350, 50 mM HEPES, and pH 7.2, centrifuged at 3000 RPM for 3 minutes in a microfuge at room temperature. The wash solution was pipetted off. The pellet was re-dissolved in 1 mL of PBS at 4° C. for 8 minutes and centrifuged at 3000 RPM for 3 minutes in a microfuge at 4° C.

HP-IEX Process

High performance ion-exchange chromatography (HP-IEX) was used to assess the charge profile of the crystalline pembrolizumab compared to non-crystallized material. An ion exchange HPLC method was performed using a Dionex ProPac WCX-10 column and a UV detector at 280 nm. Samples were diluted in purified water, and 80 µg were injected for analysis. Different charge variants were eluted using a gradient of the following mobile phases (mobile phase A: 24 mM MES, pH 6, 4% acetonitrile (v/v); mobile phase B: 20 mM phosphate, 95 mM NaCl, pH 8, 4% acetonitrile (v/v). The % area of the main peaks, representing non-degraded pembrolizumab) as well as the different charge variants for the pembrolizumab starting material and the dissolved pembrolizumab crystals are provided in Table 9. The results indicate that the % charge variants of pembrolizumab in the crystalline suspension was similar to the starting material in aqueous solution.

TABLE 9

IEX Analysis of Pembrolizumab Crystal Suspension Compared to Non-Crystallized Starting Material

| Peak | % Area Starting Material | Crystalline Suspension |
|---|---|---|
| Acidic 2 | 4.62 | 5.08 |
| Acidic 1 | 11.98 | 11.09 |
| Main | 62.07 | 62.76 |
| Basic 1 | 11.3 | 11.69 |
| Basic 2 | 10.04 | 9.37 |

Example 14

Pembrolizumab Competitive Binding ELISA

Preparation of Crystalline Suspension for Bioassay Analyses

To 333 μl of pembrolizumab (44 mg/mL) in 20 M histidine buffer, pH 5.4 was added 666 μl 10.18% PEG 3350, 50 mM HEPES, pH 7.2 at room temperature. To the resulting solution was added 100 μl of 2.5% caffeine, 20 mM histidine buffer, pH 5.4. The mixture (in solution) was incubated for 1 month at 30° C. Crystals were observed based on microscopic visible inspection.

The crystalline suspension was centrifuged at 3000 RPM for 3 minutes in a microfuge at room temperature. The mother liquor was pipetted off. The pellet was re-suspended in 1 mL of 10.18% PEG 3350, 50 mM HEPES, pH 7.2, and centrifuged at 3000 RPM for 3 minutes in a microfuge at room temperature. The wash solution was pipetted off. The pellet was re-dissolved in 1 mL of PBS at 4° C. for 8 minutes and centrifuged at 3000 RPM for 3 minutes in a microfuge at 4° C. A protein concentration of 6.061 mg/mL was determined based on Nano drop 280 nm reading; total volume of 1 mL. The sample was used for bioassay analyses, as described below.

Competitive Binding ELISA

The pembrolizumab competitive binding ELISA evaluates the ability of pembrolizumab to compete with PD-L1 (PD-1 ligand) for binding to PD-1/Fc immobilized on an ELISA plate. A sample of non-crystallized pembrolizumab ("reference") was used as a reference material to test the potency of the crystallized pembrolizumab suspension, made by the process described above ("test sample"). 4.5 μg/mL reference and test samples were serially diluted 2-fold in PBS pH 6.5, 1% BSA and mixed with an equal volume of 600 ng/mL rhPD-L1/Fc chimera ("PD-L1," Bio-techne, R & D Systems (cat. no. 156-B7), Minneapolis, MN) and then transferred to ELISA plates. The final concentrations of assay components were 2.25 μg/mL (reference and test samples) and 300 ng/mL (PD-L1). The levels of PD-L1 bound to PD-1/Fc were detected by biotinylated anti PD-L1 (Bio-techne, R & D Systems (cat. no. BAF156)), followed by peroxidase conjugated streptavidin and chemiluminescense substrate. Luminescence was measured using a microplate reader and resulting inhibition response curves were analyzed with 4-PL curve fitting software (SoftMax Pro).

The IC50 values generated from this assay are a measurement of the ability of pembrolizumab to inhibit PD-L1 binding to PD-1/Fc. Biological potency of the crystal samples is expressed as % relative potency of the pembrolizumab reference material. Geometric mean of relative potency from multiple replicates (N=3) of the same sample is reported, along with geometric standard deviation (% GSD) and 95% confidence interval. The results show the that the dissolved crystal samples had a relative potency of 95% compared to the reference (non-crystallized) pembrolizumab. See Table 10.

TABLE 10

Relative Potency of Pembrolizumab Crystals

| Dissolved Crystals mg/mL | % Relative Potency of Pembrolizumab Reference Material | % Geometric Standard Deviation | Lower Confidence Limit (95%) | Upper Confidence Limit (95%) |
|---|---|---|---|---|
| 6.061 | 95 | 3 | 87 | 103 |

Example 15

Lab Batch Crystallization Process-Non-Clean Room Conditions

A 42.7 mg/mL solution of pembrolizumab (Batch #W15-MK3475P-081) in 20 mM histidine buffer pH 5.4 (0.2 micron filtered) was prepared using sterile non pyrogenic water solution.

A solution of 10.18% PEG 3350 (50% solution Rigaku Item #10805850) mM HEPES, pH 7.0 (400 mL) was prepared by adding 20 mL of 1M HEPES (Hampton Research HR2-941-27), pH 7.4 and 81.6 mL of 50% PEG 3350 to 298.4 mL sterile water. The resulting solution was 0.2 micron filtered and stored at room temperature.

A solution of 2.5% caffeine, 20 mM histidine, pH 5.4 was prepared by adding 1.25 g caffeine (Sigma Lot #SLBK4804V) to 50 mL of 20 mM histidine (Sigma H-8000), pH 5.4. The resulting solution was heated to 60° C. until the caffeine went into solution. The solution was allowed to cool to room temperature before usage.

Four mL tubes of crystallization solution (43.72 mL scale) were prepared. To 13.32 mL of pembrolizumab (42.7 mg/mL) in 20 M histidine buffer, pH 5.4 was added 26.4 mL 10.18% PEG 3350, 50 mM HEPES, pH 7.0 at room temperature. To the resulting solution was added 4 mL of 2.5% caffeine, 20 mM histidine buffer, pH 5.4 in a 50 mL tube. The mixture (in solution) was placed on the Labnet rotisserie at room temperature. Visible turbidity was observed after 15 minutes. The batch was rotated for an additional 2 hours at room temperature. SONICC analyses were performed and confirmed crystallinity.

The 50 mL conical tubes were centrifuged in a Beckman Coulter Allegra X-15R centrifuge at 2600 RPM at room temperature for 10 minutes each 50 mL conical tube. The supernatants were decanted. The pellets in each 50 mL conical tube were re-suspended in 40 mL of 10% PEG 3350, 50 mM HEPES, pH 7.0. The process of centrifugation, decanting and resuspension was repeated. For the final centrifugation step, the bottles were centrifuged in a Beckman Coulter Allegra X-15R centrifuge at 3500 RPM at room temperature for 20 minutes. The supernatant was decanted off. The protein concentration, measured by weight:volume, 1:10, A280 reading was 216 mg/mL. Final volume 9.7 mL (92% yield). The particle size analyses measured using the Horiba particle size analyzer was 1.3 microns mean particle size.

Example 16

Batch Crystallization (43.72 mL scale)—Clean Room Conditions

A solution of 2.5% caffeine, 20 mM histidine, pH 5.4 was prepared by adding 1.25 g caffeine (Sigma Lot #SLBK4804V) to 50 mL of 20 mM histidine (Sigma H-8000), pH 5.4. The mixture was heated to 60° C. until the caffeine went into solution. The solution was allowed to cool to room temperature and sterile filtered before usage.

A solution of 10.18% PEG 3350, 50 mM HEPES, pH 7.0 solution (400 mL) was prepared by adding 20 mL of 1M HEPES (Hampton Research HR2-941-27), pH 7.4 and 81.6 mL of 50% PEG 3350 (Rigaku Item #108058) to 298.4 mL sterile water. The resulting solution was 0.2 micron filtered and stored at room temperature.

A solution of pembrolizumab at 42.7 mg/mL in 20 mM histidine buffer, pH 5.4 (0.2 micron filtered) was prepared using sterile non pyrogenic water.

To sterile, filtered 13.32 mL of pembrolizumab (42.7 mg/mL) in 20 M histidine buffer (4×50 mL tubes), pH 5.4 was added 26.4 mL 10.18% PEG 3350, 50 mM HEPES, pH 7.0 at room temperature. To this solution was added 4 mL of 2.5% caffeine, 20 mM histidine buffer, pH 5.4 in a 50 mL sterile conical tube in a clean room. After mixing, the concentrations of the components of the crystallization solution in the 4×50 mL conical tubes were: 2.28 g pembrolizumab in a 6 mM histidine, 6% PEG 3350, 30 mM HEPES, 0.23% caffeine, pH 6.8.

The mixture (in solution) was placed on the Labnet rotisserie at room temperature. Visible turbidity was observed after 15 minutes. The 4×50 mL sterile conical tubes were rotated for 2 hours at room temperature. SONICC™ analyses were performed after 2 hours and confirmed crystallinity.

The 4×50 mL sterile conical tubes were centrifuged in a Beckman Coulter Allegra X-15R centrifuge at 2600 RPM at room temperature for 10 minutes for each 50 mL conical tube. The supernatants were decanted. The pellets were re-suspended; each 50 mL conical tube in 40 mL of 10% PEG 3350, 50 mM HEPES, pH 7.0. The process was repeated. For the final centrifugation step, the conical tubes were centrifuged in a Beckman Coulter Allegra X-15R centrifuge at 3500 RPM at room temperature for 20 minutes. The supernatant was decanted off. The protein concentration, measured by weight:volume 1:10 A280 was 231 mg/mL. The sample was diluted to 0.8 mL of 10% PEG 3350, 50 mM HEPES, pH 7.0. The protein concentration, measured by weight:volume 1:10 A280 was 200.3 mg/mL final concentration. The final volume was 8.4 mL (74% yield). The protein concentration measured using an RPLC method was 192.5 mg/mL (1.2 mM) and the caffeine concentration was 0.5 mg/mL (2.5 mM). The mean particle size measured using the Horiba particle size analyzer was 1.3 microns.

Example 17

Batch Dialysis Crystallization Process

400 μl of 44 mg/mL pembrolizuab (Lot #W12123475P-17C) stock solution was place in Spectra/Por™ CE (cellulose ester) irradiated DispoDialyzer, MW cutoff: 10,000 diameter 5 mm, sample volume 500 μl. The bag was placed in a 15 mL flat bottom tube containing 10 mL of 50 mM HEPES, pH 6.8, 10% PEG 3350, 100 mM caffeine, which was stirred via a magnetic stir bar at room temperature. Slight turbidity was observed after 3 hours, the turbidity increased significantly after 18 hours. An aliquot was characterized by SONICC analyses and confirmed crystal formation. The resulting suspension was centrifuged at 3000 RPM in a microfuge for 3 minutes. The resulting pellet and washed with 1 mL of 50 mM HEPES, pH 6.8, 10% PEG 3350, and re-centrifuged in a microfuge at 3000 RPM for 3 minutes. The resulting pellet was dissolved in 10 mL of normal PBS (5 minutes at room temperature). The resulting measured A280 readings were 1.6 mg/mL (16 mg protein total). The overall yield was 91% (17.6 mg starting total mAb content). This experiment shows that a crystallization process using dialysis can produce crystalline pembrolizumab suspensions within 18 hours at room temperature in high yield.

Example 18

Pharmacokinetic Study of Pembrolizumab Crystalline Formulation

A PK comparability study in male Wistar Hen rats with pembrolizumab crystalline formulations was conducted. The dose of pembrolizumab for all groups was 50 mg/kg. Pembrolizumab at 20 mg/mL in liquid IV formulation (7% sucrose, 0.02% polysorbate 80, 10 mM histidine, pH 5.5 (group 1)) and in liquid SC formulation (7% sucrose, 0.02% polysorbate 80, 10 mM histidine, pH 5.5, 10 mM methionine (group 2)) were included as basis for bioavailability control groups (N=3 for each of groups 1 and 2).

A pembrolizumab crystalline suspension was prepared as described in EXAMPLE 16 and used for pembrolizumab crystalline formulations comprising 20 mg/mL (group 3, N=4), 40 mg/mL (group 4, N=4) and 100 mg/mL (group 5, N=4) pembrolizumab, along with 50 mM HEPES buffer, pH 7.0, and 10.18% PEG 3350 at concentrations listed in Table 11 were dosed subcutaneously. In order to ensure accurate dosing for each group, a weight/density measurement (Ig/mL) was used to accurately fill the BD Hypak 2.25 mL pre-fillable syringes for each group described in Table 11.

TABLE 11

Crystalline Formulation Groups Tested in Rat Study

| Group | Dose | Concentration (mg/mL) | Syringe fill* (g) |
|---|---|---|---|
| 3 | 50 mpk | 20 | 1.1 |
| 4 | 50 mpk | 40 | 0.7 |
| 5 | 50 mpk | 100 | 0.5 |

*0.1 g dead space in each syringe due to back filling

The specified weight of crystalline suspension was added using a sterile 10 mL positive displacement pipettor to each group to tared BD Hypak™ 2.25 mL pre-fillable glass syringes. A venting tool was used to bring the plunger cap to the liquid surface of the suspension within each filled syringe. There were a total of six syringes prepared for each group.

To control for potential caffeine effect, a pembrolizumab caffeine-free formulation (50 mM HEPES, pH 6.8, 10% PEG 3350, group 6) and a pembrolizumab-PEG free formulation (50 mM HEPES, pH 6.8, caffeine, group 7) were included in the study.

After dosing, blood was collected and serum prepared from 0.3 mL of whole blood post-dose at 0.5, 3, 6, 24, 48, 72, 96, 168, 216, 336, 408 and 504 hours. Pembrolizumab in serum was measured with a MSD (Meso Scale Discovery) immunoassay. PK parameters were calculated with a Phoenix PK software 64.6.3. Bioavailability (F) was calculated based on AUC from liquid formulation IV group (F=AUC of SC/AUC of IV*100%). Injection site was monitored throughout the study.

The results showed that the tested SC liquid formulation of pembrolizumab at 20 mg/mL resulted in similar bioavailability to that of 20 mg/mL of the crystalline formulation. See Table 12. The results also showed that maximum concentration ($C_{max}$), exposure (area under curve, AUC) and bioavailability (F) increased in a concentration dependent manner: the higher the concentration, the higher the $C_{max}$, AUC and F. The time to maximum concentration in the serum ($T_{max}$) was shorter for the highest concentration of crystalline formulation in comparison with lower concentrations, suggesting a fast absorption rate (Ka) for the highest concentration of crystalline formulation.

TABLE 12

Bioavailability of Liquid and Crystalline Formulations

| Treatment Groups | $C_{max}$ (μg/mL) Mean ± SD | $AUC_{all}$ (μg*d/mL) Mean ± SD | Tmax (Day) Mean ± SD | Bioavailability (F %) Mean ± SD |
|---|---|---|---|---|
| 1. Liquid IV formulation | 997 ± 107 | 4376 ± 169 | 0.02 ± 0 | N/A |
| 2. Liquid SC formulation | 167 ± 18 | 2104 ± 969 | 5.67 ± 2.3 | 48 ± 22 |
| 3. Crystalline formulation | 168 ± 22 | 1634 ± 407 | 3.75 ± 0.5 | 37 ± 10 |
| 4. Crystalline formulation | 242 ± 68 | 2160 ± 801 | 3.75 ± 0.5 | 49 ± 14 |
| 5. Crystalline formulation | 396 ± 28 | 2939 ± 475 | 3.00 ± 0 | 67 ± 8 |
| 6. Caffeine-free formulation | 143 ± 9 | 1821 ± 516 | 4.00 ± 0 | 42 ± 12 |
| 7. PEG-free formulation | 157 ± 22 | 2387 ± 416 | 4.00 ± 0 | 55 ± 10 |

Example 19

Solid State NMR Characterization of Pembrolizumab Crystalline Suspension

Solid-state NMR spectra are acquired on a Bruker Avance III HD 400 MHz spectrometer equipped with a 4.0 mm H/F/X magic angle spinning (MAS) probe and a Bruker Avance III 500 MHz spectrometer equipped with a 4.0 mm H/C/N MAS probe. The probes are tuned to double resonance C/H for $^{13}C$ (carbon-13) experiments on the 400 MHz spectrometer and triple-resonance C/N/H for $^{13}C$ (carbon-13) and $^{15}N$ (nitrogen-15) experiments on the 500 MHz spectrometer. The MAS frequency for all experiments is 12 kHz. The sample temperature is controlled at 10° C. on the 400 MHz spectrometer and 21° C. on the 500 MHz spectrometer. On the 400 MHz spectrometer, $^{13}C$ cross polarization (CP) MAS spectra are collected under 90.9 kHz 1H dipolar decoupling during acquisition, with a CP contact time of 1 millisecond and a recycle delay of 2 seconds. On the 500 MHz spectrometer, $^{13}C$ CP MAS spectra are collected under 71.4 kHz 1H dipolar decoupling during acquisition, with a CP contact time of 1 millisecond and a recycle delay of 2 seconds. On the 500 MHz spectrometer, $^{15}N$ CP MAS spectra are collected under 71.4 kHz 1H dipolar decoupling during acquisition, with a CP contact time of 2.5 milliseconds and a recycle delay of 2 seconds. $^{13}C$ chemical shifts are referenced to the $^{13}C$ signal of the carbonyl carbon of glycine (α-form) at 176.45 ppm. For purposes of solid-state NMR, the term "about" means±0.1 ppm.

Figure 10B:
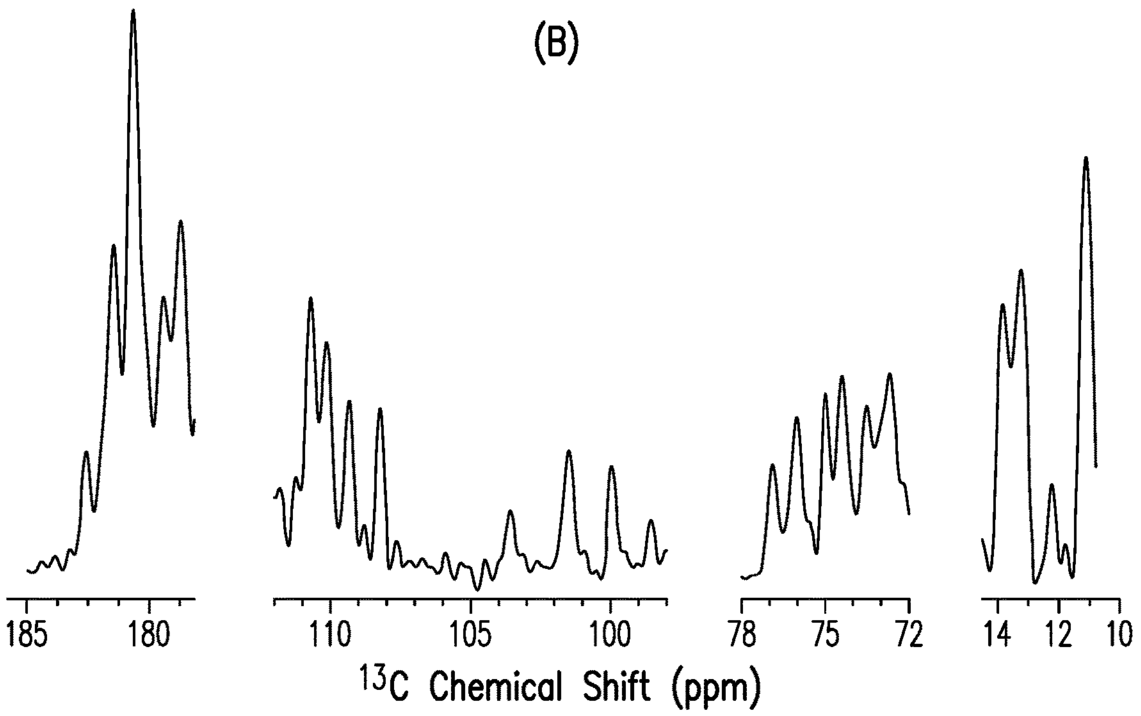
FIG. 10B depicts enlarged spectral regions of the spectra of FIG. 10A.

Using the solid state $^{13}C$ 400 MHz NMR equipment and procedures described above, the pembro-caffeine crystal has been measured. Specifically, crystalling pembrolizumab was prepared using the method described in Example 11. The $^{13}C$ (carbon-13) CP MAS NMR spectrum for the pembrolizumab-caffeine crystal was obtained. The full spectrum and a few enlarged regions are respectively shown in FIG. 10A and FIG. 10B. Characteristic peaks for the pembrolizumab-caffeine crystal are observed at about 183.07, 182.16, 181.54, 180.55, 179.99, 110.70, 110.15, 109.36, 108.23, 103.58, 101.49, 99.75, 98.56, 76.88, 76.04, 74.97, 74.41, 73.52, 72.69, 13.85, 13.27, 12.26 and 11.13 ppm.

Figure 11A:
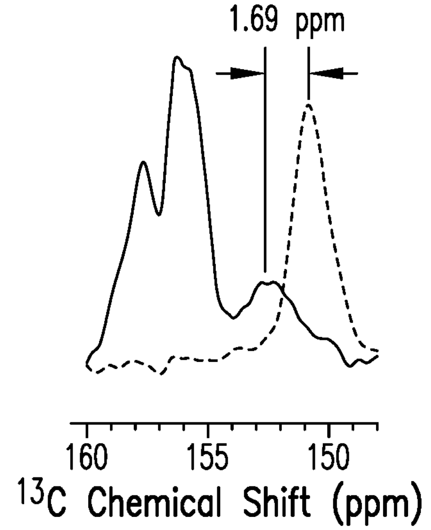
FIG. 11A and FIG. 11B depict $^{13}C$ (FIG. 11A) and $^{15}N$ (FIG. 11B) CP MAS spectra of a pembrolizumab-caffeine crystalline suspension (solid line) and caffeine-only crystal (dotted line). Isotopically 2-$^{13}C$ and 1,3-$^{15}N$ labeled caffeine was utilized in these spectra.
Figure 11B:
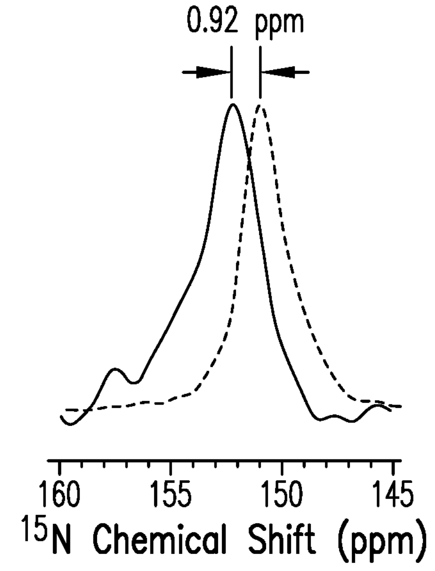

Using the solid state $^{13}C$ and $^{15}N$ 500 MHz NMR equipment and procedures described above, the pembrolizumab-caffeine crystal prepared using isotopically 2-$^{13}C$ and 1,3-$^{15}N$ labeled caffeine has been measured. The $^{13}C$ (carbon-13) and $^{15}N$ (nitrogen-15) CP MAS NMR spectra for the pembro-caffeine crystal was obtained. The enlarged spectral regions exhibiting resolved $^{13}C$ and $^{15}N$ caffeine peaks are respectively shown in FIG. 11A and FIG. 11B. Characteristic chemical shift differences of $^{13}C$ and $^{15}N$ caffeine peaks between the pembro-caffeine crystal and caffeine-only crystal are observed at about 1.69 and 0.92 ppm, respectively.

What is claimed:

1. A method for producing crystalline anti-PD-1 monoclonal antibody (mAb) comprising:

a) mixing:

i) an aqueous buffered solution comprising about 5 mg/mL to about 80 mg/mL of the anti-PD-1 mAb, wherein the anti-PD-1 mAb is pembrolizumab or a pembrolizumab variant, ii) polyethylene glycol (PEG), and iii) an additive comprising caffeine or theophylline;

to form a crystallization solution, wherein the crystallization solution has a pH of about 6.0 to about 8.8 and comprises between about 12% and about 15% weight per volume (w/v) PEG and about 0.1% to about 0.30% w/v additive, wherein, when theophylline is the additive, its concentration is between about 0.15% w/v and about 0.30% w/v, wherein, when caffeine is the additive, its concentration is between about 0.1% w/v and about 0.18% w/v;

a) incubating the crystallization solution for a period of time sufficient for crystal formation, wherein the crystallization solution is incubated a temperature between about 18° C. and about 25° C.; and b) optionally harvesting the crystalline anti-PD-1 mAb from the solution.

2. The method of claim 1, wherein the aqueous buffered solution comprising the mAb further comprises histidine buffer at a pH of about 5.0 to about 6.0.

3. The method of claim 1, wherein the PEG and the additive are mixed together to form a precipitant solution before being mixed with the aqueous buffered solution comprising the mAb.

4. The method of claim 1, wherein the solution concentration of the anti-PD-1 mAb in the crystallization solution is from about 5 mg/mL to about 50 mg/mL.

5. The method of claim 1, wherein the crystallization solution is produced by vapor diffusion, batch crystallization or dialysis.

6. A composition comprising an isolated crystal comprising pembrolizumab complexed with caffeine, wherein the crystal is characterized by space group $P222_1$ a=43.8 Å b=113.9 Å c=175.0 Å, α=β=γ=90° and a pharmaceutically acceptable carrier, further comprising about 0.01% to about 0.10% w/v non-ionic surfactant.

7. A composition comprising an isolated crystal comprising pembrolizumab complexed with caffeine, wherein the crystal is characterized by space group $P222_1$ a=43.8 Å b=113.9 Å c=175.0 Å, α=β=γ=90° and a pharmaceutically acceptable carrier, further comprising a second active pharmaceutical ingredient (API).

* * * * *

SEQUENCE LISTING

```
<160> NUMBER OF SEQ ID NOS: 10

<210> SEQ ID NO 1
<211> LENGTH: 15
<212> TYPE: PRT
<213> ORGANISM: Artificial Sequence
<220> FEATURE:
<223> OTHER INFORMATION: pembrolizumab light chain CDR1

<400> SEQUENCE: 1

Arg Ala Ser Lys Gly Val Ser Thr Ser Gly Tyr Ser Tyr Leu His
1               5                   10                  15


<210> SEQ ID NO 2
<211> LENGTH: 7
<212> TYPE: PRT
<213> ORGANISM: Artificial Sequence
<220> FEATURE:
<223> OTHER INFORMATION: pembrolizumab light chain CDR2

<400> SEQUENCE: 2

Leu Ala Ser Tyr Leu Glu Ser
1               5


<210> SEQ ID NO 3
<211> LENGTH: 9
<212> TYPE: PRT
<213> ORGANISM: Artificial Sequence
<220> FEATURE:
<223> OTHER INFORMATION: pembrolizumab light chain CDR3

<400> SEQUENCE: 3

Gln His Ser Arg Asp Leu Pro Leu Thr
1               5


<210> SEQ ID NO 4
<211> LENGTH: 5
<212> TYPE: PRT
<213> ORGANISM: Artificial Sequence
<220> FEATURE:
<223> OTHER INFORMATION: pembrolizumab heavy chain CDR1

<400> SEQUENCE: 4

Asn Tyr Tyr Met Tyr
1               5


<210> SEQ ID NO 5
<211> LENGTH: 17
<212> TYPE: PRT
<213> ORGANISM: Artificial Sequence
<220> FEATURE:
<223> OTHER INFORMATION: pembrolizumab heavy chain CDR2

<400> SEQUENCE: 5

Gly Ile Asn Pro Ser Asn Gly Gly Thr Asn Phe Asn Glu Lys Phe Lys
1               5                   10                  15

Asn


<210> SEQ ID NO 6
<211> LENGTH: 11
<212> TYPE: PRT
<213> ORGANISM: Artificial Sequence
<220> FEATURE:
<223> OTHER INFORMATION: pembrolizumab heavy chain CDR3

<400> SEQUENCE: 6
```

```
Arg Asp Tyr Arg Phe Asp Met Gly Phe Asp Tyr
1               5                   10


<210> SEQ ID NO 7
<211> LENGTH: 111
<212> TYPE: PRT
<213> ORGANISM: Artificial Sequence
<220> FEATURE:
<223> OTHER INFORMATION: pembrolizumab light chain variable region

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110


<210> SEQ ID NO 8
<211> LENGTH: 120
<212> TYPE: PRT
<213> ORGANISM: Artificial Sequence
<220> FEATURE:
<223> OTHER INFORMATION: pembrolizumab heavy chain variable region

<400> SEQUENCE: 8

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120


<210> SEQ ID NO 9
<211> LENGTH: 218
<212> TYPE: PRT
<213> ORGANISM: Artificial Sequence
<220> FEATURE:
<223> OTHER INFORMATION: pembrolizumab light chain

<400> SEQUENCE: 9

Glu Ile Val Leu Thr Gln Ser Pro Ala Thr Leu Ser Leu Ser Pro Gly
```

-continued

```
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 10
<211> LENGTH: 447
<212> TYPE: PRT
<213> ORGANISM: Artificial Sequence
<220> FEATURE:
<223> OTHER INFORMATION: pembrolizumab heavy chain

<400> SEQUENCE: 10

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
```

-continued

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```